US012668807B2

(12) United States Patent
Lippman et al.

(10) Patent No.: US 12,668,807 B2
(45) Date of Patent: Jun. 30, 2026

(54) GENE MUTATIONS IN TOMATO TO YIELD COMPACT AND EARLY YIELDING FORMS SUITABLE FOR URBAN AGRICULTURE

(71) Applicant: Cold Spring Harbor Laboratory, Cold Spring Harbor, NY (US)

(72) Inventors: Zachary Lippman, North Bellmore, NY (US); Choon-Tak Kwon, Cold Spring Harbor, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 335 days.

(21) Appl. No.: 17/779,987

(22) PCT Filed: Nov. 20, 2020

(86) PCT No.: PCT/US2020/061613
§ 371 (c)(1),
(2) Date: May 25, 2022

(87) PCT Pub. No.: WO2021/108272
PCT Pub. Date: Jun. 3, 2021

(65) Prior Publication Data

US 2022/0411809 A1 Dec. 29, 2022

Related U.S. Application Data

(60) Provisional application No. 62/952,096, filed on Dec. 20, 2019, provisional application No. 62/948,167, (Continued)

(51) Int. Cl.
*C12N 15/82* (2006.01)

(52) U.S. Cl.
CPC ..... *C12N 15/8213* (2013.01); *C12N 15/8262* (2013.01)

(58) Field of Classification Search
None
See application file for complete search history.

(56) References Cited

U.S. PATENT DOCUMENTS

| | | | |
|---|---|---|---|
| 8,865,970 | B2 | 10/2014 | Zamir et al. |
| 9,414,553 | B2 | 8/2016 | de Haan et al. |

(Continued)

FOREIGN PATENT DOCUMENTS

| | | | |
|---|---|---|---|
| EP | 2647646 | A1 | 10/2013 |
| WO | WO 2010/041190 | A1 | 4/2010 |

(Continued)

OTHER PUBLICATIONS

Villagarcia et al. ("Modification of tomato growth by expression of truncated ERECTA protein from *Arabidopsis thaliana*" 2012 J. Exp. Botany 63(18): 6493-6504; of record IDS Apr. 3, 2023) (Year: 2012).*

(Continued)

*Primary Examiner* — Matthew R Keogh
*Assistant Examiner* — Rebecca Stephens
(74) *Attorney, Agent, or Firm* — Wolf, Greenfield & Sacks, P.C.

(57) ABSTRACT

Aspects of the disclosure relate to plants containing one or more of a mutant sler (Solyc08g061560) gene or a homolog thereof, a mutant sp5g (Solyc05g053850) gene or a homolog thereof and a mutant sp (Solyc06g074350) gene or a homolog thereof, as well as methods of producing such plants. In some aspects, such plants have one or more improved traits, such as modified stem length and modified time for flowering and fruit production.

10 Claims, 52 Drawing Sheets

Specification includes a Sequence Listing.

Related U.S. Application Data filed on Dec. 13, 2019, provisional application No. 62/940,873, filed on Nov. 26, 2019.

(56) References Cited

U.S. PATENT DOCUMENTS

| | | | |
|---|---|---|---|
| 9,732,352 | B2 | 8/2017 | Lippman et al. |
| 9,896,696 | B2 | 2/2018 | Begemann et al. |
| 11,624,074 | B2 | 4/2023 | Park et al. |
| 12,270,035 | B2 | 4/2025 | Lippman et al. |
| 2010/0212046 | A1 | 8/2010 | Heldens |
| 2011/0247093 | A1 | 10/2011 | Zamir et al. |
| 2012/0144514 | A1 | 6/2012 | de Haan et al. |
| 2014/0143898 | A1 | 5/2014 | Lippman et al. |
| 2015/0011393 | A1 | 1/2015 | Tsuji et al. |
| 2015/0284732 | A1 | 10/2015 | Lippman et al. |
| 2020/0199604 | A1 | 6/2020 | Lippman et al. |
| 2020/0299705 | A1 | 9/2020 | Lippman et al. |
| 2022/0002740 | A2 | 1/2022 | Lippman et al. |

FOREIGN PATENT DOCUMENTS

| | | | |
|---|---|---|---|
| WO | WO 2014/081730 | A1 | 5/2014 |
| WO | WO 2017/180474 | A1 | 10/2017 |
| WO | WO 2018/213538 | A1 | 11/2018 |
| WO | WO 2018/213547 | A1 | 11/2018 |

OTHER PUBLICATIONS

Villagarcia et al. ("Modification of tomato growth by expression of truncated ERECTA protein from *Arabidopsis thaliana*" 2012 J. Exp. Botany 63(18):6493-6504). (Year: 2012).*

Kobayashi et al. ("Genome-Wide Analysis of Intraspecific DNA Polymorphism in 'Micro-Tom', a Model Cultivar of Tomato (*Solanum lycopersicum*" 2014 Plant Cell Physiol. 55(2):445-454). (Year: 2014).*

Morello & Breviario ("Plant Spliceosomal Introns: Not only Cut and Paste" 2008 Current Genomics 9:227-238). (Year: 2008).*

Veitia "Exploring the Molecular Etiology of Dominant-Negative Mutations" 2007 Plant Cell 19:3843-3851. (Year: 2007).*

Zhang et al. ("Phylogenetic and CRISPR/Cas9 Studies in Deciphering the Evolutionary Trajectory and Phenotypic Impacts of Rice ERECTA Genes" 2018 Frontiers in Plant Sci. 9:473 (11 total pages) doi: 10.3389/fpls.2018.00473). (Year: 2018).*

Li et al. ("Domestication of wild tomato is accelerated by genome editing" 2018 Nat. Biotech. 36(12): 1160-1163, 8 total pages). (Year: 2018).*

Shpak et al. (hereinafter SHPAK et al.2004) ("Synergistic interaction of three ERECTA-family receptor-like kinases controls *Arabidopsis* organ growth and flower development by promoting cell proliferation" 2004 Development 131(7):1491-1501). (Year: 2004).*

Torii et al. ("Regulation of Inflorescence Architecture and Organ Shape by the ERECTA Gene in *Arabidopsis*" Chapter 13 in Morphogenesis and Pattern Formation in Biological Systems (Sekimura et al. eds., Springer Japan 2003, 12 total pages). (Year: 2003).*

Bai & Lindhout "Domestication and Breeding of Tomatoes: What have We Gained and What Can We Gain in the Future?" 2007 Annals of Botany 100:1085-1094. (Year: 2007).*

Blair et al. "Identification of an ERECTA gene and its drought adaptation associations with wild and cultivated common bean" 2016 Plant Science 242:250-259. (Year: 2016).*

Extended European Search Report for Application No. EP20893126.1 mailed Dec. 6, 2023.

Soyk et al., Variation in the flowering gene Self Pruning 5G promotes day-neutrality and early yield in tomato. Nat Genet. Jan. 2017;49(1). Supplementary Information. 30 pages. doi: 10.1038/ng.3733. Epub Dec. 5, 2016.

International Preliminary Report on Patentability mailed Jun. 6, 2015 for application No. PCT/US2013/070825.

International Search Report and Written Opinion mailed Feb. 24, 2014 for application No. PCT/US2013/070825.

International Search Report and Written Opinion for Application No. PCT/US2017/026635 mailed Jul. 11, 2017.

International Preliminary Report on Patentability for Application No. PCT/US2017/026635 mailed Oct. 25, 2018.

International Search Report and Written Opinion for Application No. PCT/US2020/061613 mailed Mar. 23, 2021.

International Search Report on Patetability for Application No. PCT/US2020/061613 mailed Jun. 9, 2022.

[No Author Listed], Strains detail: tomatoma. Tomato Mutants Archive. <https://tomatoma.nbrp.jp/strainDetailAction.do?mutantId=TOMJPF00005>. Last accessed Sep. 7, 2022.

Aan Den Toorn et al., On the Origin of SERKs: Bioinformatics Analysis of the Somatic Embryogenesis Receptor Kinases. Mol Plant. May 2015;8(5):762-82. doi: 10.1016/j.molp.2015.03.015. Epub Apr. 9, 2015.

Abe et al., FD, a bZIP protein mediating signals from the floral pathway integrator FT at the shoot apex. Science. Aug. 12, 2005;309(5737):1052-6.

Ahn et al., A divergent external loop confers antagonistic activity on floral regulators FT and TFL1. EMBO J. Feb. 8, 2006;25(3):605-14. Epub Jan. 19, 2006.

Anzalone et al., Search-and-replace genome editing without double-strand breaks or donor DNA. Nature. Dec. 2019;576(7785):149-157. doi: 10.1038/s41586-019-1711-4. Epub Oct. 21, 2019.

Aoki et al., Large-scale analysis of full-length cDNAs from the tomato (*Solanum lycopersicum*) cultivar Micro-Tom, a reference system for the Solanaceae genomics. BMC Genomics. Mar. 30, 2010;11:210. doi: 10.1186/1471-2164-11-210. 210.

Banerjee et al., Up, up and away! The economics of vertical farming. J Agric Stud. 2014; 2(1): 40-60.

Benke et al., Future food-production systems: vertical farming and controlled-environment agriculture. Sustain: Science Pract Pol 2018; 13(1): 13-26.

Boch et al., Xanthomonas AvrBs3 family-type III effectors: discovery and function. Annu Rev Phytopathol. 2010;48:419-36.

BOCH,. TALEs of genome targeting. Nat Biotechnol. Feb. 2011;29(2):135-6.

Brand et al., Meristem maintenance and compound-leaf patterning utilize common genetic mechanisms in tomato. Planta. Sep. 2007;226(4):941-51. doi: 10.1007/s00425-007-0540-0. Epub May 23, 2007.

Brooks et al., Efficient gene editing in tomato in the first generation using the clustered regularly interspaced short palindromic repeats/CRISPR-associated9 system. Plant Physiol. Nov. 2014;166(3):1292-7. doi: 10.1104/p. 114.247577. Epub Sep. 15, 2014.

Burstein et al., New CRISPR-Cas systems from uncultivated microbes. Nature. Feb. 9, 2017;542(7640):237-241. doi: 10.1038/nature21059. Epub Dec. 22, 2016.

Cao et al., Four Tomato Flowering Locus T-Like Proteins Act Antagonistically to Regulate Floral Initiation. Front Plant Sci. Jan. 11, 2016;6:1213. doi: 10.3389/fpls.2015.01213. eCollection 2015.

Carmel-Goren et al., The SELF-PRUNING gene family in tomato. Plant Mol Biol. Aug. 2003;52(6):1215-22.

Cermak et al., Efficient design and assembly of custom TALEN and other TAL effector-based constructs for DNA targeting. Nucleic Acids Res. Jul. 2011;39(12):e82. doi: 10.1093/nar/gkr218. Epub Apr. 14, 2011. Erratum in: Nucleic Acids Res. Sep. 1, 2011;39(17):7879.

Christian et al., Targeting DNA double-strand breaks with TAL effector nucleases. Genetics. Oct. 2010;186(2):757-61. doi: 10.1534/genetics.110.120717. Epub Jul. 26, 2010.

Elitzur et al., Co-ordinated regulation of flowering time, plant architecture and growth by FASCICULATE: the pepper orthologue of Self Pruning. J Exp Bot. 2009;60(3):869-80. doi: 10.1093/jxb/ern334. Epub Jan. 27, 2009.

Eshed et al., Revolutions in agriculture chart a course for targeted breeding of old and new crops. Science. Nov. 8, 2019;366(6466):eaax0025. doi: 10.1126/science.aax0025. Epub Sep. 5, 2019.

Feng et al., Multigeneration analysis reveals the inheritance, specificity, and patterns of CRISPR/Cas-induced gene modifications in

(56) References Cited

OTHER PUBLICATIONS

*Arabidopsis*. Proc Natl Acad Sci U S A. Mar. 25, 2014;111(12):4632-7. doi: 10.1073/pnas.1400822111. Epub Feb. 18, 2014.
Gabsalilow et al., Site- and strand-specific nicking of DNA by fusion proteins derived from MutH and I-Scel or TALE repeats. Nucleic Acids Res. Apr. 2013;41(7):e83. doi: 10.1093/nar/gkt080. Epub Feb. 13, 2013.
Gaj et al., . ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
GENBANK Submission; NIH/NCBI, Accession No. NP_0012345345. Lifschitz et al., Nov. 30, 2014. 1 page.
Goodstein et al., Phytozome: a comparative platform for green plant genomics. Nucleic Acids Res. Jan. 2012;40(Database issue):D1178-86. doi: 10.1093/nar/gkr944. Epub Nov. 22, 2011.
Harrington et al., Programmed DNA destruction by miniature CRISPR-Cas14 enzymes. Science. Nov. 16, 2018;362(6416):839-842. doi: 10.1126/science.aav4294. Epub Oct. 18, 2018.
Hsu et al., Development and applications of CRISPR-Cas9 for genome engineering. Cell. Jun. 5, 2014;157(6):1262-1278.
Jiang et al., Demonstration of CRISPR/Cas9/sgRNA-mediated targeted gene modification in *Arabidopsis*, tobacco, sorghum and rice. Nucleic Acids Res. Nov. 2013;41(20):e188. doi: 10.1093/nar/gkt780. Epub Sep. 2, 2013.
Jiang et al., Tomato yield heterosis is triggered by a dosage sensitivity of the florigen pathway that fine-tunes shoot architecture. PLoS Genet. 2013;9(12):e1004043. doi: 10.1371/journal.pgen.1004043. Epub Dec. 26, 2013.
Juillerat et al., Optimized tuning of TALEN specificity using non-conventional RVDs. Sci Rep. Jan. 30, 2015;5:8150.
Katoh et al., MAFFT multiple sequence alignment software version 7: improvements in performance and usability. Mol Biol Evol. Apr. 2013;30(4):772-80. doi: 10.1093/molbev/mst010. Epub Jan. 16, 2013.
Kim et al., A guide to genome engineering with programmable nucleases. Nat Rev Genet. May 2014;15(5):321-34. doi: 10.1038/nrg3686. Epub Apr. 2, 2014.
Kim et al., Hybrid restriction enzymes: zinc finger fusions to Fok I cleavage domain. Proc Natl Acad Sci U S A. Feb. 6, 1996;93(3):1156-60.
Kimura et al., ERECTA-family genes coordinate stem cell functions between the epidermal and internal layers of the shoot apical meristem. Development. Jan. 8, 2018;145(1):dev156380.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.
Krieger et al., The flowering gene Single Flower Truss drives heterosis for yield in tomato. Nat Genet. May 2010;42(5):459-63. doi:10.1038/ng.550. Epub Mar. 28, 2010.
Kwon et al. Rapid customization of *Solanaceae* fruit crops for urban agriculture. Nat Biotechnol. Feb. 2020;38(2):182-188. doi: 10.1038/s41587-019-0361-2. Epub Dec. 23, 2019.
Lee et al., Homologous recombination in plant cells after Agrobacterium-mediated transformation. Plant Cell. May 1990;2(5):415-25.
Lemmon et al., Rapid improvement of domestication traits in an orphan crop by genome editing. Nat Plants. Oct. 2018;4(10):766-770. doi: 10.1038/s41477-018-0259-x. Epub Oct. 1, 2018.
Lifschitz et al., The tomato FT ortholog triggers systemic signals that regulate growth and flowering and substitute for diverse environmental stimuli. Proc Natl Acad Sci U S A. Apr. 18, 2006;103(16):6398-403. Epub Apr. 10, 2006.
Makarova et al., An updated evolutionary classification of CRISPR-Cas systems. Nat Rev Microbiol. Nov. 2015;13(11):722-36. doi: 10.1038/nrmicro3569. Epub Sep. 28, 2015.
Mandel et al., The ERECTA receptor kinase regulates *Arabidopsis* shoot apical meristem size, phyllotaxy and floral meristem identity. Development. Feb. 2014;141(4):830-41.
Martellozzo et al., Urban agriculture: a global analysis of the space constraint to meet urban vegetable demand. Envron Res Lett. 2014; 9: 064025. 8 pages.
Marti et al. Genetic and physiological characterization of tomato cv. Micro-Tom. J Exp Bot. 2006;57(9):2037-47. doi: 10.1093/jxb/erj154. Epub May 10, 2006.
Martinez, The correct application of *Physalis pruinose* L. (Solanaceae). Taxon. Feb. 1993; 42: 103-4.
Masle et al., The ERECTA gene regulates plant transpiration efficiency in *Arabidopsis*. Nature. Aug. 11, 2005;436(7052):866-70.
McCormick, Transformation of tomato with *Agrobacterium tumefaciens*. In: Plant Tissue Culture Manual, Fundamentals and Applications. 1991, Lindsey, Ed. vol. B6:1-9.
Menda et al., In silico screening of a saturated mutation library of tomato. Plant J. Jun. 2004;38(5):861-72.
Miller et al., A RESTful API for Access to Phylogenetic Tools via the CIPRES Science Gateway. Evol Bioinform Online. Mar. 16, 2015;11:43-8.
Minjuan et al., Evaluation of the growth, photosynthetic characteristics, antioxidant capacity, biomass yield and quality of tomato using aeroponics, hydroponics and porous tube-vermiculite systems in bio-regenerative life support systems. Life Sci Space Res. 2019; 22:68-75.
Molinero-Rosales et al., Single Flower Truss regulates the transition and maintenance of flowering in tomato. Planta. Jan. 2004;218(3):427-34. Epub Sep. 23, 2003.
Moscou et al., A simple cipher governs DNA recognition by TAL effectors. Science. Dec. 11, 2009;326(5959):1501.
Murovec et al., New variants of CRISPR RNA-guided genome editing enzymes. Plant Biotechnol J. Aug. 2017;15(8):917-926. doi: 10.1111/pbi.12736. Epub May 9, 2017.
Naito et al., CRISPRdirect: software for designing CRISPR/Cas guide RNA with reduced off-target sites. Bioinformatics. Apr. 1, 2015;31(7):1120-3. doi: 10.1093/bioinformatics/btu743. Epub Nov. 20, 2014.
Nguyen et al., IQ-TREE: a fast and effective stochastic algorithm for estimating maximum-likelihood phylogenies. Mol Biol Evol. Jan. 2015;32(1):268-74. doi: 10.1093/molbev/msu300. Epub Nov. 3, 2014.
Park et al., Optimization of crop productivity in tomato using induced mutations in the florigen pathway. Nat Genet. Dec. 2014;46(12):1337-42. doi: 10.1038/ng.3131. Epub Nov. 2, 2014.
Park et al., Rate of meristem maturation determines inflorescence architecture in tomato. Proc Natl Acad Sci U S A. Jan. 10, 2012;109(2):639-44. doi: 10.1073/pnas.1114963109. Epub Dec. 27, 2011.
Pearson et al., Sustainable urban agriculture: stocktake and opportunities. Int J Agric Sustain 2010; 8(1-2): 7-19.
Pnueli et al., The SELF-PRUNING gene of tomato regulates vegetative to reproductive switching of sympodial meristems and is the ortholog of CEN and TFL1. Development. Jun. 1998;125(11):1979-89.
Pnueli et al., Tomato SP-interacting proteins define a conserved signaling system that regulates shoot architecture and flowering. Plant Cell. Dec. 2001;13(12):2687-702.
Porter et al., A Practical Guide to Genome Editing Using Targeted Nuclease Technologies. Compr Physiol. Mar. 14, 2019;9(2):665-714.
Quinet et al., Transition to flowering and morphogenesis of reproductive structures in tomato. International Journal of Plant Developmental Biology. 2007;1:64-74.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ran et al., Genome engineering using the CRISPR-Cas9 system. Nat Protoc. Nov. 2013;8(11):2281-2308. doi: 10.1038/nprot.2013.143. Epub Oct. 24, 2013.
Rees et al., Base editing: precision chemistry on the genome and transcriptome of living cells. Nat Rev Genet. Dec. 2018;19(12):770-788.
Riethoven, Regulatory regions in DNA: promoters, enhancers, silencers, and insulators. Methods Mol Biol. 2010;674:33-42.

(56) References Cited

OTHER PUBLICATIONS

Rodriguez-Leal et al., Engineering Quantitative Trait Variation for Crop Improvement by Genome Editing. Cell. Oct. 5, 2017;171(2):470-480.e8. doi: 10.1016/j.cell.2017.08.030. Epub Sep. 14, 2017.

Rodriguez-Leal et al., Evolution of buffering in a genetic circuit controlling plant stem cell proliferation. Nat Genet. May 2019;51(5):786-792. doi: 10.1038/s41588-019-0389-8. Epub Apr. 15, 2019.

Saito et al., TOMATOMA: a novel tomato mutant database distributing Micro-Tom mutant collections. Plant Cell Physiol. Feb. 2011;52(2):283-96. doi: 10.1093/pcp/pcr004. Epub Jan. 21, 2011.

Samanta et al., CRISPR/Cas9: an advanced tool for editing plant genomes. Transgenic Res. Oct. 2016;25(5):561-73. doi: 10.1007/s11248-016-9953-5. Epub Mar. 24, 2016.

Sander, CRISPR-Cas systems for editing, regulating and targeting genomes. Nat Biotechnol. Apr. 2014;32(4):347-55. doi: 10.1038/nbt.2842. Epub Mar. 2, 2014.

Shi et al., Discovery of cancer drug targets by CRISPR-Cas9 screening of protein domains. Nat Biotechnol. Jun. 2015;33(6):661-7. doi: 10.1038/nbt.3235. Epub May 11, 2015.

Shmakov et al., Discovery and Functional Characterization of Diverse Class 2 CRISPR-Cas Systems. Mol Cell. Nov. 5, 2015;60(3):385-97.

Shmakov et al., Diversity and evolution of class 2 CRISPR-Cas systems. Nat Rev Microbiol. Mar. 2017;15(3):169-182.

Shpak, Diverse roles of ERECTA family genes in plant development. J Integr Plant Biol. Dec. 2013;55(12):1238-50. doi: 10.1111/jipb.12108. Epub Oct. 30, 2013.

Silva et al., Meganucleases and other tools for targeted genome engineering: perspectives and challenges for gene therapy. Curr Gene Ther. Feb. 2011;11(1):11-27.

Slaymaker et al., Rationally engineered Cas9 nucleases with improved specificity. Science. Jan. 1, 2016;351(6268):84-8. doi: 10.1126/science.aad5227. Epub Dec. 1, 2015.

Soyk et al., Duplication of a domestication locus neutralized a cryptic variant that caused a breeding barrier in tomato. Nat Plants. May 2019;5(5):471-479. doi: 10.1038/s41477-019-0422-z. Epub May 6, 2019. Erratum in: Nat Plants. Aug. 2019;5(8):903.

Soyk et al., Variation in the flowering gene Self Pruning 5G promotes day-neutrality and early yield in tomato. Nat Genet. Jan. 2017;49(1):162-168. doi: 10.1038/ng.3733. Epub Dec. 5, 2016.

Stallard. A new tomato ideal for urban gardens and even outer space. Cold Spring Harbor Laboratory. Dec. 23, 2019. Retrieved from the internet: https://www.cshl.edu/a-new-tomato-ideal-for-urban-gardens-and-even-outer-space> on Feb. 25, 2021. 1-5.

Swartwood et al., Development of plant regeneration and *Agrobacterium tumefaciens*-mediated transformation methodology for *Physalis pruinosa*. PCTOC. 2019; 137:465-72.

Taoka et al., 14-3-3 proteins act as intracellular receptors for rice Hd3a florigen. Nature. Jul. 31, 2011;476(7360):332-5. doi: 10.1038/nature10272.

Taylor et al., LAHEDES: the LAGLIDADG homing endonuclease database and engineering server. Nucleic Acids Res. Jul. 2012;40(Web Server issue): W110-6. doi: 10.1093/nar/gks365. Epub May 8, 2012.

Teo et al., New insights into the regulation of inflorescence architecture. Trends Plant Sci. Mar. 2014;19(3):158-65. doi: 10.1016/j.tplants.2013.11.001. Epub Dec. 3, 2013.

Tomlinson et al., Using CRISPR/Cas9 genome editing in tomato to create a gibberellin-responsive dominant dwarf DELLA allele. Plant Biotechnol J. Jan. 2019;17(1):132-140. doi: 10.1111/pbi.12952. Epub Jun. 22, 2018.

Torii et al., The *Arabidopsis* ERECTA gene encodes a putative receptor protein kinase with extracellular leucine-rich repeats. Plant Cell. Apr. 1996;8(4):735-46.

Touliatos et al., Vertical farming increases lettuce yield per unit area compared to conventional horizontal hydroponics. Food Energy Secur. Aug. 2016;5(3):184-191.

Tzfira et al., Genome modifications in plant cells by custom-made restriction enzymes. Plant Biotechnol J. May 2012; 10(4):373-89. doi: 10.1111/j.1467-7652.2011.00672.x. Epub Jan. 2012.

Van Eck et al., Agrobacterium tumefaciens-Mediated Transformation of Tomato. Methods Mol Biol. 2019;1864:225-234.

Varkonyi-Gasic et al., Mutagenesis of kiwifruit CENTRORADIALIS-like genes transforms a climbing woody perennial with long juvenility and axillary flowering into a compact plant with rapid terminal flowering. Plant Biotechnol J. May 2019;17(5):869-880. doi: 10.1111/pbi.13021. Epub Oct. 25, 2018.

Villagarcia et al. Modification of tomato growth by expression of truncated ERECTA protein from *Arabidopsis thaliana*. J Exp Bot. Nov. 2012;63(18):6493-504. doi: 10.1093/jxb/ers305. Epub Oct. 23, 2012.

Wang et al., Comparison of cytosine base editors and development of the BEable-GPS database for targeting pathogenic SNVs. Genome Biol. Oct. 23, 2019;20(1):218.

Wen et al., CsTFL1 inhibits determinate growth and terminal flower formation through interaction with CsNOT2a in cucumber. Development. Jul. 29, 2019;146(14):dev180166.

Werner et al., Fast track assembly of multigene constructs using Golden Gate cloning and the MoClo system. Bioeng Bugs. Jan. 1, 2012;3(1):38-43. doi: 10.4161/bbug.3.1.18223. Epub Jan. 1, 2012.

Wheeler, Agriculture for space: people and places paving the way. Open Agric. 2017; 2: 14-32.

Wigge et al., Integration of spatial and temporal information during floral induction in *Arabidopsis*. Science. Aug. 12, 2005;309(5737):1056-9.

Wigge et al., Supplement: integration of spatial and temporal information during floral induction in *Arabidopsis*. Science. Aug. 12, 2005;309(5737):S1-S8.

Xu et al., A cascade of arabinosyltransferases controls shoot meristem size in tomato. Nat Genet. Jul. 2015;47(7):784-92. doi: 10.1038/ng.3309. Epub May 25, 2015.

Yan et al., Functionally diverse type V CRISPR-Cas systems. Science. Jan. 4, 2019;363(6422):88-91. doi: 10.1126/science.aav7271. Epub Dec. 6, 2018.

Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.

Zhang et al., Phylogenetic and CRISPR/Cas9 Studies in Deciphering the Evolutionary Trajectory and Phenotypic Impacts of Rice ERECTA Genes. Front Plant Sci. Apr. 10, 2018;9:473.

Zhang et al., The emerging and uncultivated potential of CRISPR technology in plant science. Nat Plants. Aug. 2019;5(8):778-794. doi: 10.1038/s41477-019-0461-5. Epub Jul. 15, 2019.

Zhou et al., Large chromosomal deletions and heritable small genetic changes induced by CRISPR/Cas9 in rice. Nucleic Acids Res. 2014;42(17):10903-14. doi: 10.1093/nar/gku806. Epub Sep. 8, 2014.

GENBANK Submission; NIH/NCBI, Accession No. ABL84199.1. Lifschitz et al., Dec. 23, 2006. 2 pages.

* cited by examiner (SEQ ID NOs: 112-114 from Top to Bottom)

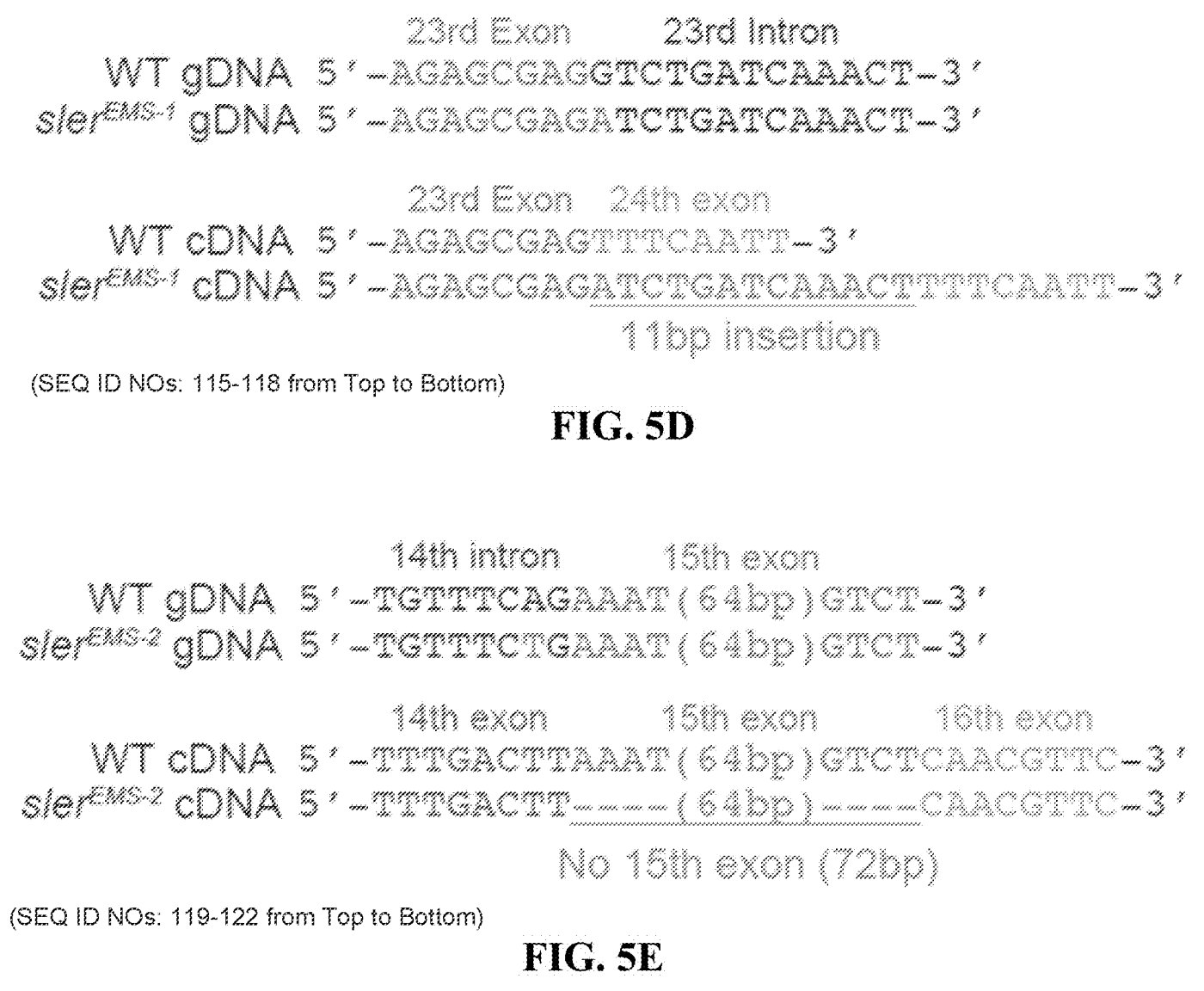

23rd Exon 23rd Intron
WT gDNA 5′-AGAGCGAGGTCTGATCAAACT-3′
$sler^{EMS-1}$ gDNA 5′-AGAGCGAGATCTGATCAAACT-3′

23rd Exon 24th exon
WT cDNA 5′-AGAGCGAGTTTCAATT-3′
$sler^{EMS-1}$ cDNA 5′-AGAGCGAGATCTGATCAAACTTTTCAATT-3′
11bp insertion (SEQ ID NOs: 115-118 from Top to Bottom)

FIG. 5D

14th intron 15th exon
WT gDNA 5′-TGTTTCAGAAAT(64bp)GTCT-3′
$sler^{EMS-2}$ gDNA 5′-TGTTTCTGAAAT(64bp)GTCT-3′

14th exon 15th exon 16th exon
WT cDNA 5′-TTTGACTTAAAT(64bp)GTCTCAACGTTC-3′
$sler^{EMS-2}$ cDNA 5′-TTTGACTT----(64bp)----CAACGTTC-3′
No 15th exon (72bp)

(SEQ ID NOs: 119-122 from Top to Bottom)

FIG. 5E

(SEQ ID NOs: 150-155 from Top to Bottom)

Sequence of $sp^{CR}$

| | |
|---|---|
| *SP* | TGT**CCA**AGTGTTAAGATGTCTGTTGTTTA(37)TTT**CCT**TCCTCAGTAACTTCTAAACCTAG |
| $sp^{CR}$ | TGT**CCA**AGTGTTAAGATGTCTGTTGTTTA(37)TTT**CCT**TCCT----AACTTCTAAACCTAG |

(SEQ ID NOs: 132-133 from Top to Bottom)

Edited sequences in *S. lycopersicum* cv. Sweet100

*SlER* TTGATGGGGAGTTGTCTCCTGCTATTGGACAGC(135)TTTCTGGCCAGATACCAGATGAGATTGGTGACT

*sler*CR-1 TTGATGGGGAGTTGTCTCCTG-TATTGGACAGC(135)TTTCTGGCCAGATACCAGAT----TTGGTGACT

*sler*CR-2 TTGATGGGGAGTTGTCT-----TATTGGACAGC(135)TTTCTGGCCAGATACCAGAT----TTGGTGACT (SEQ ID NOs: 134-136 from Top to Bottom)

Cocktail x Sweet100 *sp sp5g sler* $F_2$-derived

Grape x Sweet100 *sp sp5g sler* $F_2$-derived

*SP* TCTGTCCAAGTGTTAAGATGTCTGTTGTTTATA{33}TCTTTCCTTCCTCAGTAACTTCTAAACCTAGGG
*sp-cocktail* TCTGTCCAAGTGTTAAGATGTCTGTTGTTTATA{33}TCTTTCCTTCCATCAGTAACTTCTAAACCTAGGG
*sp-grape* TCTGTCCAAGTGTTAAGATGTCTGTTGTTTATA{33}TCTTTCCTTCCATCAGTAACTTCTAAACCTAGGG

*SP5G* TGCCTAGAGATCCTTTAATAGTTTCTGGAGTTG{48}TTTACAACAATAGGGTGGTCTATAATGGATGTT
*sp5g-cocktail* TGCCTAGAGATCCTTTAATAG--TCTGGAGTTG{48}TTTACAACAATAGGGTGGTC--TAATGGATGTT
*sp5g-grape* TGCCTAGAGATCCTTTAATAG--TCTGGAGTTG{48}TTTACAACAATAGGGTGGTC--TAATGGATGTT

*SlER* TTGATGGGGAGTTGTCTCCTGCTATTGGACAGC{135}TTTCTGGCCAGATACCAGATGAGATTGGTGACT
*sler-cocktail* TTGATGGGGAGTTGTCT-------TATTGGACAGC{135}TTTCTGGCCAGATACCAGATGAGATTGGTGACT
*sler-grape* TTGATGGGGAGTTGTCT-------TATTGGACAGC{135}TTTCTGGCCAGATACCAGATGAGATTGGTGACT (SEQ ID NOs: 137-145 from Top to Bottom)

FIG. 11C

SEQUENCE LISTING

```
<160> NUMBER OF SEQ ID NOS: 155

<210> SEQ ID NO 1
<211> LENGTH: 6324
<212> TYPE: DNA
<213> ORGANISM: Solanum lycopersicum

<400> SEQUENCE: 1

atggcatcat ttttactcca aagatgtaat cttctctttg aggttcttct tattttgggg     60

ttcttgattt tcttcagctt tggttctgtg gtgtctgatg atggtgagta gagtagagta    120

gtagaacttt ctgcttctta tgttttagtt taatgttttg tttaagatgt taaaaagaca    180

aagtgtgctt tttttaatca ttttttaaat ggtggttttt gattaatccc acgttttgta    240

gttgttattt gttaaaggtt tatttttttg tctcattatt ataataataa ttgggaaata    300

ggttctgcat tgttggaaat taagaagtca attagggacg tggagaatgt gttgtatgac    360

tggactgatt ctccttcatc tgattactgt gcctggagag gtgttacctg tgataatgtc    420

accttcaatg ttgttcaact gtaagacata actcaaaaac actatcattt gggattcttt    480

agttataaag ttgtaatctt ttgacattat cttgtagtaa tctttcgagt ttaaatcttg    540

atggggagtt gtctcctgct attggacagc tcaaaggcct tgtatctatg taatatctcc    600

tcccattatc tcacaattac cctttttgtt tgatcttttg acttagtgca cattatagac    660

tatgcctgtt aatttttttt tgaagtgata tgaggggaaa tcgcctttct ggccagatac    720

cagatgagat tggtgactgt tcagcactga aaaatttgta agtatgaaat gcttctgaat    780

cttgtgttat tgtttggaaa aataagtaac catttttttcc cttagggacc tttccttcaa    840

tgagctttat ggtgatattc ccttctccat atctaaactc aagcaactgg aatatctgta    900

agttttgata ctctccttct tctaaatgtt gtattatttg ctttccgaga ttgttagttg    960

attatgctcg tcttattcaa cttaggattt tgaagaataa tcaattgatt ggaccaattc   1020

catctacatt gtcacagatc cctaacttga aggtcttgta agtatattct ctctgctttg   1080

tcatgatatt ggtagattat gaataatttt agtttgatcc aagaacttcc tccagggacc   1140

tggctcaaaa taggttaagt ggagaaattc ctaggctgat atactggaac gaagtcctgc   1200

agtatctgtg agtgttttaa tccggtgttc ctcttcttcc tgtttgtttt aaccttagga   1260
```

-continued

```
cactttcatt tcgtatatgg atatgattac atctgttgta tgtttttatt catatagggg   1320
actgcgtggt aacaacttgg gtggatccct ttctcctgat atgtgtcagc tcaccggcct   1380
gtggtacttg taagtttgta atcctgttgc tcttaagatc ttactttagt tcctctaggt   1440
gatgacatta accattgttc attgtgttgt acagtgatgt tcggaacaat agtttgactg   1500
gttccattcc tcaaaatatt ggcaactgta ctgccttcca ggttctgtaa gtatctaaat   1560
caattgaatg aagtttgact atattctgta tgtttggttg gcataacacc ttgttttgtt   1620
ctgtcagaga tttgtcttat aatgatttga ccggagagat tcctttcaat attggtttcc   1680
tgcaagtagc gaccttgtaa gtttatgctg cttctcttca ttacaaacta ttcaatatat   1740
ggttgtttga agtgtacttt catcattcca ggtctttgca aggtaatcgt ctttcagggc   1800
agatcccttc tgtaattgga ttgatgcaag ctcttgcagt tttgtgagtg ttttgtgtct   1860
tgatatctca atctaatgct actgaatcta attcttggaa accattataa tgcatctgtt   1920
atttaagttt tctgaccctt ttactgtcag ggacttgagc tgcaatatgt tgagtggaac   1980
aattccttca attcttggga atttgactta cacagagaaa ttgttagtac ttcaacatta   2040
ttaaaagcaa tttggatcat tttgtgcttc ctaaattgtg tagtggatca attactgtaa   2100
gttcgcattg tattgcaggt atctacacgg gaacaagcta tctggttcca ttcctccaga   2160
gctgggaaat atgacaaagc tccactactt gtatgaatgc cttctatcaa tcatttttg    2220
ttagctttgt tttgttcttc ctgttcaaac ccttttaaat gaatgcttac catttagaag   2280
catttgtttg attatttagc ctttgggcaa ccacggattt gaatgataga aagctgttat   2340
gagaattttt attaagagac tttcttcaac cttaaggctc aaagatggta atttgcaggg   2400
aattgaatga taaccaactt actggacgca taccaccaga acttggaaag ctgacagaat   2460
tgtttgactt gtaaatcccg tttctcttca tcttctactt tggacttgtt aacatcatta   2520
tttatttact catgttgtat gtttcagaaa tgttgcaaac aaccacctag atgggcccat   2580
accttccaat attagctcat gtaccaattt gaatagtctg tgagtgtttt taatgtccga   2640
agtgtttcaa ttatgcacga ccatgcttgt ttggtagtta ttgacacctg attttgttgc   2700
agcaacgttc atggaaacaa attgaatggt actattccac ctgcttttca gaagctggaa   2760
agtatgacct atctgtaagt tcttactttc tgatcttttt cttttgaaga attatgttta   2820
aggttatcga agttaccgtc catgctgttg agcaagattg taaacttact gtgccttgta   2880
tataaatttt actggcgttg tattattgaa aaaatcattt tatttatatt gctctcaaat   2940
catactggct tatatccatt catgaagaat catttctact gtctgaagtt ttcagctata   3000
tgtatcgaaa aaatttagtt attatatagt ttattttgag cctctgcatc atctatttgt   3060
gaatttcatt tgcttattct gcatactctc agcattaacc gtctcttctt ttgttaattg   3120
ctttagtaat ctctcctcca acaatctcaa aggcccaatt ccaattgagc tatctcgtat   3180
tgggaatgta gatacactgt aagtgcaaac tttctcatct actttcattt ctctcattgc   3240
aattatggtt gcggggaaag cactttttgt cagtcttaag aatcttcaac atttttggc    3300
ttagggactt atcaaacaac aggatcagtg gtcctatacc tatgtccctt ggtgatttgg   3360
aacatcttct taaactgtga gcataaccgt caagttgtta tgttagcatc atatatctgt   3420
tgtacttaca tccctttgt caatgctgta ggaacttaag caagaatgaa ataaatggaa    3480
acttaccagc tgaatttggc aatttaagga gcatcatgga gatgtatgga accttgctaa   3540
attcagttac tttgaattta tggtttgctt gattttcagc tttttgactg cactcctaat   3600
```

tgtagtgatc tgtcaagcaa tcacctctct ggtcccttac ctcaggaact tggtcagctt 3660
ccaaacctgt acttgctgta agtacttcag atttactttg agactctcat cctcttagct 3720
attggtaata atctgtagag tgaataagta tgaacttcta aactcggtaa gtagatttta 3780
aaattatttt ggatgccatt ttcaaaaaag tagagatgaa gttggttgtg ttgctattgt 3840
tttatatgat ctggcttcat atgttcatta ctttggtgtt ctcagttttg ctttatattg 3900
cattattgca cggggctcaa atgcagcata tctctatctt ctttttcttg tggccttaat 3960
tattttacaa attaatgaac aggaaggtgg aaaacaacaa tttatcaggc gatgtgatgt 4020
ccttagccag ttgcctcagt ctaaatatct tgtgagtttt caagtccata gtaagacacc 4080
agtacaaaca aatgttttgt taatctaatc aacctcatgt tagcagaaat gtctcataca 4140
ataatctggg agggaatatt ccaaccggca ataatttctc tagattttca ccagacaggt 4200
aagtggagct attaagattt tacacaagtc acaagcattt attggttttt aattctttgc 4260
ttctaatttc ttcctttgc tatgtctccg aaaaagcttc ataggaaatc cagatctgtg 4320
tgggtattgg ctcacttctc cttgtcatgc atctcatccg gcagagcgag gtctgatcaa 4380
actgtaacaa tcatttggcc tttactctat tgcatttttg aagttccatt tcactttaga 4440
catctgcaac atttattaag tgtgatggac agatatattg attaatgagg aattatccct 4500
tggttgagca aacttaattc tgtgttagcc tggtagtagg gtgtaccaca aggtttgtcg 4560
tcatggtttc ctatgttcac aatccctgat tgtaacattt agatgtgtac acatatctaa 4620
ttaacatgaa ataatcttca tttgctggag ttacattgac gtaaagatgc gttagctgtc 4680
aaatgaaact gcatttgttt tatttccatc atcagtacat taattaagtg cataaatatt 4740
ttaacagttg ttgaatgata taagatgaat ttattggaca attgcagttt caatttctaa 4800
agcagcaata cttggtattg ctctgggtgg cttggtgatt cttctgatga tactagtagc 4860
agcatgccgg ccacagaaac ctgcaccttt catggaagga tctattgata aaccaggtac 4920
aatattttcc ggacggttgg atagtgtttg gagatgttca tgtcagaagg acagtcgtca 4980
gagtttattg aagttgccat gtattgattg tttaacgttt ttgatgaaca gtttattact 5040
catctccaaa acttgtgatc cttcatatga acatggcact tcatgtttac gaggacatta 5100
tgaggatgac tgagaacttg agtgagaagt atataattgg ttgtggagca tcaagtactg 5160
tatataaatg tgttttgaaa aattgcaagc ctgtagctat caagaagttg tactctcaca 5220
acccgcaata cttgaaggaa tttgagactg aacttgagac agttgggagt attaagcatc 5280
gtaatcttgt ctgtctccaa ggatattctc tttctccatc tggccatctt cttttctatg 5340
actacatgga aaatggtagc ctttgggatt tgcttcatgg ttagtaaatc caaaatggtt 5400
aaggtgattg atgcattgat tttgtgttaa agcatcaagt aatcagtcct cttgtatctt 5460
tttttgcagg tcctacaaca aagaagaaaa agcttgattg ggttactcgc cttcgaattg 5520
cattgggatc agctcaaggg cttgcatatc ttcatcatga ttgtagccct cgaataatcc 5580
accgtgatgt taaatcatct aatatcttgt tggacaaaga ctttgaggct catctgactg 5640
attttggcat agctaaaagc ttatgcatat caaagaccta tacgtccacg tacattatgg 5700
gaaccattgg ttacattgat ccagagtatg ctcgcacttc tcgcttgaca gagaagtctg 5760
atgtttacag ctatggtatt gttctattgg aattgctcac tggaaggaaa gctgtagata 5820
atgaatctaa tctacatcat ttggtaagct cttgcaattt agttaatatg aacttgtcct 5880
atgatgttta ttcatataat tatattaaga ttcaattcaa ttgatcataa cagttttgca 5940
tatatgttac agattctaac taaggcagca aacgatgctg taatggaaac agtggatcct 6000
gagataacat gcacatgcaa agatcttgca gatgtgaaga aggtttttca gcttgccctt 6060
ctatgttcca aaagacagcc tgctgagaga ccaacaatgc atgaagtggc aagagtactt 6120
gaaagcctaa tacccgtcgc tgaaacgaaa cagccaaatc caaccccctc acttgcatta 6180
ctcccatctg ctaaggtacc ttgttacatg gatgaatatg tcaacctcaa gacaccccac 6240
ctagtgaact gttcatccat gagcacttca gatgcccaac ttttcctcaa gtttggagag 6300
gtcatatccc agaatagtgg ctga 6324

<210> SEQ ID NO 2
<211> LENGTH: 2973
<212> TYPE: DNA
<213> ORGANISM: Solanum lycopersicum

<400> SEQUENCE: 2
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300
ggccttgtat ctattgatat gaggggaaat cgcctttctg gccagatacc agatgagatt 360
ggtgactgtt cagcactgaa aaatttggac ctttccttca atgagcttta tggtgatatt 420
cccttctcca tatctaaact caagcaactg gaatatctga ttttgaagaa taatcaattg 480
attggaccaa ttccatctac attgtcacag atccctaact tgaaggtctt ggacctggct 540
caaaataggt taagtggaga aattcctagg ctgatatact ggaacgaagt cctgcagtat 600
ctgggactgc gtggtaacaa cttgggtgga tccctttctc ctgatatgtg tcagctcacc 660
ggcctgtggt actttgatgt tcggaacaat agtttgactg gttccattcc tcaaaatatt 720
ggcaactgta ctgccttcca ggttctagat ttgtcttata atgatttgac cggagagatt 780
cctttcaata ttggtttcct gcaagtagcg accttgtctt tgcaaggtaa tcgtctttca 840
gggcagatcc cttctgtaat tggattgatg caagctcttg cagttttgga cttgagctgc 900
aatatgttga gtggaacaat tccttcaatt cttgggaatt tgacttacac agagaaattg 960
tatctacacg ggaacaagct atctggttcc attcctccag agctgggaaa tatgacaaag 1020
ctccactact tggaattgaa tgataaccaa cttactggac gcataccacc agaacttgga 1080
aagctgacag aattgtttga cttaaatgtt gcaaacaacc acctagatgg gcccatacct 1140
tccaatatta gctcatgtac caatttgaat agtctcaacg ttcatggaaa caaattgaat 1200
ggtactattc cacctgcttt tcagaagctg gaaagtatga cctatcttaa tctctcctcc 1260
aacaatctca aaggcccaat tccaattgag ctatctcgta ttgggaatgt agatacactg 1320
gacttatcaa acaacaggat cagtggtcct atacctatgt cccttggtga tttggaacat 1380
cttcttaaac tgaacttaag caagaatgaa ataaatggaa acttaccagc tgaatttggc 1440
aatttaagga gcatcatgga gattgatctg tcaagcaatc acctctctgg tcccttacct 1500
caggaacttg gtcagcttcc aaacctgtac ttgctgaagg tggaaaacaa caatttatca 1560
ggcgatgtga tgtccttagc cagttgcctc agtctaaata tcttaaatgt ctcatacaat 1620
aatctgggag ggaatattcc aaccggcaat aatttctcta gattttcacc agacagcttc 1680
ataggaaatc cagatctgtg tgggtattgg ctcacttctc cttgtcatgc atctcatccg 1740

```
gcagagcgag tttcaatttc taaagcagca atacttggta ttgctctggg tggcttggtg   1800

attcttctga tgatactagt agcagcatgc cggccacaga aacctgcacc tttcatggaa   1860

ggatctattg ataaaccagt ttattactca tctccaaaac ttgtgatcct tcatatgaac   1920

atggcacttc atgtttacga ggacattatg aggatgactg agaacttgag tgagaagtat   1980

ataattggtt gtggagcatc aagtactgta tataaatgtg ttttgaaaaa ttgcaagcct   2040

gtagctatca agaagttgta ctctcacaac ccgcaatact tgaaggaatt tgagactgaa   2100

cttgagacag ttgggagtat taagcatcgt aatcttgtct gtctccaagg atattctctt   2160

tctccatctg gccatcttct tttctatgac tacatggaaa atggtagcct ttgggatttg   2220

cttcatggtc ctacaacaaa gaagaaaaag cttgattggg ttactcgcct tcgaattgca   2280

ttgggatcag ctcaagggct tgcatatctt catcatgatt gtagccctcg aataatccac   2340

cgtgatgtta aatcatctaa tatcttgttg gacaaagact ttgaggctca tctgactgat   2400

tttggcatag ctaaaagctt atgcatatca aagacctata cgtccacgta cattatggga   2460

accattggtt acattgatcc agagtatgct cgcacttctc gcttgacaga gaagtctgat   2520

gtttacagct atggtattgt tctattggaa ttgctcactg gaaggaaagc tgtagataat   2580

gaatctaatc tacatcattt gattctaact aaggcagcaa acgatgctgt aatggaaaca   2640

gtggatcctg agataacatg cacatgcaaa gatcttgcag atgtgaagaa ggtttttcag   2700

cttgcccttc tatgttccaa aagacagcct gctgagagac caacaatgca tgaagtggca   2760

agagtacttg aaagcctaat acccgtcgct gaaacgaaac agccaaatcc aaccccctca   2820

cttgcattac tcccatctgc taaggtacct tgttacatgg atgaatatgt caacctcaag   2880

acaccccacc tagtgaactg ttcatccatg agcacttcag atgcccaact tttcctcaag   2940

tttggagagg tcatatccca gaatagtggc tga                                2973
```

<210> SEQ ID NO 3
<211> LENGTH: 990
<212> TYPE: PRT
<213> ORGANISM: Solanum lycopersicum

<400> SEQUENCE: 3

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160
```

```
Ile Gly Pro Ile Pro Ser Thr Leu Ser Gln Ile Pro Asn Leu Lys Val
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
        195                 200                 205

Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320

Tyr Leu His Gly Asn Lys Leu Ser Gly Ser Ile Pro Pro Glu Leu Gly
                325                 330                 335

Asn Met Thr Lys Leu His Tyr Leu Glu Leu Asn Asp Asn Gln Leu Thr
            340                 345                 350

Gly Arg Ile Pro Pro Glu Leu Gly Lys Leu Thr Glu Leu Phe Asp Leu
        355                 360                 365

Asn Val Ala Asn Asn His Leu Asp Gly Pro Ile Pro Ser Asn Ile Ser
    370                 375                 380

Ser Cys Thr Asn Leu Asn Ser Leu Asn Val His Gly Asn Lys Leu Asn
385                 390                 395                 400

Gly Thr Ile Pro Pro Ala Phe Gln Lys Leu Glu Ser Met Thr Tyr Leu
                405                 410                 415

Asn Leu Ser Ser Asn Asn Leu Lys Gly Pro Ile Pro Ile Glu Leu Ser
            420                 425                 430

Arg Ile Gly Asn Val Asp Thr Leu Asp Leu Ser Asn Asn Arg Ile Ser
        435                 440                 445

Gly Pro Ile Pro Met Ser Leu Gly Asp Leu Glu His Leu Leu Lys Leu
    450                 455                 460

Asn Leu Ser Lys Asn Glu Ile Asn Gly Asn Leu Pro Ala Glu Phe Gly
465                 470                 475                 480

Asn Leu Arg Ser Ile Met Glu Ile Asp Leu Ser Ser Asn His Leu Ser
                485                 490                 495

Gly Pro Leu Pro Gln Glu Leu Gly Gln Leu Pro Asn Leu Tyr Leu Leu
            500                 505                 510

Lys Val Glu Asn Asn Asn Leu Ser Gly Asp Val Met Ser Leu Ala Ser
        515                 520                 525

Cys Leu Ser Leu Asn Ile Leu Asn Val Ser Tyr Asn Asn Leu Gly Gly
    530                 535                 540

Asn Ile Pro Thr Gly Asn Asn Phe Ser Arg Phe Ser Pro Asp Ser Phe
545                 550                 555                 560

Ile Gly Asn Pro Asp Leu Cys Gly Tyr Trp Leu Thr Ser Pro Cys His
                565                 570                 575
```

-continued

```
Ala Ser His Pro Ala Glu Arg Val Ser Ile Ser Lys Ala Ala Ile Leu
            580                 585                 590

Gly Ile Ala Leu Gly Gly Leu Val Ile Leu Leu Met Ile Leu Val Ala
        595                 600                 605

Ala Cys Arg Pro Gln Lys Pro Ala Pro Phe Met Glu Gly Ser Ile Asp
    610                 615                 620

Lys Pro Val Tyr Tyr Ser Ser Pro Lys Leu Val Ile Leu His Met Asn
625                 630                 635                 640

Met Ala Leu His Val Tyr Glu Asp Ile Met Arg Met Thr Glu Asn Leu
                645                 650                 655

Ser Glu Lys Tyr Ile Ile Gly Cys Gly Ala Ser Ser Thr Val Tyr Lys
            660                 665                 670

Cys Val Leu Lys Asn Cys Lys Pro Val Ala Ile Lys Lys Leu Tyr Ser
        675                 680                 685

His Asn Pro Gln Tyr Leu Lys Glu Phe Glu Thr Glu Leu Glu Thr Val
    690                 695                 700

Gly Ser Ile Lys His Arg Asn Leu Val Cys Leu Gln Gly Tyr Ser Leu
705                 710                 715                 720

Ser Pro Ser Gly His Leu Leu Phe Tyr Asp Tyr Met Glu Asn Gly Ser
                725                 730                 735

Leu Trp Asp Leu Leu His Gly Pro Thr Thr Lys Lys Lys Lys Leu Asp
            740                 745                 750

Trp Val Thr Arg Leu Arg Ile Ala Leu Gly Ser Ala Gln Gly Leu Ala
        755                 760                 765

Tyr Leu His His Asp Cys Ser Pro Arg Ile Ile His Arg Asp Val Lys
    770                 775                 780

Ser Ser Asn Ile Leu Leu Asp Lys Asp Phe Glu Ala His Leu Thr Asp
785                 790                 795                 800

Phe Gly Ile Ala Lys Ser Leu Cys Ile Ser Lys Thr Tyr Thr Ser Thr
                805                 810                 815

Tyr Ile Met Gly Thr Ile Gly Tyr Ile Asp Pro Glu Tyr Ala Arg Thr
            820                 825                 830

Ser Arg Leu Thr Glu Lys Ser Asp Val Tyr Ser Tyr Gly Ile Val Leu
        835                 840                 845

Leu Glu Leu Leu Thr Gly Arg Lys Ala Val Asp Asn Glu Ser Asn Leu
    850                 855                 860

His His Leu Ile Leu Thr Lys Ala Ala Asn Asp Ala Val Met Glu Thr
865                 870                 875                 880

Val Asp Pro Glu Ile Thr Cys Thr Cys Lys Asp Leu Ala Asp Val Lys
                885                 890                 895

Lys Val Phe Gln Leu Ala Leu Leu Cys Ser Lys Arg Gln Pro Ala Glu
            900                 905                 910

Arg Pro Thr Met His Glu Val Ala Arg Val Leu Glu Ser Leu Ile Pro
        915                 920                 925

Val Ala Glu Thr Lys Gln Pro Asn Pro Thr Pro Ser Leu Ala Leu Leu
    930                 935                 940

Pro Ser Ala Lys Val Pro Cys Tyr Met Asp Glu Tyr Val Asn Leu Lys
945                 950                 955                 960

Thr Pro His Leu Val Asn Cys Ser Ser Met Ser Thr Ser Asp Ala Gln
                965                 970                 975

Leu Phe Leu Lys Phe Gly Glu Val Ile Ser Gln Asn Ser Gly
            980                 985                 990
```

<210> SEQ ID NO 4
<211> LENGTH: 6324
<212> TYPE: DNA
<213> ORGANISM: Solanum lycopersicum

<400> SEQUENCE: 4
atggcatcat ttttactcca aagatgtaat cttctctttg aggttcttct tattttgggg 60
ttcttgattt tcttcagctt tggttctgtg gtgtctgatg atggtgagta gagtagagta 120
gtagaacttt ctgcttctta tgttttagtt taatgttttg tttaagatgt taaaaagaca 180
aagtgtgctt tttttaatca ttttttaaat ggtggttttt gattaatccc acgttttgta 240
gttgttattt gttaaaggtt tatttttttg tctcattatt ataataataa ttgggaaata 300
ggttctgcat tgttggaaat taagaagtca attagggacg tggagaatgt gttgtatgac 360
tggactgatt ctccttcatc tgattactgt gcctggagag gtgttacctg tgataatgtc 420
accttcaatg ttgttcaact gtaagacata actcaaaaac actatcattt gggattcttt 480
agttataaag ttgtaatctt ttgacattat cttgtagtaa tctttcgagt ttaaatcttg 540
atggggagtt gtctcctgct attggacagc tcaaaggcct tgtatctatg taatatctcc 600
tcccattatc tcacaattac cctttttgtt tgatcttttg acttagtgca cattatagac 660
tatgcctgtt aatttttttt tgaagtgata tgaggggaaa tcgcctttct ggccagatac 720
cagatgagat tggtgactgt tcagcactga aaaatttgta agtatgaaat gcttctgaat 780
cttgtgttat tgtttggaaa aataagtaac catttttttcc cttagggacc tttccttcaa 840
tgagctttat ggtgatattc ccttctccat atctaaactc aagcaactgg aatatctgta 900
agttttgata ctctccttct tctaaatgtt gtattatttg ctttccgaga ttgttagttg 960
attatgctcg tcttattcaa cttaggattt tgaagaataa tcaattgatt ggaccaattc 1020
catctacatt gtcacagatc cctaacttga aggtcttgta agtatattct ctctgctttg 1080
tcatgatatt ggtagattat gaataatttt agtttgatcc aagaacttcc tccagggacc 1140
tggctcaaaa taggttaagt ggagaaattc ctaggctgat atactggaac gaagtcctgc 1200
agtatctgtg agtgttttaa tccggtgttc ctcttcttcc tgtttgtttt aaccttagga 1260
cactttcatt tcgtatatgg atatgattac atctgttgta tgtttttatt catatagggg 1320
actgcgtggt aacaacttgg gtggatccct ttctcctgat atgtgtcagc tcaccggcct 1380
gtggtacttg taagtttgta atcctgttgc tcttaagatc ttactttagt tcctctaggt 1440
gatgacatta accattgttc attgtgttgt acagtgatgt tcggaacaat agtttgactg 1500
gttccattcc tcaaaatatt ggcaactgta ctgccttcca ggttctgtaa gtatctaaat 1560
caattgaatg aagtttgact atattctgta tgtttggttg gcataacacc ttgttttgtt 1620
ctgtcagaga tttgtcttat aatgatttga ccggagagat tcctttcaat attggtttcc 1680
tgcaagtagc gaccttgtaa gtttatgctg cttctcttca ttacaaacta ttcaatatat 1740
ggttgtttga agtgtacttt catcattcca ggtctttgca aggtaatcgt ctttcagggc 1800
agatcccttc tgtaattgga ttgatgcaag ctcttgcagt tttgtgagtg ttttgtgtct 1860
tgatatctca atctaatgct actgaatcta attcttggaa accattataa tgcatctgtt 1920
atttaagttt tctgaccctt ttactgtcag ggacttgagc tgcaatatgt tgagtggaac 1980
aattccttca attcttggga atttgactta cacagagaaa ttgttagtac ttcaacatta 2040
ttaaaagcaa tttggatcat tttgtgcttc ctaaattgtg tagtggatca attactgtaa 2100
gttcgcattg tattgcaggt atctacacgg gaacaagcta tctggttcca ttcctccaga 2160

-continued

```
gctgggaaat atgacaaagc tccactactt gtatgaatgc cttctatcaa tcatttttg   2220
ttagctttgt tttgttcttc ctgttcaaac ccttttaaat gaatgcttac catttagaag   2280
catttgtttg attatttagc ctttgggcaa ccacggattt gaatgataga aagctgttat   2340
gagaattttt attaagagac tttcttcaac cttaaggctc aaagatggta atttgcaggg   2400
aattgaatga taaccaactt actggacgca taccaccaga acttggaaag ctgacagaat   2460
tgtttgactt gtaaatcccg tttctcttca tcttctactt tggacttgtt aacatcatta   2520
tttatttact catgttgtat gtttcagaaa tgttgcaaac aaccacctag atgggcccat   2580
accttccaat attagctcat gtaccaattt gaatagtctg tgagtgtttt taatgtccga   2640
agtgtttcaa ttatgcacga ccatgcttgt ttggtagtta ttgacacctg attttgttgc   2700
agcaacgttc atggaaacaa attgaatggt actattccac ctgcttttca gaagctggaa   2760
agtatgacct atctgtaagt tcttactttc tgatcttttt cttttgaaga attatgttta   2820
aggttatcga agttaccgtc catgctgttg agcaagattg taaacttact gtgccttgta   2880
tataaatttt actggcgttg tattattgaa aaaatcattt tatttatatt gctctcaaat   2940
catactggct tatatccatt catgaagaat catttctact gtctgaagtt ttcagctata   3000
tgtatcgaaa aaatttagtt attatatagt ttattttgag cctctgcatc atctatttgt   3060
gaatttcatt tgcttattct gcatactctc agcattaacc gtctcttctt ttgttaattg   3120
ctttagtaat ctctcctcca acaatctcaa aggcccaatt ccaattgagc tatctcgtat   3180
tgggaatgta gatacactgt aagtgcaaac tttctcatct actttcattt ctctcattgc   3240
aattatggtt gcggggaaag cactttttgt cagtcttaag aatcttcaac atttttggc   3300
ttagggactt atcaaacaac aggatcagtg gtcctatacc tatgtccctt ggtgatttgg   3360
aacatcttct taaactgtga gcataaccgt caagttgtta tgttagcatc atatatctgt   3420
tgtacttaca tccctttgt caatgctgta ggaacttaag caagaatgaa ataaatggaa   3480
acttaccagc tgaatttggc aatttaagga gcatcatgga gatgtatgga accttgctaa   3540
attcagttac tttgaattta tggtttgctt gattttcagc tttttgactg cactcctaat   3600
tgtagtgatc tgtcaagcaa tcacctctct ggtcccttac ctcaggaact tggtcagctt   3660
ccaaacctgt acttgctgta agtacttcag atttactttg agactctcat cctcttagct   3720
attggtaata atctgtagag tgaataagta tgaacttcta aactcggtaa gtagatttta   3780
aaattatttt ggatgccatt ttcaaaaaag tagagatgaa gttggttgtg ttgctattgt   3840
tttatatgat ctggcttcat atgttcatta ctttggtgtt ctcagttttg ctttatattg   3900
cattattgca cggggctcaa atgcagcata tctctatctt ctttttcttg tggccttaat   3960
tattttacaa attaatgaac aggaaggtgg aaaacaacaa tttatcaggc gatgtgatgt   4020
ccttagccag ttgcctcagt ctaaatatct tgtgagtttt caagtccata gtaagacacc   4080
agtacaaaca aatgttttgt taatctaatc aacctcatgt tagcagaaat gtctcataca   4140
ataatctggg agggaatatt ccaaccggca ataatttctc tagattttca ccagacaggt   4200
aagtggagct attaagattt tacacaagtc acaagcattt attggttttt aattctttgc   4260
ttctaatttc ttccttttgc tatgtctccg aaaaagcttc ataggaaatc cagatctgtg   4320
tgggtattgg ctcacttctc cttgtcatgc atctcatccg gcagagcgag atctgatcaa   4380
actgtaacaa tcatttggcc tttactctat tgcatttttg aagttccatt tcactttaga   4440
catctgcaac atttattaag tgtgatggac agatatattg attaatgagg aattatccct   4500
tggttgagca aacttaattc tgtgttagcc tggtagtagg gtgtaccaca aggtttgtcg   4560
```

tcatggtttc ctatgttcac aatccctgat tgtaacattt agatgtgtac acatatctaa 4620
ttaacatgaa ataatcttca tttgctggag ttacattgac gtaaagatgc gttagctgtc 4680
aaatgaaact gcatttgttt tatttccatc atcagtacat taattaagtg cataaatatt 4740
ttaacagttg ttgaatgata taagatgaat ttattggaca attgcagttt caatttctaa 4800
agcagcaata cttggtattg ctctgggtgg cttggtgatt cttctgatga tactagtagc 4860
agcatgccgg ccacagaaac ctgcaccttt catggaagga tctattgata aaccaggtac 4920
aatattttcc ggacggttgg atagtgtttg gagatgttca tgtcagaagg acagtcgtca 4980
gagtttattg aagttgccat gtattgattg tttaacgttt ttgatgaaca gtttattact 5040
catctccaaa acttgtgatc cttcatatga acatggcact tcatgtttac gaggacatta 5100
tgaggatgac tgagaacttg agtgagaagt atataattgg ttgtggagca tcaagtactg 5160
tatataaatg tgttttgaaa aattgcaagc ctgtagctat caagaagttg tactctcaca 5220
acccgcaata cttgaaggaa tttgagactg aacttgagac agttgggagt attaagcatc 5280
gtaatcttgt ctgtctccaa ggatattctc tttctccatc tggccatctt cttttctatg 5340
actacatgga aaatggtagc ctttgggatt tgcttcatgg ttagtaaatc caaaatggtt 5400
aaggtgattg atgcattgat tttgtgttaa agcatcaagt aatcagtcct cttgtatctt 5460
tttttgcagg tcctacaaca aagaagaaaa agcttgattg ggttactcgc cttcgaattg 5520
cattgggatc agctcaaggg cttgcatatc ttcatcatga ttgtagccct cgaataatcc 5580
accgtgatgt taaatcatct aatatcttgt tggacaaaga ctttgaggct catctgactg 5640
attttggcat agctaaaagc ttatgcatat caaagaccta tacgtccacg tacattatgg 5700
gaaccattgg ttacattgat ccagagtatg ctcgcacttc tcgcttgaca gagaagtctg 5760
atgtttacag ctatggtatt gttctattgg aattgctcac tggaaggaaa gctgtagata 5820
atgaatctaa tctacatcat ttggtaagct cttgcaattt agttaatatg aacttgtcct 5880
atgatgttta ttcatataat tatattaaga ttcaattcaa ttgatcataa cagttttgca 5940
tatatgttac agattctaac taaggcagca aacgatgctg taatggaaac agtggatcct 6000
gagataacat gcacatgcaa agatcttgca gatgtgaaga aggtttttca gcttgccctt 6060
ctatgttcca aaagacagcc tgctgagaga ccaacaatgc atgaagtggc aagagtactt 6120
gaaagcctaa tacccgtcgc tgaaacgaaa cagccaaatc caaccccctc acttgcatta 6180
ctcccatctg ctaaggtacc ttgttacatg gatgaatatg tcaacctcaa gacaccccac 6240
ctagtgaact gttcatccat gagcacttca gatgcccaac ttttcctcaa gtttggagag 6300
gtcatatccc agaatagtgg ctga 6324

<210> SEQ ID NO 5
<211> LENGTH: 2986
<212> TYPE: DNA
<213> ORGANISM: Solanum lycopersicum

<400> SEQUENCE: 5
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300

-continued

```
ggccttgtat ctattgatat gaggggaaat cgcctttctg gccagatacc agatgagatt    360
ggtgactgtt cagcactgaa aaatttggac ctttccttca atgagcttta tggtgatatt    420
cccttctcca tatctaaact caagcaactg gaatatctga ttttgaagaa taatcaattg    480
attggaccaa ttccatctac attgtcacag atccctaact tgaaggtctt ggacctggct    540
caaaataggt taagtggaga aattcctagg ctgatatact ggaacgaagt cctgcagtat    600
ctgggactgc gtggtaacaa cttgggtgga tccctttctc ctgatatgtg tcagctcacc    660
ggcctgtggt actttgatgt tcggaacaat agtttgactg gttccattcc tcaaaatatt    720
ggcaactgta ctgccttcca ggttctagat ttgtcttata atgatttgac cggagagatt    780
cctttcaata ttggtttcct gcaagtagcg accttgtctt tgcaaggtaa tcgtctttca    840
gggcagatcc cttctgtaat tggattgatg caagctcttg cagttttgga cttgagctgc    900
aatatgttga gtggaacaat tccttcaatt cttgggaatt tgacttacac agagaaattg    960
tatctacacg ggaacaagct atctggttcc attcctccag agctgggaaa tatgacaaag   1020
ctccactact tggaattgaa tgataaccaa cttactggac gcataccacc agaacttgga   1080
aagctgacag aattgtttga cttaaatgtt gcaaacaacc acctagatgg gcccatacct   1140
tccaatatta gctcatgtac caatttgaat agtctcaacg ttcatggaaa caaattgaat   1200
ggtactattc cacctgcttt tcagaagctg gaaagtatga cctatcttaa tctctcctcc   1260
aacaatctca aaggcccaat tccaattgag ctatctcgta ttgggaatgt agatacactg   1320
gacttatcaa acaacaggat cagtggtcct atacctatgt cccttggtga tttggaacat   1380
cttcttaaac tgaacttaag caagaatgaa ataaatggaa acttaccagc tgaatttggc   1440
aatttaagga gcatcatgga gattgatctg tcaagcaatc acctctctgg tcccttacct   1500
caggaacttg gtcagcttcc aaacctgtac ttgctgaagg tggaaaacaa caatttatca   1560
ggcgatgtga tgtccttagc cagttgcctc agtctaaata tcttaaatgt ctcatacaat   1620
aatctgggag ggaatattcc aaccggcaat aatttctcta gattttcacc agacagcttc   1680
ataggaaatc cagatctgtg tgggtattgg ctcacttctc cttgtcatgc atctcatccg   1740
gcagagcgag atctgatcaa acttttcaat ttctaaagca gcaatacttg gtattgctct   1800
gggtggcttg gtgattcttc tgatgatact agtagcagca tgccggccac agaaacctgc   1860
acctttcatg gaaggatcta ttgataaacc agtttattac tcatctccaa aacttgtgat   1920
ccttcatatg aacatggcac ttcatgttta cgaggacatt atgaggatga ctgagaactt   1980
gagtgagaag tatataattg gttgtggagc atcaagtact gtatataaat gtgttttgaa   2040
aaattgcaag cctgtagcta tcaagaagtt gtactctcac aacccgcaat acttgaagga   2100
atttgagact gaacttgaga cagttgggag tattaagcat cgtaatcttg tctgtctcca   2160
aggatattct ctttctccat ctggccatct tcttttctat gactacatgg aaaatggtag   2220
cctttgggat ttgcttcatg gtcctacaac aaagaagaaa aagcttgatt gggttactcg   2280
ccttcgaatt gcattgggat cagctcaagg gcttgcatat cttcatcatg attgtagccc   2340
tcgaataatc caccgtgatg ttaaatcatc taatatcttg ttggacaaag actttgaggc   2400
tcatctgact gattttggca tagctaaaag cttatgcata tcaaagacct atacgtccac   2460
gtacattatg ggaaccattg gttacattga tccagagtat gctcgcactt ctcgcttgac   2520
agagaagtct gatgtttaca gctatggtat tgttctattg gaattgctca ctggaaggaa   2580
agctgtagat aatgaatcta atctacatca tttgattcta actaaggcag caaacgatgc   2640
tgtaatggaa acagtggatc ctgagataac atgcacatgc aaagatcttg cagatgtgaa   2700
```

```
gaaggttttt cagcttgccc ttctatgttc caaaagacag cctgctgaga gaccaacaat   2760

gcatgaagtg gcaagagtac ttgaaagcct aatacccgtc gctgaaacga aacagccaaa   2820

tccaaccccc tcacttgcat tactcccatc tgctaaggta ccttgttaca tggatgaata   2880

tgtcaacctc aagacacccc acctagtgaa ctgttcatcc atgagcactt cagatgccca   2940

acttttcctc aagtttggag aggtcatatc ccagaatagt ggctga                  2986


<210> SEQ ID NO 6
<211> LENGTH: 591
<212> TYPE: PRT
<213> ORGANISM: Solanum lycopersicum

<400> SEQUENCE: 6

Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160

Ile Gly Pro Ile Pro Ser Thr Leu Ser Gln Ile Pro Asn Leu Lys Val
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
        195                 200                 205

Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320
```

-continued

```
Tyr Leu His Gly Asn Lys Leu Ser Gly Ser Ile Pro Pro Glu Leu Gly
            325                 330             335

Asn Met Thr Lys Leu His Tyr Leu Glu Leu Asn Asp Asn Gln Leu Thr
            340             345             350

Gly Arg Ile Pro Pro Glu Leu Gly Lys Leu Thr Glu Leu Phe Asp Leu
            355             360             365

Asn Val Ala Asn Asn His Leu Asp Gly Pro Ile Pro Ser Asn Ile Ser
        370             375             380

Ser Cys Thr Asn Leu Asn Ser Leu Asn Val His Gly Asn Lys Leu Asn
385                 390             395                 400

Gly Thr Ile Pro Pro Ala Phe Gln Lys Leu Glu Ser Met Thr Tyr Leu
                405             410             415

Asn Leu Ser Ser Asn Asn Leu Lys Gly Pro Ile Pro Ile Glu Leu Ser
            420             425             430

Arg Ile Gly Asn Val Asp Thr Leu Asp Leu Ser Asn Asn Arg Ile Ser
            435             440             445

Gly Pro Ile Pro Met Ser Leu Gly Asp Leu Glu His Leu Leu Lys Leu
        450             455             460

Asn Leu Ser Lys Asn Glu Ile Asn Gly Asn Leu Pro Ala Glu Phe Gly
465                 470             475                 480

Asn Leu Arg Ser Ile Met Glu Ile Asp Leu Ser Ser Asn His Leu Ser
            485             490             495

Gly Pro Leu Pro Gln Glu Leu Gly Gln Leu Pro Asn Leu Tyr Leu Leu
            500             505             510

Lys Val Glu Asn Asn Asn Leu Ser Gly Asp Val Met Ser Leu Ala Ser
            515             520             525

Cys Leu Ser Leu Asn Ile Leu Asn Val Ser Tyr Asn Asn Leu Gly Gly
        530             535             540

Asn Ile Pro Thr Gly Asn Asn Phe Ser Arg Phe Ser Pro Asp Ser Phe
545                 550             555                 560

Ile Gly Asn Pro Asp Leu Cys Gly Tyr Trp Leu Thr Ser Pro Cys His
            565             570             575

Ala Ser His Pro Ala Glu Arg Asp Leu Ile Lys Leu Phe Asn Phe
            580             585             590
```

<210> SEQ ID NO 7
<211> LENGTH: 6324
<212> TYPE: DNA
<213> ORGANISM: Solanum lycopersicum

<400> SEQUENCE: 7

```
atggcatcat ttttactcca aagatgtaat cttctctttg aggttcttct tattttgggg      60

ttcttgattt tcttcagctt tggttctgtg gtgtctgatg atggtgagta gagtagagta     120

gtagaacttt ctgcttctta tgttttagtt taatgttttg tttaagatgt taaaaagaca     180

aagtgtgctt tttttaatca ttttttaaat ggtggttttt gattaatccc acgttttgta     240

gttgttattt gttaaaggtt tatttttttg tctcattatt ataataataa ttgggaaata     300

ggttctgcat tgttggaaat taagaagtca attagggacg tggagaatgt gttgtatgac     360

tggactgatt ctccttcatc tgattactgt gcctggagag gtgttacctg tgataatgtc     420

accttcaatg ttgttcaact gtaagacata actcaaaaac actatcattt gggattcttt     480

agttataaag ttgtaatctt ttgacattat cttgtagtaa tctttcgagt ttaaatcttg     540

atggggagtt gtctcctgct attggacagc tcaaaggcct tgtatctatg taatatctcc     600
```

-continued

```
tcccattatc tcacaattac cctttttgtt tgatcttttg acttagtgca cattatagac      660

tatgcctgtt aatttttttt tgaagtgata tgaggggaaa tcgcctttct ggccagatac      720

cagatgagat tggtgactgt tcagcactga aaaatttgta agtatgaaat gcttctgaat      780

cttgtgttat tgtttggaaa aataagtaac cattttttcc cttagggacc tttccttcaa      840

tgagctttat ggtgatattc ccttctccat atctaaactc aagcaactgg aatatctgta      900

agttttgata ctctccttct tctaaatgtt gtattatttg ctttccgaga ttgttagttg      960

attatgctcg tcttattcaa cttaggattt tgaagaataa tcaattgatt ggaccaattc     1020

catctacatt gtcacagatc cctaacttga aggtcttgta agtatattct ctctgctttg     1080

tcatgatatt ggtagattat gaataatttt agtttgatcc aagaacttcc tccagggacc     1140

tggctcaaaa taggttaagt ggagaaattc ctaggctgat atactggaac gaagtcctgc     1200

agtatctgtg agtgttttaa tccggtgttc ctcttcttcc tgtttgtttt aaccttagga     1260

cactttcatt tcgtatatgg atatgattac atctgttgta tgtttttatt catatagggg     1320

actgcgtggt aacaacttgg gtggatccct ttctcctgat atgtgtcagc tcaccggcct     1380

gtggtacttg taagtttgta atcctgttgc tcttaagatc ttactttagt tcctctaggt     1440

gatgacatta accattgttc attgtgttgt acagtgatgt tcggaacaat agtttgactg     1500

gttccattcc tcaaaatatt ggcaactgta ctgccttcca ggttctgtaa gtatctaaat     1560

caattgaatg aagtttgact atattctgta tgtttggttg gcataacacc ttgttttgtt     1620

ctgtcagaga tttgtcttat aatgatttga ccggagagat tcctttcaat attggtttcc     1680

tgcaagtagc gaccttgtaa gtttatgctg cttctcttca ttacaaacta ttcaatatat     1740

ggttgtttga agtgtacttt catcattcca ggtctttgca aggtaatcgt ctttcagggc     1800

agatcccttc tgtaattgga ttgatgcaag ctcttgcagt tttgtgagtg ttttgtgtct     1860

tgatatctca atctaatgct actgaatcta attcttggaa accattataa tgcatctgtt     1920

atttaagttt tctgacccct ttactgtcag ggacttgagc tgcaatatgt tgagtggaac     1980

aattccttca attcttggga atttgactta cacagagaaa ttgttagtac ttcaacatta     2040

ttaaaagcaa tttggatcat tttgtgcttc ctaaattgtg tagtggatca attactgtaa     2100

gttcgcattg tattgcaggt atctacacgg gaacaagcta tctggttcca ttcctccaga     2160

gctgggaaat atgacaaagc tccactactt gtatgaatgc cttctatcaa tcattttttg     2220

ttagctttgt tttgttcttc ctgttcaaac ccttttaaat gaatgcttac catttagaag     2280

catttgtttg attatttagc ctttgggcaa ccacggattt gaatgataga aagctgttat     2340

gagaattttt attaagagac tttcttcaac cttaaggctc aaagatggta atttgcaggg     2400

aattgaatga taaccaactt actggacgca taccaccaga acttggaaag ctgacagaat     2460

tgtttgactt gtaaatcccg tttctcttca tcttctactt tggacttgtt aacatcatta     2520

tttatttact catgttgtat gtttctgaaa tgttgcaaac aaccacctag atgggcccat     2580

accttccaat attagctcat gtaccaattt gaatagtctg tgagtgtttt taatgtccga     2640

agtgtttcaa ttatgcacga ccatgcttgt ttggtagtta ttgacacctg attttgttgc     2700

agcaacgttc atggaaacaa attgaatggt actattccac ctgctttttca gaagctggaa     2760

agtatgacct atctgtaagt tcttactttc tgatcttttt cttttgaaga attatgttta     2820

aggttatcga agttaccgtc catgctgttg agcaagattg taaacttact gtgccttgta     2880

tataaatttt actggcgttg tattattgaa aaaatcattt tatttatatt gctctcaaat     2940

catactggct tatatccatt catgaagaat catttctact gtctgaagtt ttcagctata     3000
```

-continued

```
tgtatcgaaa aaatttagtt attatatagt ttattttgag cctctgcatc atctatttgt   3060
gaatttcatt tgcttattct gcatactctc agcattaacc gtctcttctt ttgttaattg   3120
ctttagtaat ctctcctcca acaatctcaa aggcccaatt ccaattgagc tatctcgtat   3180
tgggaatgta gatacactgt aagtgcaaac tttctcatct actttcattt ctctcattgc   3240
aattatggtt gcggggaaag cactttttgt cagtcttaag aatcttcaac atttttggc    3300
ttagggactt atcaaacaac aggatcagtg gtcctatacc tatgtccctt ggtgatttgg   3360
aacatcttct taaactgtga gcataaccgt caagttgtta tgttagcatc atatatctgt   3420
tgtacttaca tccctttgt caatgctgta ggaacttaag caagaatgaa ataaatggaa    3480
acttaccagc tgaatttggc aatttaagga gcatcatgga gatgtatgga accttgctaa   3540
attcagttac tttgaattta tggtttgctt gattttcagc tttttgactg cactcctaat   3600
tgtagtgatc tgtcaagcaa tcacctctct ggtcccttac ctcaggaact tggtcagctt   3660
ccaaacctgt acttgctgta agtacttcag atttactttg agactctcat cctcttagct   3720
attggtaata atctgtagag tgaataagta tgaacttcta aactcggtaa gtagatttta   3780
aaattatttt ggatgccatt ttcaaaaaag tagagatgaa gttggttgtg ttgctattgt   3840
tttatatgat ctggcttcat atgttcatta ctttggtgtt ctcagttttg ctttatattg   3900
cattattgca cggggctcaa atgcagcata tctctatctt ctttttcttg tggccttaat   3960
tattttacaa attaatgaac aggaaggtgg aaaacaacaa tttatcaggc gatgtgatgt   4020
ccttagccag ttgcctcagt ctaaatatct tgtgagtttt caagtccata gtaagacacc   4080
agtacaaaca aatgttttgt taatctaatc aacctcatgt tagcagaaat gtctcataca   4140
ataatctggg agggaatatt ccaaccggca ataatttctc tagattttca ccagacaggt   4200
aagtggagct attaagattt tacacaagtc acaagcattt attggttttt aattctttgc   4260
ttctaatttc ttccttttgc tatgtctccg aaaaagcttc ataggaaatc cagatctgtg   4320
tgggtattgg ctcacttctc cttgtcatgc atctcatccg gcagagcgag gtctgatcaa   4380
actgtaacaa tcatttggcc tttactctat tgcatttttg aagttccatt tcactttaga   4440
catctgcaac atttattaag tgtgatggac agatatattg attaatgagg aattatccct   4500
tggttgagca aacttaattc tgtgttagcc tggtagtagg gtgtaccaca aggtttgtcg   4560
tcatggtttc ctatgttcac aatccctgat tgtaacattt agatgtgtac acatatctaa   4620
ttaacatgaa ataatcttca tttgctggag ttacattgac gtaaagatgc gttagctgtc   4680
aaatgaaact gcatttgttt tatttccatc atcagtacat taattaagtg cataaatatt   4740
ttaacagttg ttgaatgata taagatgaat ttattggaca attgcagttt caatttctaa   4800
agcagcaata cttggtattg ctctgggtgg cttggtgatt cttctgatga tactagtagc   4860
agcatgccgg ccacagaaac ctgcaccttt catggaagga tctattgata aaccaggtac   4920
aatattttcc ggacggttgg atagtgtttg gagatgttca tgtcagaagg acagtcgtca   4980
gagtttattg aagttgccat gtattgattg tttaacgttt ttgatgaaca gtttattact   5040
catctccaaa acttgtgatc cttcatatga acatggcact tcatgtttac gaggacatta   5100
tgaggatgac tgagaacttg agtgagaagt atataattgg ttgtggagca tcaagtactg   5160
tatataaatg tgttttgaaa aattgcaagc ctgtagctat caagaagttg tactctcaca   5220
acccgcaata cttgaaggaa tttgagactg aacttgagac agttgggagt attaagcatc   5280
gtaatcttgt ctgtctccaa ggatattctc tttctccatc tggccatctt cttttctatg   5340
```

-continued

```
actacatgga aaatggtagc ctttgggatt tgcttcatgg ttagtaaatc caaaatggtt   5400
aaggtgattg atgcattgat tttgtgttaa agcatcaagt aatcagtcct cttgtatctt   5460
tttttgcagg tcctacaaca aagaagaaaa agcttgattg ggttactcgc cttcgaattg   5520
cattgggatc agctcaaggg cttgcatatc ttcatcatga ttgtagccct cgaataatcc   5580
accgtgatgt taaatcatct aatatcttgt tggacaaaga ctttgaggct catctgactg   5640
attttggcat agctaaaagc ttatgcatat caaagaccta tacgtccacg tacattatgg   5700
gaaccattgg ttacattgat ccagagtatg ctcgcacttc tcgcttgaca gagaagtctg   5760
atgtttacag ctatggtatt gttctattgg aattgctcac tggaaggaaa gctgtagata   5820
atgaatctaa tctacatcat ttggtaagct cttgcaattt agttaatatg aacttgtcct   5880
atgatgttta ttcatataat tatattaaga ttcaattcaa ttgatcataa cagttttgca   5940
tatatgttac agattctaac taaggcagca aacgatgctg taatggaaac agtggatcct   6000
gagataacat gcacatgcaa agatcttgca gatgtgaaga aggtttttca gcttgccctt   6060
ctatgttcca aaagacagcc tgctgagaga ccaacaatgc atgaagtggc aagagtactt   6120
gaaagcctaa tacccgtcgc tgaaacgaaa cagccaaatc caaccccctc acttgcatta   6180
ctcccatctg ctaaggtacc ttgttacatg gatgaatatg tcaacctcaa gacaccccac   6240
ctagtgaact gttcatccat gagcacttca gatgcccaac ttttcctcaa gtttggagag   6300
gtcatatccc agaatagtgg ctga                                          6324
```

<210> SEQ ID NO 8
<211> LENGTH: 2901
<212> TYPE: DNA
<213> ORGANISM: Solanum lycopersicum

<400> SEQUENCE: 8

```
atggcatcat ttttactcca aagatgtaat cttctctttg aggttcttct tattttgggg     60
ttcttgattt tcttcagctt tggttctgtg gtgtctgatg atggttctgc attgttggaa    120
attaagaagt caattaggga cgtggagaat gtgttgtatg actggactga ttctccttca    180
tctgattact gtgcctggag aggtgttacc tgtgataatg tcaccttcaa tgttgttcaa    240
cttaatcttt cgagtttaaa tcttgatggg gagttgtctc ctgctattgg acagctcaaa    300
ggccttgtat ctattgatat gaggggaaat cgcctttctg gccagatacc agatgagatt    360
ggtgactgtt cagcactgaa aaatttggac ctttccttca atgagcttta tggtgatatt    420
cccttctcca tatctaaact caagcaactg gaatatctga ttttgaagaa taatcaattg    480
attggaccaa ttccatctac attgtcacag atccctaact tgaaggtctt ggacctggct    540
caaaataggt taagtggaga aattcctagg ctgatatact ggaacgaagt cctgcagtat    600
ctgggactgc gtggtaacaa cttgggtgga tccctttctc ctgatatgtg tcagctcacc    660
ggcctgtggt actttgatgt tcggaacaat agtttgactg gttccattcc tcaaaatatt    720
ggcaactgta ctgccttcca ggttctagat ttgtcttata atgatttgac cggagagatt    780
cctttcaata ttggtttcct gcaagtagcg accttgtctt tgcaaggtaa tcgtctttca    840
gggcagatcc cttctgtaat tggattgatg caagctcttg cagttttgga cttgagctgc    900
aatatgttga gtggaacaat tccttcaatt cttgggaatt tgacttacac agagaaattg    960
tatctacacg ggaacaagct atctggttcc attcctccag agctgggaaa tatgacaaag   1020
ctccactact tggaattgaa tgataaccaa cttactggac gcataccacc agaacttgga   1080
aagctgacag aattgtttga cttcaacgtt catggaaaca aattgaatgg tactattcca   1140
```

-continued

```
cctgcttttc agaagctgga aagtatgacc tatcttaatc tctcctccaa caatctcaaa   1200

ggcccaattc caattgagct atctcgtatt gggaatgtag atacactgga cttatcaaac   1260

aacaggatca gtggtcctat acctatgtcc cttggtgatt tggaacatct tcttaaactg   1320

aacttaagca agaatgaaat aaatggaaac ttaccagctg aatttggcaa tttaaggagc   1380

atcatggaga ttgatctgtc aagcaatcac ctctctggtc ccttacctca ggaacttggt   1440

cagcttccaa acctgtactt gctgaaggtg gaaaacaaca atttatcagg cgatgtgatg   1500

tccttagcca gttgcctcag tctaaatatc ttaaatgtct catacaataa tctgggaggg   1560

aatattccaa ccggcaataa tttctctaga ttttcaccag acagcttcat aggaaatcca   1620

gatctgtgtg ggtattggct cacttctcct tgtcatgcat ctcatccggc agagcgagtt   1680

tcaatttcta aagcagcaat acttggtatt gctctgggtg gcttggtgat tcttctgatg   1740

atactagtag cagcatgccg gccacagaaa cctgcacctt tcatggaagg atctattgat   1800

aaaccagttt attactcatc tccaaaactt gtgatccttc atatgaacat ggcacttcat   1860

gtttacgagg acattatgag gatgactgag aacttgagtg agaagtatat aattggttgt   1920

ggagcatcaa gtactgtata taaatgtgtt ttgaaaaatt gcaagcctgt agctatcaag   1980

aagttgtact ctcacaaccc gcaatacttg aaggaatttg agactgaact tgagacagtt   2040

gggagtatta agcatcgtaa tcttgtctgt ctccaaggat attctctttc tccatctggc   2100

catcttcttt tctatgacta catggaaaat ggtagccttt gggatttgct tcatggtcct   2160

acaacaaaga agaaaaagct tgattgggtt actcgccttc gaattgcatt gggatcagct   2220

caagggcttg catatcttca tcatgattgt agccctcgaa taatccaccg tgatgttaaa   2280

tcatctaata tcttgttgga caaagacttt gaggctcatc tgactgattt tggcatagct   2340

aaaagcttat gcatatcaaa gacctatacg tccacgtaca ttatgggaac cattggttac   2400

attgatccag agtatgctcg cacttctcgc ttgacagaga agtctgatgt ttacagctat   2460

ggtattgttc tattggaatt gctcactgga aggaaagctg tagataatga atctaatcta   2520

catcatttga ttctaactaa ggcagcaaac gatgctgtaa tggaaacagt ggatcctgag   2580

ataacatgca catgcaaaga tcttgcagat gtgaagaagg tttttcagct tgcccttcta   2640

tgttccaaaa gacagcctgc tgagagacca acaatgcatg aagtggcaag agtacttgaa   2700

agcctaatac ccgtcgctga aacgaaacag ccaaatccaa ccccctcact tgcattactc   2760

ccatctgcta aggtaccttg ttacatggat gaatatgtca acctcaagac accccaccta   2820

gtgaactgtt catccatgag cacttcagat gcccaacttt tcctcaagtt tggagaggtc   2880

atatcccaga atagtggctg a                                             2901
```

<210> SEQ ID NO 9
<211> LENGTH: 966
<212> TYPE: PRT
<213> ORGANISM: Solanum lycopersicum

<400> SEQUENCE: 9

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
```

-continued

```
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160

Ile Gly Pro Ile Pro Ser Thr Leu Ser Gln Ile Pro Asn Leu Lys Val
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
        195                 200                 205

Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320

Tyr Leu His Gly Asn Lys Leu Ser Gly Ser Ile Pro Pro Glu Leu Gly
                325                 330                 335

Asn Met Thr Lys Leu His Tyr Leu Glu Leu Asn Asp Asn Gln Leu Thr
            340                 345                 350

Gly Arg Ile Pro Pro Glu Leu Gly Lys Leu Thr Glu Leu Phe Asp Phe
        355                 360                 365

Asn Val His Gly Asn Lys Leu Asn Gly Thr Ile Pro Pro Ala Phe Gln
    370                 375                 380

Lys Leu Glu Ser Met Thr Tyr Leu Asn Leu Ser Ser Asn Asn Leu Lys
385                 390                 395                 400

Gly Pro Ile Pro Ile Glu Leu Ser Arg Ile Gly Asn Val Asp Thr Leu
                405                 410                 415

Asp Leu Ser Asn Asn Arg Ile Ser Gly Pro Ile Pro Met Ser Leu Gly
            420                 425                 430

Asp Leu Glu His Leu Leu Lys Leu Asn Leu Ser Lys Asn Glu Ile Asn
        435                 440                 445

Gly Asn Leu Pro Ala Glu Phe Gly Asn Leu Arg Ser Ile Met Glu Ile
    450                 455                 460

Asp Leu Ser Ser Asn His Leu Ser Gly Pro Leu Pro Gln Glu Leu Gly
465                 470                 475                 480
```

-continued

```
Gln Leu Pro Asn Leu Tyr Leu Leu Lys Val Glu Asn Asn Asn Leu Ser
                485                 490                 495

Gly Asp Val Met Ser Leu Ala Ser Cys Leu Ser Leu Asn Ile Leu Asn
            500                 505                 510

Val Ser Tyr Asn Asn Leu Gly Gly Asn Ile Pro Thr Gly Asn Asn Phe
        515                 520                 525

Ser Arg Phe Ser Pro Asp Ser Phe Ile Gly Asn Pro Asp Leu Cys Gly
    530                 535                 540

Tyr Trp Leu Thr Ser Pro Cys His Ala Ser His Pro Ala Glu Arg Val
545                 550                 555                 560

Ser Ile Ser Lys Ala Ala Ile Leu Gly Ile Ala Leu Gly Gly Leu Val
                565                 570                 575

Ile Leu Leu Met Ile Leu Val Ala Ala Cys Arg Pro Gln Lys Pro Ala
            580                 585                 590

Pro Phe Met Glu Gly Ser Ile Asp Lys Pro Val Tyr Tyr Ser Ser Pro
        595                 600                 605

Lys Leu Val Ile Leu His Met Asn Met Ala Leu His Val Tyr Glu Asp
    610                 615                 620

Ile Met Arg Met Thr Glu Asn Leu Ser Glu Lys Tyr Ile Ile Gly Cys
625                 630                 635                 640

Gly Ala Ser Ser Thr Val Tyr Lys Cys Val Leu Lys Asn Cys Lys Pro
                645                 650                 655

Val Ala Ile Lys Lys Leu Tyr Ser His Asn Pro Gln Tyr Leu Lys Glu
            660                 665                 670

Phe Glu Thr Glu Leu Glu Thr Val Gly Ser Ile Lys His Arg Asn Leu
        675                 680                 685

Val Cys Leu Gln Gly Tyr Ser Leu Ser Pro Ser Gly His Leu Leu Phe
    690                 695                 700

Tyr Asp Tyr Met Glu Asn Gly Ser Leu Trp Asp Leu Leu His Gly Pro
705                 710                 715                 720

Thr Thr Lys Lys Lys Lys Leu Asp Trp Val Thr Arg Leu Arg Ile Ala
                725                 730                 735

Leu Gly Ser Ala Gln Gly Leu Ala Tyr Leu His His Asp Cys Ser Pro
            740                 745                 750

Arg Ile Ile His Arg Asp Val Lys Ser Ser Asn Ile Leu Leu Asp Lys
        755                 760                 765

Asp Phe Glu Ala His Leu Thr Asp Phe Gly Ile Ala Lys Ser Leu Cys
    770                 775                 780

Ile Ser Lys Thr Tyr Thr Ser Thr Tyr Ile Met Gly Thr Ile Gly Tyr
785                 790                 795                 800

Ile Asp Pro Glu Tyr Ala Arg Thr Ser Arg Leu Thr Glu Lys Ser Asp
                805                 810                 815

Val Tyr Ser Tyr Gly Ile Val Leu Leu Glu Leu Leu Thr Gly Arg Lys
            820                 825                 830

Ala Val Asp Asn Glu Ser Asn Leu His His Leu Ile Leu Thr Lys Ala
        835                 840                 845

Ala Asn Asp Ala Val Met Glu Thr Val Asp Pro Glu Ile Thr Cys Thr
    850                 855                 860

Cys Lys Asp Leu Ala Asp Val Lys Lys Val Phe Gln Leu Ala Leu Leu
865                 870                 875                 880

Cys Ser Lys Arg Gln Pro Ala Glu Arg Pro Thr Met His Glu Val Ala
                885                 890                 895
```

```
Arg Val Leu Glu Ser Leu Ile Pro Val Ala Glu Thr Lys Gln Pro Asn
            900                 905                 910

Pro Thr Pro Ser Leu Ala Leu Leu Pro Ser Ala Lys Val Pro Cys Tyr
        915                 920                 925

Met Asp Glu Tyr Val Asn Leu Lys Thr Pro His Leu Val Asn Cys Ser
    930                 935                 940

Ser Met Ser Thr Ser Asp Ala Gln Leu Phe Leu Lys Phe Gly Glu Val
945                 950                 955                 960

Ile Ser Gln Asn Ser Gly
                965


<210> SEQ ID NO 10
<211> LENGTH: 6325
<212> TYPE: DNA
<213> ORGANISM: Solanum lycopersicum

<400> SEQUENCE: 10

atggcatcat ttttactcca aagatgtaat cttctctttg aggttcttct tattttgggg      60

ttcttgattt tcttcagctt tggttctgtg gtgtctgatg atggtgagta gagtagagta     120

gtagaacttt ctgcttctta tgttttagtt taatgttttg tttaagatgt taaaaagaca     180

aagtgtgctt tttttaatca ttttttaaat ggtggttttt gattaatccc acgttttgta     240

gttgttattt gttaaaggtt tattttttttg tctcattatt ataataataa ttgggaaata     300

ggttctgcat tgttggaaat taagaagtca attagggacg tggagaatgt gttgtatgac     360

tggactgatt ctccttcatc tgattactgt gcctggagag gtgttacctg tgataatgtc     420

accttcaatg ttgttcaact gtaagacata actcaaaaac actatcattt gggattcttt     480

agttataaag ttgtaatctt ttgacattat cttgtagtaa tctttcgagt ttaaatcttg     540

atggggagtt gtctcctgct attggacagc tcaaaggcct tgtatctatg taatatctcc     600

tcccattatc tcacaattac ccttttttgtt tgatcttttg acttagtgca cattatagac     660

tatgcctgtt aatttttttt tgaagtgata tgaggggaaa tcgcctttct ggccagatac     720

cagatgaaga ttggtgactg ttcagcactg aaaaatttgt aagtatgaaa tgcttctgaa     780

tcttgtgtta ttgtttggaa aaataagtaa ccattttttc ccttagggac ctttccttca     840

atgagcttta tggtgatatt cccttctcca tatctaaact caagcaactg gaatatctgt     900

aagttttgat actctccttc ttctaaatgt tgtattattt gctttccgag attgttagtt     960

gattatgctc gtcttattca acttaggatt ttgaagaata atcaattgat tggaccaatt    1020

ccatctacat tgtcacagat ccctaacttg aaggtcttgt aagtatattc tctctgcttt    1080

gtcatgatat tggtagatta tgaataattt tagtttgatc caagaacttc ctccagggac    1140

ctggctcaaa ataggttaag tggagaaatt cctaggctga tatactggaa cgaagtcctg    1200

cagtatctgt gagtgtttta atccggtgtt cctcttcttc ctgtttgttt taaccttagg    1260

acactttcat ttcgtatatg gatatgatta catctgttgt atgtttttat tcatataggg    1320

gactgcgtgg taacaacttg ggtggatccc tttctcctga tatgtgtcag ctcaccggcc    1380

tgtggtactt gtaagtttgt aatcctgttg ctcttaagat cttactttag ttcctctagg    1440

tgatgacatt aaccattgtt cattgtgttg tacagtgatg ttcggaacaa tagtttgact    1500

ggttccattc ctcaaaatat tggcaactgt actgccttcc aggttctgta agtatctaaa    1560

tcaattgaat gaagtttgac tatattctgt atgtttggtt ggcataacac cttgttttgt    1620

tctgtcagag atttgtctta taatgatttg accggagaga ttcctttcaa tattggtttc    1680
```

-continued

```
ctgcaagtag cgaccttgta agtttatgct gcttctcttc attacaaact attcaatata   1740
tggttgtttg aagtgtactt tcatcattcc aggtctttgc aaggtaatcg tctttcaggg   1800
cagatccctt ctgtaattgg attgatgcaa gctcttgcag ttttgtgagt gttttgtgtc   1860
ttgatatctc aatctaatgc tactgaatct aattcttgga aaccattata atgcatctgt   1920
tatttaagtt ttctgaccct tttactgtca gggacttgag ctgcaatatg ttgagtggaa   1980
caattccttc aattcttggg aatttgactt acacagagaa attgttagta cttcaacatt   2040
attaaaagca atttggatca ttttgtgctt cctaaattgt gtagtggatc aattactgta   2100
agttcgcatt gtattgcagg tatctacacg ggaacaagct atctggttcc attcctccag   2160
agctgggaaa tatgacaaag ctccactact tgtatgaatg ccttctatca atcatttttt   2220
gttagctttg ttttgttctt cctgttcaaa cccttttaaa tgaatgctta ccatttagaa   2280
gcatttgttt gattatttag cctttgggca accacggatt tgaatgatag aaagctgtta   2340
tgagaatttt tattaagaga ctttcttcaa ccttaaggct caaagatggt aatttgcagg   2400
gaattgaatg ataaccaact tactggacgc ataccaccag aacttggaaa gctgacagaa   2460
ttgtttgact tgtaaatccc gtttctcttc atcttctact ttggacttgt taacatcatt   2520
atttatttac tcatgttgta tgtttcagaa atgttgcaaa caaccaccta gatgggccca   2580
taccttccaa tattagctca tgtaccaatt tgaatagtct gtgagtgttt ttaatgtccg   2640
aagtgtttca attatgcacg accatgcttg tttggtagtt attgacacct gattttgttg   2700
cagcaacgtt catggaaaca aattgaatgg tactattcca cctgcttttc agaagctgga   2760
aagtatgacc tatctgtaag ttcttacttt ctgatctttt tcttttgaag aattatgttt   2820
aaggttatcg aagttaccgt ccatgctgtt gagcaagatt gtaaacttac tgtgccttgt   2880
atataaattt tactggcgtt gtattattga aaaaatcatt ttatttatat tgctctcaaa   2940
tcatactggc ttatatccat tcatgaagaa tcatttctac tgtctgaagt tttcagctat   3000
atgtatcgaa aaaatttagt tattatatag tttattttga gcctctgcat catctatttg   3060
tgaatttcat ttgcttattc tgcatactct cagcattaac cgtctcttct tttgttaatt   3120
gctttagtaa tctctcctcc aacaatctca aaggcccaat tccaattgag ctatctcgta   3180
ttgggaatgt agatacactg taagtgcaaa ctttctcatc tactttcatt tctctcattg   3240
caattatggt tgcggggaaa gcactttttg tcagtcttaa gaatcttcaa catttttttgg   3300
cttagggact tatcaaacaa caggatcagt ggtcctatac ctatgtccct tggtgatttg   3360
gaacatcttc ttaaactgtg agcataaccg tcaagttgtt atgttagcat catatatctg   3420
ttgtacttac atccctttttg tcaatgctgt aggaacttaa gcaagaatga aataaatgga   3480
aacttaccag ctgaatttgg caatttaagg agcatcatgg agatgtatgg aaccttgcta   3540
aattcagtta ctttgaattt atggtttgct tgattttcag ctttttgact gcactcctaa   3600
ttgtagtgat ctgtcaagca atcacctctc tggtccctta cctcaggaac ttggtcagct   3660
tccaaacctg tacttgctgt aagtacttca gatttacttt gagactctca tcctcttagc   3720
tattggtaat aatctgtaga gtgaataagt atgaacttct aaactcggta agtagatttt   3780
aaaattattt tggatgccat tttcaaaaaa gtagagatga agttggttgt gttgctattg   3840
ttttatatga tctggcttca tatgttcatt actttggtgt tctcagtttt gctttatatt   3900
gcattattgc acggggctca aatgcagcat atctctatct tctttttctt gtggccttaa   3960
ttattttaca aattaatgaa caggaaggtg gaaaacaaca atttatcagg cgatgtgatg   4020
tccttagcca gttgcctcag tctaaatatc ttgtgagttt tcaagtccat agtaagacac   4080
```

```
cagtacaaac aaatgttttg ttaatctaat caacctcatg ttagcagaaa tgtctcatac   4140
aataatctgg gagggaatat tccaaccggc aataatttct ctagattttc accagacagg   4200
taagtggagc tattaagatt ttacacaagt cacaagcatt tattggtttt taattctttg   4260
cttctaattt cttccttttg ctatgtctcc gaaaaagctt cataggaaat ccagatctgt   4320
gtgggtattg gctcacttct ccttgtcatg catctcatcc ggcagagcga ggtctgatca   4380
aactgtaaca atcatttggc ctttactcta ttgcattttt gaagttccat ttcactttag   4440
acatctgcaa catttattaa gtgtgatgga cagatatatt gattaatgag gaattatccc   4500
ttggttgagc aaacttaatt ctgtgttagc ctggtagtag ggtgtaccac aaggtttgtc   4560
gtcatggttt cctatgttca caatccctga ttgtaacatt tagatgtgta cacatatcta   4620
attaacatga aataatcttc atttgctgga gttacattga cgtaaagatg cgttagctgt   4680
caaatgaaac tgcatttgtt ttatttccat catcagtaca ttaattaagt gcataaatat   4740
tttaacagtt gttgaatgat ataagatgaa tttattggac aattgcagtt tcaatttcta   4800
aagcagcaat acttggtatt gctctgggtg gcttggtgat tcttctgatg atactagtag   4860
cagcatgccg gccacagaaa cctgcacctt tcatggaagg atctattgat aaaccaggta   4920
caatattttc cggacggttg gatagtgttt ggagatgttc atgtcagaag gacagtcgtc   4980
agagtttatt gaagttgcca tgtattgatt gtttaacgtt tttgatgaac agtttattac   5040
tcatctccaa aacttgtgat ccttcatatg aacatggcac ttcatgttta cgaggacatt   5100
atgaggatga ctgagaactt gagtgagaag tatataattg gttgtggagc atcaagtact   5160
gtatataaat gtgttttgaa aaattgcaag cctgtagcta tcaagaagtt gtactctcac   5220
aacccgcaat acttgaagga atttgagact gaacttgaga cagttgggag tattaagcat   5280
cgtaatcttg tctgtctcca aggatattct ctttctccat ctggccatct tcttttctat   5340
gactacatgg aaaatggtag cctttgggat ttgcttcatg gttagtaaat ccaaaatggt   5400
taaggtgatt gatgcattga ttttgtgtta aagcatcaag taatcagtcc tcttgtatct   5460
ttttttgcag gtcctacaac aaagaagaaa aagcttgatt gggttactcg ccttcgaatt   5520
gcattgggat cagctcaagg gcttgcatat cttcatcatg attgtagccc tcgaataatc   5580
caccgtgatg ttaaatcatc taatatcttg ttggacaaag actttgaggc tcatctgact   5640
gattttggca tagctaaaag cttatgcata tcaaagacct atacgtccac gtacattatg   5700
ggaaccattg gttacattga tccagagtat gctcgcactt ctcgcttgac agagaagtct   5760
gatgtttaca gctatggtat tgttctattg gaattgctca ctggaaggaa agctgtagat   5820
aatgaatcta atctacatca tttggtaagc tcttgcaatt tagttaatat gaacttgtcc   5880
tatgatgttt attcatataa ttatattaag attcaattca attgatcata acagttttgc   5940
atatatgtta cagattctaa ctaaggcagc aaacgatgct gtaatggaaa cagtggatcc   6000
tgagataaca tgcacatgca aagatcttgc agatgtgaag aaggtttttc agcttgccct   6060
tctatgttcc aaaagacagc ctgctgagag accaacaatg catgaagtgg caagagtact   6120
tgaaagccta atacccgtcg ctgaaacgaa acagccaaat ccaacccccct cacttgcatt   6180
actcccatct gctaaggtac cttgttacat ggatgaatat gtcaacctca agacacccca   6240
cctagtgaac tgttcatcca tgagcacttc agatgcccaa cttttcctca agtttggaga   6300
ggtcatatcc cagaatagtg gctga                                         6325
```

<210> SEQ ID NO 11

<211> LENGTH: 2974
<212> TYPE: DNA
<213> ORGANISM: Solanum lycopersicum

<400> SEQUENCE: 11
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300
ggccttgtat ctattgatat gaggggaaat cgcctttctg gccagatacc agatgaagat 360
tggtgactgt tcagcactga aaaatttgga cctttccttc aatgagcttt atggtgatat 420
tcccttctcc atatctaaac tcaagcaact ggaatatctg attttgaaga ataatcaatt 480
gattggacca attccatcta cattgtcaca gatccctaac ttgaaggtct tggacctggc 540
tcaaaatagg ttaagtggag aaattcctag gctgatatac tggaacgaag tcctgcagta 600
tctgggactg cgtggtaaca acttgggtgg atccctttct cctgatatgt gtcagctcac 660
cggcctgtgg tactttgatg ttcggaacaa tagtttgact ggttccattc ctcaaaatat 720
tggcaactgt actgccttcc aggttctaga tttgtcttat aatgatttga ccggagagat 780
tcctttcaat attggtttcc tgcaagtagc gaccttgtct ttgcaaggta atcgtctttc 840
agggcagatc ccttctgtaa ttggattgat gcaagctctt gcagttttgg acttgagctg 900
caatatgttg agtggaacaa ttccttcaat tcttgggaat ttgacttaca cagagaaatt 960
gtatctacac gggaacaagc tatctggttc cattcctcca gagctgggaa atatgacaaa 1020
gctccactac ttggaattga atgataacca acttactgga cgcataccac cagaacttgg 1080
aaagctgaca gaattgtttg acttaaatgt tgcaaacaac cacctagatg ggcccatacc 1140
ttccaatatt agctcatgta ccaatttgaa tagtctcaac gttcatggaa acaaattgaa 1200
tggtactatt ccacctgctt ttcagaagct ggaaagtatg acctatctta atctctcctc 1260
caacaatctc aaaggcccaa ttccaattga gctatctcgt attgggaatg tagatacact 1320
ggacttatca aacaacagga tcagtggtcc tatacctatg tcccttggtg atttggaaca 1380
tcttcttaaa ctgaacttaa gcaagaatga aataaatgga aacttaccag ctgaatttgg 1440
caatttaagg agcatcatgg agattgatct gtcaagcaat cacctctctg gtcccttacc 1500
tcaggaactt ggtcagcttc caaacctgta cttgctgaag gtggaaaaca acaatttatc 1560
aggcgatgtg atgtccttag ccagttgcct cagtctaaat atcttaaatg tctcatacaa 1620
taatctggga gggaatattc caaccggcaa taatttctct agattttcac cagacagctt 1680
cataggaaat ccagatctgt gtgggtattg gctcacttct ccttgtcatg catctcatcc 1740
ggcagagcga gtttcaattt ctaaagcagc aatacttggt attgctctgg gtggcttggt 1800
gattcttctg atgatactag tagcagcatg ccggccacag aaacctgcac ctttcatgga 1860
aggatctatt gataaaccag tttattactc atctccaaaa cttgtgatcc ttcatatgaa 1920
catggcactt catgtttacg aggacattat gaggatgact gagaacttga gtgagaagta 1980
tataattggt tgtggagcat caagtactgt atataaatgt gttttgaaaa attgcaagcc 2040
tgtagctatc aagaagttgt actctcacaa cccgcaatac ttgaaggaat ttgagactga 2100
acttgagaca gttgggagta ttaagcatcg taatcttgtc tgtctccaag gatattctct 2160
ttctccatct ggccatcttc ttttctatga ctacatggaa aatggtagcc tttgggattt 2220
gcttcatggt cctacaacaa agaagaaaaa gcttgattgg gttactcgcc ttcgaattgc 2280
attgggatca gctcaagggc ttgcatatct tcatcatgat tgtagccctc gaataatcca 2340
ccgtgatgtt aaatcatcta atatcttgtt ggacaaagac tttgaggctc atctgactga 2400
ttttggcata gctaaaagct tatgcatatc aaagacctat acgtccacgt acattatggg 2460
aaccattggt tacattgatc cagagtatgc tcgcacttct cgcttgacag agaagtctga 2520
tgtttacagc tatggtattg ttctattgga attgctcact ggaaggaaag ctgtagataa 2580
tgaatctaat ctacatcatt tgattctaac taaggcagca aacgatgctg taatggaaac 2640
agtggatcct gagataacat gcacatgcaa agatcttgca gatgtgaaga aggtttttca 2700
gcttgccctt ctatgttcca aaagacagcc tgctgagaga ccaacaatgc atgaagtggc 2760
aagagtactt gaaagcctaa tacccgtcgc tgaaacgaaa cagccaaatc caaccccctc 2820
acttgcatta ctcccatctg ctaaggtacc ttgttacatg gatgaatatg tcaacctcaa 2880
gacaccccac ctagtgaact gttcatccat gagcacttca gatgcccaac ttttcctcaa 2940
gtttggagag gtcatatccc agaatagtgg ctga 2974

<210> SEQ ID NO 12
<211> LENGTH: 121
<212> TYPE: PRT
<213> ORGANISM: Solanum lycopersicum

<400> SEQUENCE: 12

Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Asp Trp
        115                 120

<210> SEQ ID NO 13
<211> LENGTH: 6320
<212> TYPE: DNA
<213> ORGANISM: Solanum lycopersicum

<400> SEQUENCE: 13
atggcatcat ttttactcca aagatgtaat cttctctttg aggttcttct tattttgggg 60
ttcttgattt tcttcagctt tggttctgtg gtgtctgatg atggtgagta gagtagagta 120
gtagaacttt ctgcttctta tgttttagtt taatgttttg tttaagatgt taaaaagaca 180
aagtgtgctt tttttaatca ttttttaaat ggtggttttt gattaatccc acgttttgta 240
gttgttattt gttaaaggtt tattttttttg tctcattatt ataataataa ttgggaaata 300
ggttctgcat tgttggaaat taagaagtca attagggacg tggagaatgt gttgtatgac 360

-continued

```
tggactgatt ctccttcatc tgattactgt gcctggagag gtgttacctg tgataatgtc    420
accttcaatg ttgttcaact gtaagacata actcaaaaac actatcattt gggattcttt    480
agttataaag ttgtaatctt ttgacattat cttgtagtaa tctttcgagt ttaaatcttg    540
atggggagtt gtctctattg gacagctcaa aggccttgta tctatgtaat atctcctccc    600
attatctcac aattaccctt tttgtttgat cttttgactt agtgcacatt atagactatg    660
cctgttaatt ttttttgaa gtgatatgag gggaaatcgc ctttctggcc agataccaga    720
tgagattggt gactgttcag cactgaaaaa tttgtaagta tgaaatgctt ctgaatcttg    780
tgttattgtt tggaaaaata agtaaccatt ttttccctta gggacctttc cttcaatgag    840
ctttatggtg atattccctt ctccatatct aaactcaagc aactggaata tctgtaagtt    900
ttgatactct ccttcttcta aatgttgtat tatttgcttt ccgagattgt tagttgatta    960
tgctcgtctt attcaactta ggattttgaa gaataatcaa ttgattggac caattccatc   1020
tacattgtca cagatcccta acttgaaggt cttgtaagta tattctctct gctttgtcat   1080
gatattggta gattatgaat aattttagtt tgatccaaga acttcctcca gggacctggc   1140
tcaaaatagg ttaagtggag aaattcctag gctgatatac tggaacgaag tcctgcagta   1200
tctgtgagtg ttttaatccg gtgttcctct tcttcctgtt tgttttaacc ttaggacact   1260
ttcatttcgt atatggatat gattacatct gttgtatgtt tttattcata taggggactg   1320
cgtggtaaca acttgggtgg atccctttct cctgatatgt gtcagctcac cggcctgtgg   1380
tacttgtaag tttgtaatcc tgttgctctt aagatcttac tttagttcct ctaggtgatg   1440
acattaacca ttgttcattg tgttgtacag tgatgttcgg aacaatagtt tgactggttc   1500
cattcctcaa aatattggca actgtactgc cttccaggtt ctgtaagtat ctaaatcaat   1560
tgaatgaagt ttgactatat tctgtatgtt tggttggcat aacaccttgt tttgttctgt   1620
cagagatttg tcttataatg atttgaccgg agagattcct ttcaatattg gtttcctgca   1680
agtagcgacc ttgtaagttt atgctgcttc tcttcattac aaactattca atatatggtt   1740
gtttgaagtg tactttcatc attccaggtc tttgcaaggt aatcgtcttt cagggcagat   1800
cccttctgta attggattga tgcaagctct tgcagttttg tgagtgtttt gtgtcttgat   1860
atctcaatct aatgctactg aatctaattc ttggaaacca ttataatgca tctgttattt   1920
aagttttctg accctttttac tgtcagggac ttgagctgca atatgttgag tggaacaatt   1980
ccttcaattc ttgggaattt gacttacaca gagaaattgt tagtacttca acattattaa   2040
aagcaatttg gatcattttg tgcttcctaa attgtgtagt ggatcaatta ctgtaagttc   2100
gcattgtatt gcaggtatct acacgggaac aagctatctg gttccattcc tccagagctg   2160
ggaaatatga caaagctcca ctacttgtat gaatgccttc tatcaatcat tttttgttag   2220
ctttgttttg ttcttcctgt tcaaaccctt ttaaatgaat gcttaccatt tagaagcatt   2280
tgtttgatta tttagccttt gggcaaccac ggatttgaat gatagaaagc tgttatgaga   2340
atttttatta agagactttc ttcaacctta aggctcaaag atggtaattt gcagggaatt   2400
gaatgataac caacttactg gacgcatacc accagaactt ggaaagctga cagaattgtt   2460
tgacttgtaa atcccgtttc tcttcatctt ctactttgga cttgttaaca tcattattta   2520
tttactcatg ttgtatgttt cagaaatgtt gcaaacaacc acctagatgg gcccatacct   2580
tccaatatta gctcatgtac caatttgaat agtctgtgag tgtttttaat gtccgaagtg   2640
tttcaattat gcacgaccat gcttgtttgg tagttattga cacctgattt tgttgcagca   2700
acgttcatgg aaacaaattg aatggtacta ttccacctgc ttttcagaag ctggaaagta   2760
```

-continued

```
tgacctatct gtaagttctt actttctgat ctttttcttt tgaagaatta tgtttaaggt   2820
tatcgaagtt accgtccatg ctgttgagca agattgtaaa cttactgtgc cttgtatata   2880
aattttactg gcgttgtatt attgaaaaaa tcattttatt tatattgctc tcaaatcata   2940
ctggcttata tccattcatg aagaatcatt tctactgtct gaagttttca gctatatgta   3000
tcgaaaaaat ttagttatta tatagtttat tttgagcctc tgcatcatct atttgtgaat   3060
ttcatttgct tattctgcat actctcagca ttaaccgtct cttcttttgt taattgcttt   3120
agtaatctct cctccaacaa tctcaaaggc ccaattccaa ttgagctatc tcgtattggg   3180
aatgtagata cactgtaagt gcaaactttc tcatctactt tcatttctct cattgcaatt   3240
atggttgcgg ggaaagcact tttgtcagt cttaagaatc ttcaacattt tttggcttag   3300
ggacttatca aacaacagga tcagtggtcc tatacctatg tcccttggtg atttggaaca   3360
tcttcttaaa ctgtgagcat aaccgtcaag ttgttatgtt agcatcatat atctgttgta   3420
cttacatccc ttttgtcaat gctgtaggaa cttaagcaag aatgaaataa atggaaactt   3480
accagctgaa tttggcaatt taaggagcat catggagatg tatggaacct tgctaaattc   3540
agttactttg aatttatggt ttgcttgatt ttcagctttt tgactgcact cctaattgta   3600
gtgatctgtc aagcaatcac ctctctggtc ccttacctca ggaacttggt cagcttccaa   3660
acctgtactt gctgtaagta cttcagattt actttgagac tctcatcctc ttagctattg   3720
gtaataatct gtagagtgaa taagtatgaa cttctaaact cggtaagtag attttaaaat   3780
tattttggat gccattttca aaaaagtaga gatgaagttg gttgtgttgc tattgtttta   3840
tatgatctgg cttcatatgt tcattacttt ggtgttctca gttttgcttt atattgcatt   3900
attgcacggg gctcaaatgc agcatatctc tatcttcttt ttcttgtggc cttaattatt   3960
ttacaaatta atgaacagga aggtggaaaa caacaattta tcaggcgatg tgatgtcctt   4020
agccagttgc ctcagtctaa atatcttgtg agtttcaag tccatagtaa gacaccagta    4080
caaacaaatg ttttgttaat ctaatcaacc tcatgttagc agaaatgtct catacaataa   4140
tctgggaggg aatattccaa ccggcaataa tttctctaga ttttcaccag acaggtaagt   4200
ggagctatta agattttaca caagtcacaa gcatttattg gtttttaatt ctttgcttct   4260
aatttcttcc ttttgctatg tctccgaaaa agcttcatag gaaatccaga tctgtgtggg   4320
tattggctca cttctccttg tcatgcatct catccggcag agcgaggtct gatcaaactg   4380
taacaatcat ttggccttta ctctattgca tttttgaagt tccatttcac tttagacatc   4440
tgcaacattt attaagtgtg atggacagat atattgatta atgaggaatt atcccttggt   4500
tgagcaaact taattctgtg ttagcctggt agtagggtgt accacaaggt ttgtcgtcat   4560
ggtttcctat gttcacaatc cctgattgta acatttagat gtgtacacat atctaattaa   4620
catgaaataa tcttcatttg ctggagttac attgacgtaa agatgcgtta gctgtcaaat   4680
gaaactgcat ttgttttatt tccatcatca gtacattaat taagtgcata aatattttaa   4740
cagttgttga atgatataag atgaatttat tggacaattg cagtttcaat ttctaaagca   4800
gcaatacttg gtattgctct gggtggcttg gtgattcttc tgatgatact agtagcagca   4860
tgccggccac agaaacctgc acctttcatg gaaggatcta ttgataaacc aggtacaata   4920
ttttccggac ggttggatag tgtttggaga tgttcatgtc agaaggacag tcgtcagagt   4980
ttattgaagt tgccatgtat tgattgttta acgtttttga tgaacagttt attactcatc   5040
tccaaaactt gtgatccttc atatgaacat ggcacttcat gtttacgagg acattatgag   5100
```

-continued

```
gatgactgag aacttgagtg agaagtatat aattggttgt ggagcatcaa gtactgtata    5160

taaatgtgtt ttgaaaaatt gcaagcctgt agctatcaag aagttgtact ctcacaaccc    5220

gcaatacttg aaggaatttg agactgaact tgagacagtt gggagtatta agcatcgtaa    5280

tcttgtctgt ctccaaggat attctctttc tccatctggc catcttcttt tctatgacta    5340

catggaaaat ggtagccttt gggatttgct tcatggttag taaatccaaa atggttaagg    5400

tgattgatgc attgattttg tgttaaagca tcaagtaatc agtcctcttg tatctttttt    5460

tgcaggtcct acaacaaaga agaaaaagct tgattgggtt actcgccttc gaattgcatt    5520

gggatcagct caagggcttg catatcttca tcatgattgt agccctcgaa taatccaccg    5580

tgatgttaaa tcatctaata tcttgttgga caaagacttt gaggctcatc tgactgattt    5640

tggcatagct aaaagcttat gcatatcaaa gacctatacg tccacgtaca ttatgggaac    5700

cattggttac attgatccag agtatgctcg cacttctcgc ttgacagaga agtctgatgt    5760

ttacagctat ggtattgttc tattggaatt gctcactgga aggaaagctg tagataatga    5820

atctaatcta catcatttgg taagctcttg caatttagtt aatatgaact tgtcctatga    5880

tgtttattca tataattata ttaagattca attcaattga tcataacagt tttgcatata    5940

tgttacagat tctaactaag gcagcaaacg atgctgtaat ggaaacagtg gatcctgaga    6000

taacatgcac atgcaaagat cttgcagatg tgaagaaggt ttttcagctt gcccttctat    6060

gttccaaaag acagcctgct gagagaccaa caatgcatga agtggcaaga gtacttgaaa    6120

gcctaatacc cgtcgctgaa acgaaacagc caaatccaac cccctcactt gcattactcc    6180

catctgctaa ggtaccttgt tacatggatg aatatgtcaa cctcaagaca ccccacctag    6240

tgaactgttc atccatgagc acttcagatg cccaactttt cctcaagttt ggagaggtca    6300

tatcccagaa tagtggctga                                                6320
```

<210> SEQ ID NO 14
<211> LENGTH: 2969
<212> TYPE: DNA
<213> ORGANISM: Solanum lycopersicum

<400> SEQUENCE: 14

```
atggcatcat ttttactcca aagatgtaat cttctctttg aggttcttct tattttgggg     60

ttcttgattt tcttcagctt tggttctgtg gtgtctgatg atggttctgc attgttggaa    120

attaagaagt caattaggga cgtggagaat gtgttgtatg actggactga ttctccttca    180

tctgattact gtgcctggag aggtgttacc tgtgataatg tcaccttcaa tgttgttcaa    240

cttaatcttt cgagtttaaa tcttgatggg gagttgtctc tattggacag ctcaaaggcc    300

ttgtatctat tgatatgagg ggaaatcgcc tttctggcca gataccagat gagattggtg    360

actgttcagc actgaaaaat ttggaccttt ccttcaatga gctttatggt gatattccct    420

tctccatatc taaactcaag caactggaat atctgatttt gaagaataat caattgattg    480

gaccaattcc atctacattg tcacagatcc ctaacttgaa ggtcttggac ctggctcaaa    540

ataggttaag tggagaaatt cctaggctga tatactggaa cgaagtcctg cagtatctgg    600

gactgcgtgg taacaacttg ggtggatccc tttctcctga tatgtgtcag ctcaccggcc    660

tgtggtactt tgatgttcgg aacaatagtt tgactggttc cattcctcaa aatattggca    720

actgtactgc cttccaggtt ctagatttgt cttataatga tttgaccgga gagattcctt    780

tcaatattgg tttcctgcaa gtagcgacct tgtctttgca aggtaatcgt ctttcagggc    840

agatcccttc tgtaattgga ttgatgcaag ctcttgcagt tttggacttg agctgcaata    900
```

-continued

```
tgttgagtgg aacaattcct tcaattcttg ggaatttgac ttacacagag aaattgtatc    960
tacacgggaa caagctatct ggttccattc ctccagagct gggaaatatg acaaagctcc   1020
actacttgga attgaatgat aaccaactta ctggacgcat accaccagaa cttggaaagc   1080
tgacagaatt gtttgactta aatgttgcaa acaaccacct agatgggccc ataccttcca   1140
atattagctc atgtaccaat ttgaatagtc tcaacgttca tggaaacaaa ttgaatggta   1200
ctattccacc tgcttttcag aagctggaaa gtatgaccta tcttaatctc tcctccaaca   1260
atctcaaagg cccaattcca attgagctat ctcgtattgg gaatgtagat acactggact   1320
tatcaaacaa caggatcagt ggtcctatac ctatgtccct tggtgatttg gaacatcttc   1380
ttaaactgaa cttaagcaag aatgaaataa atggaaactt accagctgaa tttggcaatt   1440
taaggagcat catggagatt gatctgtcaa gcaatcacct ctctggtccc ttacctcagg   1500
aacttggtca gcttccaaac ctgtacttgc tgaaggtgga aaacaacaat ttatcaggcg   1560
atgtgatgtc cttagccagt tgcctcagtc taaatatctt aaatgtctca tacaataatc   1620
tgggagggaa tattccaacc ggcaataatt tctctagatt ttcaccagac agcttcatag   1680
gaaatccaga tctgtgtggg tattggctca cttctccttg tcatgcatct catccggcag   1740
agcgagtttc aatttctaaa gcagcaatac ttggtattgc tctgggtggc ttggtgattc   1800
ttctgatgat actagtagca gcatgccggc cacagaaacc tgcacctttc atggaaggat   1860
ctattgataa accagtttat tactcatctc caaaacttgt gatccttcat atgaacatgg   1920
cacttcatgt ttacgaggac attatgagga tgactgagaa cttgagtgag aagtatataa   1980
ttggttgtgg agcatcaagt actgtatata aatgtgtttt gaaaaattgc aagcctgtag   2040
ctatcaagaa gttgtactct cacaacccgc aatacttgaa ggaatttgag actgaacttg   2100
agacagttgg gagtattaag catcgtaatc ttgtctgtct ccaaggatat tctctttctc   2160
catctggcca tcttcttttc tatgactaca tggaaaatgg tagcctttgg gatttgcttc   2220
atggtcctac aacaaagaag aaaaagcttg attgggttac tcgccttcga attgcattgg   2280
gatcagctca agggcttgca tatcttcatc atgattgtag ccctcgaata atccaccgtg   2340
atgttaaatc atctaatatc ttgttggaca aagactttga ggctcatctg actgattttg   2400
gcatagctaa aagcttatgc atatcaaaga cctatacgtc cacgtacatt atgggaacca   2460
ttggttacat tgatccagag tatgctcgca cttctcgctt gacagagaag tctgatgttt   2520
acagctatgg tattgttcta ttggaattgc tcactggaag gaaagctgta gataatgaat   2580
ctaatctaca tcatttgatt ctaactaagg cagcaaacga tgctgtaatg gaaacagtgg   2640
atcctgagat aacatgcaca tgcaaagatc ttgcagatgt gaagaaggtt tttcagcttg   2700
cccttctatg ttccaaaaga cagcctgctg agagaccaac aatgcatgaa gtggcaagag   2760
tacttgaaag cctaataccc gtcgctgaaa cgaaacagcc aaatccaacc ccctcacttg   2820
cattactccc atctgctaag gtaccttgtt acatggatga atatgtcaac ctcaagacac   2880
cccacctagt gaactgttca tccatgagca cttcagatgc ccaacttttc ctcaagtttg   2940
gagaggtcat atcccagaat agtggctga                                     2969
```

<210> SEQ ID NO 15
<211> LENGTH: 105
<212> TYPE: PRT
<213> ORGANISM: Solanum lycopersicum

<400> SEQUENCE: 15

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Leu Leu Asp
                85                  90                  95

Ser Ser Lys Ala Leu Tyr Leu Leu Ile
            100                 105
```

```
<210> SEQ ID NO 16
<211> LENGTH: 6324
<212> TYPE: DNA
<213> ORGANISM: Solanum lycopersicum

<400> SEQUENCE: 16

atggcatcat ttttactcca aagatgtaat cttctctttg aggttcttct tattttgggg      60

ttcttgattt tcttcagctt tggttctgtg gtgtctgatg atggtgagta gagtagagta     120

gtagaacttt ctgcttctta tgttttagtt taatgttttg tttaagatgt taaaaagaca     180

aagtgtgctt tttttaatca tttttttaaat ggtggttttt gattaatccc acgttttgta    240

gttgttattt gttaaaggtt tatttttttg tctcattatt ataataataa ttgggaaata     300

ggttctgcat tgttggaaat taagaagtca attagggacg tggagaatgt gttgtatgac     360

tggactgatt ctccttcatc tgattactgt gcctggagag gtgttacctg tgataatgtc     420

accttcaatg ttgttcaact gtaagacata actcaaaaac actatcattt gggattcttt     480

agttataaag ttgtaatctt ttgacattat cttgtagtaa tctttcgagt ttaaatcttg     540

atggggagtt gtctcctgct attggacagc tcaaaggcct tgtatctatg taatatctcc     600

tcccattatc tcacaattac cctttttgtt tgatcttttg acttagtgca cattatagac     660

tatgcctgtt aatttttttt tgaagtgata tgaggggaaa tcgcctttct ggccagatac     720

cagatgagat tggtgactgt tcagcactga aaaatttgta agtatgaaat gcttctgaat     780

cttgtgttat tgtttggaaa aataagtaac cattttttcc cttagggacc tttccttcaa     840

tgagctttat ggtgatattc ccttctccat atctaaactc aagcaactgg aatatctgta     900

agttttgata ctctccttct tctaaatgtt gtattatttg ctttccgaga ttgttagttg     960

attatgctcg tcttattcaa cttaggattt tgaagaataa tcaattgatt ggaccaattc    1020

catctacatt gtcacagatc cctaacttga aggtcttgta agtatattct ctctgctttg    1080

tcatgatatt ggtagattat gaataatttt agtttgatcc aagaacttcc tccagggacc    1140

tggctcaaaa taggttaagt ggagaaattc ctaggctgat atactggaac gaagtcctgc    1200

agtatctgtg agtgttttaa tccggtgttc ctcttcttcc tgtttgtttt aaccttagga    1260

cactttcatt tcgtatatgg atatgattac atctgttgta tgtttttatt catataggg     1320

actgcgtggt aacaacttgg gtggatccct ttctcctgat atgtgtcagc tcaccggcct    1380

gtggtacttg taagtttgta atcctgttgc tcttaagatc ttactttagt tcctctaggt    1440

gatgacatta accattgttc attgtgttgt acagtgatgt tcggaacaat agtttgactg    1500
```

-continued

```
gttccattcc tcaaaatatt ggcaactgta ctgccttcca ggttctgtaa gtatctaaat   1560
caattgaatg aagtttgact atattctgta tgtttggttg gcataacacc ttgttttgtt   1620
ctgtcagaga tttgtcttat aatgatttga ccggagagat tcctttcaat attggtttcc   1680
tgcaagtagc gaccttgtaa gtttatgctg cttctcttca ttacaaacta ttcaatatat   1740
ggttgtttga agtgtacttt catcattcca ggtctttgca aggtaatcgt ctttcagggc   1800
agatcccttc tgtaattgga ttgatgcaag ctcttgcagt tttgtgagtg ttttgtgtct   1860
tgatatctca atctaatgct actgaatcta attcttggaa accattataa tgcatctgtt   1920
atttaagttt tctgaccctt ttactgtcag ggacttgagc tgcaatatgt tgagtggaac   1980
aattccttca attcttggga atttgactta cacagagaaa ttgttagtac ttcaacatta   2040
ttaaaagcaa tttggatcat tttgtgcttc ctaaattgtg tagtggatca attactgtaa   2100
gttcgcattg tattgcaggt atctacacgg gaacaagcta tctggttcca ttcctccaga   2160
gctgggaaat atgacaaagc tccactactt gtatgaatgc cttctatcaa tcatttttg   2220
ttagctttgt tttgttcttc ctgttcaaac ccttttaaat gaatgcttac catttagaag   2280
catttgtttg attatttagc ctttgggcaa ccacggattt gaatgataga aagctgttat   2340
gagaattttt attaagagac tttcttcaac cttaaggctc aaagatggta atttgcaggg   2400
aattgaatga taaccaactt actggacgca taccaccaga acttggaaag ctgacagaat   2460
tgtttgactt gtaaatcccg tttctcttca tcttctactt tggacttgtt aacatcatta   2520
tttatttact catgttgtat gtttcagaaa tgttgcaaac aaccacctag atgggcccat   2580
accttccaat attagctcat gtaccaattt gaatagtctg tgagtgtttt taatgtccga   2640
agtgtttcaa ttatgcacga ccatgcttgt ttggtagtta ttgacacctg attttgttgc   2700
agcaacgttc atggaaacta attgaatggt actattccac ctgcttttca gaagctggaa   2760
agtatgacct atctgtaagt tcttactttc tgatcttttt cttttgaaga attatgttta   2820
aggttatcga agttaccgtc catgctgttg agcaagattg taaacttact gtgccttgta   2880
tataaatttt actggcgttg tattattgaa aaaatcattt tatttatatt gctctcaaat   2940
catactggct tatatccatt catgaagaat catttctact gtctgaagtt ttcagctata   3000
tgtatcgaaa aaatttagtt attatatagt ttattttgag cctctgcatc atctatttgt   3060
gaatttcatt tgcttattct gcatactctc agcattaacc gtctcttctt ttgttaattg   3120
ctttagtaat ctctcctcca acaatctcaa aggcccaatt ccaattgagc tatctcgtat   3180
tgggaatgta gatacactgt aagtgcaaac tttctcatct actttcattt ctctcattgc   3240
aattatggtt gcggggaaag cactttttgt cagtcttaag aatcttcaac atttttggc    3300
ttagggactt atcaaacaac aggatcagtg gtcctatacc tatgtccctt ggtgatttgg   3360
aacatcttct taaactgtga gcataaccgt caagttgtta tgttagcatc atatatctgt   3420
tgtacttaca tccctttgt  caatgctgta ggaacttaag caagaatgaa ataaatggaa   3480
acttaccagc tgaatttggc aatttaagga gcatcatgga gatgtatgga accttgctaa   3540
attcagttac tttgaattta tggtttgctt gattttcagc tttttgactg cactcctaat   3600
tgtagtgatc tgtcaagcaa tcacctctct ggtcccttac ctcaggaact tggtcagctt   3660
ccaaacctgt acttgctgta agtacttcag atttactttg agactctcat cctcttagct   3720
attggtaata atctgtagag tgaataagta tgaacttcta aactcggtaa gtagatttta   3780
aaattatttt ggatgccatt ttcaaaaaag tagagatgaa gttggttgtg ttgctattgt   3840
tttatatgat ctggcttcat atgttcatta ctttggtgtt ctcagttttg ctttatattg   3900
```

```
cattattgca cggggctcaa atgcagcata tctctatctt ctttttcttg tggccttaat   3960
tattttacaa attaatgaac aggaaggtgg aaaacaacaa tttatcaggc gatgtgatgt   4020
ccttagccag ttgcctcagt ctaaatatct tgtgagtttt caagtccata gtaagacacc   4080
agtacaaaca aatgttttgt taatctaatc aacctcatgt tagcagaaat gtctcataca   4140
ataatctggg agggaatatt ccaaccggca ataatttctc tagattttca ccagacaggt   4200
aagtggagct attaagattt tacacaagtc acaagcattt attggttttt aattctttgc   4260
ttctaatttc ttcctttttgc tatgtctccg aaaaagcttc ataggaaatc cagatctgtg   4320
tgggtattgg ctcacttctc cttgtcatgc atctcatccg gcagagcgag gtctgatcaa   4380
actgtaacaa tcatttggcc tttactctat tgcatttttg aagttccatt tcactttaga   4440
catctgcaac atttattaag tgtgatggac agatatattg attaatgagg aattatccct   4500
tggttgagca aacttaattc tgtgttagcc tggtagtagg gtgtaccaca aggtttgtcg   4560
tcatggtttc ctatgttcac aatccctgat tgtaacattt agatgtgtac acatatctaa   4620
ttaacatgaa ataatcttca tttgctggag ttacattgac gtaaagatgc gttagctgtc   4680
aaatgaaact gcatttgttt tatttccatc atcagtacat taattaagtg cataaatatt   4740
ttaacagttg ttgaatgata taagatgaat ttattggaca attgcagttt caatttctaa   4800
agcagcaata cttggtattg ctctgggtgg cttggtgatt cttctgatga tactagtagc   4860
agcatgccgg ccacagaaac ctgcaccttt catggaagga tctattgata aaccaggtac   4920
aatattttcc ggacggttgg atagtgtttg gagatgttca tgtcagaagg acagtcgtca   4980
gagtttattg aagttgccat gtattgattg tttaacgttt ttgatgaaca gtttattact   5040
catctccaaa acttgtgatc cttcatatga acatggcact tcatgtttac gaggacatta   5100
tgaggatgac tgagaacttg agtgagaagt atataattgg ttgtggagca tcaagtactg   5160
tatataaatg tgttttgaaa aattgcaagc ctgtagctat caagaagttg tactctcaca   5220
acccgcaata cttgaaggaa tttgagactg aacttgagac agttgggagt attaagcatc   5280
gtaatcttgt ctgtctccaa ggatattctc tttctccatc tggccatctt cttttctatg   5340
actacatgga aaatggtagc ctttgggatt tgcttcatgg ttagtaaatc caaaatggtt   5400
aaggtgattg atgcattgat tttgtgttaa agcatcaagt aatcagtcct cttgtatctt   5460
tttttgcagg tcctacaaca aagaagaaaa agcttgattg ggttactcgc cttcgaattg   5520
cattgggatc agctcaaggg cttgcatatc ttcatcatga ttgtagccct cgaataatcc   5580
accgtgatgt taaatcatct aatatcttgt tggacaaaga ctttgaggct catctgactg   5640
attttggcat agctaaaagc ttatgcatat caaagaccta tacgtccacg tacattatgg   5700
gaaccattgg ttacattgat ccagagtatg ctcgcacttc tcgcttgaca gagaagtctg   5760
atgtttacag ctatggtatt gttctattgg aattgctcac tggaaggaaa gctgtagata   5820
atgaatctaa tctacatcat ttggtaagct cttgcaattt agttaatatg aacttgtcct   5880
atgatgttta ttcatataat tatattaaga ttcaattcaa ttgatcataa cagttttgca   5940
tatatgttac agattctaac taaggcagca aacgatgctg taatggaaac agtggatcct   6000
gagataacat gcacatgcaa agatcttgca gatgtgaaga aggtttttca gcttgccctt   6060
ctatgttcca aaagacagcc tgctgagaga ccaacaatgc atgaagtggc aagagtactt   6120
gaaagcctaa tacccgtcgc tgaaacgaaa cagccaaatc caaccccctc acttgcatta   6180
ctcccatctg ctaaggtacc ttgttacatg gatgaatatg tcaacctcaa gacaccccac   6240
```

ctagtgaact gttcatccat gagcacttca gatgcccaac ttttcctcaa gtttggagag 6300
gtcatatccc agaatagtgg ctga 6324

<210> SEQ ID NO 17
<211> LENGTH: 2973
<212> TYPE: DNA
<213> ORGANISM: Solanum lycopersicum

<400> SEQUENCE: 17
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300
ggccttgtat ctattgatat gaggggaaat cgcctttctg gccagatacc agatgagatt 360
ggtgactgtt cagcactgaa aaatttggac ctttccttca atgagcttta tggtgatatt 420
cccttctcca tatctaaact caagcaactg gaatatctga ttttgaagaa taatcaattg 480
attggaccaa ttccatctac attgtcacag atccctaact tgaaggtctt ggacctggct 540
caaaataggt taagtggaga aattcctagg ctgatatact ggaacgaagt cctgcagtat 600
ctgggactgc gtggtaacaa cttgggtgga tccctttctc ctgatatgtg tcagctcacc 660
ggcctgtggt actttgatgt tcggaacaat agtttgactg gttccattcc tcaaaatatt 720
ggcaactgta ctgccttcca ggttctagat ttgtcttata atgatttgac cggagagatt 780
cctttcaata ttggtttcct gcaagtagcg accttgtctt tgcaaggtaa tcgtctttca 840
gggcagatcc cttctgtaat tggattgatg caagctcttg cagttttgga cttgagctgc 900
aatatgttga gtggaacaat tccttcaatt cttgggaatt tgacttacac agagaaattg 960
tatctacacg ggaacaagct atctggttcc attcctccag agctgggaaa tatgacaaag 1020
ctccactact tggaattgaa tgataaccaa cttactggac gcataccacc agaacttgga 1080
aagctgacag aattgtttga cttaaatgtt gcaaacaacc acctagatgg gcccatacct 1140
tccaatatta gctcatgtac caatttgaat agtctcaacg ttcatggaaa ctaattgaat 1200
ggtactattc cacctgcttt tcagaagctg gaaagtatga cctatcttaa tctctcctcc 1260
aacaatctca aaggcccaat tccaattgag ctatctcgta ttgggaatgt agatacactg 1320
gacttatcaa acaacaggat cagtggtcct atacctatgt cccttggtga tttggaacat 1380
cttcttaaac tgaacttaag caagaatgaa ataaatggaa acttaccagc tgaatttggc 1440
aatttaagga gcatcatgga gattgatctg tcaagcaatc acctctctgg tcccttacct 1500
caggaacttg gtcagcttcc aaacctgtac ttgctgaagg tggaaaacaa caatttatca 1560
ggcgatgtga tgtccttagc cagttgcctc agtctaaata tcttaaatgt ctcatacaat 1620
aatctgggag ggaatattcc aaccggcaat aatttctcta gattttcacc agacagcttc 1680
ataggaaatc cagatctgtg tgggtattgg ctcacttctc cttgtcatgc atctcatccg 1740
gcagagcgag tttcaatttc taaagcagca atacttggta ttgctctggg tggcttggtg 1800
attcttctga tgatactagt agcagcatgc cggccacaga aacctgcacc tttcatggaa 1860
ggatctattg ataaaccagt ttattactca tctccaaaac ttgtgatcct tcatatgaac 1920
atggcacttc atgtttacga ggacattatg aggatgactg agaacttgag tgagaagtat 1980
ataattggtt gtggagcatc aagtactgta tataaatgtg ttttgaaaaa ttgcaagcct 2040

```
gtagctatca agaagttgta ctctcacaac ccgcaatact tgaaggaatt tgagactgaa   2100

cttgagacag ttgggagtat taagcatcgt aatcttgtct gtctccaagg atattctctt   2160

tctccatctg gccatcttct tttctatgac tacatggaaa atggtagcct ttgggatttg   2220

cttcatggtc ctacaacaaa gaagaaaaag cttgattggg ttactcgcct tcgaattgca   2280

ttgggatcag ctcaagggct tgcatatctt catcatgatt gtagccctcg aataatccac   2340

cgtgatgtta aatcatctaa tatcttgttg gacaaagact ttgaggctca tctgactgat   2400

tttggcatag ctaaaagctt atgcatatca aagacctata cgtccacgta cattatggga   2460

accattggtt acattgatcc agagtatgct cgcacttctc gcttgacaga gaagtctgat   2520

gtttacagct atggtattgt tctattggaa ttgctcactg gaaggaaagc tgtagataat   2580

gaatctaatc tacatcattt gattctaact aaggcagcaa acgatgctgt aatggaaaca   2640

gtggatcctg agataacatg cacatgcaaa gatcttgcag atgtgaagaa ggtttttcag   2700

cttgcccttc tatgttccaa aagacagcct gctgagagac caacaatgca tgaagtggca   2760

agagtacttg aaagcctaat acccgtcgct gaaacgaaac agccaaatcc aacccccctca   2820

cttgcattac tcccatctgc taaggtacct tgttacatgg atgaatatgt caacctcaag   2880

acaccccacc tagtgaactg ttcatccatg agcacttcag atgcccaact tttcctcaag   2940

tttggagagg tcatatccca gaatagtggc tga                                2973
```

<210> SEQ ID NO 18
<211> LENGTH: 397
<212> TYPE: PRT
<213> ORGANISM: Solanum lycopersicum

<400> SEQUENCE: 18

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160

Ile Gly Pro Ile Pro Ser Thr Leu Ser Gln Ile Pro Asn Leu Lys Val
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
        195                 200                 205
```

-continued

```
Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320

Tyr Leu His Gly Asn Lys Leu Ser Gly Ser Ile Pro Pro Glu Leu Gly
                325                 330                 335

Asn Met Thr Lys Leu His Tyr Leu Glu Leu Asn Asp Asn Gln Leu Thr
            340                 345                 350

Gly Arg Ile Pro Pro Glu Leu Gly Lys Leu Thr Glu Leu Phe Asp Leu
        355                 360                 365

Asn Val Ala Asn Asn His Leu Asp Gly Pro Ile Pro Ser Asn Ile Ser
    370                 375                 380

Ser Cys Thr Asn Leu Asn Ser Leu Asn Val His Gly Asn
385                 390                 395
```

<210> SEQ ID NO 19
<211> LENGTH: 6319
<212> TYPE: DNA
<213> ORGANISM: Solanum lycopersicum

<400> SEQUENCE: 19

```
atggcatcat ttttactcca aagatgtaat cttctctttg aggttcttct tattttgggg     60

ttcttgattt tcttcagctt tggttctgtg gtgtctgatg atggtgagta gagtagagta    120

gtagaacttt ctgcttctta tgttttagtt taatgttttg tttaagatgt taaaaagaca    180

aagtgtgctt tttttaatca ttttttaaat ggtggttttt gattaatccc acgttttgta    240

gttgttattt gttaaaggtt tattttttg tctcattatt ataataataa ttgggaaata    300

ggttctgcat tgttggaaat taagaagtca attagggacg tggagaatgt gttgtatgac    360

tggactgatt ctccttcatc tgattactgt gcctggagag gtgttacctg tgataatgtc    420

accttcaatg ttgttcaact gtaagacata actcaaaaac actatcattt gggattcttt    480

agttataaag ttgtaatctt ttgacattat cttgtagtaa tctttcgagt ttaaatcttg    540

atggggagtt gtcttattgg acagctcaaa ggccttgtat ctatgtaata tctcctccca    600

ttatctcaca attacccttt ttgtttgatc ttttgactta gtgcacatta tagactatgc    660

ctgttaattt ttttttgaag tgatatgagg ggaaatcgcc tttctggcca gataccagat    720

gagattggtg actgttcagc actgaaaaat ttgtaagtat gaaatgcttc tgaatcttgt    780

gttattgttt ggaaaaataa gtaaccattt tttcccttag ggacctttcc ttcaatgagc    840

tttatggtga tattcccttc tccatatcta aactcaagca actggaatat ctgtaagttt    900

tgatactctc cttcttctaa atgttgtatt atttgctttc cgagattgtt agttgattat    960

gctcgtctta ttcaacttag gattttgaag aataatcaat tgattggacc aattccatct   1020
```

```
acattgtcac agatccctaa cttgaaggtc ttgtaagtat attctctctg ctttgtcatg   1080
atattggtag attatgaata attttagttt gatccaagaa cttcctccag ggacctggct   1140
caaaataggt taagtggaga aattcctagg ctgatatact ggaacgaagt cctgcagtat   1200
ctgtgagtgt tttaatccgg tgttcctctt cttcctgttt gttttaacct taggacactt   1260
tcatttcgta tatggatatg attacatctg ttgtatgttt ttattcatat aggggactgc   1320
gtggtaacaa cttgggtgga tccctttctc ctgatatgtg tcagctcacc ggcctgtggt   1380
acttgtaagt ttgtaatcct gttgctctta agatcttact ttagttcctc taggtgatga   1440
cattaaccat tgttcattgt gttgtacagt gatgttcgga acaatagttt gactggttcc   1500
attcctcaaa atattggcaa ctgtactgcc ttccaggttc tgtaagtatc taaatcaatt   1560
gaatgaagtt tgactatatt ctgtatgttt ggttggcata acaccttgtt ttgttctgtc   1620
agagatttgt cttataatga tttgaccgga gagattcctt tcaatattgg tttcctgcaa   1680
gtagcgacct tgtaagttta tgctgcttct cttcattaca aactattcaa tatatggttg   1740
tttgaagtgt actttcatca ttccaggtct ttgcaaggta atcgtctttc agggcagatc   1800
ccttctgtaa ttggattgat gcaagctctt gcagttttgt gagtgttttg tgtcttgata   1860
tctcaatcta atgctactga atctaattct tggaaaccat tataatgcat ctgttattta   1920
agttttctga cccttttact gtcagggact tgagctgcaa tatgttgagt ggaacaattc   1980
cttcaattct tgggaatttg acttacacag agaaattgtt agtacttcaa cattattaaa   2040
agcaatttgg atcattttgt gcttcctaaa ttgtgtagtg gatcaattac tgtaagttcg   2100
cattgtattg caggtatcta cacgggaaca agctatctgg ttccattcct ccagagctgg   2160
gaaatatgac aaagctccac tacttgtatg aatgccttct atcaatcatt ttttgttagc   2220
tttgttttgt tcttcctgtt caaacccttt taaatgaatg cttaccattt agaagcattt   2280
gtttgattat ttagcctttg ggcaaccacg gatttgaatg atagaaagct gttatgagaa   2340
tttttattaa gagactttct tcaaccttaa ggctcaaaga tggtaatttg cagggaattg   2400
aatgataacc aacttactgg acgcatacca ccagaacttg gaaagctgac agaattgttt   2460
gacttgtaaa tcccgtttct cttcatcttc tactttggac ttgttaacat cattatttat   2520
ttactcatgt tgtatgtttc agaaatgttg caaacaacca cctagatggg cccatacctt   2580
ccaatattag ctcatgtacc aatttgaata gtctgtgagt gtttttaatg tccgaagtgt   2640
ttcaattatg cacgaccatg cttgtttggt agttattgac acctgatttt gttgcagcaa   2700
cgttcatgga aacaaattga atggtactat tccacctgct tttcagaagc tggaaagtat   2760
gacctatctg taagttctta ctttctgatc tttttctttt gaagaattat gtttaaggtt   2820
atcgaagtta ccgtccatgc tgttgagcaa gattgtaaac ttactgtgcc ttgtatataa   2880
attttactgg cgttgtatta ttgaaaaaat cattttattt atattgctct caaatcatac   2940
tggcttatat ccattcatga agaatcattt ctactgtctg aagttttcag ctatatgtat   3000
cgaaaaaatt tagttattat atagtttatt ttgagcctct gcatcatcta tttgtgaatt   3060
tcatttgctt attctgcata ctctcagcat taaccgtctc ttcttttgtt aattgcttta   3120
gtaatctctc ctccaacaat ctcaaaggcc caattccaat tgagctatct cgtattggga   3180
atgtagatac actgtaagtg caaactttct catctacttt catttctctc attgcaatta   3240
tggttgcggg gaaagcactt tttgtcagtc ttaagaatct tcaacatttt ttggcttagg   3300
gacttatcaa acaacaggat cagtggtcct atacctatgt cccttggtga tttggaacat   3360
cttcttaaac tgtgagcata accgtcaagt tgttatgtta gcatcatata tctgttgtac   3420
```

```
ttacatccct tttgtcaatg ctgtaggaac ttaagcaaga atgaaataaa tggaaactta   3480
ccagctgaat ttggcaattt aaggagcatc atggagatgt atggaacctt gctaaattca   3540
gttactttga atttatggtt tgcttgattt tcagcttttt gactgcactc ctaattgtag   3600
tgatctgtca agcaatcacc tctctggtcc cttacctcag gaacttggtc agcttccaaa   3660
cctgtacttg ctgtaagtac ttcagattta ctttgagact ctcatcctct tagctattgg   3720
taataatctg tagagtgaat aagtatgaac ttctaaactc ggtaagtaga ttttaaaatt   3780
attttggatg ccattttcaa aaaagtagag atgaagttgg ttgtgttgct attgttttat   3840
atgatctggc ttcatatgtt cattactttg gtgttctcag ttttgcttta tattgcatta   3900
ttgcacgggg ctcaaatgca gcatatctct atcttctttt tcttgtggcc ttaattattt   3960
tacaaattaa tgaacaggaa ggtggaaaac aacaatttat caggcgatgt gatgtcctta   4020
gccagttgcc tcagtctaaa tatcttgtga gttttcaagt ccatagtaag acaccagtac   4080
aaacaaatgt tttgttaatc taatcaacct catgttagca gaaatgtctc atacaataat   4140
ctgggaggga atattccaac cggcaataat ttctctagat tttcaccaga caggtaagtg   4200
gagctattaa gattttacac aagtcacaag catttattgg tttttaattc tttgcttcta   4260
atttcttcct tttgctatgt ctccgaaaaa gcttcatagg aaatccagat ctgtgtgggt   4320
attggctcac ttctccttgt catgcatctc atccggcaga gcgaggtctg atcaaactgt   4380
aacaatcatt tggcctttac tctattgcat ttttgaagtt ccatttcact ttagacatct   4440
gcaacattta ttaagtgtga tggacagata tattgattaa tgaggaatta tcccttggtt   4500
gagcaaactt aattctgtgt tagcctggta gtagggtgta ccacaaggtt tgtcgtcatg   4560
gtttcctatg ttcacaatcc ctgattgtaa catttagatg tgtacacata tctaattaac   4620
atgaaataat cttcatttgc tggagttaca ttgacgtaaa gatgcgttag ctgtcaaatg   4680
aaactgcatt tgttttattt ccatcatcag tacattaatt aagtgcataa atattttaac   4740
agttgttgaa tgatataaga tgaatttatt ggacaattgc agtttcaatt tctaaagcag   4800
caatacttgg tattgctctg ggtggcttgg tgattcttct gatgatacta gtagcagcat   4860
gccggccaca gaaacctgca cctttcatgg aaggatctat tgataaacca ggtacaatat   4920
tttccggacg gttggatagt gtttggagat gttcatgtca gaaggacagt cgtcagagtt   4980
tattgaagtt gccatgtatt gattgtttaa cgtttttgat gaacagttta ttactcatct   5040
ccaaaacttg tgatccttca tatgaacatg gcacttcatg tttacgagga cattatgagg   5100
atgactgaga acttgagtga gaagtatata attggttgtg gagcatcaag tactgtatat   5160
aaatgtgttt tgaaaaattg caagcctgta gctatcaaga agttgtactc tcacaacccg   5220
caatacttga aggaatttga gactgaactt gagacagttg ggagtattaa gcatcgtaat   5280
cttgtctgtc tccaaggata ttctctttct ccatctggcc atcttctttt ctatgactac   5340
atggaaaatg gtagcctttg ggatttgctt catggttagt aaatccaaaa tggttaaggt   5400
gattgatgca ttgattttgt gttaaagcat caagtaatca gtcctcttgt atcttttttt   5460
gcaggtccta caacaaagaa gaaaaagctt gattgggtta ctcgccttcg aattgcattg   5520
ggatcagctc aagggcttgc atatcttcat catgattgta gccctcgaat aatccaccgt   5580
gatgttaaat catctaatat cttgttggac aaagactttg aggctcatct gactgatttt   5640
ggcatagcta aaagcttatg catatcaaag acctatacgt ccacgtacat tatgggaacc   5700
attggttaca ttgatccaga gtatgctcgc acttctcgct tgacagagaa gtctgatgtt   5760
```

tacagctatg gtattgttct attggaattg ctcactggaa ggaaagctgt agataatgaa 5820
tctaatctac atcatttggt aagctcttgc aatttagtta atatgaactt gtcctatgat 5880
gtttattcat ataattatat taagattcaa ttcaattgat cataacagtt ttgcatatat 5940
gttacagatt ctaactaagg cagcaaacga tgctgtaatg gaaacagtgg atcctgagat 6000
aacatgcaca tgcaaagatc ttgcagatgt gaagaaggtt tttcagcttg cccttctatg 6060
ttccaaaaga cagcctgctg agagaccaac aatgcatgaa gtggcaagag tacttgaaag 6120
cctaataccc gtcgctgaaa cgaaacagcc aaatccaacc ccctcacttg cattactccc 6180
atctgctaag gtaccttgtt acatggatga atatgtcaac ctcaagacac cccacctagt 6240
gaactgttca tccatgagca cttcagatgc ccaacttttc ctcaagtttg gagaggtcat 6300
atcccagaat agtggctga 6319

<210> SEQ ID NO 20
<211> LENGTH: 2968
<212> TYPE: DNA
<213> ORGANISM: Solanum lycopersicum

<400> SEQUENCE: 20
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctt attggacagc tcaaaggcct 300
tgtatctatt gatatgaggg gaaatcgcct ttctggccag ataccagatg agattggtga 360
ctgttcagca ctgaaaaatt tggacctttc cttcaatgag ctttatggtg atattccctt 420
ctccatatct aaactcaagc aactggaata tctgattttg aagaataatc aattgattgg 480
accaattcca tctacattgt cacagatccc taacttgaag gtcttggacc tggctcaaaa 540
taggttaagt ggagaaattc ctaggctgat atactggaac gaagtcctgc agtatctggg 600
actgcgtggt aacaacttgg gtggatccct ttctcctgat atgtgtcagc tcaccggcct 660
gtggtacttt gatgttcgga acaatagttt gactggttcc attcctcaaa atattggcaa 720
ctgtactgcc ttccaggttc tagatttgtc ttataatgat ttgaccggag agattccttt 780
caatattggt ttcctgcaag tagcgacctt gtctttgcaa ggtaatcgtc tttcagggca 840
gatcccttct gtaattggat tgatgcaagc tcttgcagtt ttggacttga gctgcaatat 900
gttgagtgga acaattcctt caattcttgg gaatttgact tacacagaga aattgtatct 960
acacgggaac aagctatctg gttccattcc tccagagctg ggaaatatga caaagctcca 1020
ctacttggaa ttgaatgata accaacttac tggacgcata ccaccagaac ttggaaagct 1080
gacagaattg tttgacttaa atgttgcaaa caaccaccta gatgggccca taccttccaa 1140
tattagctca tgtaccaatt tgaatagtct caacgttcat ggaaacaaat tgaatggtac 1200
tattccacct gcttttcaga agctggaaag tatgacctat cttaatctct cctccaacaa 1260
tctcaaaggc ccaattccaa ttgagctatc tcgtattggg aatgtagata cactggactt 1320
atcaaacaac aggatcagtg gtcctatacc tatgtccctt ggtgatttgg aacatcttct 1380
taaactgaac ttaagcaaga atgaaataaa tggaaactta ccagctgaat ttggcaattt 1440
aaggagcatc atggagattg atctgtcaag caatcacctc tctggtccct tacctcagga 1500
acttggtcag cttccaaacc tgtacttgct gaaggtggaa aacaacaatt tatcaggcga 1560

```
tgtgatgtcc ttagccagtt gcctcagtct aaatatctta aatgtctcat acaataatct   1620

gggagggaat attccaaccg gcaataattt ctctagattt tcaccagaca gcttcatagg   1680

aaatccagat ctgtgtgggt attggctcac ttctccttgt catgcatctc atccggcaga   1740

gcgagtttca atttctaaag cagcaatact tggtattgct ctgggtggct tggtgattct   1800

tctgatgata ctagtagcag catgccggcc acagaaacct gcacctttca tggaaggatc   1860

tattgataaa ccagtttatt actcatctcc aaaacttgtg atccttcata tgaacatggc   1920

acttcatgtt tacgaggaca ttatgaggat gactgagaac ttgagtgaga agtatataat   1980

tggttgtgga gcatcaagta ctgtatataa atgtgttttg aaaaattgca agcctgtagc   2040

tatcaagaag ttgtactctc acaacccgca atacttgaag gaatttgaga ctgaacttga   2100

gacagttggg agtattaagc atcgtaatct tgtctgtctc caaggatatt ctctttctcc   2160

atctggccat cttcttttct atgactacat ggaaaatggt agcctttggg atttgcttca   2220

tggtcctaca acaaagaaga aaaagcttga ttgggttact cgccttcgaa ttgcattggg   2280

atcagctcaa gggcttgcat atcttcatca tgattgtagc cctcgaataa tccaccgtga   2340

tgttaaatca tctaatatct tgttggacaa agactttgag gctcatctga ctgattttgg   2400

catagctaaa agcttatgca tatcaaagac ctatacgtcc acgtacatta tgggaaccat   2460

tggttacatt gatccagagt atgctcgcac ttctcgcttg acagagaagt ctgatgttta   2520

cagctatggt attgttctat tggaattgct cactggaagg aaagctgtag ataatgaatc   2580

taatctacat catttgattc taactaaggc agcaaacgat gctgtaatgg aaacagtgga   2640

tcctgagata acatgcacat gcaaagatct tgcagatgtg aagaaggttt ttcagcttgc   2700

ccttctatgt tccaaaagac agcctgctga gagaccaaca atgcatgaag tggcaagagt   2760

acttgaaagc ctaatacccg tcgctgaaac gaaacagcca aatccaaccc cctcacttgc   2820

attactccca tctgctaagg taccttgtta catggatgaa tatgtcaacc tcaagacacc   2880

ccacctagtg aactgttcat ccatgagcac ttcagatgcc caacttttcc tcaagtttgg   2940

agaggtcata tcccagaata gtggctga                                       2968
```

<210> SEQ ID NO 21
<211> LENGTH: 103
<212> TYPE: PRT
<213> ORGANISM: Solanum lycopersicum

<400> SEQUENCE: 21

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Tyr Trp Thr
                85                  90                  95

Ala Gln Arg Pro Cys Ile Tyr
            100
```

<210> SEQ ID NO 22
<211> LENGTH: 6319
<212> TYPE: DNA
<213> ORGANISM: Solanum lycopersicum

<400> SEQUENCE: 22
atggcatcat ttttactcca aagatgtaat cttctctttg aggttcttct tattttgggg 60
ttcttgattt tcttcagctt tggttctgtg gtgtctgatg atggtgagta gagtagagta 120
gtagaacttt ctgcttctta tgttttagtt taatgttttg tttaagatgt taaaaagaca 180
aagtgtgctt tttttaatca ttttttaaat ggtggttttt gattaatccc acgttttgta 240
gttgttattt gttaaaggtt tatttttttg tctcattatt ataataataa ttgggaaata 300
ggttctgcat tgttggaaat taagaagtca attagggacg tggagaatgt gttgtatgac 360
tggactgatt ctccttcatc tgattactgt gcctggagag gtgttacctg tgataatgtc 420
accttcaatg ttgttcaact gtaagacata actcaaaaac actatcattt gggattcttt 480
agttataaag ttgtaatctt ttgacattat cttgtagtaa tctttcgagt ttaaatcttg 540
atggggagtt gtcttattgg acagctcaaa ggccttgtat ctatgtaata tctcctccca 600
ttatctcaca attacccttt ttgtttgatc ttttgactta gtgcacatta tagactatgc 660
ctgttaattt ttttttgaag tgatatgagg ggaaatcgcc tttctggcca gataccagat 720
gagattggtg actgttcagc actgaaaaat ttgtaagtat gaaatgcttc tgaatcttgt 780
gttattgttt ggaaaaataa gtaaccattt tttcccttag ggacctttcc ttcaatgagc 840
tttatggtga tattcccttc tccatatcta aactcaagca actggaatat ctgtaagttt 900
tgatactctc cttcttctaa atgttgtatt atttgctttc cgagattgtt agttgattat 960
gctcgtctta ttcaacttag gattttgaag aataatcaat tgattggacc aattccatct 1020
acattgtcac agatccctaa cttgaaggtc ttgtaagtat attctctctg ctttgtcatg 1080
atattggtag attatgaata attttagttt gatccaagaa cttcctccag ggacctggct 1140
caaaataggt taagtggaga aattcctagg ctgatatact ggaacgaagt cctgcagtat 1200
ctgtgagtgt tttaatccgg tgttcctctt cttcctgttt gttttaacct taggacactt 1260
tcatttcgta tatggatatg attacatctg ttgtatgttt ttattcatat aggggactgc 1320
gtggtaacaa cttgggtgga tccctttctc ctgatatgtg tcagctcacc ggcctgtggt 1380
acttgtaagt ttgtaatcct gttgctctta agatcttact ttagttcctc taggtgatga 1440
cattaaccat tgttcattgt gttgtacagt gatgttcgga acaatagttt gactggttcc 1500
attcctcaaa atattggcaa ctgtactgcc ttccaggttc tgtaagtatc taaatcaatt 1560
gaatgaagtt tgactatatt ctgtatgttt ggttggcata acaccttgtt ttgttctgtc 1620
agagatttgt cttataatga tttgaccgga gagattcctt tcaatattgg tttcctgcaa 1680
gtagcgacct tgtaagttta tgctgcttct cttcattaca aactattcaa tatatggttg 1740
tttgaagtgt actttcatca ttccaggtct ttgcaaggta atcgtctttc agggcagatc 1800
ccttctgtaa ttggattgat gcaagctctt gcagttttgt gagtgttttg tgtcttgata 1860
tctcaatcta atgctactga atctaattct tggaaaccat tataatgcat ctgttattta 1920
agttttctga ccctttttact gtcagggact tgagctgcaa tatgttgagt ggaacaattc 1980
cttcaattct tgggaatttg acttacacag agaaattgtt agtacttcaa cattattaaa 2040
agcaatttgg atcattttgt gcttcctaaa ttgtgtagtg gatcaattac tgtaagttcg 2100
cattgtattg caggtatcta cacgggaaca agctatctgg ttccattcct ccagagctgg 2160

-continued

```
gaaatatgac aaagctccac tacttgtatg aatgccttct atcaatcatt ttttgttagc   2220
tttgttttgt tcttcctgtt caaacccttt taaatgaatg cttaccattt agaagcattt   2280
gtttgattat ttagcctttg ggcaaccacg gatttgaatg atagaaagct gttatgagaa   2340
tttttattaa gagactttct tcaaccttaa ggctcaaaga tggtaatttg cagggaattg   2400
aatgataacc aacttactgg acgcatacca ccagaacttg gaaagctgac agaattgttt   2460
gacttgtaaa tcccgtttct cttcatcttc tactttggac ttgttaacat cattatttat   2520
ttactcatgt tgtatgtttc agaaatgttg caaacaacca cctagatggg cccatacctt   2580
ccaatattag ctcatgtacc aatttgaata gtctgtgagt gtttttaatg tccgaagtgt   2640
ttcaattatg cacgaccatg cttgtttggt agttattgac acctgatttt gttgcagcaa   2700
cgttcatgga aacaaattga atggtactat tccacctgct tttcagaagc tggaaagtat   2760
gacctatctg taagttctta ctttctgatc tttttctttt gaagaattat gtttaaggtt   2820
atcgaagtta ccgtccatgc tgttgagcaa gattgtaaac ttactgtgcc ttgtatataa   2880
atttactgg cgttgtatta ttgaaaaaat catttttattt atattgctct caaatcatac   2940
tggcttatat ccattcatga agaatcattt ctactgtctg aagttttcag ctatatgtat   3000
cgaaaaaatt tagttattat atagtttatt ttgagcctct gcatcatcta tttgtgaatt   3060
tcatttgctt attctgcata ctctcagcat taaccgtctc ttcttttgtt aattgcttta   3120
gtaatctctc ctccaacaat ctcaaaggcc caattccaat tgagctatct cgtattggga   3180
atgtagatac actgtaagtg caaactttct catctacttt catttctctc attgcaatta   3240
tggttgcggg gaaagcactt tttgtcagtc ttaagaatct tcaacatttt ttggcttagg   3300
gacttatcaa acaacaggat cagtggtcct atacctatgt cccttggtga tttggaacat   3360
cttcttaaac tgtgagcata accgtcaagt tgttatgtta gcatcatata tctgttgtac   3420
ttacatccct tttgtcaatg ctgtaggaac ttaagcaaga atgaaataaa tggaaactta   3480
ccagctgaat ttggcaattt aaggagcatc atggagatgt atggaacctt gctaaattca   3540
gttactttga atttatggtt tgcttgattt tcagcttttt gactgcactc ctaattgtag   3600
tgatctgtca agcaatcacc tctctggtcc cttacctcag gaacttggtc agcttccaaa   3660
cctgtacttg ctgtaagtac ttcagattta ctttgagact ctcatcctct tagctattgg   3720
taataatctg tagagtgaat aagtatgaac ttctaaactc ggtaagtaga ttttaaaatt   3780
attttggatg ccattttcaa aaaagtagag atgaagttgg ttgtgttgct attgttttat   3840
atgatctggc ttcatatgtt cattactttg gtgttctcag ttttgcttta tattgcatta   3900
ttgcacgggg ctcaaatgca gcatatctct atcttctttt tcttgtggcc ttaattattt   3960
tacaaattaa tgaacaggaa ggtggaaaac aacaatttat caggcgatgt gatgtcctta   4020
gccagttgcc tcagtctaaa tatcttgtga gttttcaagt ccatagtaag acaccagtac   4080
aaacaaatgt tttgttaatc taatcaacct catgttagca gaaatgtctc atacaataat   4140
ctgggaggga atattccaac cggcaataat ttctctagat tttcaccaga caggtaagtg   4200
gagctattaa gattttacac aagtcacaag catttattgg tttttaattc tttgcttcta   4260
atttcttcct tttgctatgt ctccgaaaaa gcttcatagg aaatccagat ctgtgtgggt   4320
attggctcac ttctccttgt catgcatctc atccggcaga gcgaggtctg atcaaactgt   4380
aacaatcatt tggcctttac tctattgcat ttttgaagtt ccatttcact ttagacatct   4440
gcaacattta ttaagtgtga tggacagata tattgattaa tgaggaatta tcccttggtt   4500
gagcaaactt aattctgtgt tagcctggta gtagggtgta ccacaaggtt tgtcgtcatg   4560
```

gtttcctatg ttcacaatcc ctgattgtaa catttagatg tgtacacata tctaattaac 4620
atgaaataat cttcatttgc tggagttaca ttgacgtaaa gatgcgttag ctgtcaaatg 4680
aaactgcatt tgttttattt ccatcatcag tacattaatt aagtgcataa atattttaac 4740
agttgttgaa tgatataaga tgaatttatt ggacaattgc agtttcaatt tctaaagcag 4800
caatacttgg tattgctctg ggtggcttgg tgattcttct gatgatacta gtagcagcat 4860
gccggccaca gaaacctgca cctttcatgg aaggatctat tgataaacca ggtacaatat 4920
tttccggacg gttggatagt gtttggagat gttcatgtca gaaggacagt cgtcagagtt 4980
tattgaagtt gccatgtatt gattgtttaa cgtttttgat gaacagttta ttactcatct 5040
ccaaaacttg tgatccttca tatgaacatg gcacttcatg tttacgagga cattatgagg 5100
atgactgaga acttgagtga gaagtatata attggttgtg gagcatcaag tactgtatat 5160
aaatgtgttt tgaaaaattg caagcctgta gctatcaaga agttgtactc tcacaacccg 5220
caatacttga aggaatttga gactgaactt gagacagttg ggagtattaa gcatcgtaat 5280
cttgtctgtc tccaaggata ttctctttct ccatctggcc atcttctttt ctatgactac 5340
atggaaaatg gtagcctttg ggatttgctt catggttagt aaatccaaaa tggttaaggt 5400
gattgatgca ttgattttgt gttaaagcat caagtaatca gtcctcttgt atcttttttt 5460
gcaggtccta caacaaagaa gaaaaagctt gattgggtta ctcgccttcg aattgcattg 5520
ggatcagctc aagggcttgc atatcttcat catgattgta gccctcgaat aatccaccgt 5580
gatgttaaat catctaatat cttgttggac aaagactttg aggctcatct gactgatttt 5640
ggcatagcta aaagcttatg catatcaaag acctatacgt ccacgtacat tatgggaacc 5700
attggttaca ttgatccaga gtatgctcgc acttctcgct tgacagagaa gtctgatgtt 5760
tacagctatg gtattgttct attggaattg ctcactggaa ggaaagctgt agataatgaa 5820
tctaatctac atcatttggt aagctcttgc aatttagtta atatgaactt gtcctatgat 5880
gtttattcat ataattatat taagattcaa ttcaattgat cataacagtt ttgcatatat 5940
gttacagatt ctaactaagg cagcaaacga tgctgtaatg gaaacagtgg atcctgagat 6000
aacatgcaca tgcaaagatc ttgcagatgt gaagaaggtt tttcagcttg cccttctatg 6060
ttccaaaaga cagcctgctg agagaccaac aatgcatgaa gtggcaagag tacttgaaag 6120
cctaataccc gtcgctgaaa cgaaacagcc aaatccaacc ccctcacttg cattactccc 6180
atctgctaag gtaccttgtt acatggatga atatgtcaac ctcaagacac cccacctagt 6240
gaactgttca tccatgagca cttcagatgc ccaacttttc ctcaagtttg gagaggtcat 6300
atcccagaat agtggctga 6319

<210> SEQ ID NO 23
<211> LENGTH: 2968
<212> TYPE: DNA
<213> ORGANISM: Solanum lycopersicum

<400> SEQUENCE: 23
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctt attggacagc tcaaaggcct 300

-continued

```
tgtatctatt gatatgaggg gaaatcgcct ttctggccag ataccagatg agattggtga    360
ctgttcagca ctgaaaaatt tggacctttc cttcaatgag ctttatggtg atattccctt    420
ctccatatct aaactcaagc aactggaata tctgattttg aagaataatc aattgattgg    480
accaattcca tctacattgt cacagatccc taacttgaag gtcttggacc tggctcaaaa    540
taggttaagt ggagaaattc ctaggctgat atactggaac gaagtcctgc agtatctggg    600
actgcgtggt aacaacttgg gtggatccct ttctcctgat atgtgtcagc tcaccggcct    660
gtggtacttt gatgttcgga acaatagttt gactggttcc attcctcaaa atattggcaa    720
ctgtactgcc ttccaggttc tagatttgtc ttataatgat ttgaccggag agattccttt    780
caatattggt ttcctgcaag tagcgacctt gtctttgcaa ggtaatcgtc tttcagggca    840
gatcccttct gtaattggat tgatgcaagc tcttgcagtt ttggacttga gctgcaatat    900
gttgagtgga acaattcctt caattcttgg gaatttgact tacacagaga aattgtatct    960
acacgggaac aagctatctg gttccattcc tccagagctg ggaaatatga caaagctcca   1020
ctacttggaa ttgaatgata accaacttac tggacgcata ccaccagaac ttggaaagct   1080
gacagaattg tttgacttaa atgttgcaaa caaccaccta gatgggccca taccttccaa   1140
tattagctca tgtaccaatt tgaatagtct caacgttcat ggaaacaaat tgaatggtac   1200
tattccacct gcttttcaga agctggaaag tatgacctat cttaatctct cctccaacaa   1260
tctcaaaggc ccaattccaa ttgagctatc tcgtattggg aatgtagata cactggactt   1320
atcaaacaac aggatcagtg gtcctatacc tatgtccctt ggtgatttgg aacatcttct   1380
taaactgaac ttaagcaaga atgaaataaa tggaaactta ccagctgaat ttggcaattt   1440
aaggagcatc atggagattg atctgtcaag caatcacctc tctggtccct tacctcagga   1500
acttggtcag cttccaaacc tgtacttgct gaaggtggaa aacaacaatt tatcaggcga   1560
tgtgatgtcc ttagccagtt gcctcagtct aaatatctta aatgtctcat acaataatct   1620
gggagggaat attccaaccg gcaataattt ctctagattt tcaccagaca gcttcatagg   1680
aaatccagat ctgtgtgggt attggctcac ttctccttgt catgcatctc atccggcaga   1740
gcgagtttca atttctaaag cagcaatact tggtattgct ctgggtggct tggtgattct   1800
tctgatgata ctagtagcag catgccggcc acagaaacct gcacctttca tggaaggatc   1860
tattgataaa ccagtttatt actcatctcc aaaacttgtg atccttcata tgaacatggc   1920
acttcatgtt tacgaggaca ttatgaggat gactgagaac ttgagtgaga agtatataat   1980
tggttgtgga gcatcaagta ctgtatataa atgtgttttg aaaaattgca agcctgtagc   2040
tatcaagaag ttgtactctc acaacccgca atacttgaag gaatttgaga ctgaacttga   2100
gacagttggg agtattaagc atcgtaatct tgtctgtctc caaggatatt ctctttctcc   2160
atctggccat cttcttttct atgactacat ggaaaatggt agcctttggg atttgcttca   2220
tggtcctaca acaaagaaga aaaagcttga ttgggttact cgccttcgaa ttgcattggg   2280
atcagctcaa gggcttgcat atcttcatca tgattgtagc cctcgaataa tccaccgtga   2340
tgttaaatca tctaatatct tgttggacaa agactttgag gctcatctga ctgattttgg   2400
catagctaaa agcttatgca tatcaaagac ctatacgtcc acgtacatta tgggaaccat   2460
tggttacatt gatccagagt atgctcgcac ttctcgcttg acagagaagt ctgatgttta   2520
cagctatggt attgttctat tggaattgct cactggaagg aaagctgtag ataatgaatc   2580
taatctacat catttgattc taactaaggc agcaaacgat gctgtaatgg aaacagtgga   2640
tcctgagata acatgcacat gcaaagatct tgcagatgtg aagaaggttt ttcagcttgc   2700
```

```
ccttctatgt tccaaaagac agcctgctga gagaccaaca atgcatgaag tggcaagagt   2760

acttgaaagc ctaataccccg tcgctgaaac gaaacagcca aatccaaccc cctcacttgc   2820

attactccca tctgctaagg taccttgtta catggatgaa tatgtcaacc tcaagacacc   2880

ccacctagtg aactgttcat ccatgagcac ttcagatgcc caacttttcc tcaagtttgg   2940

agaggtcata tcccagaata gtggctga                                      2968
```

<210> SEQ ID NO 24
<211> LENGTH: 103
<212> TYPE: PRT
<213> ORGANISM: Solanum lycopersicum

<400> SEQUENCE: 24

```
Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Tyr Trp Thr
                85                  90                  95

Ala Gln Arg Pro Cys Ile Tyr
            100
```

<210> SEQ ID NO 25
<211> LENGTH: 7278
<212> TYPE: DNA
<213> ORGANISM: Solanum lycopersicum

<400> SEQUENCE: 25

```
ttttcgagtt gacatagtac cttcgcagtt gaagaagaag aaattgatta agaagataaa     60

ttcgacattg gaacttgata attaagaaga aatcaatgaa aaagagatat aatataatga    120

ggtaaagaaa ataaataatg atgaagagaa acaaaagagg agaaataatg gaagaatggg    180

agaaattagg gttaaaaggg ggaagaagat cgttggtggg tggttcaaga tccacatgtg    240

cgcttttaaa gagtttgcac gcgcttaaag gacgtgagat cacgtttggc tccacatcag    300

ccaagaatat ttaaaaggat caaattatag ggggttaaag gatttaatag gaatcttggt    360

tagttaaggt atctggggga aaagcgcgaa caactttagg gacctgcata tgtatttggc    420

caagaaaaaa taaacaaata atgagagaaa gagtgaatat atgtgtatgg actagcaata    480

aaagtggcac tagtaattga aaagcaagtg tatagagaga gataatgaga gagaaagagt    540

aagtacacta ctactgctac tatcccatat acctgtaatg ttgcaggtct gaattttgca    600

gttgcagacc cccttctctt ggcacaagct cttttaactt ttatcttctc aaataattct    660

ctctctctct cttttctatc attttttttt acattgagag taaacttaat atccgttgta    720

tgtattagtg tgaggcctat ctgccacaag gatgtgatgg aacactatgc ttcctctgct    780

aaaaccccac aaccccaaaa ctctctttca cttcacattt aagcacaatt cctcagtaaa    840

attatccttt tgatctctct aacatcaatg ttggttagtt caagaattgg tttttccatt    900

tcaaaggagc tgagttagtg aggttttgag ttttgactga gacttgagtc taccatggca    960
```

```
tcatttttac tccaaagatg taatcttctc tttgaggttc ttcttatttt ggggttcttg   1020
attttcttca gctttggttc tgtggtgtct gatgatggtg agtagagtag agtagtagaa   1080
ctttctgctt cttatgtttt agtttaatgt tttgtttaag atgttaaaaa gacaaagtgt   1140
gcttttttta atcatttttt aaatggtggt ttttgattaa tcccacgttt tgtagttgtt   1200
atttgttaaa ggtttatttt tttgtctcat tattataata ataattggga aataggttct   1260
gcattgttgg aaattaagaa gtcaattagg gacgtggaga atgtgttgta tgactggact   1320
gattctcctt catctgatta ctgtgcctgg agaggtgtta cctgtgataa tgtcaccttc   1380
aatgttgttc aactgtaaga cataactcaa aaacactatc atttgggatt ctttagttat   1440
aaagttgtaa tcttttgaca ttatcttgta gtaatctttc gagtttaaat cttgatgggg   1500
agttgtctcc tgctattgga cagctcaaag gccttgtatc tatgtaatat ctcctcccat   1560
tatctcacaa ttaccctttt tgtttgatct tttgacttag tgcacattat agactatgcc   1620
tgttaatttt tttttgaagt gatatgaggg gaaatcgcct ttctggccag ataccagatg   1680
agattggtga ctgttcagca ctgaaaaatt tgtaagtatg aaatgcttct gaatcttgtg   1740
ttattgtttg gaaaaataag taaccatttt ttcccttagg gacctttcct tcaatgagct   1800
ttatggtgat attcccttct ccatatctaa actcaagcaa ctggaatatc tgtaagtttt   1860
gatactctcc ttcttctaaa tgttgtatta tttgctttcc gagattgtta gttgattatg   1920
ctcgtcttat tcaacttagg attttgaaga ataatcaatt gattggacca attccatcta   1980
cattgtcaca gatccctaac ttgaaggtct tgtaagtata ttctctctgc tttgtcatga   2040
tattggtaga ttatgaataa ttttagtttg atccaagaac ttcctccagg gacctggctc   2100
aaaataggtt aagtggagaa attcctaggc tgatatactg gaacgaagtc ctgcagtatc   2160
tgtgagtgtt ttaatccggt gttcctcttc ttcctgtttg ttttaacctt aggacacttt   2220
catttcgtat atggatatga ttacatctgt tgtatgtttt tattcatata ggggactgcg   2280
tggtaacaac ttgggtggat ccctttctcc tgatatgtgt cagctcaccg gcctgtggta   2340
cttgtaagtt tgtaatcctg ttgctcttaa gatcttactt tagttcctct aggtgatgac   2400
attaaccatt gttcattgtg ttgtacagtg atgttcggaa caatagtttg actggttcca   2460
ttcctcaaaa tattggcaac tgtactgcct tccaggttct gtaagtatct aaatcaattg   2520
aatgaagttt gactatattc tgtatgtttg gttggcataa caccttgttt tgttctgtca   2580
gagatttgtc ttataatgat ttgaccggag agattccttt caatattggt ttcctgcaag   2640
tagcgacctt gtaagtttat gctgcttctc ttcattacaa actattcaat atatggttgt   2700
ttgaagtgta ctttcatcat tccaggtctt tgcaaggtaa tcgtctttca gggcagatcc   2760
cttctgtaat tggattgatg caagctcttg cagttttgtg agtgttttgt gtcttgatat   2820
ctcaatctaa tgctactgaa tctaattctt ggaaaccatt ataatgcatc tgttatttaa   2880
gttttctgac ccttttactg tcagggactt gagctgcaat atgttgagtg gaacaattcc   2940
ttcaattctt gggaatttga cttacacaga gaaattgtta gtacttcaac attattaaaa   3000
gcaatttgga tcattttgtg cttcctaaat tgtgtagtgg atcaattact gtaagttcgc   3060
attgtattgc aggtatctac acgggaacaa gctatctggt tccattcctc cagagctggg   3120
aaatatgaca aagctccact acttgtatga atgccttcta tcaatcattt tttgttagct   3180
ttgttttgtt cttcctgttc aaaccctttt aaatgaatgc ttaccattta gaagcatttg   3240
tttgattatt tagcctttgg gcaaccacgg atttgaatga tagaaagctg ttatgagaat   3300
```

-continued

```
ttttattaag agactttctt caaccttaag gctcaaagat ggtaatttgc agggaattga   3360
atgataacca acttactgga cgcataccac cagaacttgg aaagctgaca gaattgtttg   3420
acttgtaaat cccgtttctc ttcatcttct actttggact tgttaacatc attatttatt   3480
tactcatgtt gtatgtttca gaaatgttgc aaacaaccac ctagatgggc ccataccttc   3540
caatattagc tcatgtacca atttgaatag tctgtgagtg tttttaatgt ccgaagtgtt   3600
tcaattatgc acgaccatgc ttgtttggta gttattgaca cctgattttg ttgcagcaac   3660
gttcatggaa acaaattgaa tggtactatt ccacctgctt ttcagaagct ggaaagtatg   3720
acctatctgt aagttcttac tttctgatct ttttcttttg aagaattatg tttaaggtta   3780
tcgaagttac cgtccatgct gttgagcaag attgtaaact tactgtgcct tgtatataaa   3840
ttttactggc gttgtattat tgaaaaaatc attttattta tattgctctc aaatcatact   3900
ggcttatatc cattcatgaa gaatcatttc tactgtctga agttttcagc tatatgtatc   3960
gaaaaaattt agttattata tagtttattt tgagcctctg catcatctat ttgtgaattt   4020
catttgctta ttctgcatac tctcagcatt aaccgtctct tcttttgtta attgctttag   4080
taatctctcc tccaacaatc tcaaaggccc aattccaatt gagctatctc gtattgggaa   4140
tgtagataca ctgtaagtgc aaactttctc atctactttc atttctctca ttgcaattat   4200
ggttgcgggg aaagcacttt ttgtcagtct taagaatctt caacattttt tggcttaggg   4260
acttatcaaa caacaggatc agtggtccta tacctatgtc ccttggtgat ttggaacatc   4320
ttcttaaact gtgagcataa ccgtcaagtt gttatgttag catcatatat ctgttgtact   4380
tacatccctt ttgtcaatgc tgtaggaact taagcaagaa tgaaataaat ggaaacttac   4440
cagctgaatt tggcaattta aggagcatca tggagatgta tggaaccttg ctaaattcag   4500
ttactttgaa tttatggttt gcttgatttt cagctttttg actgcactcc taattgtagt   4560
gatctgtcaa gcaatcacct ctctggtccc ttacctcagg aacttggtca gcttccaaac   4620
ctgtacttgc tgtaagtact tcagatttac tttgagactc tcatcctctt agctattggt   4680
aataatctgt agagtgaata agtatgaact tctaaactcg gtaagtagat tttaaaatta   4740
ttttggatgc cattttcaaa aaagtagaga tgaagttggt tgtgttgcta ttgttttata   4800
tgatctggct tcatatgttc attactttgg tgttctcagt tttgctttat attgcattat   4860
tgcacggggc tcaaatgcag catatctcta tcttcttttt cttgtggcct taattatttt   4920
acaaattaat gaacaggaag gtggaaaaca acaatttatc aggcgatgtg atgtccttag   4980
ccagttgcct cagtctaaat atcttgtgag ttttcaagtc catagtaaga caccagtaca   5040
aacaaatgtt ttgttaatct aatcaacctc atgttagcag aaatgtctca tacaataatc   5100
tgggagggaa tattccaacc ggcaataatt tctctagatt ttcaccagac aggtaagtgg   5160
agctattaag attttacaca agtcacaagc atttattggt ttttaattct ttgcttctaa   5220
tttcttcctt ttgctatgtc tccgaaaaag cttcatagga aatccagatc tgtgtgggta   5280
ttggctcact tctccttgtc atgcatctca tccggcagag cgaggtctga tcaaactgta   5340
acaatcattt ggcctttact ctattgcatt tttgaagttc catttcactt tagacatctg   5400
caacatttat taagtgtgat ggacagatat attgattaat gaggaattat cccttggttg   5460
agcaaactta attctgtgtt agcctggtag tagggtgtac cacaaggttt gtcgtcatgg   5520
tttcctatgt tcacaatccc tgattgtaac atttagatgt gtacacatat ctaattaaca   5580
tgaaataatc ttcatttgct ggagttacat tgacgtaaag atgcgttagc tgtcaaatga   5640
aactgcattt gttttatttc catcatcagt acattaatta agtgcataaa tattttaaca   5700
```

-continued

```
gttgttgaat gatataagat gaatttattg gacaattgca gtttcaattt ctaaagcagc    5760

aatacttggt attgctctgg gtggcttggt gattcttctg atgatactag tagcagcatg    5820

ccggccacag aaacctgcac ctttcatgga aggatctatt gataaaccag gtacaatatt    5880

ttccggacgg ttggatagtg tttggagatg ttcatgtcag aaggacagtc gtcagagttt    5940

attgaagttg ccatgtattg attgtttaac gtttttgatg aacagtttat tactcatctc    6000

caaaacttgt gatccttcat atgaacatgg cacttcatgt ttacgaggac attatgagga    6060

tgactgagaa cttgagtgag aagtatataa ttggttgtgg agcatcaagt actgtatata    6120

aatgtgtttt gaaaaattgc aagcctgtag ctatcaagaa gttgtactct cacaacccgc    6180

aatacttgaa ggaatttgag actgaacttg agacagttgg gagtattaag catcgtaatc    6240

ttgtctgtct ccaaggatat tctctttctc catctggcca tcttcttttc tatgactaca    6300

tggaaaatgg tagcctttgg gatttgcttc atggttagta aatccaaaat ggttaaggtg    6360

attgatgcat tgattttgtg ttaaagcatc aagtaatcag tcctcttgta tctttttttg    6420

caggtcctac aacaaagaag aaaaagcttg attgggttac tcgccttcga attgcattgg    6480

gatcagctca agggcttgca tatcttcatc atgattgtag ccctcgaata atccaccgtg    6540

atgttaaatc atctaatatc ttgttggaca aagactttga ggctcatctg actgattttg    6600

gcatagctaa aagcttatgc atatcaaaga cctatacgtc cacgtacatt atgggaacca    6660

ttggttacat tgatccagag tatgctcgca cttctcgctt gacagagaag tctgatgttt    6720

acagctatgg tattgttcta ttggaattgc tcactggaag gaaagctgta gataatgaat    6780

ctaatctaca tcatttggta agctcttgca atttagttaa tatgaacttg tcctatgatg    6840

tttattcata taattatatt aagattcaat tcaattgatc ataacagttt tgcatatatg    6900

ttacagattc taactaaggc agcaaacgat gctgtaatgg aaacagtgga tcctgagata    6960

acatgcacat gcaaagatct tgcagatgtg aagaaggttt ttcagcttgc ccttctatgt    7020

tccaaaagac agcctgctga gagaccaaca atgcatgaag tggcaagagt acttgaaagc    7080

ctaatacccg tcgctgaaac gaaacagcca aatccaaccc cctcacttgc attactccca    7140

tctgctaagg taccttgtta catggatgaa tatgtcaacc tcaagacacc ccacctagtg    7200

aactgttcat ccatgagcac ttcagatgcc caacttttcc tcaagtttgg agaggtcata    7260

tcccagaata gtggctga                                                  7278
```

<210> SEQ ID NO 26
<211> LENGTH: 2973
<212> TYPE: DNA
<213> ORGANISM: Solanum lycopersicum

<400> SEQUENCE: 26

```
atggcatcat ttttactcca aagatgtaat cttctctttg aggttcttct tattttgggg      60

ttcttgattt tcttcagctt tggttctgtg gtgtctgatg atggttctgc attgttggaa     120

attaagaagt caattaggga cgtggagaat gtgttgtatg actggactga ttctccttca     180

tctgattact gtgcctggag aggtgttacc tgtgataatg tcaccttcaa tgttgttcaa     240

cttaatcttt cgagtttaaa tcttgatggg gagttgtctc ctgctattgg acagctcaaa     300

ggccttgtat ctattgatat gaggggaaat cgcctttctg gccagatacc agatgagatt     360

ggtgactgtt cagcactgaa aaatttggac ctttccttca atgagcttta tggtgatatt     420

cccttctcca tatctaaact caagcaactg gaatatctga ttttgaagaa taatcaattg     480
```

-continued

```
attggaccaa ttccatctac attgtcacag atccctaact tgaaggtctt ggacctggct    540
caaaataggt taagtggaga aattcctagg ctgatatact ggaacgaagt cctgcagtat    600
ctgggactgc gtggtaacaa cttgggtgga tccctttctc ctgatatgtg tcagctcacc    660
ggcctgtggt actttgatgt tcggaacaat agtttgactg gttccattcc tcaaaatatt    720
ggcaactgta ctgccttcca ggttctagat ttgtcttata atgatttgac cggagagatt    780
cctttcaata ttggtttcct gcaagtagcg accttgtctt tgcaaggtaa tcgtctttca    840
gggcagatcc cttctgtaat tggattgatg caagctcttg cagttttgga cttgagctgc    900
aatatgttga gtggaacaat tccttcaatt cttgggaatt tgacttacac agagaaattg    960
tatctacacg ggaacaagct atctggttcc attcctccag agctgggaaa tatgacaaag   1020
ctccactact tggaattgaa tgataaccaa cttactggac gcataccacc agaacttgga   1080
aagctgacag aattgtttga cttaaatgtt gcaaacaacc acctagatgg gcccatacct   1140
tccaatatta gctcatgtac caatttgaat agtctcaacg ttcatggaaa caaattgaat   1200
ggtactattc cacctgcttt tcagaagctg gaaagtatga cctatcttaa tctctcctcc   1260
aacaatctca aaggcccaat tccaattgag ctatctcgta ttgggaatgt agatacactg   1320
gacttatcaa acaacaggat cagtggtcct atacctatgt cccttggtga tttggaacat   1380
cttcttaaac tgaacttaag caagaatgaa ataaatggaa acttaccagc tgaatttggc   1440
aatttaagga gcatcatgga gattgatctg tcaagcaatc acctctctgg tcccttacct   1500
caggaacttg gtcagcttcc aaacctgtac ttgctgaagg tggaaaacaa caatttatca   1560
ggcgatgtga tgtccttagc cagttgcctc agtctaaata tcttaaatgt ctcatacaat   1620
aatctgggag ggaatattcc aaccggcaat aatttctcta gattttcacc agacagcttc   1680
ataggaaatc cagatctgtg tgggtattgg ctcacttctc cttgtcatgc atctcatccg   1740
gcagagcgag tttcaatttc taaagcagca atacttggta ttgctctggg tggcttggtg   1800
attcttctga tgatactagt agcagcatgc cggccacaga aacctgcacc tttcatggaa   1860
ggatctattg ataaaccagt ttattactca tctccaaaac ttgtgatcct tcatatgaac   1920
atggcacttc atgtttacga ggacattatg aggatgactg agaacttgag tgagaagtat   1980
ataattggtt gtggagcatc aagtactgta tataaatgtg ttttgaaaaa ttgcaagcct   2040
gtagctatca agaagttgta ctctcacaac ccgcaatact tgaaggaatt tgagactgaa   2100
cttgagacag ttgggagtat taagcatcgt aatcttgtct gtctccaagg atattctctt   2160
tctccatctg gccatcttct tttctatgac tacatggaaa atggtagcct ttgggatttg   2220
cttcatggtc ctacaacaaa gaagaaaaag cttgattggg ttactcgcct tcgaattgca   2280
ttgggatcag ctcaagggct tgcatatctt catcatgatt gtagccctcg aataatccac   2340
cgtgatgtta aatcatctaa tatcttgttg gacaaagact ttgaggctca tctgactgat   2400
tttggcatag ctaaaagctt atgcatatca aagacctata cgtccacgta cattatggga   2460
accattggtt acattgatcc agagtatgct cgcacttctc gcttgacaga gaagtctgat   2520
gtttacagct atggtattgt tctattggaa ttgctcactg gaaggaaagc tgtagataat   2580
gaatctaatc tacatcattt gattctaact aaggcagcaa acgatgctgt aatggaaaca   2640
gtggatcctg agataacatg cacatgcaaa gatcttgcag atgtgaagaa ggtttttcag   2700
cttgcccttc tatgttccaa aagacagcct gctgagagac caacaatgca tgaagtggca   2760
agagtacttg aaagcctaat acccgtcgct gaaacgaaac agccaaatcc aacccccctca   2820
cttgcattac tcccatctgc taaggtacct tgttacatgg atgaatatgt caacctcaag   2880
```

acaccccacc tagtgaactg ttcatccatg agcacttcag atgcccaact tttcctcaag 2940
tttggagagg tcatatccca gaatagtggc tga 2973

<210> SEQ ID NO 27
<211> LENGTH: 990
<212> TYPE: PRT
<213> ORGANISM: Solanum lycopersicum

<400> SEQUENCE: 27

Met Ala Ser Phe Leu Leu Gln Arg Cys Asn Leu Leu Phe Glu Val Leu
1 5 10 15

Leu Ile Leu Gly Phe Leu Ile Phe Phe Ser Phe Gly Ser Val Val Ser
20 25 30

Asp Asp Gly Ser Ala Leu Leu Glu Ile Lys Lys Ser Ile Arg Asp Val
35 40 45

Glu Asn Val Leu Tyr Asp Trp Thr Asp Ser Pro Ser Ser Asp Tyr Cys
50 55 60

Ala Trp Arg Gly Val Thr Cys Asp Asn Val Thr Phe Asn Val Val Gln
65 70 75 80

Leu Asn Leu Ser Ser Leu Asn Leu Asp Gly Glu Leu Ser Pro Ala Ile
85 90 95

Gly Gln Leu Lys Gly Leu Val Ser Ile Asp Met Arg Gly Asn Arg Leu
100 105 110

Ser Gly Gln Ile Pro Asp Glu Ile Gly Asp Cys Ser Ala Leu Lys Asn
115 120 125

Leu Asp Leu Ser Phe Asn Glu Leu Tyr Gly Asp Ile Pro Phe Ser Ile
130 135 140

Ser Lys Leu Lys Gln Leu Glu Tyr Leu Ile Leu Lys Asn Asn Gln Leu
145 150 155 160

Ile Gly Pro Ile Pro Ser Thr Leu Ser Gln Ile Pro Asn Leu Lys Val
165 170 175

Leu Asp Leu Ala Gln Asn Arg Leu Ser Gly Glu Ile Pro Arg Leu Ile
180 185 190

Tyr Trp Asn Glu Val Leu Gln Tyr Leu Gly Leu Arg Gly Asn Asn Leu
195 200 205

Gly Gly Ser Leu Ser Pro Asp Met Cys Gln Leu Thr Gly Leu Trp Tyr
210 215 220

Phe Asp Val Arg Asn Asn Ser Leu Thr Gly Ser Ile Pro Gln Asn Ile
225 230 235 240

Gly Asn Cys Thr Ala Phe Gln Val Leu Asp Leu Ser Tyr Asn Asp Leu
245 250 255

Thr Gly Glu Ile Pro Phe Asn Ile Gly Phe Leu Gln Val Ala Thr Leu
260 265 270

Ser Leu Gln Gly Asn Arg Leu Ser Gly Gln Ile Pro Ser Val Ile Gly
275 280 285

Leu Met Gln Ala Leu Ala Val Leu Asp Leu Ser Cys Asn Met Leu Ser
290 295 300

Gly Thr Ile Pro Ser Ile Leu Gly Asn Leu Thr Tyr Thr Glu Lys Leu
305 310 315 320

Tyr Leu His Gly Asn Lys Leu Ser Gly Ser Ile Pro Pro Glu Leu Gly
325 330 335

Asn Met Thr Lys Leu His Tyr Leu Glu Leu Asn Asp Asn Gln Leu Thr
340 345 350

-continued

```
Gly Arg Ile Pro Pro Glu Leu Gly Lys Leu Thr Glu Leu Phe Asp Leu
        355                 360                 365

Asn Val Ala Asn Asn His Leu Asp Gly Pro Ile Pro Ser Asn Ile Ser
    370                 375                 380

Ser Cys Thr Asn Leu Asn Ser Leu Asn Val His Gly Asn Lys Leu Asn
385                 390                 395                 400

Gly Thr Ile Pro Pro Ala Phe Gln Lys Leu Glu Ser Met Thr Tyr Leu
                405                 410                 415

Asn Leu Ser Ser Asn Asn Leu Lys Gly Pro Ile Pro Ile Glu Leu Ser
            420                 425                 430

Arg Ile Gly Asn Val Asp Thr Leu Asp Leu Ser Asn Asn Arg Ile Ser
        435                 440                 445

Gly Pro Ile Pro Met Ser Leu Gly Asp Leu Glu His Leu Leu Lys Leu
    450                 455                 460

Asn Leu Ser Lys Asn Glu Ile Asn Gly Asn Leu Pro Ala Glu Phe Gly
465                 470                 475                 480

Asn Leu Arg Ser Ile Met Glu Ile Asp Leu Ser Ser Asn His Leu Ser
                485                 490                 495

Gly Pro Leu Pro Gln Glu Leu Gly Gln Leu Pro Asn Leu Tyr Leu Leu
            500                 505                 510

Lys Val Glu Asn Asn Asn Leu Ser Gly Asp Val Met Ser Leu Ala Ser
        515                 520                 525

Cys Leu Ser Leu Asn Ile Leu Asn Val Ser Tyr Asn Asn Leu Gly Gly
    530                 535                 540

Asn Ile Pro Thr Gly Asn Asn Phe Ser Arg Phe Ser Pro Asp Ser Phe
545                 550                 555                 560

Ile Gly Asn Pro Asp Leu Cys Gly Tyr Trp Leu Thr Ser Pro Cys His
                565                 570                 575

Ala Ser His Pro Ala Glu Arg Val Ser Ile Ser Lys Ala Ala Ile Leu
            580                 585                 590

Gly Ile Ala Leu Gly Gly Leu Val Ile Leu Leu Met Ile Leu Val Ala
        595                 600                 605

Ala Cys Arg Pro Gln Lys Pro Ala Pro Phe Met Glu Gly Ser Ile Asp
    610                 615                 620

Lys Pro Val Tyr Tyr Ser Ser Pro Lys Leu Val Ile Leu His Met Asn
625                 630                 635                 640

Met Ala Leu His Val Tyr Glu Asp Ile Met Arg Met Thr Glu Asn Leu
                645                 650                 655

Ser Glu Lys Tyr Ile Ile Gly Cys Gly Ala Ser Ser Thr Val Tyr Lys
            660                 665                 670

Cys Val Leu Lys Asn Cys Lys Pro Val Ala Ile Lys Lys Leu Tyr Ser
        675                 680                 685

His Asn Pro Gln Tyr Leu Lys Glu Phe Glu Thr Glu Leu Glu Thr Val
    690                 695                 700

Gly Ser Ile Lys His Arg Asn Leu Val Cys Leu Gln Gly Tyr Ser Leu
705                 710                 715                 720

Ser Pro Ser Gly His Leu Leu Phe Tyr Asp Tyr Met Glu Asn Gly Ser
                725                 730                 735

Leu Trp Asp Leu Leu His Gly Pro Thr Thr Lys Lys Lys Lys Leu Asp
            740                 745                 750

Trp Val Thr Arg Leu Arg Ile Ala Leu Gly Ser Ala Gln Gly Leu Ala
        755                 760                 765

Tyr Leu His His Asp Cys Ser Pro Arg Ile Ile His Arg Asp Val Lys
```

-continued

```
    770                 775                 780

Ser Ser Asn Ile Leu Leu Asp Lys Asp Phe Glu Ala His Leu Thr Asp
785                 790                 795                 800

Phe Gly Ile Ala Lys Ser Leu Cys Ile Ser Lys Thr Tyr Thr Ser Thr
                805                 810                 815

Tyr Ile Met Gly Thr Ile Gly Tyr Ile Asp Pro Glu Tyr Ala Arg Thr
            820                 825                 830

Ser Arg Leu Thr Glu Lys Ser Asp Val Tyr Ser Tyr Gly Ile Val Leu
        835                 840                 845

Leu Glu Leu Leu Thr Gly Arg Lys Ala Val Asp Asn Glu Ser Asn Leu
    850                 855                 860

His His Leu Ile Leu Thr Lys Ala Ala Asn Asp Ala Val Met Glu Thr
865                 870                 875                 880

Val Asp Pro Glu Ile Thr Cys Thr Cys Lys Asp Leu Ala Asp Val Lys
                885                 890                 895

Lys Val Phe Gln Leu Ala Leu Leu Cys Ser Lys Arg Gln Pro Ala Glu
            900                 905                 910

Arg Pro Thr Met His Glu Val Ala Arg Val Leu Glu Ser Leu Ile Pro
        915                 920                 925

Val Ala Glu Thr Lys Gln Pro Asn Pro Thr Pro Ser Leu Ala Leu Leu
    930                 935                 940

Pro Ser Ala Lys Val Pro Cys Tyr Met Asp Glu Tyr Val Asn Leu Lys
945                 950                 955                 960

Thr Pro His Leu Val Asn Cys Ser Ser Met Ser Thr Ser Asp Ala Gln
                965                 970                 975

Leu Phe Leu Lys Phe Gly Glu Val Ile Ser Gln Asn Ser Gly
            980                 985                 990
```

<210> SEQ ID NO 28
<211> LENGTH: 8295
<212> TYPE: DNA
<213> ORGANISM: Solanum lycopersicum

<400> SEQUENCE: 28

```
ttttcgagtt gacatagtac cttcgcagtt gaagaagaag aaattgatta agaagataaa     60

ttcgacattg gaacttgata attaagaaga aatcaatgaa aaagagatat aatataatga    120

ggtaaagaaa ataaataatg atgaagagaa acaaaagagg agaaataatg gaagaatggg    180

agaaattagg gttaaaaggg ggaagaagat cgttggtggg tggttcaaga tccacatgtg    240

cgcttttaaa gagtttgcac gcgcttaaag gacgtgagat cacgtttggc tccacatcag    300

ccaagaatat ttaaaaggat caaattatag ggggttaaag gatttaatag gaatcttggt    360

tagttaaggt atctggggga aaagcgcgaa caactttagg gacctgcata tgtatttggc    420

caagaaaaaa taaacaaata atgagagaaa gagtgaatat atataaacaa tggtatagtc    480

cctctgtcac tttaacactc acacgtcaag attgttgtag ttaaatcttg aagagcccgt    540

gaaaggtgtt tcatttttac tcaaatatat tgatgaaata attacttaag tggagaacaa    600

ataactttat aataatttat catatgattt tacagttttt ttttatttga taaatttgaa    660

taaacaattg aggttatttt aatagtttta gaacttatga gatttttatg tttatgagaa    720

aatatacatt accaaaattt catatcgcat gtccaaacaa aacatcaatt ttagtatgat    780

tccatatcat aataccatat cgaatgacca aacggaccgt tagaataact ttataatagt    840

tattatactt tcattatgaa tttttgctta tttagtaaga ttgtatgaat aaagttagga    900
```

-continued

```
caatatttgg tgagattttg atttatgagc taacaataga atttcaaaat cataatttct    960
atatggctaa gcaaaacttc aatttcatgt taaacgaatg aaaagtaagt aggcgtttgg   1020
tcatgtgata tcatatcacg atatgaaatc gtgagaagga atcagcgttt gaacatgcga   1080
ttatacattg attctatatc atgagatgta attccatatt cttcaaaaac catgatatgg   1140
aaatttcata tcatgatttg atatattttt aatacaaaaa ttgatccaca tatttgtatt   1200
ttgttaaaac aacccatatt taattttttg ggtaagccat cgacgttttg tatttatatt   1260
aaaatctgat taaatttgaa gctgatttat atttagaatg aaacttcagc ttaaaaataa   1320
gaaaatagtt tatgatttca ttagaattaa ggcgtagtca ctgtcaaact tgagaaagga   1380
ttaccccttt aagctttgcc cttgtttgca gagacagtga cttgtgatga aatgaagcca   1440
gagaaggcac tctgttatca cacttaaatg ataatacatg tgtatggact agcaataaaa   1500
gtggcactag taattgaaaa gcaagtgtat agagagagat aatgagagag aaagagtaag   1560
tacactacta ctgctactat cccatatacc tgtaatgttg caggtctgaa ttttgcagtt   1620
gcagaccccc ttctcttggc acaagctctt ttaactttta tcttctcaaa taattctctc   1680
tctctctctt ttctatcatt ttttttaca ttgagagtaa acttaatatc cgttgtatgt   1740
attagtgtga ggcctatctg ccacaaggat gtgatggaac actatgcttc ctctgctaaa   1800
accccacaac cccaaaactc tctttcactt cacatttaag cacaattcct cagtaaaatt   1860
atccttttga tctctctaac atcaatgttg gttagttcaa gaattggttt ttccatttca   1920
aaggagctga gttagtgagg ttttgagttt tgactgagac ttgagtctac catggcatca   1980
tttttactcc aaagatgtaa tcttctcttt gaggttcttc ttattttggg gttcttgatt   2040
ttcttcagct ttggttctgt ggtgtctgat gatggtgagt agagtagagt agtagaactt   2100
tctgcttctt atgttttagt ttaatgtttt gtttaagatg ttaaaaagac aaagtgtgct   2160
ttttttaatc atttttttaaa tggtggtttt tgattaatcc cacgttttgt agttgttatt   2220
tgttaaaggt ttattttttt gtctcattat tataataata attgggaaat aggttctgca   2280
ttgttggaaa ttaagaagtc aattagggac gtggagaatg tgttgtatga ctggactgat   2340
tctccttcat ctgattactg tgcctggaga ggtgttacct gtgataatgt caccttcaat   2400
gttgttcaac tgtaagacat aactcaaaaa cactatcatt tgggattctt tagttataaa   2460
gttgtaatct tttgacatta tcttgtagta atctttcgag tttaaatctt gatggggagt   2520
tgtctcctgc tattggacag ctcaaaggcc ttgtatctat gtaatatctc ctcccattat   2580
ctcacaatta cccttttttgt ttgatctttt gacttagtgc acattataga ctatgcctgt   2640
taattttttt ttgaagtgat atgaggggaa atcgcctttc tggccagata ccagatgaga   2700
ttggtgactg ttcagcactg aaaaatttgt aagtatgaaa tgcttctgaa tcttgtgtta   2760
ttgtttggaa aaataagtaa ccattttttc ccttagggac ctttccttca atgagcttta   2820
tggtgatatt cccttctcca tatctaaact caagcaactg gaatatctgt aagttttgat   2880
actctccttc ttctaaatgt tgtattattt gctttccgag attgttagtt gattatgctc   2940
gtcttattca acttaggatt ttgaagaata atcaattgat tggaccaatt ccatctacat   3000
tgtcacagat ccctaacttg aaggtcttgt aagtatattc tctctgcttt gtcatgatat   3060
tggtagatta tgaataattt tagtttgatc caagaacttc ctccagggac ctggctcaaa   3120
ataggttaag tggagaaatt cctaggctga tatactggaa cgaagtcctg cagtatctgt   3180
gagtgtttta atccggtgtt cctcttcttc ctgtttgttt taaccttagg acactttcat   3240
ttcgtatatg gatatgatta catctgttgt atgtttttat tcatataggg gactgcgtgg   3300
```

```
taacaacttg ggtggatccc tttctcctga tatgtgtcag ctcaccggcc tgtggtactt   3360
gtaagtttgt aatcctgttg ctcttaagat cttactttag ttcctctagg tgatgacatt   3420
aaccattgtt cattgtgttg tacagtgatg ttcggaacaa tagtttgact ggttccattc   3480
ctcaaaatat tggcaactgt actgccttcc aggttctgta agtatctaaa tcaattgaat   3540
gaagtttgac tatattctgt atgtttggtt ggcataacac cttgttttgt tctgtcagag   3600
atttgtctta taatgatttg accggagaga ttcctttcaa tattggtttc ctgcaagtag   3660
cgaccttgta agtttatgct gcttctcttc attacaaact attcaatata tggttgtttg   3720
aagtgtactt tcatcattcc aggtctttgc aaggtaatcg tctttcaggg cagatccctt   3780
ctgtaattgg attgatgcaa gctcttgcag ttttgtgagt gttttgtgtc ttgatatctc   3840
aatctaatgc tactgaatct aattcttgga aaccattata atgcatctgt tatttaagtt   3900
ttctgaccct tttactgtca gggacttgag ctgcaatatg ttgagtggaa caattccttc   3960
aattcttggg aatttgactt acacagagaa attgttagta cttcaacatt attaaaagca   4020
atttggatca ttttgtgctt cctaaattgt gtagtggatc aattactgta agttcgcatt   4080
gtattgcagg tatctacacg ggaacaagct atctggttcc attcctccag agctgggaaa   4140
tatgacaaag ctccactact tgtatgaatg ccttctatca atcatttttt gttagctttg   4200
ttttgttctt cctgttcaaa ccccttttaaa tgaatgctta ccatttagaa gcatttgttt   4260
gattatttag cctttgggca accacggatt tgaatgatag aaagctgtta tgagaatttt   4320
tattaagaga ctttcttcaa ccttaaggct caaagatggt aatttgcagg gaattgaatg   4380
ataaccaact tactggacgc ataccaccag aacttggaaa gctgacagaa ttgtttgact   4440
tgtaaatccc gtttctcttc atcttctact ttggacttgt taacatcatt atttatttac   4500
tcatgttgta tgtttcagaa atgttgcaaa caaccaccta gatgggccca taccttccaa   4560
tattagctca tgtaccaatt tgaatagtct gtgagtgttt ttaatgtccg aagtgtttca   4620
attatgcacg accatgcttg tttggtagtt attgacacct gattttgttg cagcaacgtt   4680
catggaaaca aattgaatgg tactattcca cctgcttttc agaagctgga aagtatgacc   4740
tatctgtaag ttcttacttt ctgatctttt tcttttgaag aattatgttt aaggttatcg   4800
aagttaccgt ccatgctgtt gagcaagatt gtaaacttac tgtgccttgt atataaattt   4860
tactggcgtt gtattattga aaaaatcatt ttatttatat tgctctcaaa tcatactggc   4920
ttatatccat tcatgaagaa tcatttctac tgtctgaagt tttcagctat atgtatcgaa   4980
aaaatttagt tattatatag tttattttga gcctctgcat catctatttg tgaatttcat   5040
ttgcttattc tgcatactct cagcattaac cgtctcttct tttgttaatt gctttagtaa   5100
tctctcctcc aacaatctca aaggcccaat tccaattgag ctatctcgta ttgggaatgt   5160
agatacactg taagtgcaaa ctttctcatc tactttcatt tctctcattg caattatggt   5220
tgcggggaaa gcactttttg tcagtcttaa gaatcttcaa catttttttgg cttagggact   5280
tatcaaacaa caggatcagt ggtcctatac ctatgtccct tggtgatttg gaacatcttc   5340
ttaaactgtg agcataaccg tcaagttgtt atgttagcat catatatctg ttgtacttac   5400
atccctttttg tcaatgctgt aggaacttaa gcaagaatga aataaatgga aacttaccag   5460
ctgaatttgg caatttaagg agcatcatgg agatgtatgg aaccttgcta aattcagtta   5520
ctttgaattt atggtttgct tgattttcag ctttttgact gcactcctaa ttgtagtgat   5580
ctgtcaagca atcacctctc tggtccctta cctcaggaac ttggtcagct tccaaacctg   5640
```

-continued

```
tacttgctgt aagtacttca gatttacttt gagactctca tcctcttagc tattggtaat   5700
aatctgtaga gtgaataagt atgaacttct aaactcggta agtagatttt aaaattattt   5760
tggatgccat tttcaaaaaa gtagagatga agttggttgt gttgctattg ttttatatga   5820
tctggcttca tatgttcatt actttggtgt tctcagtttt gctttatatt gcattattgc   5880
acggggctca aatgcagcat atctctatct tctttttctt gtggccttaa ttattttaca   5940
aattaatgaa caggaaggtg gaaaacaaca atttatcagg cgatgtgatg tccttagcca   6000
gttgcctcag tctaaatatc ttgtgagttt tcaagtccat agtaagacac cagtacaaac   6060
aaatgttttg ttaatctaat caacctcatg ttagcagaaa tgtctcatac aataatctgg   6120
gagggaatat tccaaccggc aataatttct ctagattttc accagacagg taagtggagc   6180
tattaagatt ttacacaagt cacaagcatt tattggtttt taattctttg cttctaattt   6240
cttccttttg ctatgtctcc gaaaaagctt cataggaaat ccagatctgt gtgggtattg   6300
gctcacttct ccttgtcatg catctcatcc ggcagagcga ggtctgatca aactgtaaca   6360
atcatttggc ctttactcta ttgcattttt gaagttccat ttcactttag acatctgcaa   6420
catttattaa gtgtgatgga cagatatatt gattaatgag gaattatccc ttggttgagc   6480
aaacttaatt ctgtgttagc ctggtagtag ggtgtaccac aaggtttgtc gtcatggttt   6540
cctatgttca caatccctga ttgtaacatt tagatgtgta cacatatcta attaacatga   6600
aataatcttc atttgctgga gttacattga cgtaaagatg cgttagctgt caaatgaaac   6660
tgcatttgtt ttatttccat catcagtaca ttaattaagt gcataaatat tttaacagtt   6720
gttgaatgat ataagatgaa tttattggac aattgcagtt tcaatttcta aagcagcaat   6780
acttggtatt gctctgggtg gcttggtgat tcttctgatg atactagtag cagcatgccg   6840
gccacagaaa cctgcacctt tcatggaagg atctattgat aaaccaggta caatattttc   6900
cggacggttg gatagtgttt ggagatgttc atgtcagaag gacagtcgtc agagtttatt   6960
gaagttgcca tgtattgatt gtttaacgtt tttgatgaac agtttattac tcatctccaa   7020
aacttgtgat ccttcatatg aacatggcac ttcatgttta cgaggacatt atgaggatga   7080
ctgagaactt gagtgagaag tatataattg gttgtggagc atcaagtact gtatataaat   7140
gtgttttgaa aaattgcaag cctgtagcta tcaagaagtt gtactctcac aacccgcaat   7200
acttgaagga atttgagact gaacttgaga cagttgggag tattaagcat cgtaatcttg   7260
tctgtctcca aggatattct ctttctccat ctggccatct tcttttctat gactacatgg   7320
aaaatggtag cctttgggat ttgcttcatg gttagtaaat ccaaaatggt taaggtgatt   7380
gatgcattga ttttgtgtta aagcatcaag taatcagtcc tcttgtatct ttttttgcag   7440
gtcctacaac aaagaagaaa aagcttgatt gggttactcg ccttcgaatt gcattgggat   7500
cagctcaagg gcttgcatat cttcatcatg attgtagccc tcgaataatc caccgtgatg   7560
ttaaatcatc taatatcttg ttggacaaag actttgaggc tcatctgact gattttggca   7620
tagctaaaag cttatgcata tcaaagacct atacgtccac gtacattatg ggaaccattg   7680
gttacattga tccagagtat gctcgcactt ctcgcttgac agagaagtct gatgtttaca   7740
gctatggtat tgttctattg gaattgctca ctggaaggaa agctgtagat aatgaatcta   7800
atctacatca tttggtaagc tcttgcaatt tagttaatat gaacttgtcc tatgatgttt   7860
attcatataa ttatattaag attcaattca attgatcata acagttttgc atatatgtta   7920
cagattctaa ctaaggcagc aaacgatgct gtaatggaaa cagtggatcc tgagataaca   7980
tgcacatgca aagatcttgc agatgtgaag aaggtttttc agcttgccct tctatgttcc   8040
```

aaaagacagc ctgctgagag accaacaatg catgaagtgg caagagtact tgaaagccta 8100
atacccgtcg ctgaaacgaa acagccaaat ccaacccccct cacttgcatt actcccatct 8160
gctaaggtac cttgttacat ggatgaatat gtcaacctca agacacccca cctagtgaac 8220
tgttcatcca tgagcacttc agatgcccaa cttttcctca agtttggaga ggtcatatcc 8280
cagaatagtg gctga 8295

<210> SEQ ID NO 29
<211> LENGTH: 2973
<212> TYPE: DNA
<213> ORGANISM: Solanum lycopersicum

<400> SEQUENCE: 29
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300
ggccttgtat ctattgatat gaggggaaat cgcctttctg gccagatacc agatgagatt 360
ggtgactgtt cagcactgaa aaatttggac ctttccttca atgagcttta tggtgatatt 420
cccttctcca tatctaaact caagcaactg gaatatctga ttttgaagaa taatcaattg 480
attggaccaa ttccatctac attgtcacag atccctaact tgaaggtctt ggacctggct 540
caaaataggt taagtggaga aattcctagg ctgatatact ggaacgaagt cctgcagtat 600
ctgggactgc gtggtaacaa cttgggtgga tccctttctc ctgatatgtg tcagctcacc 660
ggcctgtggt actttgatgt tcggaacaat agtttgactg gttccattcc tcaaaatatt 720
ggcaactgta ctgccttcca ggttctagat ttgtcttata atgatttgac cggagagatt 780
cctttcaata ttggtttcct gcaagtagcg accttgtctt tgcaaggtaa tcgtctttca 840
gggcagatcc cttctgtaat tggattgatg caagctcttg cagttttgga cttgagctgc 900
aatatgttga gtggaacaat tccttcaatt cttgggaatt tgacttacac agagaaattg 960
tatctacacg ggaacaagct atctggttcc attcctccag agctgggaaa tatgacaaag 1020
ctccactact tggaattgaa tgataaccaa cttactggac gcataccacc agaacttgga 1080
aagctgacag aattgtttga cttaaatgtt gcaaacaacc acctagatgg gcccatacct 1140
tccaatatta gctcatgtac caatttgaat agtctcaacg ttcatggaaa caaattgaat 1200
ggtactattc cacctgcttt tcagaagctg gaaagtatga cctatcttaa tctctcctcc 1260
aacaatctca aaggcccaat tccaattgag ctatctcgta ttgggaatgt agatacactg 1320
gacttatcaa acaacaggat cagtggtcct atacctatgt cccttggtga tttggaacat 1380
cttcttaaac tgaacttaag caagaatgaa ataaatggaa acttaccagc tgaatttggc 1440
aatttaagga gcatcatgga gattgatctg tcaagcaatc acctctctgg tcccttacct 1500
caggaacttg gtcagcttcc aaacctgtac ttgctgaagg tggaaaacaa caatttatca 1560
ggcgatgtga tgtccttagc cagttgcctc agtctaaata tcttaaatgt ctcatacaat 1620
aatctgggag ggaatattcc aaccggcaat aatttctcta gattttcacc agacagcttc 1680
ataggaaatc cagatctgtg tgggtattgg ctcacttctc cttgtcatgc atctcatccg 1740
gcagagcgag tttcaatttc taaagcagca atacttggta ttgctctggg tggcttggtg 1800

```
attcttctga tgatactagt agcagcatgc cggccacaga aacctgcacc tttcatggaa   1860

ggatctattg ataaaccagt ttattactca tctccaaaac ttgtgatcct tcatatgaac   1920

atggcacttc atgtttacga ggacattatg aggatgactg agaacttgag tgagaagtat   1980

ataattggtt gtggagcatc aagtactgta tataaatgtg ttttgaaaaa ttgcaagcct   2040

gtagctatca agaagttgta ctctcacaac ccgcaatact tgaaggaatt tgagactgaa   2100

cttgagacag ttgggagtat taagcatcgt aatcttgtct gtctccaagg atattctctt   2160

tctccatctg gccatcttct tttctatgac tacatggaaa atggtagcct ttgggatttg   2220

cttcatggtc ctacaacaaa gaagaaaaag cttgattggg ttactcgcct tcgaattgca   2280

ttgggatcag ctcaagggct tgcatatctt catcatgatt gtagccctcg aataatccac   2340

cgtgatgtta aatcatctaa tatcttgttg gacaaagact ttgaggctca tctgactgat   2400

tttggcatag ctaaaagctt atgcatatca aagacctata cgtccacgta cattatggga   2460

accattggtt acattgatcc agagtatgct cgcacttctc gcttgacaga gaagtctgat   2520

gtttacagct atggtattgt tctattggaa ttgctcactg gaaggaaagc tgtagataat   2580

gaatctaatc tacatcattt gattctaact aaggcagcaa acgatgctgt aatggaaaca   2640

gtggatcctg agataacatg cacatgcaaa gatcttgcag atgtgaagaa ggtttttcag   2700

cttgcccttc tatgttccaa aagacagcct gctgagagac caacaatgca tgaagtggca   2760

agagtacttg aaagcctaat acccgtcgct gaaacgaaac agccaaatcc aacccccctca   2820

cttgcattac tcccatctgc taaggtacct tgttacatgg atgaatatgt caacctcaag   2880

acaccccacc tagtgaactg ttcatccatg agcacttcag atgcccaact tttcctcaag   2940

tttggagagg tcatatccca gaatagtggc tga                                2973

<210> SEQ ID NO 30
<211> LENGTH: 990
<212> TYPE: PRT
<213> ORGANISM: Solanum lycopersicum

<400> SEQUENCE: 30

Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160

Ile Gly Pro Ile Pro Ser Thr Leu Ser Gln Ile Pro Asn Leu Lys Val
```

-continued

```
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
        195                 200                 205

Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320

Tyr Leu His Gly Asn Lys Leu Ser Gly Ser Ile Pro Pro Glu Leu Gly
                325                 330                 335

Asn Met Thr Lys Leu His Tyr Leu Glu Leu Asn Asp Asn Gln Leu Thr
            340                 345                 350

Gly Arg Ile Pro Pro Glu Leu Gly Lys Leu Thr Glu Leu Phe Asp Leu
        355                 360                 365

Asn Val Ala Asn Asn His Leu Asp Gly Pro Ile Pro Ser Asn Ile Ser
    370                 375                 380

Ser Cys Thr Asn Leu Asn Ser Leu Asn Val His Gly Asn Lys Leu Asn
385                 390                 395                 400

Gly Thr Ile Pro Pro Ala Phe Gln Lys Leu Glu Ser Met Thr Tyr Leu
                405                 410                 415

Asn Leu Ser Ser Asn Asn Leu Lys Gly Pro Ile Pro Ile Glu Leu Ser
            420                 425                 430

Arg Ile Gly Asn Val Asp Thr Leu Asp Leu Ser Asn Asn Arg Ile Ser
        435                 440                 445

Gly Pro Ile Pro Met Ser Leu Gly Asp Leu Glu His Leu Leu Lys Leu
    450                 455                 460

Asn Leu Ser Lys Asn Glu Ile Asn Gly Asn Leu Pro Ala Glu Phe Gly
465                 470                 475                 480

Asn Leu Arg Ser Ile Met Glu Ile Asp Leu Ser Ser Asn His Leu Ser
                485                 490                 495

Gly Pro Leu Pro Gln Glu Leu Gly Gln Leu Pro Asn Leu Tyr Leu Leu
            500                 505                 510

Lys Val Glu Asn Asn Asn Leu Ser Gly Asp Val Met Ser Leu Ala Ser
        515                 520                 525

Cys Leu Ser Leu Asn Ile Leu Asn Val Ser Tyr Asn Asn Leu Gly Gly
    530                 535                 540

Asn Ile Pro Thr Gly Asn Asn Phe Ser Arg Phe Ser Pro Asp Ser Phe
545                 550                 555                 560

Ile Gly Asn Pro Asp Leu Cys Gly Tyr Trp Leu Thr Ser Pro Cys His
                565                 570                 575

Ala Ser His Pro Ala Glu Arg Val Ser Ile Ser Lys Ala Ala Ile Leu
            580                 585                 590
```

```
Gly Ile Ala Leu Gly Gly Leu Val Ile Leu Leu Met Ile Leu Val Ala
        595                 600                 605

Ala Cys Arg Pro Gln Lys Pro Ala Pro Phe Met Glu Gly Ser Ile Asp
    610                 615                 620

Lys Pro Val Tyr Tyr Ser Ser Pro Lys Leu Val Ile Leu His Met Asn
625                 630                 635                 640

Met Ala Leu His Val Tyr Glu Asp Ile Met Arg Met Thr Glu Asn Leu
                645                 650                 655

Ser Glu Lys Tyr Ile Ile Gly Cys Gly Ala Ser Ser Thr Val Tyr Lys
            660                 665                 670

Cys Val Leu Lys Asn Cys Lys Pro Val Ala Ile Lys Lys Leu Tyr Ser
        675                 680                 685

His Asn Pro Gln Tyr Leu Lys Glu Phe Glu Thr Glu Leu Glu Thr Val
    690                 695                 700

Gly Ser Ile Lys His Arg Asn Leu Val Cys Leu Gln Gly Tyr Ser Leu
705                 710                 715                 720

Ser Pro Ser Gly His Leu Leu Phe Tyr Asp Tyr Met Glu Asn Gly Ser
                725                 730                 735

Leu Trp Asp Leu Leu His Gly Pro Thr Thr Lys Lys Lys Lys Leu Asp
            740                 745                 750

Trp Val Thr Arg Leu Arg Ile Ala Leu Gly Ser Ala Gln Gly Leu Ala
        755                 760                 765

Tyr Leu His His Asp Cys Ser Pro Arg Ile Ile His Arg Asp Val Lys
    770                 775                 780

Ser Ser Asn Ile Leu Leu Asp Lys Asp Phe Glu Ala His Leu Thr Asp
785                 790                 795                 800

Phe Gly Ile Ala Lys Ser Leu Cys Ile Ser Lys Thr Tyr Thr Ser Thr
                805                 810                 815

Tyr Ile Met Gly Thr Ile Gly Tyr Ile Asp Pro Glu Tyr Ala Arg Thr
            820                 825                 830

Ser Arg Leu Thr Glu Lys Ser Asp Val Tyr Ser Tyr Gly Ile Val Leu
        835                 840                 845

Leu Glu Leu Leu Thr Gly Arg Lys Ala Val Asp Asn Glu Ser Asn Leu
    850                 855                 860

His His Leu Ile Leu Thr Lys Ala Ala Asn Asp Ala Val Met Glu Thr
865                 870                 875                 880

Val Asp Pro Glu Ile Thr Cys Thr Cys Lys Asp Leu Ala Asp Val Lys
                885                 890                 895

Lys Val Phe Gln Leu Ala Leu Leu Cys Ser Lys Arg Gln Pro Ala Glu
            900                 905                 910

Arg Pro Thr Met His Glu Val Ala Arg Val Leu Glu Ser Leu Ile Pro
        915                 920                 925

Val Ala Glu Thr Lys Gln Pro Asn Pro Thr Pro Ser Leu Ala Leu Leu
    930                 935                 940

Pro Ser Ala Lys Val Pro Cys Tyr Met Asp Glu Tyr Val Asn Leu Lys
945                 950                 955                 960

Thr Pro His Leu Val Asn Cys Ser Ser Met Ser Thr Ser Asp Ala Gln
                965                 970                 975

Leu Phe Leu Lys Phe Gly Glu Val Ile Ser Gln Asn Ser Gly
            980                 985                 990
```

<210> SEQ ID NO 31
<211> LENGTH: 6324

<212> TYPE: DNA
<213> ORGANISM: Solanum lycopersicum

<400> SEQUENCE: 31
atggcatcat ttttactcca aagatgtaat cttctctttg aggttcttct tattttgggg 60
ttcttgattt tcttcagctt tggttctgtg gtgtctgatg atggtgagta gagtagagta 120
gtagaacttt ctgcttctta tgttttagtt taatgttttg tttaagatgt taaaaagaca 180
aagtgtgctt tttttaatca ttttttaaat ggtggttttt gattaatccc acgttttgta 240
gttgttattt gttaaaggtt tatttttttg tctcattatt ataataataa ttgggaaata 300
ggttctgcat tgttggaaat taagaagtca attagggacg tggagaatgt gttgtatgac 360
tggactgatt ctccttcatc tgattactgt gcctggagag gtgttacctg tgataatgtc 420
accttcaatg ttgttcaact gtaagacata actcaaaaac actatcattt gggattcttt 480
agttataaag ttgtaatctt ttgacattat cttgtagtaa tctttcgagt ttaaatcttg 540
atggggagtt gtctcctgct attggacagc tcaaaggcct tgtatctatg taatatctcc 600
tcccattatc tcacaattac cctttttgtt tgatcttttg acttagtgca cattatagac 660
tatgcctgtt aatttttttt tgaagtgata tgaggggaaa tcgcctttct ggccagatac 720
cagatgagat tggtgactgt tcagcactga aaaatttgta agtatgaaat gcttctgaat 780
cttgtgttat tgtttggaaa aataagtaac catttttttcc cttagggacc tttccttcaa 840
tgagctttat ggtgatattc ccttctccat atctaaactc aagcaactgg aatatctgta 900
agttttgata ctctccttct tctaaatgtt gtattatttg ctttccgaga ttgttagttg 960
attatgctcg tcttattcaa cttaggattt tgaagaataa tcaattgatt ggaccaattc 1020
catctacatt gtcacagatc cctaacttga aggtcttgta agtatattct ctctgctttg 1080
tcatgatatt ggtagattat gaataatttt agtttgatcc aagaacttcc tccagggacc 1140
tggctcaaaa taggttaagt ggagaaattc ctaggctgat atactggaac gaagtcctgc 1200
agtatctgtg agtgttttaa tccggtgttc ctcttcttcc tgtttgtttt aaccttagga 1260
cactttcatt tcgtatatgg atatgattac atctgttgta tgtttttatt catatagggg 1320
actgcgtggt aacaacttgg gtggatccct ttctcctgat atgtgtcagc tcaccggcct 1380
gtggtacttg taagtttgta atcctgttgc tcttaagatc ttactttagt tcctctaggt 1440
gatgacatta accattgttc attgtgttgt acagtgatgt tcggaacaat agtttgactg 1500
gttccattcc tcaaaatatt ggcaactgta ctgccttcca ggttctgtaa gtatctaaat 1560
caattgaatg aagtttgact atattctgta tgtttggttg gcataacacc ttgttttgtt 1620
ctgtcagaga tttgtcttat aatgatttga ccggagagat tcctttcaat attggtttcc 1680
tgcaagtagc gaccttgtaa gtttatgctg cttctcttca ttacaaacta ttcaatatat 1740
ggttgtttga agtgtacttt catcattcca ggtctttgca aggtaatcgt ctttcagggc 1800
agatcccttc tgtaattgga ttgatgcaag ctcttgcagt tttgtgagtg ttttgtgtct 1860
tgatatctca atctaatgct actgaatcta attcttggaa accattataa tgcatctgtt 1920
atttaagttt tctgaccctt ttactgtcag ggacttgagc tgcaatatgt tgagtggaac 1980
aattccttca attcttggga atttgactta cacagagaaa ttgttagtac ttcaacatta 2040
ttaaaagcaa tttggatcat tttgtgcttc ctaaattgtg tagtggatca attactgtaa 2100
gttcgcattg tattgcaggt atctacacgg gaacaagcta tctggttcca ttcctccaga 2160
gctgggaaat atgacaaagc tccactactt gtatgaatgc cttctatcaa tcattttttg 2220

-continued

```
ttagctttgt tttgttcttc ctgttcaaac ccttttaaat gaatgcttac catttagaag   2280
catttgtttg attatttagc ctttgggcaa ccacggattt gaatgataga aagctgttat   2340
gagaattttt attaagagac tttcttcaac cttaaggctc aaagatggta atttgcaggg   2400
aattgaatga taaccaactt actggacgca taccaccaga acttggaaag ctgacagaat   2460
tgtttgactt gtaaatcccg tttctcttca tcttctactt tggacttgtt aacatcatta   2520
tttatttact catgttgtat gtttcagaaa tgttgcaaac aaccacctag atgggcccat   2580
accttccaat attagctcat gtaccaattt gaatagtctg tgagtgtttt taatgtccga   2640
agtgtttcaa ttatgcacga ccatgcttgt ttggtagtta ttgacacctg attttgttgc   2700
agcaacgttc atggaaacaa attgaatggt actattccac ctgcttttca gaagctggaa   2760
agtatgacct atctgtaagt tcttactttc tgatcttttt cttttgaaga attatgttta   2820
aggttatcga agttaccgtc catgctgttg agcaagattg taaacttact gtgccttgta   2880
tataaatttt actggcgttg tattattgaa aaaatcattt tatttatatt gctctcaaat   2940
catactggct tatatccatt catgaagaat catttctact gtctgaagtt ttcagctata   3000
tgtatcgaaa aaatttagtt attatatagt ttattttgag cctctgcatc atctatttgt   3060
gaatttcatt tgcttattct gcatactctc agcattaacc gtctcttctt ttgttaattg   3120
ctttagtaat ctctcctcca acaatctcaa aggcccaatt ccaattgagc tatctcgtat   3180
tgggaatgta gatacactgt aagtgcaaac tttctcatct actttcattt ctctcattgc   3240
aattatggtt gcggggaaag cactttttgt cagtcttaag aatcttcaac atttttggc    3300
ttagggactt atcaaacaac aggatcagtg gtcctatacc tatgtccctt ggtgatttgg   3360
aacatcttct taaactgtga gcataaccgt caagttgtta tgttagcatc atatatctgt   3420
tgtacttaca tccctttgt caatgctgta ggaacttaag caagaatgaa ataaatggaa    3480
acttaccagc tgaatttggc aatttaagga gcatcatgga gatgtatgga accttgctaa   3540
attcagttac tttgaattta tggtttgctt gattttcagc tttttgactg cactcctaat   3600
tgtagtgatc tgtcaagcaa tcacctctct ggtcccttac ctcaggaact tggtcagctt   3660
ccaaacctgt acttgctgta agtacttcag atttactttg agactctcat cctcttagct   3720
attggtaata atctgtagag tgaataagta tgaacttcta aactcggtaa gtagatttta   3780
aaattatttt ggatgccatt ttcaaaaaag tagagatgaa gttggttgtg ttgctattgt   3840
tttatatgat ctggcttcat atgttcatta ctttggtgtt ctcagttttg ctttatattg   3900
cattattgca cggggctcaa atgcagcata tctctatctt ctttttcttg tggccttaat   3960
tattttacaa attaatgaac aggaaggtgg aaaacaacaa tttatcaggc gatgtgatgt   4020
ccttagccag ttgcctcagt ctaaatatct tgtgagtttt caagtccata gtaagacacc   4080
agtacaaaca aatgttttgt taatctaatc aacctcatgt tagcagaaat gtctcataca   4140
ataatctggg agggaatatt ccaaccggca ataatttctc tagattttca ccagacaggt   4200
aagtggagct attaagattt tacacaagtc acaagcattt attggttttt aattctttgc   4260
ttctaatttc ttccttttgc tatgtctccg aaaaagcttc ataggaaatc cagatctgtg   4320
tgggtattgg ctcacttctc cttgtcatgc atctcatccg gcagagcgag gtctgatcaa   4380
actgtaacaa tcatttggcc tttactctat tgcatttttg aagttccatt tcactttaga   4440
catctgcaac atttattaag tgtgatggac agatatattg attaatgagg aattatccct   4500
tggttgagca aacttaattc tgtgttagcc tggtagtagg gtgtaccaca aggtttgtcg   4560
tcatggtttc ctatgttcac aatccctgat tgtaacattt agatgtgtac acatatctaa   4620
```

ttaacatgaa ataatcttca tttgctggag ttacattgac gtaaagatgc gttagctgtc 4680
aaatgaaact gcatttgttt tatttccatc atcagtacat taattaagtg cataaatatt 4740
ttaacagttg ttgaatgata taagatgaat ttattggaca attgcagttt caatttctaa 4800
agcagcaata cttggtattg ctctgggtgg cttggtgatt cttctgatga tactagtagc 4860
agcatgccgg ccacagaaac ctgcaccttt catggaagga tctattgata aaccaggtac 4920
aatattttcc ggacggttgg atagtgtttg gagatgttca tgtcagaagg acagtcgtca 4980
gagtttattg aagttgccat gtattgattg tttaacgttt ttgatgaaca gtttattact 5040
catctccaaa acttgtgatc cttcatatga acatggcact tcatgtttac gaggacatta 5100
tgaggatgac tgagaacttg agtgagaagt atataattgg ttgtggagca tcaagtactg 5160
tatataaatg tgttttgaaa aattgcaagc ctgtagctat caagaagttg tactctcaca 5220
acccgcaata cttgaaggaa tttgagactg aacttgagac agttgggagt attaagcatc 5280
gtaatcttgt ctgtctccaa ggatattctc tttctccatc tggccatctt cttttctatg 5340
actacatgga aaatggtagc ctttgggatt tgcttcatgg ttagtaaatc caaaatggtt 5400
aaggtgattg atgcattgat tttgtgttaa agcatcaagt aatcagtcct cttgtatctt 5460
tttttgcagg tcctacaaca aagaagaaaa agcttgattg ggttactcgc cttcgaattg 5520
cattgggatc agctcaaggg cttgcatatc ttcatcatga ttgtagccct cgaataatcc 5580
accgtgatgt taaatcatct aatatcttgt tggacaaaga ctttgaggct catctgactg 5640
attttggcat agctaaaagc ttatgcatat caaagaccta tacgtccacg tacattatgg 5700
gaaccattgg ttacattgat ccagagtatg ctcgcacttc tcgcttgaca gagaagtctg 5760
atgtttacag ctatggtatt gttctattgg aattgctcac tggaaggaaa gctgtagata 5820
atgaatctaa tctacatcat ttggtaagct cttgcaattt agttaatatg aacttgtcct 5880
atgatgttta ttcatataat tatattaaga ttcaattcaa ttgatcataa cagttttgca 5940
tatatgttac agattctaac taaggcagca aacgatgctg taatggaaac agtggatcct 6000
gagataacat gcacatgcaa agatcttgca gatgtgaaga aggtttttca gcttgccctt 6060
ctatgttcca aaagacagcc tgctgagaga ccaacaatgc atgaagtggc aagagtactt 6120
gaaagcctaa tacccgtcgc tgaaacgaaa cagccaaatc caaccccctc acttgcatta 6180
ctcccatctg ctaaggtacc ttgttacatg gatgaatatg tcaacctcaa gacaccccac 6240
ctagtgaact gttcatccat gagcacttca gatgcccaac ttttcctcaa gtttggagag 6300
gtcatatccc agaatagtgg ctga 6324

<210> SEQ ID NO 32
<211> LENGTH: 2973
<212> TYPE: DNA
<213> ORGANISM: Solanum lycopersicum

<400> SEQUENCE: 32
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgctattgg acagctcaaa 300
ggccttgtat ctattgatat gaggggaaat cgcctttctg gccagatacc agatgagatt 360

-continued

```
ggtgactgtt cagcactgaa aaatttggac ctttccttca atgagcttta tggtgatatt    420
cccttctcca tatctaaact caagcaactg gaatatctga ttttgaagaa taatcaattg    480
attggaccaa ttccatctac attgtcacag atccctaact tgaaggtctt ggacctggct    540
caaaataggt taagtggaga aattcctagg ctgatatact ggaacgaagt cctgcagtat    600
ctgggactgc gtggtaacaa cttgggtgga tccctttctc ctgatatgtg tcagctcacc    660
ggcctgtggt actttgatgt tcggaacaat agtttgactg gttccattcc tcaaaatatt    720
ggcaactgta ctgccttcca ggttctagat ttgtcttata atgatttgac cggagagatt    780
cctttcaata ttggtttcct gcaagtagcg accttgtctt tgcaaggtaa tcgtctttca    840
gggcagatcc cttctgtaat tggattgatg caagctcttg cagttttgga cttgagctgc    900
aatatgttga gtggaacaat tccttcaatt cttgggaatt tgacttacac agagaaattg    960
tatctacacg ggaacaagct atctggttcc attcctccag agctgggaaa tatgacaaag   1020
ctccactact tggaattgaa tgataaccaa cttactggac gcataccacc agaacttgga   1080
aagctgacag aattgtttga cttaaatgtt gcaaacaacc acctagatgg gcccatacct   1140
tccaatatta gctcatgtac caatttgaat agtctcaacg ttcatggaaa caaattgaat   1200
ggtactattc cacctgcttt tcagaagctg gaaagtatga cctatcttaa tctctcctcc   1260
aacaatctca aaggcccaat tccaattgag ctatctcgta ttgggaatgt agatacactg   1320
gacttatcaa acaacaggat cagtggtcct atacctatgt cccttggtga tttggaacat   1380
cttcttaaac tgaacttaag caagaatgaa ataaatggaa acttaccagc tgaatttggc   1440
aatttaagga gcatcatgga gattgatctg tcaagcaatc acctctctgg tcccttacct   1500
caggaacttg gtcagcttcc aaacctgtac ttgctgaagg tggaaaacaa caatttatca   1560
ggcgatgtga tgtccttagc cagttgcctc agtctaaata tcttaaatgt ctcatacaat   1620
aatctgggag ggaatattcc aaccggcaat aatttctcta gattttcacc agacagcttc   1680
ataggaaatc cagatctgtg tgggtattgg ctcacttctc cttgtcatgc atctcatccg   1740
gcagagcgag tttcaatttc taaagcagca atacttggta ttgctctggg tggcttggtg   1800
attcttctga tgatactagt agcagcatgc cggccacaga aacctgcacc tttcatggaa   1860
ggatctattg ataaaccagt ttattactca tctccaaaac ttgtgatcct tcatatgaac   1920
atggcacttc atgtttacga ggacattatg aggatgactg agaacttgag tgagaagtat   1980
ataattggtt gtggagcatc aagtactgta tataaatgtg ttttgaaaaa ttgcaagcct   2040
gtagctatca agaagttgta ctctcacaac ccgcaatact tgaaggaatt tgagactgaa   2100
cttgagacag ttgggagtat taagcatcgt aatcttgtct gtctccaagg atattctctt   2160
tctccatctg gccatcttct tttctatgac tacatggaaa atggtagcct ttgggatttg   2220
cttcatggtc ctacaacaaa gaagaaaaag cttgattggg ttactcgcct tcgaattgca   2280
ttgggatcag ctcaagggct tgcatatctt catcatgatt gtagccctcg aataatccac   2340
cgtgatgtta aatcatctaa tatcttgttg gacaaagact ttgaggctca tctgactgat   2400
tttggcatag ctaaaagctt atgcatatca aagacctata cgtccacgta cattatggga   2460
accattggtt acattgatcc agagtatgct cgcacttctc gcttgacaga gaagtctgat   2520
gtttacagct atggtattgt tctattggaa ttgctcactg gaaggaaagc tgtagataat   2580
gaatctaatc tacatcattt gattctaact aaggcagcaa acgatgctgt aatggaaaca   2640
gtggatcctg agataacatg cacatgcaaa gatcttgcag atgtgaagaa ggtttttcag   2700
cttgcccttc tatgttccaa aagacagcct gctgagagac caacaatgca tgaagtggca   2760
```

-continued

```
agagtacttg aaagcctaat acccgtcgct gaaacgaaac agccaaatcc aaccccctca    2820

cttgcattac tcccatctgc taaggtacct tgttacatgg atgaatatgt caacctcaag    2880

acaccccacc tagtgaactg ttcatccatg agcacttcag atgcccaact tttcctcaag    2940

tttggagagg tcatatccca gaatagtggc tga                                 2973
```

```
<210> SEQ ID NO 33
<211> LENGTH: 990
<212> TYPE: PRT
<213> ORGANISM: Solanum lycopersicum

<400> SEQUENCE: 33

Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Pro Ala Ile
                85                  90                  95

Gly Gln Leu Lys Gly Leu Val Ser Ile Asp Met Arg Gly Asn Arg Leu
            100                 105                 110

Ser Gly Gln Ile Pro Asp Glu Ile Gly Asp Cys Ser Ala Leu Lys Asn
        115                 120                 125

Leu Asp Leu Ser Phe Asn Glu Leu Tyr Gly Asp Ile Pro Phe Ser Ile
    130                 135                 140

Ser Lys Leu Lys Gln Leu Glu Tyr Leu Ile Leu Lys Asn Asn Gln Leu
145                 150                 155                 160

Ile Gly Pro Ile Pro Ser Thr Leu Ser Gln Ile Pro Asn Leu Lys Val
                165                 170                 175

Leu Asp Leu Ala Gln Asn Arg Leu Ser Gly Glu Ile Pro Arg Leu Ile
            180                 185                 190

Tyr Trp Asn Glu Val Leu Gln Tyr Leu Gly Leu Arg Gly Asn Asn Leu
            195                 200                 205

Gly Gly Ser Leu Ser Pro Asp Met Cys Gln Leu Thr Gly Leu Trp Tyr
    210                 215                 220

Phe Asp Val Arg Asn Asn Ser Leu Thr Gly Ser Ile Pro Gln Asn Ile
225                 230                 235                 240

Gly Asn Cys Thr Ala Phe Gln Val Leu Asp Leu Ser Tyr Asn Asp Leu
                245                 250                 255

Thr Gly Glu Ile Pro Phe Asn Ile Gly Phe Leu Gln Val Ala Thr Leu
            260                 265                 270

Ser Leu Gln Gly Asn Arg Leu Ser Gly Gln Ile Pro Ser Val Ile Gly
        275                 280                 285

Leu Met Gln Ala Leu Ala Val Leu Asp Leu Ser Cys Asn Met Leu Ser
    290                 295                 300

Gly Thr Ile Pro Ser Ile Leu Gly Asn Leu Thr Tyr Thr Glu Lys Leu
305                 310                 315                 320

Tyr Leu His Gly Asn Lys Leu Ser Gly Ser Ile Pro Pro Glu Leu Gly
                325                 330                 335
```

```
Asn Met Thr Lys Leu His Tyr Leu Glu Leu Asn Asp Asn Gln Leu Thr
            340                 345                 350

Gly Arg Ile Pro Pro Glu Leu Gly Lys Leu Thr Glu Leu Phe Asp Leu
        355                 360                 365

Asn Val Ala Asn Asn His Leu Asp Gly Pro Ile Pro Ser Asn Ile Ser
    370                 375                 380

Ser Cys Thr Asn Leu Asn Ser Leu Asn Val His Gly Asn Lys Leu Asn
385                 390                 395                 400

Gly Thr Ile Pro Pro Ala Phe Gln Lys Leu Glu Ser Met Thr Tyr Leu
                405                 410                 415

Asn Leu Ser Ser Asn Asn Leu Lys Gly Pro Ile Pro Ile Glu Leu Ser
            420                 425                 430

Arg Ile Gly Asn Val Asp Thr Leu Asp Leu Ser Asn Asn Arg Ile Ser
        435                 440                 445

Gly Pro Ile Pro Met Ser Leu Gly Asp Leu Glu His Leu Leu Lys Leu
    450                 455                 460

Asn Leu Ser Lys Asn Glu Ile Asn Gly Asn Leu Pro Ala Glu Phe Gly
465                 470                 475                 480

Asn Leu Arg Ser Ile Met Glu Ile Asp Leu Ser Ser Asn His Leu Ser
                485                 490                 495

Gly Pro Leu Pro Gln Glu Leu Gly Gln Leu Pro Asn Leu Tyr Leu Leu
            500                 505                 510

Lys Val Glu Asn Asn Asn Leu Ser Gly Asp Val Met Ser Leu Ala Ser
        515                 520                 525

Cys Leu Ser Leu Asn Ile Leu Asn Val Ser Tyr Asn Asn Leu Gly Gly
    530                 535                 540

Asn Ile Pro Thr Gly Asn Asn Phe Ser Arg Phe Ser Pro Asp Ser Phe
545                 550                 555                 560

Ile Gly Asn Pro Asp Leu Cys Gly Tyr Trp Leu Thr Ser Pro Cys His
                565                 570                 575

Ala Ser His Pro Ala Glu Arg Val Ser Ile Ser Lys Ala Ala Ile Leu
            580                 585                 590

Gly Ile Ala Leu Gly Gly Leu Val Ile Leu Leu Met Ile Leu Val Ala
        595                 600                 605

Ala Cys Arg Pro Gln Lys Pro Ala Pro Phe Met Glu Gly Ser Ile Asp
    610                 615                 620

Lys Pro Val Tyr Tyr Ser Ser Pro Lys Leu Val Ile Leu His Met Asn
625                 630                 635                 640

Met Ala Leu His Val Tyr Glu Asp Ile Met Arg Met Thr Glu Asn Leu
                645                 650                 655

Ser Glu Lys Tyr Ile Ile Gly Cys Gly Ala Ser Ser Thr Val Tyr Lys
            660                 665                 670

Cys Val Leu Lys Asn Cys Lys Pro Val Ala Ile Lys Lys Leu Tyr Ser
        675                 680                 685

His Asn Pro Gln Tyr Leu Lys Glu Phe Glu Thr Glu Leu Glu Thr Val
    690                 695                 700

Gly Ser Ile Lys His Arg Asn Leu Val Cys Leu Gln Gly Tyr Ser Leu
705                 710                 715                 720

Ser Pro Ser Gly His Leu Leu Phe Tyr Asp Tyr Met Glu Asn Gly Ser
                725                 730                 735

Leu Trp Asp Leu Leu His Gly Pro Thr Thr Lys Lys Lys Lys Leu Asp
            740                 745                 750
```

```
Trp Val Thr Arg Leu Arg Ile Ala Leu Gly Ser Ala Gln Gly Leu Ala
        755                 760                 765

Tyr Leu His His Asp Cys Ser Pro Arg Ile Ile His Arg Asp Val Lys
    770                 775                 780

Ser Ser Asn Ile Leu Leu Asp Lys Asp Phe Glu Ala His Leu Thr Asp
785                 790                 795                 800

Phe Gly Ile Ala Lys Ser Leu Cys Ile Ser Lys Thr Tyr Thr Ser Thr
                805                 810                 815

Tyr Ile Met Gly Thr Ile Gly Tyr Ile Asp Pro Glu Tyr Ala Arg Thr
            820                 825                 830

Ser Arg Leu Thr Glu Lys Ser Asp Val Tyr Ser Tyr Gly Ile Val Leu
        835                 840                 845

Leu Glu Leu Leu Thr Gly Arg Lys Ala Val Asp Asn Glu Ser Asn Leu
    850                 855                 860

His His Leu Ile Leu Thr Lys Ala Ala Asn Asp Ala Val Met Glu Thr
865                 870                 875                 880

Val Asp Pro Glu Ile Thr Cys Thr Cys Lys Asp Leu Ala Asp Val Lys
                885                 890                 895

Lys Val Phe Gln Leu Ala Leu Leu Cys Ser Lys Arg Gln Pro Ala Glu
            900                 905                 910

Arg Pro Thr Met His Glu Val Ala Arg Val Leu Glu Ser Leu Ile Pro
        915                 920                 925

Val Ala Glu Thr Lys Gln Pro Asn Pro Thr Pro Ser Leu Ala Leu Leu
    930                 935                 940

Pro Ser Ala Lys Val Pro Cys Tyr Met Asp Glu Tyr Val Asn Leu Lys
945                 950                 955                 960

Thr Pro His Leu Val Asn Cys Ser Ser Met Ser Thr Ser Asp Ala Gln
                965                 970                 975

Leu Phe Leu Lys Phe Gly Glu Val Ile Ser Gln Asn Ser Gly
            980                 985                 990


<210> SEQ ID NO 34
<211> LENGTH: 6319
<212> TYPE: DNA
<213> ORGANISM: Solanum lycopersicum

<400> SEQUENCE: 34

atggcatcat ttttactcca aagatgtaat cttctctttg aggttcttct tattttgggg      60

ttcttgattt tcttcagctt tggttctgtg gtgtctgatg atggtgagta gagtagagta     120

gtagaacttt ctgcttctta tgttttagtt taatgttttg tttaagatgt taaaaagaca     180

aagtgtgctt tttttaatca ttttttaaat ggtggttttt gattaatccc acgttttgta     240

gttgttattt gttaaaggtt tattttttttg tctcattatt ataataataa ttgggaaata     300

ggttctgcat tgttggaaat taagaagtca attagggacg tggagaatgt gttgtatgac     360

tggactgatt ctccttcatc tgattactgt gcctggagag gtgttacctg tgataatgtc     420

accttcaatg ttgttcaact gtaagacata actcaaaaac actatcattt gggattcttt     480

agttataaag ttgtaatctt ttgacattat cttgtagtaa tctttcgagt ttaaatcttg     540

atggggagtt gtctcctgta ttggacagct caaaggcctt gtatctatgt aatatctcct     600

cccattatct cacaattacc ctttttgttt gatcttttga cttagtgcac attatagact     660

atgcctgtta attttttttt gaagtgatat gaggggaaat cgcctttctg gccagatacc     720

agatttggtg actgttcagc actgaaaaat ttgtaagtat gaaatgcttc tgaatcttgt     780
```

-continued

```
gttattgttt ggaaaaataa gtaaccattt tttcccttag ggacctttcc ttcaatgagc    840
tttatggtga tattcccttc tccatatcta aactcaagca actggaatat ctgtaagttt    900
tgatactctc cttcttctaa atgttgtatt atttgctttc cgagattgtt agttgattat    960
gctcgtctta ttcaacttag gattttgaag aataatcaat tgattggacc aattccatct   1020
acattgtcac agatccctaa cttgaaggtc ttgtaagtat attctctctg ctttgtcatg   1080
atattggtag attatgaata attttagttt gatccaagaa cttcctccag ggacctggct   1140
caaaataggt taagtggaga aattcctagg ctgatatact ggaacgaagt cctgcagtat   1200
ctgtgagtgt tttaatccgg tgttcctctt cttcctgttt gttttaacct taggacactt   1260
tcatttcgta tatggatatg attacatctg ttgtatgttt ttattcatat aggggactgc   1320
gtggtaacaa cttgggtgga tccctttctc ctgatatgtg tcagctcacc ggcctgtggt   1380
acttgtaagt ttgtaatcct gttgctctta agatcttact ttagttcctc taggtgatga   1440
cattaaccat tgttcattgt gttgtacagt gatgttcgga acaatagttt gactggttcc   1500
attcctcaaa atattggcaa ctgtactgcc ttccaggttc tgtaagtatc taaatcaatt   1560
gaatgaagtt tgactatatt ctgtatgttt ggttggcata acaccttgtt ttgttctgtc   1620
agagatttgt cttataatga tttgaccgga gagattcctt tcaatattgg tttcctgcaa   1680
gtagcgacct tgtaagttta tgctgcttct cttcattaca aactattcaa tatatggttg   1740
tttgaagtgt actttcatca ttccaggtct ttgcaaggta atcgtctttc agggcagatc   1800
ccttctgtaa ttggattgat gcaagctctt gcagttttgt gagtgttttg tgtcttgata   1860
tctcaatcta atgctactga atctaattct tggaaaccat tataatgcat ctgttattta   1920
agttttctga cccttttact gtcagggact tgagctgcaa tatgttgagt ggaacaattc   1980
cttcaattct tgggaatttg acttacacag agaaattgtt agtacttcaa cattattaaa   2040
agcaatttgg atcattttgt gcttcctaaa ttgtgtagtg gatcaattac tgtaagttcg   2100
cattgtattg caggtatcta cacgggaaca agctatctgg ttccattcct ccagagctgg   2160
gaaatatgac aaagctccac tacttgtatg aatgccttct atcaatcatt ttttgttagc   2220
tttgttttgt tcttcctgtt caaacccttt taaatgaatg cttaccattt agaagcattt   2280
gtttgattat ttagcctttg ggcaaccacg gatttgaatg atagaaagct gttatgagaa   2340
tttttattaa gagactttct tcaaccttaa ggctcaaaga tggtaatttg cagggaattg   2400
aatgataacc aacttactgg acgcatacca ccagaacttg gaaagctgac agaattgttt   2460
gacttgtaaa tcccgtttct cttcatcttc tactttggac ttgttaacat cattatttat   2520
ttactcatgt tgtatgtttc agaaatgttg caaacaacca cctagatggg cccatacctt   2580
ccaatattag ctcatgtacc aatttgaata gtctgtgagt gtttttaatg tccgaagtgt   2640
ttcaattatg cacgaccatg cttgtttggt agttattgac acctgatttt gttgcagcaa   2700
cgttcatgga aacaaattga atggtactat tccacctgct tttcagaagc tggaaagtat   2760
gacctatctg taagttctta ctttctgatc tttttctttt gaagaattat gtttaaggtt   2820
atcgaagtta ccgtccatgc tgttgagcaa gattgtaaac ttactgtgcc ttgtatataa   2880
attttactgg cgttgtatta ttgaaaaaat cattttattt atattgctct caaatcatac   2940
tggcttatat ccattcatga agaatcattt ctactgtctg aagttttcag ctatatgtat   3000
cgaaaaaatt tagttattat atagtttatt ttgagcctct gcatcatcta tttgtgaatt   3060
tcatttgctt attctgcata ctctcagcat taaccgtctc ttcttttgtt aattgcttta   3120
gtaatctctc ctccaacaat ctcaaaggcc caattccaat tgagctatct cgtattggga   3180
```

atgtagatac actgtaagtg caaactttct catctacttt catttctctc attgcaatta 3240
tggttgcggg gaaagcactt tttgtcagtc ttaagaatct tcaacatttt ttggcttagg 3300
gacttatcaa acaacaggat cagtggtcct atacctatgt cccttggtga tttggaacat 3360
cttcttaaac tgtgagcata accgtcaagt tgttatgtta gcatcatata tctgttgtac 3420
ttacatccct tttgtcaatg ctgtaggaac ttaagcaaga atgaaataaa tggaaactta 3480
ccagctgaat ttggcaattt aaggagcatc atggagatgt atggaacctt gctaaattca 3540
gttactttga atttatggtt tgcttgattt tcagcttttt gactgcactc ctaattgtag 3600
tgatctgtca agcaatcacc tctctggtcc cttacctcag gaacttggtc agcttccaaa 3660
cctgtacttg ctgtaagtac ttcagattta ctttgagact ctcatcctct tagctattgg 3720
taataatctg tagagtgaat aagtatgaac ttctaaactc ggtaagtaga ttttaaaatt 3780
attttggatg ccattttcaa aaaagtagag atgaagttgg ttgtgttgct attgttttat 3840
atgatctggc ttcatatgtt cattactttg gtgttctcag ttttgcttta tattgcatta 3900
ttgcacgggg ctcaaatgca gcatatctct atcttctttt tcttgtggcc ttaattattt 3960
tacaaattaa tgaacaggaa ggtggaaaac aacaatttat caggcgatgt gatgtcctta 4020
gccagttgcc tcagtctaaa tatcttgtga gttttcaagt ccatagtaag acaccagtac 4080
aaacaaatgt tttgttaatc taatcaacct catgttagca gaaatgtctc atacaataat 4140
ctgggaggga atattccaac cggcaataat ttctctagat tttcaccaga caggtaagtg 4200
gagctattaa gattttacac aagtcacaag catttattgg tttttaattc tttgcttcta 4260
atttcttcct tttgctatgt ctccgaaaaa gcttcatagg aaatccagat ctgtgtgggt 4320
attggctcac ttctccttgt catgcatctc atccggcaga gcgaggtctg atcaaactgt 4380
aacaatcatt tggcctttac tctattgcat ttttgaagtt ccatttcact ttagacatct 4440
gcaacattta ttaagtgtga tggacagata tattgattaa tgaggaatta tcccttggtt 4500
gagcaaactt aattctgtgt tagcctggta gtagggtgta ccacaaggtt tgtcgtcatg 4560
gtttcctatg ttcacaatcc ctgattgtaa catttagatg tgtacacata tctaattaac 4620
atgaaataat cttcatttgc tggagttaca ttgacgtaaa gatgcgttag ctgtcaaatg 4680
aaactgcatt tgttttattt ccatcatcag tacattaatt aagtgcataa atattttaac 4740
agttgttgaa tgatataaga tgaatttatt ggacaattgc agtttcaatt tctaaagcag 4800
caatacttgg tattgctctg ggtggcttgg tgattcttct gatgatacta gtagcagcat 4860
gccggccaca gaaacctgca cctttcatgg aaggatctat tgataaacca ggtacaatat 4920
tttccggacg gttggatagt gtttggagat gttcatgtca gaaggacagt cgtcagagtt 4980
tattgaagtt gccatgtatt gattgtttaa cgtttttgat gaacagttta ttactcatct 5040
ccaaaacttg tgatccttca tatgaacatg gcacttcatg tttacgagga cattatgagg 5100
atgactgaga acttgagtga gaagtatata attggttgtg gagcatcaag tactgtatat 5160
aaatgtgttt tgaaaaattg caagcctgta gctatcaaga agttgtactc tcacaacccg 5220
caatacttga aggaatttga gactgaactt gagacagttg ggagtattaa gcatcgtaat 5280
cttgtctgtc tccaaggata ttctctttct ccatctggcc atcttctttt ctatgactac 5340
atggaaaatg gtagcctttg ggatttgctt catggttagt aaatccaaaa tggttaaggt 5400
gattgatgca ttgattttgt gttaaagcat caagtaatca gtcctcttgt atcttttttt 5460
gcaggtccta caacaaagaa gaaaaagctt gattgggtta ctcgccttcg aattgcattg 5520

-continued ggatcagctc aagggcttgc atatcttcat catgattgta gccctcgaat aatccaccgt 5580
gatgttaaat catctaatat cttgttggac aaagactttg aggctcatct gactgatttt 5640
ggcatagcta aaagcttatg catatcaaag acctatacgt ccacgtacat tatgggaacc 5700
attggttaca ttgatccaga gtatgctcgc acttctcgct tgacagagaa gtctgatgtt 5760
tacagctatg gtattgttct attggaattg ctcactggaa ggaaagctgt agataatgaa 5820
tctaatctac atcatttggt aagctcttgc aatttagtta atatgaactt gtcctatgat 5880
gtttattcat ataattatat taagattcaa ttcaattgat cataacagtt ttgcatatat 5940
gttacagatt ctaactaagg cagcaaacga tgctgtaatg gaaacagtgg atcctgagat 6000
aacatgcaca tgcaaagatc ttgcagatgt gaagaaggtt tttcagcttg cccttctatg 6060
ttccaaaaga cagcctgctg agagaccaac aatgcatgaa gtggcaagag tacttgaaag 6120
cctaataccc gtcgctgaaa cgaaacagcc aaatccaacc ccctcacttg cattactccc 6180
atctgctaag gtaccttgtt acatggatga atatgtcaac ctcaagacac cccacctagt 6240
gaactgttca tccatgagca cttcagatgc ccaacttttc ctcaagtttg gagaggtcat 6300
atcccagaat agtggctga 6319

<210> SEQ ID NO 35
<211> LENGTH: 2968
<212> TYPE: DNA
<213> ORGANISM: Solanum lycopersicum

<400> SEQUENCE: 35
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtctc ctgtattgga cagctcaaag 300
gccttgtatc tattgatatg aggggaaatc gcctttctgg ccagatacca gatttggtga 360
ctgttcagca ctgaaaaatt tggacctttc cttcaatgag ctttatggtg atattccctt 420
ctccatatct aaactcaagc aactggaata tctgattttg aagaataatc aattgattgg 480
accaattcca tctacattgt cacagatccc taacttgaag gtcttggacc tggctcaaaa 540
taggttaagt ggagaaattc ctaggctgat atactggaac gaagtcctgc agtatctggg 600
actgcgtggt aacaacttgg gtggatccct ttctcctgat atgtgtcagc tcaccggcct 660
gtggtacttt gatgttcgga acaatagttt gactggttcc attcctcaaa atattggcaa 720
ctgtactgcc ttccaggttc tagatttgtc ttataatgat ttgaccggag agattccttt 780
caatattggt ttcctgcaag tagcgacctt gtctttgcaa ggtaatcgtc tttcagggca 840
gatcccttct gtaattggat tgatgcaagc tcttgcagtt ttggacttga gctgcaatat 900
gttgagtgga acaattcctt caattcttgg gaatttgact tacacagaga aattgtatct 960
acacgggaac aagctatctg gttccattcc tccagagctg ggaaatatga caaagctcca 1020
ctacttggaa ttgaatgata accaacttac tggacgcata ccaccagaac ttggaaagct 1080
gacagaattg tttgacttaa atgttgcaaa caaccaccta gatgggccca taccttccaa 1140
tattagctca tgtaccaatt tgaatagtct caacgttcat ggaaacaaat tgaatggtac 1200
tattccacct gcttttcaga agctggaaag tatgacctat cttaatctct cctccaacaa 1260
tctcaaaggc ccaattccaa ttgagctatc tcgtattggg aatgtagata cactggactt 1320
atcaaacaac aggatcagtg gtcctatacc tatgtccctt ggtgatttgg aacatcttct 1380
taaactgaac ttaagcaaga atgaaataaa tggaaactta ccagctgaat ttggcaattt 1440
aaggagcatc atggagattg atctgtcaag caatcacctc tctggtccct tacctcagga 1500
acttggtcag cttccaaacc tgtacttgct gaaggtggaa aacaacaatt tatcaggcga 1560
tgtgatgtcc ttagccagtt gcctcagtct aaatatctta aatgtctcat acaataatct 1620
gggagggaat attccaaccg gcaataattt ctctagattt tcaccagaca gcttcatagg 1680
aaatccagat ctgtgtgggt attggctcac ttctccttgt catgcatctc atccggcaga 1740
gcgagtttca atttctaaag cagcaatact tggtattgct ctgggtggct tggtgattct 1800
tctgatgata ctagtagcag catgccggcc acagaaacct gcacctttca tggaaggatc 1860
tattgataaa ccagtttatt actcatctcc aaaacttgtg atccttcata tgaacatggc 1920
acttcatgtt tacgaggaca ttatgaggat gactgagaac ttgagtgaga agtatataat 1980
tggttgtgga gcatcaagta ctgtatataa atgtgttttg aaaaattgca agcctgtagc 2040
tatcaagaag ttgtactctc acaacccgca atacttgaag gaatttgaga ctgaacttga 2100
gacagttggg agtattaagc atcgtaatct tgtctgtctc caaggatatt ctctttctcc 2160
atctggccat cttcttttct atgactacat ggaaaatggt agcctttggg atttgcttca 2220
tggtcctaca acaaagaaga aaaagcttga ttgggttact cgccttcgaa ttgcattggg 2280
atcagctcaa gggcttgcat atcttcatca tgattgtagc cctcgaataa tccaccgtga 2340
tgttaaatca tctaatatct tgttggacaa agactttgag gctcatctga ctgattttgg 2400
catagctaaa agcttatgca tatcaaagac ctatacgtcc acgtacatta tgggaaccat 2460
tggttacatt gatccagagt atgctcgcac ttctcgcttg acagagaagt ctgatgttta 2520
cagctatggt attgttctat tggaattgct cactggaagg aaagctgtag ataatgaatc 2580
taatctacat catttgattc taactaaggc agcaaacgat gctgtaatgg aaacagtgga 2640
tcctgagata acatgcacat gcaaagatct tgcagatgtg aagaaggttt ttcagcttgc 2700
ccttctatgt tccaaaagac agcctgctga gagaccaaca atgcatgaag tggcaagagt 2760
acttgaaagc ctaatacccg tcgctgaaac gaaacagcca aatccaaccc cctcacttgc 2820
attactccca tctgctaagg taccttgtta catggatgaa tatgtcaacc tcaagacacc 2880
ccacctagtg aactgttcat ccatgagcac ttcagatgcc caacttttcc tcaagtttgg 2940
agaggtcata tcccagaata gtggctga 2968

<210> SEQ ID NO 36
<211> LENGTH: 106
<212> TYPE: PRT
<213> ORGANISM: Solanum lycopersicum

<400> SEQUENCE: 36

Met Ala Ser Phe Leu Leu Gln Arg Cys Asn Leu Leu Phe Glu Val Leu
1 5 10 15

Leu Ile Leu Gly Phe Leu Ile Phe Phe Ser Phe Gly Ser Val Val Ser
20 25 30

Asp Asp Gly Ser Ala Leu Leu Glu Ile Lys Lys Ser Ile Arg Asp Val
35 40 45

Glu Asn Val Leu Tyr Asp Trp Thr Asp Ser Pro Ser Ser Asp Tyr Cys
50 55 60

Ala Trp Arg Gly Val Thr Cys Asp Asn Val Thr Phe Asn Val Val Gln
65 70 75 80

-continued

```
Leu Asn Leu Ser Ser Leu Asn Leu Asp Gly Glu Leu Ser Pro Val Leu
                85                  90                  95

Asp Ser Ser Lys Ala Leu Tyr Leu Leu Ile
            100                 105

<210> SEQ ID NO 37
<211> LENGTH: 6315
<212> TYPE: DNA
<213> ORGANISM: Solanum lycopersicum

<400> SEQUENCE: 37

atggcatcat ttttactcca aagatgtaat cttctctttg aggttcttct tattttgggg      60

ttcttgattt tcttcagctt tggttctgtg gtgtctgatg atggtgagta gagtagagta     120

gtagaacttt ctgcttctta tgttttagtt taatgttttg tttaagatgt taaaaagaca     180

aagtgtgctt tttttaatca ttttttaaat ggtggttttt gattaatccc acgttttgta     240

gttgttattt gttaaaggtt tatttttttg tctcattatt ataataataa ttgggaaata     300

ggttctgcat tgttggaaat taagaagtca attagggacg tggagaatgt gttgtatgac     360

tggactgatt ctccttcatc tgattactgt gcctggagag gtgttacctg tgataatgtc     420

accttcaatg ttgttcaact gtaagacata actcaaaaac actatcattt gggattcttt     480

agttataaag ttgtaatctt ttgacattat cttgtagtaa tctttcgagt ttaaatcttg     540

atggggagtt gtcttattgg acagctcaaa ggccttgtat ctatgtaata tctcctccca     600

ttatctcaca attacccttt ttgtttgatc ttttgactta gtgcacatta tagactatgc     660

ctgttaattt ttttttgaag tgatatgagg ggaaatcgcc tttctggcca gataccagat     720

ttggtgactg ttcagcactg aaaaatttgt aagtatgaaa tgcttctgaa tcttgtgtta     780

ttgtttggaa aaataagtaa ccattttttc ccttagggac ctttccttca atgagcttta     840

tggtgatatt cccttctcca tatctaaact caagcaactg gaatatctgt aagttttgat     900

actctccttc ttctaaatgt tgtattattt gctttccgag attgttagtt gattatgctc     960

gtcttattca acttaggatt ttgaagaata atcaattgat tggaccaatt ccatctacat    1020

tgtcacagat ccctaacttg aaggtcttgt aagtatattc tctctgcttt gtcatgatat    1080

tggtagatta tgaataattt tagtttgatc caagaacttc ctccagggac ctggctcaaa    1140

ataggttaag tggagaaatt cctaggctga tatactggaa cgaagtcctg cagtatctgt    1200

gagtgtttta atccggtgtt cctcttcttc ctgtttgttt taaccttagg acactttcat    1260

ttcgtatatg gatatgatta catctgttgt atgtttttat tcatataggg gactgcgtgg    1320

taacaacttg ggtggatccc tttctcctga tatgtgtcag ctcaccggcc tgtggtactt    1380

gtaagtttgt aatcctgttg ctcttaagat cttactttag ttcctctagg tgatgacatt    1440

aaccattgtt cattgtgttg tacagtgatg ttcggaacaa tagtttgact ggttccattc    1500

ctcaaaatat tggcaactgt actgccttcc aggttctgta agtatctaaa tcaattgaat    1560

gaagtttgac tatattctgt atgtttggtt ggcataacac cttgttttgt tctgtcagag    1620

atttgtctta taatgatttg accggagaga ttcctttcaa tattggtttc ctgcaagtag    1680

cgaccttgta agtttatgct gcttctcttc attacaaact attcaatata tggttgtttg    1740

aagtgtactt tcatcattcc aggtctttgc aaggtaatcg tctttcaggg cagatccctt    1800

ctgtaattgg attgatgcaa gctcttgcag ttttgtgagt gttttgtgtc ttgatatctc    1860

aatctaatgc tactgaatct aattcttgga aaccattata atgcatctgt tatttaagtt    1920
```

-continued

```
ttctgaccct tttactgtca gggacttgag ctgcaatatg ttgagtggaa caattccttc   1980
aattcttggg aatttgactt acacagagaa attgttagta cttcaacatt attaaaagca   2040
atttggatca ttttgtgctt cctaaattgt gtagtggatc aattactgta agttcgcatt   2100
gtattgcagg tatctacacg ggaacaagct atctggttcc attcctccag agctgggaaa   2160
tatgacaaag ctccactact tgtatgaatg ccttctatca atcatttttt gttagctttg   2220
ttttgttctt cctgttcaaa cccttttaaa tgaatgctta ccatttagaa gcatttgttt   2280
gattatttag cctttgggca accacggatt tgaatgatag aaagctgtta tgagaatttt   2340
tattaagaga ctttcttcaa ccttaaggct caaagatggt aatttgcagg gaattgaatg   2400
ataaccaact tactggacgc ataccaccag aacttggaaa gctgacagaa ttgtttgact   2460
tgtaaatccc gtttctcttc atcttctact ttggacttgt taacatcatt atttatttac   2520
tcatgttgta tgtttcagaa atgttgcaaa caaccaccta gatgggccca taccttccaa   2580
tattagctca tgtaccaatt tgaatagtct gtgagtgttt ttaatgtccg aagtgtttca   2640
attatgcacg accatgcttg tttggtagtt attgacacct gattttgttg cagcaacgtt   2700
catggaaaca aattgaatgg tactattcca cctgcttttc agaagctgga aagtatgacc   2760
tatctgtaag ttcttacttt ctgatctttt tcttttgaag aattatgttt aaggttatcg   2820
aagttaccgt ccatgctgtt gagcaagatt gtaaacttac tgtgccttgt atataaattt   2880
tactggcgtt gtattattga aaaaatcatt ttatttatat tgctctcaaa tcatactggc   2940
ttatatccat tcatgaagaa tcatttctac tgtctgaagt tttcagctat atgtatcgaa   3000
aaaatttagt tattatatag tttattttga gcctctgcat catctatttg tgaatttcat   3060
ttgcttattc tgcatactct cagcattaac cgtctcttct tttgttaatt gctttagtaa   3120
tctctcctcc aacaatctca aaggcccaat tccaattgag ctatctcgta ttgggaatgt   3180
agatacactg taagtgcaaa ctttctcatc tactttcatt tctctcattg caattatggt   3240
tgcggggaaa gcactttttg tcagtcttaa gaatcttcaa catttttttgg cttagggact   3300
tatcaaacaa caggatcagt ggtcctatac ctatgtccct tggtgatttg gaacatcttc   3360
ttaaactgtg agcataaccg tcaagttgtt atgttagcat catatatctg ttgtacttac   3420
atccctttttg tcaatgctgt aggaacttaa gcaagaatga aataaatgga aacttaccag   3480
ctgaatttgg caatttaagg agcatcatgg agatgtatgg aaccttgcta aattcagtta   3540
ctttgaattt atggtttgct tgattttcag ctttttgact gcactcctaa ttgtagtgat   3600
ctgtcaagca atcacctctc tggtccctta cctcaggaac ttggtcagct tccaaacctg   3660
tacttgctgt aagtacttca gatttacttt gagactctca tcctcttagc tattggtaat   3720
aatctgtaga gtgaataagt atgaacttct aaactcggta agtagatttt aaaattattt   3780
tggatgccat tttcaaaaaa gtagagatga agttggttgt gttgctattg ttttatatga   3840
tctggcttca tatgttcatt actttggtgt tctcagtttt gctttatatt gcattattgc   3900
acggggctca aatgcagcat atctctatct tctttttctt gtggccttaa ttattttaca   3960
aattaatgaa caggaaggtg gaaaacaaca atttatcagg cgatgtgatg tccttagcca   4020
gttgcctcag tctaaatatc ttgtgagttt tcaagtccat agtaagacac cagtacaaac   4080
aaatgttttg ttaatctaat caacctcatg ttagcagaaa tgtctcatac aataatctgg   4140
gagggaatat tccaaccggc aataatttct ctagattttc accagacagg taagtggagc   4200
tattaagatt ttacacaagt cacaagcatt tattggtttt taattctttg cttctaattt   4260
cttccttttg ctatgtctcc gaaaaagctt cataggaaat ccagatctgt gtgggtattg   4320
```

gctcacttct ccttgtcatg catctcatcc ggcagagcga ggtctgatca aactgtaaca 4380
atcatttggc ctttactcta ttgcattttt gaagttccat ttcactttag acatctgcaa 4440
catttattaa gtgtgatgga cagatatatt gattaatgag gaattatccc ttggttgagc 4500
aaacttaatt ctgtgttagc ctggtagtag ggtgtaccac aaggtttgtc gtcatggttt 4560
cctatgttca caatccctga ttgtaacatt tagatgtgta cacatatcta attaacatga 4620
aataatcttc atttgctgga gttacattga cgtaaagatg cgttagctgt caaatgaaac 4680
tgcatttgtt ttatttccat catcagtaca ttaattaagt gcataaatat tttaacagtt 4740
gttgaatgat ataagatgaa tttattggac aattgcagtt tcaatttcta aagcagcaat 4800
acttggtatt gctctgggtg gcttggtgat tcttctgatg atactagtag cagcatgccg 4860
gccacagaaa cctgcacctt tcatggaagg atctattgat aaaccaggta caatattttc 4920
cggacggttg gatagtgttt ggagatgttc atgtcagaag gacagtcgtc agagtttatt 4980
gaagttgcca tgtattgatt gtttaacgtt tttgatgaac agtttattac tcatctccaa 5040
aacttgtgat ccttcatatg aacatggcac ttcatgttta cgaggacatt atgaggatga 5100
ctgagaactt gagtgagaag tatataattg gttgtggagc atcaagtact gtatataaat 5160
gtgttttgaa aaattgcaag cctgtagcta tcaagaagtt gtactctcac aacccgcaat 5220
acttgaagga atttgagact gaacttgaga cagttgggag tattaagcat cgtaatcttg 5280
tctgtctcca aggatattct ctttctccat ctggccatct tcttttctat gactacatgg 5340
aaaatggtag cctttgggat ttgcttcatg gttagtaaat ccaaaatggt taaggtgatt 5400
gatgcattga ttttgtgtta aagcatcaag taatcagtcc tcttgtatct ttttttgcag 5460
gtcctacaac aaagaagaaa aagcttgatt gggttactcg ccttcgaatt gcattgggat 5520
cagctcaagg gcttgcatat cttcatcatg attgtagccc tcgaataatc caccgtgatg 5580
ttaaatcatc taatatcttg ttggacaaag actttgaggc tcatctgact gatttttggca 5640 tagctaaaag cttatgcata tcaaagacct atacgtccac gtacattatg ggaaccattg 5700
gttacattga tccagagtat gctcgcactt ctcgcttgac agagaagtct gatgtttaca 5760
gctatggtat tgttctattg gaattgctca ctggaaggaa agctgtagat aatgaatcta 5820
atctacatca tttggtaagc tcttgcaatt tagttaatat gaacttgtcc tatgatgttt 5880
attcatataa ttatattaag attcaattca attgatcata acagttttgc atatatgtta 5940
cagattctaa ctaaggcagc aaacgatgct gtaatggaaa cagtggatcc tgagataaca 6000
tgcacatgca aagatcttgc agatgtgaag aaggtttttc agcttgccct tctatgttcc 6060
aaaagacagc ctgctgagag accaacaatg catgaagtgg caagagtact tgaaagccta 6120
atacccgtcg ctgaaacgaa acagccaaat ccaacccccct cacttgcatt actcccatct 6180
gctaaggtac cttgttacat ggatgaatat gtcaacctca agacacccca cctagtgaac 6240
tgttcatcca tgagcacttc agatgcccaa cttttcctca agtttggaga ggtcatatcc 6300
cagaatagtg gctga 6315

<210> SEQ ID NO 38
<211> LENGTH: 2964
<212> TYPE: DNA
<213> ORGANISM: Solanum lycopersicum

<400> SEQUENCE: 38
atggcatcat ttttactcca aagatgtaat cttctctttg aggttcttct tattttgggg 60

-continued

```
ttcttgattt tcttcagctt tggttctgtg gtgtctgatg atggttctgc attgttggaa    120
attaagaagt caattaggga cgtggagaat gtgttgtatg actggactga ttctccttca    180
tctgattact gtgcctggag aggtgttacc tgtgataatg tcaccttcaa tgttgttcaa    240
cttaatcttt cgagtttaaa tcttgatggg gagttgtctt attggacagc tcaaaggcct    300
tgtatctatt gatatgaggg gaaatcgcct ttctggccag ataccagatt tggtgactgt    360
tcagcactga aaaatttgga cctttccttc aatgagcttt atggtgatat tcccttctcc    420
atatctaaac tcaagcaact ggaatatctg attttgaaga ataatcaatt gattggacca    480
attccatcta cattgtcaca gatccctaac ttgaaggtct tggacctggc tcaaaatagg    540
ttaagtggag aaattcctag gctgatatac tggaacgaag tcctgcagta tctgggactg    600
cgtggtaaca acttgggtgg atccctttct cctgatatgt gtcagctcac cggcctgtgg    660
tactttgatg ttcggaacaa tagtttgact ggttccattc ctcaaaatat tggcaactgt    720
actgccttcc aggttctaga tttgtcttat aatgatttga ccggagagat tcctttcaat    780
attggtttcc tgcaagtagc gaccttgtct ttgcaaggta atcgtctttc agggcagatc    840
ccttctgtaa ttggattgat gcaagctctt gcagttttgg acttgagctg caatatgttg    900
agtggaacaa ttccttcaat tcttgggaat ttgacttaca cagagaaatt gtatctacac    960
gggaacaagc tatctggttc cattcctcca gagctgggaa atatgacaaa gctccactac   1020
ttggaattga atgataacca acttactgga cgcataccac cagaacttgg aaagctgaca   1080
gaattgtttg acttaaatgt tgcaaacaac cacctagatg ggcccatacc ttccaatatt   1140
agctcatgta ccaatttgaa tagtctcaac gttcatggaa acaaattgaa tggtactatt   1200
ccacctgctt ttcagaagct ggaaagtatg acctatctta atctctcctc caacaatctc   1260
aaaggcccaa ttccaattga gctatctcgt attgggaatg tagatacact ggacttatca   1320
aacaacagga tcagtggtcc tatacctatg tcccttggtg atttggaaca tcttcttaaa   1380
ctgaacttaa gcaagaatga aataaatgga aacttaccag ctgaatttgg caatttaagg   1440
agcatcatgg agattgatct gtcaagcaat cacctctctg gtcccttacc tcaggaactt   1500
ggtcagcttc caaacctgta cttgctgaag gtggaaaaca acaatttatc aggcgatgtg   1560
atgtccttag ccagttgcct cagtctaaat atcttaaatg tctcatacaa taatctggga   1620
gggaatattc caaccggcaa taatttctct agattttcac cagacagctt cataggaaat   1680
ccagatctgt gtgggtattg gctcacttct ccttgtcatg catctcatcc ggcagagcga   1740
gtttcaattt ctaaagcagc aatacttggt attgctctgg gtggcttggt gattcttctg   1800
atgatactag tagcagcatg ccggccacag aaacctgcac ctttcatgga aggatctatt   1860
gataaaccag tttattactc atctccaaaa cttgtgatcc ttcatatgaa catggcactt   1920
catgtttacg aggacattat gaggatgact gagaacttga gtgagaagta tataattggt   1980
tgtggagcat caagtactgt atataaatgt gttttgaaaa attgcaagcc tgtagctatc   2040
aagaagttgt actctcacaa cccgcaatac ttgaaggaat ttgagactga acttgagaca   2100
gttgggagta ttaagcatcg taatcttgtc tgtctccaag gatattctct ttctccatct   2160
ggccatcttc ttttctatga ctacatggaa aatggtagcc tttgggattt gcttcatggt   2220
cctacaacaa agaagaaaaa gcttgattgg gttactcgcc ttcgaattgc attgggatca   2280
gctcaagggc ttgcatatct tcatcatgat tgtagccctc gaataatcca ccgtgatgtt   2340
aaatcatcta atatcttgtt ggacaaagac tttgaggctc atctgactga ttttggcata   2400
gctaaaagct tatgcatatc aaagacctat acgtccacgt acattatggg aaccattggt   2460
```

tacattgatc cagagtatgc tcgcacttct cgcttgacag agaagtctga tgtttacagc 2520
tatggtattg ttctattgga attgctcact ggaaggaaag ctgtagataa tgaatctaat 2580
ctacatcatt tgattctaac taaggcagca aacgatgctg taatggaaac agtggatcct 2640
gagataacat gcacatgcaa agatcttgca gatgtgaaga aggtttttca gcttgccctt 2700
ctatgttcca aaagacagcc tgctgagaga ccaacaatgc atgaagtggc aagagtactt 2760
gaaagcctaa tacccgtcgc tgaaacgaaa cagccaaatc caaccccctc acttgcatta 2820
ctcccatctg ctaaggtacc ttgttacatg gatgaatatg tcaacctcaa gacaccccac 2880
ctagtgaact gttcatccat gagcacttca gatgcccaac ttttcctcaa gtttggagag 2940
gtcatatccc agaatagtgg ctga 2964

<210> SEQ ID NO 39
<211> LENGTH: 103
<212> TYPE: PRT
<213> ORGANISM: Solanum lycopersicum

<400> SEQUENCE: 39

Met Ala Ser Phe Leu Leu Gln Arg Cys Asn Leu Leu Phe Glu Val Leu
1 5 10 15

Leu Ile Leu Gly Phe Leu Ile Phe Phe Ser Phe Gly Ser Val Val Ser
20 25 30

Asp Asp Gly Ser Ala Leu Leu Glu Ile Lys Lys Ser Ile Arg Asp Val
35 40 45

Glu Asn Val Leu Tyr Asp Trp Thr Asp Ser Pro Ser Ser Asp Tyr Cys
50 55 60

Ala Trp Arg Gly Val Thr Cys Asp Asn Val Thr Phe Asn Val Val Gln
65 70 75 80

Leu Asn Leu Ser Ser Leu Asn Leu Asp Gly Glu Leu Ser Tyr Trp Thr
85 90 95

Ala Gln Arg Pro Cys Ile Tyr
100

<210> SEQ ID NO 40
<211> LENGTH: 6318
<212> TYPE: DNA
<213> ORGANISM: Solanum lycopersicum

<400> SEQUENCE: 40
atggcatcat ttttactcca aagatgtaat cttctctttg aggttcttct tattttgggg 60
ttcttgattt tcttcagctt tggttctgtg gtgtctgatg atggtgagta gagtagagta 120
gtagaacttt ctgcttctta tgttttagtt taatgttttg tttaagatgt taaaaagaca 180
aagtgtgctt tttttaatca ttttttaaat ggtggttttt gattaatccc acgttttgta 240
gttgttattt gttaaaggtt tattttttttg tctcattatt ataataataa ttgggaaata 300
ggttctgcat tgttggaaat taagaagtca attagggacg tggagaatgt gttgtatgac 360
tggactgatt ctccttcatc tgattactgt gcctggagag gtgttacctg tgataatgtc 420
accttcaatg ttgttcaact gtaagacata actcaaaaac actatcattt gggattcttt 480
agttataaag ttgtaatctt ttgacattat cttgtagtaa tctttcgagt ttaaatcttg 540
atggggagtt gtctattgga cagctcaaag gccttgtatc tatgtaatat ctcctcccat 600
tatctcacaa ttaccctttt tgtttgatct tttgacttag tgcacattat agactatgcc 660
tgttaatttt tttttgaagt gatatgaggg gaaatcgcct ttctggccag ataccagatg 720

-continued

```
agattggtga ctgttcagca ctgaaaaatt tgtaagtatg aaatgcttct gaatcttgtg    780
ttattgtttg gaaaaataag taaccatttt ttcccttagg gacctttcct tcaatgagct    840
ttatggtgat attcccttct ccatatctaa actcaagcaa ctggaatatc tgtaagtttt    900
gatactctcc ttcttctaaa tgttgtatta tttgctttcc gagattgtta gttgattatg    960
ctcgtcttat tcaacttagg attttgaaga ataatcaatt gattggacca attccatcta   1020
cattgtcaca gatccctaac ttgaaggtct tgtaagtata ttctctctgc tttgtcatga   1080
tattggtaga ttatgaataa ttttagtttg atccaagaac ttcctccagg gacctggctc   1140
aaaataggtt aagtggagaa attcctaggc tgatatactg gaacgaagtc ctgcagtatc   1200
tgtgagtgtt ttaatccggt gttcctcttc ttcctgtttg ttttaacctt aggacacttt   1260
catttcgtat atggatatga ttacatctgt tgtatgtttt tattcatata ggggactgcg   1320
tggtaacaac ttgggtggat ccctttctcc tgatatgtgt cagctcaccg gcctgtggta   1380
cttgtaagtt tgtaatcctg ttgctcttaa gatcttactt tagttcctct aggtgatgac   1440
attaaccatt gttcattgtg ttgtacagtg atgttcggaa caatagtttg actggttcca   1500
ttcctcaaaa tattggcaac tgtactgcct tccaggttct gtaagtatct aaatcaattg   1560
aatgaagttt gactatattc tgtatgtttg gttggcataa caccttgttt tgttctgtca   1620
gagatttgtc ttataatgat ttgaccggag agattccttt caatattggt ttcctgcaag   1680
tagcgacctt gtaagtttat gctgcttctc ttcattacaa actattcaat atatggttgt   1740
ttgaagtgta ctttcatcat tccaggtctt tgcaaggtaa tcgtctttca gggcagatcc   1800
cttctgtaat tggattgatg caagctcttg cagttttgtg agtgttttgt gtcttgatat   1860
ctcaatctaa tgctactgaa tctaattctt ggaaaccatt ataatgcatc tgttatttaa   1920
gttttctgac ccttttactg tcagggactt gagctgcaat atgttgagtg gaacaattcc   1980
ttcaattctt gggaatttga cttacacaga gaaattgtta gtacttcaac attattaaaa   2040
gcaatttgga tcattttgtg cttcctaaat tgtgtagtgg atcaattact gtaagttcgc   2100
attgtattgc aggtatctac acgggaacaa gctatctggt tccattcctc cagagctggg   2160
aaatatgaca aagctccact acttgtatga atgccttcta tcaatcattt tttgttagct   2220
ttgttttgtt cttcctgttc aaaccctttt aaatgaatgc ttaccattta gaagcatttg   2280
tttgattatt tagcctttgg gcaaccacgg atttgaatga tagaaagctg ttatgagaat   2340
ttttattaag agactttctt caaccttaag gctcaaagat ggtaatttgc agggaattga   2400
atgataacca acttactgga cgcataccac cagaacttgg aaagctgaca gaattgtttg   2460
acttgtaaat cccgtttctc ttcatcttct actttggact tgttaacatc attatttatt   2520
tactcatgtt gtatgtttca gaaatgttgc aaacaaccac ctagatgggc ccataccttc   2580
caatattagc tcatgtacca atttgaatag tctgtgagtg tttttaatgt ccgaagtgtt   2640
tcaattatgc acgaccatgc ttgtttggta gttattgaca cctgattttg ttgcagcaac   2700
gttcatggaa acaaattgaa tggtactatt ccacctgctt ttcagaagct ggaaagtatg   2760
acctatctgt aagttcttac tttctgatct ttttcttttg aagaattatg tttaaggtta   2820
tcgaagttac cgtccatgct gttgagcaag attgtaaact tactgtgcct tgtatataaa   2880
ttttactggc gttgtattat tgaaaaaatc attttattta tattgctctc aaatcatact   2940
ggcttatatc cattcatgaa gaatcatttc tactgtctga agttttcagc tatatgtatc   3000
gaaaaaattt agttattata tagtttattt tgagcctctg catcatctat ttgtgaattt   3060
```

-continued

```
catttgctta ttctgcatac tctcagcatt aaccgtctct tcttttgtta attgctttag   3120
taatctctcc tccaacaatc tcaaaggccc aattccaatt gagctatctc gtattgggaa   3180
tgtagataca ctgtaagtgc aaactttctc atctactttc atttctctca ttgcaattat   3240
ggttgcgggg aaagcacttt ttgtcagtct taagaatctt caacattttt tggcttaggg   3300
acttatcaaa caacaggatc agtggtccta tacctatgtc ccttggtgat ttggaacatc   3360
ttcttaaact gtgagcataa ccgtcaagtt gttatgttag catcatatat ctgttgtact   3420
tacatccctt ttgtcaatgc tgtaggaact taagcaagaa tgaaataaat ggaaacttac   3480
cagctgaatt tggcaattta aggagcatca tggagatgta tggaaccttg ctaaattcag   3540
ttactttgaa tttatggttt gcttgatttt cagctttttg actgcactcc taattgtagt   3600
gatctgtcaa gcaatcacct ctctggtccc ttacctcagg aacttggtca gcttccaaac   3660
ctgtacttgc tgtaagtact tcagatttac tttgagactc tcatcctctt agctattggt   3720
aataatctgt agagtgaata agtatgaact tctaaactcg gtaagtagat tttaaaatta   3780
ttttggatgc cattttcaaa aaagtagaga tgaagttggt tgtgttgcta ttgttttata   3840
tgatctggct tcatatgttc attactttgg tgttctcagt tttgctttat attgcattat   3900
tgcacggggc tcaaatgcag catatctcta tcttcttttt cttgtggcct taattatttt   3960
acaaattaat gaacaggaag gtggaaaaca acaatttatc aggcgatgtg atgtccttag   4020
ccagttgcct cagtctaaat atcttgtgag ttttcaagtc catagtaaga caccagtaca   4080
aacaaatgtt ttgttaatct aatcaacctc atgttagcag aaatgtctca tacaataatc   4140
tgggagggaa tattccaacc ggcaataatt tctctagatt ttcaccagac aggtaagtgg   4200
agctattaag attttacaca agtcacaagc atttattggt ttttaattct ttgcttctaa   4260
tttcttcctt ttgctatgtc tccgaaaaag cttcatagga aatccagatc tgtgtgggta   4320
ttggctcact tctccttgtc atgcatctca tccggcagag cgaggtctga tcaaactgta   4380
acaatcattt ggcctttact ctattgcatt tttgaagttc catttcactt tagacatctg   4440
caacatttat taagtgtgat ggacagatat attgattaat gaggaattat cccttggttg   4500
agcaaactta attctgtgtt agcctggtag tagggtgtac cacaaggttt gtcgtcatgg   4560
tttcctatgt tcacaatccc tgattgtaac atttagatgt gtacacatat ctaattaaca   4620
tgaaataatc ttcatttgct ggagttacat tgacgtaaag atgcgttagc tgtcaaatga   4680
aactgcattt gttttatttc catcatcagt acattaatta agtgcataaa tattttaaca   4740
gttgttgaat gatataagat gaatttattg gacaattgca gtttcaattt ctaaagcagc   4800
aatacttggt attgctctgg gtggcttggt gattcttctg atgatactag tagcagcatg   4860
ccggccacag aaacctgcac ctttcatgga aggatctatt gataaaccag gtacaatatt   4920
ttccggacgg ttggatagtg tttggagatg ttcatgtcag aaggacagtc gtcagagttt   4980
attgaagttg ccatgtattg attgtttaac gtttttgatg aacagtttat tactcatctc   5040
caaaacttgt gatccttcat atgaacatgg cacttcatgt ttacgaggac attatgagga   5100
tgactgagaa cttgagtgag aagtatataa ttggttgtgg agcatcaagt actgtatata   5160
aatgtgtttt gaaaaattgc aagcctgtag ctatcaagaa gttgtactct cacaacccgc   5220
aatacttgaa ggaatttgag actgaacttg agacagttgg gagtattaag catcgtaatc   5280
ttgtctgtct ccaaggatat tctctttctc catctggcca tcttcttttc tatgactaca   5340
tggaaaatgg tagcctttgg gatttgcttc atggttagta aatccaaaat ggttaaggtg   5400
attgatgcat tgattttgtg ttaaagcatc aagtaatcag tcctcttgta tcttttttg    5460
```

caggtcctac aacaaagaag aaaaagcttg attgggttac tcgccttcga attgcattgg 5520
gatcagctca agggcttgca tatcttcatc atgattgtag ccctcgaata atccaccgtg 5580
atgttaaatc atctaatatc ttgttggaca aagactttga ggctcatctg actgattttg 5640
gcatagctaa aagcttatgc atatcaaaga cctatacgtc cacgtacatt atgggaacca 5700
ttggttacat tgatccagag tatgctcgca cttctcgctt gacagagaag tctgatgttt 5760
acagctatgg tattgttcta ttggaattgc tcactggaag gaaagctgta gataatgaat 5820
ctaatctaca tcatttggta agctcttgca atttagttaa tatgaacttg tcctatgatg 5880
tttattcata taattatatt aagattcaat tcaattgatc ataacagttt tgcatatatg 5940
ttacagattc taactaaggc agcaaacgat gctgtaatgg aaacagtgga tcctgagata 6000
acatgcacat gcaaagatct tgcagatgtg aagaaggttt ttcagcttgc ccttctatgt 6060
tccaaaagac agcctgctga gagaccaaca atgcatgaag tggcaagagt acttgaaagc 6120 ctaataccccg tcgctgaaac gaaacagcca aatccaaccc cctcacttgc attactccca 6180
tctgctaagg taccttgtta catggatgaa tatgtcaacc tcaagacacc ccacctagtg 6240
aactgttcat ccatgagcac ttcagatgcc caacttttcc tcaagtttgg agaggtcata 6300
tcccagaata gtggctga 6318

<210> SEQ ID NO 41
<211> LENGTH: 2967
<212> TYPE: DNA
<213> ORGANISM: Solanum lycopersicum

<400> SEQUENCE: 41
atggcatcat ttttactcca aagatgtaat cttctctttg aggttcttct tattttgggg 60
ttcttgattt tcttcagctt tggttctgtg gtgtctgatg atggttctgc attgttggaa 120
attaagaagt caattaggga cgtggagaat gtgttgtatg actggactga ttctccttca 180
tctgattact gtgcctggag aggtgttacc tgtgataatg tcaccttcaa tgttgttcaa 240
cttaatcttt cgagtttaaa tcttgatggg gagttgtcta ttggacagct caaaggcctt 300
gtatctattg atatgagggg aaatcgcctt tctggccaga taccagatga gattggtgac 360
tgttcagcac tgaaaaattt ggacctttcc ttcaatgagc tttatggtga tattcccttc 420
tccatatcta aactcaagca actggaatat ctgattttga agaataatca attgattgga 480
ccaattccat ctacattgtc acagatccct aacttgaagg tcttggacct ggctcaaaat 540
aggttaagtg gagaaattcc taggctgata tactggaacg aagtcctgca gtatctggga 600
ctgcgtggta acaacttggg tggatccctt tctcctgata tgtgtcagct caccggcctg 660
tggtactttg atgttcggaa caatagtttg actggttcca ttcctcaaaa tattggcaac 720
tgtactgcct tccaggttct agatttgtct tataatgatt tgaccggaga gattcctttc 780
aatattggtt tcctgcaagt agcgaccttg tctttgcaag gtaatcgtct ttcagggcag 840
atcccttctg taattggatt gatgcaagct cttgcagttt tggacttgag ctgcaatatg 900
ttgagtggaa caattccttc aattcttggg aatttgactt acacagagaa attgtatcta 960
cacgggaaca agctatctgg ttccattcct ccagagctgg gaaatatgac aaagctccac 1020
tacttggaat tgaatgataa ccaacttact ggacgcatac caccagaact tggaaagctg 1080
acagaattgt ttgacttaaa tgttgcaaac aaccacctag atgggcccat accttccaat 1140
attagctcat gtaccaattt gaatagtctc aacgttcatg gaaacaaatt gaatggtact 1200
attccacctg cttttcagaa gctggaaagt atgacctatc ttaatctctc ctccaacaat 1260
ctcaaaggcc caattccaat tgagctatct cgtattggga atgtagatac actggactta 1320
tcaaacaaca ggatcagtgg tcctatacct atgtcccttg gtgatttgga acatcttctt 1380
aaactgaact taagcaagaa tgaaataaat ggaaacttac cagctgaatt tggcaattta 1440
aggagcatca tggagattga tctgtcaagc aatcacctct ctggtccctt acctcaggaa 1500
cttggtcagc ttccaaacct gtacttgctg aaggtggaaa acaacaattt atcaggcgat 1560
gtgatgtcct tagccagttg cctcagtcta aatatcttaa atgtctcata caataatctg 1620
ggagggaata ttccaaccgg caataatttc tctagatttt caccagacag cttcatagga 1680
aatccagatc tgtgtgggta ttggctcact tctccttgtc atgcatctca tccggcagag 1740
cgagtttcaa tttctaaagc agcaatactt ggtattgctc tgggtggctt ggtgattctt 1800
ctgatgatac tagtagcagc atgccggcca cagaaacctg cacctttcat ggaaggatct 1860
attgataaac cagtttatta ctcatctcca aaacttgtga tccttcatat gaacatggca 1920
cttcatgttt acgaggacat tatgaggatg actgagaact tgagtgagaa gtatataatt 1980
ggttgtggag catcaagtac tgtatataaa tgtgttttga aaaattgcaa gcctgtagct 2040
atcaagaagt tgtactctca caacccgcaa tacttgaagg aatttgagac tgaacttgag 2100
acagttggga gtattaagca tcgtaatctt gtctgtctcc aaggatattc tctttctcca 2160
tctggccatc ttcttttcta tgactacatg gaaaatggta gcctttggga tttgcttcat 2220
ggtcctacaa caaagaagaa aaagcttgat tgggttactc gccttcgaat tgcattggga 2280
tcagctcaag ggcttgcata tcttcatcat gattgtagcc ctcgaataat ccaccgtgat 2340
gttaaatcat ctaatatctt gttggacaaa gactttgagg ctcatctgac tgattttggc 2400
atagctaaaa gcttatgcat atcaaagacc tatacgtcca cgtacattat gggaaccatt 2460
ggttacattg atccagagta tgctcgcact tctcgcttga cagagaagtc tgatgtttac 2520
agctatggta ttgttctatt ggaattgctc actggaagga aagctgtaga taatgaatct 2580
aatctacatc atttgattct aactaaggca gcaaacgatg ctgtaatgga aacagtggat 2640
cctgagataa catgcacatg caaagatctt gcagatgtga agaaggtttt tcagcttgcc 2700
cttctatgtt ccaaaagaca gcctgctgag agaccaacaa tgcatgaagt ggcaagagta 2760
cttgaaagcc taatacccgt cgctgaaacg aaacagccaa atccaacccc ctcacttgca 2820
ttactcccat ctgctaaggt accttgttac atggatgaat atgtcaacct caagacaccc 2880
cacctagtga actgttcatc catgagcact tcagatgccc aacttttcct caagtttgga 2940
gaggtcatat cccagaatag tggctga 2967

<210> SEQ ID NO 42
<211> LENGTH: 988
<212> TYPE: PRT
<213> ORGANISM: Solanum lycopersicum

<400> SEQUENCE: 42

Met Ala Ser Phe Leu Leu Gln Arg Cys Asn Leu Leu Phe Glu Val Leu
1               5                   10                  15

Leu Ile Leu Gly Phe Leu Ile Phe Phe Ser Phe Gly Ser Val Val Ser
            20                  25                  30

Asp Asp Gly Ser Ala Leu Leu Glu Ile Lys Lys Ser Ile Arg Asp Val
        35                  40                  45

Glu Asn Val Leu Tyr Asp Trp Thr Asp Ser Pro Ser Ser Asp Tyr Cys
    50                  55                  60

-continued

```
Ala Trp Arg Gly Val Thr Cys Asp Asn Val Thr Phe Asn Val Val Gln
65                  70                  75                  80

Leu Asn Leu Ser Ser Leu Asn Leu Asp Gly Glu Leu Ser Ile Gly Gln
                85                  90                  95

Leu Lys Gly Leu Val Ser Ile Asp Met Arg Gly Asn Arg Leu Ser Gly
            100                 105                 110

Gln Ile Pro Asp Glu Ile Gly Asp Cys Ser Ala Leu Lys Asn Leu Asp
        115                 120                 125

Leu Ser Phe Asn Glu Leu Tyr Gly Asp Ile Pro Phe Ser Ile Ser Lys
    130                 135                 140

Leu Lys Gln Leu Glu Tyr Leu Ile Leu Lys Asn Asn Gln Leu Ile Gly
145                 150                 155                 160

Pro Ile Pro Ser Thr Leu Ser Gln Ile Pro Asn Leu Lys Val Leu Asp
                165                 170                 175

Leu Ala Gln Asn Arg Leu Ser Gly Glu Ile Pro Arg Leu Ile Tyr Trp
            180                 185                 190

Asn Glu Val Leu Gln Tyr Leu Gly Leu Arg Gly Asn Asn Leu Gly Gly
        195                 200                 205

Ser Leu Ser Pro Asp Met Cys Gln Leu Thr Gly Leu Trp Tyr Phe Asp
    210                 215                 220

Val Arg Asn Asn Ser Leu Thr Gly Ser Ile Pro Gln Asn Ile Gly Asn
225                 230                 235                 240

Cys Thr Ala Phe Gln Val Leu Asp Leu Ser Tyr Asn Asp Leu Thr Gly
                245                 250                 255

Glu Ile Pro Phe Asn Ile Gly Phe Leu Gln Val Ala Thr Leu Ser Leu
            260                 265                 270

Gln Gly Asn Arg Leu Ser Gly Gln Ile Pro Ser Val Ile Gly Leu Met
        275                 280                 285

Gln Ala Leu Ala Val Leu Asp Leu Ser Cys Asn Met Leu Ser Gly Thr
    290                 295                 300

Ile Pro Ser Ile Leu Gly Asn Leu Thr Tyr Thr Glu Lys Leu Tyr Leu
305                 310                 315                 320

His Gly Asn Lys Leu Ser Gly Ser Ile Pro Pro Glu Leu Gly Asn Met
                325                 330                 335

Thr Lys Leu His Tyr Leu Glu Leu Asn Asp Asn Gln Leu Thr Gly Arg
            340                 345                 350

Ile Pro Pro Glu Leu Gly Lys Leu Thr Glu Leu Phe Asp Leu Asn Val
        355                 360                 365

Ala Asn Asn His Leu Asp Gly Pro Ile Pro Ser Asn Ile Ser Ser Cys
    370                 375                 380

Thr Asn Leu Asn Ser Leu Asn Val His Gly Asn Lys Leu Asn Gly Thr
385                 390                 395                 400

Ile Pro Pro Ala Phe Gln Lys Leu Glu Ser Met Thr Tyr Leu Asn Leu
                405                 410                 415

Ser Ser Asn Asn Leu Lys Gly Pro Ile Pro Ile Glu Leu Ser Arg Ile
            420                 425                 430

Gly Asn Val Asp Thr Leu Asp Leu Ser Asn Asn Arg Ile Ser Gly Pro
        435                 440                 445

Ile Pro Met Ser Leu Gly Asp Leu Glu His Leu Leu Lys Leu Asn Leu
    450                 455                 460

Ser Lys Asn Glu Ile Asn Gly Asn Leu Pro Ala Glu Phe Gly Asn Leu
465                 470                 475                 480
```

```
Arg Ser Ile Met Glu Ile Asp Leu Ser Ser Asn His Leu Ser Gly Pro
                485                 490                 495

Leu Pro Gln Glu Leu Gly Gln Leu Pro Asn Leu Tyr Leu Leu Lys Val
            500                 505                 510

Glu Asn Asn Asn Leu Ser Gly Asp Val Met Ser Leu Ala Ser Cys Leu
        515                 520                 525

Ser Leu Asn Ile Leu Asn Val Ser Tyr Asn Asn Leu Gly Gly Asn Ile
    530                 535                 540

Pro Thr Gly Asn Asn Phe Ser Arg Phe Ser Pro Asp Ser Phe Ile Gly
545                 550                 555                 560

Asn Pro Asp Leu Cys Gly Tyr Trp Leu Thr Ser Pro Cys His Ala Ser
                565                 570                 575

His Pro Ala Glu Arg Val Ser Ile Ser Lys Ala Ala Ile Leu Gly Ile
            580                 585                 590

Ala Leu Gly Gly Leu Val Ile Leu Leu Met Ile Leu Val Ala Ala Cys
        595                 600                 605

Arg Pro Gln Lys Pro Ala Pro Phe Met Glu Gly Ser Ile Asp Lys Pro
    610                 615                 620

Val Tyr Tyr Ser Ser Pro Lys Leu Val Ile Leu His Met Asn Met Ala
625                 630                 635                 640

Leu His Val Tyr Glu Asp Ile Met Arg Met Thr Glu Asn Leu Ser Glu
                645                 650                 655

Lys Tyr Ile Ile Gly Cys Gly Ala Ser Ser Thr Val Tyr Lys Cys Val
            660                 665                 670

Leu Lys Asn Cys Lys Pro Val Ala Ile Lys Lys Leu Tyr Ser His Asn
        675                 680                 685

Pro Gln Tyr Leu Lys Glu Phe Glu Thr Glu Leu Glu Thr Val Gly Ser
    690                 695                 700

Ile Lys His Arg Asn Leu Val Cys Leu Gln Gly Tyr Ser Leu Ser Pro
705                 710                 715                 720

Ser Gly His Leu Leu Phe Tyr Asp Tyr Met Glu Asn Gly Ser Leu Trp
                725                 730                 735

Asp Leu Leu His Gly Pro Thr Thr Lys Lys Lys Lys Leu Asp Trp Val
            740                 745                 750

Thr Arg Leu Arg Ile Ala Leu Gly Ser Ala Gln Gly Leu Ala Tyr Leu
        755                 760                 765

His His Asp Cys Ser Pro Arg Ile Ile His Arg Asp Val Lys Ser Ser
    770                 775                 780

Asn Ile Leu Leu Asp Lys Asp Phe Glu Ala His Leu Thr Asp Phe Gly
785                 790                 795                 800

Ile Ala Lys Ser Leu Cys Ile Ser Lys Thr Tyr Thr Ser Thr Tyr Ile
                805                 810                 815

Met Gly Thr Ile Gly Tyr Ile Asp Pro Glu Tyr Ala Arg Thr Ser Arg
            820                 825                 830

Leu Thr Glu Lys Ser Asp Val Tyr Ser Tyr Gly Ile Val Leu Leu Glu
        835                 840                 845

Leu Leu Thr Gly Arg Lys Ala Val Asp Asn Glu Ser Asn Leu His His
    850                 855                 860

Leu Ile Leu Thr Lys Ala Ala Asn Asp Ala Val Met Glu Thr Val Asp
865                 870                 875                 880

Pro Glu Ile Thr Cys Thr Cys Lys Asp Leu Ala Asp Val Lys Lys Val
                885                 890                 895

Phe Gln Leu Ala Leu Leu Cys Ser Lys Arg Gln Pro Ala Glu Arg Pro
```

-continued

```
            900                 905                 910

Thr Met His Glu Val Ala Arg Val Leu Glu Ser Leu Ile Pro Val Ala
        915                 920                 925

Glu Thr Lys Gln Pro Asn Pro Thr Pro Ser Leu Ala Leu Leu Pro Ser
    930                 935                 940

Ala Lys Val Pro Cys Tyr Met Asp Glu Tyr Val Asn Leu Lys Thr Pro
945                 950                 955                 960

His Leu Val Asn Cys Ser Ser Met Ser Thr Ser Asp Ala Gln Leu Phe
                965                 970                 975

Leu Lys Phe Gly Glu Val Ile Ser Gln Asn Ser Gly
            980                 985


<210> SEQ ID NO 43
<211> LENGTH: 5721
<212> TYPE: DNA
<213> ORGANISM: Solanum lycopersicum

<400> SEQUENCE: 43

atggaagtga gcctgaaaat gaaattccgc tcgcaagcgc tactgttggt tctattgctt     60

gttttcccga tcgttttggc tctcaccgaa gaaggtaact atttttttca acacctaata    120

gctgtttcgg tattgcgttg tgtgctattt aggaaataag gaagttattg ttcgaattta    180

gttttgtatt ttcagtttct ggagctgcat tccatgctgt tttaactttg attacgaaaa    240

atccgtgtta tttgagatat atttaggctt cagtttatgg cttaaccacc ggaatactac    300

ttgataaata ctaaaaatgg ttatgactgc ttgcgcaggc aaagcattaa tgtcgatcaa    360

ggcatcgttt agcaacgtag caaacgtgtt gctggattgg gatgatatcc acgacgagga    420

tttttgctca tggagaggcg tgttgtgtgg aaatttctcc atgtccgtcg ttgcactgta    480

ggtgtttcat cctttgtttc ctaactttca ctgatacacc aggaaaaaag cagtagctga    540

attctgatga cctgctagct attgtatagc actttgttag tttagctaat agttatacgt    600

cttttatata aatttacctt ctctgcttgt gaaggaatct gtctaatctg aacttgggcg    660

gggaaatttc accagacatt ggagagttga agaatctgga gacattgtat ggtgcagttt    720

ctcttttact gttcttggtc cattgactgt cattttacct ctctgatatt acattccaat    780

gttaatgaca gagaccttca gggaaataaa ttaactggtc aagtcccaga tgaaattggc    840

aactgcattt cactgatcta tctgtaagta aaatagtttt taacctatga ttttaatatt    900

tttttcttgc atgtcagtaa atttcaagtg ctcacactaa ttgatttgct attgtctgca    960

gtgatttgtc tgataacttg ttctatggag atataccatt ctcaatttct aagctcaagc   1020

agctagagtt gttgtgagtt atttaatcac atgacattga tgttttctga taactagttg   1080

atatggttat gatgaattaa ttcattatgt ggtgcagaaa ctttaaaaac aaccagttgt   1140

ccggcccaat cccgtccaca ttaactcaaa ttcctaatct aaagacgctg tgagttccat   1200

gactttcgtt ttatctccct caaaatttag tccaatatac atgcttaaca aatggttgtt   1260

tgaatggtga agtgatctgg ctcgaaacca gctcattggt gagataccaa ggttgatcta   1320

ttggaatgaa gttctacaat atctgtgagt gcattttcct ggtgttttgg aggttttcat   1380

tttttgtttg agaaatttaa gatgtttctt taccttctgt attgcagagg attaagaggc   1440

aacatgttga caggaacatt gtcccctgat atgtgccagt tgactggctt gtggtatttg   1500

tatgtgctct gctacatgat atctatacgg gatgctctgt tgtctgtttg gtgtaatatt   1560

tatgtatatt ctaacattag aagtttcata ttatttcagt gatgtgcggg gcaataacct   1620
```

-continued

```
cagcggaata attccagata atattgggaa ttgtacaagc tttgagatac tgtcagtgtt   1680
gtcttcttgc tctgattatg ttaagctaca gttcttctcc tactgctgcc caattctaac   1740
aaaatctatt ttttcgtgat ttcaggata tctcatacaa tcagataact ggagaaattc   1800
cctacaatat tgggttttta caagtggcta ccttgttagt aaattcaact ttgtcagttc   1860
taccttgtct gttctgttat ggggttcgtt tctgtaaatg gtaaatggag attatggtcc   1920
tttcaacagg tctttgcaag gaaataggct aactggcagg atcccagaag tgattggtct   1980
tatgcaagct cttgctgttc tgtgagtatt catactagta caagaattgt ttattttttc   2040
caactccatt cttactagtt actgcttgca agtaagaagg ttcatgatgt ccgtctcctc   2100
tgtagggact tgagtgaaaa tgagttggtg ggaccaatcc ctccaatctt tggcaattta   2160
tcttacacag ggaagctgta agttttcact cctattttaa tgcatatacc tttctatgtg   2220
aggctcgttt atctgattca tttgtacatt caacaggtac ctgcacggca acaaacttac   2280
agggccagtt ccaccggagc taggaaatat gtctaaactt agttacttgt aagagcctaa   2340
gaggattaat tcacagtttc agatacatga tgtggtcacc ttgttttgct tcatgcattg   2400
agctatctta tttacaggca attaaatgac aatcagctaa tgggtcgaat tccccctgaa   2460
cttggcaaac tggaccagtt atttgaattg tgagcctttt atttttgtag taaatatttc   2520
tggttccact tcctcttgga atattgaggt cttagctatc ctctaccagg aatcttgcaa   2580
ataacaagtt ggagggacca attcctgaaa atatcagctc ctgttctgca ttgaatcagc   2640
tgtaagattg ttctgtttcc ttttgaaact tcattttttt ctctttctct tttgctagtc   2700
tattcattct gagtctcaac atatttgttt ttttctttca gtaatgttca tggcaacaac   2760
ttaaacgagt ccattccttc agggtttaag aatctggaga gcttgacgta tctgtatgtt   2820
atagtcttct gttttggcta gtggtcatga taatgatttt gaatttcttt catatggtac   2880
taacttatta gtgatatttg ttgatattta cctggcagaa atctttcagc taataaattt   2940
aagggtcaca taccttctca acttgggcga atcatcaacc ttgatacatt gtgagttctt   3000
gattgtcaag gccgataaaa tttattagtt cacgtgattc cttgtactaa aacttttatt   3060
ctttagggat ctctctggca acaatttttc tgggtctatc cctggttcta ttggagattt   3120
ggagcatctc ctcacattgt aagatattaa acatttcgat gtacaagatg tttgtatcat   3180
attgagactg gaacataatc acaatatcat tgcacattgt aggaatctga gcagcaatca   3240
tcttgatgga caaattcctg tagaatttgg caatctaaaa agtatacaga ccatgtaagt   3300
ttctgctgag agctttggtt acactgcctt caaaatgtgt actttttgta tactgatttt   3360
catgtgctga gattggcttc tatactgcct tcaacatgtg tatttttata ctgatcttct   3420
tgcgctgaga ctggcttcta ttctttcagt gatatgtcaa gcaacaagat ctctggtggc   3480
atcccaaaag agctgggaca gctgcagacc atgataactc tgtaagtaca ttagtttttg   3540
tcaagtaaat tgatgtagtg tttaatcagt tttccttaat atcacaatca attctaataa   3600
aattttgatt gactttgttt ctttttgtag tactttgaca ggtaactatc ttactggagc   3660
aatccctgac caattgacca attgtttcag cctaactagt ttgtgagttc atctatcttt   3720
gcctttaaca tcatagacag tctaattctt tgtacagtta ctgatcttat gtcattctcc   3780
ttcaggaata tatcctacaa caattttagt ggtgttgttc ctctttcacg gaatttctcg   3840
cggtttgcac ctgacaggta ttttccgaat agaatgaagc tttatcatta tatttgtgct   3900
ttagtactct agctaatgac caccttatta tggtcatcag ctttttaggg aacccatttc   3960
tttgtggcaa ctggaaaggt tcaatatgtg acccctatgc accaaggtct aacggtatga   4020
```

cttcattttt gtgcattggt tagcgaatct cttggtatgc agagtcatgt gcatcaaaat 4080
gacttgttac ttttgcagcc ttgttctcca gaacagctgt tgtttgcaca gcactgggtt 4140
tcattgcact cttatccatg gttgtagtgg ctgtgtataa gtccaaccaa ccacaccagt 4200
ttttgaaggg gcctaagacc aatcaaggta aaaattagta catgtacact ctgttctttt 4260
gtttttcagt actttcaggt atttatgttt gctttttgtc ttgtttccct ctaattccat 4320
aggctccccc aaacttgtgg ttcttcacat ggatatggcc atccatacat atgatgacat 4380
tatgaggatt accgagaact tcaatgagaa attcataata ggatatggtg cgtccagcac 4440
tgtatataaa tgtgatttga aagattcccg accaattgca gttaagcgac tttacaccgc 4500
acatccgcac agcttgcgag agtttgagac tgaactggag acaattggaa gcattaggca 4560
tagaaacctt gttagcttgc atggttactc cctttcccct catgggaatc tcctttgtta 4620
cgactacatg gagaatggtt cactctggga tctacttcat ggttagtaac ccacctttcc 4680
ttgtaatctt ttatgaagtt tcttcatgta agacagtgtt gactattggt tgatgttaat 4740
tactagtttc tctgtcggag aacagttcta ttagccaaga tttttgtgaa aatggctaat 4800
tatcaactga atacatgtca atagggcctt ccaaaaaggt gaagcttgac tgggaaacac 4860
gtctgaagat tgctgttggt gctgctcagg gtcttgctta tcttcaccac gattgcaacc 4920
caagaataat acacagagat gtaaaatctt caaacatcct tgttgatgaa aattttgagg 4980
ctcatctatc tgattttggg gttgcaaaat gcatccctac tgcaaaaact catgcatcaa 5040
ctttggtgtt gggcaccata ggttacattg accctgagta tgccaggact tccaggttaa 5100
ctgaaaagtc agacgtctac agctttggca ttgttctcct agagcttttg acaggaaaga 5160
aaccggttga taatgacttg aacctgcatc agctggtatt attctccact tatactctac 5220
gttgttactt gtaaaaaaga tttaactcag actggatata gaaaagaaca acttagctca 5280
aattatccca tcttcctata gcatttgcaa taatgtcttt tgtctattaa ctcctgtatt 5340
acatttgtct ttgaagtaat tcgatttgtg ttacagataa tgtcaaaggc ggatgataac 5400
accgtgatgg atgctgttga tcctgaggta tctgttacat gtatggattt aatgcatgtt 5460
aggaaaactt ttcagcttgc gttgctgtgt gcaaaaagat tcccatgtga gaggccaaca 5520
atgcatgagg ttgctagggt acttgtttcc ttgcttcctc ccccaccaac caaaccttgt 5580
ttagacccac ctcccaaatc cattgattat acaaaatttg tgattggtaa aggactaccg 5640
caagtccagc agggtgacaa ttcctccgaa gctcagtggc ttgttagatt tcaagaagct 5700
atatccaaaa actccctttg a 5721

<210> SEQ ID NO 44
<211> LENGTH: 2928
<212> TYPE: DNA
<213> ORGANISM: Solanum lycopersicum

<400> SEQUENCE: 44
atggaagtga gcctgaaaat gaaattccgc tcgcaagcgc tactgttggt tctattgctt 60
gttttcccga tcgttttggc tctcaccgaa gaaggcaaag cattaatgtc gatcaaggca 120
tcgtttagca acgtagcaaa cgtgttgctg gattgggatg atatccacga cgaggatttt 180
tgctcatgga gaggcgtgtt gtgtggaaat ttctccatgt ccgtcgttgc actgaatctg 240
tctaatctga acttgggcgg ggaaatttca ccagacattg gagagttgaa gaatctggag 300
acattagacc ttcagggaaa taaattaact ggtcaagtcc cagatgaaat tggcaactgc 360

-continued

```
atttcactga tctatcttga tttgtctgat aacttgttct atggagatat accattctca    420
atttctaagc tcaagcagct agagttgtta aactttaaaa acaaccagtt gtccggccca    480
atcccgtcca cattaactca aattcctaat ctaaagacgc ttgatctggc tcgaaaccag    540
ctcattggtg agataccaag gttgatctat tggaatgaag ttctacaata tctaggatta    600
agaggcaaca tgttgacagg aacattgtcc cctgatatgt gccagttgac tggcttgtgg    660
tattttgatg tgcggggcaa taacctcagc ggaataattc cagataatat tgggaattgt    720
acaagctttg agatactgga tatctcatac aatcagataa ctggagaaat tccctacaat    780
attgggtttt tacaagtggc taccttgtct ttgcaaggaa ataggctaac tggcaggatc    840
ccagaagtga ttggtcttat gcaagctctt gctgttctgg acttgagtga aaatgagttg    900
gtgggaccaa tccctccaat ctttggcaat ttatcttaca cagggaagct gtacctgcac    960
ggcaacaaac ttacagggcc agttccaccg gagctaggaa atatgtctaa acttagttac   1020
ttgcaattaa atgacaatca gctaatgggt cgaattcccc ctgaacttgg caaactggac   1080
cagttatttg aattgaatct tgcaaataac aagttggagg gaccaattcc tgaaaatatc   1140
agctcctgtt ctgcattgaa tcagcttaat gttcatggca acaacttaaa cgagtccatt   1200
ccttcagggt ttaagaatct ggagagcttg acgtatctaa atctttcagc taataaattt   1260
aagggtcaca taccttctca acttgggcga atcatcaacc ttgatacatt ggatctctct   1320
ggcaacaatt tttctgggtc tatccctggt tctattggag atttggagca tctcctcaca   1380
ttgaatctga gcagcaatca tcttgatgga caaattcctg tagaatttgg caatctaaaa   1440
agtatacaga ccattgatat gtcaagcaac aagatctctg gtggcatccc aaaagagctg   1500
ggacagctgc agaccatgat aactcttact ttgacaggta actatcttac tggagcaatc   1560
cctgaccaat tgaccaattg tttcagccta actagtttga atatatccta caacaatttt   1620
agtggtgttg ttcctctttc acggaatttc tcgcggtttg cacctgacag ctttttaggg   1680
aacccatttc tttgtggcaa ctggaaaggt tcaatatgtg acccctatgc accaaggtct   1740
aacgccttgt tctccagaac agctgttgtt tgcacagcac tgggtttcat tgcactctta   1800
tccatggttg tagtggctgt gtataagtcc aaccaaccac accagttttt gaaggggcct   1860
aagaccaatc aaggctcccc caaacttgtg gttcttcaca tggatatggc catccataca   1920
tatgatgaca ttatgaggat taccgagaac ttcaatgaga aattcataat aggatatggt   1980
gcgtccagca ctgtatataa atgtgatttg aaagattccc gaccaattgc agttaagcga   2040
ctttacaccg cacatccgca cagcttgcga gagtttgaga ctgaactgga gacaattgga   2100
agcattaggc atagaaacct tgttagcttg catggttact ccctttcccc tcatgggaat   2160
ctcctttgtt acgactacat ggagaatggt tcactctggg atctacttca tgggccttcc   2220
aaaaaggtga agcttgactg ggaaacacgt ctgaagattg ctgttggtgc tgctcagggt   2280
cttgcttatc ttcaccacga ttgcaaccca agaataatac acagagatgt aaaatcttca   2340
aacatccttg ttgatgaaaa ttttgaggct catctatctg attttggggt tgcaaaatgc   2400
atccctactg caaaaaactca tgcatcaact ttggtgttgg gcaccatagg ttacattgac   2460
cctgagtatg ccaggacttc caggttaact gaaaagtcag acgtctacag ctttggcatt   2520
gttctcctag agcttttgac aggaaagaaa ccggttgata atgacttgaa cctgcatcag   2580
ctgataatgt caaaggcgga tgataacacc gtgatggatg ctgttgatcc tgaggtatct   2640
gttacatgta tggatttaat gcatgttagg aaaacttttc agcttgcgtt gctgtgtgca   2700
aaaagattcc catgtgagag gccaacaatg catgaggttg ctagggtact tgtttccttg   2760
```

cttcctcccc caccaaccaa accttgttta gacccacctc ccaaatccat tgattataca 2820
aaatttgtga ttggtaaagg actaccgcaa gtccagcagg gtgacaattc ctccgaagct 2880
cagtggcttg ttagatttca agaagctata tccaaaaact ccctttga 2928

<210> SEQ ID NO 45
<211> LENGTH: 975
<212> TYPE: PRT
<213> ORGANISM: Solanum lycopersicum

<400> SEQUENCE: 45

```
Met Glu Val Ser Leu Lys Met Lys Phe Arg Ser Gln Ala Leu Leu Leu
1               5                   10                  15

Val Leu Leu Leu Val Phe Pro Ile Val Leu Ala Leu Thr Glu Glu Gly
            20                  25                  30

Lys Ala Leu Met Ser Ile Lys Ala Ser Phe Ser Asn Val Ala Asn Val
        35                  40                  45

Leu Leu Asp Trp Asp Asp Ile His Asp Glu Asp Phe Cys Ser Trp Arg
    50                  55                  60

Gly Val Leu Cys Gly Asn Phe Ser Met Ser Val Val Ala Leu Asn Leu
65                  70                  75                  80

Ser Asn Leu Asn Leu Gly Gly Glu Ile Ser Pro Asp Ile Gly Glu Leu
                85                  90                  95

Lys Asn Leu Glu Thr Leu Asp Leu Gln Gly Asn Lys Leu Thr Gly Gln
            100                 105                 110

Val Pro Asp Glu Ile Gly Asn Cys Ile Ser Leu Ile Tyr Leu Asp Leu
        115                 120                 125

Ser Asp Asn Leu Phe Tyr Gly Asp Ile Pro Phe Ser Ile Ser Lys Leu
    130                 135                 140

Lys Gln Leu Glu Leu Leu Asn Phe Lys Asn Asn Gln Leu Ser Gly Pro
145                 150                 155                 160

Ile Pro Ser Thr Leu Thr Gln Ile Pro Asn Leu Lys Thr Leu Asp Leu
                165                 170                 175

Ala Arg Asn Gln Leu Ile Gly Glu Ile Pro Arg Leu Ile Tyr Trp Asn
            180                 185                 190

Glu Val Leu Gln Tyr Leu Gly Leu Arg Gly Asn Met Leu Thr Gly Thr
        195                 200                 205

Leu Ser Pro Asp Met Cys Gln Leu Thr Gly Leu Trp Tyr Phe Asp Val
    210                 215                 220

Arg Gly Asn Asn Leu Ser Gly Ile Ile Pro Asp Asn Ile Gly Asn Cys
225                 230                 235                 240

Thr Ser Phe Glu Ile Leu Asp Ile Ser Tyr Asn Gln Ile Thr Gly Glu
                245                 250                 255

Ile Pro Tyr Asn Ile Gly Phe Leu Gln Val Ala Thr Leu Ser Leu Gln
            260                 265                 270

Gly Asn Arg Leu Thr Gly Arg Ile Pro Glu Val Ile Gly Leu Met Gln
        275                 280                 285

Ala Leu Ala Val Leu Asp Leu Ser Glu Asn Glu Leu Val Gly Pro Ile
    290                 295                 300

Pro Pro Ile Phe Gly Asn Leu Ser Tyr Thr Gly Lys Leu Tyr Leu His
305                 310                 315                 320

Gly Asn Lys Leu Thr Gly Pro Val Pro Pro Glu Leu Gly Asn Met Ser
                325                 330                 335

Lys Leu Ser Tyr Leu Gln Leu Asn Asp Asn Gln Leu Met Gly Arg Ile
```

-continued

```
            340                 345                 350

Pro Pro Glu Leu Gly Lys Leu Asp Gln Leu Phe Glu Leu Asn Leu Ala
        355                 360                 365

Asn Asn Lys Leu Glu Gly Pro Ile Pro Glu Asn Ile Ser Ser Cys Ser
    370                 375                 380

Ala Leu Asn Gln Leu Asn Val His Gly Asn Asn Leu Asn Glu Ser Ile
385                 390                 395                 400

Pro Ser Gly Phe Lys Asn Leu Glu Ser Leu Thr Tyr Leu Asn Leu Ser
                405                 410                 415

Ala Asn Lys Phe Lys Gly His Ile Pro Ser Gln Leu Gly Arg Ile Ile
            420                 425                 430

Asn Leu Asp Thr Leu Asp Leu Ser Gly Asn Asn Phe Ser Gly Ser Ile
        435                 440                 445

Pro Gly Ser Ile Gly Asp Leu Glu His Leu Leu Thr Leu Asn Leu Ser
    450                 455                 460

Ser Asn His Leu Asp Gly Gln Ile Pro Val Glu Phe Gly Asn Leu Lys
465                 470                 475                 480

Ser Ile Gln Thr Ile Asp Met Ser Ser Asn Lys Ile Ser Gly Gly Ile
                485                 490                 495

Pro Lys Glu Leu Gly Gln Leu Gln Thr Met Ile Thr Leu Thr Leu Thr
            500                 505                 510

Gly Asn Tyr Leu Thr Gly Ala Ile Pro Asp Gln Leu Thr Asn Cys Phe
        515                 520                 525

Ser Leu Thr Ser Leu Asn Ile Ser Tyr Asn Asn Phe Ser Gly Val Val
    530                 535                 540

Pro Leu Ser Arg Asn Phe Ser Arg Phe Ala Pro Asp Ser Phe Leu Gly
545                 550                 555                 560

Asn Pro Phe Leu Cys Gly Asn Trp Lys Gly Ser Ile Cys Asp Pro Tyr
                565                 570                 575

Ala Pro Arg Ser Asn Ala Leu Phe Ser Arg Thr Ala Val Val Cys Thr
            580                 585                 590

Ala Leu Gly Phe Ile Ala Leu Leu Ser Met Val Val Val Ala Val Tyr
        595                 600                 605

Lys Ser Asn Gln Pro His Gln Phe Leu Lys Gly Pro Lys Thr Asn Gln
    610                 615                 620

Gly Ser Pro Lys Leu Val Val Leu His Met Asp Met Ala Ile His Thr
625                 630                 635                 640

Tyr Asp Asp Ile Met Arg Ile Thr Glu Asn Phe Asn Glu Lys Phe Ile
                645                 650                 655

Ile Gly Tyr Gly Ala Ser Ser Thr Val Tyr Lys Cys Asp Leu Lys Asp
            660                 665                 670

Ser Arg Pro Ile Ala Val Lys Arg Leu Tyr Thr Ala His Pro His Ser
        675                 680                 685

Leu Arg Glu Phe Glu Thr Glu Leu Glu Thr Ile Gly Ser Ile Arg His
    690                 695                 700

Arg Asn Leu Val Ser Leu His Gly Tyr Ser Leu Ser Pro His Gly Asn
705                 710                 715                 720

Leu Leu Cys Tyr Asp Tyr Met Glu Asn Gly Ser Leu Trp Asp Leu Leu
                725                 730                 735

His Gly Pro Ser Lys Lys Val Lys Leu Asp Trp Glu Thr Arg Leu Lys
            740                 745                 750

Ile Ala Val Gly Ala Ala Gln Gly Leu Ala Tyr Leu His His Asp Cys
        755                 760                 765
```

```
Asn Pro Arg Ile Ile His Arg Asp Val Lys Ser Ser Asn Ile Leu Val
    770                 775                 780

Asp Glu Asn Phe Glu Ala His Leu Ser Asp Phe Gly Val Ala Lys Cys
785                 790                 795                 800

Ile Pro Thr Ala Lys Thr His Ala Ser Thr Leu Val Leu Gly Thr Ile
                805                 810                 815

Gly Tyr Ile Asp Pro Glu Tyr Ala Arg Thr Ser Arg Leu Thr Glu Lys
            820                 825                 830

Ser Asp Val Tyr Ser Phe Gly Ile Val Leu Leu Glu Leu Leu Thr Gly
        835                 840                 845

Lys Lys Pro Val Asp Asn Asp Leu Asn Leu His Gln Leu Ile Met Ser
    850                 855                 860

Lys Ala Asp Asp Asn Thr Val Met Asp Ala Val Asp Pro Glu Val Ser
865                 870                 875                 880

Val Thr Cys Met Asp Leu Met His Val Arg Lys Thr Phe Gln Leu Ala
                885                 890                 895

Leu Leu Cys Ala Lys Arg Phe Pro Cys Glu Arg Pro Thr Met His Glu
            900                 905                 910

Val Ala Arg Val Leu Val Ser Leu Leu Pro Pro Pro Pro Thr Lys Pro
        915                 920                 925

Cys Leu Asp Pro Pro Pro Lys Ser Ile Asp Tyr Thr Lys Phe Val Ile
    930                 935                 940

Gly Lys Gly Leu Pro Gln Val Gln Gln Gly Asp Asn Ser Ser Glu Ala
945                 950                 955                 960

Gln Trp Leu Val Arg Phe Gln Glu Ala Ile Ser Lys Asn Ser Leu
                965                 970                 975


<210> SEQ ID NO 46
<211> LENGTH: 5720
<212> TYPE: DNA
<213> ORGANISM: Solanum lycopersicum

<400> SEQUENCE: 46

atggaagtga gcctgaaaat gaaattccgc tcgcaagcgc tactgttggt tctattgctt      60

gttttcccga tcgttttggc tctcaccgaa gaaggtaact attttttca acacctaata     120

gctgtttcgg tattgcgttg tgtgctattt aggaaataag gaagttattg ttcgaattta    180

gttttgtatt ttcagtttct ggagctgcat tccatgctgt tttaactttg attacgaaaa    240

atccgtgtta tttgagatat atttaggctt cagtttatgg cttaaccacc ggaatactac    300

ttgataaata ctaaaaatgg ttatgactgc ttgcgcaggc aaagcattaa tgtcgatcaa    360

ggcatcgttt agcaacgtag caaacgtgtt gctggattgg gatgatatcc acgacgagga    420

tttttgctca tggagaggcg tgttgtgtgg aaatttctcc atgtccgtcg ttgcactgta    480

ggtgtttcat cctttgtttc ctaactttca ctgatacacc aggaaaaaag cagtagctga    540

attctgatga cctgctagct attgtatagc actttgttag tttagctaat agttatacgt    600

cttttatata aatttacctt ctctgcttgt gaaggaatct gtctaatctg aacttgggcg    660

gggaaatttc accagacatt ggagagttga agaatctgga gacattgtat ggtgcagttt    720

ctcttttact gttcttggtc cattgactgt cattttacct ctctgatatt acattccaat    780

gttaatgaca gagacctcag ggaaataaat taactggtca agtcccagat gaaattggca    840

actgcatttc actgatctat ctgtaagtaa aatagttttt aacctatgat tttaatattt    900

ttttcttgca tgtcagtaaa tttcaagtgc tcacactaat tgatttgcta ttgtctgcag    960
```

-continued

```
tgatttgtct gataacttgt tctatggaga tataccattc tcaatttcta agctcaagca   1020
gctagagttg ttgtgagtta tttaatcaca tgacattgat gttttctgat aactagttga   1080
tatggttatg atgaattaat tcattatgtg gtgcagaaac tttaaaaaca accagttgtc   1140
cggcccaatc ccgtccacat taactcaaat tcctaatcta aagacgctgt gagttccatg   1200
actttcgttt tatctccctc aaaatttagt ccaatataca tgcttaacaa atggttgttt   1260
gaatggtgaa gtgatctggc tcgaaaccag ctcattggtg agataccaag gttgatctat   1320
tggaatgaag ttctacaata tctgtgagtg cattttcctg gtgttttgga ggttttcatt   1380
ttttgtttga gaaatttaag atgtttcttt accttctgta ttgcagagga ttaagaggca   1440
acatgttgac aggaacattg tcccctgata tgtgccagtt gactggcttg tggtatttgt   1500
atgtgctctg ctacatgata tctatacggg atgctctgtt gtctgtttgg tgtaatattt   1560
atgtatattc taacattaga agtttcatat tatttcagtg atgtgcgggg caataacctc   1620
agcggaataa ttccagataa tattgggaat tgtacaagct ttgagatact gtcagtgttg   1680
tcttcttgct ctgattatgt taagctacag ttcttctcct actgctgccc aattctaaca   1740
aaatctattt tttcgtgatt tcagggatat ctcatacaat cagataactg gagaaattcc   1800
ctacaatatt gggtttttac aagtggctac cttgttagta aattcaactt tgtcagttct   1860
accttgtctg ttctgttatg gggttcgttt ctgtaaatgg taaatggaga ttatggtcct   1920
ttcaacaggt ctttgcaagg aaataggcta actggcagga tcccagaagt gattggtctt   1980
atgcaagctc ttgctgttct gtgagtattc atactagtac aagaattgtt tattttttcc   2040
aactccattc ttactagtta ctgcttgcaa gtaagaaggt tcatgatgtc cgtctcctct   2100
gtagggactt gagtgaaaat gagttggtgg gaccaatccc tccaatcttt ggcaatttat   2160
cttacacagg gaagctgtaa gttttcactc ctattttaat gcatatacct ttctatgtga   2220
ggctcgttta tctgattcat ttgtacattc aacaggtacc tgcacggcaa caaacttaca   2280
gggccagttc caccggagct aggaaatatg tctaaactta gttacttgta agagcctaag   2340
aggattaatt cacagtttca gatacatgat gtggtcacct tgttttgctt catgcattga   2400
gctatcttat ttacaggcaa ttaaatgaca atcagctaat gggtcgaatt ccccctgaac   2460
ttggcaaact ggaccagtta tttgaattgt gagcctttta tttttgtagt aaatatttct   2520
ggttccactt cctcttggaa tattgaggtc ttagctatcc tctaccagga atcttgcaaa   2580
taacaagttg gagggaccaa ttcctgaaaa tatcagctcc tgttctgcat tgaatcagct   2640
gtaagattgt tctgtttcct tttgaaactt cattttttc tctttctctt ttgctagtct    2700
attcattctg agtctcaaca tatttgtttt tttctttcag taatgttcat ggcaacaact   2760
taaacgagtc cattccttca gggtttaaga atctggagag cttgacgtat ctgtatgtta   2820
tagtcttctg ttttggctag tggtcatgat aatgattttg aatttctttc atatggtact   2880
aacttattag tgatatttgt tgatatttac ctggcagaaa tctttcagct aataaattta   2940
agggtcacat accttctcaa cttgggcgaa tcatcaacct tgatacattg tgagttcttg   3000
attgtcaagg ccgataaaat ttattagttc acgtgattcc ttgtactaaa acttttattc   3060
tttagggatc tctctggcaa caatttttct gggtctatcc ctggttctat tggagatttg   3120
gagcatctcc tcacattgta agatattaaa catttcgatg tacaagatgt ttgtatcata   3180
ttgagactgg aacataatca caatatcatt gcacattgta ggaatctgag cagcaatcat   3240
cttgatggac aaattcctgt agaatttggc aatctaaaaa gtatacagac catgtaagtt   3300
```

```
tctgctgaga gctttggtta cactgccttc aaaatgtgta ctttttgtat actgattttc   3360
atgtgctgag attggcttct atactgcctt caacatgtgt atttttatac tgatcttctt   3420
gcgctgagac tggcttctat tctttcagtg atatgtcaag caacaagatc tctggtggca   3480
tcccaaaaga gctgggacag ctgcagacca tgataactct gtaagtacat tagtttttgt   3540
caagtaaatt gatgtagtgt ttaatcagtt ttccttaata tcacaatcaa ttctaataaa   3600
attttgattg actttgtttc tttttgtagt actttgacag gtaactatct tactggagca   3660
atccctgacc aattgaccaa ttgtttcagc ctaactagtt tgtgagttca tctatctttg   3720
cctttaacat catagacagt ctaattcttt gtacagttac tgatcttatg tcattctcct   3780
tcaggaatat atcctacaac aattttagtg gtgttgttcc tctttcacgg aatttctcgc   3840
ggtttgcacc tgacaggtat tttccgaata gaatgaagct ttatcattat atttgtgctt   3900
tagtactcta gctaatgacc accttattat ggtcatcagc tttttaggga acccatttct   3960
ttgtggcaac tggaaaggtt caatatgtga cccctatgca ccaaggtcta acggtatgac   4020
ttcatttttg tgcattggtt agcgaatctc ttggtatgca gagtcatgtg catcaaaatg   4080
acttgttact tttgcagcct tgttctccag aacagctgtt gtttgcacag cactgggttt   4140
cattgcactc ttatccatgg ttgtagtggc tgtgtataag tccaaccaac cacaccagtt   4200
tttgaagggg cctaagacca atcaaggtaa aaattagtac atgtacactc tgttcttttg   4260
tttttcagta ctttcaggta tttatgtttg ctttttgtct tgtttccctc taattccata   4320
ggctccccca aacttgtggt tcttcacatg gatatggcca tccatacata tgatgacatt   4380
atgaggatta ccgagaactt caatgagaaa ttcataatag gatatggtgc gtccagcact   4440
gtatataaat gtgatttgaa agattcccga ccaattgcag ttaagcgact ttacaccgca   4500
catccgcaca gcttgcgaga gtttgagact gaactggaga caattggaag cattaggcat   4560
agaaaccttg ttagcttgca tggttactcc ctttcccctc atgggaatct cctttgttac   4620
gactacatgg agaatggttc actctgggat ctacttcatg gttagtaacc cacctttcct   4680
tgtaatcttt tatgaagttt cttcatgtaa gacagtgttg actattggtt gatgttaatt   4740
actagtttct ctgtcggaga acagttctat tagccaagat tttgtgaaa atggctaatt   4800
atcaactgaa tacatgtcaa tagggccttc caaaaaggtg aagcttgact gggaaacacg   4860
tctgaagatt gctgttggtg ctgctcaggg tcttgcttat cttcaccacg attgcaaccc   4920
aagaataata cacagagatg taaaatcttc aaacatcctt gttgatgaaa attttgaggc   4980
tcatctatct gattttgggg ttgcaaaatg catccctact gcaaaaactc atgcatcaac   5040
tttggtgttg ggcaccatag gttacattga ccctgagtat gccaggactt ccaggttaac   5100
tgaaaagtca gacgtctaca gctttggcat tgttctccta gagcttttga caggaaagaa   5160
accggttgat aatgacttga acctgcatca gctggtatta ttctccactt atactctacg   5220
ttgttacttg taaaaaagat ttaactcaga ctggatatag aaaagaacaa cttagctcaa   5280
attatcccat cttcctatag catttgcaat aatgtctttt gtctattaac tcctgtatta   5340
catttgtctt tgaagtaatt cgatttgtgt tacagataat gtcaaaggcg gatgataaca   5400
ccgtgatgga tgctgttgat cctgaggtat ctgttacatg tatggattta atgcatgtta   5460
ggaaaacttt tcagcttgcg ttgctgtgtg caaaaagatt cccatgtgag aggccaacaa   5520
tgcatgaggt tgctagggta cttgtttcct tgcttcctcc cccaccaacc aaaccttgtt   5580
tagacccacc tcccaaatcc attgattata caaaatttgt gattggtaaa ggactaccgc   5640
aagtccagca gggtgacaat tcctccgaag ctcagtggct tgttagattt caagaagcta   5700
```

tatccaaaaa ctccctttga 5720

<210> SEQ ID NO 47
<211> LENGTH: 2927
<212> TYPE: DNA
<213> ORGANISM: Solanum lycopersicum

<400> SEQUENCE: 47
atggaagtga gcctgaaaat gaaattccgc tcgcaagcgc tactgttggt tctattgctt 60
gttttcccga tcgttttggc tctcaccgaa gaaggcaaag cattaatgtc gatcaaggca 120
tcgtttagca acgtagcaaa cgtgttgctg gattgggatg atatccacga cgaggatttt 180
tgctcatgga gaggcgtgtt gtgtggaaat ttctccatgt ccgtcgttgc actgaatctg 240
tctaatctga acttgggcgg ggaaatttca ccagacattg gagagttgaa gaatctggag 300
acattagacc tcagggaaat aaattaactg gtcaagtccc agatgaaatt ggcaactgca 360
tttcactgat ctatcttgat ttgtctgata acttgttcta tggagatata ccattctcaa 420
tttctaagct caagcagcta gagttgttaa actttaaaaa caaccagttg tccggcccaa 480
tcccgtccac attaactcaa attcctaatc taaagacgct tgatctggct cgaaaccagc 540
tcattggtga gataccaagg ttgatctatt ggaatgaagt tctacaatat ctaggattaa 600
gaggcaacat gttgacagga acattgtccc ctgatatgtg ccagttgact ggcttgtggt 660
attttgatgt gcggggcaat aacctcagcg gaataattcc agataatatt gggaattgta 720
caagctttga gatactggat atctcataca atcagataac tggagaaatt ccctacaata 780
ttgggttttt acaagtggct accttgtctt tgcaaggaaa taggctaact ggcaggatcc 840
cagaagtgat tggtcttatg caagctcttg ctgttctgga cttgagtgaa aatgagttgg 900
tgggaccaat ccctccaatc tttggcaatt tatcttacac agggaagctg tacctgcacg 960
gcaacaaact tacagggcca gttccaccgg agctaggaaa tatgtctaaa cttagttact 1020
tgcaattaaa tgacaatcag ctaatgggtc gaattccccc tgaacttggc aaactggacc 1080
agttatttga attgaatctt gcaaataaca agttggaggg accaattcct gaaaatatca 1140
gctcctgttc tgcattgaat cagcttaatg ttcatggcaa caacttaaac gagtccattc 1200
cttcagggtt taagaatctg gagagcttga cgtatctaaa tctttcagct aataaattta 1260
agggtcacat accttctcaa cttgggcgaa tcatcaacct tgatacattg gatctctctg 1320
gcaacaattt ttctgggtct atccctggtt ctattggaga tttggagcat ctcctcacat 1380
tgaatctgag cagcaatcat cttgatggac aaattcctgt agaatttggc aatctaaaaa 1440
gtatacagac cattgatatg tcaagcaaca agatctctgg tggcatccca aaagagctgg 1500
gacagctgca gaccatgata actcttactt tgacaggtaa ctatcttact ggagcaatcc 1560
ctgaccaatt gaccaattgt ttcagcctaa ctagtttgaa tatatcctac aacaatttta 1620
gtggtgttgt tcctctttca cggaatttct cgcggtttgc acctgacagc tttttaggga 1680
acccatttct ttgtggcaac tggaaaggtt caatatgtga cccctatgca ccaaggtcta 1740
acgccttgtt ctccagaaca gctgttgttt gcacagcact gggtttcatt gcactcttat 1800
ccatggttgt agtggctgtg tataagtcca accaaccaca ccagtttttg aaggggccta 1860
agaccaatca aggctccccc aaacttgtgg ttcttcacat ggatatggcc atccatacat 1920
atgatgacat tatgaggatt accgagaact tcaatgagaa attcataata ggatatggtg 1980
cgtccagcac tgtatataaa tgtgatttga aagattcccg accaattgca gttaagcgac 2040

```
tttacaccgc acatccgcac agcttgcgag agtttgagac tgaactggag acaattggaa   2100

gcattaggca tagaaacctt gttagcttgc atggttactc cctttcccct catgggaatc   2160

tcctttgtta cgactacatg gagaatggtt cactctggga tctacttcat gggccttcca   2220

aaaaggtgaa gcttgactgg gaaacacgtc tgaagattgc tgttggtgct gctcagggtc   2280

ttgcttatct tcaccacgat tgcaacccaa gaataataca cagagatgta aaatcttcaa   2340

acatccttgt tgatgaaaat tttgaggctc atctatctga ttttggggtt gcaaaatgca   2400

tccctactgc aaaaactcat gcatcaactt tggtgttggg caccataggt tacattgacc   2460

ctgagtatgc caggacttcc aggttaactg aaaagtcaga cgtctacagc tttggcattg   2520

ttctcctaga gcttttgaca ggaaagaaac cggttgataa tgacttgaac ctgcatcagc   2580

tgataatgtc aaaggcggat gataacaccg tgatggatgc tgttgatcct gaggtatctg   2640

ttacatgtat ggatttaatg catgttagga aaacttttca gcttgcgttg ctgtgtgcaa   2700

aaagattccc atgtgagagg ccaacaatgc atgaggttgc tagggtactt gtttccttgc   2760

ttcctccccc accaaccaaa ccttgtttag acccacctcc caaatccatt gattatacaa   2820

aatttgtgat tggtaaagga ctaccgcaag tccagcaggg tgacaattcc tccgaagctc   2880

agtggcttgt tagatttcaa gaagctatat ccaaaaactc cctttga                 2927
```

```
<210> SEQ ID NO 48
<211> LENGTH: 108
<212> TYPE: PRT
<213> ORGANISM: Solanum lycopersicum

<400> SEQUENCE: 48

Met Glu Val Ser Leu Lys Met Lys Phe Arg Ser Gln Ala Leu Leu Leu
1               5                   10                  15

Val Leu Leu Leu Val Phe Pro Ile Val Leu Ala Leu Thr Glu Glu Gly
            20                  25                  30

Lys Ala Leu Met Ser Ile Lys Ala Ser Phe Ser Asn Val Ala Asn Val
        35                  40                  45

Leu Leu Asp Trp Asp Asp Ile His Asp Glu Asp Phe Cys Ser Trp Arg
    50                  55                  60

Gly Val Leu Cys Gly Asn Phe Ser Met Ser Val Val Ala Leu Asn Leu
65                  70                  75                  80

Ser Asn Leu Asn Leu Gly Gly Glu Ile Ser Pro Asp Ile Gly Glu Leu
                85                  90                  95

Lys Asn Leu Glu Thr Leu Asp Leu Arg Glu Ile Asn
            100                 105
```

```
<210> SEQ ID NO 49
<211> LENGTH: 5722
<212> TYPE: DNA
<213> ORGANISM: Solanum lycopersicum

<400> SEQUENCE: 49

atggaagtga gcctgaaaat gaaattccgc tcgcaagcgc tactgttggt tctattgctt     60

gttttcccga tcgttttggc tctcaccgaa gaaggtaact atttttttca acacctaata    120

gctgtttcgg tattgcgttg tgtgctattt aggaaataag gaagttattg ttcgaattta    180

gttttgtatt ttcagtttct ggagctgcat tccatgctgt tttaactttg attacgaaaa    240

atccgtgtta tttgagatat atttaggctt cagtttatgg cttaaccacc ggaatactac    300

ttgataaata ctaaaaatgg ttatgactgc ttgcgcaggc aaagcattaa tgtcgatcaa    360
```

```
ggcatcgttt agcaacgtag caaacgtgtt tgctggattg ggatgatatc cacgacgagg    420
atttttgctc atggagaggc gtgttgtgtg gaaatttctc catgtccgtc gttgcactgt    480
aggtgtttca tcctttgttt cctaactttc actgatacac caggaaaaaa gcagtagctg    540
aattctgatg acctgctagc tattgtatag cactttgtta gtttagctaa tagttatacg    600
tcttttatat aaatttacct tctctgcttg tgaaggaatc tgtctaatct gaacttgggc    660
ggggaaattt caccagacat tggagagttg aagaatctgg agacattgta tggtgcagtt    720
tctcttttac tgttcttggt ccattgactg tcattttacc tctctgatat tacattccaa    780
tgttaatgac agagaccttc agggaaataa attaactggt caagtcccag atgaaattgg    840
caactgcatt tcactgatct atctgtaagt aaaatagttt ttaacctatg attttaatat    900
tttttcttg catgtcagta aatttcaagt gctcacacta attgatttgc tattgtctgc    960
agtgatttgt ctgataactt gttctatgga gatataccat tctcaatttc taagctcaag   1020
cagctagagt tgttgtgagt tatttaatca catgacattg atgttttctg ataactagtt   1080
gatatggtta tgatgaatta attcattatg tggtgcagaa actttaaaaa caaccagttg   1140
tccggcccaa tcccgtccac attaactcaa attcctaatc taaagacgct gtgagttcca   1200
tgactttcgt tttatctccc tcaaaattta gtccaatata catgcttaac aaatggttgt   1260
ttgaatggtg aagtgatctg gctcgaaacc agctcattgg tgagatacca aggttgatct   1320
attggaatga agttctacaa tatctgtgag tgcattttcc tggtgttttg gaggttttca   1380
tttttgttt gagaaattta agatgtttct ttaccttctg tattgcagag gattaagagg   1440
caacatgttg acaggaacat tgtcccctga tatgtgccag ttgactggct tgtggtattt   1500
gtatgtgctc tgctacatga tatctatacg ggatgctctg ttgtctgttt ggtgtaatat   1560
ttatgtatat tctaacatta gaagtttcat attatttcag tgatgtgcgg ggcaataacc   1620
tcagcggaat aattccagat aatattggga attgtacaag ctttgagata ctgtcagtgt   1680
tgtcttcttg ctctgattat gttaagctac agttcttctc ctactgctgc ccaattctaa   1740
caaaatctat tttttcgtga tttcagggat atctcataca atcagataac tggagaaatt   1800
ccctacaata ttgggttttt acaagtggct accttgttag taaattcaac tttgtcagtt   1860
ctaccttgtc tgttctgtta tggggttcgt ttctgtaaat ggtaaatgga gattatggtc   1920
ctttcaacag gtctttgcaa ggaaatagc taactggcag gatcccagaa gtgattggtc   1980
ttatgcaagc tcttgctgtt ctgtgagtat tcatactagt acaagaattg tttattttt    2040
ccaactccat tcttactagt tactgcttgc aagtaagaag gttcatgatg tccgtctcct   2100
ctgtagggac ttgagtgaaa atgagttggt gggaccaatc cctccaatct ttggcaattt   2160
atcttacaca gggaagctgt aagttttcac tcctatttta atgcatatac ctttctatgt   2220
gaggctcgtt tatctgattc atttgtacat tcaacaggta cctgcacggc aacaaactta   2280
cagggccagt tccaccggag ctaggaaata tgtctaaact tagttacttg taagagccta   2340
agaggattaa ttcacagttt cagatacatg atgtggtcac cttgttttgc ttcatgcatt   2400
gagctatctt atttacaggc aattaaatga caatcagcta atgggtcgaa ttccccctga   2460
acttggcaaa ctggaccagt tatttgaatt gtgagccttt tatttttgta gtaaatattt   2520
ctggttccac ttcctcttgg aatattgagg tcttagctat cctctaccag gaatcttgca   2580
aataacaagt tggagggacc aattcctgaa aatatcagct cctgttctgc attgaatcag   2640
ctgtaagatt gttctgtttc cttttgaaac ttcatttttt tctctttctc ttttgctagt   2700
ctattcattc tgagtctcaa catatttgtt tttttctttc agtaatgttc atggcaacaa   2760
```

cttaaacgag tccattcctt cagggtttaa gaatctggag agcttgacgt atctgtatgt 2820
tatagtcttc tgttttggct agtggtcatg ataatgattt tgaatttctt tcatatggta 2880
ctaacttatt agtgatattt gttgatattt acctggcaga aatctttcag ctaataaatt 2940
taagggtcac ataccttctc aacttgggcg aatcatcaac cttgatacat tgtgagttct 3000
tgattgtcaa ggccgataaa atttattagt tcacgtgatt ccttgtacta aaacttttat 3060
tctttaggga tctctctggc aacaattttt ctgggtctat ccctggttct attggagatt 3120
tggagcatct cctcacattg taagatatta aacatttcga tgtacaagat gtttgtatca 3180
tattgagact ggaacataat cacaatatca ttgcacattg taggaatctg agcagcaatc 3240
atcttgatgg acaaattcct gtagaatttg gcaatctaaa aagtatacag accatgtaag 3300
tttctgctga gagctttggt tacactgcct tcaaaatgtg tactttttgt atactgattt 3360
tcatgtgctg agattggctt ctatactgcc ttcaacatgt gtatttttat actgatcttc 3420
ttgcgctgag actggcttct attctttcag tgatatgtca agcaacaaga tctctggtgg 3480
catcccaaaa gagctgggac agctgcagac catgataact ctgtaagtac attagttttt 3540
gtcaagtaaa ttgatgtagt gtttaatcag ttttccttaa tatcacaatc aattctaata 3600
aaattttgat tgactttgtt tctttttgta gtactttgac aggtaactat cttactggag 3660
caatccctga ccaattgacc aattgtttca gcctaactag tttgtgagtt catctatctt 3720
tgcctttaac atcatagaca gtctaattct ttgtacagtt actgatctta tgtcattctc 3780
cttcaggaat atatcctaca acaattttag tggtgttgtt cctctttcac ggaatttctc 3840
gcggtttgca cctgacaggt attttccgaa tagaatgaag ctttatcatt atatttgtgc 3900
tttagtactc tagctaatga ccaccttatt atggtcatca gctttttagg gaacccattt 3960
ctttgtggca actggaaagg ttcaatatgt gacccctatg caccaaggtc taacggtatg 4020
acttcatttt tgtgcattgg ttagcgaatc tcttggtatg cagagtcatg tgcatcaaaa 4080
tgacttgtta cttttgcagc cttgttctcc agaacagctg ttgtttgcac agcactgggt 4140
ttcattgcac tcttatccat ggttgtagtg gctgtgtata agtccaacca accacaccag 4200
tttttgaagg ggcctaagac caatcaaggt aaaaaattagt acatgtacac tctgttcttt 4260
tgtttttcag tactttcagg tatttatgtt tgctttttgt cttgtttccc tctaattcca 4320
taggctcccc caaacttgtg gttcttcaca tggatatggc catccataca tatgatgaca 4380
ttatgaggat taccgagaac ttcaatgaga aattcataat aggatatggt gcgtccagca 4440
ctgtatataa atgtgatttg aaagattccc gaccaattgc agttaagcga ctttacaccg 4500
cacatccgca cagcttgcga gagtttgaga ctgaactgga gacaattgga agcattaggc 4560
atagaaacct tgttagcttg catggttact ccctttcccc tcatgggaat ctcctttgtt 4620
acgactacat ggagaatggt tcactctggg atctacttca tggttagtaa cccacctttc 4680
cttgtaatct tttatgaagt ttcttcatgt aagacagtgt tgactattgg ttgatgttaa 4740
ttactagttt ctctgtcgga gaacagttct attagccaag atttttgtga aaatggctaa 4800
ttatcaactg aatacatgtc aatagggcct tccaaaaagg tgaagcttga ctgggaaaca 4860
cgtctgaaga ttgctgttgg tgctgctcag ggtcttgctt atcttcacca cgattgcaac 4920
ccaagaataa tacacagaga tgtaaaatct tcaaacatcc ttgttgatga aaattttgag 4980
gctcatctat ctgattttgg ggttgcaaaa tgcatcccta ctgcaaaaac tcatgcatca 5040
actttggtgt tgggcaccat aggttacatt gaccctgagt atgccaggac ttccaggtta 5100

-continued

```
actgaaaagt cagacgtcta cagctttggc attgttctcc tagagctttt gacaggaaag   5160

aaaccggttg ataatgactt gaacctgcat cagctggtat tattctccac ttatactcta   5220

cgttgttact tgtaaaaaag atttaactca gactggatat agaaaagaac aacttagctc   5280

aaattatccc atcttcctat agcatttgca ataatgtctt ttgtctatta actcctgtat   5340

tacatttgtc tttgaagtaa ttcgatttgt gttacagata atgtcaaagg cggatgataa   5400

caccgtgatg gatgctgttg atcctgaggt atctgttaca tgtatggatt taatgcatgt   5460

taggaaaact tttcagcttg cgttgctgtg tgcaaaaaga ttcccatgtg agaggccaac   5520

aatgcatgag gttgctaggg tacttgtttc cttgcttcct cccccaccaa ccaaaccttg   5580

tttagaccca cctcccaaat ccattgatta tacaaaattt gtgattggta aaggactacc   5640

gcaagtccag cagggtgaca attcctccga agctcagtgg cttgttagat ttcaagaagc   5700

tatatccaaa aactcccttt ga                                            5722
```

<210> SEQ ID NO 50
<211> LENGTH: 2929
<212> TYPE: DNA
<213> ORGANISM: Solanum lycopersicum

<400> SEQUENCE: 50

```
atggaagtga gcctgaaaat gaaattccgc tcgcaagcgc tactgttggt tctattgctt     60

gttttcccga tcgttttggc tctcaccgaa gaaggcaaag cattaatgtc gatcaaggca    120

tcgtttagca acgtagcaaa cgtgtttgct ggattgggat gatatccacg acgaggattt    180

ttgctcatgg agaggcgtgt tgtgtggaaa tttctccatg tccgtcgttg cactgaatct    240

gtctaatctg aacttgggcg gggaaatttc accagacatt ggagagttga agaatctgga    300

gacattagac cttcagggaa ataaattaac tggtcaagtc ccagatgaaa ttggcaactg    360

catttcactg atctatcttg atttgtctga taacttgttc tatggagata taccattctc    420

aatttctaag ctcaagcagc tagagttgtt aaactttaaa aacaaccagt tgtccggccc    480

aatcccgtcc acattaactc aaattcctaa tctaaagacg cttgatctgg ctcgaaacca    540

gctcattggt gagataccaa ggttgatcta ttggaatgaa gttctacaat atctaggatt    600

aagaggcaac atgttgacag gaacattgtc ccctgatatg tgccagttga ctggcttgtg    660

gtattttgat gtgcggggca ataacctcag cggaataatt ccagataata ttgggaattg    720

tacaagcttt gagatactgg atatctcata caatcagata actggagaaa ttccctacaa    780

tattgggttt ttacaagtgg ctaccttgtc tttgcaagga aataggctaa ctggcaggat    840

cccagaagtg attggtctta tgcaagctct tgctgttctg gacttgagtg aaaatgagtt    900

ggtgggacca atccctccaa tctttggcaa tttatcttac acagggaagc tgtacctgca    960

cggcaacaaa cttacagggc cagttccacc ggagctagga aatatgtcta aacttagtta   1020

cttgcaatta aatgacaatc agctaatggg tcgaattccc cctgaacttg gcaaactgga   1080

ccagttattt gaattgaatc ttgcaaataa caagttggag ggaccaattc ctgaaaatat   1140

cagctcctgt tctgcattga atcagcttaa tgttcatggc aacaacttaa acgagtccat   1200

tccttcaggg tttaagaatc tggagagctt gacgtatcta aatctttcag ctaataaatt   1260

taagggtcac ataccttctc aacttgggcg aatcatcaac cttgatacat tggatctctc   1320

tggcaacaat tttctgggt ctatccctgg ttctattgga gatttggagc atctcctcac   1380

attgaatctg agcagcaatc atcttgatgg acaaattcct gtagaatttg gcaatctaaa   1440

aagtatacag accattgata tgtcaagcaa caagatctct ggtggcatcc caaaagagct   1500
```

```
gggacagctg cagaccatga taactcttac tttgacaggt aactatctta ctggagcaat   1560
ccctgaccaa ttgaccaatt gtttcagcct aactagtttg aatatatcct acaacaattt   1620
tagtggtgtt gttcctcttt cacggaattt ctcgcggttt gcacctgaca gctttttagg   1680
gaacccattt ctttgtggca actggaaagg ttcaatatgt gacccctatg caccaaggtc   1740
taacgccttg ttctccagaa cagctgttgt ttgcacagca ctgggtttca ttgcactctt   1800
atccatggtt gtagtggctg tgtataagtc caaccaacca caccagtttt tgaaggggcc   1860
taagaccaat caaggctccc ccaaacttgt ggttcttcac atggatatgg ccatccatac   1920
atatgatgac attatgagga ttaccgagaa cttcaatgag aaattcataa taggatatgg   1980
tgcgtccagc actgtatata aatgtgattt gaaagattcc cgaccaattg cagttaagcg   2040
actttacacc gcacatccgc acagcttgcg agagtttgag actgaactgg agacaattgg   2100
aagcattagg catagaaacc ttgttagctt gcatggttac tccctttccc ctcatgggaa   2160
tctcctttgt tacgactaca tggagaatgg ttcactctgg gatctacttc atgggccttc   2220
caaaaaggtg aagcttgact gggaaacacg tctgaagatt gctgttggtg ctgctcaggg   2280
tcttgcttat cttcaccacg attgcaaccc aagaataata cacagagatg taaaatcttc   2340
aaacatcctt gttgatgaaa attttgaggc tcatctatct gattttgggg ttgcaaaatg   2400
catccctact gcaaaaactc atgcatcaac tttggtgttg ggcaccatag gttacattga   2460
ccctgagtat gccaggactt ccaggttaac tgaaaagtca gacgtctaca gctttggcat   2520
tgttctccta gagcttttga caggaaagaa accggttgat aatgacttga acctgcatca   2580
gctgataatg tcaaaggcgg atgataacac cgtgatggat gctgttgatc ctgaggtatc   2640
tgttacatgt atggatttaa tgcatgttag gaaaactttt cagcttgcgt tgctgtgtgc   2700
aaaaagattc ccatgtgaga ggccaacaat gcatgaggtt gctagggtac ttgtttcctt   2760
gcttcctccc ccaccaacca aaccttgttt agacccacct cccaaatcca ttgattatac   2820
aaaatttgtg attggtaaag gactaccgca agtccagcag ggtgacaatt cctccgaagc   2880
tcagtggctt gttagatttc aagaagctat atccaaaaac tccctttga               2929
```

<210> SEQ ID NO 51
<211> LENGTH: 53
<212> TYPE: PRT
<213> ORGANISM: Solanum lycopersicum

<400> SEQUENCE: 51

```
Met Glu Val Ser Leu Lys Met Lys Phe Arg Ser Gln Ala Leu Leu Leu
1               5                   10                  15

Val Leu Leu Leu Val Phe Pro Ile Val Leu Ala Leu Thr Glu Glu Gly
            20                  25                  30

Lys Ala Leu Met Ser Ile Lys Ala Ser Phe Ser Asn Val Ala Asn Val
        35                  40                  45

Phe Ala Gly Leu Gly
    50
```

<210> SEQ ID NO 52
<211> LENGTH: 1663
<212> TYPE: DNA
<213> ORGANISM: Solanum lycopersicum

<400> SEQUENCE: 52

```
atgcctagag atcctttaat agtttctgga gttgttggag atgttgttga tccattcaca     60
```

```
agatgtgtag actttggtgt ggtttacaac aatagggtgg tctataatgg atgttccttg    120
aggccttcac aagttgtcaa tcaacctagg gttgacattg atggagacga tcttcgtact    180
ttttacactc tggtataaac tcatcgtttt atttcatatg atatacatat atatatatat    240
atatatatat atatatatat atattttctt tctatttata cattttaata tctctaaatt    300
attaaccttt tgtcaattga ttatgagtag aagatcaaaa ggacaatatg tgcaaaggct    360
tctaattatg tgaatttgtg ttagttttaa ttttgattca ccatctaagt acttgttttg    420
tggtttttat ttgaatttga gaactcataa catactattt atgataataa aaaatgttag    480
taacatgtat gtttaatatt gcaagcttga aaatatacaa tatttttaaa ttactaataa    540
tgtcatgtaa tacatttgga tatacaatat ggaaaattat ttttcctaat tttcaaaata    600
tttgaaatgt ttcttttctt tttggaagat tatggtggat cctgatgctc caaaccctag    660
caacccaaac ctgagggaat atttgcactg gtaagtcatc tagcttatat tatatatata    720
tatatatata tatatatata ttatataaat agataaaaat attcattttg ttatatactt    780
cttatttctc ttaaatcaat cgtcgatagc gaagacaaaa atgtatgtga gattatataa    840
gaacctaagg aaagtattat ttcataaaat gataactttc tgatacacaa attaatcaat    900
atttcaaata aataccaaat atcgaataac aacgtaaaaa aataataact attatcgatt    960
gcttaatccc cttacaatta atgtacctaa acctcttttt tttttaaaa aaaaaataat    1020
aataataatg tttaacacat tattttttta ataggttggt cacagatatc ccagcagcca    1080
caggagcaac ctttggtaag tttttcttac attattacct aatggctcgt aattacgcag    1140
tgacgaagca agaaatttaa atatacttta tatttacgat acattgtatc cgtatcacta    1200
catttttaat ataagacggt tagtaatata caaaatacaa cttgtatcat catcacctta    1260
gtagtacatt attagtacta taggcccaat tatgactact aataaaataa gacttaaaaa    1320
gaaacataaa atcaaaatga agtatatact atgtatataa atgtttttga aacaaggaaa    1380
atacgcgtat tgaatgtctt tgttactaaa ctcaaactct cgttatacag gcaatgaagt    1440
cgtgggctac gagagcccac gaccctcaat gggaatccat cgttatattt tcgtgttgta    1500
tcgacaattg ggctgcgatg ccatcgatgc accggacata atcgattcta gacaaaattt    1560
caacacaaga gactttgcta ggtttcacaa tctaggtttg cctgttgctg ctgtttactt    1620
caattgcaat agggaaggtg gtaccggtgg tcgtcgccta taa                      1663
```

<210> SEQ ID NO 53
<211> LENGTH: 528
<212> TYPE: DNA
<213> ORGANISM: Solanum lycopersicum

<400> SEQUENCE: 53

```
atgcctagag atcctttaat agtttctgga gttgttggag atgttgttga tccattcaca     60
agatgtgtag actttggtgt ggtttacaac aatagggtgg tctataatgg atgttccttg    120
aggccttcac aagttgtcaa tcaacctagg gttgacattg atggagacga tcttcgtact    180
ttttacactc tgattatggt ggatcctgat gctccaaacc ctagcaaccc aaacctgagg    240
gaatatttgc actggttggt cacagatatc ccagcagcca caggagcaac ctttggcaat    300
gaagtcgtgg gctacgagag cccacgaccc tcaatgggaa tccatcgtta tattttcgtg    360
ttgtatcgac aattgggctg cgatgccatc gatgcaccgg acataatcga ttctagacaa    420
aatttcaaca caagagactt tgctaggttt cacaatctag gtttgcctgt tgctgctgtt    480
tacttcaatt gcaataggga aggtggtacc ggtggtcgtc gcctataa                 528
```

<210> SEQ ID NO 54
<211> LENGTH: 175
<212> TYPE: PRT
<213> ORGANISM: Solanum lycopersicum

<400> SEQUENCE: 54

```
Met Pro Arg Asp Pro Leu Ile Val Ser Gly Val Val Gly Asp Val Val
1               5                   10                  15

Asp Pro Phe Thr Arg Cys Val Asp Phe Gly Val Val Tyr Asn Asn Arg
            20                  25                  30

Val Val Tyr Asn Gly Cys Ser Leu Arg Pro Ser Gln Val Val Asn Gln
        35                  40                  45

Pro Arg Val Asp Ile Asp Gly Asp Asp Leu Arg Thr Phe Tyr Thr Leu
    50                  55                  60

Ile Met Val Asp Pro Asp Ala Pro Asn Pro Ser Asn Pro Asn Leu Arg
65                  70                  75                  80

Glu Tyr Leu His Trp Leu Val Thr Asp Ile Pro Ala Ala Thr Gly Ala
                85                  90                  95

Thr Phe Gly Asn Glu Val Val Gly Tyr Glu Ser Pro Arg Pro Ser Met
            100                 105                 110

Gly Ile His Arg Tyr Ile Phe Val Leu Tyr Arg Gln Leu Gly Cys Asp
        115                 120                 125

Ala Ile Asp Ala Pro Asp Ile Ile Asp Ser Arg Gln Asn Phe Asn Thr
    130                 135                 140

Arg Asp Phe Ala Arg Phe His Asn Leu Gly Leu Pro Val Ala Ala Val
145                 150                 155                 160

Tyr Phe Asn Cys Asn Arg Glu Gly Gly Thr Gly Gly Arg Arg Leu
                165                 170                 175
```

<210> SEQ ID NO 55
<211> LENGTH: 1575
<212> TYPE: DNA
<213> ORGANISM: Solanum lycopersicum

<400> SEQUENCE: 55

```
atgcctagag atcctttaat ggatgttcct tgaggccttc acaagttgtc aatcaaccta     60

gggttgacat tgatggagac gatcttcgta ctttttacac tctggtataa actcatcgtt    120

ttatttcata tgatatacat atatatatat atatatatat atatatatat atatattttc    180

tttctattta tacattttaa tatctctaaa ttattaacct tttgtcaatt gattatgagt    240

agaagatcaa aaggacaata tgtgcaaagg cttctaatta tgtgaatttg tgttagtttt    300

aattttgatt caccatctaa gtacttgttt tgtggttttt atttgaattt gagaactcat    360

aacatactat ttatgataat aaaaaatgtt agtaacatgt atgtttaata ttgcaagctt    420

gaaaatatac aatattttta aattactaat aatgtcatgt aatacatttg gatatacaat    480

atggaaaatt atttttccta attttcaaaa tatttgaaat gtttcttttc tttttggaag    540

attatggtgg atcctgatgc tccaaaccct agcaacccaa acctgaggga atatttgcac    600

tggtaagtca tctagcttat attatatata tatatatata tatatatata tattatataa    660

atagataaaa atattcattt tgttatatac ttcttatttc tcttaaatca atcgtcgata    720

gcgaagacaa aaatgtatgt gagattatat aagaacctaa ggaaagtatt atttcataaa    780

atgataactt tctgatacac aaattaatca atatttcaaa taaataccaa atatcgaata    840

acaacgtaaa aaaataataa ctattatcga ttgcttaatc cccttacaat taatgtacct    900
```

aaacctcttt ttttttttaa aaaaaaaata ataataataa tgtttaacac attatttttt 960
taataggttg gtcacagata tcccagcagc cacaggagca acctttggta agtttttctt 1020
acattattac ctaatggctc gtaattacgc agtgacgaag caagaaattt aaatatactt 1080
tatatttacg atacattgta tccgtatcac tacattttta atataagacg gttagtaata 1140
tacaaaatac aacttgtatc atcatcacct tagtagtaca ttattagtac tataggccca 1200
attatgacta ctaataaaat aagacttaaa aagaaacata aaatcaaaat gaagtatata 1260
ctatgtatat aaatgttttt gaaacaagga aaatacgcgt attgaatgtc tttgttacta 1320
aactcaaact ctcgttatac aggcaatgaa gtcgtgggct acgagagccc acgaccctca 1380
atgggaatcc atcgttatat tttcgtgttg tatcgacaat tgggctgcga tgccatcgat 1440
gcaccggaca taatcgattc tagacaaaat ttcaacacaa gagactttgc taggtttcac 1500
aatctaggtt tgcctgttgc tgctgtttac ttcaattgca atagggaagg tggtaccggt 1560
ggtcgtcgcc tataa 1575

<210> SEQ ID NO 56
<211> LENGTH: 440
<212> TYPE: DNA
<213> ORGANISM: Solanum lycopersicum

<400> SEQUENCE: 56
atgcctagag atcctttaat ggatgttcct tgaggccttc acaagttgtc aatcaaccta 60
gggttgacat tgatggagac gatcttcgta ctttttacac tctgattatg gtggatcctg 120
atgctccaaa ccctagcaac ccaaacctga gggaatattt gcactggttg gtcacagata 180
tcccagcagc cacaggagca acctttggca atgaagtcgt gggctacgag agcccacgac 240
cctcaatggg aatccatcgt tatattttcg tgttgtatcg acaattgggc tgcgatgcca 300
tcgatgcacc ggacataatc gattctagac aaaatttcaa cacaagagac tttgctaggt 360
ttcacaatct aggtttgcct gttgctgctg tttacttcaa ttgcaatagg gaaggtggta 420
ccggtggtcg tcgcctataa 440

<210> SEQ ID NO 57
<211> LENGTH: 10
<212> TYPE: PRT
<213> ORGANISM: Solanum lycopersicum

<400> SEQUENCE: 57

Met Pro Arg Asp Pro Leu Met Asp Val Pro
1 5 10

<210> SEQ ID NO 58
<211> LENGTH: 1659
<212> TYPE: DNA
<213> ORGANISM: Solanum lycopersicum

<400> SEQUENCE: 58
atgcctagag atcctttaat agtctggagt tgttggagat gttgttgatc cattcacaag 60
atgtgtagac tttggtgtgg tttacaacaa tagggtggtc taatggatgt tccttgaggc 120
cttcacaagt tgtcaatcaa cctagggttg acattgatgg agacgatctt cgtacttttt 180
acactctggt ataaactcat cgttttattt catatgatat acatatatat atatatatat 240
atatatatat atatatatat tttctttcta tttatacatt ttaatatctc taaattatta 300
accttttgtc aattgattat gagtagaaga tcaaaaggac aatatgtgca aaggcttcta 360

-continued

```
attatgtgaa tttgtgttag ttttaatttt gattcaccat ctaagtactt gttttgtggt     420

ttttatttga atttgagaac tcataacata ctatttatga taataaaaaa tgttagtaac     480

atgtatgttt aatattgcaa gcttgaaaat atacaatatt tttaaattac taataatgtc     540

atgtaataca tttggatata caatatggaa aattattttt cctaattttc aaaatatttg     600

aaatgtttct tttctttttg gaagattatg gtggatcctg atgctccaaa ccctagcaac     660

ccaaacctga gggaatattt gcactggtaa gtcatctagc ttatattata tatatatata     720

tatatatata tatatattat ataaatagat aaaaatattc attttgttat atacttctta     780

tttctcttaa atcaatcgtc gatagcgaag acaaaaatgt atgtgagatt atataagaac     840

ctaaggaaag tattatttca taaaatgata actttctgat acacaaatta atcaatattt     900

caaataaata ccaaatatcg aataacaacg taaaaaaata ataactatta tcgattgctt     960

aatcccctta caattaatgt acctaaacct cttttttttt ttaaaaaaaa aataataata    1020

ataatgttta acacattatt tttttaatag gttggtcaca gatatcccag cagccacagg    1080

agcaaccttt ggtaagtttt tcttacatta ttacctaatg gctcgtaatt acgcagtgac    1140

gaagcaagaa atttaaatat actttatatt tacgatacat tgtatccgta tcactacatt    1200

tttaatataa gacggttagt aatatacaaa atacaacttg tatcatcatc accttagtag    1260

tacattatta gtactatagg cccaattatg actactaata aaataagact taaaaagaaa    1320

cataaaatca aaatgaagta tatactatgt atataaatgt ttttgaaaca aggaaaatac    1380

gcgtattgaa tgtctttgtt actaaactca aactctcgtt atacaggcaa tgaagtcgtg    1440

ggctacgaga gcccacgacc ctcaatggga atccatcgtt atattttcgt gttgtatcga    1500

caattgggct gcgatgccat cgatgcaccg gacataatcg attctagaca aaatttcaac    1560

acaagagact ttgctaggtt tcacaatcta ggtttgcctg ttgctgctgt ttacttcaat    1620

tgcaataggg aaggtggtac cggtggtcgt cgcctataa                           1659
```

<210> SEQ ID NO 59
<211> LENGTH: 524
<212> TYPE: DNA
<213> ORGANISM: Solanum lycopersicum

<400> SEQUENCE: 59

```
atgcctagag atcctttaat agtctggagt tgttggagat gttgttgatc cattcacaag      60

atgtgtagac tttggtgtgg tttacaacaa tagggtggtc taatggatgt tccttgaggc     120

cttcacaagt tgtcaatcaa cctagggttg acattgatgg agacgatctt cgtacttttt     180

acactctgat tatggtggat cctgatgctc caaaccctag caacccaaac ctgagggaat     240

atttgcactg gttggtcaca gatatcccag cagccacagg agcaaccttt ggcaatgaag     300

tcgtgggcta cgagagccca cgaccctcaa tgggaatcca tcgttatatt ttcgtgttgt     360

atcgacaatt gggctgcgat gccatcgatg caccggacat aatcgattct agacaaaatt     420

tcaacacaag agactttgct aggtttcaca atctaggttt gcctgttgct gctgtttact     480

tcaattgcaa tagggaaggt ggtaccggtg gtcgtcgcct ataa                      524
```

<210> SEQ ID NO 60
<211> LENGTH: 15
<212> TYPE: PRT
<213> ORGANISM: Solanum lycopersicum

<400> SEQUENCE: 60

-continued

```
Met Pro Arg Asp Pro Leu Ile Val Trp Ser Cys Trp Arg Cys Cys
1               5                   10                  15


<210> SEQ ID NO 61
<211> LENGTH: 1659
<212> TYPE: DNA
<213> ORGANISM: Solanum lycopersicum

<400> SEQUENCE: 61

atgcctagag atcctttaat agtctggagt tgttggagat gttgttgatc cattcacaag     60

atgtgtagac tttggtgtgg tttacaacaa tagggtggtc taatggatgt tccttgaggc    120

cttcacaagt tgtcaatcaa cctagggttg acattgatgg agacgatctt cgtacttttt    180

acactctggt ataaactcat cgttttattt catatgatat acatatatat atatatatat    240

atatatatat atatatatat tttctttcta tttatacatt ttaatatctc taaattatta    300

acctttttgtc aattgattat gagtagaaga tcaaaaggac aatatgtgca aaggcttcta    360

attatgtgaa tttgtgttag ttttaatttt gattcaccat ctaagtactt gttttgtggt    420

ttttatttga atttgagaac tcataacata ctatttatga taataaaaaa tgttagtaac    480

atgtatgttt aatattgcaa gcttgaaaat atacaatatt tttaaattac taataatgtc    540

atgtaataca tttggatata caatatggaa aattattttt cctaattttc aaaatatttg    600

aaatgtttct tttctttttg gaagattatg gtggatcctg atgctccaaa ccctagcaac    660

ccaaacctga gggaatattt gcactggtaa gtcatctagc ttatattata tatatatata    720

tatatatata tatatattat ataaatagat aaaaatattc attttgttat atacttctta    780

tttctcttaa atcaatcgtc gatagcgaag acaaaaatgt atgtgagatt atataagaac    840

ctaaggaaag tattatttca taaaatgata actttctgat acacaaatta atcaatattt    900

caaataaata ccaaatatcg aataacaacg taaaaaaata ataactatta tcgattgctt    960

aatcccctta caattaatgt acctaaacct cttttttttt ttaaaaaaaa aataataata   1020

ataatgttta acacattatt tttttaatag gttggtcaca gatatcccag cagccacagg   1080

agcaaccttt ggtaagtttt tcttacatta ttacctaatg gctcgtaatt acgcagtgac   1140

gaagcaagaa atttaaatat actttatatt tacgatacat tgtatccgta tcactacatt   1200

tttaatataa gacggttagt aatatacaaa atacaacttg tatcatcatc accttagtag   1260

tacattatta gtactatagg cccaattatg actactaata aaataagact taaaaagaaa   1320

cataaaatca aaatgaagta tatactatgt atataaatgt ttttgaaaca aggaaaatac   1380

gcgtattgaa tgtctttgtt actaaactca aactctcgtt atacaggcaa tgaagtcgtg   1440

ggctacgaga gcccacgacc ctcaatggga atccatcgtt atattttcgt gttgtatcga   1500

caattgggct gcgatgccat cgatgcaccg gacataatcg attctagaca aaatttcaac   1560

acaagagact ttgctaggtt tcacaatcta ggtttgcctg ttgctgctgt ttacttcaat   1620

tgcaataggg aaggtggtac cggtggtcgt cgcctataa                          1659


<210> SEQ ID NO 62
<211> LENGTH: 524
<212> TYPE: DNA
<213> ORGANISM: Solanum lycopersicum

<400> SEQUENCE: 62

atgcctagag atcctttaat agtctggagt tgttggagat gttgttgatc cattcacaag     60

atgtgtagac tttggtgtgg tttacaacaa tagggtggtc taatggatgt tccttgaggc    120
```

```
cttcacaagt tgtcaatcaa cctagggttg acattgatgg agacgatctt cgtacttttt    180

acactctgat tatggtggat cctgatgctc caaaccctag caacccaaac ctgagggaat    240

atttgcactg gttggtcaca gatatcccag cagccacagg agcaaccttt ggcaatgaag    300

tcgtgggcta cgagagccca cgaccctcaa tgggaatcca tcgttatatt ttcgtgttgt    360

atcgacaatt gggctgcgat gccatcgatg caccggacat aatcgattct agacaaaatt    420

tcaacacaag agactttgct aggtttcaca atctaggttt gcctgttgct gctgtttact    480

tcaattgcaa tagggaaggt ggtaccggtg gtcgtcgcct ataa                     524
```

<210> SEQ ID NO 63
<211> LENGTH: 15
<212> TYPE: PRT
<213> ORGANISM: Solanum lycopersicum

<400> SEQUENCE: 63

```
Met Pro Arg Asp Pro Leu Ile Val Trp Ser Cys Trp Arg Cys Cys
1               5                   10                  15
```

<210> SEQ ID NO 64
<211> LENGTH: 1659
<212> TYPE: DNA
<213> ORGANISM: Solanum lycopersicum

<400> SEQUENCE: 64

```
atgcctagag atcctttaat agtctggagt tgttggagat gttgttgatc cattcacaag     60

atgtgtagac tttggtgtgg tttacaacaa tagggtggtc taatggatgt tccttgaggc    120

cttcacaagt tgtcaatcaa cctagggttg acattgatgg agacgatctt cgtacttttt    180

acactctggt ataaactcat cgttttattt catatgatat acatatatat atatatatat    240

atatatatat atatatatat tttctttcta tttatacatt ttaatatctc taaattatta    300

accttttgtc aattgattat gagtagaaga tcaaaaggac aatatgtgca aaggcttcta    360

attatgtgaa tttgtgttag ttttaatttt gattcaccat ctaagtactt gttttgtggt    420

ttttatttga atttgagaac tcataacata ctatttatga taataaaaaa tgttagtaac    480

atgtatgttt aatattgcaa gcttgaaaat atacaatatt tttaaattac taataatgtc    540

atgtaataca tttggatata caatatggaa aattattttt cctaattttc aaaatatttg    600

aaatgtttct tttctttttg gaagattatg gtggatcctg atgctccaaa ccctagcaac    660

ccaaacctga gggaatattt gcactggtaa gtcatctagc ttatattata tatatatata    720

tatatatata tatatattat ataaatagat aaaaatattc attttgttat atacttctta    780

tttctcttaa atcaatcgtc gatagcgaag acaaaaatgt atgtgagatt atataagaac    840

ctaaggaaag tattatttca taaaatgata actttctgat acacaaatta atcaatattt    900

caaataaata ccaaatatcg aataacaacg taaaaaaata ataactatta tcgattgctt    960

aatcccctta caattaatgt acctaaacct cttttttttt ttaaaaaaaa aataataata   1020

ataatgttta acacattatt tttttaatag gttggtcaca gatatcccag cagccacagg   1080

agcaaccttt ggtaagtttt tcttacatta ttacctaatg gctcgtaatt acgcagtgac   1140

gaagcaagaa atttaaatat actttatatt tacgatacat tgtatccgta tcactacatt   1200

tttaatataa gacggttagt aatatacaaa atacaacttg tatcatcatc accttagtag   1260

tacattatta gtactatagg cccaattatg actactaata aaataagact taaaaagaaa   1320

cataaaatca aaatgaagta tatactatgt atataaatgt ttttgaaaca aggaaaatac   1380
```

gcgtattgaa tgtctttgtt actaaactca aactctcgtt atacaggcaa tgaagtcgtg 1440
ggctacgaga gcccacgacc ctcaatggga atccatcgtt atattttcgt gttgtatcga 1500
caattgggct gcgatgccat cgatgcaccg gacataatcg attctagaca aaatttcaac 1560
acaagagact ttgctaggtt tcacaatcta ggtttgcctg ttgctgctgt ttacttcaat 1620
tgcaataggg aaggtggtac cggtggtcgt cgcctataa 1659

<210> SEQ ID NO 65
<211> LENGTH: 524
<212> TYPE: DNA
<213> ORGANISM: Solanum lycopersicum

<400> SEQUENCE: 65
atgcctagag atcctttaat agtctggagt tgttggagat gttgttgatc cattcacaag 60
atgtgtagac tttggtgtgg tttacaacaa tagggtggtc taatggatgt tccttgaggc 120
cttcacaagt tgtcaatcaa cctagggttg acattgatgg agacgatctt cgtacttttt 180
acactctgat tatggtggat cctgatgctc caaaccctag caacccaaac ctgagggaat 240
atttgcactg gttggtcaca gatatcccag cagccacagg agcaaccttt ggcaatgaag 300
tcgtgggcta cgagagccca cgaccctcaa tgggaatcca tcgttatatt ttcgtgttgt 360
atcgacaatt gggctgcgat gccatcgatg caccggacat aatcgattct agacaaaatt 420
tcaacacaag agactttgct aggtttcaca atctaggttt gcctgttgct gctgtttact 480
tcaattgcaa tagggaaggt ggtaccggtg gtcgtcgcct ataa 524

<210> SEQ ID NO 66
<211> LENGTH: 15
<212> TYPE: PRT
<213> ORGANISM: Solanum lycopersicum

<400> SEQUENCE: 66

Met Pro Arg Asp Pro Leu Ile Val Trp Ser Cys Trp Arg Cys Cys
1 5 10 15

<210> SEQ ID NO 67
<211> LENGTH: 1930
<212> TYPE: DNA
<213> ORGANISM: Solanum lycopersicum

<400> SEQUENCE: 67
atggcttcca aaatgtgtga acccccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actggtatat attaatcttc aacacttcca atttactccg 240
tctgtctgtc ctaatttatg tcacacattt tctatgatat atagttttag aaattattca 300
agaccataac tttttaaaga aaaaatcata gactttctta gtcaacgtca aataaattga 360
gacggacaag atgacatgat tagtacattt atcttctatt attgacctct catttctttt 420
tatacattat ttgacagatc atgatagatc cagatgttcc tggtcctagt gatccatatc 480
tcagggaaca tctacactgg tatagacaac atatgcctta aaactaactc agtcaatttt 540
atcttcaatt gtttactttg gaaggggaaa tgacatgatc attatatcat agtacaaatt 600
attatgtaat ttctgttcgt ctaaaaaatg tcactttaga aaaaactgat aatcatatac 660
aataccacaa taaagataga agaacatgta ctaatattga acttaaataa tgagtactag 720

-continued

```
gagtattatt aattaacttt aaaaatgcta gtcaatatac ctatgtttat atgttaaaaa    780

atcctttata tttggaaaca tgagtactcc tataccatac aatgttgtcg tacagttgat    840

tagacgggca aattaaacaa atgtccaata attgtactaa ttaataacta cttgttctct    900

tcatctatta ttagttatta ccaaaaaaag aggactgcaa aatggtgata ttattatgtg    960

taacggaaaa aaacgtactc tatttaatat gatagaatca aagtgacata ttttgttcta   1020

gttagacaaa taagtaactg aaaagaggat ttgaccatct ttacaggatt gtcacagaca   1080

ttccaggcac tacagattgc tcttttggta tgtatcctta acccataaat caaaataatg   1140

tactttcttt ttatttgcca ttaatatctc tagtacaaaa aagaaatatt ataaaaaaaa   1200

ttaatttcaa tttttatatt ataggtttaa gataataata ttaaacgata ttttagtctc   1260

taccaaatag acgagcaaat taaaactaag aaagcactac atgttttctt tatattatta   1320

gtataaaaat atattataat ttgcctggtg gtaataggat caaagtattg attcttaatt   1380

attattatat aattaataat aatggtaaac aaaaagatat aaagtgctta cctcctaatt   1440

ccctatatga aaaaatatac ttacttaatt actcttttta cacgtaagca tgcatttaaa   1500

aaaatattaa aaaattattc cagaggttat atataatatg tatggataaa aaaaaaattc   1560

acctatatac ataataatat aattttcgag tgaattgacc gcccttcagc atcattatat   1620

aatgttatcg atctaggtct ttgtgtgaaa ttaaaagtta tttatacggt tagtacgatc   1680

gcgtaataac gaaggtaaaa atatttcagg aagagaagtg gttgggtatg aaatgccaag   1740

gccaaatatt ggaatccaca ggtttgtatt tttgctgttt aagcagaaga aaaggcaaac   1800

aatatcgagt gcaccagtgt ccagagatca atttagtagt agaaaatttt cagaagaaaa   1860

tgaacttggc tcaccagttg ctgctgtttt cttcaattgt cagagggaaa ctgccgctag   1920

aaggcgttga                                                          1930
```

<210> SEQ ID NO 68
<211> LENGTH: 528
<212> TYPE: DNA
<213> ORGANISM: Solanum lycopersicum

<400> SEQUENCE: 68

```
atggcttcca aaatgtgtga accccttgtg attggtagag tgattggtga agttgttgat     60

tatttctgtc caagtgttaa gatgtctgtt gtttataaca acaacaaaca tgtctataat    120

ggacatgaat tctttccttc ctcagtaact tctaaaccta gggttgaagt tcatggtggt    180

gatctcagat ccttcttcac actgatcatg atagatccag atgttcctgg tcctagtgat    240

ccatatctca gggaacatct acactggatt gtcacagaca ttccaggcac tacagattgc    300

tcttttggaa gagaagtggt tgggtatgaa atgccaaggc caaatattgg aatccacagg    360

tttgtatttt tgctgtttaa gcagaagaaa aggcaaacaa tatcgagtgc accagtgtcc    420

agagatcaat ttagtagtag aaaattttca gaagaaaatg aacttggctc accagttgct    480

gctgttttct tcaattgtca gagggaaact gccgctagaa ggcgttga                 528
```

<210> SEQ ID NO 69
<211> LENGTH: 175
<212> TYPE: PRT
<213> ORGANISM: Solanum lycopersicum

<400> SEQUENCE: 69

```
Met Ala Ser Lys Met Cys Glu Pro Leu Val Ile Gly Arg Val Ile Gly
1               5                   10                  15
```

Glu Val Val Asp Tyr Phe Cys Pro Ser Val Lys Met Ser Val Val Tyr
20 25 30

Asn Asn Asn Lys His Val Tyr Asn Gly His Glu Phe Phe Pro Ser Ser
35 40 45

Val Thr Ser Lys Pro Arg Val Glu Val His Gly Gly Asp Leu Arg Ser
50 55 60

Phe Phe Thr Leu Ile Met Ile Asp Pro Asp Val Pro Gly Pro Ser Asp
65 70 75 80

Pro Tyr Leu Arg Glu His Leu His Trp Ile Val Thr Asp Ile Pro Gly
85 90 95

Thr Thr Asp Cys Ser Phe Gly Arg Glu Val Val Gly Tyr Glu Met Pro
100 105 110

Arg Pro Asn Ile Gly Ile His Arg Phe Val Phe Leu Leu Phe Lys Gln
115 120 125

Lys Lys Arg Gln Thr Ile Ser Ser Ala Pro Val Ser Arg Asp Gln Phe
130 135 140

Ser Ser Arg Lys Phe Ser Glu Glu Asn Glu Leu Gly Ser Pro Val Ala
145 150 155 160

Ala Val Phe Phe Asn Cys Gln Arg Glu Thr Ala Ala Arg Arg Arg
165 170 175

<210> SEQ ID NO 70
<211> LENGTH: 1930
<212> TYPE: DNA
<213> ORGANISM: Solanum lycopersicum

<400> SEQUENCE: 70
atggcttcca aaatgtgtga accccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actggtatat attaatcttc aacacttcca atttactccg 240
tctgtctgtc ctaatttatg tcacacattt tctatgatat atagttttag aaattattca 300
agaccataac tttttaaaga aaaaatcata gactttctta gtcaacgtca aataaattga 360
gacggacaag atgacatgat tagtacattt atcttctatt attgacctct cattttcttt 420
tatacattat ttgacagatc atgatagatc cagatgttct tggtcctagt gatccatatc 480
tcagggaaca tctacactgg tatagacaac atatgcctta aaactaactc agtcaatttt 540
atcttcaatt gtttactttg gaaggggaaa tgacatgatc attatatcat agtacaaatt 600
attatgtaat ttctgttcgt ctaaaaaatg tcactttaga aaaaactgat aatcatatac 660
aataccacaa taaagataga agaacatgta ctaatattga acttaaataa tgagtactag 720
gagtattatt aattaacttt aaaaatgcta gtcaatatac ctatgtttat atgttaaaaa 780
atcctttata tttggaaaca tgagtactcc tataccatac aatgttgtcg tacagttgat 840
tagacgggca aattaaacaa atgtccaata attgtactaa ttaataacta cttgttctct 900
tcatctatta ttagttatta ccaaaaaaag aggactgcaa aatggtgata ttattatgtg 960
taacggaaaa aaacgtactc tatttaatat gatagaatca aagtgacata ttttgttcta 1020
gttagacaaa taagtaactg aaaagaggat ttgaccatct ttacaggatt gtcacagaca 1080
ttccaggcac tacagattgc tcttttggta tgtatcctta acccataaat caaaataatg 1140
tactttcttt ttatttgcca ttaatatctc tagtacaaaa aagaaatatt ataaaaaaaa 1200
ttaatttcaa tttttatatt ataggtttaa gataataata ttaaacgata ttttagtctc 1260
taccaaatag acgagcaaat taaaactaag aaagcactac atgttttctt tatattatta 1320
gtataaaaat atattataat ttgcctggtg gtaataggat caaagtattg attcttaatt 1380
attattatat aattaataat aatggtaaac aaaaagatat aaagtgctta cctcctaatt 1440
ccctatatga aaaaatatac ttacttaatt actcttttta cacgtaagca tgcatttaaa 1500
aaaatattaa aaaattattc cagaggttat atataatatg tatggataaa aaaaaaattc 1560
acctatatac ataataatat aattttcgag tgaattgacc gcccttcagc atcattatat 1620
aatgttatcg atctaggtct ttgtgtgaaa ttaaaagtta tttatacggt tagtacgatc 1680
gcgtaataac gaaggtaaaa atatttcagg aagagaagtg gttgggtatg aaatgccaag 1740
gccaaatatt ggaatccaca ggtttgtatt tttgctgttt aagcagaaga aaaggcaaac 1800
aatatcgagt gcaccagtgt ccagagatca atttagtagt agaaaatttt cagaagaaaa 1860
tgaacttggc tcaccagttg ctgctgtttt cttcaattgt cagagggaaa ctgccgctag 1920
aaggcgttga 1930

<210> SEQ ID NO 71
<211> LENGTH: 528
<212> TYPE: DNA
<213> ORGANISM: Solanum lycopersicum

<400> SEQUENCE: 71
atggcttcca aaatgtgtga accccttgtg attggtagag tgattggtga agttgttgat 60
tatttctgtc caagtgttaa gatgtctgtt gtttataaca acaacaaaca tgtctataat 120
ggacatgaat tctttccttc ctcagtaact tctaaaccta gggttgaagt tcatggtggt 180
gatctcagat ccttcttcac actgatcatg atagatccag atgttcttgg tcctagtgat 240
ccatatctca gggaacatct acactggatt gtcacagaca ttccaggcac tacagattgc 300
tcttttggaa gagaagtggt tgggtatgaa atgccaaggc caaatattgg aatccacagg 360
tttgtatttt tgctgtttaa gcagaagaaa aggcaaacaa tatcgagtgc accagtgtcc 420
agagatcaat ttagtagtag aaaattttca gaagaaaatg aacttggctc accagttgct 480
gctgttttct tcaattgtca gagggaaact gccgctagaa ggcgttga 528

<210> SEQ ID NO 72
<211> LENGTH: 175
<212> TYPE: PRT
<213> ORGANISM: Solanum lycopersicum

<400> SEQUENCE: 72

Met Ala Ser Lys Met Cys Glu Pro Leu Val Ile Gly Arg Val Ile Gly
1 5 10 15

Glu Val Val Asp Tyr Phe Cys Pro Ser Val Lys Met Ser Val Val Tyr
20 25 30

Asn Asn Asn Lys His Val Tyr Asn Gly His Glu Phe Phe Pro Ser Ser
35 40 45

Val Thr Ser Lys Pro Arg Val Glu Val His Gly Gly Asp Leu Arg Ser
50 55 60

Phe Phe Thr Leu Ile Met Ile Asp Pro Asp Val Leu Gly Pro Ser Asp
65 70 75 80

Pro Tyr Leu Arg Glu His Leu His Trp Ile Val Thr Asp Ile Pro Gly
85 90 95

Thr Thr Asp Cys Ser Phe Gly Arg Glu Val Val Gly Tyr Glu Met Pro
100 105 110

-continued

Arg Pro Asn Ile Gly Ile His Arg Phe Val Phe Leu Leu Phe Lys Gln
115 120 125

Lys Lys Arg Gln Thr Ile Ser Ser Ala Pro Val Ser Arg Asp Gln Phe
130 135 140

Ser Ser Arg Lys Phe Ser Glu Glu Asn Glu Leu Gly Ser Pro Val Ala
145 150 155 160

Ala Val Phe Phe Asn Cys Gln Arg Glu Thr Ala Ala Arg Arg Arg
165 170 175

<210> SEQ ID NO 73
<211> LENGTH: 1926
<212> TYPE: DNA
<213> ORGANISM: Solanum lycopersicum

<400> SEQUENCE: 73
atggcttcca aaatgtgtga accccttgtg attggtagag tgattggtga agttgttgat 60
tatttctgtc caagtgttaa gatgtctgtt gtttataaca acaacaaaca tgtctataat 120
ggacatgaat tctttccttc ctaacttcta aacctagggt tgaagttcat ggtggtgatc 180
tcagatcctt cttcacactg gtatatatta atcttcaaca cttccaattt actccgtctg 240
tctgtcctaa tttatgtcac acattttcta tgatatatag ttttagaaat tattcaagac 300
cataactttt taaagaaaaa atcatagact ttcttagtca acgtcaaata aattgagacg 360
gacaagatga catgattagt acatttatct tctattattg acctctcatt ttcttttata 420
cattatttga cagatcatga tagatccaga tgttcctggt cctagtgatc catatctcag 480
ggaacatcta cactggtata gacaacatat gccttaaaac taactcagtc aattttatct 540
tcaattgttt actttggaag gggaaatgac atgatcatta tatcatagta caaattatta 600
tgtaatttct gttcgtctaa aaaatgtcac tttagaaaaa actgataatc atatacaata 660
ccacaataaa gatagaagaa catgtactaa tattgaactt aaataatgag tactaggagt 720
attattaatt aactttaaaa atgctagtca atatacctat gtttatatgt taaaaaatcc 780
tttatatttg gaaacatgag tactcctata ccatacaatg ttgtcgtaca gttgattaga 840
cgggcaaatt aaacaaatgt ccaataattg tactaattaa taactacttg ttctcttcat 900
ctattattag ttattaccaa aaaaagagga ctgcaaaatg gtgatattat tatgtgtaac 960
ggaaaaaaac gtactctatt taatatgata gaatcaaagt gacatatttt gttctagtta 1020
gacaaataag taactgaaaa gaggatttga ccatctttac aggattgtca cagacattcc 1080
aggcactaca gattgctctt ttggtatgta tccttaaccc ataaatcaaa ataatgtact 1140
ttctttttat ttgccattaa tatctctagt acaaaaaaga aatattataa aaaaaattaa 1200
tttcaatttt tatattatag gtttaagata ataatattaa acgatatttt agtctctacc 1260
aaatagacga gcaaattaaa actaagaaag cactacatgt tttctttata ttattagtat 1320
aaaaatatat tataatttgc ctggtggtaa taggatcaaa gtattgattc ttaattatta 1380
ttatataatt aataataatg gtaaacaaaa agatataaag tgcttacctc ctaattccct 1440
atatgaaaaa atatacttac ttaattactc tttttacacg taagcatgca tttaaaaaaa 1500
tattaaaaaa ttattccaga ggttatatat aatatgtatg gataaaaaaa aaattcacct 1560
atatacataa taatataatt ttcgagtgaa ttgaccgccc ttcagcatca ttatataatg 1620
ttatcgatct aggtctttgt gtgaaattaa aagttattta tacggttagt acgatcgcgt 1680
aataacgaag gtaaaaatat ttcaggaaga gaagtggttg ggtatgaaat gccaaggcca 1740
aatattggaa tccacaggtt tgtatttttg ctgtttaagc agaagaaaag gcaaacaata 1800
tcgagtgcac cagtgtccag agatcaattt agtagtagaa aattttcaga agaaaatgaa 1860
cttggctcac cagttgctgc tgttttcttc aattgtcaga gggaaactgc cgctagaagg 1920
cgttga 1926

<210> SEQ ID NO 74
<211> LENGTH: 524
<212> TYPE: DNA
<213> ORGANISM: Solanum lycopersicum

<400> SEQUENCE: 74
atggcttcca aaatgtgtga acccettgtg attggtagag tgattggtga agttgttgat 60
tatttctgtc caagtgttaa gatgtctgtt gtttataaca acaacaaaca tgtctataat 120
ggacatgaat tctttccttc ctaacttcta aacctagggt tgaagttcat ggtggtgatc 180
tcagatcctt cttcacactg atcatgatag atccagatgt tcctggtcct agtgatccat 240
atctcaggga acatctacac tggattgtca cagacattcc aggcactaca gattgctctt 300
ttggaagaga agtggttggg tatgaaatgc caaggccaaa tattggaatc cacaggtttg 360
tatttttgct gtttaagcag aagaaaaggc aaacaatatc gagtgcacca gtgtccagag 420
atcaatttag tagtagaaaa ttttcagaag aaaatgaact tggctcacca gttgctgctg 480
ttttcttcaa ttgtcagagg gaaactgccg ctagaaggcg ttga 524

<210> SEQ ID NO 75
<211> LENGTH: 47
<212> TYPE: PRT
<213> ORGANISM: Solanum lycopersicum

<400> SEQUENCE: 75

Met Ala Ser Lys Met Cys Glu Pro Leu Val Ile Gly Arg Val Ile Gly
1 5 10 15

Glu Val Val Asp Tyr Phe Cys Pro Ser Val Lys Met Ser Val Val Tyr
20 25 30

Asn Asn Asn Lys His Val Tyr Asn Gly His Glu Phe Phe Pro Ser
35 40 45

<210> SEQ ID NO 76
<211> LENGTH: 1931
<212> TYPE: DNA
<213> ORGANISM: Solanum lycopersicum

<400> SEQUENCE: 76
atggcttcca aaatgtgtga acccettgtg attggtagag tgattggtga agttgttgat 60
tatttctgtc caagtgttaa gatgtctgtt gtttataaca acaacaaaca tgtctataat 120
ggacatgaat tctttccttc catcagtaac ttctaaacct agggttgaag ttcatggtgg 180
tgatctcaga tccttcttca cactggtata tattaatctt caacacttcc aatttactcc 240
gtctgtctgt cctaatttat gtcacacatt ttctatgata tatagtttta gaaattattc 300
aagaccataa ctttttaaag aaaaaatcat agactttctt agtcaacgtc aaataaattg 360
agacggacaa gatgacatga ttagtacatt tatcttctat tattgacctc tcattttctt 420
ttatacatta tttgacagat catgatagat ccagatgttc ctggtcctag tgatccatat 480
ctcagggaac atctacactg gtatagacaa catatgcctt aaaactaact cagtcaattt 540
tatcttcaat tgtttacttt ggaaggggaa atgacatgat cattatatca tagtacaaat 600

```
tattatgtaa tttctgttcg tctaaaaaat gtcactttag aaaaaactga taatcatata    660
caataccaca ataaagatag aagaacatgt actaatattg aacttaaata atgagtacta    720
ggagtattat taattaactt taaaaatgct agtcaatata cctatgttta tatgttaaaa    780
aatcctttat atttggaaac atgagtactc ctataccata caatgttgtc gtacagttga    840
ttagacgggc aaattaaaca aatgtccaat aattgtacta attaataact acttgttctc    900
ttcatctatt attagttatt accaaaaaaa gaggactgca aaatggtgat attattatgt    960
gtaacggaaa aaaacgtact ctatttaata tgatagaatc aaagtgacat attttgttct   1020
agttagacaa ataagtaact gaaaagagga tttgaccatc tttacaggat tgtcacagac   1080
attccaggca ctacagattg ctcttttggt atgtatcctt aacccataaa tcaaaataat   1140
gtactttctt tttatttgcc attaatatct ctagtacaaa aaagaaatat tataaaaaaa   1200
attaatttca atttttatat tataggttta agataataat attaaacgat attttagtct   1260
ctaccaaata gacgagcaaa ttaaaactaa gaaagcacta catgttttct ttatattatt   1320
agtataaaaa tatattataa tttgcctggt ggtaatagga tcaaagtatt gattcttaat   1380
tattattata taattaataa taatggtaaa caaaaagata taaagtgctt acctcctaat   1440
tccctatatg aaaaaatata cttacttaat tactcttttt acacgtaagc atgcatttaa   1500
aaaaatatta aaaaattatt ccagaggtta tatataatat gtatggataa aaaaaaaatt   1560
cacctatata cataataata taattttcga gtgaattgac cgcccttcag catcattata   1620
taatgttatc gatctaggtc tttgtgtgaa attaaaagtt atttatacgg ttagtacgat   1680
cgcgtaataa cgaaggtaaa aatatttcag gaagagaagt ggttgggtat gaaatgccaa   1740
ggccaaatat tggaatccac aggtttgtat ttttgctgtt taagcagaag aaaaggcaaa   1800
caatatcgag tgcaccagtg tccagagatc aatttagtag tagaaaattt tcagaagaaa   1860
atgaacttgg ctcaccagtt gctgctgttt tcttcaattg tcagagggaa actgccgcta   1920
gaaggcgttg a                                                         1931
```

<210> SEQ ID NO 77
<211> LENGTH: 529
<212> TYPE: DNA
<213> ORGANISM: Solanum lycopersicum

<400> SEQUENCE: 77

```
atggcttcca aaatgtgtga acccccttgtg attggtagag tgattggtga agttgttgat    60
tatttctgtc caagtgttaa gatgtctgtt gtttataaca acaacaaaca tgtctataat   120
ggacatgaat tctttccttc catcagtaac ttctaaacct agggttgaag ttcatggtgg   180
tgatctcaga tccttcttca cactgatcat gatagatcca gatgttcctg gtcctagtga   240
tccatatctc agggaacatc tacactggat tgtcacagac attccaggca ctacagattg   300
ctcttttgga agagaagtgg ttgggtatga aatgccaagg ccaaatattg gaatccacag   360
gtttgtattt ttgctgttta agcagaagaa aaggcaaaca atatcgagtg caccagtgtc   420
cagagatcaa tttagtagta gaaaattttc agaagaaaat gaacttggct caccagttgc   480
tgctgttttc ttcaattgtc agagggaaac tgccgctaga aggcgttga                529
```

<210> SEQ ID NO 78
<211> LENGTH: 51
<212> TYPE: PRT
<213> ORGANISM: Solanum lycopersicum

<400> SEQUENCE: 78

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ile
        35                  40                  45

Ser Asn Phe
    50
```

<210> SEQ ID NO 79
<211> LENGTH: 1931
<212> TYPE: DNA
<213> ORGANISM: Solanum lycopersicum

<400> SEQUENCE: 79

```
atggcttcca aaatgtgtga accccttgtg attggtagag tgattggtga agttgttgat     60
tatttctgtc caagtgttaa gatgtctgtt gtttataaca acaacaaaca tgtctataat    120
ggacatgaat tctttccttc catcagtaac ttctaaacct agggttgaag ttcatggtgg    180
tgatctcaga tccttcttca cactggtata tattaatctt caacacttcc aatttactcc    240
gtctgtctgt cctaatttat gtcacacatt ttctatgata tatagtttta gaaattattc    300
aagaccataa ctttttaaag aaaaaatcat agactttctt agtcaacgtc aaataaattg    360
agacggacaa gatgacatga ttagtacatt tatcttctat tattgacctc tcattttctt    420
ttatacatta tttgacagat catgatagat ccagatgttc ctggtcctag tgatccatat    480
ctcagggaac atctacactg gtatagacaa catatgcctt aaaactaact cagtcaattt    540
tatcttcaat tgtttacttt ggaaggggaa atgacatgat cattatatca tagtacaaat    600
tattatgtaa tttctgttcg tctaaaaaat gtcactttag aaaaaactga taatcatata    660
caataccaca ataaagatag aagaacatgt actaatattg aacttaaata atgagtacta    720
ggagtattat taattaactt taaaaatgct agtcaatata cctatgttta tatgttaaaa    780
aatcctttat atttggaaac atgagtactc ctataccata caatgttgtc gtacagttga    840
ttagacgggc aaattaaaca aatgtccaat aattgtacta attaataact acttgttctc    900
ttcatctatt attagttatt accaaaaaaa gaggactgca aaatggtgat attattatgt    960
gtaacggaaa aaaacgtact ctatttaata tgatagaatc aaagtgacat attttgttct   1020
agttagacaa ataagtaact gaaaagagga tttgaccatc tttacaggat tgtcacagac   1080
attccaggca ctacagattg ctcttttggt atgtatcctt aacccataaa tcaaaataat   1140
gtactttctt tttatttgcc attaatatct ctagtacaaa aaagaaatat tataaaaaaa   1200
attaatttca atttttatat tataggttta agataataat attaaacgat attttagtct   1260
ctaccaaata gacgagcaaa ttaaaactaa gaaagcacta catgttttct ttatattatt   1320
agtataaaaa tatattataa tttgcctggt ggtaatagga tcaaagtatt gattcttaat   1380
tattattata taattaataa taatggtaaa caaaaagata taaagtgctt acctcctaat   1440
tccctatatg aaaaaatata cttacttaat tactcttttt acacgtaagc atgcatttaa   1500
aaaaatatta aaaaattatt ccagaggtta tatataatat gtatggataa aaaaaaaatt   1560
cacctatata cataataata taattttcga gtgaattgac cgcccttcag catcattata   1620
taatgttatc gatctaggtc tttgtgtgaa attaaaagtt atttatacgg ttagtacgat   1680
cgcgtaataa cgaaggtaaa aatatttcag gaagagaagt ggttgggtat gaaatgccaa   1740
```

```
ggccaaatat tggaatccac aggtttgtat ttttgctgtt taagcagaag aaaaggcaaa   1800

caatatcgag tgcaccagtg tccagagatc aatttagtag tagaaaattt tcagaagaaa   1860

atgaacttgg ctcaccagtt gctgctgttt tcttcaattg tcagagggaa actgccgcta   1920

gaaggcgttg a                                                        1931
```

<210> SEQ ID NO 80
<211> LENGTH: 529
<212> TYPE: DNA
<213> ORGANISM: Solanum lycopersicum

<400> SEQUENCE: 80

```
atggcttcca aaatgtgtga accccttgtg attggtagag tgattggtga agttgttgat     60

tatttctgtc caagtgttaa gatgtctgtt gtttataaca acaacaaaca tgtctataat    120

ggacatgaat tctttccttc catcagtaac ttctaaacct agggttgaag ttcatggtgg    180

tgatctcaga tccttcttca cactgatcat gatagatcca gatgttcctg gtcctagtga    240

tccatatctc agggaacatc tacactggat tgtcacagac attccaggca ctacagattg    300

ctcttttgga agagaagtgg ttgggtatga aatgccaagg ccaaatattg gaatccacag    360

gtttgtattt ttgctgttta agcagaagaa aaggcaaaca atatcgagtg caccagtgtc    420

cagagatcaa tttagtagta gaaaattttc agaagaaaat gaacttggct caccagttgc    480

tgctgttttc ttcaattgtc agagggaaac tgccgctaga aggcgttga                529
```

<210> SEQ ID NO 81
<211> LENGTH: 51
<212> TYPE: PRT
<213> ORGANISM: Solanum lycopersicum

<400> SEQUENCE: 81

```
Met Ala Ser Lys Met Cys Glu Pro Leu Val Ile Gly Arg Val Ile Gly
1               5                   10                  15

Glu Val Val Asp Tyr Phe Cys Pro Ser Val Lys Met Ser Val Val Tyr
            20                  25                  30

Asn Asn Asn Lys His Val Tyr Asn Gly His Glu Phe Phe Pro Ser Ile
        35                  40                  45

Ser Asn Phe
    50
```

<210> SEQ ID NO 82
<211> LENGTH: 1931
<212> TYPE: DNA
<213> ORGANISM: Solanum lycopersicum

<400> SEQUENCE: 82

```
atggcttcca aaatgtgtga accccttgtg attggtagag tgattggtga agttgttgat     60

tatttctgtc caagtgttaa gatgtctgtt gtttataaca acaacaaaca tgtctataat    120

ggacatgaat tctttccttc catcagtaac ttctaaacct agggttgaag ttcatggtgg    180

tgatctcaga tccttcttca cactggtata tattaatctt caacacttcc aatttactcc    240

gtctgtctgt cctaatttat gtcacacatt ttctatgata tatagtttta gaaattattc    300

aagaccataa ctttttaaag aaaaaatcat agactttctt agtcaacgtc aaataaattg    360

agacggacaa gatgacatga ttagtacatt tatcttctat tattgacctc tcattttctt    420

ttatacatta tttgacagat catgatagat ccagatgttc ctggtcctag tgatccatat    480

ctcagggaac atctacactg gtatagacaa catatgcctt aaaactaact cagtcaattt    540
```

```
tatcttcaat tgtttacttt ggaaggggaa atgacatgat cattatatca tagtacaaat    600

tattatgtaa tttctgttcg tctaaaaaat gtcactttag aaaaaactga taatcatata    660

caataccaca ataaagatag aagaacatgt actaatattg aacttaaata atgagtacta    720

ggagtattat taattaactt taaaaatgct agtcaatata cctatgttta tatgttaaaa    780

aatcctttat atttggaaac atgagtactc ctataccata caatgttgtc gtacagttga    840

ttagacgggc aaattaaaca aatgtccaat aattgtacta attaataact acttgttctc    900

ttcatctatt attagttatt accaaaaaaa gaggactgca aaatggtgat attattatgt    960

gtaacggaaa aaaacgtact ctatttaata tgatagaatc aaagtgacat attttgttct   1020

agttagacaa ataagtaact gaaaagagga tttgaccatc tttacaggat tgtcacagac   1080

attccaggca ctacagattg ctcttttggt atgtatcctt aacccataaa tcaaaataat   1140

gtactttctt tttatttgcc attaatatct ctagtacaaa aaagaaatat tataaaaaaa   1200

attaatttca atttttatat tataggttta agataataat attaaacgat attttagtct   1260

ctaccaaata gacgagcaaa ttaaaactaa gaaagcacta catgttttct ttatattatt   1320

agtataaaaa tatattataa tttgcctggt ggtaatagga tcaaagtatt gattcttaat   1380

tattattata taattaataa taatggtaaa caaaaagata taaagtgctt acctcctaat   1440

tccctatatg aaaaaatata cttacttaat tactcttttt acacgtaagc atgcatttaa   1500

aaaaatatta aaaaattatt ccagaggtta tatataatat gtatggataa aaaaaaaatt   1560

cacctatata cataataata taattttcga gtgaattgac cgcccttcag catcattata   1620

taatgttatc gatctaggtc tttgtgtgaa attaaaagtt atttatacgg ttagtacgat   1680

cgcgtaataa cgaaggtaaa aatatttcag gaagagaagt ggttgggtat gaaatgccaa   1740

ggccaaatat tggaatccac aggtttgtat ttttgctgtt taagcagaag aaaaggcaaa   1800

caatatcgag tgcaccagtg tccagagatc aatttagtag tagaaaattt tcagaagaaa   1860

atgaacttgg ctcaccagtt gctgctgttt tcttcaattg tcagagggaa actgccgcta   1920

gaaggcgttg a                                                        1931
```

<210> SEQ ID NO 83
<211> LENGTH: 529
<212> TYPE: DNA
<213> ORGANISM: Solanum lycopersicum

<400> SEQUENCE: 83

```
atggcttcca aaatgtgtga accccttgtg attggtagag tgattggtga agttgttgat     60

tatttctgtc caagtgttaa gatgtctgtt gtttataaca acaacaaaca tgtctataat    120

ggacatgaat tctttccttc catcagtaac ttctaaacct agggttgaag ttcatggtgg    180

tgatctcaga tccttcttca cactgatcat gatagatcca gatgttcctg gtcctagtga    240

tccatatctc agggaacatc tacactggat tgtcacagac attccaggca ctacagattg    300

ctcttttgga agagaagtgg ttgggtatga aatgccaagg ccaaatattg gaatccacag    360

gtttgtattt ttgctgttta agcagaagaa aaggcaaaca atatcgagtg caccagtgtc    420

cagagatcaa tttagtagta gaaaattttc agaagaaaat gaacttggct caccagttgc    480

tgctgttttc ttcaattgtc agagggaaac tgccgctaga aggcgttga                529
```

<210> SEQ ID NO 84
<211> LENGTH: 51
<212> TYPE: PRT

<213> ORGANISM: Solanum lycopersicum

<400> SEQUENCE: 84

Met Ala Ser Lys Met Cys Glu Pro Leu Val Ile Gly Arg Val Ile Gly
1 5 10 15

Glu Val Val Asp Tyr Phe Cys Pro Ser Val Lys Met Ser Val Val Tyr
20 25 30

Asn Asn Asn Lys His Val Tyr Asn Gly His Glu Phe Phe Pro Ser Ile
35 40 45

Ser Asn Phe
50

<210> SEQ ID NO 85
<211> LENGTH: 6296
<212> TYPE: DNA
<213> ORGANISM: Solanum lycopersicum

<400> SEQUENCE: 85
atggtgaagg tgatggagaa ggatactgtg gtggtatcac tggtggtatg gctaatcttg 60
gttgtatatc atcttaagct catttatgct aatatggaag gtttgtgggc ccatcatcct 120
catttagtta attttaggtc tatatttgat gttctatttt gtgagatgag tttcaaatgt 180
cgaaactttt cgtactagaa ataaaatata tgctaaaagt gaaattggta tgtgcaaaat 240
tggattttga atttgactaa tgtgtgagtt gttgaatttt cccaaaaggg taagcaagat 300
gtacaatgag ttccctgcac tgttacagtg acaagcagtt tagttttaat gtcagttaaa 360
tgtgaaagtt tttagttatc attgccattc aaccttagtg cattatgttt cctatacaag 420
cttgagtaat ttgatgtgat ttaatttggt tgtttgccaa aatcttgata aactgttttg 480
ttcagtcaat agattaaatt tttatgcgca tttaggtggt tgaaaattgt ctatgttttc 540
ctaaatgaat acacgaacag gtgatgcatt gcacagtcta cgcgtcaatt tacaagatcc 600
taacaatgtg ctacagagct gggacccaac ccttgttaat ccttgcacat ggtttcacgt 660
tacctgcaac aatgacaaca gtgttataag agtgtaagaa tctgttttct ggtctacctc 720
catttgaatg gatttgcaat tccactctct tgtggtggtg agcaatctaa ttgcagtttg 780
tgctcccata acacttgtta tatgatcaac ctttccagtg atttaggaaa tgcagcttta 840
tctggtttgt tagttccaca gcttggcctt ttgaagaatt tgcagtactt gtaagtctca 900
cttcatgaac tatgtttgga attattttac aaatttagag ttggaaaact ggcattgagt 960
gtattggttt ttccagctgt tgaagatttt catattacct ctagaattcg ctgcatgaaa 1020
ataatgtagg tggcttgcat attaactttt gcataaaaac aaagctgttg taagtggcaa 1080
aaatgagcag agaacacttt ctcctctcca tctcttgttt cacttgatgt tgtagtcgat 1140
ggcatagttg ttgatgtgtt ccctgaacaa cacaaatttg aatgtgtact tcataaaaaa 1200
agatttaaat atttgtttca cattacatac tagtaaatta agtaactcag atacttggat 1260
gagactagca atgaagtaac ttatgtggca aagtagtgtc tgtaattgct tgtgaaaaca 1320
ttgtagttga acttaaattt ttgtcataca ctcccttata taaagataag cagagtaatc 1380
gttaactttt ttatgaactc ttaaacagag tattattcta aatattatta ctaatgccag 1440
taccctaagc actcttaatt tggaatgaca aacttcaact catatcaaat cctttattcc 1500
ctctttcctt gttccatgta gactctaatc acgatttagg atgatggaat aggataaaac 1560
aaacaagaga aacaagtcca ttgtaaaagt aaagcaaaat ctagacttaa aaagaggaaa 1620
tatggcatga gggtaggttg atgtcttgga ggagaagatc tgaagttttc tggtcatata 1680
acagatgcta ttctggtttt caccaagagt tcgaatcatg attcaattaa gcatagattt 1740
tgtacaagtg ttaagcttag tttggagttc aatataccgt tcacttaaat tacatctcaa 1800
atttcattgt tcttattgta acccatgctc ttttgaagct gcaactgtat ggaagttcac 1860
agagacagta tgtgcatgtg cacctggtga agcagggcat tacatgatgt ataaccatgc 1920
atcagacaat gttataatga tggtataat tattacctag tgactgcttc atcctgctca 1980
cacattaata tattcctatg gatgcctaga tttgcttgag gcttgtgtag tacgcgtgct 2040
aagtattttc ctagtgtatg caagtgacaa tcacatcaag aatgaaacaa tataaaaaga 2100
acatcaaaag tataacatta tctttgtcaa aaaaaaaaag aaagaacatc aagagtgctg 2160
atggaattta acaatcaccg ggcatacaca ctgtttagat gaagttcgaa attaacataa 2220
tgacagacgt taaattttta ttgatgagtt atatagattg tataaaatgt ttgacgagct 2280
gattctttgc agcacatggg acgacaggtt tttatataga aaagtgcttg taaccaaata 2340
taagaaaata cctccatgaa atagacatcg gtaactagtt ataattgcta tcttggaact 2400
cctagacctt tctcatttgt tgacttttaa ttgtcgcttg atgccagtat tgatggatgt 2460
gagaattctc cttcattatc ttggttgtcc cattatccta gggatgtcat tggtatgata 2520
tgtggaattg actcattctc tggttttctt gtcacaggga gctttacagt aataaatataa 2580
gtggtctgat accgagtgat cttgggaatt tgactaatct ggtcagcttg gatctctact 2640
tgaacaactt cgtcggtccc atcccagatt ccttgggcaa gctgtcgaaa ttgagattcc 2700
tgtatgtatt tttgttctat attagattta tgtggatatt gtgatgccaa atgtatattt 2760
catcaaccaa gatggaccta ctcttactgg catgttgaga aaggaaagga agcctgaatt 2820
cttttctagg tttcacataa gatgacctct attagtatta tgtttcactc ttaagttttg 2880
atggtagaag gtatttgagg acttcatggg tctgatatca ttcataaaac cgatcttaca 2940
taagtctttt aattttctcc ctttgttcta atccttgtat aaaggaaaag aatagaagcc 3000
tatgctttgt ctgatactga tattgtaaaa ttaatcagag tttagtaatg ggtgttggga 3060
tccttttcta gaagagagaa gaagtttaga atcccatgct tcatcttgca tttttcactg 3120
ctgaagtttc tcttgcttaa tgctccacaa acttctttct tttggcttga ctgtctaaga 3180
agtgtgccaa attgttctat catgcagact cagcatgaaa cctcattaac tgcatcttgg 3240
gacttactat agaactattg cagtactgca acgttgacta acatgattta gtccaaaagg 3300
tgtttcaagt ctgtttatcg gggggggggg atgttttgag gctctttatc gtggttctga 3360
actgacgcct tcatttccag ctgaagtgcc ggttctggct cgaagttgaa tatgttttac 3420
atccacatat taataattta ttaagatgat tctccttgtc aaataataaa taaattaaga 3480
tgattcaatt agtagccttt tcttctgttt tattctccat tatttacttg taccaaagat 3540
gaagctcatt cctgtaaacc tttgtgtttt cttgcaagga tagtcggctc aacaataata 3600
gcttgactgg taacatccca atgtcactga ctaatatctc atcactgcaa gtgttgtaag 3660
tacactgatt attttgtgac ttgatttaga taattctttc tgtcttccat atcttctcat 3720
gcatttcctt ttccttctaa tgcatataca gatttactta tgctcaattc ttgtctcacc 3780
tgtatgtagg gatctgtcaa acaaccgtct ctcaggtgct gttccagata atggttcatt 3840
ttctctattc acgcctatca ggtatatttc atttaaggcg gtgcaccatc taactggctg 3900
gtggttttag catgctacta tttgctaata tatttttctt gtttacagtt ttgcgaataa 3960
tttagatctt tgcgggcctg taactggacg cccttgccct ggatctcctc cattctcccc 4020

-continued

```
tccgcctcca tttgttccac caccaccaat ttctgctcca ggtggttctc taaattggtg   4080
tggataaatt gttctccttt ctttttcttt ttgttttttt tgcttttttg cggttagtga   4140
ttttagtttg tccatccaac gtaagtgaga atttgtgcta tagaagctaa agtactgaca   4200
agaaaggggg cagaagagga aaacccatct taactagtca ggcattagtt ctgatgggaa   4260
actggtatgc acgagactac atttagtctc taagcattct ggtctttata caaatttaat   4320
tcagcattgt ggacatcttt tctttggtcc ccttgtaaat tattatctgt ggtatttgaa   4380
gtcatgtgtc tgaatgaaat taatcatatt tatgccagaa cttgtgaaga ttttcttttc   4440
tttgtaaaaa ctgtcctgga aattagatct gatgatagat acaaatttgt ctactaattt   4500
ctttttgaag tgatttaatt aatgaagggc cggccaaaat tatgtgttaa atatagtcta   4560
gatcatatga aggaaattaa tcaaatttat gggaacttca ggaggaaatg gtgcaactgg   4620
agcaattgct ggaggtgtag ctgctggtgc tgctctacta tttgctgctc ctgccattgc   4680
atttgcctgg tggcgccgta gaaagccaca agaatatttc tttgacgtac caggttagca   4740
gtattcaaat acccaaccat aagtccataa ctcctactta ctctctcacg tgtttatggt   4800
ttctcttgca tgttttattt tttggctcca taattaacgt ctttgcttaa acttattgca   4860
gccgaagaag atcctgaagt tcacttaggt caactgaaaa ggttctccct ccgagagcta   4920
caagttgcaa ctgacagttt tagcaataaa aatatactgg gtcgaggtgg atttggtaag   4980
gtatacaaag gacgcttagc agatggatca ttggtggctg ttaagcggct aaaggaagag   5040
cgtactcctg gaggggagtt gcaatttcaa acagaagttg agatgattag catggcagtg   5100
cataggaatc ttctacgatt gcgtggtttc tgtatgacac caactgaaag actgcttgtc   5160
taccccctaca tggcgaatgg aagtgttgca tcatgcctga gaggtgacac tttctgaaat   5220
ctatcactcc ataaatgttc tcacctttaa tttggagggt attattgcat aatgcaagaa   5280
tgtctttcgc tggttaacat tctatcttgg cataacttac tctttataac aaaacatatt   5340
cttgttagtt attttcctgt aactttttaa aaggtagaag tataatttgt attgtattct   5400
cttgacaaca taatttattt tatcagaacg accgccttct gaaccaccac ttgattggcc   5460
aacgcgaaaa cgtattgctt tggggtctgc caggggatta tcgtatttgc atgatcattg   5520
tgaccctaag attatccatc gtgatgtgaa ggctgcaaat atattgctag atgaagaatt   5580
tgaggctgtt gttggagact ttggtttggc taaacttatg gactacaagg atacacatgt   5640
tacaactgct gtgcgtggta caatcgggca tatagctcca gaataccttt ccacagggaa   5700
gtcttcagaa aagactgatg tttttgggta tgggatcatg cttctggagc taatcaccgg   5760
ccaacgtgct tttgatcttg ctcggctggc aaatgatgac gatgtcatgt tgcttgactg   5820
ggtatgttgt catacctgct ttacatgtga acatgacacg agtaccataa tgtgttcatt   5880
ttttaatctg tacatcacaa cactagctga ctaataagta tttgtgcctt tagcaggaat   5940
atttaagtct atgactaaac ttgttgaggt tcttgtttca ggtgaaagga ctcctcaaag   6000
agaagaaact ggaaatgctg gttgaccctg atcttcagaa caaatatgtg gaggctgagg   6060
tggagcaact gatccaggta gcattgcttt gtacacaaag caacccaatg gatcggccta   6120
agatgtcgga agtggtgaga atgcttgaag gtgatggttt ggctgaaaga tgggatgagt   6180
ggcagaaggt agaagttctc cggcaggaag tggaacttgc accacatcct ggttctgatt   6240
ggcttgttga ctcgacagag aatttacatg cagttgaatt atcgggtcca aggtga       6296
```

<210> SEQ ID NO 86
<211> LENGTH: 1890

<212> TYPE: DNA
<213> ORGANISM: Solanum lycopersicum

<400> SEQUENCE: 86
atggtgaagg tgatggagaa ggatactgtg gtggtatcac tggtggtatg gctaatcttg 60
gttgtatatc atcttaagct catttatgct aatatggaag gtgatgcatt gcacagtcta 120
cgcgtcaatt tacaagatcc taacaatgtg ctacagagct gggacccaac ccttgttaat 180
ccttgcacat ggtttcacgt tacctgcaac aatgacaaca gtgttataag agttgattta 240
ggaaatgcag ctttatctgg tttgttagtt ccacagcttg gccttttgaa gaatttgcag 300
tacttggagc tttacagtaa taatataagt ggtctgatac cgagtgatct tgggaatttg 360
actaatctgg tcagcttgga tctctacttg aacaacttcg tcggtcccat cccagattcc 420
ttgggcaagc tgtcgaaatt gagattcctt cggctcaaca ataatagctt gactggtaac 480
atcccaatgt cactgactaa tatctcatca ctgcaagtgt tggatctgtc aaacaaccgt 540
ctctcaggtg ctgttccaga taatggttca ttttctctat tcacgcctat cagttttgcg 600
aataatttag atctttgcgg gcctgtaact ggacgccctt gccctggatc tcctccattc 660
tcccctccgc ctccatttgt tccaccacca ccaatttctg ctccaggagg aaatggtgca 720
actggagcaa ttgctggagg tgtagctgct ggtgctgctc tactatttgc tgctcctgcc 780
attgcatttg cctggtggcg ccgtagaaag ccacaagaat atttctttga cgtaccagcc 840
gaagaagatc ctgaagttca cttaggtcaa ctgaaaaggt tctccctccg agagctacaa 900
gttgcaactg acagttttag caataaaaat atactgggtc gaggtggatt tggtaaggta 960
tacaaaggac gcttagcaga tggatcattg gtggctgtta agcggctaaa ggaagagcgt 1020
actcctggag gggagttgca atttcaaaca gaagttgaga tgattagcat ggcagtgcat 1080
aggaatcttc tacgattgcg tggtttctgt atgacaccaa ctgaaagact gcttgtctac 1140
ccctacatgg cgaatggaag tgttgcatca tgcctgagag aacgaccgcc ttctgaacca 1200
ccacttgatt ggccaacgcg aaaacgtatt gctttggggt ctgccagggg attatcgtat 1260
ttgcatgatc attgtgaccc taagattatc catcgtgatg tgaaggctgc aaatatattg 1320
ctagatgaag aatttgaggc tgttgttgga gactttggtt tggctaaact tatggactac 1380
aaggatacac atgttacaac tgctgtgcgt ggtacaatcg ggcatatagc tccagaatac 1440
ctttccacag ggaagtcttc agaaaagact gatgtttttg ggtatgggat catgcttctg 1500
gagctaatca ccggccaacg tgcttttgat cttgctcggc tggcaaatga tgacgatgtc 1560
atgttgcttg actgggtgaa aggactcctc aaagagaaga aactggaaat gctggttgac 1620
cctgatcttc agaacaaata tgtggaggct gaggtggagc aactgatcca ggtagcattg 1680
ctttgtacac aaagcaaccc aatggatcgg cctaagatgt cggaagtggt gagaatgctt 1740
gaaggtgatg gtttggctga aagatgggat gagtggcaga aggtagaagt tctccggcag 1800
gaagtggaac ttgcaccaca tcctggttct gattggcttg ttgactcgac agagaattta 1860
catgcagttg aattatcggg tccaaggtga 1890

<210> SEQ ID NO 87
<211> LENGTH: 629
<212> TYPE: PRT
<213> ORGANISM: Solanum lycopersicum

<400> SEQUENCE: 87

Met Val Lys Val Met Glu Lys Asp Thr Val Val Val Ser Leu Val Val
1 5 10 15

```
Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Leu Val Asn Pro Cys Thr Trp
    50                  55                  60

Phe His Val Thr Cys Asn Asn Asp Asn Ser Val Ile Arg Val Asp Leu
65                  70                  75                  80

Gly Asn Ala Ala Leu Ser Gly Leu Leu Val Pro Gln Leu Gly Leu Leu
                85                  90                  95

Lys Asn Leu Gln Tyr Leu Glu Leu Tyr Ser Asn Asn Ile Ser Gly Leu
            100                 105                 110

Ile Pro Ser Asp Leu Gly Asn Leu Thr Asn Leu Val Ser Leu Asp Leu
        115                 120                 125

Tyr Leu Asn Asn Phe Val Gly Pro Ile Pro Asp Ser Leu Gly Lys Leu
    130                 135                 140

Ser Lys Leu Arg Phe Leu Arg Leu Asn Asn Asn Ser Leu Thr Gly Asn
145                 150                 155                 160

Ile Pro Met Ser Leu Thr Asn Ile Ser Ser Leu Gln Val Leu Asp Leu
                165                 170                 175

Ser Asn Asn Arg Leu Ser Gly Ala Val Pro Asp Asn Gly Ser Phe Ser
            180                 185                 190

Leu Phe Thr Pro Ile Ser Phe Ala Asn Asn Leu Asp Leu Cys Gly Pro
        195                 200                 205

Val Thr Gly Arg Pro Cys Pro Gly Ser Pro Pro Phe Ser Pro Pro Pro
    210                 215                 220

Pro Phe Val Pro Pro Pro Pro Ile Ser Ala Pro Gly Gly Asn Gly Ala
225                 230                 235                 240

Thr Gly Ala Ile Ala Gly Gly Val Ala Ala Gly Ala Ala Leu Leu Phe
                245                 250                 255

Ala Ala Pro Ala Ile Ala Phe Ala Trp Trp Arg Arg Arg Lys Pro Gln
            260                 265                 270

Glu Tyr Phe Phe Asp Val Pro Ala Glu Glu Asp Pro Glu Val His Leu
        275                 280                 285

Gly Gln Leu Lys Arg Phe Ser Leu Arg Glu Leu Gln Val Ala Thr Asp
    290                 295                 300

Ser Phe Ser Asn Lys Asn Ile Leu Gly Arg Gly Gly Phe Gly Lys Val
305                 310                 315                 320

Tyr Lys Gly Arg Leu Ala Asp Gly Ser Leu Val Ala Val Lys Arg Leu
                325                 330                 335

Lys Glu Glu Arg Thr Pro Gly Gly Glu Leu Gln Phe Gln Thr Glu Val
            340                 345                 350

Glu Met Ile Ser Met Ala Val His Arg Asn Leu Leu Arg Leu Arg Gly
        355                 360                 365

Phe Cys Met Thr Pro Thr Glu Arg Leu Leu Val Tyr Pro Tyr Met Ala
    370                 375                 380

Asn Gly Ser Val Ala Ser Cys Leu Arg Glu Arg Pro Pro Ser Glu Pro
385                 390                 395                 400

Pro Leu Asp Trp Pro Thr Arg Lys Arg Ile Ala Leu Gly Ser Ala Arg
                405                 410                 415

Gly Leu Ser Tyr Leu His Asp His Cys Asp Pro Lys Ile Ile His Arg
            420                 425                 430
```

-continued

```
Asp Val Lys Ala Ala Asn Ile Leu Leu Asp Glu Glu Phe Glu Ala Val
        435                 440                 445

Val Gly Asp Phe Gly Leu Ala Lys Leu Met Asp Tyr Lys Asp Thr His
    450                 455                 460

Val Thr Thr Ala Val Arg Gly Thr Ile Gly His Ile Ala Pro Glu Tyr
465                 470                 475                 480

Leu Ser Thr Gly Lys Ser Ser Glu Lys Thr Asp Val Phe Gly Tyr Gly
                485                 490                 495

Ile Met Leu Leu Glu Leu Ile Thr Gly Gln Arg Ala Phe Asp Leu Ala
            500                 505                 510

Arg Leu Ala Asn Asp Asp Asp Val Met Leu Leu Asp Trp Val Lys Gly
        515                 520                 525

Leu Leu Lys Glu Lys Lys Leu Glu Met Leu Val Asp Pro Asp Leu Gln
    530                 535                 540

Asn Lys Tyr Val Glu Ala Glu Val Glu Gln Leu Ile Gln Val Ala Leu
545                 550                 555                 560

Leu Cys Thr Gln Ser Asn Pro Met Asp Arg Pro Lys Met Ser Glu Val
                565                 570                 575

Val Arg Met Leu Glu Gly Asp Gly Leu Ala Glu Arg Trp Asp Glu Trp
            580                 585                 590

Gln Lys Val Glu Val Leu Arg Gln Glu Val Glu Leu Ala Pro His Pro
        595                 600                 605

Gly Ser Asp Trp Leu Val Asp Ser Thr Glu Asn Leu His Ala Val Glu
    610                 615                 620

Leu Ser Gly Pro Arg
625
```

<210> SEQ ID NO 88
<211> LENGTH: 6296
<212> TYPE: DNA
<213> ORGANISM: Solanum lycopersicum

<400> SEQUENCE: 88

```
atggtgaagg tgatggagaa ggatactgtg gtggtatcac tggtggtatg gctaatcttg     60

gttgtatatc atcttaagct catttatgct aatatggaag gtttgtgggc ccatcatcct    120

catttagtta attttaggtc tatatttgat gttctatttt gtgagatgag tttcaaatgt    180

cgaaactttt cgtactagaa ataaaatata tgctaaaagt gaaattggta tgtgcaaaat    240

tggattttga atttgactaa tgtgtgagtt gttgaatttt cccaaaaggg taagcaagat    300

gtacaatgag ttccctgcac tgttacagtg acaagcagtt tagttttaat gtcagttaaa    360

tgtgaaagtt tttagttatc attgccattc aaccttagtg cattatgttt cctatacaag    420

cttgagtaat ttgatgtgat ttaatttggt tgtttgccaa aatcttgata aactgttttg    480

ttcagtcaat agattaaatt tttatgcgca tttaggtggt tgaaaattgt ctatgttttc    540

ctaaatgaat acacgaacag gtgatgcatt gcacagtcta cgcgtcaatt tacaagatcc    600

taacaatgtg ctacagagct gggacccaac ccttgttaat ccttgcacat ggtttcacgt    660

tacctgcaac aatgacaaca gtgttataag agtgtaagaa tctgttttct ggtctacctc    720

catttgaatg gatttgcaat tccactctct tgtggtggtg agcaatctaa ttgcagtttg    780

tgctcccata acacttgtta tatgatcaac ctttccagtg atttaggaaa tgcagcttta    840

tctggtttgt tagttccaca gcttggcctt ttgaagaatt tgcagtactt gtaagtctca    900

cttcatgaac tatgtttgga attattttac aaatttagag ttggaaaact ggcattgagt    960
```

gtattggttt ttccagctgt tgaagatttt catattacct ctagaattcg ctgcatgaaa 1020
ataatgtagg tggcttgcat attaactttt gcataaaaac aaagctgttg taagtggcaa 1080
aaatgagcag agaacacttt ctcctctcca tctcttgttt cacttgatgt tgtagtcgat 1140
ggcatagttg ttgatgtgtt ccctgaacaa cacaaatttg aatgtgtact tcataaaaaa 1200
agatttaaat atttgtttca cattacatac tagtaaatta agtaactcag atacttggat 1260
gagactagca atgaagtaac ttatgtggca aagtagtgtc tgtaattgct tgtgaaaaca 1320
ttgtagttga acttaaattt ttgtcataca ctcccttata taaagataag cagagtaatc 1380
gttaactttt ttatgaactc ttaaacagag tattattcta aatattatta ctaatgccag 1440
taccctaagc actcttaatt tggaatgaca aacttcaact catatcaaat cctttattcc 1500
ctctttcctt gttccatgta gactctaatc acgatttagg atgatggaat aggataaaac 1560
aaacaagaga aacaagtcca ttgtaaaagt aaagcaaaat ctagacttaa aaagaggaaa 1620
tatggcatga gggtaggttg atgtcttgga ggagaagatc tgaagttttc tggtcatata 1680
acagatgcta ttctggtttt caccaagagt tcgaatcatg attcaattaa gcatagattt 1740
tgtacaagtg ttaagcttag tttggagttc aatataccgt tcacttaaat tacatctcaa 1800
atttcattgt tcttattgta acccatgctc ttttgaagct gcaactgtat ggaagttcac 1860
agagacagta tgtgcatgtg cacctggtga agcagggcat tacatgatgt ataaccatgc 1920
atcagacaat gttataatga tgggtataat tattacctag tgactgcttc atcctgctca 1980
cacattaata tattcctatg gatgcctaga tttgcttgag gcttgtgtag tacgcgtgct 2040
aagtattttc ctagtgtatg caagtgacaa tcacatcaag aatgaaacaa tataaaaaga 2100
acatcaaaag tataacatta tctttgtcaa aaaaaaaaag aaagaacatc aagagtgctg 2160
atggaattta acaatcaccg ggcatacaca ctgtttagat gaagttcgaa attaacataa 2220
tgacagacgt taaattttta ttgatgagtt atatagattg tataaaatgt ttgacgagct 2280
gattctttgc agcacatggg acgacaggtt tttatataga aaagtgcttg taaccaaata 2340
taagaaaata cctccatgaa atagacatcg gtaactagtt ataattgcta tcttggaact 2400
cctagacctt tctcatttgt tgacttttaa ttgtcgcttg atgccagtat tgatggatgt 2460
gagaattctc cttcattatc ttggttgtcc cattatccta gggatgtcat tggtatgata 2520
tgtggaattg actcattctc tggttttctt gtcacaggga gctttacagt aataaatataa 2580 gtggtctgat accgagtgat cttgggaatt tgactaatct ggtcagcttg gatctctact 2640
tgaacaactt cgtcggtccc atcccagatt ccttgggcaa gctgtcgaaa ttgagattcc 2700
tgtatgtatt tttgttctat attagattta tgtggatatt gtgatgccaa atgtatattt 2760
catcaaccaa gatggaccta ctcttactgg catgttgaga aaggaaagga agcctgaatt 2820
cttttctagg tttcacataa gatgacctct attagtatta tgtttcactc ttaagttttg 2880
atggtagaag gtatttgagg acttcatggg tctgatatca ttcataaaac cgatcttaca 2940
taagtctttt aattttctcc ctttgttcta atccttgtat aaaggaaaag aatagaagcc 3000
tatgctttgt ctgatactga tattgtaaaa ttaatcagag tttagtaatg ggtgttggga 3060
tccttttcta gaagagagaa gaagtttaga atcccatgct tcatcttgca tttttcactg 3120
ctgaagtttc tcttgcttaa tgctccacaa acttctttct tttggcttga ctgtctaaga 3180
agtgtgccaa attgttctat catgcagact cagcatgaaa cctcattaac tgcatcttgg 3240
gacttactat agaactattg cagtactgca acgttgacta acatgattta gtccaaaagg 3300
tgtttcaagt ctgtttatcg gggggggggg atgttttgag gctctttatc gtggttctga 3360

-continued

```
actgacgcct tcatttccag ctgaagtgcc ggttctggct cgaagttgaa tatgttttac   3420
atccacatat taataattta ttaagatgat tctccttgtc aaataataaa taaattaaga   3480
tgattcaatt agtagccttt tcttctgttt tattctccat tatttacttg taccaaagat   3540
gaagctcatt cctgtaaacc tttgtgtttt cttgcaagga tagtcggctc aacaataata   3600
gcttgactgg taacatccca atgtcactga ctaatatctc atcactgcaa gtgttgtaag   3660
tacactgatt attttgtgac ttgatttaga taattctttc tgtcttccat atcttctcat   3720
gcatttcctt ttccttctaa tgcatataca gatttactta tgctcaattc ttgtctcacc   3780
tgtatgtagg gatctgtcaa acaaccgtct ctcaggtgct gttccagata atggttcatt   3840
ttctctattc acgcctatca ggtatatttc atttaaggcg gtgcaccatc taactggctg   3900
gtggttttag catgctacta tttgctaata tatttttctt gtttacagtt ttgcgaataa   3960
tttagatctt tgcgggcctg taactggacg cccttgccct ggatctcctc cattctcccc   4020
tccgcctcca tttgttccac caccaccaat ttctgctcca ggtggttctc taaattggtg   4080
tggataaatt gttctccttt cttttttctt ttgttttttt tgcttttttg cggttagtga   4140
ttttagtttg tccatccaac gtaagtgaga atttgtgcta tagaagctaa agtactgaca   4200
agaaaggggg cagaagagga aaacccatct taactagtca ggcattagtt ctgatgggaa   4260
actggtatgc acgagactac atttagtctc taagcattct ggtctttata caaatttaat   4320
tcagcattgt ggacatcttt tctttggtcc ccttgtaaat tattatctgt ggtatttgaa   4380
gtcatgtgtc tgaatgaaat taatcatatt tatgccagaa cttgtgaaga ttttcttttc   4440
tttgtaaaaa ctgtcctgga aattagatct gatgatagat acaaatttgt ctactaattt   4500
ctttttgaag tgatttaatt aatgaagggc cggccaaaat tatgtgttaa atatagtcta   4560
gatcatatga aggaaattaa tcaaatttat gggaacttca ggaggaaatg gtgcaactgg   4620
agcaattgct ggaggtgtag ctgctggtgc tgctctacta tttgctgctc ctgccattgc   4680
atttgcctgg tggcgccgta gaaagccaca agaatatttc tttgacgtac caggttagca   4740
gtattcaaat acccaaccat aagtccataa ctcctactta ctctctcacg tgtttatggt   4800
ttctcttgca tgttttattt tttggctcca taattaacgt ctttgcttaa acttattgca   4860
gccgaagaag atcctgaagt tcacttaggt caactgaaaa ggttctccct ccgagagcta   4920
caagttgcaa ctgacagttc tagcaataaa aatatactgg gtcgaggtgg atttggtaag   4980
gtatacaaag gacgcttagc agatggatca ttggtggctg ttaagcggct aaaggaagag   5040
cgtactcctg gaggggagtt gcaatttcaa acagaagttg agatgattag catggcagtg   5100
cataggaatc ttctacgatt gcgtggtttc tgtatgacac caactgaaag actgcttgtc   5160
taccccctaca tggcgaatgg aagtgttgca tcatgcctga gaggtgacac tttctgaaat   5220
ctatcactcc ataaatgttc tcacctttaa tttggagggt attattgcat aatgcaagaa   5280
tgtctttcgc tggttaacat tctatcttgg cataacttac tctttataac aaaacatatt   5340
cttgttagtt attttcctgt aactttttaa aaggtagaag tataatttgt attgtattct   5400
cttgacaaca taatttattt tatcagaacg accgccttct gaaccaccac ttgattggcc   5460
aacgcgaaaa cgtattgctt tggggtctgc caggggatta tcgtatttgc atgatcattg   5520
tgaccctaag attatccatc gtgatgtgaa ggctgcaaat atattgctag atgaagaatt   5580
tgaggctgtt gttggagact ttggtttggc taaacttatg gactacaagg atacacatgt   5640
tacaactgct gtgcgtggta caatcgggca tatagctcca gaataccttt ccacagggaa   5700
```

gtcttcagaa aagactgatg tttttgggta tgggatcatg cttctggagc taatcaccgg 5760
ccaacgtgct tttgatcttg ctcggctggc aaatgatgac gatgtcatgt tgcttgactg 5820
ggtatgttgt catacctgct ttacatgtga acatgacacg agtaccataa tgtgttcatt 5880
ttttaatctg tacatcacaa cactagctga ctaataagta tttgtgcctt tagcaggaat 5940
atttaagtct atgactaaac ttgttgaggt tcttgtttca ggtgaaagga ctcctcaaag 6000
agaagaaact ggaaatgctg gttgaccctg atcttcagaa caaatatgtg gaggctgagg 6060
tggagcaact gatccaggta gcattgcttt gtacacaaag caacccaatg gatcggccta 6120
agatgtcgga agtggtgaga atgcttgaag gtgatggttt ggctgaaaga tgggatgagt 6180
ggcagaaggt agaagttctc cggcaggaag tggaacttgc accacatcct ggttctgatt 6240
ggcttgttga ctcgacagag aatttacatg cagttgaatt atcgggtcca aggtga 6296

<210> SEQ ID NO 89
<211> LENGTH: 1890
<212> TYPE: DNA
<213> ORGANISM: Solanum lycopersicum

<400> SEQUENCE: 89
atggtgaagg tgatggagaa ggatactgtg gtggtatcac tggtggtatg gctaatcttg 60
gttgtatatc atcttaagct catttatgct aatatggaag gtgatgcatt gcacagtcta 120
cgcgtcaatt tacaagatcc taacaatgtg ctacagagct gggacccaac ccttgttaat 180
ccttgcacat ggtttcacgt tacctgcaac aatgacaaca gtgttataag agttgattta 240
ggaaatgcag ctttatctgg tttgttagtt ccacagcttg gccttttgaa gaatttgcag 300
tacttggagc tttacagtaa taatataagt ggtctgatac cgagtgatct tgggaatttg 360
actaatctgg tcagcttgga tctctacttg aacaacttcg tcggtcccat cccagattcc 420
ttgggcaagc tgtcgaaatt gagattcctt cggctcaaca ataatagctt gactggtaac 480
atcccaatgt cactgactaa tatctcatca ctgcaagtgt tggatctgtc aaacaaccgt 540
ctctcaggtg ctgttccaga taatggttca ttttctctat tcacgcctat cagttttgcg 600
aataatttag atctttgcgg gcctgtaact ggacgccctt gccctggatc tcctccattc 660
tcccctccgc ctccatttgt tccaccacca ccaatttctg ctccaggagg aaatggtgca 720
actggagcaa ttgctggagg tgtagctgct ggtgctgctc tactatttgc tgctcctgcc 780
attgcatttg cctggtggcg ccgtagaaag ccacaagaat atttctttga cgtaccagcc 840
gaagaagatc ctgaagttca cttaggtcaa ctgaaaaggt tctccctccg agagctacaa 900
gttgcaactg acagttctag caataaaaat atactgggtc gaggtggatt tggtaaggta 960
tacaaaggac gcttagcaga tggatcattg gtggctgtta agcggctaaa ggaagagcgt 1020
actcctggag gggagttgca atttcaaaca gaagttgaga tgattagcat ggcagtgcat 1080
aggaatcttc tacgattgcg tggtttctgt atgacaccaa ctgaaagact gcttgtctac 1140
ccctacatgg cgaatggaag tgttgcatca tgcctgagag aacgaccgcc ttctgaacca 1200
ccacttgatt ggccaacgcg aaaacgtatt gctttggggt ctgccagggg attatcgtat 1260
ttgcatgatc attgtgaccc taagattatc catcgtgatg tgaaggctgc aaatatattg 1320
ctagatgaag aatttgaggc tgttgttgga gactttggtt tggctaaact tatggactac 1380
aaggatacac atgttacaac tgctgtgcgt ggtacaatcg ggcatatagc tccagaatac 1440
ctttccacag ggaagtcttc agaaaagact gatgtttttg ggtatgggat catgcttctg 1500
gagctaatca ccggccaacg tgcttttgat cttgctcggc tggcaaatga tgacgatgtc 1560

```
atgttgcttg actgggtgaa aggactcctc aaagagaaga aactggaaat gctggttgac   1620

cctgatcttc agaacaaata tgtggaggct gaggtggagc aactgatcca ggtagcattg   1680

ctttgtacac aaagcaaccc aatggatcgg cctaagatgt cggaagtggt gagaatgctt   1740

gaaggtgatg gtttggctga aagatgggat gagtggcaga aggtagaagt tctccggcag   1800

gaagtggaac ttgcaccaca tcctggttct gattggcttg ttgactcgac agagaattta   1860

catgcagttg aattatcggg tccaaggtga                                    1890


<210> SEQ ID NO 90
<211> LENGTH: 629
<212> TYPE: PRT
<213> ORGANISM: Solanum lycopersicum

<400> SEQUENCE: 90

Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Leu Val Asn Pro Cys Thr Trp
    50                  55                  60

Phe His Val Thr Cys Asn Asn Asp Asn Ser Val Ile Arg Val Asp Leu
65                  70                  75                  80

Gly Asn Ala Ala Leu Ser Gly Leu Leu Val Pro Gln Leu Gly Leu Leu
                85                  90                  95

Lys Asn Leu Gln Tyr Leu Glu Leu Tyr Ser Asn Asn Ile Ser Gly Leu
            100                 105                 110

Ile Pro Ser Asp Leu Gly Asn Leu Thr Asn Leu Val Ser Leu Asp Leu
        115                 120                 125

Tyr Leu Asn Asn Phe Val Gly Pro Ile Pro Asp Ser Leu Gly Lys Leu
    130                 135                 140

Ser Lys Leu Arg Phe Leu Arg Leu Asn Asn Asn Ser Leu Thr Gly Asn
145                 150                 155                 160

Ile Pro Met Ser Leu Thr Asn Ile Ser Ser Leu Gln Val Leu Asp Leu
                165                 170                 175

Ser Asn Asn Arg Leu Ser Gly Ala Val Pro Asp Asn Gly Ser Phe Ser
            180                 185                 190

Leu Phe Thr Pro Ile Ser Phe Ala Asn Asn Leu Asp Leu Cys Gly Pro
        195                 200                 205

Val Thr Gly Arg Pro Cys Pro Gly Ser Pro Pro Phe Ser Pro Pro Pro
    210                 215                 220

Pro Phe Val Pro Pro Pro Pro Ile Ser Ala Pro Gly Gly Asn Gly Ala
225                 230                 235                 240

Thr Gly Ala Ile Ala Gly Gly Val Ala Ala Gly Ala Ala Leu Leu Phe
                245                 250                 255

Ala Ala Pro Ala Ile Ala Phe Ala Trp Trp Arg Arg Arg Lys Pro Gln
            260                 265                 270

Glu Tyr Phe Phe Asp Val Pro Ala Glu Glu Asp Pro Glu Val His Leu
        275                 280                 285

Gly Gln Leu Lys Arg Phe Ser Leu Arg Glu Leu Gln Val Ala Thr Asp
    290                 295                 300

Ser Ser Ser Asn Lys Asn Ile Leu Gly Arg Gly Gly Phe Gly Lys Val
```

305 310 315 320

Tyr Lys Gly Arg Leu Ala Asp Gly Ser Leu Val Ala Val Lys Arg Leu
325 330 335

Lys Glu Glu Arg Thr Pro Gly Gly Glu Leu Gln Phe Gln Thr Glu Val
340 345 350

Glu Met Ile Ser Met Ala Val His Arg Asn Leu Leu Arg Leu Arg Gly
355 360 365

Phe Cys Met Thr Pro Thr Glu Arg Leu Leu Val Tyr Pro Tyr Met Ala
370 375 380

Asn Gly Ser Val Ala Ser Cys Leu Arg Glu Arg Pro Pro Ser Glu Pro
385 390 395 400

Pro Leu Asp Trp Pro Thr Arg Lys Arg Ile Ala Leu Gly Ser Ala Arg
405 410 415

Gly Leu Ser Tyr Leu His Asp His Cys Asp Pro Lys Ile Ile His Arg
420 425 430

Asp Val Lys Ala Ala Asn Ile Leu Leu Asp Glu Glu Phe Glu Ala Val
435 440 445

Val Gly Asp Phe Gly Leu Ala Lys Leu Met Asp Tyr Lys Asp Thr His
450 455 460

Val Thr Thr Ala Val Arg Gly Thr Ile Gly His Ile Ala Pro Glu Tyr
465 470 475 480

Leu Ser Thr Gly Lys Ser Ser Glu Lys Thr Asp Val Phe Gly Tyr Gly
485 490 495

Ile Met Leu Leu Glu Leu Ile Thr Gly Gln Arg Ala Phe Asp Leu Ala
500 505 510

Arg Leu Ala Asn Asp Asp Asp Val Met Leu Leu Asp Trp Val Lys Gly
515 520 525

Leu Leu Lys Glu Lys Lys Leu Glu Met Leu Val Asp Pro Asp Leu Gln
530 535 540

Asn Lys Tyr Val Glu Ala Glu Val Glu Gln Leu Ile Gln Val Ala Leu
545 550 555 560

Leu Cys Thr Gln Ser Asn Pro Met Asp Arg Pro Lys Met Ser Glu Val
565 570 575

Val Arg Met Leu Glu Gly Asp Gly Leu Ala Glu Arg Trp Asp Glu Trp
580 585 590

Gln Lys Val Glu Val Leu Arg Gln Glu Val Glu Leu Ala Pro His Pro
595 600 605

Gly Ser Asp Trp Leu Val Asp Ser Thr Glu Asn Leu His Ala Val Glu
610 615 620

Leu Ser Gly Pro Arg
625

<210> SEQ ID NO 91
<211> LENGTH: 6296
<212> TYPE: DNA
<213> ORGANISM: Solanum lycopersicum

<400> SEQUENCE: 91
atggtgaagg tgatggagaa ggatactgtg gtggtatcac tggtggtatg gctaatcttg 60
gttgtatatc atcttaagct catttatgct aatatggaag gtttgtgggc ccatcatcct 120
catttagtta attttaggtc tatatttgat gttctatttt gtgagatgag tttcaaatgt 180
cgaaactttt cgtactagaa ataaaatata tgctaaaagt gaaattggta tgtgcaaaat 240
tggattttga atttgactaa tgtgtgagtt gttgaatttt cccaaaaggg taagcaagat 300

-continued

```
gtacaatgag ttccctgcac tgttacagtg acaagcagtt tagttttaat gtcagttaaa    360
tgtgaaagtt tttagttatc attgccattc aaccttagtg cattatgttt cctatacaag    420
cttgagtaat ttgatgtgat ttaatttggt tgtttgccaa aatcttgata aactgttttg    480
ttcagtcaat agattaaatt tttatgcgca tttaggtggt tgaaaattgt ctatgttttc    540
ctaaatgaat acacgaacag gtgatgcatt gcacagtcta cgcgtcaatt tacaagatcc    600
taacaatgtg ctacagagct gggacccaac ccttgttaat ccttgcacat ggtttcacgt    660
tacctgcaac aatgacaaca gtgttataag agtgtaagaa tctgttttct ggtctacctc    720
catttgaatg gatttgcaat tccactctct tgtggtggtg agcaatctaa ttgcagtttg    780
tgctcccata acacttgtta tatgatcaac ctttccagtg atttaggaaa tgcagcttta    840
tctggtttgt tagttccaca gcttggcctt ttgaagaatt tgcagtactt gtaagtctca    900
cttcatgaac tatgtttgga attattttac aaatttagag ttggaaaact ggcattgagt    960
gtattggttt ttccagctgt tgaagatttt catattacct ctagaattcg ctgcatgaaa   1020
ataatgtagg tggcttgcat attaactttt gcataaaaac aaagctgttg taagtggcaa   1080
aaatgagcag agaacacttt ctcctctcca tctcttgttt cacttgatgt tgtagtcgat   1140
ggcatagttg ttgatgtgtt ccctgaacaa cacaaatttg aatgtgtact tcataaaaaa   1200
agatttaaat atttgtttca cattacatac tagtaaatta agtaactcag atacttggat   1260
gagactagca atgaagtaac ttatgtggca aagtagtgtc tgtaattgct tgtgaaaaca   1320
ttgtagttga acttaaattt ttgtcataca ctcccttata taaagataag cagagtaatc   1380
gttaactttt ttatgaactc ttaaacagag tattattcta aatattatta ctaatgccag   1440
taccctaagc actcttaatt tggaatgaca aacttcaact catatcaaat cctttattcc   1500
ctctttcctt gttccatgta gactctaatc acgatttagg atgatggaat aggataaaac   1560
aaacaagaga aacaagtcca ttgtaaaagt aaagcaaaat ctagacttaa aaagaggaaa   1620
tatggcatga gggtaggttg atgtcttgga ggagaagatc tgaagttttc tggtcatata   1680
acagatgcta ttctggtttt caccaagagt tcgaatcatg attcaattaa gcatagattt   1740
tgtacaagtg ttaagcttag tttggagttc aatataccgt tcacttaaat tacatctcaa   1800
atttcattgt tcttattgta acccatgctc ttttgaagct gcaactgtat ggaagttcac   1860
agagacagta tgtgcatgtg cacctggtga agcagggcat tacatgatgt ataaccatgc   1920
atcagacaat gttataatga tgggtataat tattacctag tgactgcttc atcctgctca   1980
cacattaata tattcctatg gatgcctaga tttgcttgag gcttgtgtag tacgcgtgct   2040
aagtattttc ctagtgtatg caagtgacaa tcacatcaag aatgaaacaa tataaaaaga   2100
acatcaaaag tataacatta tctttgtcaa aaaaaaaaag aaagaacatc aagagtgctg   2160
atggaattta acaatcaccg ggcatacaca ctgtttagat gaagttcgaa attaacataa   2220
tgacagacgt taaattttta ttgatgagtt atatagattg tataaaatgt ttgacgagct   2280
gattctttgc agcacatggg acgacaggtt tttatataga aaagtgcttg taaccaaata   2340
taagaaaata cctccatgaa atagacatcg gtaactagtt ataattgcta tcttggaact   2400
cctagacctt tctcatttgt tgacttttaa ttgtcgcttg atgccagtat tgatggatgt   2460
gagaattctc cttcattatc ttggttgtcc cattatccta gggatgtcat tggtatgata   2520
tgtggaattg actcattctc tggttttctt gtcacaggga gctttacagt aataatataa   2580
gtggtctgat accgagtgat cttgggaatt tgactaatct ggtcagcttg gatctctact   2640
```

-continued

```
tgaacaactt cgtcggtccc atcccagatt ccttgggcaa gctgtcgaaa ttgagattcc   2700
tgtatgtatt tttgttctat attagattta tgtggatatt gtgatgccaa atgtatattt   2760
catcaaccaa gatggaccta ctcttactgg catgttgaga aaggaaagga agcctgaatt   2820
cttttctagg tttcacataa gatgacctct attagtatta tgtttcactc ttaagttttg   2880
atggtagaag gtatttgagg acttcatggg tctgatatca ttcataaaac cgatcttaca   2940
taagtctttt aattttctcc ctttgttcta atccttgtat aaaggaaaag aatagaagcc   3000
tatgctttgt ctgatactga tattgtaaaa ttaatcagag tttagtaatg ggtgttggga   3060
tcctttttcta gaagagagaa gaagtttaga atcccatgct tcatcttgca tttttcactg   3120
ctgaagtttc tcttgcttaa tgctccacaa acttctttct tttggcttga ctgtctaaga   3180
agtgtgccaa attgttctat catgcagact cagcatgaaa cctcattaac tgcatcttgg   3240
gacttactat agaactattg cagtactgca acgttgacta acatgattta gtccaaaagg   3300
tgtttcaagt ctgtttatcg gggggggggg atgttttgag gctctttatc gtggttctga   3360
actgacgcct tcatttccag ctgaagtgcc ggttctggct cgaagttgaa tatgttttac   3420
atccacatat taataattta ttaagatgat tctccttgtc aaataataaa taaattaaga   3480
tgattcaatt agtagccttt tcttctgttt tattctccat tatttacttg taccaaagat   3540
gaagctcatt cctgtaaacc tttgtgtttt cttgcaagga tagtcggctc aacaataata   3600
gcttgactgg taacatccca atgtcactga ctaatatctc atcactgcaa gtgttgtaag   3660
tacactgatt attttgtgac ttgatttaga taattctttc tgtcttccat atcttctcat   3720
gcatttcctt ttccttctaa tgcatataca gatttactta tgctcaattc ttgtctcacc   3780
tgtatgtagg gatctgtcaa acaaccgtct ctcaggtgct gttccagata atggttcatt   3840
ttctctattc acgcctatca ggtatatttc atttaaggcg gtgcaccatc taactggctg   3900
gtggttttag catgctacta tttgctaata tatttttctt gtttacagtt ttgcgaataa   3960
tttagatctt tgcgggcctg taactggacg cccttgccct ggatctcctc cattctcccc   4020
tccgcctcca tttgttccac caccaccaat ttctgctcca ggtggttctc taaattggtg   4080
tggataaatt gttctccttt cttttttctt ttgttttttt tgcttttttg cggttagtga   4140
ttttagtttg tccatccaac gtaagtgaga atttgtgcta tagaagctaa agtactgaca   4200
agaaaggggg cagaagagga aaacccatct taactagtca ggcattagtt ctgatgggaa   4260
actggtatgc acgagactac atttagtctc taagcattct ggtctttata caaatttaat   4320
tcagcattgt ggacatcttt tctttggtcc ccttgtaaat tattatctgt ggtatttgaa   4380
gtcatgtgtc tgaatgaaat taatcatatt tatgccagaa cttgtgaaga ttttcttttc   4440
tttgtaaaaa ctgtcctgga aattagatct gatgatagat acaaatttgt ctactaattt   4500
ctttttgaag tgatttaatt aatgaagggc cggccaaaat tatgtgttaa atatagtcta   4560
gatcatatga aggaaattaa tcaaatttat gggaacttca ggaggaaatg gtgcaactgg   4620
agcaattgct ggaggtgtag ctgctggtgc tgctctacta tttgctgctc ctgccattgc   4680
atttgcctgg tggcgccgta gaaagccaca agaatatttc tttgacgtac caggttagca   4740
gtattcaaat acccaaccat aagtccataa ctcctactta ctctctcacg tgtttatggt   4800
ttctcttgca tgttttattt tttggctcca taattaacgt ctttgcttaa acttattgca   4860
gccgaagaag atcctgaagt tcacttaggt caactgaaaa ggttctccct ccgagagcta   4920
caagttgcaa ctgacagttt tagcaataaa aatatactgg gtcgaggtgg atttggtaag   4980
gtatacaaag gacgcttagc agatggatca ttggtggctg ttaagcggct aaaggaagag   5040
```

cgtactcctg gaggggagtt gcaatttcaa acaaaagttg agatgattag catggcagtg 5100
cataggaatc ttctacgatt gcgtggtttc tgtatgacac caactgaaag actgcttgtc 5160 taccccctaca tggcgaatgg aagtgttgca tcatgcctga gaggtgacac tttctgaaat 5220
ctatcactcc ataaatgttc tcacctttaa tttggagggt attattgcat aatgcaagaa 5280
tgtctttcgc tggttaacat tctatcttgg cataacttac tctttataac aaaacatatt 5340
cttgttagtt attttcctgt aactttttaa aaggtagaag tataatttgt attgtattct 5400
cttgacaaca taatttattt tatcagaacg accgccttct gaaccaccac ttgattggcc 5460
aacgcgaaaa cgtattgctt tggggtctgc caggggatta tcgtatttgc atgatcattg 5520
tgaccctaag attatccatc gtgatgtgaa ggctgcaaat atattgctag atgaagaatt 5580
tgaggctgtt gttggagact ttggtttggc taaacttatg gactacaagg atacacatgt 5640
tacaactgct gtgcgtggta caatcgggca tatagctcca gaataccttt ccacagggaa 5700
gtcttcagaa aagactgatg tttttgggta tgggatcatg cttctggagc taatcaccgg 5760
ccaacgtgct tttgatcttg ctcggctggc aaatgatgac gatgtcatgt tgcttgactg 5820
ggtatgttgt catacctgct ttacatgtga acatgacacg agtaccataa tgtgttcatt 5880
ttttaatctg tacatcacaa cactagctga ctaataagta tttgtgcctt tagcaggaat 5940
atttaagtct atgactaaac ttgttgaggt tcttgtttca ggtgaaagga ctcctcaaag 6000
agaagaaact ggaaatgctg gttgaccctg atcttcagaa caaatatgtg gaggctgagg 6060
tggagcaact gatccaggta gcattgcttt gtacacaaag caacccaatg gatcggccta 6120
agatgtcgga agtggtgaga atgcttgaag gtgatggttt ggctgaaaga tgggatgagt 6180
ggcagaaggt agaagttctc cggcaggaag tggaacttgc accacatcct ggttctgatt 6240
ggcttgttga ctcgacagag aatttacatg cagttgaatt atcgggtcca aggtga 6296

<210> SEQ ID NO 92
<211> LENGTH: 1890
<212> TYPE: DNA
<213> ORGANISM: Solanum lycopersicum

<400> SEQUENCE: 92
atggtgaagg tgatggagaa ggatactgtg gtggtatcac tggtggtatg gctaatcttg 60
gttgtatatc atcttaagct catttatgct aatatggaag gtgatgcatt gcacagtcta 120
cgcgtcaatt tacaagatcc taacaatgtg ctacagagct gggacccaac ccttgttaat 180
ccttgcacat ggtttcacgt tacctgcaac aatgacaaca gtgttataag agttgattta 240
ggaaatgcag ctttatctgg tttgttagtt ccacagcttg gccttttgaa gaatttgcag 300
tacttggagc tttacagtaa taatataagt ggtctgatac cgagtgatct tgggaatttg 360
actaatctgg tcagcttgga tctctacttg aacaacttcg tcggtcccat cccagattcc 420
ttgggcaagc tgtcgaaatt gagattcctt cggctcaaca ataatagctt gactggtaac 480
atcccaatgt cactgactaa tatctcatca ctgcaagtgt tggatctgtc aaacaaccgt 540
ctctcaggtg ctgttccaga taatggttca ttttctctat tcacgcctat cagttttgcg 600
aataatttag atctttgcgg gcctgtaact ggacgccctt gccctggatc tcctccattc 660
tcccctccgc ctccatttgt tccaccacca ccaatttctg ctccaggagg aaatggtgca 720
actggagcaa ttgctggagg tgtagctgct ggtgctgctc tactatttgc tgctcctgcc 780
attgcatttg cctggtggcg ccgtagaaag ccacaagaat atttctttga cgtaccagcc 840

-continued

```
gaagaagatc ctgaagttca cttaggtcaa ctgaaaaggt tctccctccg agagctacaa    900

gttgcaactg acagttttag caataaaaat atactgggtc gaggtggatt tggtaaggta    960

tacaaaggac gcttagcaga tggatcattg gtggctgtta agcggctaaa ggaagagcgt   1020

actcctggag gggagttgca atttcaaaca aaagttgaga tgattagcat ggcagtgcat   1080

aggaatcttc tacgattgcg tggtttctgt atgacaccaa ctgaaagact gcttgtctac   1140

ccctacatgg cgaatggaag tgttgcatca tgcctgagag aacgaccgcc ttctgaacca   1200

ccacttgatt ggccaacgcg aaaacgtatt gctttggggt ctgccagggg attatcgtat   1260

ttgcatgatc attgtgaccc taagattatc catcgtgatg tgaaggctgc aaatatattg   1320

ctagatgaag aatttgaggc tgttgttgga gactttggtt tggctaaact tatggactac   1380

aaggatacac atgttacaac tgctgtgcgt ggtacaatcg ggcatatagc tccagaatac   1440

ctttccacag ggaagtcttc agaaaagact gatgtttttg ggtatgggat catgcttctg   1500

gagctaatca ccggccaacg tgcttttgat cttgctcggc tggcaaatga tgacgatgtc   1560

atgttgcttg actgggtgaa aggactcctc aaagagaaga aactggaaat gctggttgac   1620

cctgatcttc agaacaaata tgtggaggct gaggtggagc aactgatcca ggtagcattg   1680

ctttgtacac aaagcaaccc aatggatcgg cctaagatgt cggaagtggt gagaatgctt   1740

gaaggtgatg gtttggctga aagatgggat gagtggcaga aggtagaagt tctccggcag   1800

gaagtggaac ttgcaccaca tcctggttct gattggcttg ttgactcgac agagaattta   1860

catgcagttg aattatcggg tccaaggtga                                     1890
```

<210> SEQ ID NO 93
<211> LENGTH: 629
<212> TYPE: PRT
<213> ORGANISM: Solanum lycopersicum

<400> SEQUENCE: 93

```
Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Leu Val Asn Pro Cys Thr Trp
    50                  55                  60

Phe His Val Thr Cys Asn Asn Asp Asn Ser Val Ile Arg Val Asp Leu
65                  70                  75                  80

Gly Asn Ala Ala Leu Ser Gly Leu Leu Val Pro Gln Leu Gly Leu Leu
                85                  90                  95

Lys Asn Leu Gln Tyr Leu Glu Leu Tyr Ser Asn Asn Ile Ser Gly Leu
            100                 105                 110

Ile Pro Ser Asp Leu Gly Asn Leu Thr Asn Leu Val Ser Leu Asp Leu
        115                 120                 125

Tyr Leu Asn Asn Phe Val Gly Pro Ile Pro Asp Ser Leu Gly Lys Leu
    130                 135                 140

Ser Lys Leu Arg Phe Leu Arg Leu Asn Asn Asn Ser Leu Thr Gly Asn
145                 150                 155                 160

Ile Pro Met Ser Leu Thr Asn Ile Ser Ser Leu Gln Val Leu Asp Leu
                165                 170                 175

Ser Asn Asn Arg Leu Ser Gly Ala Val Pro Asp Asn Gly Ser Phe Ser
            180                 185                 190
```

```
Leu Phe Thr Pro Ile Ser Phe Ala Asn Asn Leu Asp Leu Cys Gly Pro
        195                 200                 205

Val Thr Gly Arg Pro Cys Pro Gly Ser Pro Pro Phe Ser Pro Pro Pro
    210                 215                 220

Pro Phe Val Pro Pro Pro Pro Ile Ser Ala Pro Gly Gly Asn Gly Ala
225                 230                 235                 240

Thr Gly Ala Ile Ala Gly Gly Val Ala Ala Gly Ala Ala Leu Leu Phe
                245                 250                 255

Ala Ala Pro Ala Ile Ala Phe Ala Trp Trp Arg Arg Arg Lys Pro Gln
            260                 265                 270

Glu Tyr Phe Phe Asp Val Pro Ala Glu Glu Asp Pro Glu Val His Leu
        275                 280                 285

Gly Gln Leu Lys Arg Phe Ser Leu Arg Glu Leu Gln Val Ala Thr Asp
    290                 295                 300

Ser Phe Ser Asn Lys Asn Ile Leu Gly Arg Gly Gly Phe Gly Lys Val
305                 310                 315                 320

Tyr Lys Gly Arg Leu Ala Asp Gly Ser Leu Val Ala Val Lys Arg Leu
                325                 330                 335

Lys Glu Glu Arg Thr Pro Gly Gly Glu Leu Gln Phe Gln Thr Lys Val
            340                 345                 350

Glu Met Ile Ser Met Ala Val His Arg Asn Leu Leu Arg Leu Arg Gly
        355                 360                 365

Phe Cys Met Thr Pro Thr Glu Arg Leu Leu Val Tyr Pro Tyr Met Ala
    370                 375                 380

Asn Gly Ser Val Ala Ser Cys Leu Arg Glu Arg Pro Pro Ser Glu Pro
385                 390                 395                 400

Pro Leu Asp Trp Pro Thr Arg Lys Arg Ile Ala Leu Gly Ser Ala Arg
                405                 410                 415

Gly Leu Ser Tyr Leu His Asp His Cys Asp Pro Lys Ile Ile His Arg
            420                 425                 430

Asp Val Lys Ala Ala Asn Ile Leu Leu Asp Glu Glu Phe Glu Ala Val
        435                 440                 445

Val Gly Asp Phe Gly Leu Ala Lys Leu Met Asp Tyr Lys Asp Thr His
    450                 455                 460

Val Thr Thr Ala Val Arg Gly Thr Ile Gly His Ile Ala Pro Glu Tyr
465                 470                 475                 480

Leu Ser Thr Gly Lys Ser Ser Glu Lys Thr Asp Val Phe Gly Tyr Gly
                485                 490                 495

Ile Met Leu Leu Glu Leu Ile Thr Gly Gln Arg Ala Phe Asp Leu Ala
            500                 505                 510

Arg Leu Ala Asn Asp Asp Asp Val Met Leu Leu Asp Trp Val Lys Gly
        515                 520                 525

Leu Leu Lys Glu Lys Lys Leu Glu Met Leu Val Asp Pro Asp Leu Gln
    530                 535                 540

Asn Lys Tyr Val Glu Ala Glu Val Glu Gln Leu Ile Gln Val Ala Leu
545                 550                 555                 560

Leu Cys Thr Gln Ser Asn Pro Met Asp Arg Pro Lys Met Ser Glu Val
                565                 570                 575

Val Arg Met Leu Glu Gly Asp Gly Leu Ala Glu Arg Trp Asp Glu Trp
            580                 585                 590

Gln Lys Val Glu Val Leu Arg Gln Glu Val Glu Leu Ala Pro His Pro
        595                 600                 605
```

```
Gly Ser Asp Trp Leu Val Asp Ser Thr Glu Asn Leu His Ala Val Glu
    610                 615                 620

Leu Ser Gly Pro Arg
625


<210> SEQ ID NO 94
<211> LENGTH: 6296
<212> TYPE: DNA
<213> ORGANISM: Solanum lycopersicum

<400> SEQUENCE: 94

atggtgaagg tgatggagaa ggatactgtg gtggtatcac tggtggtatg gctaatcttg     60

gttgtatatc atcttaagct catttatgct aatatggaag gtttgtgggc ccatcatcct    120

catttagtta attttaggtc tatatttgat gttctatttt gtgagatgag tttcaaatgt    180

cgaaactttt cgtactagaa ataaaatata tgctaaaagt gaaattggta tgtgcaaaat    240

tggattttga atttgactaa tgtgtgagtt gttgaatttt cccaaaaggg taagcaagat    300

gtacaatgag ttccctgcac tgttacagtg acaagcagtt tagttttaat gtcagttaaa    360

tgtgaaagtt tttagttatc attgccattc aaccttagtg cattatgttt cctatacaag    420

cttgagtaat ttgatgtgat ttaatttggt tgtttgccaa aatcttgata aactgttttg    480

ttcagtcaat agattaaatt tttatgcgca tttaggtggt tgaaaattgt ctatgttttc    540

ctaaatgaat acacgaacag gtgatgcatt gcacagtcta cgcgtcaatt tacaagatcc    600

taacaatgtg ctacagagct gggacccaac ccttgttaat ccttgcacat ggtttcacgt    660

tacctgcaac aatgacaaca gtgttataag agtgtaagaa tctgttttct ggtctacctc    720

catttgaatg gatttgcaat tccactctct tgtggtggtg agcaatctaa ttgcagtttg    780

tgctcccata acacttgtta tatgatcaac ctttccagtg atttaggaaa tgcagcttta    840

tctggtttgt tagttccaca gcttggcctt ttgaagaatt tgcagtactt gtaagtctca    900

cttcatgaac tatgtttgga attattttac aaatttagag ttggaaaact ggcattgagt    960

gtattggttt ttccagctgt tgaagatttt catattacct ctagaattcg ctgcatgaaa   1020

ataatgtagg tggcttgcat attaactttt gcataaaaac aaagctgttg taagtggcaa   1080

aaatgagcag agaacacttt ctcctctcca tctcttgttt cacttgatgt tgtagtcgat   1140

ggcatagttg ttgatgtgtt ccctgaacaa cacaaattg  aatgtgtact tcataaaaaa   1200

agatttaaat atttgtttca cattacatac tagtaaatta agtaactcag atacttggat   1260

gagactagca atgaagtaac ttatgtggca aagtagtgtc tgtaattgct tgtgaaaaca   1320

ttgtagttga acttaaattt ttgtcataca ctcccttata taaagataag cagagtaatc   1380

gttaactttt ttatgaactc ttaaacagag tattattcta aatattatta ctaatgccag   1440

taccctaagc actcttaatt tggaatgaca aacttcaact catatcaaat cctttattcc   1500

ctctttcctt gttccatgta gactctaatc acgatttagg atgatggaat aggataaaac   1560

aaacaagaga aacaagtcca ttgtaaaagt aaagcaaaat ctagacttaa aaagaggaaa   1620

tatggcatga gggtaggttg atgtcttgga ggagaagatc tgaagttttc tggtcatata   1680

acagatgcta ttctggtttt caccaagagt tcgaatcatg attcaattaa gcatagattt   1740

tgtacaagtg ttaagcttag tttggagttc aatataccgt tcacttaaat tacatctcaa   1800

atttcattgt tcttattgta acccatgctc ttttgaagct gcaactgtat ggaagttcac   1860

agagacagta tgtgcatgtg cacctggtga agcagggcat tacatgatgt ataaccatgc   1920

atcagacaat gttataatga tgggtataat tattacctag tgactgcttc atcctgctca   1980
```

```
cacattaata tattcctatg gatgcctaga tttgcttgag gcttgtgtag tacgcgtgct   2040
aagtattttc ctagtgtatg caagtgacaa tcacatcaag aatgaaacaa tataaaaaga   2100
acatcaaaag tataacatta tctttgtcaa aaaaaaaaag aaagaacatc aagagtgctg   2160
atggaattta acaatcaccg ggcatacaca ctgtttagat gaagttcgaa attaacataa   2220
tgacagacgt taaattttta ttgatgagtt atatagattg tataaaatgt ttgacgagct   2280
gattctttgc agcacatggg acgacaggtt tttatataga aaagtgcttg taaccaaata   2340
taagaaaata cctccatgaa atagacatcg gtaactagtt ataattgcta tcttggaact   2400
cctagacctt tctcatttgt tgacttttaa ttgtcgcttg atgccagtat tgatggatgt   2460
gagaattctc cttcattatc ttggttgtcc cattatccta gggatgtcat tggtatgata   2520
tgtggaattg actcattctc tggttttctt gtcacaggga gctttacagt aataatataa   2580
gtggtctgat accgagtgat cttgggaatt tgactaatct ggtcagcttg gatctctact   2640
tgaacaactt cgtcggtccc atcccagatt ccttgggcaa gctgtcgaaa ttgagattcc   2700
tgtatgtatt tttgttctat attagattta tgtggatatt gtgatgccaa atgtatattt   2760
catcaaccaa gatggaccta ctcttactgg catgttgaga aaggaaagga agcctgaatt   2820
cttttctagg tttcacataa gatgacctct attagtatta tgtttcactc ttaagttttg   2880
atggtagaag gtatttgagg acttcatggg tctgatatca ttcataaaac cgatcttaca   2940
taagtctttt aatttctcc ctttgttcta atccttgtat aaaggaaaag aatagaagcc   3000
tatgctttgt ctgatactga tattgtaaaa ttaatcagag tttagtaatg ggtgttggga   3060
tccttttcta gaagagagaa gaagtttaga atcccatgct tcatcttgca tttttcactg   3120
ctgaagtttc tcttgcttaa tgctccacaa acttctttct tttggcttga ctgtctaaga   3180
agtgtgccaa attgttctat catgcagact cagcatgaaa cctcattaac tgcatcttgg   3240
gacttactat agaactattg cagtactgca acgttgacta acatgattta gtccaaaagg   3300
tgtttcaagt ctgtttatcg gggggggggg atgttttgag gctctttatc gtggttctga   3360
actgacgcct tcatttccag ctgaagtgcc ggttctggct cgaagttgaa tatgttttac   3420
atccacatat taataattta ttaagatgat tctccttgtc aaataataaa taaattaaga   3480
tgattcaatt agtagccttt tcttctgttt tattctccat tatttacttg taccaaagat   3540
gaagctcatt cctgtaaacc tttgtgtttt cttgcaagga tagtcggctc aacaataata   3600
gcttgactgg taacatccca atgtcactga ctaatatctc atcactgcaa gtgttgtaag   3660
tacactgatt attttgtgac ttgatttaga taattctttc tgtcttccat atcttctcat   3720
gcatttcctt ttccttctaa tgcatataca gatttactta tgctcaattc ttgtctcacc   3780
tgtatgtagg gatctgtcaa acaaccgtct ctcaggtgct gttccagata atggttcatt   3840
ttctctattc acgcctatca ggtatatttc atttaaggcg gtgcaccatc taactggctg   3900
gtggttttag catgctacta tttgctaata tatttttctt gtttacagtt ttgcgaataa   3960
tttagatctt tgcgggcctg taactggacg cccttgccct ggatctcctc cattctcccc   4020
tccgcctcca tttgttccac caccaccaat ttctgctcca ggtggttctc taaattggtg   4080
tggataaatt gttctccttt cttttttctt ttgttttttt tgcttttttg cggttagtga   4140
ttttagtttg tccatccaac gtaagtgaga atttgtgcta tagaagctaa agtactgaca   4200
agaaaggggg cagaagagga aaacccatct taactagtca ggcattagtt ctgatgggaa   4260
actggtatgc acgagactac atttagtctc taagcattct ggtctttata caaatttaat   4320
```

-continued tcagcattgt ggacatcttt tctttggtcc ccttgtaaat tattatctgt ggtatttgaa 4380
gtcatgtgtc tgaatgaaat taatcatatt tatgccagaa cttgtgaaga ttttcttttc 4440
tttgtaaaaa ctgtcctgga aattagatct gatgatagat acaaatttgt ctactaattt 4500
ctttttgaag tgatttaatt aatgaagggc cggccaaaat tatgtgttaa atatagtcta 4560
gatcatatga aggaaattaa tcaaatttat gggaacttca ggaggaaatg gtgcaactgg 4620
agcaattgct ggaggtgtag ctgctggtgc tgctctacta tttgctgctc ctgccattgc 4680
atttgcctgg tggcgccgta gaaagccaca agaatatttc tttgacgtac caggttagca 4740
gtattcaaat acccaaccat aagtccataa ctcctactta ctctctcacg tgtttatggt 4800
ttctcttgca tgttttattt tttggctcca taattaacgt ctttgcttaa acttattgca 4860
gccgaagaag atcctgaagt tcacttaggt caactgaaaa ggttctccct ccgagagcta 4920
caagttgcaa ctgacagttt tagcaataaa aatatactgg atcgaggtgg atttggtaag 4980
gtatacaaag gacgcttagc agatggatca ttggtggctg ttaagcggct aaaggaagag 5040
cgtactcctg gaggggagtt gcaatttcaa acagaagttg agatgattag catggcagtg 5100
cataggaatc ttctacgatt gcgtggtttc tgtatgacac caactgaaag actgcttgtc 5160 taccccctaca tggcgaatgg aagtgttgca tcatgcctga gaggtgacac tttctgaaat 5220
ctatcactcc ataaatgttc tcacctttaa tttggagggt attattgcat aatgcaagaa 5280
tgtctttcgc tggttaacat tctatcttgg cataacttac tctttataac aaaacatatt 5340
cttgttagtt attttcctgt aactttttaa aaggtagaag tataatttgt attgtattct 5400
cttgacaaca taatttattt tatcagaacg accgccttct gaaccaccac ttgattggcc 5460
aacgcgaaaa cgtattgctt tggggtctgc caggggatta tcgtatttgc atgatcattg 5520
tgaccctaag attatccatc gtgatgtgaa ggctgcaaat atattgctag atgaagaatt 5580
tgaggctgtt gttggagact ttggtttggc taaacttatg gactacaagg atacacatgt 5640
tacaactgct gtgcgtggta caatcgggca tatagctcca gaatacctttt ccacagggaa 5700 gtcttcagaa aagactgatg tttttgggta tgggatcatg cttctggagc taatcaccgg 5760
ccaacgtgct tttgatcttg ctcggctggc aaatgatgac gatgtcatgt tgcttgactg 5820
ggtatgttgt catacctgct ttacatgtga acatgacacg agtaccataa tgtgttcatt 5880
ttttaatctg tacatcacaa cactagctga ctaataagta tttgtgcctt tagcaggaat 5940
atttaagtct atgactaaac ttgttgaggt tcttgtttca ggtgaaagga ctcctcaaag 6000
agaagaaact ggaaatgctg gttgaccctg atcttcagaa caaatatgtg gaggctgagg 6060
tggagcaact gatccaggta gcattgcttt gtacacaaag caacccaatg gatcggccta 6120
agatgtcgga agtggtgaga atgcttgaag gtgatggttt ggctgaaaga tgggatgagt 6180
ggcagaaggt agaagttctc cggcaggaag tggaacttgc accacatcct ggttctgatt 6240
ggcttgttga ctcgacagag aatttacatg cagttgaatt atcgggtcca aggtga 6296

<210> SEQ ID NO 95
<211> LENGTH: 1890
<212> TYPE: DNA
<213> ORGANISM: Solanum lycopersicum

<400> SEQUENCE: 95
atggtgaagg tgatggagaa ggatactgtg gtggtatcac tggtggtatg gctaatcttg 60
gttgtatatc atcttaagct catttatgct aatatggaag gtgatgcatt gcacagtcta 120
cgcgtcaatt tacaagatcc taacaatgtg ctacagagct gggacccaac ccttgttaat 180
ccttgcacat ggtttcacgt tacctgcaac aatgacaaca gtgttataag agttgattta 240
ggaaatgcag ctttatctgg tttgttagtt ccacagcttg gccttttgaa gaatttgcag 300
tacttggagc tttacagtaa taatataagt ggtctgatac cgagtgatct tgggaatttg 360
actaatctgg tcagcttgga tctctacttg aacaacttcg tcggtcccat cccagattcc 420
ttgggcaagc tgtcgaaatt gagattcctt cggctcaaca ataatagctt gactggtaac 480
atcccaatgt cactgactaa tatctcatca ctgcaagtgt tggatctgtc aaacaaccgt 540
ctctcaggtg ctgttccaga taatggttca ttttctctat tcacgcctat cagttttgcg 600
aataatttag atctttgcgg gcctgtaact ggacgccctt gccctggatc tcctccattc 660
tcccctccgc ctccatttgt tccaccacca ccaatttctg ctccaggagg aaatggtgca 720
actggagcaa ttgctggagg tgtagctgct ggtgctgctc tactatttgc tgctcctgcc 780
attgcatttg cctggtggcg ccgtagaaag ccacaagaat atttctttga cgtaccagcc 840
gaagaagatc ctgaagttca cttaggtcaa ctgaaaaggt tctccctccg agagctacaa 900
gttgcaactg acagttttag caataaaaat atactggatc gaggtggatt tggtaaggta 960
tacaaaggac gcttagcaga tggatcattg gtggctgtta agcggctaaa ggaagagcgt 1020
actcctggag gggagttgca atttcaaaca gaagttgaga tgattagcat ggcagtgcat 1080
aggaatcttc tacgattgcg tggtttctgt atgacaccaa ctgaaagact gcttgtctac 1140
ccctacatgg cgaatggaag tgttgcatca tgcctgagag aacgaccgcc ttctgaacca 1200
ccacttgatt ggccaacgcg aaaacgtatt gctttggggt ctgccagggg attatcgtat 1260
ttgcatgatc attgtgaccc taagattatc catcgtgatg tgaaggctgc aaatatattg 1320
ctagatgaag aatttgaggc tgttgttgga gactttggtt tggctaaact tatggactac 1380
aaggatacac atgttacaac tgctgtgcgt ggtacaatcg ggcatatagc tccagaatac 1440
ctttccacag ggaagtcttc agaaaagact gatgtttttg ggtatgggat catgcttctg 1500
gagctaatca ccggccaacg tgcttttgat cttgctcggc tggcaaatga tgacgatgtc 1560
atgttgcttg actgggtgaa aggactcctc aaagagaaga aactggaaat gctggttgac 1620
cctgatcttc agaacaaata tgtggaggct gaggtggagc aactgatcca ggtagcattg 1680
ctttgtacac aaagcaaccc aatggatcgg cctaagatgt cggaagtggt gagaatgctt 1740
gaaggtgatg gtttggctga aagatgggat gagtggcaga aggtagaagt tctccggcag 1800
gaagtggaac ttgcaccaca tcctggttct gattggcttg ttgactcgac agagaattta 1860
catgcagttg aattatcggg tccaaggtga 1890

<210> SEQ ID NO 96
<211> LENGTH: 629
<212> TYPE: PRT
<213> ORGANISM: Solanum lycopersicum

<400> SEQUENCE: 96

Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Leu Val Asn Pro Cys Thr Trp
    50                  55                  60

-continued

```
Phe His Val Thr Cys Asn Asn Asp Asn Ser Val Ile Arg Val Asp Leu
65                  70                  75                  80

Gly Asn Ala Ala Leu Ser Gly Leu Leu Val Pro Gln Leu Gly Leu Leu
                85                  90                  95

Lys Asn Leu Gln Tyr Leu Glu Leu Tyr Ser Asn Asn Ile Ser Gly Leu
            100                 105                 110

Ile Pro Ser Asp Leu Gly Asn Leu Thr Asn Leu Val Ser Leu Asp Leu
        115                 120                 125

Tyr Leu Asn Asn Phe Val Gly Pro Ile Pro Asp Ser Leu Gly Lys Leu
    130                 135                 140

Ser Lys Leu Arg Phe Leu Arg Leu Asn Asn Asn Ser Leu Thr Gly Asn
145                 150                 155                 160

Ile Pro Met Ser Leu Thr Asn Ile Ser Ser Leu Gln Val Leu Asp Leu
                165                 170                 175

Ser Asn Asn Arg Leu Ser Gly Ala Val Pro Asp Asn Gly Ser Phe Ser
            180                 185                 190

Leu Phe Thr Pro Ile Ser Phe Ala Asn Asn Leu Asp Leu Cys Gly Pro
        195                 200                 205

Val Thr Gly Arg Pro Cys Pro Gly Ser Pro Pro Phe Ser Pro Pro Pro
    210                 215                 220

Pro Phe Val Pro Pro Pro Pro Ile Ser Ala Pro Gly Gly Asn Gly Ala
225                 230                 235                 240

Thr Gly Ala Ile Ala Gly Gly Val Ala Ala Gly Ala Ala Leu Leu Phe
                245                 250                 255

Ala Ala Pro Ala Ile Ala Phe Ala Trp Trp Arg Arg Arg Lys Pro Gln
            260                 265                 270

Glu Tyr Phe Phe Asp Val Pro Ala Glu Glu Asp Pro Glu Val His Leu
        275                 280                 285

Gly Gln Leu Lys Arg Phe Ser Leu Arg Glu Leu Gln Val Ala Thr Asp
    290                 295                 300

Ser Phe Ser Asn Lys Asn Ile Leu Asp Arg Gly Gly Phe Gly Lys Val
305                 310                 315                 320

Tyr Lys Gly Arg Leu Ala Asp Gly Ser Leu Val Ala Val Lys Arg Leu
                325                 330                 335

Lys Glu Glu Arg Thr Pro Gly Gly Glu Leu Gln Phe Gln Thr Glu Val
            340                 345                 350

Glu Met Ile Ser Met Ala Val His Arg Asn Leu Leu Arg Leu Arg Gly
        355                 360                 365

Phe Cys Met Thr Pro Thr Glu Arg Leu Leu Val Tyr Pro Tyr Met Ala
    370                 375                 380

Asn Gly Ser Val Ala Ser Cys Leu Arg Glu Arg Pro Pro Ser Glu Pro
385                 390                 395                 400

Pro Leu Asp Trp Pro Thr Arg Lys Arg Ile Ala Leu Gly Ser Ala Arg
                405                 410                 415

Gly Leu Ser Tyr Leu His Asp His Cys Asp Pro Lys Ile Ile His Arg
            420                 425                 430

Asp Val Lys Ala Ala Asn Ile Leu Leu Asp Glu Glu Phe Glu Ala Val
        435                 440                 445

Val Gly Asp Phe Gly Leu Ala Lys Leu Met Asp Tyr Lys Asp Thr His
    450                 455                 460

Val Thr Thr Ala Val Arg Gly Thr Ile Gly His Ile Ala Pro Glu Tyr
465                 470                 475                 480

Leu Ser Thr Gly Lys Ser Ser Glu Lys Thr Asp Val Phe Gly Tyr Gly
```

-continued

```
                485                 490                 495

Ile Met Leu Leu Glu Leu Ile Thr Gly Gln Arg Ala Phe Asp Leu Ala
            500                 505                 510

Arg Leu Ala Asn Asp Asp Asp Val Met Leu Leu Asp Trp Val Lys Gly
        515                 520                 525

Leu Leu Lys Glu Lys Lys Leu Glu Met Leu Val Asp Pro Asp Leu Gln
    530                 535                 540

Asn Lys Tyr Val Glu Ala Glu Val Glu Gln Leu Ile Gln Val Ala Leu
545                 550                 555                 560

Leu Cys Thr Gln Ser Asn Pro Met Asp Arg Pro Lys Met Ser Glu Val
                565                 570                 575

Val Arg Met Leu Glu Gly Asp Gly Leu Ala Glu Arg Trp Asp Glu Trp
            580                 585                 590

Gln Lys Val Glu Val Leu Arg Gln Glu Val Glu Leu Ala Pro His Pro
        595                 600                 605

Gly Ser Asp Trp Leu Val Asp Ser Thr Glu Asn Leu His Ala Val Glu
    610                 615                 620

Leu Ser Gly Pro Arg
625


<210> SEQ ID NO 97
<211> LENGTH: 6178
<212> TYPE: DNA
<213> ORGANISM: Solanum lycopersicum

<400> SEQUENCE: 97

atggtgaagg tgatggagaa ggatactgtg gtggtatcac tggtggtatg gctaatcttg      60

gttgtatatc atcttaagct catttatgct aatatggaag gtttgtgggc ccatcatcct     120

catttagtta attttaggtc tatatttgat gttctatttt gtgagatgag tttcaaatgt     180

cgaaactttt cgtactagaa ataaaatata tgctaaaagt gaaattggta tgtgcaaaat     240

tggattttga atttgactaa tgtgtgagtt gttgaatttt cccaaaaggg taagcaagat     300

gtacaatgag ttccctgcac tgttacagtg acaagcagtt tagttttaat gtcagttaaa     360

tgtgaaagtt tttagttatc attgccattc aaccttagtg cattatgttt cctatacaag     420

cttgagtaat ttgatgtgat ttaatttggt tgtttgccaa aatcttgata aactgttttg     480

ttcagtcaat agattaaatt tttatgcgca tttaggtggt tgaaaattgt ctatgttttc     540

ctaaatgaat acacgaacag gtgtgttata agagtgtaag aatctgtttt ctggtctacc     600

tccatttgaa tggatttgca attccactct cttgtggtgg tgagcaatct aattgcagtt     660

tgtgctccca taacacttgt tatatgatca acctttccag tgatttagga aatgcagctt     720

tatctggttt gttagttcca cagcttggcc ttttgaagaa tttgcagtac ttgtaagtct     780

cacttcatga actatgtttg gaattatttt acaaatttag agttggaaaa ctggcattga     840

gtgtattggt ttttccagct gttgaagatt ttcatattac ctctagaatt cgctgcatga     900

aaataatgta ggtggcttgc atattaactt ttgcataaaa acaaagctgt tgtaagtggc     960

aaaaatgagc agagaacact ttctcctctc catctcttgt ttcacttgat gttgtagtcg    1020

atggcatagt tgttgatgtg ttccctgaac aacacaaatt tgaatgtgta cttcataaaa    1080

aaagatttaa atatttgttt cacattacat actagtaaat taagtaactc agatacttgg    1140

atgagactag caatgaagta acttatgtgg caaagtagtg tctgtaattg cttgtgaaaa    1200

cattgtagtt gaacttaaat ttttgtcata cactccctta tataaagata agcagagtaa    1260
```

```
tcgttaactt ttttatgaac tcttaaacag agtattattc taaatattat tactaatgcc   1320
agtaccctaa gcactcttaa tttggaatga caaacttcaa ctcatatcaa atcctttatt   1380
ccctctttcc ttgttccatg tagactctaa tcacgattta ggatgatgga ataggataaa   1440
acaaacaaga gaaacaagtc cattgtaaaa gtaaagcaaa atctagactt aaaaagagga   1500
aatatggcat gagggtaggt tgatgtcttg gaggagaaga tctgaagttt tctggtcata   1560
taacagatgc tattctggtt ttcaccaaga gttcgaatca tgattcaatt aagcatagat   1620
tttgtacaag tgttaagctt agtttggagt tcaatatacc gttcacttaa attacatctc   1680
aaatttcatt gttcttattg taacccatgc tcttttgaag ctgcaactgt atggaagttc   1740
acagagacag tatgtgcatg tgcacctggt gaagcagggc attacatgat gtataaccat   1800
gcatcagaca atgttataat gatgggtata attattacct agtgactgct tcatcctgct   1860
cacacattaa tatattccta tggatgccta gatttgcttg aggcttgtgt agtacgcgtg   1920
ctaagtattt tcctagtgta tgcaagtgac aatcacatca agaatgaaac aatataaaaa   1980
gaacatcaaa agtataacat tatctttgtc aaaaaaaaaa agaaagaaca tcaagagtgc   2040
tgatggaatt taacaatcac cgggcataca cactgtttag atgaagttcg aaattaacat   2100
aatgacagac gttaaatttt tattgatgag ttatatagat tgtataaaat gtttgacgag   2160
ctgattcttt gcagcacatg ggacgacagg tttttatata gaaaagtgct tgtaaccaaa   2220
tataagaaaa tacctccatg aaatagacat cggtaactag ttataattgc tatcttggaa   2280
ctcctagacc tttctcattt gttgactttt aattgtcgct tgatgccagt attgatggat   2340
gtgagaattc tccttcatta tcttggttgt cccattatcc tagggatgtc attggtatga   2400
tatgtggaat tgactcattc tctggttttc ttgtcacagg gagctttaca gtaataatat   2460
aagtggtctg ataccgagtg atcttgggaa tttgactaat ctggtcagct tggatctcta   2520
cttgaacaac ttcgtcggtc ccatcccaga ttccttgggc aagctgtcga aattgagatt   2580
cctgtatgta tttttgttct atattagatt tatgtggata ttgtgatgcc aaatgtatat   2640
ttcatcaacc aagatggacc tactcttact ggcatgttga gaaaggaaag gaagcctgaa   2700
ttcttttcta ggtttcacat aagatgacct ctattagtat tatgtttcac tcttaagttt   2760
tgatggtaga aggtatttga ggacttcatg ggtctgatat cattcataaa accgatctta   2820
cataagtctt ttaatttctc ccctttgttc taatccttgt ataaaggaaa agaatagaag   2880
cctatgcttt gtctgatact gatattgtaa aattaatcag agtttagtaa tgggtgttgg   2940
gatccttttc tagaagagag aagaagttta gaatcccatg cttcatcttg catttttcac   3000
tgctgaagtt tctcttgctt aatgctccac aaacttcttt cttttggctt gactgtctaa   3060
gaagtgtgcc aaattgttct atcatgcaga ctcagcatga aacctcatta actgcatctt   3120
gggacttact atagaactat tgcagtactg caacgttgac taacatgatt tagtccaaaa   3180
ggtgtttcaa gtctgtttat cggggggggg ggatgttttg aggctcttta tcgtggttct   3240
gaactgacgc cttcatttcc agctgaagtg ccggttctgg ctcgaagttg aatatgtttt   3300
acatccacat attaataatt tattaagatg attctccttg tcaaataata aataaattaa   3360
gatgattcaa ttagtagcct tttcttctgt tttattctcc attatttact tgtaccaaag   3420
atgaagctca ttcctgtaaa cctttgtgtt ttcttgcaag gatagtcggc tcaacaataa   3480
tagcttgact ggtaacatcc caatgtcact gactaatatc tcatcactgc aagtgttgta   3540
agtacactga ttattttgtg acttgattta gataattctt tctgtcttcc atatcttctc   3600
atgcatttcc ttttccttct aatgcatata cagatttact tatgctcaat tcttgtctca   3660
```

-continued

```
cctgtatgta gggatctgtc aaacaaccgt ctctcaggtg ctgttccaga taatggttca   3720
ttttctctat tcacgcctat caggtatatt tcatttaagg cggtgcacca tctaactggc   3780
tggtggtttt agcatgctac tatttgctaa tatatttttc ttgtttacag ttttgcgaat   3840
aatttagatc tttgcgggcc tgtaactgga cgcccttgcc ctggatctcc tccattctcc   3900
cctccgcctc catttgttcc accaccacca atttctgctc caggtggttc tctaaattgg   3960
tgtggataaa ttgttctcct ttcttttttc ttttgttttt tttgcttttt tgcggttagt   4020
gattttagtt tgtccatcca acgtaagtga gaatttgtgc tatagaagct aaagtactga   4080
caagaaaggg ggcagaagag gaaaacccat cttaactagt caggcattag ttctgatggg   4140
aaactggtat gcacgagact acatttagtc tctaagcatt ctggtcttta tacaaattta   4200
attcagcatt gtggacatct tttctttggt ccccttgtaa attattatct gtggtatttg   4260
aagtcatgtg tctgaatgaa attaatcata tttatgccag aacttgtgaa gattttcttt   4320
tctttgtaaa aactgtcctg gaaattagat ctgatgatag atacaaattt gtctactaat   4380
ttctttttga agtgatttaa ttaatgaagg gccggccaaa attatgtgtt aaatatagtc   4440
tagatcatat gaaggaaatt aatcaaattt atgggaactt caggaggaaa tggtgcaact   4500
ggagcaattg ctggaggtgt agctgctggt gctgctctac tatttgctgc tcctgccatt   4560
gcatttgcct ggtggcgccg tagaaagcca caagaatatt tctttgacgt accaggttag   4620
cagtattcaa atacccaacc ataagtccat aactcctact tactctctca cgtgtttatg   4680
gtttctcttg catgttttat tttttggctc cataattaac gtctttgctt aaacttattg   4740
cagccgaaga agatcctgaa gttcacttag gtcaactgaa aaggttctcc ctccgagagc   4800
tacaagttgc aactgacagt tttagcaata aaaatatact gggtcgaggt ggatttggta   4860
aggtatacaa aggacgctta gcagatggat cattggtggc tgttaagcgg ctaaaggaag   4920
agcgtactcc tggaggggag ttgcaatttc aaacagaagt tgagatgatt agcatggcag   4980
tgcataggaa tcttctacga ttgcgtggtt tctgtatgac accaactgaa agactgcttg   5040
tctaccccta catggcgaat ggaagtgttg catcatgcct gagaggtgac actttctgaa   5100
atctatcact ccataaatgt tctcaccttt aatttggagg gtattattgc ataatgcaag   5160
aatgtctttc gctggttaac attctatctt ggcataactt actctttata acaaaacata   5220
ttcttgttag ttattttcct gtaacttttt aaaaggtaga agtataattt gtattgtatt   5280
ctcttgacaa cataatttat tttatcagaa cgaccgcctt ctgaaccacc acttgattgg   5340
ccaacgcgaa aacgtattgc tttggggtct gccaggggat tatcgtattt gcatgatcat   5400
tgtgacccta agattatcca tcgtgatgtg aaggctgcaa atatattgct agatgaagaa   5460
tttgaggctg ttgttggaga ctttggtttg gctaaactta tggactacaa ggatacacat   5520
gttacaactg ctgtgcgtgg tacaatcggg catatagctc cagaatacct ttccacaggg   5580
aagtcttcag aaaagactga tgtttttggg tatgggatca tgcttctgga gctaatcacc   5640
ggccaacgtg cttttgatct tgctcggctg gcaaatgatg acgatgtcat gttgcttgac   5700
tgggtatgtt gtcatacctg ctttacatgt gaacatgaca cgagtaccat aatgtgttca   5760
ttttttaatc tgtacatcac aacactagct gactaataag tatttgtgcc tttagcagga   5820
atatttaagt ctatgactaa acttgttgag gttcttgttt caggtgaaag gactcctcaa   5880
agagaagaaa ctggaaatgc tggttgaccc tgatcttcag aacaaatatg tggaggctga   5940
ggtggagcaa ctgatccagg tagcattgct ttgtacacaa agcaacccaa tggatcggcc   6000
```

```
taagatgtcg gaagtggtga gaatgcttga aggtgatggt ttggctgaaa gatgggatga   6060

gtggcagaag gtagaagttc tccggcagga agtggaactt gcaccacatc ctggttctga   6120

ttggcttgtt gactcgacag agaatttaca tgcagttgaa ttatcgggtc caaggtga     6178
```

<210> SEQ ID NO 98
<211> LENGTH: 1772
<212> TYPE: DNA
<213> ORGANISM: Solanum lycopersicum

<400> SEQUENCE: 98

```
atggtgaagg tgatggagaa ggatactgtg gtggtatcac tggtggtatg gctaatcttg     60

gttgtatatc atcttaagct catttatgct aatatggaag gtgtgttata agagttgatt    120

taggaaatgc agctttatct ggtttgttag ttccacagct tggccttttg aagaatttgc    180

agtacttgga gctttacagt aataatataa gtggtctgat accgagtgat cttgggaatt    240

tgactaatct ggtcagcttg gatctctact tgaacaactt cgtcggtccc atcccagatt    300

ccttgggcaa gctgtcgaaa ttgagattcc ttcggctcaa caataatagc ttgactggta    360

acatcccaat gtcactgact aatatctcat cactgcaagt gttggatctg tcaaacaacc    420

gtctctcagg tgctgttcca gataatggtt catttctct attcacgcct atcagttttg    480

cgaataattt agatctttgc gggcctgtaa ctggacgccc ttgccctgga tctcctccat    540

tctcccctcc gcctccattt gttccaccac caccaatttc tgctccagga ggaaatggtg    600

caactggagc aattgctgga ggtgtagctg ctggtgctgc tctactattt gctgctcctg    660

ccattgcatt tgcctggtgg cgccgtagaa agccacaaga atatttcttt gacgtaccag    720

ccgaagaaga tcctgaagtt cacttaggtc aactgaaaag gttctccctc cgagagctac    780

aagttgcaac tgacagtttt agcaataaaa atatactggg tcgaggtgga tttggtaagg    840

tatacaaagg acgcttagca gatggatcat tggtggctgt taagcggcta aaggaagagc    900

gtactcctgg aggggagttg caatttcaaa cagaagttga gatgattagc atggcagtgc    960

ataggaatct tctacgattg cgtggtttct gtatgacacc aactgaaaga ctgcttgtct   1020

acccctacat ggcgaatgga agtgttgcat catgcctgag agaacgaccg ccttctgaac   1080

caccacttga ttggccaacg cgaaaacgta ttgctttggg gtctgccagg ggattatcgt   1140

atttgcatga tcattgtgac cctaagatta tccatcgtga tgtgaaggct gcaaatatat   1200

tgctagatga agaatttgag gctgttgttg gagactttgg tttggctaaa cttatggact   1260

acaaggatac acatgttaca actgctgtgc gtggtacaat cgggcatata gctccagaat   1320

acctttccac agggaagtct tcagaaaaga ctgatgtttt tgggtatggg atcatgcttc   1380

tggagctaat caccggccaa cgtgcttttg atcttgctcg gctggcaaat gatgacgatg   1440

tcatgttgct tgactgggtg aaaggactcc tcaaagagaa gaaactggaa atgctggttg   1500

accctgatct tcagaacaaa tatgtggagg ctgaggtgga gcaactgatc caggtagcat   1560

tgctttgtac acaaagcaac ccaatggatc ggcctaagat gtcggaagtg gtgagaatgc   1620

ttgaaggtga tggtttggct gaaagatggg atgagtggca gaaggtagaa gttctccggc   1680

aggaagtgga acttgcacca catcctggtt ctgattggct tgttgactcg acagagaatt   1740

tacatgcagt tgaattatcg ggtccaaggt ga                                  1772
```

<210> SEQ ID NO 99
<211> LENGTH: 36
<212> TYPE: PRT
<213> ORGANISM: Solanum lycopersicum

<400> SEQUENCE: 99

Met Val Lys Val Met Glu Lys Asp Thr Val Val Val Ser Leu Val Val
1 5 10 15

Trp Leu Ile Leu Val Val Tyr His Leu Lys Leu Ile Tyr Ala Asn Met
20 25 30

Glu Gly Val Leu
35

<210> SEQ ID NO 100
<211> LENGTH: 6280
<212> TYPE: DNA
<213> ORGANISM: Solanum lycopersicum

<400> SEQUENCE: 100
atggtgaagg tgatggagaa ggatactgtg gtggtatcac tggtggtatg gctaatcttg 60
gttgtatatc atcttaagct catttatgct aatatggaag gtttgtgggc ccatcatcct 120
catttagtta attttaggtc tatatttgat gttctatttt gtgagatgag tttcaaatgt 180
cgaaactttt cgtactagaa ataaaatata tgctaaaagt gaaattggta tgtgcaaaat 240
tggattttga atttgactaa tgtgtgagtt gttgaatttt cccaaaaggg taagcaagat 300
gtacaatgag ttccctgcac tgttacagtg acaagcagtt tagttttaat gtcagttaaa 360
tgtgaaagtt tttagttatc attgccattc aaccttagtg cattatgttt cctatacaag 420
cttgagtaat ttgatgtgat ttaatttggt tgtttgccaa aatcttgata aactgttttg 480
ttcagtcaat agattaaatt tttatgcgca tttaggtggt tgaaaattgt ctatgttttc 540
ctaaatgaat acacgaacag gtgatgcatt gcacagtcta cgcgtcaatt tacaagatcc 600
taacaatgtg ctacagagct gggtccttgc acatggtttc acgttacctg caacaatgac 660
aacagtgtta taagagtgta agaatctgtt ttctggtcta cctccatttg aatggatttg 720
caattccact ctcttgtggt ggtgagcaat ctaattgcag tttgtgctcc cataacactt 780
gttatatgat caacctttcc agtgatttag gaaatgcagc tttatctggt ttgttagttc 840
cacagcttgg ccttttgaag aatttgcagt acttgtaagt ctcacttcat gaactatgtt 900
tggaattatt ttacaaattt agagttggaa aactggcatt gagtgtattg gtttttccag 960
ctgttgaaga ttttcatatt acctctagaa ttcgctgcat gaaaataatg taggtggctt 1020
gcatattaac ttttgcataa aaacaaagct gttgtaagtg gcaaaaatga gcagagaaca 1080
ctttctcctc tccatctctt gtttcacttg atgttgtagt cgatggcata gttgttgatg 1140
tgttccctga acaacacaaa tttgaatgtg tacttcataa aaaaagattt aaatatttgt 1200
ttcacattac atactagtaa attaagtaac tcagatactt ggatgagact agcaatgaag 1260
taacttatgt ggcaaagtag tgtctgtaat tgcttgtgaa aacattgtag ttgaacttaa 1320
atttttgtca tacactccct tatataaaga taagcagagt aatcgttaac ttttttatga 1380
actcttaaac agagtattat tctaaatatt attactaatg ccagtaccct aagcactctt 1440
aatttggaat gacaaacttc aactcatatc aaatccttta ttccctcttt ccttgttcca 1500
tgtagactct aatcacgatt taggatgatg gaataggata aaacaaacaa gagaaacaag 1560
tccattgtaa aagtaaagca aaatctagac ttaaaaagag gaaatatggc atgagggtag 1620
gttgatgtct tggaggagaa gatctgaagt tttctggtca tataacagat gctattctgg 1680
ttttcaccaa gagttcgaat catgattcaa ttaagcatag attttgtaca agtgttaagc 1740
ttagtttgga gttcaatata ccgttcactt aaattacatc tcaaatttca ttgttcttat 1800
tgtaacccat gctcttttga agctgcaact gtatggaagt tcacagagac agtatgtgca 1860
tgtgcacctg gtgaagcagg gcattacatg atgtataacc atgcatcaga caatgttata 1920
atgatgggta taattattac ctagtgactg cttcatcctg ctcacacatt aatatattcc 1980
tatggatgcc tagatttgct tgaggcttgt gtagtacgcg tgctaagtat tttcctagtg 2040
tatgcaagtg acaatcacat caagaatgaa acaatataaa aagaacatca aaagtataac 2100
attatctttg tcaaaaaaaa aaagaaagaa catcaagagt gctgatggaa tttaacaatc 2160
accgggcata cacactgttt agatgaagtt cgaaattaac ataatgacag acgttaaatt 2220
tttattgatg agttatatag attgtataaa atgtttgacg agctgattct ttgcagcaca 2280
tgggacgaca ggtttttata tagaaaagtg cttgtaacca aatataagaa aatacctcca 2340
tgaaatagac atcggtaact agttataatt gctatcttgg aactcctaga cctttctcat 2400
ttgttgactt ttaattgtcg cttgatgcca gtattgatgg atgtgagaat tctccttcat 2460
tatcttggtt gtcccattat cctagggatg tcattggtat gatatgtgga attgactcat 2520
tctctggttt tcttgtcaca gggagcttta cagtaataat ataagtggtc tgataccgag 2580
tgatcttggg aatttgacta atctggtcag cttggatctc tacttgaaca acttcgtcgg 2640
tcccatccca gattccttgg gcaagctgtc gaaattgaga ttcctgtatg tatttttgtt 2700
ctatattaga tttatgtgga tattgtgatg ccaaatgtat atttcatcaa ccaagatgga 2760
cctactctta ctggcatgtt gagaaaggaa aggaagcctg aattcttttc taggtttcac 2820
ataagatgac ctctattagt attatgtttc actcttaagt tttgatggta gaaggtattt 2880
gaggacttca tgggtctgat atcattcata aaaccgatct tacataagtc ttttaatttt 2940
ctccctttgt tctaatcctt gtataaagga aaagaataga agcctatgct ttgtctgata 3000
ctgatattgt aaaattaatc agagtttagt aatgggtgtt gggatccttt tctagaagag 3060
agaagaagtt tagaatccca tgcttcatct tgcatttttc actgctgaag tttctcttgc 3120
ttaatgctcc acaaacttct ttcttttggc ttgactgtct aagaagtgtg ccaaattgtt 3180
ctatcatgca gactcagcat gaaacctcat taactgcatc ttgggactta ctatagaact 3240
attgcagtac tgcaacgttg actaacatga tttagtccaa aaggtgtttc aagtctgttt 3300
atcggggggg ggggatgttt tgaggctctt tatcgtggtt ctgaactgac gccttcattt 3360
ccagctgaag tgccggttct ggctcgaagt tgaatatgtt ttacatccac atattaataa 3420
tttattaaga tgattctcct tgtcaaataa taaataaatt aagatgattc aattagtagc 3480
cttttcttct gttttattct ccattattta cttgtaccaa agatgaagct cattcctgta 3540
aacctttgtg ttttcttgca aggatagtcg gctcaacaat aatagcttga ctggtaacat 3600
cccaatgtca ctgactaata tctcatcact gcaagtgttg taagtacact gattattttg 3660
tgacttgatt tagataattc tttctgtctt ccatatcttc tcatgcattt ccttttcctt 3720
ctaatgcata tacagattta cttatgctca attcttgtct cacctgtatg tagggatctg 3780
tcaaacaacc gtctctcagg tgctgttcca gataatggtt cattttctct attcacgcct 3840
atcaggtata tttcatttaa ggcggtgcac catctaactg gctggtggtt ttagcatgct 3900
actatttgct aatatatttt tcttgtttac agttttgcga ataatttaga tctttgcggg 3960
cctgtaactg gacgcccttg ccctggatct cctccattct cccctccgcc tccatttgtt 4020
ccaccaccac caatttctgc tccaggtggt tctctaaatt ggtgtggata aattgttctc 4080
ctttcttttt tcttttgttt tttttgcttt tttgcggtta gtgattttag tttgtccatc 4140
caacgtaagt gagaatttgt gctatagaag ctaaagtact gacaagaaag ggggcagaag 4200
aggaaaaccc atcttaacta gtcaggcatt agttctgatg ggaaactggt atgcacgaga 4260
ctacatttag tctctaagca ttctggtctt tatacaaatt taattcagca ttgtggacat 4320
cttttctttg gtccccttgt aaattattat ctgtggtatt tgaagtcatg tgtctgaatg 4380
aaattaatca tatttatgcc agaacttgtg aagattttct tttctttgta aaaactgtcc 4440
tggaaattag atctgatgat agatacaaat ttgtctacta atttcttttt gaagtgattt 4500
aattaatgaa gggccggcca aaattatgtg ttaaatatag tctagatcat atgaaggaaa 4560
ttaatcaaat ttatgggaac ttcaggagga aatggtgcaa ctggagcaat tgctggaggt 4620
gtagctgctg gtgctgctct actatttgct gctcctgcca ttgcatttgc ctggtggcgc 4680
cgtagaaagc cacaagaata tttctttgac gtaccaggtt agcagtattc aaatacccaa 4740
ccataagtcc ataactccta cttactctct cacgtgttta tggtttctct tgcatgtttt 4800
attttttggc tccataatta acgtctttgc ttaaacttat tgcagccgaa gaagatcctg 4860
aagttcactt aggtcaactg aaaaggttct ccctccgaga gctacaagtt gcaactgaca 4920
gttttagcaa taaaaatata ctgggtcgag gtggatttgg taaggtatac aaaggacgct 4980
tagcagatgg atcattggtg gctgttaagc ggctaaagga agagcgtact cctggagggg 5040
agttgcaatt tcaaacagaa gttgagatga ttagcatggc agtgcatagg aatcttctac 5100
gattgcgtgg tttctgtatg acaccaactg aaagactgct tgtctacccc tacatggcga 5160
atggaagtgt tgcatcatgc ctgagaggtg acactttctg aaatctatca ctccataaat 5220
gttctcacct ttaatttgga gggtattatt gcataatgca agaatgtctt tcgctggtta 5280
acattctatc ttggcataac ttactcttta taacaaaaca tattcttgtt agttattttc 5340
ctgtaacttt ttaaaaggta gaagtataat ttgtattgta ttctcttgac aacataattt 5400
attttatcag aacgaccgcc ttctgaacca ccacttgatt ggccaacgcg aaaacgtatt 5460
gctttggggt ctgccagggg attatcgtat ttgcatgatc attgtgaccc taagattatc 5520
catcgtgatg tgaaggctgc aaatatattg ctagatgaag aatttgaggc tgttgttgga 5580
gactttggtt tggctaaact tatggactac aaggatacac atgttacaac tgctgtgcgt 5640
ggtacaatcg ggcatatagc tccagaatac ctttccacag ggaagtcttc agaaaagact 5700
gatgtttttg ggtatgggat catgcttctg gagctaatca ccggccaacg tgcttttgat 5760
cttgctcggc tggcaaatga tgacgatgtc atgttgcttg actgggtatg ttgtcatacc 5820
tgctttacat gtgaacatga cacgagtacc ataatgtgtt catttttaa tctgtacatc 5880
acaacactag ctgactaata agtatttgtg cctttagcag gaatatttaa gtctatgact 5940
aaacttgttg aggttcttgt ttcaggtgaa aggactcctc aaagagaaga aactggaaat 6000
gctggttgac cctgatcttc agaacaaata tgtggaggct gaggtggagc aactgatcca 6060
ggtagcattg ctttgtacac aaagcaaccc aatggatcgg cctaagatgt cggaagtggt 6120
gagaatgctt gaaggtgatg gtttggctga aagatgggat gagtggcaga aggtagaagt 6180
tctccggcag gaagtggaac ttgcaccaca tcctggttct gattggcttg ttgactcgac 6240
agagaattta catgcagttg aattatcggg tccaaggtga 6280

<210> SEQ ID NO 101
<211> LENGTH: 1874
<212> TYPE: DNA
<213> ORGANISM: Solanum lycopersicum

<400> SEQUENCE: 101
atggtgaagg tgatggagaa ggatactgtg gtggtatcac tggtggtatg gctaatcttg 60
gttgtatatc atcttaagct catttatgct aatatggaag gtgatgcatt gcacagtcta 120
cgcgtcaatt tacaagatcc taacaatgtg ctacagagct gggtccttgc acatggtttc 180
acgttacctg caacaatgac aacagtgtta taagagttga tttaggaaat gcagctttat 240
ctggtttgtt agttccacag cttggccttt tgaagaattt gcagtacttg gagctttaca 300
gtaataatat aagtggtctg ataccgagtg atcttgggaa tttgactaat ctggtcagct 360
tggatctcta cttgaacaac ttcgtcggtc ccatcccaga ttccttgggc aagctgtcga 420
aattgagatt ccttcggctc aacaataata gcttgactgg taacatccca atgtcactga 480
ctaatatctc atcactgcaa gtgttggatc tgtcaaacaa ccgtctctca ggtgctgttc 540
cagataatgg ttcattttct ctattcacgc ctatcagttt tgcgaataat ttagatcttt 600
gcgggcctgt aactggacgc ccttgccctg gatctcctcc attctcccct ccgcctccat 660
ttgttccacc accaccaatt tctgctccag gaggaaatgg tgcaactgga gcaattgctg 720
gaggtgtagc tgctggtgct gctctactat ttgctgctcc tgccattgca tttgcctggt 780
ggcgccgtag aaagccacaa gaatatttct ttgacgtacc agccgaagaa gatcctgaag 840
ttcacttagg tcaactgaaa aggttctccc tccgagagct acaagttgca actgacagtt 900
ttagcaataa aaatatactg ggtcgaggtg gatttggtaa ggtatacaaa ggacgcttag 960
cagatggatc attggtggct gttaagcggc taaaggaaga gcgtactcct ggaggggagt 1020
tgcaatttca aacagaagtt gagatgatta gcatggcagt gcataggaat cttctacgat 1080
tgcgtggttt ctgtatgaca ccaactgaaa gactgcttgt ctacccctac atggcgaatg 1140
gaagtgttgc atcatgcctg agagaacgac cgccttctga accaccactt gattggccaa 1200
cgcgaaaacg tattgctttg ggtctgccca ggggattatc gtatttgcat gatcattgtg 1260
accctaagat tatccatcgt gatgtgaagg ctgcaaatat attgctagat gaagaatttg 1320
aggctgttgt tggagacttt ggtttggcta aacttatgga ctacaaggat acacatgtta 1380
caactgctgt gcgtggtaca atcgggcata tagctccaga atacctttcc acagggaagt 1440
cttcagaaaa gactgatgtt tttgggtatg ggatcatgct tctggagcta atcaccggcc 1500
aacgtgcttt tgatcttgct cggctggcaa atgatgacga tgtcatgttg cttgactggg 1560
tgaaaggact cctcaaagag aagaaactgg aaatgctggt tgaccctgat cttcagaaca 1620
aatatgtgga ggctgaggtg gagcaactga tccaggtagc attgctttgt acacaaagca 1680
acccaatgga tcggcctaag atgtcggaag tggtgagaat gcttgaaggt gatggtttgg 1740
ctgaaagatg ggatgagtgg cagaaggtag aagttctccg gcaggaagtg gaacttgcac 1800
cacatcctgg ttctgattgg cttgttgact cgacagagaa tttacatgca gttgaattat 1860
cgggtccaag gtga 1874

<210> SEQ ID NO 102
<211> LENGTH: 70
<212> TYPE: PRT
<213> ORGANISM: Solanum lycopersicum

<400> SEQUENCE: 102

Met Val Lys Val Met Glu Lys Asp Thr Val Val Val Ser Leu Val Val
1 5 10 15

Trp Leu Ile Leu Val Val Tyr His Leu Lys Leu Ile Tyr Ala Asn Met
20 25 30

-continued

```
Glu Gly Asp Ala Leu His Ser Leu Arg Val Asn Leu Gln Asp Pro Asn
        35                  40                  45

Asn Val Leu Gln Ser Trp Val Leu Ala His Gly Phe Thr Leu Pro Ala
    50                  55                  60

Thr Met Thr Thr Val Leu
65                  70


<210> SEQ ID NO 103
<211> LENGTH: 6276
<212> TYPE: DNA
<213> ORGANISM: Solanum lycopersicum

<400> SEQUENCE: 103

atggtgaagg tgatggagaa ggatactgtg gtggtatcac tggtggtatg gctaatcttg      60

gttgtatatc atcttaagct catttatgct aatatggaag gtttgtgggc ccatcatcct     120

catttagtta attttaggtc tatatttgat gttctatttt gtgagatgag tttcaaatgt     180

cgaaactttt cgtactagaa ataaaatata tgctaaaagt gaaattggta tgtgcaaaat     240

tggattttga atttgactaa tgtgtgagtt gttgaatttt cccaaaaggg taagcaagat     300

gtacaatgag ttccctgcac tgttacagtg acaagcagtt tagttttaat gtcagttaaa     360

tgtgaaagtt tttagttatc attgccattc aaccttagtg cattatgttt cctatacaag     420

cttgagtaat ttgatgtgat ttaatttggt tgtttgccaa aatcttgata aactgttttg     480

ttcagtcaat agattaaatt tttatgcgca tttaggtggt tgaaaattgt ctatgttttc     540

ctaaatgaat acacgaacag gtgatgcatt gcacagtcta cgcgtcaatt tacaagatcc     600

taacaatgtg ctacagagct gggacccaac cgtttcacgt tacctgcaac aatgacaaca     660

gtgttataag agtgtaagaa tctgttttct ggtctacctc catttgaatg gatttgcaat     720

tccactctct tgtggtggtg agcaatctaa ttgcagtttg tgctcccata acacttgtta     780

tatgatcaac ctttccagtg atttaggaaa tgcagcttta tctggtttgt tagttccaca     840

gcttggcctt ttgaagaatt tgcagtactt gtaagtctca cttcatgaac tatgtttgga     900

attattttac aaatttagag ttggaaaact ggcattgagt gtattggttt ttccagctgt     960

tgaagatttt catattacct ctagaattcg ctgcatgaaa ataatgtagg tggcttgcat    1020

attaactttt gcataaaaac aaagctgttg taagtggcaa aaatgagcag agaacacttt    1080

ctcctctcca tctcttgttt cacttgatgt tgtagtcgat ggcatagttg ttgatgtgtt    1140

ccctgaacaa cacaaatttg aatgtgtact tcataaaaaa agatttaaat atttgtttca    1200

cattacatac tagtaaatta agtaactcag atacttggat gagactagca atgaagtaac    1260

ttatgtggca aagtagtgtc tgtaattgct tgtgaaaaca ttgtagttga acttaaattt    1320

ttgtcataca ctcccttata taaagataag cagagtaatc gttaactttt ttatgaactc    1380

ttaaacagag tattattcta aatattatta ctaatgccag taccctaagc actcttaatt    1440

tggaatgaca aacttcaact catatcaaat cctttattcc ctctttcctt gttccatgta    1500

gactctaatc acgatttagg atgatggaat aggataaaac aaacaagaga aacaagtcca    1560

ttgtaaaagt aaagcaaaat ctagacttaa aaagaggaaa tatggcatga gggtaggttg    1620

atgtcttgga ggagaagatc tgaagttttc tggtcatata acagatgcta ttctggtttt    1680

caccaagagt tcgaatcatg attcaattaa gcatagattt tgtacaagtg ttaagcttag    1740

tttggagttc aatataccgt tcacttaaat tacatctcaa atttcattgt tcttattgta    1800

acccatgctc ttttgaagct gcaactgtat ggaagttcac agagacagta tgtgcatgtg    1860
```

-continued cacctggtga agcagggcat tacatgatgt ataaccatgc atcagacaat gttataatga 1920
tgggtataat tattacctag tgactgcttc atcctgctca cacattaata tattcctatg 1980
gatgcctaga tttgcttgag gcttgtgtag tacgcgtgct aagtattttc ctagtgtatg 2040
caagtgacaa tcacatcaag aatgaaacaa tataaaaaga acatcaaaag tataacatta 2100
tctttgtcaa aaaaaaaaag aaagaacatc aagagtgctg atggaattta acaatcaccg 2160
ggcatacaca ctgtttagat gaagttcgaa attaacataa tgacagacgt taaattttta 2220
ttgatgagtt atatagattg tataaaatgt ttgacgagct gattctttgc agcacatggg 2280
acgacaggtt tttatataga aaagtgcttg taaccaaata taagaaaata cctccatgaa 2340
atagacatcg gtaactagtt ataattgcta tcttggaact cctagacctt tctcatttgt 2400
tgacttttaa ttgtcgcttg atgccagtat tgatggatgt gagaattctc cttcattatc 2460
ttggttgtcc cattatccta gggatgtcat tggtatgata tgtggaattg actcattctc 2520 tggtttttctt gtcacaggga gctttacagt aataatataa gtggtctgat accgagtgat 2580
cttgggaatt tgactaatct ggtcagcttg gatctctact tgaacaactt cgtcggtccc 2640
atcccagatt ccttgggcaa gctgtcgaaa ttgagattcc tgtatgtatt tttgttctat 2700
attagattta tgtggatatt gtgatgccaa atgtatattt catcaaccaa gatggaccta 2760
ctcttactgg catgttgaga aaggaaagga agcctgaatt cttttctagg tttcacataa 2820
gatgacctct attagtatta tgtttcactc ttaagttttg atggtagaag gtatttgagg 2880
acttcatggg tctgatatca ttcataaaac cgatcttaca taagtctttt aattttctcc 2940
ctttgttcta atccttgtat aaaggaaaag aatagaagcc tatgctttgt ctgatactga 3000
tattgtaaaa ttaatcagag tttagtaatg ggtgttggga tccttttcta gaagagagaa 3060
gaagtttaga atcccatgct tcatcttgca tttttcactg ctgaagtttc tcttgcttaa 3120
tgctccacaa acttctttct tttggcttga ctgtctaaga agtgtgccaa attgttctat 3180
catgcagact cagcatgaaa cctcattaac tgcatcttgg gacttactat agaactattg 3240
cagtactgca acgttgacta acatgattta gtccaaaagg tgtttcaagt ctgtttatcg 3300
gggggggggg atgttttgag gctctttatc gtggttctga actgacgcct tcatttccag 3360
ctgaagtgcc ggttctggct cgaagttgaa tatgttttac atccacatat taataattta 3420
ttaagatgat tctccttgtc aaataataaa taaattaaga tgattcaatt agtagccttt 3480
tcttctgttt tattctccat tatttacttg taccaaagat gaagctcatt cctgtaaacc 3540
tttgtgtttt cttgcaagga tagtcggctc aacaataata gcttgactgg taacatccca 3600
atgtcactga ctaatatctc atcactgcaa gtgttgtaag tacactgatt attttgtgac 3660
ttgatttaga taattctttc tgtcttccat atcttctcat gcatttcctt ttccttctaa 3720
tgcatataca gatttactta tgctcaattc ttgtctcacc tgtatgtagg gatctgtcaa 3780
acaaccgtct ctcaggtgct gttccagata atggttcatt ttctctattc acgcctatca 3840
ggtatatttc atttaaggcg gtgcaccatc taactggctg gtggttttag catgctacta 3900
tttgctaata tatttttctt gtttacagtt ttgcgaataa tttagatctt tgcgggcctg 3960
taactggacg cccttgccct ggatctcctc cattctcccc tccgcctcca tttgttccac 4020
caccaccaat ttctgctcca ggtggttctc taaattggtg tggataaatt gttctccttt 4080 ctttttctt ttgtttttttt tgctttttttg cggttagtga ttttagtttg tccatccaac 4140
gtaagtgaga atttgtgcta tagaagctaa agtactgaca agaaaggggg cagaagagga 4200
aaacccatct taactagtca ggcattagtt ctgatgggaa actggtatgc acgagactac 4260

```
atttagtctc taagcattct ggtctttata caaatttaat tcagcattgt ggacatcttt   4320

tctttggtcc ccttgtaaat tattatctgt ggtatttgaa gtcatgtgtc tgaatgaaat   4380

taatcatatt tatgccagaa cttgtgaaga ttttcttttc tttgtaaaaa ctgtcctgga   4440

aattagatct gatgatagat acaaatttgt ctactaattt ctttttgaag tgatttaatt   4500

aatgaagggc cggccaaaat tatgtgttaa atatagtcta gatcatatga aggaaattaa   4560

tcaaatttat gggaacttca ggaggaaatg gtgcaactgg agcaattgct ggaggtgtag   4620

ctgctggtgc tgctctacta tttgctgctc ctgccattgc atttgcctgg tggcgccgta   4680

gaaagccaca agaatatttc tttgacgtac caggttagca gtattcaaat acccaaccat   4740

aagtccataa ctcctactta ctctctcacg tgtttatggt ttctcttgca tgttttattt   4800

tttggctcca taattaacgt ctttgcttaa acttattgca gccgaagaag atcctgaagt   4860

tcacttaggt caactgaaaa ggttctccct ccgagagcta caagttgcaa ctgacagttt   4920

tagcaataaa aatatactgg gtcgaggtgg atttggtaag gtatacaaag gacgcttagc   4980

agatggatca ttggtggctg ttaagcggct aaaggaagag cgtactcctg gaggggagtt   5040

gcaatttcaa acagaagttg agatgattag catggcagtg cataggaatc ttctacgatt   5100

gcgtggtttc tgtatgacac caactgaaag actgcttgtc taccccctaca tggcgaatgg   5160

aagtgttgca tcatgcctga gaggtgacac tttctgaaat ctatcactcc ataaatgttc   5220

tcacctttaa tttggagggt attattgcat aatgcaagaa tgtctttcgc tggttaacat   5280

tctatcttgg cataacttac tctttataac aaaacatatt cttgttagtt attttcctgt   5340

aactttttaa aaggtagaag tataatttgt attgtattct cttgacaaca taatttattt   5400

tatcagaacg accgccttct gaaccaccac ttgattggcc aacgcgaaaa cgtattgctt   5460

tggggtctgc caggggatta tcgtatttgc atgatcattg tgaccctaag attatccatc   5520

gtgatgtgaa ggctgcaaat atattgctag atgaagaatt tgaggctgtt gttggagact   5580

ttggtttggc taaacttatg gactacaagg atacacatgt tacaactgct gtgcgtggta   5640

caatcgggca tatagctcca gaataccttt ccacagggaa gtcttcagaa aagactgatg   5700

tttttgggta tgggatcatg cttctggagc taatcaccgg ccaacgtgct tttgatcttg   5760

ctcggctggc aaatgatgac gatgtcatgt tgcttgactg ggtatgttgt catacctgct   5820

ttacatgtga acatgacacg agtaccataa tgtgttcatt ttttaatctg tacatcacaa   5880

cactagctga ctaataagta tttgtgcctt tagcaggaat atttaagtct atgactaaac   5940

ttgttgaggt tcttgtttca ggtgaaagga ctcctcaaag agaagaaact ggaaatgctg   6000

gttgaccctg atcttcagaa caaatatgtg gaggctgagg tggagcaact gatccaggta   6060

gcattgcttt gtacacaaag caacccaatg gatcggccta agatgtcgga agtggtgaga   6120

atgcttgaag gtgatggttt ggctgaaaga tgggatgagt ggcagaaggt agaagttctc   6180

cggcaggaag tggaacttgc accacatcct ggttctgatt ggcttgttga ctcgacagag   6240

aatttacatg cagttgaatt atcgggtcca aggtga                             6276
```

<210> SEQ ID NO 104
<211> LENGTH: 1870
<212> TYPE: DNA
<213> ORGANISM: Solanum lycopersicum

<400> SEQUENCE: 104

```
atggtgaagg tgatggagaa ggatactgtg gtggtatcac tggtggtatg gctaatcttg     60
```

-continued

```
gttgtatatc atcttaagct catttatgct aatatggaag gtgatgcatt gcacagtcta    120

cgcgtcaatt tacaagatcc taacaatgtg ctacagagct gggacccaac cgtttcacgt    180

tacctgcaac aatgacaaca gtgttataag agttgattta ggaaatgcag ctttatctgg    240

tttgttagtt ccacagcttg gccttttgaa gaatttgcag tacttggagc tttacagtaa    300

taatataagt ggtctgatac cgagtgatct tgggaatttg actaatctgg tcagcttgga    360

tctctacttg aacaacttcg tcggtcccat cccagattcc ttgggcaagc tgtcgaaatt    420

gagattcctt cggctcaaca ataatagctt gactggtaac atcccaatgt cactgactaa    480

tatctcatca ctgcaagtgt tggatctgtc aaacaaccgt ctctcaggtg ctgttccaga    540

taatggttca ttttctctat tcacgcctat cagttttgcg aataatttag atctttgcgg    600

gcctgtaact ggacgccctt gccctggatc tcctccattc tcccctccgc ctccatttgt    660

tccaccacca ccaatttctg ctccaggagg aaatggtgca actggagcaa ttgctggagg    720

tgtagctgct ggtgctgctc tactatttgc tgctcctgcc attgcatttg cctggtggcg    780

ccgtagaaag ccacaagaat atttctttga cgtaccagcc gaagaagatc ctgaagttca    840

cttaggtcaa ctgaaaaggt tctccctccg agagctacaa gttgcaactg acagttttag    900

caataaaaat atactgggtc gaggtggatt tggtaaggta tacaaaggac gcttagcaga    960

tggatcattg gtggctgtta agcggctaaa ggaagagcgt actcctggag gggagttgca   1020

atttcaaaca gaagttgaga tgattagcat ggcagtgcat aggaatcttc tacgattgcg   1080

tggtttctgt atgacaccaa ctgaaagact gcttgtctac ccctacatgg cgaatggaag   1140

tgttgcatca tgcctgagag aacgaccgcc ttctgaacca ccacttgatt ggccaacgcg   1200

aaaacgtatt gctttggggt ctgccagggg attatcgtat ttgcatgatc attgtgaccc   1260

taagattatc catcgtgatg tgaaggctgc aaatatattg ctagatgaag aatttgaggc   1320

tgttgttgga gactttggtt tggctaaact tatggactac aaggatacac atgttacaac   1380

tgctgtgcgt ggtacaatcg ggcatatagc tccagaatac ctttccacag ggaagtcttc   1440

agaaaagact gatgtttttg ggtatgggat catgcttctg gagctaatca ccggccaacg   1500

tgcttttgat cttgctcggc tggcaaatga tgacgatgtc atgttgcttg actgggtgaa   1560

aggactcctc aaagagaaga aactggaaat gctggttgac cctgatcttc agaacaaata   1620

tgtggaggct gaggtggagc aactgatcca ggtagcattg ctttgtacac aaagcaaccc   1680

aatggatcgg cctaagatgt cggaagtggt gagaatgctt gaaggtgatg gtttggctga   1740

aagatgggat gagtggcaga aggtagaagt tctccggcag gaagtggaac ttgcaccaca   1800

tcctggttct gattggcttg ttgactcgac agagaattta catgcagttg aattatcggg   1860

tccaaggtga                                                          1870
```

<210> SEQ ID NO 105
<211> LENGTH: 64
<212> TYPE: PRT
<213> ORGANISM: Solanum lycopersicum

<400> SEQUENCE: 105

```
Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45
```

-continued

```
Asn Val Leu Gln Ser Trp Asp Pro Thr Val Ser Arg Tyr Leu Gln Gln
    50                  55                  60


<210> SEQ ID NO 106
<211> LENGTH: 6067
<212> TYPE: DNA
<213> ORGANISM: Solanum lycopersicum

<400> SEQUENCE: 106

atggtgaagg tgatggagaa ggatactgtg gtggtatcac tggtggtatg gctaatcttg     60

gttgtatatc atcttaagct catttatgct aatatggaag gtttgtgggc ccatcatcct    120

catttagtta attttaggtc tatatttgat gttctatttt gtgagatgag tttcaaatgt    180

cgaaactttt cgtactagaa ataaaatata tgctaaaagt gaaattggta tgtgcaaaat    240

tggattttga atttgactaa tgtgtgagtt gttgaatttt cccaaaaggg taagcaagat    300

gtacaatgag ttccctgcac tgttacagtg acaagcagtt tagttttaat gtcagttaaa    360

tgtgaaagtt tttagttatc attgccattc aaccttagtg cattatgttt cctatacaag    420

cttgagtaat ttgatgtgat ttaatttggt tgtttgccaa aatcttgata aactgttttg    480

ttcagtcaat agattaaatt tttatgcgca tttaggtggt tgaaaattgt ctatgttttc    540

ctaaatgaat acacgaacag gtgatgcatt gcacagtcta cgcgtcaatt tacaagatcc    600

taacaatgtg ctacagagct gggacccaac cgcttggcct tttgaagaat ttgcagtact    660

tgtaagtctc acttcatgaa ctatgtttgg aattatttta caaatttaga gttggaaaac    720

tggcattgag tgtattggtt tttccagctg ttgaagattt tcatattacc tctagaattc    780

gctgcatgaa aataatgtag gtggcttgca tattaacttt tgcataaaaa caaagctgtt    840

gtaagtggca aaaatgagca gagaacactt tctcctctcc atctcttgtt tcacttgatg    900

ttgtagtcga tggcatagtt gttgatgtgt tccctgaaca acacaaattt gaatgtgtac    960

ttcataaaaa aagatttaaa tatttgtttc acattacata ctagtaaatt aagtaactca   1020

gatacttgga tgagactagc aatgaagtaa cttatgtggc aaagtagtgt ctgtaattgc   1080

ttgtgaaaac attgtagttg aacttaaatt tttgtcatac actcccttat ataaagataa   1140

gcagagtaat cgttaacttt tttatgaact cttaaacaga gtattattct aaatattatt   1200

actaatgcca gtaccctaag cactcttaat ttggaatgac aaacttcaac tcatatcaaa   1260

tcctttattc cctctttcct tgttccatgt agactctaat cacgatttag gatgatggaa   1320

taggataaaa caaacaagag aaacaagtcc attgtaaaag taaagcaaaa tctagactta   1380

aaaagaggaa atatggcatg agggtaggtt gatgtcttgg aggagaagat ctgaagtttt   1440

ctggtcatat aacagatgct attctggttt tcaccaagag ttcgaatcat gattcaatta   1500

agcatagatt ttgtacaagt gttaagctta gtttggagtt caatataccg ttcacttaaa   1560

ttacatctca aatttcattg ttcttattgt aacccatgct cttttgaagc tgcaactgta   1620

tggaagttca cagagacagt atgtgcatgt gcacctggtg aagcagggca ttacatgatg   1680

tataaccatg catcagacaa tgttataatg atgggtataa ttattaccta gtgactgctt   1740

catcctgctc acacattaat atattcctat ggatgcctag atttgcttga ggcttgtgta   1800

gtacgcgtgc taagtatttt cctagtgtat gcaagtgaca atcacatcaa gaatgaaaca   1860

atataaaaag aacatcaaaa gtataacatt atctttgtca aaaaaaaaaa gaaagaacat   1920

caagagtgct gatggaattt aacaatcacc gggcatacac actgtttaga tgaagttcga   1980

aattaacata atgacagacg ttaaattttt attgatgagt tatatagatt gtataaaatg   2040
```

-continued

```
tttgacgagc tgattctttg cagcacatgg gacgacaggt ttttatatag aaaagtgctt   2100
gtaaccaaat ataagaaaat acctccatga aatagacatc ggtaactagt tataattgct   2160
atcttggaac tcctagacct ttctcatttg ttgactttta attgtcgctt gatgccagta   2220
ttgatggatg tgagaattct ccttcattat cttggttgtc ccattatcct agggatgtca   2280
ttggtatgat atgtggaatt gactcattct ctggttttct tgtcacaggg agctttacag   2340
taataatata agtggtctga taccgagtga tcttgggaat ttgactaatc tggtcagctt   2400
ggatctctac ttgaacaact tcgtcggtcc catcccagat tccttgggca agctgtcgaa   2460
attgagattc ctgtatgtat ttttgttcta tattagattt atgtggatat tgtgatgcca   2520
aatgtatatt tcatcaacca agatggacct actcttactg gcatgttgag aaaggaaagg   2580
aagcctgaat tcttttctag gtttcacata agatgacctc tattagtatt atgtttcact   2640
cttaagtttt gatggtagaa ggtatttgag gacttcatgg gtctgatatc attcataaaa   2700
ccgatcttac ataagtcttt taattttctc cctttgttct aatccttgta taaaggaaaa   2760
gaatagaagc ctatgctttg tctgatactg atattgtaaa attaatcaga gtttagtaat   2820
gggtgttggg atccttttct agaagagaga agaagtttag aatcccatgc ttcatcttgc   2880
atttttcact gctgaagttt ctcttgctta atgctccaca aacttctttc ttttggcttg   2940
actgtctaag aagtgtgcca aattgttcta tcatgcagac tcagcatgaa acctcattaa   3000
ctgcatcttg ggacttacta tagaactatt gcagtactgc aacgttgact aacatgattt   3060
agtccaaaag gtgtttcaag tctgtttatc gggggggggg gatgttttga ggctctttat   3120
cgtggttctg aactgacgcc ttcatttcca gctgaagtgc cggttctggc tcgaagttga   3180
atatgtttta catccacata ttaataattt attaagatga ttctccttgt caaataataa   3240
ataaattaag atgattcaat tagtagcctt ttcttctgtt ttattctcca ttatttactt   3300
gtaccaaaga tgaagctcat tcctgtaaac ctttgtgttt tcttgcaagg atagtcggct   3360
caacaataat agcttgactg gtaacatccc aatgtcactg actaatatct catcactgca   3420
agtgttgtaa gtacactgat tattttgtga cttgatttag ataattcttt ctgtcttcca   3480
tatcttctca tgcatttcct tttccttcta atgcatatac agatttactt atgctcaatt   3540
cttgtctcac ctgtatgtag ggatctgtca aacaaccgtc tctcaggtgc tgttccagat   3600
aatggttcat tttctctatt cacgcctatc aggtatattt catttaaggc ggtgcaccat   3660
ctaactggct ggtggtttta gcatgctact atttgctaat atatttttct tgtttacagt   3720
tttgcgaata atttagatct ttgcgggcct gtaactggac gcccttgccc tggatctcct   3780
ccattctccc ctccgcctcc atttgttcca ccaccaccaa tttctgctcc aggtggttct   3840
ctaaattggt gtggataaat tgttctcctt tctttttttct tttgtttttt ttgctttttt   3900
gcggttagtg attttagttt gtccatccaa cgtaagtgag aatttgtgct atagaagcta   3960
aagtactgac aagaaagggg gcagaagagg aaaacccatc ttaactagtc aggcattagt   4020
tctgatggga aactggtatg cacgagacta catttagtct ctaagcattc tggtctttat   4080
acaaatttaa ttcagcattg tggacatctt ttctttggtc cccttgtaaa ttattatctg   4140
tggtatttga agtcatgtgt ctgaatgaaa ttaatcatat ttatgccaga acttgtgaag   4200
attttctttt ctttgtaaaa actgtcctgg aaattagatc tgatgataga tacaaatttg   4260
tctactaatt tctttttgaa gtgatttaat taatgaaggg ccggccaaaa ttatgtgtta   4320
aatatagtct agatcatatg aaggaaatta atcaaattta tgggaacttc aggaggaaat   4380
ggtgcaactg gagcaattgc tggaggtgta gctgctggtg ctgctctact atttgctgct   4440
```

```
cctgccattg catttgcctg gtggcgccgt agaaagccac aagaatattt ctttgacgta   4500
ccaggttagc agtattcaaa tacccaacca taagtccata actcctactt actctctcac   4560
gtgtttatgg tttctcttgc atgttttatt ttttggctcc ataattaacg tctttgctta   4620
aacttattgc agccgaagaa gatcctgaag ttcacttagg tcaactgaaa aggttctccc   4680
tccgagagct acaagttgca actgacagtt ttagcaataa aaatatactg ggtcgaggtg   4740
gatttggtaa ggtatacaaa ggacgcttag cagatggatc attggtggct gttaagcggc   4800
taaaggaaga gcgtactcct ggaggggagt tgcaatttca aacagaagtt gagatgatta   4860
gcatggcagt gcataggaat cttctacgat tgcgtggttt ctgtatgaca ccaactgaaa   4920
gactgcttgt ctacccctac atggcgaatg gaagtgttgc atcatgcctg agaggtgaca   4980
ctttctgaaa tctatcactc cataaatgtt ctcaccttta atttggaggg tattattgca   5040
taatgcaaga atgtctttcg ctggttaaca ttctatcttg gcataactta ctctttataa   5100
caaaacatat tcttgttagt tattttcctg taacttttta aaaggtagaa gtataatttg   5160
tattgtattc tcttgacaac ataatttatt ttatcagaac gaccgccttc tgaaccacca   5220
cttgattggc caacgcgaaa acgtattgct ttggggtctg ccaggggatt atcgtatttg   5280
catgatcatt gtgaccctaa gattatccat cgtgatgtga aggctgcaaa tatattgcta   5340
gatgaagaat ttgaggctgt tgttggagac tttggtttgg ctaaacttat ggactacaag   5400
gatacacatg ttacaactgc tgtgcgtggt acaatcgggc atatagctcc agaatacctt   5460
tccacaggga agtcttcaga aaagactgat gtttttgggt atgggatcat gcttctggag   5520
ctaatcaccg gccaacgtgc ttttgatctt gctcggctgg caaatgatga cgatgtcatg   5580
ttgcttgact gggtatgttg tcatacctgc tttacatgtg aacatgacac gagtaccata   5640
atgtgttcat tttttaatct gtacatcaca acactagctg actaataagt atttgtgcct   5700
ttagcaggaa tatttaagtc tatgactaaa cttgttgagg ttcttgtttc aggtgaaagg   5760
actcctcaaa gagaagaaac tggaaatgct ggttgaccct gatcttcaga acaaatatgt   5820
ggaggctgag gtggagcaac tgatccaggt agcattgctt tgtacacaaa gcaacccaat   5880
ggatcggcct aagatgtcgg aagtggtgag aatgcttgaa ggtgatggtt tggctgaaag   5940
atgggatgag tggcagaagg tagaagttct ccggcaggaa gtggaacttg caccacatcc   6000
tggttctgat tggcttgttg actcgacaga gaatttacat gcagttgaat tatcgggtcc   6060
aaggtga                                                             6067
```

<210> SEQ ID NO 107
<211> LENGTH: 1786
<212> TYPE: DNA
<213> ORGANISM: Solanum lycopersicum

<400> SEQUENCE: 107

```
atggtgaagg tgatggagaa ggatactgtg gtggtatcac tggtggtatg gctaatcttg     60
gttgtatatc atcttaagct catttatgct aatatggaag gtgatgcatt gcacagtcta    120
cgcgtcaatt tacaagatcc taacaatgtg ctacagagct gggacccaac cgcttggcct    180
tttgaagaat ttgcagtact tggagcttta cagtaataat ataagtggtc tgataccgag    240
tgatcttggg aatttgacta atctggtcag cttggatctc tacttgaaca acttcgtcgg    300
tcccatccca gattccttgg gcaagctgtc gaaattgaga ttccttcggc tcaacaataa    360
tagcttgact ggtaacatcc caatgtcact gactaatatc tcatcactgc aagtgttgga    420
```

-continued

```
tctgtcaaac aaccgtctct caggtgctgt tccagataat ggttcatttt ctctattcac    480

gcctatcagt tttgcgaata atttagatct ttgcgggcct gtaactggac gcccttgccc    540

tggatctcct ccattctccc ctccgcctcc atttgttcca ccaccaccaa tttctgctcc    600

aggaggaaat ggtgcaactg gagcaattgc tggaggtgta gctgctggtg ctgctctact    660

atttgctgct cctgccattg catttgcctg gtggcgccgt agaaagccac aagaatattt    720

ctttgacgta ccagccgaag aagatcctga agttcactta ggtcaactga aaaggttctc    780

cctccgagag ctacaagttg caactgacag ttttagcaat aaaaatatac tgggtcgagg    840

tggatttggt aaggtataca aaggacgctt agcagatgga tcattggtgg ctgttaagcg    900

gctaaaggaa gagcgtactc ctggagggga gttgcaattt caaacagaag ttgagatgat    960

tagcatggca gtgcatagga atcttctacg attgcgtggt ttctgtatga caccaactga   1020

aagactgctt gtctacccct acatggcgaa tggaagtgtt gcatcatgcc tgagagaacg   1080

accgccttct gaaccaccac ttgattggcc aacgcgaaaa cgtattgctt tggggtctgc   1140

caggggatta tcgtatttgc atgatcattg tgaccctaag attatccatc gtgatgtgaa   1200

ggctgcaaat atattgctag atgaagaatt tgaggctgtt gttggagact ttggtttggc   1260

taaacttatg gactacaagg atacacatgt tacaactgct gtgcgtggta caatcgggca   1320

tatagctcca gaatacctt ccacagggaa gtcttcagaa aagactgatg tttttgggta   1380

tgggatcatg cttctggagc taatcaccgg ccaacgtgct tttgatcttg ctcggctggc   1440

aaatgatgac gatgtcatgt tgcttgactg ggtgaaagga ctcctcaaag agaagaaact   1500

ggaaatgctg gttgaccctg atcttcagaa caaatatgtg gaggctgagg tggagcaact   1560

gatccaggta gcattgcttt gtacacaaag caacccaatg gatcggccta agatgtcgga   1620

agtggtgaga atgcttgaag gtgatggttt ggctgaaaga tgggatgagt ggcagaaggt   1680

agaagttctc cggcaggaag tggaacttgc accacatcct ggttctgatt ggcttgttga   1740

ctcgacagag aatttacatg cagttgaatt atcgggtcca aggtga                  1786
```

<210> SEQ ID NO 108
<211> LENGTH: 71
<212> TYPE: PRT
<213> ORGANISM: Solanum lycopersicum

<400> SEQUENCE: 108

```
Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Ala Trp Pro Phe Glu Glu Phe
    50                  55                  60

Ala Val Leu Gly Ala Leu Gln
65                  70
```

<210> SEQ ID NO 109
<211> LENGTH: 6293
<212> TYPE: DNA
<213> ORGANISM: Solanum lycopersicum

<400> SEQUENCE: 109

```
atggtgaagg tgatggagaa ggatactgtg gtggtatcac tggtggtatg gctaatcttg     60
```

-continued

```
gttgtatatc atcttaagct catttatgct aatatggaag gtttgtgggc ccatcatcct    120
catttagtta attttaggtc tatatttgat gttctatttt gtgagatgag tttcaaatgt    180
cgaaactttt cgtactagaa ataaaatata tgctaaaagt gaaattggta tgtgcaaaat    240
tggattttga atttgactaa tgtgtgagtt gttgaatttt cccaaaaggg taagcaagat    300
gtacaatgag ttccctgcac tgttacagtg acaagcagtt tagttttaat gtcagttaaa    360
tgtgaaagtt tttagttatc attgccattc aaccttagtg cattatgttt cctatacaag    420
cttgagtaat ttgatgtgat ttaatttggt tgtttgccaa aatcttgata aactgttttg    480
ttcagtcaat agattaaatt tttatgcgca tttaggtggt tgaaaattgt ctatgttttc    540
ctaaatgaat acacgaacag gtgatgcatt gcacagtcta cgcgtcaatt tacaagatcc    600
taacaatgtg ctacagagct gggacccaac ctgttaatcc ttgcacatgg tttcacgtta    660
cctgcaacaa tgacaacagt gttataagag tgtaagaatc tgttttctgg tctacctcca    720
tttgaatgga tttgcaattc cactctcttg tggtggtgag caatctaatt gcagtttgtg    780
ctcccataac acttgttata tgatcaacct ttccagtgat ttaggaaatg cagctttatc    840
tggtttgtta gttccacact tggccttttg aagaatttgc agtacttgta agtctcactt    900
catgaactat gtttggaatt attttacaaa tttagagttg gaaaactggc attgagtgta    960
ttggtttttc cagctgttga agattttcat attacctcta gaattcgctg catgaaaata   1020
atgtaggtgg cttgcatatt aacttttgca taaaaacaaa gctgttgtaa gtggcaaaaa   1080
tgagcagaga acactttctc ctctccatct cttgtttcac ttgatgttgt agtcgatggc   1140
atagttgttg atgtgttccc tgaacaacac aaatttgaat gtgtacttca taaaaaaaga   1200
tttaaatatt tgtttcacat tacatactag taaattaagt aactcagata cttggatgag   1260
actagcaatg aagtaactta tgtggcaaag tagtgtctgt aattgcttgt gaaaacattg   1320
tagttgaact taaatttttg tcatacactc ccttatataa agataagcag agtaatcgtt   1380
aacttttttta tgaactctta aacagagtat tattctaaat attattacta atgccagtac   1440
cctaagcact cttaatttgg aatgacaaac ttcaactcat atcaaatcct ttattccctc   1500
tttccttgtt ccatgtagac tctaatcacg atttaggatg atggaatagg ataaaacaaa   1560
caagagaaac aagtccattg taaaagtaaa gcaaaatcta gacttaaaaa gaggaaatat   1620
ggcatgaggg taggttgatg tcttggagga gaagatctga agttttctgg tcatataaca   1680
gatgctattc tggttttcac caagagttcg aatcatgatt caattaagca tagattttgt   1740
acaagtgtta agcttagttt ggagttcaat ataccgttca cttaaattac atctcaaatt   1800
tcattgttct tattgtaacc catgctcttt tgaagctgca actgtatgga agttcacaga   1860
gacagtatgt gcatgtgcac ctggtgaagc agggcattac atgatgtata accatgcatc   1920
agacaatgtt ataatgatgg gtataattat tacctagtga ctgcttcatc ctgctcacac   1980
attaatatat tcctatggat gcctagattt gcttgaggct tgtgtagtac gcgtgctaag   2040
tattttccta gtgtatgcaa gtgacaatca catcaagaat gaaacaatat aaaaagaaca   2100
tcaaaagtat aacattatct ttgtcaaaaa aaaaaagaaa gaacatcaag agtgctgatg   2160
gaatttaaca atcaccgggc atacacactg tttagatgaa gttcgaaatt aacataatga   2220
cagacgttaa atttttattg atgagttata tagattgtat aaaatgtttg acgagctgat   2280
tctttgcagc acatgggacg acaggttttt atatagaaaa gtgcttgtaa ccaaatataa   2340
gaaaatacct ccatgaaata gacatcggta actagttata attgctatct tggaactcct   2400
agacctttct catttgttga cttttaattg tcgcttgatg ccagtattga tggatgtgag   2460
```

-continued

```
aattctcctt cattatcttg gttgtcccat tatcctaggg atgtcattgg tatgatatgt   2520
ggaattgact cattctctgg ttttcttgtc acagggagct ttacagtaat aatataagtg   2580
gtctgatacc gagtgatctt gggaatttga ctaatctggt cagcttggat ctctacttga   2640
acaacttcgt cggtcccatc ccagattcct tgggcaagct gtcgaaattg agattcctgt   2700
atgtattttt gttctatatt agatttatgt ggatattgtg atgccaaatg tatatttcat   2760
caaccaagat ggacctactc ttactggcat gttgagaaag gaaaggaagc ctgaattctt   2820
ttctaggttt cacataagat gacctctatt agtattatgt ttcactctta agttttgatg   2880
gtagaaggta tttgaggact tcatgggtct gatatcattc ataaaaccga tcttacataa   2940
gtcttttaat tttctccctt tgttctaatc cttgtataaa ggaaaagaat agaagcctat   3000
gctttgtctg atactgatat tgtaaaatta atcagagttt agtaatgggt gttgggatcc   3060
ttttctagaa gagagaagaa gtttagaatc ccatgcttca tcttgcattt ttcactgctg   3120
aagtttctct tgcttaatgc tccacaaact tctttctttt ggcttgactg tctaagaagt   3180
gtgccaaatt gttctatcat gcagactcag catgaaacct cattaactgc atcttgggac   3240
ttactataga actattgcag tactgcaacg ttgactaaca tgatttagtc caaaaggtgt   3300
ttcaagtctg tttatcgggg ggggggg atg ttttgaggct ctttatcgtg gttctgaact   3360
gacgccttca tttccagctg aagtgccggt tctggctcga agttgaatat gttttacatc   3420
cacatattaa taatttatta agatgattct ccttgtcaaa taataaataa attaagatga   3480
ttcaattagt agccttttct tctgttttat tctccattat ttacttgtac caaagatgaa   3540
gctcattcct gtaaaccttt gtgttttctt gcaaggatag tcggctcaac aataatagct   3600
tgactggtaa catcccaatg tcactgacta atatctcatc actgcaagtg ttgtaagtac   3660
actgattatt ttgtgacttg atttagataa ttctttctgt cttccatatc ttctcatgca   3720
tttccttttc cttctaatgc atatacagat ttacttatgc tcaattcttg tctcacctgt   3780
atgtagggat ctgtcaaaca accgtctctc aggtgctgtt ccagataatg gttcattttc   3840
tctattcacg cctatcaggt atatttcatt taaggcggtg caccatctaa ctggctggtg   3900
gttttagcat gctactattt gctaatatat ttttcttgtt tacagttttg cgaataattt   3960
agatctttgc gggcctgtaa ctggacgccc ttgccctgga tctcctccat tctcccctcc   4020
gcctccattt gttccaccac caccaatttc tgctccaggt ggttctctaa attggtgtgg   4080
ataaattgtt ctcctttctt ttttcttttg ttttttttgc ttttttgcgg ttagtgattt   4140
tagtttgtcc atccaacgta agtgagaatt tgtgctatag aagctaaagt actgacaaga   4200
aagggggcag aagaggaaaa cccatcttaa ctagtcaggc attagttctg atgggaaact   4260
ggtatgcacg agactacatt tagtctctaa gcattctggt ctttatacaa atttaattca   4320
gcattgtgga catcttttct ttggtcccct tgtaaattat tatctgtggt atttgaagtc   4380
atgtgtctga atgaaattaa tcatatttat gccagaactt gtgaagattt tcttttcttt   4440
gtaaaaactg tcctggaaat tagatctgat gatagataca aatttgtcta ctaatttctt   4500
tttgaagtga tttaattaat gaagggccgg ccaaaattat gtgttaaata tagtctagat   4560
catatgaagg aaattaatca aatttatggg aacttcagga ggaaatggtg caactggagc   4620
aattgctgga ggtgtagctg ctggtgctgc tctactattt gctgctcctg ccattgcatt   4680
tgcctggtgg cgccgtagaa agccacaaga atatttcttt gacgtaccag gttagcagta   4740
ttcaaatacc caaccataag tccataactc ctacttactc tctcacgtgt ttatggtttc   4800
```

-continued

```
tcttgcatgt tttatttttt ggctccataa ttaacgtctt tgcttaaact tattgcagcc   4860

gaagaagatc ctgaagttca cttaggtcaa ctgaaaaggt tctccctccg agagctacaa   4920

gttgcaactg acagttttag caataaaaat atactgggtc gaggtggatt tggtaaggta   4980

tacaaaggac gcttagcaga tggatcattg gtggctgtta agcggctaaa ggaagagcgt   5040

actcctggag gggagttgca atttcaaaca gaagttgaga tgattagcat ggcagtgcat   5100

aggaatcttc tacgattgcg tggtttctgt atgacaccaa ctgaaagact gcttgtctac   5160

ccctacatgg cgaatggaag tgttgcatca tgcctgagag gtgacacttt ctgaaatcta   5220

tcactccata aatgttctca cctttaattt ggagggtatt attgcataat gcaagaatgt   5280

ctttcgctgg ttaacattct atcttggcat aacttactct ttataacaaa acatattctt   5340

gttagttatt ttcctgtaac tttttaaaag gtagaagtat aatttgtatt gtattctctt   5400

gacaacataa tttattttat cagaacgacc gccttctgaa ccaccacttg attggccaac   5460

gcgaaaacgt attgctttgg ggtctgccag gggattatcg tatttgcatg atcattgtga   5520

ccctaagatt atccatcgtg atgtgaaggc tgcaaatata ttgctagatg aagaatttga   5580

ggctgttgtt ggagactttg gtttggctaa acttatggac tacaaggata cacatgttac   5640

aactgctgtg cgtggtacaa tcgggcatat agctccagaa tacctttcca cagggaagtc   5700

ttcagaaaag actgatgttt ttgggtatgg gatcatgctt ctggagctaa tcaccggcca   5760

acgtgctttt gatcttgctc ggctggcaaa tgatgacgat gtcatgttgc ttgactgggt   5820

atgttgtcat acctgcttta catgtgaaca tgacacgagt accataatgt gttcattttt   5880

taatctgtac atcacaacac tagctgacta ataagtattt gtgcctttag caggaatatt   5940

taagtctatg actaaacttg ttgaggttct tgtttcaggt gaaaggactc ctcaaagaga   6000

agaaactgga aatgctggtt gaccctgatc ttcagaacaa atatgtggag gctgaggtgg   6060

agcaactgat ccaggtagca ttgctttgta cacaaagcaa cccaatggat cggcctaaga   6120

tgtcggaagt ggtgagaatg cttgaaggtg atggtttggc tgaaagatgg gatgagtggc   6180

agaaggtaga agttctccgg caggaagtgg aacttgcacc acatcctggt tctgattggc   6240

ttgttgactc gacagagaat ttacatgcag ttgaattatc gggtccaagg tga          6293
```

<210> SEQ ID NO 110
<211> LENGTH: 1887
<212> TYPE: DNA
<213> ORGANISM: Solanum lycopersicum

<400> SEQUENCE: 110

```
atggtgaagg tgatggagaa ggatactgtg gtggtatcac tggtggtatg gctaatcttg     60

gttgtatatc atcttaagct catttatgct aatatggaag gtgatgcatt gcacagtcta    120

cgcgtcaatt tacaagatcc taacaatgtg ctacagagct gggacccaac ctgttaatcc    180

ttgcacatgg tttcacgtta cctgcaacaa tgacaacagt gttataagag ttgatttagg    240

aaatgcagct ttatctggtt tgttagttcc acacttggcc ttttgaagaa tttgcagtac    300

ttggagcttt acagtaataa tataagtggt ctgataccga gtgatcttgg gaatttgact    360

aatctggtca gcttggatct ctacttgaac aacttcgtcg gtcccatccc agattccttg    420

ggcaagctgt cgaaattgag attccttcgg ctcaacaata atagcttgac tggtaacatc    480

ccaatgtcac tgactaatat ctcatcactg caagtgttgg atctgtcaaa caaccgtctc    540

tcaggtgctg ttccagataa tggttcattt tctctattca cgcctatcag ttttgcgaat    600

aatttagatc tttgcgggcc tgtaactgga cgcccttgcc ctggatctcc tccattctcc    660
```

```
cctccgcctc catttgttcc accaccacca atttctgctc caggaggaaa tggtgcaact    720

ggagcaattg ctggaggtgt agctgctggt gctgctctac tatttgctgc tcctgccatt    780

gcatttgcct ggtggcgccg tagaaagcca caagaatatt tctttgacgt accagccgaa    840

gaagatcctg aagttcactt aggtcaactg aaaaggttct ccctccgaga gctacaagtt    900

gcaactgaca gttttagcaa taaaaatata ctgggtcgag gtggatttgg taaggtatac    960

aaaggacgct tagcagatgg atcattggtg gctgttaagc ggctaaagga agagcgtact   1020

cctggagggg agttgcaatt tcaaacagaa gttgagatga ttagcatggc agtgcatagg   1080

aatcttctac gattgcgtgg tttctgtatg acaccaactg aaagactgct tgtctacccc   1140

tacatggcga atggaagtgt tgcatcatgc ctgagagaac gaccgccttc tgaaccacca   1200

cttgattggc caacgcgaaa acgtattgct ttggggtctg ccaggggatt atcgtatttg   1260

catgatcatt gtgaccctaa gattatccat cgtgatgtga aggctgcaaa tatattgcta   1320

gatgaagaat ttgaggctgt tgttggagac tttggtttgg ctaaacttat ggactacaag   1380

gatacacatg ttacaactgc tgtgcgtggt acaatcgggc atatagctcc agaatacctt   1440

tccacaggga agtcttcaga aaagactgat gtttttgggt atgggatcat gcttctggag   1500

ctaatcaccg gccaacgtgc ttttgatctt gctcggctgg caaatgatga cgatgtcatg   1560

ttgcttgact gggtgaaagg actcctcaaa gagaagaaac tggaaatgct ggttgaccct   1620

gatcttcaga acaaatatgt ggaggctgag gtggagcaac tgatccaggt agcattgctt   1680

tgtacacaaa gcaacccaat ggatcggcct aagatgtcgg aagtggtgag aatgcttgaa   1740

ggtgatggtt tggctgaaag atgggatgag tggcagaagg tagaagttct ccggcaggaa   1800

gtggaacttg caccacatcc tggttctgat tggcttgttg actcgacaga gaatttacat   1860

gcagttgaat tatcgggtcc aaggtga                                       1887
```

<210> SEQ ID NO 111
<211> LENGTH: 58
<212> TYPE: PRT
<213> ORGANISM: Solanum lycopersicum

<400> SEQUENCE: 111

```
Met Val Lys Val Met Glu Lys Asp Thr Val Val Val Ser Leu Val Val
1               5                   10                  15

Trp Leu Ile Leu Val Val Tyr His Leu Lys Leu Ile Tyr Ala Asn Met
            20                  25                  30

Glu Gly Asp Ala Leu His Ser Leu Arg Val Asn Leu Gln Asp Pro Asn
        35                  40                  45

Asn Val Leu Gln Ser Trp Asp Pro Thr Cys
    50                  55
```

<210> SEQ ID NO 112
<211> LENGTH: 87
<212> TYPE: DNA
<213> ORGANISM: Solanum lycopersicum

<400> SEQUENCE: 112

```
tagcaacgta gcaaacgtgt tgctggattt ctgtctaatc tgaacttggg cggggaaaaa     60

tgttaatgac agagaccttc agggaaa                                         87
```

<210> SEQ ID NO 113
<211> LENGTH: 86
<212> TYPE: DNA

<213> ORGANISM: Solanum lycopersicum

<400> SEQUENCE: 113
tagcaacgta gcaaacgtgt tgctggattt ctgtctaatc tgaacttggg cggggaaaaa 60
tgttaatgac agagacctca gggaaa 86

<210> SEQ ID NO 114
<211> LENGTH: 88
<212> TYPE: DNA
<213> ORGANISM: Solanum lycopersicum

<400> SEQUENCE: 114
tagcaacgta gcaaacgtgt ttgctggatt tctgtctaat ctgaacttgg gcggggaaaa 60
atgttaatga cagagacctt cagggaaa 88

<210> SEQ ID NO 115
<211> LENGTH: 21
<212> TYPE: DNA
<213> ORGANISM: Solanum lycopersicum

<400> SEQUENCE: 115
agagcgaggt ctgatcaaac t 21

<210> SEQ ID NO 116
<211> LENGTH: 22
<212> TYPE: DNA
<213> ORGANISM: Solanum lycopersicum

<400> SEQUENCE: 116
agagcgagag tctgatcaaa ct 22

<210> SEQ ID NO 117
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 117
agagcgagtt tcaatt 16

<210> SEQ ID NO 118
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 118
agagcgagat ctgatcaaac ttttcaatt 29

<210> SEQ ID NO 119
<211> LENGTH: 16
<212> TYPE: DNA
<213> ORGANISM: Solanum lycopersicum

<400> SEQUENCE: 119
tgtttcagaa atgtct 16

<210> SEQ ID NO 120
<211> LENGTH: 16
<212> TYPE: DNA
<213> ORGANISM: Solanum lycopersicum

<400> SEQUENCE: 120
tgtttctgaa atgtct 16

<210> SEQ ID NO 121
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 121
tttgacttaa atgtctcaac gttc 24

<210> SEQ ID NO 122
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 122
tttgacttca acgttc 16

<210> SEQ ID NO 123
<211> LENGTH: 87
<212> TYPE: DNA
<213> ORGANISM: Solanum lycopersicum

<400> SEQUENCE: 123
ctccttcatc tgattactgt gcctggagag atggggagtt gtctcctgct attggacatc 60
tggccagata ccagatgaga ttggtga 87

<210> SEQ ID NO 124
<211> LENGTH: 88
<212> TYPE: DNA
<213> ORGANISM: Solanum lycopersicum

<400> SEQUENCE: 124
ctccttcatc tgattactgt gcctggagag atggggagtt gtctcctgct attggacatc 60
tggccagata ccagatgaag attggtga 88

<210> SEQ ID NO 125
<211> LENGTH: 83
<212> TYPE: DNA
<213> ORGANISM: Solanum lycopersicum

<400> SEQUENCE: 125
ctccttcatc tgattactgt gcctggagag atggggagtt gtctctattg gacatctggc 60
cagataccag atgagattgg tga 83

<210> SEQ ID NO 126
<211> LENGTH: 94
<212> TYPE: DNA
<213> ORGANISM: Solanum lycopersicum

<400> SEQUENCE: 126
gtggacccaa cccttgttaa tccttgcaca tggtttcacg ttacctgcaa caatgacaac 60
agtgttctgg tttgttagtt ccacagcttg gcct 94

<210> SEQ ID NO 127

<211> LENGTH: 32
<212> TYPE: DNA
<213> ORGANISM: Solanum lycopersicum

<400> SEQUENCE: 127
tgttctggtt tgttagttcc acagcttggc ct 32

<210> SEQ ID NO 128
<211> LENGTH: 78
<212> TYPE: DNA
<213> ORGANISM: Solanum lycopersicum

<400> SEQUENCE: 128
gtggtccttg cacatggttt cacgttacct gcaacaatga caacagtgtt ctggtttgtt 60
agttccacag cttggcct 78

<210> SEQ ID NO 129
<211> LENGTH: 74
<212> TYPE: DNA
<213> ORGANISM: Solanum lycopersicum

<400> SEQUENCE: 129
gtggacccaa ccgtttcacg ttacctgcaa caatgacaac agtgttctgg tttgttagtt 60
ccacagcttg gcct 74

<210> SEQ ID NO 130
<211> LENGTH: 21
<212> TYPE: DNA
<213> ORGANISM: Solanum lycopersicum

<400> SEQUENCE: 130
gtggacccaa ccgcttggcc t 21

<210> SEQ ID NO 131
<211> LENGTH: 91
<212> TYPE: DNA
<213> ORGANISM: Solanum lycopersicum

<400> SEQUENCE: 131
gtggacccaa cctgttaatc cttgcacatg gtttcacgtt acctgcaaca atgacaacag 60
tgttctggtt tgttagttcc acacttggcc t 91

<210> SEQ ID NO 132
<211> LENGTH: 58
<212> TYPE: DNA
<213> ORGANISM: Solanum lycopersicum

<400> SEQUENCE: 132
tgtccaagtg ttaagatgtc tgttgtttat ttccttcctc agtaacttct aaacctag 58

<210> SEQ ID NO 133
<211> LENGTH: 54
<212> TYPE: DNA
<213> ORGANISM: Solanum lycopersicum

<400> SEQUENCE: 133
tgtccaagtg ttaagatgtc tgttgtttat ttccttccta acttctaaac ctag 54

<210> SEQ ID NO 134
<211> LENGTH: 66
<212> TYPE: DNA
<213> ORGANISM: Solanum lycopersicum

<400> SEQUENCE: 134
ttgatgggga gttgtctcct gctattggac agctttctgg ccagatacca gatgagattg 60
gtgact 66

<210> SEQ ID NO 135
<211> LENGTH: 61
<212> TYPE: DNA
<213> ORGANISM: Solanum lycopersicum

<400> SEQUENCE: 135
ttgatgggga gttgtctcct gtattggaca gctttctggc cagataccag atttggtgac 60
t 61

<210> SEQ ID NO 136
<211> LENGTH: 57
<212> TYPE: DNA
<213> ORGANISM: Solanum lycopersicum

<400> SEQUENCE: 136
ttgatgggga gttgtcttat tggacagctt tctggccaga taccagattt ggtgact 57

<210> SEQ ID NO 137
<211> LENGTH: 66
<212> TYPE: DNA
<213> ORGANISM: Solanum lycopersicum

<400> SEQUENCE: 137
tctgtccaag tgttaagatg tctgttgttt atatctttcc ttcctcagta acttctaaac 60
ctaggg 66

<210> SEQ ID NO 138
<211> LENGTH: 67
<212> TYPE: DNA
<213> ORGANISM: Solanum lycopersicum

<400> SEQUENCE: 138
tctgtccaag tgttaagatg tctgttgttt atatctttcc ttccatcagt aacttctaaa 60
cctaggg 67

<210> SEQ ID NO 139
<211> LENGTH: 67
<212> TYPE: DNA
<213> ORGANISM: Solanum lycopersicum

<400> SEQUENCE: 139
tctgtccaag tgttaagatg tctgttgttt atatctttcc ttccatcagt aacttctaaa 60
cctaggg 67

<210> SEQ ID NO 140
<211> LENGTH: 66
<212> TYPE: DNA
<213> ORGANISM: Solanum lycopersicum

<400> SEQUENCE: 140
tgcctagaga tcctttaata gtttctggag ttgtttacaa caatagggtg gtctataatg 60
gatgtt 66

<210> SEQ ID NO 141

<211> LENGTH: 62
<212> TYPE: DNA
<213> ORGANISM: Solanum lycopersicum

<400> SEQUENCE: 141
tgcctagaga tcctttaata gtctggagtt gtttacaaca atagggtggt ctaatggatg 60
tt 62

<210> SEQ ID NO 142
<211> LENGTH: 62
<212> TYPE: DNA
<213> ORGANISM: Solanum lycopersicum

<400> SEQUENCE: 142
tgcctagaga tcctttaata gtctggagtt gtttacaaca atagggtggt ctaatggatg 60
tt 62

<210> SEQ ID NO 143
<211> LENGTH: 66
<212> TYPE: DNA
<213> ORGANISM: Solanum lycopersicum

<400> SEQUENCE: 143
ttgatgggga gttgtctcct gctattggac agctttctgg ccagatacca gatgagattg 60
gtgact 66

<210> SEQ ID NO 144
<211> LENGTH: 61
<212> TYPE: DNA
<213> ORGANISM: Solanum lycopersicum

<400> SEQUENCE: 144
ttgatgggga gttgtcttat tggacagctt tctggccaga taccagatga gattggtgac 60
t 61

<210> SEQ ID NO 145
<211> LENGTH: 61
<212> TYPE: DNA
<213> ORGANISM: Solanum lycopersicum

<400> SEQUENCE: 145
ttgatgggga gttgtcttat tggacagctt tctggccaga taccagatga gattggtgac 60
t 61

<210> SEQ ID NO 146
<211> LENGTH: 60
<212> TYPE: DNA
<213> ORGANISM: Solanum lycopersicum

<400> SEQUENCE: 146
ttgatgggga gttgtctatt ggacagcttt ctggccagat accagatgag attggtgact 60

<210> SEQ ID NO 147
<211> LENGTH: 4672
<212> TYPE: DNA
<213> ORGANISM: Solanum lycopersicum

<400> SEQUENCE: 147
ttttcgagtt gacatagtac cttcgcagtt gaagaagaag aaattgatta agaagataaa 60
ttcgacattg gaacttgata attaagaaga aatcaatgaa aaagagatat aatataatga 120

```
ggtaaagaaa ataaataatg atgaagagaa acaaaagagg agaaataatg gaagaatggg    180
agaaattagg gttaaaaggg ggaagaagat cgttggtggg tggttcaaga tccacatgtg    240
cgcttttaaa gagtttgcac gcgcttaaag gacgtgagat cacgtttggc tccacatcag    300
ccaagaatat ttaaaaggat caaattatag gggttaaag gatttaatag gaatcttggt     360
tagttaaggt atctggggga aaagcgcgaa caactttagg gacctgcata tgtatttggc    420
caagaaaaaa taaacaaata atgagagaaa gagtgaatat atataaacaa tggtatagtc    480
cctctatttg aactttttgg tcaaaattca tagtggcatt acaattgcac aatatgactt    540
tgggtgcttt gactacgctc catgttagtt tcttctttgc cataatgttt cttagtaaag    600
aatcaaataa ttatagaatc gcctttagtg tgataatcac tattcctttt gtaccaattt    660
aagtatgttt ttttttaaa ttagtatatg taccgggagt tttgatatat aatattattt     720
tttaatctaa aattattttg gacatttgat aattttgaat tctctaacaa gtttgatata    780
taaaattttg accgataact ttatattttg taaaaaaaaa atccatcatt atgtatgaca    840
tttgttttta caagaatatc aaaggaatga tgaaatattt atggaatatg aacatgatat    900
ataattacta atgatattga ttatgttcga ctttttaaa gaaaagttca ttgtttataa     960
tcacggttca atttatcttt ttattgaact aaagttttat caataaatgt tatcctagtc   1020
tgagtaggca tttgaccata tgatagcata ttaccagagg tggatctagt atttgaaggt   1080
cctgagtgtc acattgtcca aataagataa gttggtcagt tgctttaatt ttgatttaca   1140
atcgaatcat ttatcttttt tcgatcttta taaacaaatc gatcaaacat gcatgttagt   1200
aatttttctt ttagatatca tgagattagg gcttagtaac catttaattt ttatttattg   1260
ttaggaatta gtagccttat tcgctgaaac tttgaggaaa aaaaattgac actaaaattt   1320
gagcttgtat aaactatcaa atagtgttaa ctcaatatat tcatattcta ttgagttgtt   1380
gcaaaataca acaaaagaga atacaaattt tagttcattt agtcatctta cttaacaaga   1440
atattggtga agatcgaaga accttcaaat taaaagaatt ctaataataa tatttatcat   1500
ttttaaattt atgtttttta aatttactat tgaaatatag tcttaataat atttatgtca   1560
tgttcataat ttaattgata aagtataaac acgtgacact catatcaaaa gattaataat   1620
tagtaaaaaa agaaagtaga agaacttaaa aattaattat agtgaatagg aatcaatttg   1680
aattaacaaa aaatacttgt aaataaataa gaatgaatgg aaggggaaaa taactcacac   1740
attttaaaaa aagaaaagaa aagaaaaagc ttccaaaaat taatgctgca aatgaggttc   1800
gaattggtgt tgtctgtgtg gtagattaac tattttgcca attgaactat taaccatttt   1860
attcaaagag tggaaaagaa aatatatact cattttctta aacatgtata ctatatatac   1920
aaagtttaga gatcagtggg tgccgtgaca ttaccacata aattcataaa tccgcccctg   1980
catattacga tatagtatca tgagatggaa tcagcgtttg gacgtgcaat tttacattga   2040
ttcgatctta tgattctata tcatgagata tgattgcata ttctccataa accatgatat   2100
gaaatcatat gggaatacca cttcatgatt tgagttactt taatacaaaa attgatccac   2160
gagtttatat tttgttaaca taaccccgca tttatatcta ctaacaattt atttcacatg   2220
taaataaaat ttataatcac atcattactt tttaaattta ttattctcac agacataaag   2280
tttattatta ttctcaccaa cctatagtca ctttaacact cacacgtcaa gattgttgta   2340
gttaaatctt gaagagcccg tgaaaggtgt ttcattttta ctcaaatata ttgatgaaat   2400
aattacttaa gtggagaaca aataacttta taataattta tcatatgatt ttacagtttt   2460
```

```
tttttatttg ataaatttga ataaacaatt gaggttattt taatagtttt agaacttatg   2520
agatttttat gtttatgaga aaatatacat taccaaaatt tcatatcgca tgtccaaaca   2580
aaacatcaat tttagtatga ttccatatca taataccata tcgaatgacc aaacggaccg   2640
ttagaataac tttataatag ttattatact ttcattatga atttttgctt atttagtaag   2700
attgtatgaa taaagttagg acaatatttg gtgagatttt gatttatgag ctaacaatag   2760
aatttcaaaa tcataatttc tatatggcta agcaaaactt caatttcatg ttaaacgaat   2820
gaaaagtaag taggcgtttg gtcatgtgat atcatatcac gatatgaaat cgtgagaagg   2880
aatcagcgtt tgaacatgcg attatacatt gattctatat catgagatgt aattccatat   2940
tcttcaaaaa ccatgatatg gaaatttcat atcatgattt gatatatttt taatacaaaa   3000
attgatccac atatttgtat tttgttaaaa caacccatat ttatatctac taaccattta   3060
tttcatttgt aaataaaatt tataatcaga tcattacttt caaaatttat tattctcacg   3120
acataaaatt tatttttctt accaacatat aattacttta actcacacca atcgattgtt   3180
gagttaataa atttgttctc ttcatttatt tcaacaccta atttattatt ttttaccgtt   3240
ttatatttat tacaacttaa aagtaacaat attggttctt cttctcaatc acatgatcga   3300
gaaatacaag ttcaacatga ggaaatgtcc agacgatgtg agaagattat attaaaaatt   3360
agtacattat aatttatgtt caattttttt attgaactaa agttagatga aacagttacc   3420
gtagtggaaa acaagtaact ttgtgataat ttaaatgcga tcttatgatt tttttttattt   3480
gataagactg aataaaaaat tgagattatg ttaatagttt tacaatttat gagattcata   3540
tacaaaacaa tttttttat catatatcta aataaaattt taattttata ttatgatttc   3600
atattataat atcatatcaa caaactagct attaaatttt ataaatgata aattatagcc   3660
aaaacactta aattaaaact gagagaagta gcatttttac cttaaatgat gataggacag   3720
ttgctagcta aatatgaaga aaagaaacaa atgtgtaggt aaaaccctcc catcattact   3780
tgtgataata tcctatggct tcataaatca tataacactg atcgagacaa acaacgcatt   3840
accccactga aaaggttgaa accccatttc tcgtgagtac ataactgcac atgttgggta   3900
gtgaagagta gtcattgtca aacatttttt gggtaagcca tcgacgtttt gtatttatat   3960
taaaatctga ttaaatttga agctgattta tatttagaat gaaacttcag cttaaaaata   4020
agaaaatagt ttatgatttc attagaatta aggcgtagtc actgtcaaac ttgagaaagg   4080
attacccctt taagctttgc ccttgtttgc agagacagtg acttgtgatg aaatgaagcc   4140
agagaaggca ctctgttatc acacttaaat gataatacat gtgtatggac tagcaataaa   4200
agtggcacta gtaattgaaa agcaagtgta tagagagaga taatgagaga gaaagagtaa   4260
gtacactact actgctacta tcccatatac ctgtaatgtt gcaggtctga attttgcagt   4320
tgcagacccc cttctcttgg cacaagctct tttaactttt atcttctcaa ataattctct   4380
ctctctctct tttctatcat ttttttttac attgagagta aacttaatat ccgttgtatg   4440
tattagtgtg aggcctatct gccacaagga tgtgatggaa cactatgctt cctctgctaa   4500
aaccccacaa ccccaaaact ctctttcact tcacatttaa gcacaattcc tcagtaaaat   4560
tatccttttg atctctctaa catcaatgtt ggttagttca agaattggtt tttccatttc   4620
aaaggagctg agttagtgag gttttgagtt ttgactgaga cttgagtcta cc           4672
```

<210> SEQ ID NO 148
<211> LENGTH: 4060
<212> TYPE: DNA
<213> ORGANISM: Solanum lycopersicum

<400> SEQUENCE: 148
aataagacaa agagaattgc gatatgggga taatttttct agttagatta gagataaaag 60
gggatcgaat ttagatttga aagcagatat gattattaga taattttaat aattagttag 120
ggattaatta agaataaaat aaagttagca aaagaaaagt taattaattt aaaaaataaa 180
aaaaatataa aattataatt tctaacgtgg tgctgatgtg acactgatgt agcagtaagt 240
gtaatacatc acatacatgt gatggcggta ttacatgtct caaggtgata ttaaattcac 300
tttaactaat aaaagtatgt tgttataaaa tcatcataat aattaaaacg tgtaattaat 360
tattcgatat aatttttttaa gaggaaattt atgtcttttc actaaaaaaa aaacaaaaaa 420
aatcaaatat tgtgaatcag gctgtccact aaaataggta tttattttat agccacatta 480
aacctcaaga ggatatcttt caaattcttt atggcctaaa aaataataat ttttttttcc 540
tgcaaaccgt ttaattcata ggtttccaaa gggagaaaag aaaaatagaa ttaagaaaaa 600
aaaaactagc aatattcttt ctttcactca tctttacatc tcacaatcgg atcgcatagc 660
cgttactctt taggtatgca tcggataatt ttgctcttat ccattaactt gtaaaataca 720
ttagattata gaatatgttt agttggacca gctactcgat aggaagtcga cttaaaattc 780
attattatta caacaaaagc aattctaatg gtaatatatc atgcgcatca acaaagaaca 840
ctagatcctt tatcaacgtt agttaattgt tattagatct aatgttgcta taaactttag 900
cgacatttac aaaaaatgtt aattgtctct aaaaaaatat atttaactat aattagctat 960
tatcgccaaa aaattcctta atttacagta taacacacca gctcctggtg taccacccaa 1020
aatccaccta catataaata aactacactt aaaataagaa attaacaacc gacaaaattt 1080
tgcgataaaa gttcaaataa tttaaaattt atataattat atatattagc tagagattat 1140
cgataaattt catagctgat tattaccaat cactttccat gtccccacac ttgtagtaac 1200
cctaccccca ctcttactga actttgatca ctatgaggag aaagaaaagg aatgttgttt 1260
tgtgtggaga ggctatcaaa tgcttctgat attattgatt ctctctagac acaatttgaa 1320
cacaaagaaa cttgtgaaaa tggacaaaag agctaatatt ctttatttcc tcatatgtac 1380
atcttaatta aaaaaaagtc acatatatct tttttttttg ccattaggaa tatcaattaa 1440
tattatatag aattgtagtt gttcgacgta aaaataagag agacagaaat tttatcaagg 1500
agtgttatga agtaaaaaaa taaataagaa gcgacacaca aagaaatcgg gaagtataca 1560
tatatcgtat atatacataa atttagtatc gtgacctagt taaataacgt aattttctga 1620
tgaaaaggtg tcaagaatat caattaatat catatagatt tgttgttatt cgacataaaa 1680
taagagagat ataaatttta tcaaagagtg tcataaaata aaaaaataag aagagacaca 1740
caaagaattg agaagtatac atatagtata gatacataaa tttaatatcg tgacctaatt 1800
aaataatata attttctggt gaaaagtcgt caagacatcc cttaccataa ggtggctcga 1860
ccactcgtcc aaattagtct tctttttgga gaggccgtag atgtaagctg aagaagaatt 1920
tgggatgatg gttacataag atgttatata ttttcaactt atcgaggaca taacctagat 1980
aaaaagatag aaaaatcgaa gattaaaata atagagtagt agataaatat taccttactt 2040
ttacatggga gagactgggt gctagactcc tcttctccta attttgtata atatctttat 2100
cttctattta cataattagt tgttgcttta tttactttgt ttattttgct attttattgt 2160
tattttaatt tcttttgcgc tcatgcttta atttttattt cttttaagct aaggatctat 2220
tgaaaaaaaa catcttcatt tcacaaagac aaaagtattg ttcgtgtaca ttctattctc 2280
ctagatctcc tgtcataagg ttcattgatt tgttattatt tttgtaaatt cagtataaat 2340
acaaattcta atctctcatc gaagacgagt caataatttc tgtaggtcaa cggattgtat 2400
gtaaaatata accgacttca attttttttt taatttttca aataaaattt ctaatttcgc 2460
tactaaataa tataaagagc ggcgggcctc tctagaggtg cattccttct tataattttt 2520
tcaccttcat tattattaat taaaagtccc aataaacaaa ggaaaaagtt ctatcacttt 2580
tttacaattg gaaaaaagag attcttttaa ggaatgtgtg gtgacaaata agcatcctat 2640
tttcttctgt tactaaagcc tctaaaaaaa taaaaaataa aaatatatat acttaaactc 2700
acaagtttag ggcaattttg atgcatcttt attttgttta tcaaactcta tatatagtca 2760
ttcataaaaa tgatagtacg acacataaat cactccatat tttattatat tgtaattatg 2820
attcgagaaa ggatttaatt tctcaaaata taatataaat agactatcgt aatataaata 2880
ttagtactat ctaatgaagt acgatttgat gaagtgtaaa gttaacttac atatgaccta 2940
gagaaaccac ttaagtagca atgaataatc caagatatat atatacttaa actcacaagt 3000
tacatttttg acgtatcttt attttgttta ttaaactcta tatatagtca ttcataaaaa 3060 tgataaatatg acgcataaat cattccatat tttattaaat tataattaag atttgaaaaa 3120
agaatttact tcttcaaaat ataatctaaa tagtctatcg taatataaat attaatgtta 3180
tctagtgaag tatgatttaa tgaagtgtaa agttaactta catatgacct agagaaatca 3240
cttaagtagc gatgaataat ccaagaatat gtttggtcct ttattctttc ttgtcatggc 3300
tcatgtatcc atgcacttta ttataacaat tcgagaagtg ttataattat ggtgattctc 3360
ttatttaaaa ttttttcgaa ctattaataa agtaaatgaa taataataat aataatatga 3420
attaggaaaa tatttatgta tataattttt atgtcaaaat tacttgattc tccactttac 3480
agctcaacaa ttaacatata tggtttcccc ttaaagaaaa acttcaaaaa gattcctatg 3540
atggtaaaga aacgtttggc cataaaaatt aaatattttt caattttcaa atcgaaattt 3600
ttttgatcac tatggatctg atataaacag tctccctatt acgaaaaagt aagagtaagg 3660
tctgcataca tcttatcctc tttaaacctc acagtttgaa gatgcgactt tgtttgatta 3720
tactttttcc aaaggagaga attaagagat tatatttgga attacgcaga caaaatttga 3780
aagacatctt ataagtttga aatccaatta caagtggaat ttaaaatttt cacgacttgt 3840
caaccattga ttctcaaata aagtgaaaaa ttattccaaa aacaaataaa tattttttttt 3900 atgaccaaat atgtcctcaa gaacatatga aagctctcta gtcatgagta taaataacaa 3960
gggctagcta gctcttgtct actcataaaa tatcatccat ccatctcatg taataaacaa 4020
aaattgagct tattaattat aattgagaag aaaaaaaatc 4060

<210> SEQ ID NO 149
<211> LENGTH: 4080
<212> TYPE: DNA
<213> ORGANISM: Solanum lycopersicum

<400> SEQUENCE: 149
gatgattgtt cttttgatta tgattactca tgtgattcat ccttttatga tatcaatcct 60
gatatacatg tttgtcctac ttcacctcat cttggatctg attcatattc tgatgcacat 120
atgatgccta cttcagtaga agttgcttca gtagaggttc ctattatacc ttctactgat 180
agttcctata atcctccaag aaggtctcaa agagtgtcct ctagacctct ctggatgaca 240
gattatgtga ctgcaccatc tgggaattct gtacaatatc ccatacaaga ctatatgtcc 300
tatataggct tgtcagcttc acactatagt tttttgagca tgctgaacac tgtggttgaa 360

-continued

```
ccatctactt atcaacaggc ttcacaagac cctcgttgga tagatgctat gaatgctgag    420
atacaagcct tgcaggataa tcatacttgg gactctttac ctcaagggaa acatcctata    480
ggttgtaaat gggtatataa agttaaactt caggccaatg gtgacataga aaggtttaag    540
gctcgtcttg tggcaaaagg gtataatcaa acggaaggtc ttgattacaa tgagactttt    600
tctccagttg tcaaaattgc tactgcgaga actgtattat ctatagctgc tcaacatgac    660
tggcatattc atcaacttga tgtctataat gcatttcttc aaggggatct tcatgatgaa    720
gtatatatgc agttgccaca aggttttcca agtcaggggg agtctatagt ttgtagactt    780
gttaaatcct tgtatgggct caagcaagca agtagacaat ggaatgtaaa gttaacagaa    840
gccttgctgc attctcaatt tcaacagagc aaattggatc attcattgtt tataaaaaga    900
gaaggtaaaa gcactgtgat catccttatt tatgtggatg atatgttggt aacagggaat    960
gatttggagt tgattagaag gaccaaggaa gaattacaca aagcattcaa gatcaaagat   1020
ttaggaaatt tgaaatattt tcttggtatg gagtttagca ggtaaaagaa aggaatatta   1080
atcaatcaaa gaaaatacgc attagagata atctcagaaa caggactagg gggagctaaa   1140
cctgcatgga caccattaga aataaatgag aagttgacag caattgagtt agacaagctt   1200
actggaaagg aagatgatga catgttagaa gatgtaggat agtatcaaag agtcattgga   1260
agattattgt acttgacttt aacaagacct gatatagcat tctcagtaca aactcttagt   1320
caatttttac agcagccaaa gaaatctcat tgggatgcag caatgaggat aatcagatat   1380
gtcaagagac agccaggcct tggaattttg atgagtagtt aataaatcta atactatggt   1440
agtatactgt gattcagatt gggcatcatg tccaaataca agaaggtcgg tatcaggttt   1500
tttggtcaag tatggagatt cattgatttc ttggaagtca aagaaacaaa ccactgtgtc   1560
taggagttca gcagaggctg aatacagaag tatgggaagt gcagtagctg agatagtatg   1620
gttgacaact ctaatgaaag aattggaggc tggaattgag atacctgtta aagtttacag   1680
tgacagcaaa gctgcattgc aaattgctgc aaaccctgtg tttcacgaga gaacaaagca   1740
cattgaaatt gattgccatt ttattaggca gaaaattcaa gaggggttag taaagactga   1800
acatgtggga actaaggatc aaacagcaga catattgaca aaagggcttc caagagtaca   1860
acatgaacat ttagttggca agctgggaat gcttaacatt tttgcacctg ccagcttgag   1920
ggggagtgat gaaataggaa taggttgaag taaatataat tagtgagtta gttagtcttt   1980
tatcaagtta gttagaaatt agttattagc atcttaactt gcacatgata ggtagttaga   2040
tataattagt cacattataa atatgctgta acaaaccaat attgtaattc aattttctgc   2100
aatatacaat acacagtttt ctcaatgatt ttttcttctt cttcatcttc tccatcttct   2160
attctcttca tcttcataga tttagttaca gattttcaat aattcaacaa ccatcaccat   2220
actcacaatt actaccacct ccaccatcac tatcaaccac tacaatcctt gcgatcaatc   2280
tctactacaa accaatgaac cattttcatt atcataacta gcacagctac tatcatcaac   2340
acatcatcaa ttaccatata tattcttcac ccatcgctgt taatatcact aactattaat   2400
atcaatcaac ttcaccagga caatcaccat caccactatt aaatgtcatc atcacaccag   2460
tcattacaaa actaacagtc tccaacatta ccagtaatca ctaacaacaa ccattattac   2520
aaacaatctc tacttattta cttttattca aatatttatt tagacaaaac tgattttagt   2580
aaaacaaatg agatcaatct ttttctcgtg attaattttt aagttggaat tagttccaaa   2640
atacatttaa tatagacaaa tatgatactc ccaccgtccc attttatgta aaaaaacacg   2700
```

tctcattttc ttatatggta agtatttaaa ggtataattt ctctttttta cctttattga 2760
tcttaatttt ctaatacatt tatgagaaga gagaaaaatg agttactttt ttaaagaacg 2820
atttgataaa tattttaaaa tcttcattat ttcttaaatt ttgtgccaga tcaaatgttg 2880
tcacataaaa tgagacggaa aaagtaaaac atatcaaaca cacccttaat ttaaaatagt 2940
gtaggtacta cctaaaagtg gaagttaatt atttgtttcc ccaaaattaa attttaccct 3000
tggacagcaa ttcctgttta agggttaatt gtatagggac atacattttc ttctaatagt 3060
ccagggtagt ttggttttcg atatgtggaa aattatctcg acataaaatg ctacagtaac 3120
taattagtac aatatttagt ttgtatttac cattacattt agctccacat tcacataaat 3180
tggtagtaca acatttaatc ttctaatttg tactataaca ttttcattaa taaaaagtat 3240
ggtttctatc ttcaccatta gcgtaacgtt cgagtagaga tatacatatt tattattata 3300
atatacgatt gcaaatgcca aagatggcta attttgtttt gagagactac tgcattaagt 3360 aaatttttc agagacatgt ataagattaa gtctattgcc aattctcaaa tattactctt 3420
ttttacttat tgtggttatt tatacatatt aagtgaactt tcttttaaga caaaaatgtg 3480
aaagaaatga atttcaaatt tgattcaatt ccataaaata gctcaaatcg gaggaggaat 3540
taatattcaa gtcttataag gaaattattc atcgatcatg attattttc catgttaaat 3600 tgattaaatc tttttcatt cttcaacata tctaatcttc taccctacaa caagctctca 3660
cctttcatag tatttatata gactatatat tcgtataaaa tatttttctt catatcgaac 3720
acacatgatc tttttaggat agagggagta ttttttaaaa aaaaaataat ggggcaaacg 3780
caaataaaat agaacacata tatattcttt ctctagctgc taattaagct atgactttat 3840
aattttgtag cacgagaaga gaataacctt tttgtgcttt tcatttcttt aatttggttc 3900
cccatttttt gaactatcaa tattttagtc cctatcccat ctgactctct aatgatctta 3960
gggccactat aaatattggt attttgctct tcttttctcc accaaaaaac aactacaact 4020
ctttaagtag attttgtttt gtttcttata attaattaat aattaactct aaatatatat 4080

<210> SEQ ID NO 150
<211> LENGTH: 99
<212> TYPE: DNA
<213> ORGANISM: Solanum lycopersicum

<400> SEQUENCE: 150
ttgatgtgga cccaaccctt gttaatcctt gcacatggtt tcacgttacc tgcaacaatg 60
acaacagtgt tctggtttgt tagttccaca gcttggcct 99

<210> SEQ ID NO 151
<211> LENGTH: 32
<212> TYPE: DNA
<213> ORGANISM: Solanum lycopersicum

<400> SEQUENCE: 151
tgttctggtt tgttagttcc acagcttggc ct 32

<210> SEQ ID NO 152
<211> LENGTH: 83
<212> TYPE: DNA
<213> ORGANISM: Solanum lycopersicum

<400> SEQUENCE: 152
ttgatgtggt ccttgcacat ggtttcacgt tacctgcaac aatgacaaca gtgttctggt 60
ttgttagttc cacagcttgg cct 83

-continued

```
<210> SEQ ID NO 153
<211> LENGTH: 79
<212> TYPE: DNA
<213> ORGANISM: Solanum lycopersicum

<400> SEQUENCE: 153

ttgatgtgga cccaaccgtt tcacgttacc tgcaacaatg acaacagtgt tctggtttgt     60

tagttccaca gcttggcct                                                  79


<210> SEQ ID NO 154
<211> LENGTH: 26
<212> TYPE: DNA
<213> ORGANISM: Solanum lycopersicum

<400> SEQUENCE: 154

ttgatgtgga cccaaccgct tggcct                                          26


<210> SEQ ID NO 155
<211> LENGTH: 97
<212> TYPE: DNA
<213> ORGANISM: Solanum lycopersicum

<400> SEQUENCE: 155

ttgatgtgga cccaaacccg ttaatccttg cacatggttt cacgttacct gcaacaatga     60

caacagtgtt ctggtttgtt agttccacac ttggcct                              97
```

GENE MUTATIONS IN TOMATO TO YIELD COMPACT AND EARLY YIELDING FORMS SUITABLE FOR URBAN AGRICULTURE

RELATED APPLICATIONS

This application is a national stage filing under 35 U.S.C. § 371 of International Application No. PCT/US2020/061613, filed Nov. 20, 2020, entitled "GENE MUTATIONS IN TOMATO TO YIELD COMPACT AND EARLY YIELDING FORMS SUITABLE FOR URBAN AGRICULTURE", which claims the benefit of the filing date under 35 U.S.C. § 119(e) of each of the following: U.S. Provisional Application Ser. No. 62/940,873, filed Nov. 26, 2019, entitled "GENE MUTATIONS IN TOMATO TO YIELD COMPACT AND EARLY YIELDING FORMS SUITABLE FOR URBAN AGRICULTURE"; U.S. Provisional Application Ser. No. 62/948,167, filed Dec. 13, 2019, entitled "GENE MUTATIONS IN TOMATO TO YIELD COMPACT AND EARLY YIELDING FORMS SUITABLE FOR URBAN AGRICULTURE"; and U.S. Provisional Application Ser. No. 62/952,096, filed Dec. 20, 2019, entitled "GENE MUTATIONS IN TOMATO TO YIELD COMPACT AND EARLY YIELDING FORMS SUITABLE FOR URBAN AGRICULTURE." The entire contents of each of the referenced applications are herein incorporated by reference in their entireties.

GOVERNMENT SUPPORT

This invention was made with government support under Grant No. IOS-1546837 awarded by the National Science Foundation Plant Genome Research Program. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on May 16, 2022, is named C130070036US03-SEQ-DQB and is 476,723 bytes in size.

BACKGROUND

A significant challenge for the future of agriculture is the loss of arable land, driven by population growth, diminishing water resources, and climate change. Part of the solution will require increasing yield in the staple crops that feed humans and their livestock, such as corn, rice, soybean, and wheat, which are bred for high productivity in large-scale field conditions. A complementary approach that can promote sustainable agriculture is to grow more food in urban environments (Benke, et al. *Sustain Sci Pract Policy* (2017) 13:13-26; Pearson, et al. *Int J Agric Sustain* (2010) 8:7-19). For example, although initial infrastructure costs can be high, rooftop farms and climate-controlled automated vertical farming systems optimize land use and are designed to be more environmentally friendly and sustainable than traditional farming (Benke, et al., *Sustain Sci Pract Policy* (2017) 13:13-26; Martellozzo, et al. *Environ Res Lett* (2014) 9:064025; and Banerjee, et al., *J Agric Stud* (2014) 2:40-60). However, the benefits of urban agriculture and its expansion are limited by the few crops that can be cultivated under highly restrictive growth parameters.

SUMMARY

A modern revolution in agriculture is emerging that allows cultivation in urban environments to provide local low input food production (Benke, et al. *Sustain Sci Pract Policy* (2017) 13:13-26; Pearson, et al. Int JAgric Sustain (2010) 8:7-19; Martellozzo, et al. *Environ Res Lett* (2014) 9:064025; and Banerjee, et al., *J Agric Stud* (2014) 2:40-60). However, space restrictions and the need for rapid crop cycling have limited these systems to lettuce and related "leafy green" vegetables (Touliatos, et al. *Food Energy Secur* (2016) 5:184-191). Fruit crops are highly desired, but developing new varieties whose architectures and productivities are optimized for these specific growth parameters is challenging (Benke, et al. *Sustain Sci Pract Policy* (2017) 13:13-26; Touliatos, et al. *Food Energy Secur* (2016) 5:184-191). Crop varieties that are both compact and rapid cycling are needed to optimize efficiency and productivity, and for these reasons, urban agriculture is currently dominated by lettuce and related leafy green vegetables (Benke, et al. *Sustain Sci Pract Policy* (2017) 13:13-26; Touliatos, et al. *Food Energy Secur* (2016) 5:184-191).

The present disclosure relates to novel genetic plant variants and methods for generating novel genetic variants of plants having traits, such as compact architecture and early-yield. In some embodiments, a novel genetic plant variant has one or more mutations that result in one or more traits (e.g., rapid flowering, precocious growth termination, condensed shoots, etc.) useful for fruit production in less favorable conditions, such as in an urban setting. In some embodiments, mutation(s) in one or more of the genes of a novel genetic plant variant can be used to generate weak allele variants for customizing plant compactness, where a more subtle phenotypic change (e.g., stem length and/or pedicel length) is beneficial.

According to some aspects, genetically-altered Solanaceae plants disclosed are contemplated. In some embodiments, the genetically altered Solanaceae plant comprises a mutant sler (Solyc08g061560) gene or a homolog thereof, a mutant sp5g (SolycO5gO53850) gene or a homolog thereof, and a mutant sp (SolycO6gO74350) gene or a homolog thereof.

In some embodiments, the genetically-altered Solanaceae plant comprises a mutant sler (Solyc08g061560) gene or a homolog thereof and a mutant sp (SolycO6gO74350) gene or a homolog thereof.

In some embodiments, the genetically-altered Solanaceae plant comprises a mutant sler (Solyc08gf061560) gene or a homolog thereof and a mutant sp5g (SolycO5gO53850) gene or a homolog thereof.

In some embodiments, the genetically-altered Solanaceae plant further comprises a mutant slerl1 (Solyc03g007050) gene or a homolog thereof, or a mutant slserk] (Solyc04gO72570) gene or a homolog thereof.

In some embodiments, the mutant sler (Solyc08gf061560) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant sler (Solyc08gt061560) gene or a homolog thereof is a null allele or a hypomorphic allele.

In some embodiments, the mutant sp5g (SolycO5gO53850) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant sp (SolycO6gO74350) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant slerl1 (Solyc03g007050) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant slserk1 (Solyc04g072570) gene or the homolog thereof comprises a missense mutation, a frameshift mutation, a nonsense mutation, a mutation resulting in an early stop codon, a splicing error mutation, an insertion, a deletion or a duplication.

In some embodiments, the genetically-altered Solanaceae plant is heterozygous or homozygous for the mutant sler (Solyc08g061560) gene or a homolog thereof.

In some embodiments, the genetically-altered plant is heterozygous or homozygous for the mutant slerl1 (Solyc03g007050) gene or a homolog thereof. In some embodiments, the mutant slerl1 (Solyc03g007050) gene or homolog thereof is a null allele or a hypomorphic allele.

In some embodiments, the genetically-altered Solanaceae plant is heterozygous or homozygous for the mutant sp5g (Solyc05g053850) gene or a homolog thereof. In some embodiments, the mutant sp5g (Solyc05g053850) gene or homolog thereof is a null allele or a hypomorphic allele.

In some embodiments, the genetically-altered Solanaceae plant is heterozygous or homozygous for the mutant sp (Solyc06g074350) gene or a homolog thereof. In some embodiments, the mutant sp (Solyc06g074350) gene or homolog thereof is a null allele or a hypomorphic allele.

In some embodiments, the genetically-altered plant is heterozygous or homozygous for the mutant slserk1 (Solyc04g072570) gene. In some embodiments, the mutant slserk1 (Solyc04g072570) gene or homolog thereof is a null allele or a hypomorphic allele.

In some embodiments, the genetically-altered Solanaceae plant is homozygous for the mutant sp5g (Solyc05g053850) gene or a homolog thereof and is a null allele or a hypomorphic allele, and homozygous for the mutant sp (Solyc06g074350) gene or a homolog thereof and is a null allele or a hypomorphic allele.

In some embodiments, the genetically-altered Solanaceae plant is homozygous for the mutant sp5g (Solyc05g053850) gene or a homolog thereof and homozygous for the mutant sp (Solyc06g074350) gene or a homolog thereof, and wherein each is a null allele.

In some embodiments, the genetically-altered Solanaceae plant is homozygous for the mutant sp5g (Solyc05g053850) gene or a homolog thereof and homozygous for the mutant sp (Solyc06g074350) gene or a homolog thereof, and wherein each is a hypomorphic allele.

In some embodiments, the Solanaceae plant is a tomato (*Solanum lycopersicum*) plant.

In some embodiments, one or more of the mutant sler (Solyc08g061560) gene or a homolog thereof, the mutant slerl1 (Solyc03g007050) gene or a homolog thereof, the mutant sp5g (Solyc05g053850) gene or a homolog thereof, the mutant sp (Solyc06g074350) gene or a homolog thereof, and the mutant slserk1 (Solyc04g072570) gene or a homolog thereof is introduced by chemical or physical means.

In some embodiments, one or more of the mutant sler (Solyc08g061560) gene or a homolog thereof, the mutant slerl1 (Solyc03g007050) gene or a homolog thereof, the mutant sp5g (Solyc05g053850) gene or a homolog thereof, the mutant sp (Solyc06g074350) gene or a homolog thereof, or the mutant slserk1 (Solyc04g072570) gene or a homolog thereof is introduced using CRISPR/Cas9, chemical mutagenesis, radiation, *Agrobacterium*-mediated recombination, viral-vector mediated recombination, or transposon mutagenesis.

In some embodiments, Solanaceae plants exclusively obtained by means of an essentially biological process are excluded.

In some embodiments, the mutant sler (Solyc08g061560) gene or a homolog thereof comprises a mutant coding sequence that encodes a mutant polypeptide with a mutation in a leucine-rich repeat (LRR) domain or comprises a mutation in a regulatory region of the sler (Solyc08g061560) gene or a homolog thereof.

In some embodiments, the mutation in the mutant sler (Solyc08g061560) gene or the homolog thereof is a CRISPR/Cas9-induced heritable allele.

According to some aspects, crops harvested from genetically-altered Solanaceae plants disclosed are contemplated. According to some aspects, seeds for producing a genetically-altered Solanaceae plants are contemplated.

According to some aspects, methods for producing genetically altered Solanaceae plants are contemplated.

In some embodiments, the method comprises introducing a mutation into a sler (Solyc08g061560) gene or a homolog thereof in a Solanaceae plant, introducing a mutation into a sp5g (Solyc05g053850) gene or a homolog thereof in a Solanaceae plant, and introducing a mutation into a sp (Solyc06g074350) gene or a homolog thereof in a Solanaceae plant, thereby producing a genetically-altered Solanaceae plant containing a mutant sler (Solyc08g061560) gene or homolog thereof, a mutant sp5g (Solyc05g053850) gene or a homolog thereof, and a mutant sp (Solyc06g074350) gene or a homolog thereof.

In some embodiments, the method comprises introducing a mutation into a sler (Solyc08g061560) gene or a homolog thereof in a Solanaceae plant, and introducing a mutation into a sp (Solyc06g074350) gene or a homolog thereof in a Solanaceae plant, thereby producing a genetically-altered Solanaceae plant containing a mutant sler (Solyc08g061560) gene or homolog thereof and a mutant sp (Solyc06g074350) gene or a homolog thereof.

In some embodiments, the method comprises introducing a mutation into a sler (Solyc08g061560) gene or a homolog thereof in a Solanaceae plant, and introducing a mutation into a sp5g (Solyc05g053850) gene or a homolog thereof in a Solanaceae plant, thereby producing a genetically-altered Solanaceae plant containing a mutant sler (Solyc08g061560) gene or a homolog thereof and a mutant sp5g (Solyc05g053850) gene or a homolog thereof.

In some embodiments, the mutation is introduced using any gene editing nuclease(s) (e.g., CRISPR/Cas9) or ethyl methanesulfonate (EMS). In some embodiments, the mutation produces a null allele or a hypomorphic allele of the sler (Solyc08g061560) gene or a homolog thereof.

In some embodiments, the method further comprises introducing into the Solanaceae plant a mutation into a slerl1 (Solyc03g007050) gene or a homolog thereof, or introducing into the Solanaceae plant a mutation into a slserk1 (Solyc04g072570) gene or a homolog thereof, thereby producing a genetically-altered Solanaceae plant further containing a mutant slerl1 (Solyc03g007050) gene or a homolog thereof and a mutant slserk1 (Solyc04g072570) gene or a homolog thereof.

In some embodiments, the mutation(s) is/are introduced using CRISPR/Cas9 or EMS.

In some embodiments, the genetically-altered Solanaceae plant containing the mutant sler (Solyc08g061560) gene or a homolog thereof, containing a mutant sp5g (Solyc05g053850) gene or a homolog thereof, and a mutant sp (Solyc06g074350) gene or a homolog thereof is crossed with another genetically-altered Solanaceae plant comprising a mutant slerl1 (Solyc03g007050) gene or a homolog thereof, a mutant slserk1 (Solyc04g072570) gene or a homolog thereof, or both a mutant slerl1 (Solyc03g007050) gene or a homolog thereof and a mutant slserk1 (Solyc04g072570) gene or a homolog thereof.

In some embodiments, the genetically-altered Solanaceae plant containing a mutant sler (Solyc08g061560) gene or homolog thereof and a mutant sp (Solyc06g074350) gene or a homolog thereof is crossed with another genetically-altered Solanaceae plant comprising a mutant slerl1 (Solyc03g007050) gene or a homolog thereof, a mutant slserk1 (Solyc04g072570) gene or a homolog thereof, or both a mutant slerl1 (Solyc03g007050) gene or a homolog thereof and a mutant slserk1 (Solyc04g072570) gene or a homolog thereof.

In some embodiments, the genetically-altered Solanaceae plant containing the mutant sler (Solyc08g061560) gene or a homolog thereof and a mutant sp5g (Solyc05g053850) gene or a homolog thereof is crossed with another genetically-altered Solanaceae plant comprising a mutant slerl1 (Solyc03g007050) gene or a homolog thereof, a mutant slserk1 (Solyc04g072570) gene or a homolog thereof, or both a mutant slerl1 (Solyc03g007050) gene or a homolog thereof and a mutant slserk1 (Solyc04g072570) gene or a homolog thereof.

In some embodiments, the genetically-altered Solanaceae plant is a tomato (*Solanum lycopersicum*) plant.

In some embodiments, the genetically-altered Solanaceae plant is produced or obtainable by a method disclosed.

According to some aspects, methods of reducing stem length between leaves and flowers (internodes) in a Solanaceae plant are disclosed.

In some embodiments, the method comprises producing a genetically-altered Solanaceae plant, genetically-altered Solanaceae seed or genetically-altered Solanaceae plant part comprising a mutant sler (Solyc08g061560) gene or a homolog thereof in a mutant sp5g (Solyc05g053850) gene or a homolog thereof and a mutant sp (Solyc06g074350) gene or a homolog thereof background and maintaining the genetically-altered Solanaceae plant, genetically-altered Solanaceae seed or genetically-altered Solanaceae plant part under conditions under which the genetically-altered Solanaceae plant, the genetically-altered Solanaceae seed or the genetically-altered Solanaceae plant part grows.

In some embodiments, the method comprises producing a genetically-altered Solanaceae plant, genetically-altered Solanaceae seed or genetically-altered Solanaceae plant part comprising a mutant sler (Solyc08g061560) gene or a homolog thereof in a mutant sp (Solyc06g074350) gene or a homolog thereof background and maintaining the genetically-altered Solanaceae plant, genetically-altered Solanaceae seed or genetically-altered Solanaceae plant part under conditions under which the genetically-altered Solanaceae plant, the genetically-altered Solanaceae seed or the genetically-altered Solanaceae plant part grows.

In some embodiments, the method comprises producing a genetically-altered Solanaceae plant, genetically-altered Solanaceae seed or genetically-altered Solanaceae plant part comprising a mutant sler (Solyc08g061560) gene or a homolog thereof in a mutant sp5g (Solyc05g053850) gene or a homolog thereof background and maintaining the genetically-altered Solanaceae plant, genetically-altered Solanaceae seed or genetically-altered Solanaceae plant part under conditions under which the genetically-altered Solanaceae plant, the genetically-altered Solanaceae seed or the genetically-altered Solanaceae plant part grows.

In some embodiments, the genetically-altered Solanaceae plant is a tomato (*Solanum lycopersicum*) plant.

According to some aspects, genetically-altered tomato plants are contemplated.

In some embodiments, the genetically-altered tomato plant comprises a mutant sler (Solyc08g061560) gene or a homolog thereof, wherein the mutant sler (Solyc08g061560) gene comprises a mutation in a noncoding region of the sler (Solyc08g061560) gene and a mutant sp (Solyc06g074350) gene or a homolog thereof.

In some embodiments, the genetically-altered tomato plant further comprises a mutant sp5g (Solyc05g053850) gene or a homolog thereof.

In some embodiments, the genetically-altered tomato plant further comprising a mutant slerl1 (Solyc03g007050) gene or a homolog thereof, or a mutant slserk1 (Solyc04g072570) gene or a homolog thereof.

In some embodiments, the mutant sler (Solyc08g061560) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant sler (Solyc08g061560) gene or a homolog thereof is a null allele or a hypomorphic allele.

In some embodiments, the mutant sp5g (Solyc05g053850) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant sp (Solyc06g074350) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant slerl1 (Solyc03g007050) gene or the homolog thereof comprises a missense mutation, a frameshift mutation, a nonsense mutation, a mutation resulting in an early stop codon, a splicing error mutation, an insertion, a deletion or a duplication.

In some embodiments, the mutant slserk1 (Solyc04g072570) gene or the homolog thereof comprises a missense mutation, a frameshift mutation, a nonsense mutation, a mutation resulting in an early stop codon, a splicing error mutation, an insertion, a deletion or a duplication.

In some embodiments, the genetically-altered tomato plant is heterozygous or homozygous for the mutant sler (Solyc08g061560) gene or a homolog thereof.

In some embodiments, the genetically-altered plant is heterozygous or homozygous for the mutant slerl1 (Solyc03g007050) gene or a homolog thereof.

In some embodiments, the mutant slerl1 (Solyc03g007050) gene or homolog thereof is a null allele or a hypomorphic allele.

In some embodiments, the genetically-altered tomato plant is heterozygous or homozygous for the mutant sp5g (Solyc05g053850) gene or a homolog thereof. In some embodiments, the mutant sp5g (Solyc05g053850) gene or homolog thereof is a null allele or a hypomorphic allele.

In some embodiments, the genetically-altered tomato plant is heterozygous or homozygous for the mutant sp (Solyc06g074350) gene or a homolog thereof. In some embodiments, the mutant sp (Solyc06g074350) gene or homolog thereof is a null allele or a hypomorphic allele.

In some embodiments, the genetically-altered plant is heterozygous or homozygous for the mutant slserk1 (Solyc04g072570) gene. In some embodiments, the mutant slserk1 (Solyc04g072570) gene or homolog thereof is a null allele or a hypomorphic allele.

In some embodiments, the genetically-altered tomato plant is homozygous for the mutant sp5g (Solyc05g053850) gene or a homolog thereof and is a null allele or a hypomorphic allele, and homozygous for the mutant sp (Solyc06g074350) gene or a homolog thereof and is a null allele or a hypomorphic allele.

In some embodiments, the genetically-altered tomato plant is homozygous for the mutant sp5g (Solyc05g053850) gene or a homolog thereof and homozygous for the mutant sp (Solyc06g074350) gene or a homolog thereof, and wherein each is a null allele.

In some embodiments, the genetically-altered tomato plant is homozygous for the mutant sp5g (Solyc05g053850) gene or a homolog thereof and homozygous for the mutant sp (Solyc06g074350) gene or a homolog thereof, and wherein each is a hypomorphic allele.

In some embodiments, one or more of the mutant sler (Solyc08g061560) gene or a homolog thereof, the mutant slerl1 (Solyc03g007050) gene or a homolog thereof, the mutant sp5g (Solyc05g053850) gene or a homolog thereof, the mutant sp (Solyc06g074350) gene or a homolog thereof, and the mutant slserk1 (Solyc04g072570) gene or a homolog thereof is introduced by chemical or physical means.

In some embodiments, one or more of the mutant sler (Solyc08g061560) gene or a homolog thereof, the mutant slerl1 (Solyc03g007050) gene or a homolog thereof, the mutant sp5g (Solyc05g053850) gene or a homolog thereof, the mutant sp (Solyc06g074350) gene or a homolog thereof, or the mutant slserk1 (Solyc04g072570) gene or a homolog thereof is introduced using a gene editing nuclease system (e.g., CRISPR/Cas9, prime editing, etc.), chemical mutagenesis, radiation, *Agrobacterium*-mediated recombination, viral-vector mediated recombination, or transposon mutagenesis.

In some embodiments, plants (e.g., tomato) plants exclusively obtained by means of an essentially biological process are excluded.

In some embodiments, the mutant sler (Solyc08g061560) gene or a homolog thereof comprises a mutation in a regulatory region of the sler (Solyc08g061560) gene or a homolog thereof.

In some embodiments, the mutation in the mutant sler (Solyc08g061560) gene or the homolog thereof is a CRISPR/Cas9-induced heritable allele.

According to some aspects, crops harvested from genetically-altered tomato plants disclosed are contemplated.

According to some aspects, seeds for producing a genetically-altered tomato plants disclosed are contemplated.

According to some aspects, methods for producing a genetically altered tomato plant are contemplated.

In some embodiments, the method comprises introducing a mutation into a sler (Solyc08g061560) gene or a homolog thereof in a tomato plant, and introducing a mutation into a sp (Solyc06g074350) gene or a homolog thereof in a tomato plant, thereby producing a genetically-altered tomato plant containing a mutant sler (Solyc08g061560) gene or homolog thereof, and a mutant sp (Solyc06g074350) gene or a homolog thereof.

In some embodiments, the method further comprises introducing a mutation into a sp5g (Solyc05g053850) gene or a homolog thereof in a tomato plant, thereby producing a genetically-altered tomato plant further containing a mutant sp5g (Solyc05g053850) gene or a homolog thereof.

In some embodiments, the mutation is introduced using CRISPR/Cas9 or ethyl methanesulfonate (EMS).

In some embodiments, the mutation produces a null allele or a hypomorphic allele of the sler (Solyc08g061560) gene or a homolog thereof.

In some embodiments, the method further comprises introducing into the tomato plant a mutation into a slerl1 (Solyc03g007050) gene or a homolog thereof, or introducing into the tomato plant a mutation into a slserk1 (Solyc04g072570) gene or a homolog thereof, thereby producing a genetically-altered tomato plant further containing a mutant slerl1 (Solyc03g007050) gene or a homolog thereof and a mutant slserk1 (Solyc04g072570) gene or a homolog thereof.

In some embodiments, the mutation(s) is/are introduced using CRISPR/Cas9 or EMS.

In some embodiments, the genetically-altered tomato plant containing the mutant sler (Solyc08g061560) gene or a homolog thereof, containing a mutant sp5g (Solyc05g053850) gene or a homolog thereof, and a mutant sp (Solyc06g074350) gene or a homolog thereof is crossed with another genetically-altered tomato plant comprising a mutant slerl1 (Solyc03g007050) gene or a homolog thereof, a mutant slserk1 (Solyc04g072570) gene or a homolog thereof, or both a mutant slerl1 (Solyc03g007050) gene or a homolog thereof and a mutant slserk1 (Solyc04g072570) gene or a homolog thereof.

According to some aspects, a genetically-altered tomato plant is produced or obtainable by a method disclosed.

According to some aspects, methods of reducing stem length between leaves and flowers (internodes) in tomato plant are disclosed.

In some embodiments, the method comprises producing a genetically-altered tomato plant, genetically-altered tomato seed or genetically-altered tomato plant part comprising a mutant sler (Solyc08g061560) gene or a homolog thereof in a mutant sp (Solyc06g074350) gene or a homolog thereof background and maintaining the genetically-altered tomato plant, genetically-altered tomato seed or genetically-altered tomato plant part under conditions under which the genetically-altered tomato plant, the genetically-altered tomato seed or the genetically-altered tomato plant part grows.

In some embodiments, the method further comprises a mutant sp5g (Solyc05g053850) gene or a homolog thereof background and maintaining the genetically-altered tomato plant, genetically-altered tomato seed or genetically-altered tomato plant part under conditions under which the genetically-altered tomato plant, the genetically-altered tomato seed or the genetically-altered tomato plant part grows.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 1A shows shoots and inflorescences of WT and si mutants. Arrowheads indicate inflorescences. FIG. 1B shows quantification of shoot lengths in WT, si and si heterozygotes (si/+). Prim., primary shoot and Axil, basal axillary shoot (Length between $1^{st}$ inflorescence and $1^{st}$ leaf); Symp., sympodial shoot (Length between $1^{st}$ and $2^{nd}$ inflorescence); n, number of plants. FIG. 1C shows inflorescences and mature fruits. DP, distal section of $1^{st}$ pedicel; PP, proximal section of $1^{st}$ pedicel; INT, $1^{st}$ inflorescence internode; AZ, abscission zone. FIG. 1D shows quantification of inflorescence stem sections. n, number of inflorescences. FIG. 1E shows the tomato *ERECTA* gene (SlER) and various ethyl methanesulfonate (EMS) and CRISPR-Cas9 generated alleles. The plants resulting from the EMS and CRISPR-Cas9 generated alleles have identical phenotypes. FIG. 1F shows normalized expression (RPKM) for SlER and its paralog SlER-like 1 (SlERL1) in meristems and major tissues. Sym. inflo., sympodial inflorescence; Sym. shoot; sympodial shoot. FIG. 1G shows the SlERL1 gene and CRISPR-Cas9 generated mutations. Guide RNA and protospacer-adjacent motif (PAM) sequences are light gray and bold underlined, respectively. Dash and dark gray letter indicate deletion and insertion. Numbers in parentheses indicate gap lengths (SEQ ID NOs: 112-114 from Top to Bottom). FIG. 1H shows shoots and inflorescences of slerl1 mutants compared to WT and sler. Arrowheads indicate inflorescences. FIG. 11 shows quantification of WT and slerl1 inflorescence stem sections. n, number of inflorescences. FIG. 1J shows sler slerl1 double mutants. DAT, days after transplanting in FIG. 1A, FIG. 1H, and FIG. 1J. Box plots, $25^{th}$-$75^{th}$ percentile; center line, median; whiskers, full data range in FIG. 1B, FIG. 1D, and FIG. 11. P values (two-tailed, two-sample t-test) in FIG. 1B, FIG. 1D, and FIG. 11.

FIG. 2A shows a trait stacking strategy that combines mutations that cause precocious growth termination, rapid flowering, and shorter stems to create "triple-determinate" tomato varieties. FIG. 2B shows a comparison of double (sp sp5g) and triple (sp sp5g sler) determinate tomato genotypes. Basal axillary shoots of sp sp5g and sp sp5g sler. Arrowheads indicate inflorescences. FIG. 2C shows mature plants and fruits (left) and associated shoots and inflorescences (right) from field-grown plants of double and triple determinate genotypes. Leaves were removed to expose fruits. Arrowheads indicate inflorescences. FIG. 2D shows quantification of primary shoot height (length between first leaf and last inflorescence of primary shoot) and a field-based productivity trial comparing all three determinate genotypes. Harvest index, total yield/plant weight. n, number of plants, or inflorescences (for flower number). Box plots, $25^{th}$-$75^{th}$ percentile; center line, median; whiskers, full data range. P values (two-tailed, two-sample t-test).

FIG. 3A shows shoots and inflorescences comparing double and triple determinate cultivars of cherry tomato variety Sweet100. Arrowheads indicate inflorescences. FIG. 3B shows quantification of shoot lengths and inflorescence stem sections, as in FIG. 1. n, number of plants and inflorescences. FIG. 3C shows field-grown plants of Sweet100 sp determinate, sp sp5g double-determinate and sp sp5g sler triple-determinate plants at 50 days after transplanting. Both the double-determinate and triple-determinate plants show ripe fruits, but not determinate plants. FIG. 3D shows days after transplanting to first ripe fruit, primary shoot height and total yield in all three genotypes. FIG. 3E shows Sweet100 triple-determinate plants producing ripe fruits in an LED growth chamber at 68 days after sowing (DAS). FIG. 3F shows more than 1000 Sweet100 triple-determinate plants cultivated in a hydroponic vertical farm system. The triple-determinate plants produced open flowers 50 DAS. n, number of plants. Box plots, $25^{th}$-$75^{th}$ percentile; center line, median; whiskers, full data range in FIG. 3B and FIG. 3D. the numbers represent P values (two-tailed, two-sample t-test) in FIG. 3B and FIG. 3D.

FIGS. 5A-5L show mapping of the short internode (si) mutant and characterization of multiple loss-of-function alleles in the causative gene SlERECTA (SlER). FIGS. 5A-5B show length of shoot internodes, distal and proximal section of flower pedicels, peduncles and inflorescence internodes in WT, si and si/+ heterozygotes. $5^{th}$, internode between $5^{th}$ and $6^{th}$ leaf of primary shoot; $6^{th}$, internode between $6^{th}$ and $7^{th}$ leaf; $7^{th}$, internode between $7^{th}$ and $8^{th}$ leaf. n, number of plants and inflorescences. Box plots, $25^{th}$-$75^{th}$ percentile; center line, median; whiskers, full data range. The numbers indicate P values (two-tailed, two-sample t-test). FIG. 5C shows mapping-by-sequencing of the si mutant generated by EMS mutagenesis. Differences in SNP index between pools of si and WT individuals derived from a segregating $F_2$ population are shown. Dotted lines indicate 95% cut-off in SNP index. SlER is located on chromosome 8. FIG. 5D shows genomic DNA and transcript sequences of $sler^{EMS\text{-}1}$ (Sequences corresponding to SEQ ID NOs: 115-118 are shown, from Top to Bottom). FIG. 5E shows genomic DNA and transcript sequences of $sler^{EMS\text{-}2}$ (Sequences corresponding to SEQ ID NOs: 119-122 are shown, from Top to Bottom). FIG. 5F shows RT-PCR analysis showing an 11bp insertion in the transcript from of $sler^{EMS\text{-}1}$. FIG. 5G shows RT-PCR analysis showing a 72 bp deletion in the transcript of $sler^{EMS\text{-}2}$. FIG. 5H shows SlER protein models of WT, $sler^{EMS\text{-}1}$ and $sler^{EMS\text{-}2}$. FIG. 5I shows schematic showing targeting of SlER by CRISPR-Cas9 (Sequences corresponding to SEQ ID NOs: 123-125 are shown, from Top to Bottom). FIG. 5J shows complementation test between $sler^{EMS\text{-}1}$ and the CRISPR-generated null allele $sler^{CR\text{-}1}$. FIG. 5K shows complementation test between $sler^{CR\text{-}1}$ and $sler^{EMS\text{-}2}$. FIG. 5L shows complementation test between $sler^{EMS\text{-}1}$ and $sler^{EMS\text{-}2}$.

FIG. 6A shows a shoot of MicroTom and $sler^{MT}$. DAS, days after sowing. FIG. 6B shows quantification of shoot and internode lengths in MicroTom, $sler^{MT}$ and $sler^{MT}$/+ heterozygotes. Prim., primary (Length between $1^{st}$ inflorescence and $1^{st}$ leaf of primary shoot); Axil., basal axillary (Length between $1^{st}$ inflorescence and $1^{st}$ leaf of basal axillary shoot); Symp., sympodial (Length between $1^{st}$ and $2^{nd}$ inflorescence of primary shoot). $3^{rd}$, internode between $3^{rd}$ and $4^{th}$ leaf of primary shoot; $4^{th}$, internode between $4^{th}$ leaf and $5^{th}$ leaf of primary shoot. n, number of plants. FIG. 6C shows inflorescences of WT and $sler^{MT}$. FIG. 6D shows length of flower pedicels, peduncles and inflorescence internodes in MicroTom, $sler^{MT}$ and $sler^{MT}$/+ heterozygotes. n, number of inflorescences. Box plots, $25^{th}$-$75^{th}$ percentile; center line, median; whiskers, full data range in FIG. 6B and FIG. 6D. The numbers represent P values (two-tailed, two-sample t-test) in FIG. 6B and FIG. 6D.

FIG. 7A shows three independent alleles of slserk1 (previously designated spd2) obtained from EMS mutagenesis. Two of the alleles (slserk1$^{S1}$ and slserk1$^{S2}$) were missense mutations in the kinase domain and showed identical strong pleiotropic phenotypes. The third allele showed a weaker phenotype and was caused by a missense mutation outside of the kinase domain (slserk1$^{W}$). FIG. 7B shows sequential stages of growth for slserk1$^{S1}$ plants. FIG. 7C shows normalized RNA-seq expression (RPKM) for SlSERK1 in meristems and major tissues. Sym. inflo., sympodial inflorescence; Sym. shoot; sympodial shoot. FIG. 7D shows seedling stage and flowering plant of sler slserk1$^{S1}$sdouble mutants. FIG. 7E shows inflorescence of slserk1$^{W}$. FIG. 7F shows PCR analysis of first-generation ($T_0$) CRISPR-Cas9 transgenic plants targeting SlSERK1. FIG. 7G shows shoot and inflorescence of slserk1$^{CR}$ To plants. FIG. 7H shows sequences of slserk1$^{CR}$ alleles identified from two To plants 5 and 7. sgRNA and PAM sequences are represented by light gray and bold underlined font, respectively. Dashes and the numbers in parentheses indicate deletions and sequence gap lengths, respectively (Sequences corresponding to SEQ ID NOs: 150-155 are shown, from Top to Bottom). FIG. 7I shows lengths of shoots, shoot internodes, distal and proximal section of pedicels, peduncles and inflorescence internodes in WT plants and slerl1 homozygous mutants. Prim., primary (Length between 1$^{st}$ inflorescence and 1$^{st}$ leaf of the primary shoot); Symp., sympodial (Length between 1$^{st}$ and 2$^{nd}$ inflorescence of primary shoot). n, number of plants and inflorescences. Box plots, 25$^{th}$-75$^{th}$ percentile; center line, median; whiskers, full data range. The numbers indicate P values (two-tailed, two-sample t-test). FIG. 7J shows early seedling stage of WT, sler and sler slerl1 from plants 16 days after sowing (DAS). FIG. 7K shows plants of WT, sler and sler slerl1 41 DAS. DAT, days after transplanting in FIG. 7B, FIG. 7D, and FIG. 7G.

FIG. 8A shows the sequence of a CRISPR-generated null mutation in self pruning (sp$^{CR}$). Light gray and bold underlined font indicate guide RNA and PAM sequences, respectively. Deletions and sequence gap lengths are indicated by dashes and the numbers in parentheses, respectively (Sequences corresponding to SEQ ID NOs: 132-133 are shown, from Top to Bottom). FIG. 8B shows representative field-grown mature plants of sp$^{CR}$ and sp$^{CR}$ sler$^{CR\text{-}1}$. Leaves were removed to show fruit set. DAT, days after transplanting. FIG. 8C shows a productivity trial of sp$^{CR}$ and sp$^{CR}$ sler$^{CR\text{-}1}$. FIG. 8D shows quantification of leaves to first inflorescence, inflorescence numbers for both primary and basal axillary shoots, and flower number per inflorescence in single-, double- and triple-determinate plants. Box plots, 25$^{th}$-75$^{th}$ percentile; center line, median; whiskers, full data range. The numbers above bars indicate P values (two-tailed, two-sample t-test). n, number of plants. Harvest index, total yield/plant weight.

FIG. 9A shows the sequences of two sler$^{CR}$ alleles of Sweet100. sgRNA and PAM sequences are indicated by light gray and bold underlined font, respectively. The numbers in parentheses and dashes and indicate sequence gap lengths and deletions, respectively (Sequences corresponding to SEQ ID NOs: 134-136 are shown, from Top to Bottom). FIG. 9B shows quantification of shoot internode, inflorescence stem sections and peduncle lengths in Sweet100 sp sp5g double mutant and sp sp5g sler triple mutant genotypes. 4$^{th}$, internode between 4$^{th}$ and 5$^{th}$ leaf of primary shoot; 5$^{th}$, internode between 5$^{th}$ and 6$^{th}$ leaf of primary shoot. DP, distal section of 2$^{nd}$ pedicel; PP, proximal section of 2$^{nd}$ pedicel; INT, 2$^{nd}$ inflorescence internode. FIG. 9C shows quantification of a primary shoot, leaves to first inflorescence, flower number per inflorescence, inflorescence per shoot and sugar content (brix) in Sweet100 sp determinate, sp sp5g double-determinate and sp sp5g sler triple-determinate plants. FIG. 9D shows mature fruits of all three genotypes. FIG. 9E shows quantification of fruit size, fruit height to width ratio, and fruit weight in all three genotypes. n, number of plants, inflorescence and fruits in FIGS. 9B, FIG. 9C, and FIG. 9E. Box plots, 25$^{th}$-75$^{th}$ percentile; center line, median; whiskers, full data range in FIG. 9B, FIG. 9C, and FIG. 9E. The numbers above bars indicate P values (two-tailed, two-sample t-test) in FIG. 9B, FIG. 9C, and FIG. 9E.

FIG. 10A shows representative field-grown plants of Sweet100 single-, double- and triple-determinate plants. DAT, days after transplanting. FIG. 10B shows data on yield components for individual plants. Plant weight, harvest index and percentage of red fruits at harvesting. n, number of plants. FIG. 10C shows yield trial in blocks (eight plants) of Sweet100 single-, double- and triple-determinate plants. Fruit drop per total yield, weight of fruit drop/total yield of a block. n, number of blocks. Box plots, 25$^{th}$-75$^{th}$ percentile; center line, median; whiskers, full data range. Numbers above bars represent P values (two-tailed, two-sample t-test). Harvest index, total yield/plant weight. Red fruits per total yield, red fruit weight/total fruit weight. All data of yield components were obtained at 65 DAT.

FIGS. 11A-11C show selection for triple-determinate genotypes with different fruit traits from crossbred $F_2$ populations. FIG. 11A shows a selected triple-determinate plant with larger fruits derived from a cross between "cocktail" and Sweet100 sp sp5g sler triple-determinate varieties. FIG. 11B shows a selected triple-determinate plant with elongated (ovate) fruits derived from a cross between "grape" and Sweet100 sp sp5g sler triple-determinate varieties. FIG. 11C shows sequences of inherited mutated alleles of sp, sp5g and sler in "cocktail" and "grape" triple-determinate plants (Sequences corresponding to SEQ ID NOs: 137-145 are shown, from Top to Bottom).

FIG. 12A shows a concept for generating intermediates between double- and triple-determinate plants by quantitatively modifying shoot and inflorescence internode lengths. FIG. 12B shows PCR analysis of $T_0$ transgenic plants targeting promoter region of SlER by CRISPR-Cas9, following the approach of previous study[22]. FIG. 12C shows sequences of two SlER$^{CR\text{-}pro}$ promoter alleles and one sler$^{CR\text{-}3}$ coding sequence in-frame allele from $T_2$ plants. Arrows, dark gray and light gray squares indicate guide RNAs, exons and 5' UTR, respectively. FIG. 12D shows representative field-grown plants of Sweet100 sp sp5g, sp sp5g SlER$^{CR\text{-}pro\text{-}4}$, sp sp5g sler$^{CR\text{-}3}$ and sp sp5g sler$^{CR\text{-}1}$ Leaves were removed to show fruits. DAT, days after transplanting. FIG. 12E shows primary shoot lengths (Length between 1$^{st}$ leaf and 1$^{st}$ inflorescence of the primary shoot) of Sweet100 sp sp5g, sp sp5g SlER$^{CR\text{-}pro\text{-}14}$, sp sp5g SlER$^{CR\text{-}pro\text{-}4}$, sp sp5g slerCR-$^{3}$ and sp sp5g sler$^{CR\text{-}1}$plants. n, number of plants. Data of Sweet100 sp sp5g and sp sp5g sler$^{CR\text{-}1}$ are from FIG. 3B. FIG. 12F shows representative first inflorescences of Sweet100 sp sp5g, sp sp5g SlER$^{CR\text{-}pro\text{-}4}$, sp sp5g sler$^{CR\text{-}3}$ and sp sp5g sler$^{CR\text{-}1}$ (left) and enlarged photo for of Sweet100 sp sp5g and sp sp5g SlER$^{CR\text{-}pro\text{-}4}$ (right) plants. DP3r, 3$^{rd}$ distal pedicel from distal region of the first inflorescence. DP4r, 4$^{th}$ distal pedicel from distal region of the first inflorescence. PP3r, 3$^{rd}$ proximal pedicel from distal region of the first inflorescence. PP4r, 4$^{th}$ proximal pedicel from distal region of the first inflorescence. INT2r, 2$^{nd}$ internode from distal region of the first inflorescence. INT3r, 3$^{rd}$ internode from distal region of the first inflorescence. FIG. 12G shows quantification of pedicels and inflorescence internodes from the proximal region of the first inflorescences in Sweet100 sp sp5g, sp sp5g SlER$^{CR\text{-}pro\text{-}14}$, sp sp5g SlER$^{CR\text{-}pro\text{-}4}$, sp sp5g slerCR-$^{3}$ and sp sp5g sler$^{CR\text{-}1}$ plants. FIG. 12H shows quantification of pedicels and inflorescence internodes from distal region of the first inflorescences in Sweet100 sp sp5g, sp sp5g SlER$^{CR\text{-}pro\text{-}14}$ and sp sp5g SlER$^{CRpro\text{-}4}$.n, number of inflorescences in FIG. 12G and FIG. 12H. Box plots, 25$^{th}$-75$^{th}$ percentile; center line, median; whiskers, full data range in FIG. 12E, FIG. 12G, and FIG. 12H. The letters indicate the significance groups at P<0.01 (One-way ANOVA and Tukey test) in FIG. 12E, FIG. 12G, and FIG. 12H.

SEQUENCES

Figure 1B:
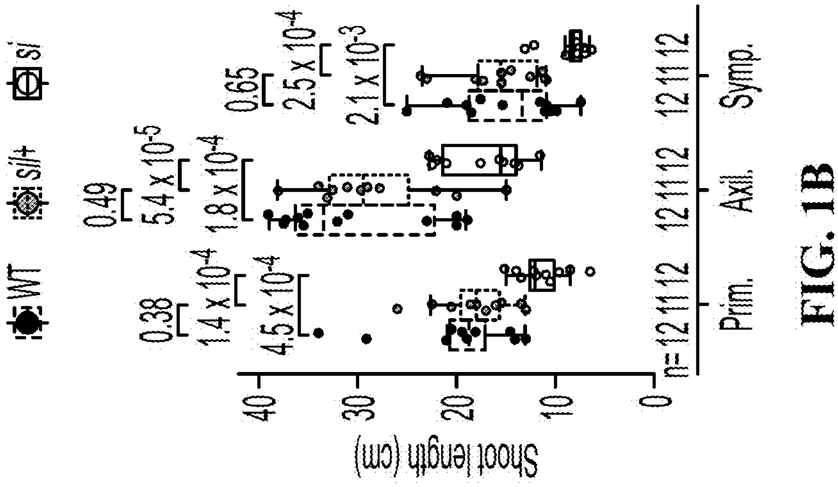
FIGS. 1A-1J show condensed shoots of the tomato short internode (si) mutant and identification of the underlying gene.
Figure 1A:
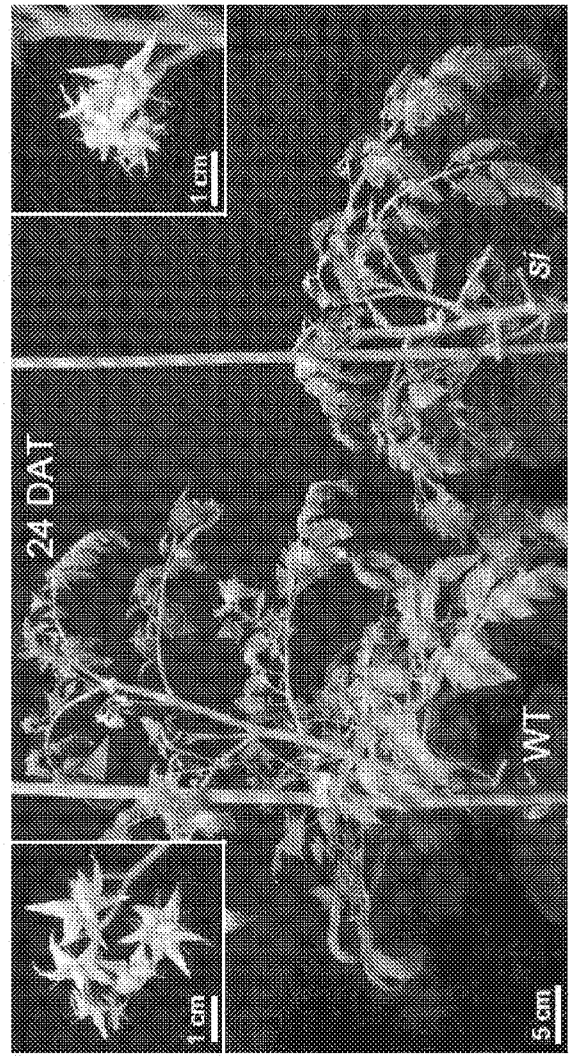
Figure 1D:
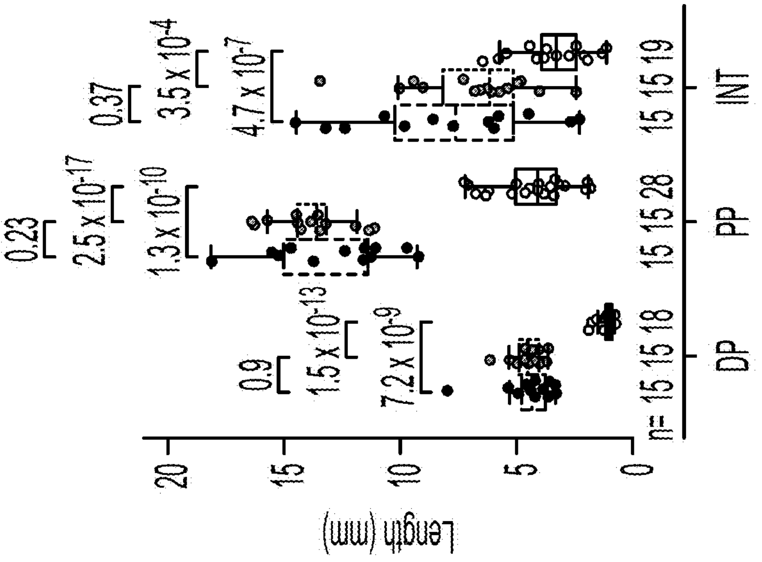
Figure 1C:
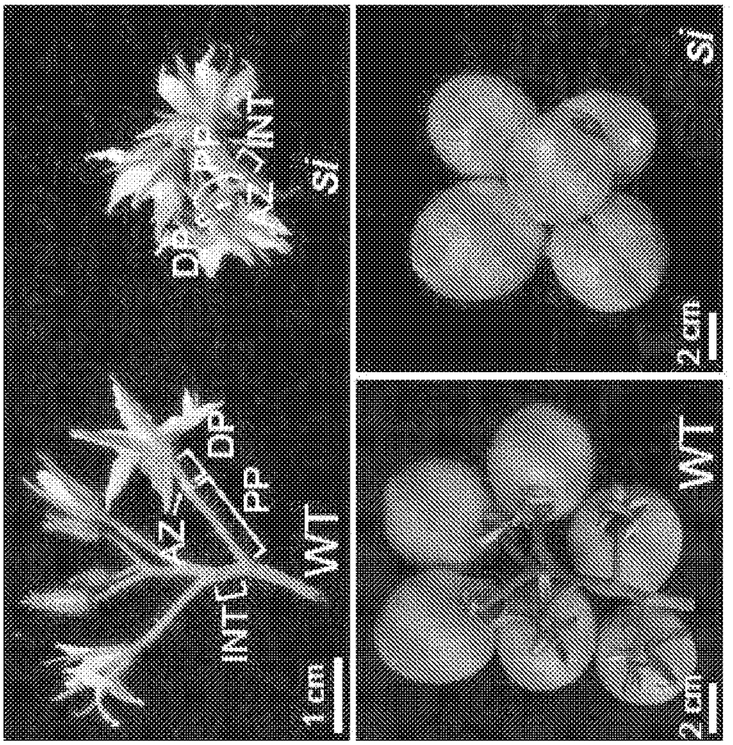
Figure 1E:
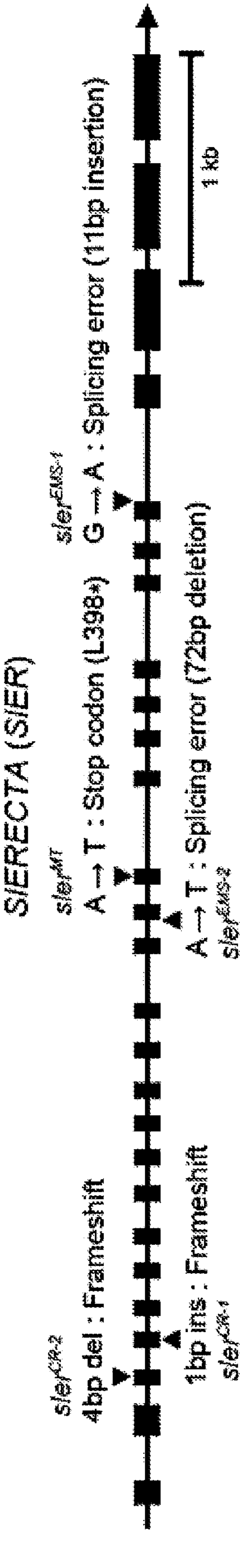

Below is a brief description of certain sequences disclosed:

SEQ ID NO: 1 is a nucleic acid sequence of a wild-type SlER gene encoded by a Solyc08g061560 gene.

SEQ ID NO: 2 is a nucleic acid sequence of a wild-type SlER gene encoded by a Solyc08g061560 coding sequence.

SEQ ID NO: 3 is an amino acid sequence of a polypeptide encoded by the wild-type SlER gene encoded by a Solyc08g061560 coding sequence.

SEQ ID NO: 4 is a nucleic acid sequence of a mutant Solyc08g061560 gene allele sler$^{EMS\text{-}1}$ (*S lycopersicum* cv. M82).

SEQ ID NO: 5 is a nucleic acid sequence of a mutant Solyc08g061560 gene allele sler$^{EMS\text{-}1}$ coding sequence (*S. lycopersicum* cv. M82).

SEQ ID NO: 6 is an amino acid sequence of a mutant polypeptide encoded by a mutant Solyc08g061560 gene allele sler$^{EMS\text{-}1}$ coding sequence (*S. lycopersicum* cv. M82).

SEQ ID NO: 7 is a nucleic acid sequence of a mutant Solyc08g061560 gene allele sler$^{EMS\text{-}2}$ (*S. lycopersicum* cv. M82).

SEQ ID NO: 8 is a nucleic acid sequence of a mutant Solyc08g061560 gene allele sler$^{EMS\text{-}2}$ coding sequence (*S. lycopersicum* cv. M82).

SEQ ID NO: 9 is an amino acid sequence of a mutant polypeptide encoded by a mutant Solyc08g061560 gene allele sler$^{EMS\text{-}2}$ coding sequence (*S. lycopersicum* cv. M82).

SEQ ID NO: 10 is a nucleic acid sequence of a mutant Solyc08g061560 gene allele sler$^{CR\text{-}1}$ (*S lycopersicum* cv. M82).

SEQ ID NO: 11 is a nucleic acid sequence of a mutant Solyc08g061560 gene allele sler$^{CR\text{-}1}$ coding sequence (*S. lycopersicum* cv. M82).

SEQ ID NO: 12 is an amino acid sequence of a mutant polypeptide encoded by a mutant Solyc08g061560 gene allele sler$^{CR\text{-}1}$ coding sequence (*S. lycopersicum* cv. M82).

SEQ ID NO: 13 is a nucleic acid sequence of a mutant Solyc08g061560 gene allele sler$^{CR\text{-}2}$ (*S. lycopersicum* cv. M82).

SEQ ID NO: 14 is a nucleic acid sequence of a mutant Solyc08g061560 gene allele sler$^{CR\text{-}2}$ coding sequence (*S. lycopersicum* cv. M82).

SEQ ID NO: 15 is an amino acid sequence of a mutant polypeptide encoded by a mutant Solyc08g061560 gene allele sler$^{CR\text{-}2}$ coding sequence (*S. lycopersicum* cv. M82).

SEQ ID NO: 16 is a nucleic acid sequence of a mutant Solyc08g061560 gene allele sler$^{MT}$.

SEQ ID NO: 17 is a nucleic acid sequence of a mutant Solyc08g061560 gene allele sler$^{MT}$ coding sequence.

SEQ ID NO: 18 is an amino acid sequence of a mutant polypeptide encoded by a mutant Solyc08g061560 gene allele sler$^{MT}$ coding sequence.

SEQ ID NO: 19 is a nucleic acid sequence of a mutant Solyc08g061560 gene allele sler-cocktail.

SEQ ID NO: 20 is a nucleic acid sequence of a mutant Solyc08g061560 gene allele sler-cocktail coding sequence.

SEQ ID NO: 21 is an amino acid sequence of a mutant polypeptide encoded by a mutant Solyc08g061560 gene allele sler-cocktail coding sequence.

SEQ ID NO: 22 is a nucleic acid sequence of a mutant Solyc08g061560 gene allele sler-grape.

SEQ ID NO: 23 is a nucleic acid sequence of a mutant Solyc08g061560 gene allele sler-grape coding sequence.

SEQ ID NO: 24 is an amino acid sequence of a mutant polypeptide encoded by a mutant Solyc08g061560 gene allele sler-grape coding sequence.

SEQ ID NO: 25 is a nucleic acid sequence of a mutant Solyc08g061560 promoter allele SlER$^{CR\text{-}pro\text{-}4}$ (*S. lycopersicum* cv. Sweet100).

SEQ ID NO: 26 is a nucleic acid sequence of a mutant Solyc08g061560 promoter allele SlER$^{CR\text{-}pro\text{-}4}$ coding sequence (*S. lycopersicum* cv. Sweet100).

SEQ ID NO: 27 is an amino acid sequence of a mutant polypeptide encoded by a mutant Solyc08g061560 promoter allele SlER$^{CR\text{-}pro\text{-}4}$ coding sequence (*S. lycopersicum* cv. Sweet100).

SEQ ID NO: 28 is a nucleic acid sequence of a mutant Solyc08g061560 promoter allele SlER$^{CR\text{-}pro\text{-}14}$ (*S. lycopersicum* cv. Sweet100).

SEQ ID NO: 29 is a nucleic acid sequence of a mutant Solyc08g061560 promoter allele SlER$^{CR\text{-}pro\text{-}14}$ coding sequence (*S. lycopersicum* cv. Sweet100).

SEQ ID NO: 30 is an amino acid sequence of a mutant polypeptide encoded by a mutant Solyc08g061560 promoter allele SlER$^{CR\text{-}pro\text{-}14}$ coding sequence (*S. lycopersicum* cv. Sweet100).

SEQ ID NO: 31 is a nucleic acid sequence of a *S. lycopersicum* cv. Sweet100 SlER gene.

SEQ ID NO: 32 is a nucleic acid sequence of a *S. lycopersicum* cv. Sweet100 SlER coding sequence.

SEQ ID NO: 33 is an amino acid sequence of a polypeptide encoded by a *S. lycopersicum* cv. Sweet100 SlER coding sequence.

SEQ ID NO: 34 is a nucleic acid sequence of a *S. lycopersicum* cv. Sweet100 gene allele sler$^{CR\text{-}1}$.

SEQ ID NO: 35 is a nucleic acid sequence of a *S. lycopersicum* cv. Sweet100 gene allele sler$^{CR-1}$ coding sequence.

SEQ ID NO: 36 is an amino acid sequence of a polypeptide encoded by a *S. lycopersicum* cv. Sweet100 gene allele sler$^{CR-1}$ coding sequence.

SEQ ID NO: 37 is a nucleic acid sequence of a *S. lycopersicum* cv. Sweet100 gene allele sler$^{CR-2}$.

SEQ ID NO: 38 is a nucleic acid sequence of a *S. lycopersicum* cv. Sweet100 gene allele sler$^{CR-2}$ coding sequence.

SEQ ID NO: 39 is an amino acid sequence of a polypeptide encoded by a *S. lycopersicum* cv. Sweet100 gene allele sler$^{CR-2}$ coding sequence.

SEQ ID NO: 40 is a nucleic acid sequence of a *S. lycopersicum* cv. Sweet100 gene allele sler$^{CR-3}$.

SEQ ID NO: 41 is a nucleic acid sequence of a *S. lycopersicum* cv. Sweet100 gene allele sler$^{CR-3}$ coding sequence.

SEQ ID NO: 42 is an amino acid sequence of a polypeptide encoded by a *S. lycopersicum* cv. Sweet100 gene allele sler$^{CR-3}$ coding sequence.

SEQ ID NO: 43 is a nucleic acid sequence of a wild-type SlERL1 gene encoded by a Solyc03g007050 gene.

SEQ ID NO: 44 is a nucleic acid sequence of a wild-type SlERL1 gene encoded by a Solyc03g007050 coding sequence.

SEQ ID NO: 45 is an amino acid sequence of a polypeptide encoded by a wild-type SlERL1 gene encoded by a Solyc03g007050 coding sequence.

SEQ ID NO: 46 is a nucleic acid sequence of a mutant Solyc03g007050 gene allele slerl1$^{CR-1}$ SEQ ID NO: 47 is a nucleic acid sequence of a mutant Solyc03g007050 gene allele slerl1$^{CR-1}$ coding sequence.

SEQ ID NO: 48 is an amino acid sequence of a mutant polypeptide encoded by a mutant Solyc03g007050 gene allele slerl1$^{CR-1}$ coding sequence.

SEQ ID NO: 49 is a nucleic acid sequence of a mutant Solyc03g007050 gene allele slerl1$^{CR-2}$.

SEQ ID NO: 50 is a nucleic acid sequence of a mutant Solyc03g007050 gene allele slerl1$^{CR-2}$ coding sequence.

SEQ ID NO: 51 is an amino acid sequence of a mutant polypeptide encoded by a mutant Solyc03g007050 gene allele slerl1$^{CR-2}$ coding sequence.

SEQ ID NO: 52 is a nucleic acid sequence of a wild-type SP5G gene encoded by a Solyc05g053850 gene.

SEQ ID NO: 53 is a nucleic acid sequence of a wild-type SP5G gene encoded by a Solyc05g053850 coding sequence.

SEQ ID NO: 54 is an amino acid sequence of a polypeptide encoded by a wild-type SP5G gene encoded by a Solyc05g053850 coding sequence.

SEQ ID NO: 55 is a nucleic acid sequence of a mutant Solyc05g053850 gene allele sp5g (M82

BACKGROUND

SEQ ID NO: 56 is a nucleic acid sequence of a mutant Solyc05g053850 gene allele sp5g coding sequence (M82 background).

SEQ ID NO: 57 is an amino acid sequence of a mutant polypeptide encoded by a mutant Solyc05g053850 gene allele sp5g coding sequence (M82 background).

SEQ ID NO: 58 is a nucleic acid sequence of a mutant Solyc05g053850 gene allele sp5g (Sweet100 background).

SEQ ID NO: 59 is a nucleic acid sequence of a mutant Solyc05g053850 gene allele sp5g coding sequence (Sweet100 background).

SEQ ID NO: 60 is an amino acid sequence of a mutant polypeptide encoded by a mutant Solyc05g053850 gene allele sp5g coding sequence (Sweet100 background).

SEQ ID NO: 61 is a nucleic acid sequence of a mutant Solyc05g053850 gene allele sp5g-cocktail.

SEQ ID NO: 62 is a nucleic acid sequence of a mutant Solyc05g053850 gene allele sp5g-cocktail coding sequence.

SEQ ID NO: 63 is an amino acid sequence of a mutant polypeptide encoded by a mutant Solyc05g053850 gene allele sp5g-cocktail coding sequence.

SEQ ID NO: 64 is a nucleic acid sequence of a mutant Solyc05g053850 gene allele sp5g-grape.

SEQ ID NO: 65 is a nucleic acid sequence of a mutant Solyc05g053850 gene allele sp5g-grape coding sequence.

SEQ ID NO: 66 is an amino acid sequence of a mutant polypeptide encoded by a mutant Solyc05g053850 gene allele sp5g-grape coding sequence.

SEQ ID NO: 67 is a nucleic acid sequence of a wild-type SP gene encoded by a Solyc06g074350 gene in tomato.

SEQ ID NO: 68 is a nucleic acid sequence of a wild-type SP gene encoded by a Solyc06g074350 coding sequence in tomato.

SEQ ID NO: 69 is an amino acid sequence of a polypeptide encoded by a wild-type SP gene encoded by a Solyc06g074350 coding sequence in tomato.

SEQ ID NO: 70 is a nucleic acid sequence of a mutant Solyc06g074350 gene allele sp (M82 background).

SEQ ID NO: 71 is a nucleic acid sequence of a mutant Solyc06g074350 gene allele sp coding sequence (M82 background).

SEQ ID NO: 72 is an amino acid sequence of a mutant polypeptide encoded by a mutant Solyc06g074350 gene allele sp coding sequence (M82 background).

SEQ ID NO: 73 is a nucleic acid sequence of a mutant Solyc06g074350 gene allele sp$^{CR}$ (M82 background).

SEQ ID NO: 74 is a nucleic acid sequence of a mutant Solyc06g074350 gene allele sp$^{CR}$ coding sequence (M82 background).

SEQ ID NO: 75 is an amino acid sequence of a mutant polypeptide encoded by a mutant Solyc06g074350 gene allele sp$^{CR}$ coding sequence (M82 background).

SEQ ID NO: 76 is a nucleic acid sequence of a mutant Solyc06g074350 gene allele sp (Sweet100 background).

SEQ ID NO: 77 is a nucleic acid sequence of a mutant Solyc06g074350 gene allele sp coding sequence (Sweet100 background).

SEQ ID NO: 78 is an amino acid sequence of a mutant polypeptide encoded by a mutant Solyc06g074350 gene allele sp coding sequence (Sweet100 background).

SEQ ID NO: 79 is a nucleic acid sequence of a mutant Solyc06g074350 gene allele sp-cocktail.

SEQ ID NO: 80 is a nucleic acid sequence of a mutant Solyc06g074350 gene allele sp-cocktail coding sequence.

SEQ ID NO: 81 is an amino acid sequence of a mutant polypeptide encoded by a mutant Solyc06g074350 gene allele sp-cocktail coding sequence.

SEQ ID NO: 82 is a nucleic acid sequence of a mutant Solyc06g074350 gene allele sp-grape.

SEQ ID NO: 83 is a nucleic acid sequence of a mutant Solyc06g074350 gene allele sp-grape coding sequence.

SEQ ID NO: 84 is an amino acid sequence of a mutant polypeptide encoded by a mutant Solyc06g074350 gene allele sp-grape coding sequence.

SEQ ID NO: 85 is a nucleic acid sequence of a wild-type SlSERK1 gene encoded by a Solyc04g072570 gene.

SEQ ID NO: 86 is a nucleic acid sequence of a wild-type SlSERK1 gene encoded by a Solyc04g072570 coding sequence.

SEQ ID NO: 87 is an amino acid sequence of a polypeptide encoded by the wild-type SlSERK1 gene encoded by a Solyc04g072570 coding sequence.

SEQ ID NO: 88 is a nucleic acid sequence of a mutant Solyc04g072570 gene allele slserk1$^{w}$.

SEQ ID NO: 89 is a nucleic acid sequence of a mutant Solyc04g072570 gene allele slserk1$^{w}$ coding sequence.

SEQ ID NO: 90 is an amino acid sequence of a mutant polypeptide encoded by a mutant Solyc04g072570 gene allele slserk1$^{w}$ coding sequence.

SEQ ID NO: 91 is a nucleic acid sequence of a mutant Solyc04g072570 gene allele slserk1$^{S1}$.

SEQ ID NO: 92 is a nucleic acid sequence of a mutant Solyc04g072570 gene allele slserk1$^{S1}$ coding sequence.

SEQ ID NO: 93 is an amino acid sequence of a mutant polypeptide encoded by a mutant Solyc04g072570 gene allele slserk1$^{S1}$ coding sequence.

SEQ ID NO: 94 is a nucleic acid sequence of a mutant Solyc04g072570 gene allele slserk1s2.

SEQ ID NO: 95 is a nucleic acid sequence of a mutant Solyc04g072570 gene allele slserk1s2 coding sequence.

SEQ ID NO: 96 is an amino acid sequence of a mutant polypeptide encoded by a mutant Solyc04g072570 gene allele slserk1$^{S2}$ coding sequence.

SEQ ID NO: 97 is a nucleic acid sequence of a mutant Solyc04g072570 gene allele slserk1$^{CR\text{-}5\text{-}a1}$.

SEQ ID NO: 98 is a nucleic acid sequence of a mutant Solyc04g072570 gene allele slserkCR-5-a1 coding sequence.

SEQ ID NO: 99 is an amino acid sequence of a mutant polypeptide encoded by a mutant Solyc04g072570 gene allele slserk$^{CR\text{-}5\text{-}a1}$ coding sequence.

SEQ ID NO: 100 is a nucleic acid sequence of a mutant Solyc04g072570 gene allele slserk1$^{CR\text{-}5\text{-}a2}$. SEQ ID NO: 101 is a nucleic acid sequence of a mutant Solyc04g072570 gene allele slserk1$^{CR\text{-}5\text{-}a2}$ coding sequence.

SEQ ID NO: 102 is an amino acid sequence of a mutant polypeptide encoded by a mutant Solyc04g072570 gene allele slserk1$^{CR\text{-}5\text{-}a2}$ coding sequence.

SEQ ID NO: 103 is a nucleic acid sequence of a mutant Solyc04g072570 gene allele slserk1$^{CR\text{-}5\text{-}a3}$.

SEQ ID NO: 104 is a nucleic acid sequence of a mutant Solyc04g072570 gene allele slserk1$^{CR\text{-}5\text{-}a3}$ coding sequence.

SEQ ID NO: 105 is an amino acid sequence of a mutant polypeptide encoded by a mutant Solyc04g072570 gene allele slserk1$^{CR\text{-}5\text{-}a3}$ coding sequence.

SEQ ID NO: 106 is a nucleic acid sequence of a mutant Solyc04g072570 gene allele slserk1$^{CR\text{-}7\text{-}a1}$.

SEQ ID NO: 107 is a nucleic acid sequence of a mutant Solyc04g072570 gene allele slserk1$^{CR\text{-}7\text{-}a1}$ coding sequence.

SEQ ID NO: 108 is an amino acid sequence of a mutant polypeptide encoded by a mutant Solyc04g072570 gene allele slserk1$^{CR\text{-}7\text{-}a1}$ coding sequence.

SEQ ID NO: 109 is a nucleic acid sequence of a mutant Solyc04g072570 gene allele slserk1$^{CR\text{-}7\text{-}a2}$.

SEQ ID NO: 110 is a nucleic acid sequence of a mutant Solyc04g072570 gene allele slserk1$^{CR\text{-}7\text{-}a2}$ coding sequence.

SEQ ID NO: 111 is an amino acid sequence of a mutant polypeptide encoded by a mutant Solyc04g072570 gene allele slserk1$^{CR\text{-}7\text{-}a2}$ coding sequence.

SEQ ID NO: 147 is a nucleic acid sequence of a wild-type Solyc08g061560 SlER promoter.

SEQ ID NO: 148 is a nucleic acid sequence of a wild-type Solyc05g053850 SP5G promoter.

SEQ ID NO: 149 is a nucleic acid sequence of a wild-type Solyc06g074350 SP promoter.

DETAILED DESCRIPTION

A significant challenge for the future of agriculture is the loss of arable land, driven by population growth, diminishing water resources, and climate change. Part of the solution will require increasing yield in the staple crops that feed humans and their livestock, such as corn, rice, soybean, and wheat, which are bred for high productivity in large-scale field conditions. A complementary approach that can promote sustainable agriculture is to grow more food in urban environments[1,2]. For example, although initial infrastructure costs can be high, rooftop farms and climate-controlled automated vertical farming systems optimize land use and are designed to be more environmentally friendly and sustainable than traditional farming[1,3,4]. However, the benefits of urban agriculture and its expansion are limited by the few crops that can be cultivated under highly restrictive growth parameters. Crop varieties that are both compact and rapid cycling are needed to optimize efficiency and productivity, and for these reasons, urban agriculture is currently dominated by lettuce and related leafy green vegetables[1,5].

There is great interest in fruits and berries for urban agriculture; such crops will require dramatic modification of existing varieties, which were and continue to be, bred for maximum productivity under typical greenhouse and field parameters. As an important component of the human diet and a major fruit crop, a promising opportunity is tomato. It was previously shown that mutating two regulators of flowering in the universal florigen hormone system can convert tall, continuously growing "indeterminate" tomato plants into early yielding, compact "determinate" varieties. Natural and CRISPR-Cas9-induced mutations in the classical flowering repressor gene SELF PRUNING (SP) confer a determinate growth habit, and mutating its paralog SP5G in the sp background accelerates flowering and enhances plant compactness[6,7]. These sp sp5g "double-determinate" genotypes are rapid cycling and productive when grown at high density in greenhouses and fields (Soyk, S. et al. *Nat. Genet.* (2017) 49:162-8); even smaller plants that still yield well would be more beneficial for urban agriculture.

Disclosed are genes that regulate stem length in plants and mutants thereof (e.g., a Solanaceae plant, such as *Solanum lycopersicum*), which can be combined with mutations in genes that control flowering and/or growth termination, to yield compact plants (e.g., plants that are shorter in height, plants that grow more densely, and/or plants that occupy a smaller area, etc.) relative to a reference plant, which are suitable for growth in restrictive conditions, such as in an urban setting. For instance, using a genome editing tool (e.g., CRISPR-Cas9), continuous vine-like growth of plants, such as in Solanaceae plants, can quite surprisingly be restructured into a compact, early yielding form suitable for urban agriculture. From the identification of a new regulator of stem length in a plant, such as tomato, a trait stacking strategy was devised that uses one or more mutations in one or more of the genes disclosed to yield compact plants suitable for growth in restrictive conditions. Similar approaches according to the methods disclosed, targeting homologs of the genes disclosed, can be used to expand the repertoire of crops for urban agriculture.

In some embodiments, one or more mutations result in the traits of rapid flowering (e.g., a mutation in a SP5G protein), precocious growth termination (e.g., a mutation in a SP protein), condensed shoots (e.g., a mutation in a SlER protein) or a combination of any two or three of these traits (e.g., rapid flowering and precocious growth termination; rapid flowering and condensed shoots; precocious growth termination and condensed shoots; or rapid flowering, precocious growth termination, and condensed shoots). Combining two or more mutations in genes that regulate stem length in the absence or presence of one or more gene(s) that regulate flowering and growth termination, in homozygous and heterozygous combinations, allowed for the creation of a range of compact plants, and the development of weaker allele hybrids with traits, such as customized flower and fruit production. In particular, data described here in a Solanaceae plant (e.g., *Solanum lycopersicum*), demonstrates the utility of mutant stem length regulator genes, such as mutant *ERECTA* family gene homologs, and the interaction between such mutant genes with one or more mutant genes that regulate flowering and growth termination, to alter plant structure into compact and early-yielding forms.

Mutants of one or more of the gene Solyc08g061560 (also referred to herein as SlER; or a homolog thereof), the gene Solyc03g007050 (also referred to herein as SlERL1; or a homolog thereof), the gene Solyc05g053850 gene (also referred to herein as SP5G; or a homolog thereof), the gene Solyc06g074350 (also referred to herein as SP; or a homolog thereof), the gene Solyc04g072570 (also referred to herein as SlSERK1; or a homolog thereof), altered one or more of stem length, pedicel length, flowering time, and growth termination in plants (e.g., a Solanaceae plant, such as *Solanum lycopersicum*). Specifically, it was found that mixing and matching the presence of these mutations in various homozygous combinations resulted in compact and early-yielding plants. In some embodiments, plant weight, fruit weight, total yield, harvest index or any combination of two or more (two, three or four) of these characteristics were unaffected in the compact and early-yielding plants. In some embodiments, plant compactness (e.g., plant height, growth density, and/or area occupied, etc.) is customized with weak alleles with a more subtle phenotype (e.g., stem and/or pedicel length), for instance, to meet specific agronomic needs (e.g., agronomic needs of larger-fruited varieties where more subtle changes in internode length are beneficial).

In some aspects, the present disclosure relates to plants (e.g., a Solanaceae plant) comprising one or more mutant genes, such as one or more mutant *ERECTA* family gene homologs, in the absence or presence of one or more mutations in genes that regulate flowering and growth termination, and exhibit a compact plant architecture. In specific embodiments, there is not a significant difference in plant weight, fruit weight, total yield, harvest index or any combination of two or more (two, three or four) of these characteristics, relative to a reference plant. In some embodiments (e.g., in the case of combined or higher-order mutations, for example in the triple-determinate mutant), one or more of the following occurs: fruit size is smaller, plant weight is reduced, or total yield per plant is down (e.g., reduced relative to a reference plant). In these embodiments, harvest index is increased and yield per unit area can compensate for the reduced fruit weight and reduced total yield per plant because plants can be planted much more tightly, such as in a smaller space. In a specific embodiment, in a triple-determinate mutant, fruit size is smaller, plant weight is reduced, and total yield per plant is down (e.g., reduced relative to a reference plant). Further, harvest index is increased and yield per unit area compensates for reduced fruit weight and reduced yield because plants can be planted much more tightly in a given area than is possible with corresponding plants that are not genetic plant variants.

In some aspects, provided herein are genetically-altered plants, such as genetically-altered Solanaceae (e.g., *Solanum lycopersicum*) plants comprising one or more of (at least one of) a mutant Solyc08g061560 gene (or a homolog thereof), a mutant Solyc03g007050 gene (or a homolog thereof), a mutant Solyc05g053850 gene (or a homolog thereof), a mutant Solyc06g074350 gene (or a homolog thereof), and a mutant Solyc04g072570 gene (or a homolog thereof), which exhibit characteristics different from those of a reference plant. The characteristics exhibited that are different in the genetically-altered plant from those in the reference plant include, but are not limited to, one or more of the following: modified stem length, modified pedicel length, modified number of leaves, modified number of leaves to first inflorescence, or any combination of two or three or four of these characteristics, a combination of which, according to some aspects, yields a compact plant architecture form, an early-yielding form or a compact plant architecture, early-yielding form.

In some embodiments, the term a "reference plant" refers to a corresponding plant, which does not contain a mutation in one or more of the genes disclosed in a genetically-altered (e.g., mutant) plant. In some embodiments, the term a "reference plant" refers to: a corresponding plant (e.g., tomato, a Solanaceae plant), which does not have the mutation(s) in a SlER gene or in a homolog thereof (e.g., an *ERECTA* gene in *A. thaliana*, etc.) that are present in the genetically-altered (e.g., mutant) plant; a corresponding plant (e.g., tomato, a Solanaceae plant), which does not have the mutation(s) in a SP gene or in a homolog thereof that are present in the genetically-altered (e.g., mutant) plant; a corresponding plant (e.g., tomato, a Solanaceae plant), which does not have the mutation(s) in a SP5G gene or in a homolog thereof that are present in the genetically-altered (e.g., mutant) plant; a corresponding plant (e.g., tomato, a Solanaceae plant), which does not have the mutation(s) in a SlERL1 gene or in a homolog thereof that are present in the genetically-altered (e.g., mutant) plant; a corresponding plant (e.g., tomato, a Solanaceae plant), which does not have the mutation(s) in a SlSERK1 gene or in a homolog thereof that are present in the genetically-altered (e.g., mutant) plant. In some embodiments, a reference plant refers to the corresponding wild-type (WT) plant (e.g., a WT Solanaceae plant), which has not been genetically-altered.

In some embodiments, the term a "reference allele" refers to a corresponding allele, which does not contain one or more of the mutations disclosed in a genetically-altered (e.g., mutant) plant. In some embodiments, a reference allele refers to: a corresponding allele in a plant (e.g., tomato, a Solanaceae plant), which does not have the mutation(s) in a SlER gene or in a homolog thereof (e.g., an *ERECTA* gene in *A. thaliana*, etc.) that are present in one or both alleles of the genetically-altered (e.g., mutant) plant; a corresponding allele in a plant (e.g., tomato, a Solanaceae plant), which does not have the mutation(s) in a SP gene or in a homolog thereof that are present in one or both alleles of the genetically-altered (e.g., mutant) plant; a corresponding allele in a plant (e.g., tomato, a Solanaceae plant), which does not have the mutation(s) in a SP5G gene or in a homolog thereof that are present in one or both alleles of the genetically-altered (e.g., mutant) plant; a corresponding allele in a plant (e.g., tomato, a Solanaceae plant), which does not have the mutation(s) in a SlERL1 gene or in a homolog thereof that are present in one or both alleles of the genetically-altered (e.g., mutant) plant; a corresponding allele in a plant (e.g., tomato, a Solanaceae plant), which does not have the mutation(s) in a SlSERK1 gene or in a homolog thereof that are present in one or both alleles of the genetically-altered (e.g., mutant) plant. In some embodiments, a reference allele refers to the corresponding wild-type (WT) allele in a plant (e.g., a WT Solanaceae plant), which has not been genetically-altered.

In some embodiments, genetically-altered Solanaceae plants, e.g., tomato plants (such as *Solanum lycopersicum*), comprise one or more of a mutant Solyc08g061560 gene (or a homolog thereof) that is homozygous or heterozygous, a mutant Solyc03g007050 gene (or a homolog thereof) that is homozygous or heterozygous, a mutant Solyc05g053850 gene (or a homolog thereof) that is homozygous or heterozygous, a mutant Solyc06g074350 gene (or a homolog thereof) that is homozygous or heterozygous, and a mutant Solyc04g072570 gene (or a homolog thereof) that is homozygous or heterozygous.

In some embodiments, the plants comprise combinations of the different mutant gene alleles, such as, for example, a mutant Solyc08g061560 gene (or a homolog thereof) and a mutant Solyc05g053850 gene (or a homolog thereof); a mutant Solyc08g061560 gene (or a homolog thereof) and a mutant Solyc06g074350 gene (or a homolog thereof); a mutant Solyc08g061560 gene (or a homolog thereof) and a mutant Solyc03g007050 gene (or a homolog thereof); a mutant Solyc08g061560 gene (or a homolog thereof) and a mutant Solyc04g072570 gene (or a homolog thereof); or a mutant Solyc08g061560 gene (or a homolog thereof), a mutant Solyc05g053850 gene (or a homolog thereof), and a mutant Solyc06g074350 gene (or a homolog thereof).

The genetically-altered plants may be heterozygotes or homozygotes and, in some embodiments, may be double heterozygotes, double homozygotes, triple heterozygotes, or triple homozygotes. In some embodiments, such a plant comprises a mutant Solyc08g061560 gene (or a homolog thereof). In some embodiments, such a plant comprises a mutant Solyc08g061560 gene and a mutant Solyc05g053850 gene (or a homolog thereof). In some embodiments, such a plant comprises a mutant Solyc08g061560 gene and a mutant Solyc06g074350 gene (or a homolog thereof). In some embodiments, such a plant comprises a mutant Solyc08g061560 gene (or a homolog thereof), a mutant Solyc05g053850 gene (or a homolog thereof), and a mutant Solyc06g074350 gene (or a homolog thereof).

Mutant Solyc08g061560 (SlER) Gene

Other aspects of the disclosure relate to mutants of the Solyc08g061560 gene (or a homolog thereof) as well as plants, plant cells, and seeds comprising such mutant genes, and nucleic acids comprising such mutant genes. The Solyc08g061560 gene is also referred to herein as SlERECTA or SlER. The Solyc08g061560 gene is a homolog of *ERECTA* in *Arabidopsis thaliana*. Homologs of SlER can be readily identified using tools, such as a Basic Local Alignment Search Tool (BLAST), known to those of ordinary skill in the art. In some embodiments, a Solyc08g061560 gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 1 or SEQ ID NO: 2 or has 85%, 90%, 91%, 92%, 93%, 94%, 95%, 96%, 97%, 98%, 98.5%, 99%, 99.5% or 99.9% identity with the nucleic acid sequence of SEQ ID NO: 1 or SEQ ID NO: 2. In some embodiments, the homolog of the Solyc08g061560 gene is not a *Solanum lycopersicum* gene.

In some embodiments, the mutant Solyc08g061560 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (see, e.g., Riethoven et al., Methods Mol Biol (2010) 674:33-42). In some embodiments, the promoter is a region upstream of the start codon (e.g., ATG).

In some embodiments, the mutant Solyc08g061560 gene (or homolog thereof) comprises one or more mutations in the promoter of the Solyc08g061560 gene. In some embodiments, the promoter of the Solyc08g061560 gene comprises or consists of the nucleic acid sequence of SEQ ID NO: 147. In some embodiments, the promoter of the Solyc08g061560 gene comprising one or more mutations comprises a nucleic acid sequence with at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 147. In some embodiments, the promoter of the Solyc08g061560 gene comprises one or more of a missense, frameshift, nonsense, insertion, deletion, duplication, inversion or indel mutation. In some embodiments, the promoter of the Solyc08g061560 gene comprises a deletion of or at least 10, 20, 30, 40, 50, 60, 70, 80, 90, 100, 150, 200, 250, 300, 250, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, or any range or combination thereof, of the nucleotides from the nucleic acid sequence comprising the promoter. In some embodiments, one continuous nucleic acid sequence is deleted from the promoter. In some embodiments, two or more nucleic acid sequences are deleted from the promoter, wherein the sequences are not contiguous.

In some embodiments, the mutant Solyc08g061560 gene (or homolog thereof) contains a mutation in an exon (e.g., exon 15, exon 24, etc.). In some embodiments, the mutant Solyc08g061560 gene (or homolog thereof) contains a mutation in an intron (e.g., intron 23, etc.). In some embodiments, the mutant Solyc08g061560 gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant Solyc08g061560 gene (or homolog thereof) is a hypomorphic allele or a null allele. In some embodiments, a hypomorphic allele of the mutant Solyc08g061560 gene (or homolog thereof) is an allele that encodes a mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, lower than a mRNA or protein level of expression encoded by a corresponding reference allele.

In some embodiments, a Solanaceae plant (e.g., *Solanum lycopersicum*) comprising the mutant Solyc08g061560 gene, or homolog thereof, (e.g., a hypomorphic, knock-out or null allele disclosed) is heterozygous for the mutant Solyc08g061560 gene. In some embodiments, a Solanaceae plant (e.g., *Solanum lycopersicum*) comprising the mutant Solyc08g061560 gene, or homolog thereof, (e.g., a hypomorphic, knock-out or null allele disclosed) is homozygous for the mutant Solyc08g061560 gene.

In some embodiments, the mutant $sler^{EMS-1}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 4 or SEQ ID NO: 5 or has 85%, 90%, 91%, 92%, 93%, 94%, 95%, 96%, 97%, 98%, 98.5%, 99%, 99.5% or 99.9% identity with the nucleic acid sequence of SEQ ID NO: 4 or SEQ ID NO: 5. In some embodiments, the homolog of the mutant $sler^{EMS-1}$ gene is not a *Solanum lycopersicum* gene.

In some embodiments, the mutant $sler^{EMS-1}$ gene comprises, for example, a nucleic acid (e.g., DNA) having the sequence of SEQ ID NO: 4; a portion of SEQ ID NO: 4 that exhibits substantially the same activity (e.g., encodes the same polypeptide or substantially the same polypeptide that has the same activity) as a nucleic acid (e.g., DNA) having the nucleic acid sequence of SEQ ID NO: 4; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 4 or has 85%, 90%, 91%, 92%, 93%, 94%, 95%, 96%, 97%, 98%, 98.5%, 99%, 99.5% or 99.9% identity with the nucleic acid sequence of SEQ ID NO: 4, or any range or combination thereof; a homolog of the nucleic acid having the sequence of SEQ ID NO: 4.

In some embodiments, the mutant $sler^{EMS-1}$ gene comprises a coding sequence that comprises, for example, a nucleic acid (e.g., DNA) having the sequence of SEQ ID NO: 5; a portion of SEQ ID NO: 5 that exhibits substantially the same activity (e.g., encodes the same polypeptide or substantially the same polypeptide that has the same activity) as a nucleic acid (e.g., DNA) having the nucleic acid sequence of SEQ ID NO: 5; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 5 or has 85%, 90%, 91%, 92%, 93%, 94%, 95%, 96%, 97%, 98%, 98.5%, 99%, 99.5% or 99.9% identity with the nucleic acid sequence of SEQ ID NO: 5, or any range or combination thereof; a homolog of the nucleic acid having the sequence of SEQ ID NO: 5.

In some embodiments, the mutant $sler^{EMS-1}$ gene comprises a coding sequence that encodes a protein or polypeptide (e.g., amino acid sequence) having the sequence of SEQ ID NO: 6; a portion of SEQ ID NO: 6 that exhibits substantially the same activity as a protein or polypeptide having the amino acid sequence of SEQ ID NO: 6; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 6 or has 85%, 90%, 91%, 92%, 93%, 94%, 95%, 96%, 97%, 98%, 98.5%, 99%, 99.5% or 99.9% identity with the amino acid sequence of SEQ ID NO: 6, or any range or combination thereof; a homolog of the amino acid having the sequence of SEQ ID NO: 6.

In some embodiments, the mutant $sler^{EMS-2}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 7 or SEQ ID NO: 8 or has 85%, 90%, 91%, 92%, 93%, 94%, 95%, 96%, 97%, 98%, 98.5%, 99%, 99.5% or 99.9% identity with the nucleic acid sequence of SEQ ID NO: 7 or SEQ ID NO: 8. In some embodiments, the homolog of the mutant $sler^{EMS-2}$ gene is not a *Solanum lycopersicum* gene.

In some embodiments, the mutant $sler^{EMS-2}$ gene comprises, for example, a nucleic acid (e.g., DNA) having the sequence of SEQ ID NO: 7; a portion of SEQ ID NO: 7 that exhibits substantially the same activity (e.g., encodes the same polypeptide or substantially the same polypeptide that has the same activity) as a nucleic acid (e.g., DNA) having the nucleic acid sequence of SEQ ID NO: 7; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 7 or has 85%, 90%, 91%, 92%, 93%, 94%, 95%, 96%, 97%, 98%, 98.5%, 99%, 99.5% or 99.9% identity with the nucleic acid sequence of SEQ ID NO: 7, or any range or combination thereof; a homolog of the nucleic acid having the sequence of SEQ ID NO: 7.

In some embodiments, the mutant $sler^{EMS-2}$ gene comprises a coding sequence that comprises, for example, a nucleic acid (e.g., DNA) having the sequence of SEQ ID NO: 8; a portion of SEQ ID NO: 8 that exhibits substantially the same activity (e.g., encodes the same polypeptide or substantially the same polypeptide that has the same activity) as a nucleic acid (e.g., DNA) having the nucleic acid sequence of SEQ ID NO: 8; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 8 or has 85%, 90%, 91%, 92%, 93%, 94%, 95%, 96%, 97%, 98%, 98.5%, 99%, 99.5% or 99.9% identity with the nucleic acid sequence of SEQ ID NO: 8, or any range or combination thereof; a homolog of the nucleic acid having the sequence of SEQ ID NO: 8.

In some embodiments, the mutant $sler^{EMS-2}$ gene comprises a coding sequence that encodes a protein or polypeptide (e.g., amino acid sequence) having the sequence of SEQ ID NO: 9; a portion of SEQ ID NO: 9 that exhibits substantially the same activity as a protein or polypeptide having the amino acid sequence of SEQ ID NO: 9; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 9 or has 85%, 90%, 91%, 92%, 93%, 94%, 95%, 96%, 97%, 98%, 98.5%, 99%, 99.5% or 99.9% identity with the amino acid sequence of SEQ ID NO: 9, or any range or combination thereof; a homolog of the amino acid having the sequence of SEQ ID NO: 9.

In some embodiments, the mutant $sler^{CR-1}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 10 or SEQ ID NO: 11 or has 85%, 90%, 91%, 92%, 93%, 94%, 95%, 96%, 97%, 98%, 98.5%, 99%, 99.5% or 99.9% identity with the nucleic acid sequence of SEQ ID NO: 10 or SEQ ID NO: 11. In some embodiments, the homolog of the mutant sler$^{CR-1}$ gene is not a *Solanum lycopersicum* gene.

In some embodiments, the mutant sler$^{CR-1}$ gene comprises, for example, a nucleic acid (e.g., DNA) having the sequence of SEQ ID NO: 10; a portion of SEQ ID NO: 10 that exhibits substantially the same activity (e.g., encodes the same polypeptide or substantially the same polypeptide that has the same activity) as a nucleic acid (e.g., DNA) having the nucleic acid sequence of SEQ ID NO: 10; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 10 or has 85%, 90%, 91%, 92%, 93%, 94%, 95%, 96%, 97%, 98%, 98.5%, 99%, 99.5% or 99.9% identity with the nucleic acid sequence of SEQ ID NO: 10, or any range or combination thereof; a homolog of the nucleic acid having the sequence of SEQ ID NO: 10.

In some embodiments, the mutant sler$^{CR-1}$ gene comprises a coding sequence that comprises, for example, a nucleic acid (e.g., DNA) having the sequence of SEQ ID NO: 11; a portion of SEQ ID NO: 11 that exhibits substantially the same activity (e.g., encodes the same polypeptide or substantially the same polypeptide that has the same activity) as a nucleic acid (e.g., DNA) having the nucleic acid sequence of SEQ ID NO: 11; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 11 or has 85%, 90%, 91%, 92%, 93%, 94%, 95%, 96%, 97%, 98%, 98.5%, 99%, 99.5% or 99.9% identity with the nucleic acid sequence of SEQ ID NO: 11, or any range or combination thereof; a homolog of the nucleic acid having the sequence of SEQ ID NO: 11.

In some embodiments, the mutant sler$^{CR-1}$ gene comprises a coding sequence that encodes a protein or polypeptide (e.g., amino acid sequence) having the sequence of SEQ ID NO: 12; a portion of SEQ ID NO: 12 that exhibits substantially the same activity as a protein or polypeptide having the amino acid sequence of SEQ ID NO: 12; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 12 or has 85%, 90%, 91%, 92%, 93%, 94%, 95%, 96%, 97%, 98%, 98.5%, 99%, 99.5% or 99.9% identity with the amino acid sequence of SEQ ID NO: 12, or any range or combination thereof; a homolog of the amino acid having the sequence of SEQ ID NO: 12.

In some embodiments, the mutant sler$^{CR-2}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 13 or SEQ ID NO: 14 or has 85%, 90%, 91%, 92%, 93%, 94%, 95%, 96%, 97%, 98%, 98.5%, 99%, 99.5% or 99.9% identity with the nucleic acid sequence of SEQ ID NO: 13 or SEQ ID NO: 14. In some embodiments, the homolog of the mutant sler$^{CR-2}$ gene is not a *Solanum lycopersicum* gene.

In some embodiments, the mutant sler$^{CR-2}$ gene comprises, for example, a nucleic acid (e.g., DNA) having the sequence of SEQ ID NO: 13; a portion of SEQ ID NO: 13 that exhibits substantially the same activity (e.g., encodes the same polypeptide or substantially the same polypeptide that has the same activity) as a nucleic acid (e.g., DNA) having the nucleic acid sequence of SEQ ID NO: 13; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 13 or has 85%, 90%, 91%, 92%, 93%, 94%, 95%, 96%, 97%, 98%, 98.5%, 99%, 99.5% or 99.9% identity with the nucleic acid sequence of SEQ ID NO: 13, or any range or combination thereof; a homolog of the nucleic acid having the sequence of SEQ ID NO: 13.

In some embodiments, the mutant sler$^{CR-2}$ gene comprises a coding sequence that comprises, for example, a nucleic acid (e.g., DNA) having the sequence of SEQ ID NO: 14; a portion of SEQ ID NO: 14 that exhibits substantially the same activity (e.g., encodes the same polypeptide or substantially the same polypeptide that has the same activity) as a nucleic acid (e.g., DNA) having the nucleic acid sequence of SEQ ID NO: 14; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 14 or has 85%, 90%, 91%, 92%, 93%, 94%, 95%, 96%, 97%, 98%, 98.5%, 99%, 99.5% or 99.9% identity with the nucleic acid sequence of SEQ ID NO: 14, or any range or combination thereof; a homolog of the nucleic acid having the sequence of SEQ ID NO: 14.

In some embodiments, the mutant sler$^{CR-2}$ gene comprises a coding sequence that encodes a protein or polypeptide (e.g., amino acid sequence) having the sequence of SEQ ID NO: 15; a portion of SEQ ID NO: 15 that exhibits substantially the same activity as a protein or polypeptide having the amino acid sequence of SEQ ID NO: 15; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 15 or has 85%, 90%, 91%, 92%, 93%, 94%, 95%, 96%, 97%, 98%, 98.5%, 99%, 99.5% or 99.9% identity with the amino acid sequence of SEQ ID NO: 15, or any range or combination thereof; a homolog of the amino acid having the sequence of SEQ ID NO: 15.

In some embodiments, the mutant sler$^{MT}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 16 or SEQ ID NO: 17 or has 85%, 90%, 91%, 92%, 93%, 94%, 95%, 96%, 97%, 98%, 98.5%, 99%, 99.5% or 99.9% identity with the nucleic acid sequence of SEQ ID NO: 16 or SEQ ID NO: 17. In some embodiments, the homolog of the mutant sler$^{MT}$ gene is not a *Solanum lycopersicum* gene.

In some embodiments, the mutant sler$^{MT}$ gene comprises, for example, a nucleic acid (e.g., DNA) having the sequence of SEQ ID NO: 16; a portion of SEQ ID NO: 16 that exhibits substantially the same activity (e.g., encodes the same polypeptide or substantially the same polypeptide that has the same activity) as a nucleic acid (e.g., DNA) having the nucleic acid sequence of SEQ ID NO: 16; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 16 or has 85%, 90%, 91%, 92%, 93%, 94%, 95%, 96%, 97%, 98%, 98.5%, 99%, 99.5% or 99.9% identity with the nucleic acid sequence of SEQ ID NO: 16, or any range or combination thereof; a homolog of the nucleic acid having the sequence of SEQ ID NO: 16.

In some embodiments, the mutant sler$^{MT}$ gene comprises a coding sequence that comprises, for example, a nucleic acid (e.g., DNA) having the sequence of SEQ ID NO: 17; a portion of SEQ ID NO: 17 that exhibits substantially the same activity (e.g., encodes the same polypeptide or substantially the same polypeptide that has the same activity) as a nucleic acid (e.g., DNA) having the nucleic acid sequence of SEQ ID NO: 17; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 17 or has 85%, 90%, 91%, 92%, 93%, 94%, 95%, 96%, 97%, 98%, 98.5%, 99%, 99.5% or 99.9% identity with the nucleic acid sequence of SEQ ID NO: 17, or any range or combination thereof; a homolog of the nucleic acid having the sequence of SEQ ID NO: 17.

In some embodiments, the mutant sler$^{MT}$ gene comprises a coding sequence that encodes a protein or polypeptide (e.g., amino acid sequence) having the sequence of SEQ ID NO: 18; a portion of SEQ ID NO: 18 that exhibits substantially the same activity as a protein or polypeptide having the amino acid sequence of SEQ ID NO: 18; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 18 or has 85%, 90%, 91%, 92%, 93%, 94%, 95%, 96%, 97%, 98%, 98.5%, 99%, 99.5% or 99.9% identity with the amino acid sequence of SEQ ID NO: 18, or any range or combination thereof; a homolog of the amino acid having the sequence of SEQ ID NO: 18.

In some embodiments, the mutant sler-cocktail gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 19 or SEQ ID NO: 20 or has 85%, 90%, 91%, 92%, 93%, 94%, 95%, 96%, 97%, 98%, 98.5%, 99%, 99.5% or 99.9% identity with the nucleic acid sequence of SEQ ID NO: 19 or SEQ ID NO: 20. In some embodiments, the homolog of the mutant sler-cocktail gene is not a *Solanum lycopersicum* gene.

In some embodiments, the mutant sler-cocktail gene comprises, for example, a nucleic acid (e.g., DNA) having the sequence of SEQ ID NO: 19; a portion of SEQ ID NO: 19 that exhibits substantially the same activity (e.g., encodes the same polypeptide or substantially the same polypeptide that has the same activity) as a nucleic acid (e.g., DNA) having the nucleic acid sequence of SEQ ID NO: 19; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 19 or has 85%, 90%, 91%, 92%, 93%, 94%, 95%, 96%, 97%, 98%, 98.5%, 99%, 99.5% or 99.9% identity with the nucleic acid sequence of SEQ ID NO: 19, or any range or combination thereof; a homolog of the nucleic acid having the sequence of SEQ ID NO: 19.

In some embodiments, the mutant sler-cocktail gene comprises a coding sequence that comprises, for example, a nucleic acid (e.g., DNA) having the sequence of SEQ ID NO: 20; a portion of SEQ ID NO: 20 that exhibits substantially the same activity (e.g., encodes the same polypeptide or substantially the same polypeptide that has the same activity) as a nucleic acid (e.g., DNA) having the nucleic acid sequence of SEQ ID NO: 20; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 20 or has 85%, 90%, 91%, 92%, 93%, 94%, 95%, 96%, 97%, 98%, 98.5%, 99%, 99.5% or 99.9% identity with the nucleic acid sequence of SEQ ID NO: 20, or any range or combination thereof; a homolog of the nucleic acid having the sequence of SEQ ID NO: 20.

In some embodiments, the mutant sler-cocktail gene comprises a coding sequence that encodes a protein or polypeptide (e.g., amino acid sequence) having the sequence of SEQ ID NO: 21; a portion of SEQ ID NO: 21 that exhibits substantially the same activity as a protein or polypeptide having the amino acid sequence of SEQ ID NO: 21; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 21 or has 85%, 90%, 91%, 92%, 93%, 94%, 95%, 96%, 97%, 98%, 98.5%, 99%, 99.5% or 99.9% identity with the amino acid sequence of SEQ ID NO: 21, or any range or combination thereof; a homolog of the amino acid having the sequence of SEQ ID NO: 21.

In some embodiments, the mutant sler-grape gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 22 or SEQ ID NO: 23 or has 85%, 90%, 91%, 92%, 93%, 94%, 95%, 96%, 97%, 98%, 98.5%, 99%, 99.5% or 99.9% identity with the nucleic acid sequence of SEQ ID NO: 22 or SEQ ID NO: 23. In some embodiments, the homolog of the mutant sler-grape gene is not a *Solanum lycopersicum* gene.

In some embodiments, the mutant sler-grape gene comprises, for example, a nucleic acid (e.g., DNA) having the sequence of SEQ ID NO: 22; a portion of SEQ ID NO: 22 that exhibits substantially the same activity (e.g., encodes the same polypeptide or substantially the same polypeptide that has the same activity) as a nucleic acid (e.g., DNA) having the nucleic acid sequence of SEQ ID NO: 22; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 22 or has 85%, 90%, 91%, 92%, 93%, 94%, 95%, 96%, 97%, 98%, 98.5%, 99%, 99.5% or 99.9% identity with the nucleic acid sequence of SEQ ID NO: 22, or any range or combination thereof; a homolog of the nucleic acid having the sequence of SEQ ID NO: 22.

In some embodiments, the mutant sler-grape gene comprises a coding sequence that comprises, for example, a nucleic acid (e.g., DNA) having the sequence of SEQ ID NO: 23; a portion of SEQ ID NO: 23 that exhibits substantially the same activity (e.g., encodes the same polypeptide or substantially the same polypeptide that has the same activity) as a nucleic acid (e.g., DNA) having the nucleic acid sequence of SEQ ID NO: 23; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 23 or has 85%, 90%, 91%, 92%, 93%, 94%, 95%, 96%, 97%, 98%, 98.5%, 99%, 99.5% or 99.9% identity with the nucleic acid sequence of SEQ ID NO: 23, or any range or combination thereof; a homolog of the nucleic acid having the sequence of SEQ ID NO: 23.

In some embodiments, the mutant sler-grape gene comprises a coding sequence that encodes a protein or polypeptide (e.g., amino acid sequence) having the sequence of SEQ ID NO: 24; a portion of SEQ ID NO: 24 that exhibits substantially the same activity as a protein or polypeptide having the amino acid sequence of SEQ ID NO: 24; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 24 or has 85%, 90%, 91%, 92%, 93%, 94%, 95%, 96%, 97%, 98%, 98.5%, 99%, 99.5% or 99.9% identity with the amino acid sequence of SEQ ID NO: 24, or any range or combination thereof; a homolog of the amino acid having the sequence of SEQ ID NO: 24.

In some embodiments, the mutant sler$^{CR\text{-}pro\text{-}4}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 25 or SEQ ID NO: 26 or has 85%, 90%, 91%, 92%, 93%, 94%, 95%, 96%, 97%, 98%, 98.5%, 99%, 99.5% or 99.9% identity with the nucleic acid sequence of SEQ ID NO: 25 or SEQ ID NO: 26. In some embodiments, the homolog of the mutant sler$^{CR\text{-}pro\text{-}4}$ gene is not a *Solanum lycopersicum* gene.

In some embodiments, the mutant sler$^{CR\text{-}pro\text{-}4}$ gene comprises, for example, a nucleic acid (e.g., DNA) having the sequence of SEQ ID NO: 25; a portion of SEQ ID NO: 25 that exhibits substantially the same activity (e.g., encodes the same polypeptide or substantially the same polypeptide that has the same activity) as a nucleic acid (e.g., DNA) having the nucleic acid sequence of SEQ ID NO: 25; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 25 or has 85%, 90%, 91%, 92%, 93%, 94%, 95%, 96%, 97%, 98%, 98.5%, 99%, 99.5% or 99.9% identity with the nucleic acid sequence of SEQ ID NO: 25, or any range or combination thereof; a homolog of the nucleic acid having the sequence of SEQ ID NO: 25.

In some embodiments, the mutant sler$^{CR\text{-}pro\text{-}4}$ gene comprises a coding sequence that comprises, for example, a nucleic acid (e.g., DNA) having the sequence of SEQ ID NO: 26; a portion of SEQ ID NO: 26 that exhibits substantially the same activity (e.g., encodes the same polypeptide or substantially the same polypeptide that has the same activity) as a nucleic acid (e.g., DNA) having the nucleic acid sequence of SEQ ID NO: 26; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 26 or has 85%, 90%, 91%, 92%, 93%, 94%, 95%, 96%, 97%, 98%, 98.5%, 99%, 99.5% or 99.9% identity with the nucleic acid sequence of SEQ ID NO: 26, or any range or combination thereof; a homolog of the nucleic acid having the sequence of SEQ ID NO: 26.

In some embodiments, the mutant sler$^{CR\text{-}pro\text{-}4}$ gene comprises a coding sequence that encodes a protein or polypeptide (e.g., amino acid sequence) having the sequence of SEQ ID NO: 27; a portion of SEQ ID NO: 27 that exhibits substantially the same activity as a protein or polypeptide having the amino acid sequence of SEQ ID NO: 27; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 27 or has 85%, 90%, 91%, 92%, 93%, 94%, 95%, 96%, 97%, 98%, 98.5%, 99%, 99.5% or 99.9% identity with the amino acid sequence of SEQ ID NO: 27, or any range or combination thereof; a homolog of the amino acid having the sequence of SEQ ID NO: 27.

In some embodiments, the mutant sler$^{CR\text{-}pro\text{-}14}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 28 or SEQ ID NO: 29 or has 85%, 90%, 91%, 92%, 93%, 94%, 95%, 96%, 97%, 98%, 98.5%, 99%, 99.5% or 99.9% identity with the nucleic acid sequence of SEQ ID NO: 28 or SEQ ID NO: 29. In some embodiments, the homolog of the mutant sler$^{CR\text{-}pro\text{-}14}$ gene is not a *Solanum lycopersicum* gene.

In some embodiments, the mutant sler$^{CR\text{-}pro\text{-}14}$ gene comprises, for example, a nucleic acid (e.g., DNA) having the sequence of SEQ ID NO: 28; a portion of SEQ ID NO: 28 that exhibits substantially the same activity (e.g., encodes the same polypeptide or substantially the same polypeptide that has the same activity) as a nucleic acid (e.g., DNA) having the nucleic acid sequence of SEQ ID NO: 28; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 28 or has 85%, 90%, 91%, 92%, 93%, 94%, 95%, 96%, 97%, 98%, 98.5%, 99%, 99.5% or 99.9% identity with the nucleic acid sequence of SEQ ID NO: 28, or any range or combination thereof; a homolog of the nucleic acid having the sequence of SEQ ID NO: 28.

In some embodiments, the mutant sler$^{CR\text{-}pro\text{-}14}$ gene comprises a coding sequence that comprises, for example, a nucleic acid (e.g., DNA) having the sequence of SEQ ID NO: 29; a portion of SEQ ID NO: 29 that exhibits substantially the same activity (e.g., encodes the same polypeptide or substantially the same polypeptide that has the same activity) as a nucleic acid (e.g., DNA) having the nucleic acid sequence of SEQ ID NO: 29; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 29 or has 85%, 90%, 91%, 92%, 93%, 94%, 95%, 96%, 97%, 98%, 98.5%, 99%, 99.5% or 99.9% identity with the nucleic acid sequence of SEQ ID NO: 29, or any range or combination thereof; a homolog of the nucleic acid having the sequence of SEQ ID NO: 29.

In some embodiments, the mutant sler$^{CR\text{-}pro\text{-}14}$ gene comprises a coding sequence that encodes a protein or polypeptide (e.g., amino acid sequence) having the sequence of SEQ ID NO: 30; a portion of SEQ ID NO: 30 that exhibits substantially the same activity as a protein or polypeptide having the amino acid sequence of SEQ ID NO: 30; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 30 or has 85%, 90%, 91%, 92%, 93%, 94%, 95%, 96%, 97%, 98%, 98.5%, 99%, 99.5% or 99.9% identity with the amino acid sequence of SEQ ID NO: 30, or any range or combination thereof; a homolog of the amino acid having the sequence of SEQ ID NO: 30.

In some embodiments, the mutant *S. lycopersicum* cv. Sweet100 sler$^{CR-1}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 34 or SEQ ID NO: 35 or has 85%, 90%, 91%, 92%, 93%, 94%, 95%, 96%, 97%, 98%, 98.5%, 99%, 99.5% or 99.9% identity with the nucleic acid sequence of SEQ ID NO: 34 or SEQ ID NO: 35. In some embodiments, the homolog of the mutant *S. lycopersicum* cv. Sweet100 sler$^{CR-1}$ gene is not a *Solanum lycopersicum* gene.

In some embodiments, the mutant *S. lycopersicum* cv. Sweet100 sler$^{CR-1}$ gene comprises, for example, a nucleic acid (e.g., DNA) having the sequence of SEQ ID NO: 34; a portion of SEQ ID NO: 34 that exhibits substantially the same activity (e.g., encodes the same polypeptide or substantially the same polypeptide that has the same activity) as a nucleic acid (e.g., DNA) having the nucleic acid sequence of SEQ ID NO: 34; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 34 or has 85%, 90%, 91%, 92%, 93%, 94%, 95%, 96%, 97%, 98%, 98.5%, 99%, 99.5% or 99.9% identity with the nucleic acid sequence of SEQ ID NO: 34, or any range or combination thereof; a homolog of the nucleic acid having the sequence of SEQ ID NO: 34.

In some embodiments, the mutant *S. lycopersicum* cv. Sweet100 sler$^{CR-1}$ gene comprises a coding sequence that comprises, for example, a nucleic acid (e.g., DNA) having the sequence of SEQ ID NO: 35; a portion of SEQ ID NO: 35 that exhibits substantially the same activity (e.g., encodes the same polypeptide or substantially the same polypeptide that has the same activity) as a nucleic acid (e.g., DNA) having the nucleic acid sequence of SEQ ID NO: 35; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 35 or has 85%, 90%, 91%, 92%, 93%, 94%, 95%, 96%, 97%, 98%, 98.5%, 99%, 99.5% or 99.9% identity with the nucleic acid sequence of SEQ ID NO: 35, or any range or combination thereof; a homolog of the nucleic acid having the sequence of SEQ ID NO: 35.

In some embodiments, the mutant *S. lycopersicum* cv. Sweet100 sler$^{CR-1}$ gene comprises a coding sequence that encodes a protein or polypeptide (e.g., amino acid sequence) having the sequence of SEQ ID NO: 36; a portion of SEQ ID NO: 36 that exhibits substantially the same activity as a protein or polypeptide having the amino acid sequence of SEQ ID NO: 36; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 36 or has 85%, 90%, 91%, 92%, 93%, 94%, 95%, 96%, 97%, 98%, 98.5%, 99%, 99.5% or 99.9% identity with the amino acid sequence of SEQ ID NO: 36, or any range or combination thereof; a homolog of the amino acid having the sequence of SEQ ID NO: 36.

In some embodiments, the mutant *S. lycopersicum* cv. Sweet100 sler$^{CR-2}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 37 or SEQ ID NO: 38 or has 85%, 90%, 91%, 92%, 93%, 94%, 95%, 96%, 97%, 98%, 98.5%, 99%, 99.5% or 99.9% identity with the nucleic acid sequence of SEQ ID NO: 37 or SEQ ID NO: 38. In some embodiments, the homolog of the mutant *S. lycopersicum* cv. Sweet100 sler$^{CR-2}$ gene is not a *Solanum lycopersicum* gene.

In some embodiments, the mutant *S. lycopersicum* cv. Sweet100 sler$^{CR-2}$ gene comprises, for example, a nucleic acid (e.g., DNA) having the sequence of SEQ ID NO: 37; a portion of SEQ ID NO: 37 that exhibits substantially the same activity (e.g., encodes the same polypeptide or substantially the same polypeptide that has the same activity) as a nucleic acid (e.g., DNA) having the nucleic acid sequence of SEQ ID NO: 37; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 37 or has 85%, 90%, 91%, 92%, 93%, 94%, 95%, 96%, 97%, 98%, 98.5%, 99%, 99.5% or 99.9% identity with the nucleic acid sequence of SEQ ID NO: 37, or any range or combination thereof; a homolog of the nucleic acid having the sequence of SEQ ID NO: 37.

In some embodiments, the mutant *S. lycopersicum* cv. Sweet100 sler$^{CR-2}$ gene comprises a coding sequence that comprises, for example, a nucleic acid (e.g., DNA) having the sequence of SEQ ID NO: 38; a portion of SEQ ID NO: 38 that exhibits substantially the same activity (e.g., encodes the same polypeptide or substantially the same polypeptide that has the same activity) as a nucleic acid (e.g., DNA) having the nucleic acid sequence of SEQ ID NO: 38; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 38 or has 85%, 90%, 91%, 92%, 93%, 94%, 95%, 96%, 97%, 98%, 98.5%, 99%, 99.5% or 99.9% identity with the nucleic acid sequence of SEQ ID NO: 38, or any range or combination thereof; a homolog of the nucleic acid having the sequence of SEQ ID NO: 38.

In some embodiments, the mutant *S. lycopersicum* cv. Sweet100 sler$^{CR-2}$ gene comprises a coding sequence that encodes a protein or polypeptide (e.g., amino acid sequence) having the sequence of SEQ ID NO: 39; a portion of SEQ ID NO: 39 that exhibits substantially the same activity as a protein or polypeptide having the amino acid sequence of SEQ ID NO: 39; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 39 or has 85%, 90%, 91%, 92%, 93%, 94%, 95%, 96%, 97%, 98%, 98.5%, 99%, 99.5% or 99.9% identity with the amino acid sequence of SEQ ID NO: 39, or any range or combination thereof; a homolog of the amino acid having the sequence of SEQ ID NO: 39.

In some embodiments, the mutant *S. lycopersicum* cv. Sweet100 sler$^{CR-3}$ gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 40 or SEQ ID NO: 41 or has 85%, 90%, 91%, 92%, 93%, 94%, 95%, 96%, 97%, 98%, 98.5%, 99%, 99.5% or 99.9% identity with the nucleic acid sequence of SEQ ID NO: 40 or SEQ ID NO: 41. In some embodiments, the homolog of the mutant *S. lycopersicum* cv. Sweet100 sler$^{CR-3}$ gene is not a *Solanum lycopersicum* gene.

In some embodiments, the mutant *S. lycopersicum* cv. Sweet100 sler$^{CR-3}$ gene comprises, for example, a nucleic acid (e.g., DNA) having the sequence of SEQ ID NO: 40; a portion of SEQ ID NO: 40 that exhibits substantially the same activity (e.g., encodes the same polypeptide or substantially the same polypeptide that has the same activity) as a nucleic acid (e.g., DNA) having the nucleic acid sequence of SEQ ID NO: 40; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 40 or has 85%, 90%, 91%, 92%, 93%, 94%, 95%, 96%, 97%, 98%, 98.5%, 99%, 99.5% or 99.9% identity with the nucleic acid sequence of SEQ ID NO: 40, or any range or combination thereof; a homolog of the nucleic acid having the sequence of SEQ ID NO: 40.

In some embodiments, the mutant *S. lycopersicum* cv. Sweet100 sler$^{CR-3}$ gene comprises a coding sequence that comprises, for example, a nucleic acid (e.g., DNA) having the sequence of SEQ ID NO: 41; a portion of SEQ ID NO: 41 that exhibits substantially the same activity (e.g., encodes the same polypeptide or substantially the same polypeptide that has the same activity) as a nucleic acid (e.g., DNA) having the nucleic acid sequence of SEQ ID NO: 41; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 41 or has 85%, 90%, 91%, 92%, 93%, 94%, 95%, 96%, 97%, 98%, 98.5%, 99%, 99.5% or 99.9% identity with the nucleic acid sequence of SEQ ID NO: 41, or any range or combination thereof; a homolog of the nucleic acid having the sequence of SEQ ID NO: 41.

In some embodiments, the mutant *S. lycopersicum* cv. Sweet100 sler$^{CR-3}$ gene comprises a coding sequence that encodes a protein or polypeptide (e.g., amino acid sequence) having the sequence of SEQ ID NO: 42; a portion of SEQ ID NO: 42 that exhibits substantially the same activity as a protein or polypeptide having the amino acid sequence of SEQ ID NO: 42; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 42 or has 85%, 90%, 91%, 92%, 93%, 94%, 95%, 96%, 97%, 98%, 98.5%, 99%, 99.5% or 99.9% identity with the amino acid sequence of SEQ ID NO: 42, or any range or combination thereof; a homolog of the amino acid having the sequence of SEQ ID NO: 42.

In some embodiments, a mutant Solyc08g061560 gene (or homolog thereof) comprises a nucleic acid sequence that encodes a mutant SlER protein or polypeptide that comprises a mutant leucine-rich repeat (LRR) domain. In some embodiments, the mutant LRR domain has at least 85% identity with the amino acid sequence of the LRR domain of SlER or to the LRR domain of a homolog thereof In some embodiments, the mutant LRR domain has at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of the LRR domain of SlER or to the LRR domain of a homolog thereof. In some embodiments, the amino acid sequence of the mutant LRR domain has 85%, 90%, 91%, 92%, 93%, 94%, 95%, 96%, 97%, 98%, 98.5%, 99%, 99.5% or 99.9% identity, or any range or combination thereof, with the amino acid sequence of the LRR domain of SlER or to the LRR domain of a homolog thereof In some embodiments, a mutant Solyc08g061560 gene (or homolog thereof) comprises a nucleic acid sequence that encodes a mutant SlER protein or polypeptide that comprises a mutant kinase domain. In some embodiments, the mutant kinase domain has at least 85% identity with the amino acid sequence of the kinase domain of SlER or to the kinase domain of a homolog thereof. In some embodiments, the amino acid sequence of the mutant kinase domain has at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of the kinase domain of SlER or to the kinase domain of a homolog thereof. In some embodiments, the amino acid sequence of the mutant kinase domain has 85%, 90%, 91%, 92%, 93%, 94%, 95%, 96%, 97%, 98%, 98.5%, 99%, 99.5% or 99.9% identity, or any range or combination thereof, with the amino acid sequence of the kinase domain of SlER or to the kinase domain of a homolog thereof.

Mutant Solyc03g007050 (SlERL1) Gene

Other aspects of the disclosure relate to mutants of the Solyc03g007050 gene (or a homolog thereof) as well as plants, plant cells, and seeds comprising such mutant genes, and nucleic acids comprising such mutant genes. The Solyc03g007050 gene is also referred to herein as SlER-like 1 or SlERL1. Homologs of SlERL1 can be readily identified using tools, such as BLAST, available to one of ordinary skill in the art. In some embodiments, a Solyc03g007050 gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 43 or SEQ ID NO: 44 or has 85%, 90%, 91%, 92%, 93%, 94%, 95%, 96%, 97%, 98%, 98.5%, 99%, 99.5% or 99.9% identity with the nucleic acid sequence of SEQ ID NO: 43 or SEQ ID NO: 44. In some embodiments, the homolog of the Solyc03g007050 gene is not a *Solanum lycopersicum* gene.

In some embodiments, the mutant Solyc03g007050 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (See e.g., Riethoven et al., Methods Mol Biol (2010) 674:33-42). In some embodiments, the mutant Solyc03g007050 gene (or homolog thereof) contains a mutation in an exon. In some embodiments, the mutant Solyc03g007050 gene (or homolog thereof) contains a mutation in an intron. In some embodiments, the mutant Solyc03g007050 gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant Solyc03g007050 gene (or homolog thereof) is a hypomorphic allele or a null allele. In some embodiments, a hypomorphic allele of the mutant Solyc03g007050 gene (or homolog thereof) is an allele that encodes a mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a Solanaceae plant (e.g., *Solanum lycopersicum*) comprising the mutant Solyc03g007050 gene, or homolog thereof, (e.g., a hypomorphic, knock-out or null allele disclosed) is heterozygous for the mutant Solyc03g007050 gene. In some embodiments, a Solanaceae plant (e.g., *Solanum lycopersicum*) comprising the mutant Solyc03g007050 gene, or homolog thereof, (e.g., a hypomorphic, knock-out or null allele disclosed) is homozygous for the mutant Solyc03g007050 gene.

In some embodiments, the mutant slerl1$^{CR-1}$ gene comprises, for example, a nucleic acid (e.g., DNA) having the sequence of SEQ ID NO: 46; a portion of SEQ ID NO: 46 that exhibits substantially the same activity (e.g., encodes the same polypeptide or substantially the same polypeptide that has the same activity) as a nucleic acid (e.g., DNA) having the nucleic acid sequence of SEQ ID NO: 46; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 46 or has 85%, 90%, 91%, 92%, 93%, 94%, 95%, 96%, 97%, 98%, 98.5%, 99%, 99.5% or 99.9% identity with the nucleic acid sequence of SEQ ID NO: 46, or any range or combination thereof; a homolog of the nucleic acid having the sequence of SEQ ID NO: 46.

In some embodiments, the mutant slerl1$^{CR-1}$ gene comprises a coding sequence that comprises, for example, a nucleic acid (e.g., DNA) having the sequence of SEQ ID NO: 47; a portion of SEQ ID NO: 47 that exhibits substantially the same activity (e.g., encodes the same polypeptide or substantially the same polypeptide that has the same activity) as a nucleic acid (e.g., DNA) having the nucleic acid sequence of SEQ ID NO: 47; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 47 or has 85%, 90%, 91%, 92%, 93%, 94%, 95%, 96%, 97%, 98%, 98.5%, 99%, 99.5% or 99.9% identity with the nucleic acid sequence of SEQ ID NO: 47, or any range or combination thereof; a homolog of the nucleic acid having the sequence of SEQ ID NO: 47.

In some embodiments, the mutant slerl1$^{CR-1}$ gene comprises a coding sequence that encodes a protein or polypeptide (e.g., amino acid sequence) having the sequence of SEQ ID NO: 48; a portion of SEQ ID NO: 48 that exhibits substantially the same activity as a protein or polypeptide having the amino acid sequence of SEQ ID NO: 48; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 48 or has 85%, 90%, 91%, 92%, 93%, 94%, 95%, 96%, 97%, 98%, 98.5%, 99%, 99.5% or 99.9% identity with the amino acid sequence of SEQ ID NO: 48, or any range or combination thereof; a homolog of the amino acid having the sequence of SEQ ID NO: 48.

In some embodiments, the mutant slerl1$^{CR-2}$ gene comprises, for example, a nucleic acid (e.g., DNA) having the sequence of SEQ ID NO: 49; a portion of SEQ ID NO: 49 that exhibits substantially the same activity (e.g., encodes the same polypeptide or substantially the same polypeptide that has the same activity) as a nucleic acid (e.g., DNA) having the nucleic acid sequence of SEQ ID NO: 49; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 49 or has 85%, 90%, 91%, 92%, 93%, 94%, 95%, 96%, 97%, 98%, 98.5%, 99%, 99.5% or 99.9% identity with the nucleic acid sequence of SEQ ID NO: 49, or any range or combination thereof; a homolog of the nucleic acid having the sequence of SEQ ID NO: 49.

In some embodiments, the mutant slerl1$^{CR-2}$ gene comprises a coding sequence that comprises, for example, a nucleic acid (e.g., DNA) having the sequence of SEQ ID NO: 50; a portion of SEQ ID NO: 50 that exhibits substantially the same activity (e.g., encodes the same polypeptide or substantially the same polypeptide that has the same activity) as a nucleic acid (e.g., DNA) having the nucleic acid sequence of SEQ ID NO: 50; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 50 or has 85%, 90%, 91%, 92%, 93%, 94%, 95%, 96%, 97%, 98%, 98.5%, 99%, 99.5% or 99.9% identity with the nucleic acid sequence of SEQ ID NO: 62, or any range or combination thereof; a homolog of the nucleic acid having the sequence of SEQ ID NO: 50.

In some embodiments, the mutant slerl1$^{CR-2}$ gene comprises a coding sequence that encodes a protein or polypeptide (e.g., amino acid sequence) having the sequence of SEQ ID NO: 51; a portion of SEQ ID NO: 51 that exhibits substantially the same activity as a protein or polypeptide having the amino acid sequence of SEQ ID NO: 51; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 51 or has 85%, 90%, 91%, 92%, 93%, 94%, 95%, 96%, 97%, 98%, 98.5%, 99%, 99.5% or 99.9% identity with the amino acid sequence of SEQ ID NO: 51, or any range or combination thereof; a homolog of the amino acid having the sequence of SEQ ID NO: 51.

Mutant Solyc05g053850 (SP5G) Gene

Other aspects of the disclosure relate to mutants of the Solyc05g053850 gene (or a homolog thereof) as well as plants, plant cells, and seeds comprising such mutant genes, and nucleic acids comprising such mutant genes. The Solyc05g053850 gene is also referred to herein as SP5G. Homologs of Solyc05g053850 can be readily identified using tools, such as BLAST, available to one of ordinary skill in the art. In some embodiments, a Solyc05g053850 gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 52 or SEQ ID NO: 53 or has 85%, 90%, 91%, 92%, 93%, 94%, 95%, 96%, 97%, 98%, 98.5%, 99%, 99.5% or 99.9% identity with the nucleic acid sequence of SEQ ID NO: 52 or SEQ ID NO: 53. In some embodiments, the homolog of the Solyc05g053850 gene is not a *Solanum lycopersicum* gene.

In some embodiments, the mutant Solyc05g053850 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (See e.g., Riethoven et al., Methods Mol Biol (2010) 674:33-42). In some embodiments, the promoter is a region upstream of the start codon (e.g., ATG).

In some embodiments, the mutant Solyc05g053850 gene (or homolog thereof) comprises one or more mutations in the promoter of the Solyc05g053850 gene. In some embodiments, the promoter of the Solyc05g053850 gene comprises or consists of the nucleic acid sequence of SEQ ID NO: 148. In some embodiments, the promoter of the Solyc05g053850 gene comprising one or more mutations comprises a nucleic acid sequence with at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 148. In some embodiments, the promoter of the Solyc05g053850 gene comprises one or more of a missense, frameshift, nonsense, insertion, deletion, duplication, inversion or indel mutation. In some embodiments, the promoter of the Solyc05g053850 gene comprises a deletion of or at least 10, 20, 30, 40, 50, 60, 70, 80, 90, 100, 150, 200, 250, 300, 250, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, or any range or combination thereof, of the nucleotides from the nucleic acid sequence comprising the promoter. In some embodiments, one continuous nucleic acid sequence is deleted from the promoter. In some embodiments, two or more nucleic acid sequences are deleted from the promoter, wherein the sequences are not contiguous.

In some embodiments, the mutant Solyc05g053850 gene (or homolog thereof) contains a mutation in an exon. In some embodiments, the mutant Solyc05g053850 gene (or homolog thereof) contains a mutation in an intron. In some embodiments, the mutant Solyc05g053850 gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant Solyc05g053850 gene (or homolog thereof) is a hypomorphic allele or a null allele. In some embodiments, a hypomorphic allele of the mutant Solyc05g053850 gene (or homolog thereof) is an allele that encodes a mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a Solanaceae plant (e.g., *Solanum lycopersicum*) comprising the mutant Solyc05g053850 gene, or homolog thereof, (e.g., a hypomorphic, knock-out or null allele disclosed) is heterozygous for the mutant Solyc05g053850 gene. In some embodiments, a Solanaceae plant (e.g., *Solanum lycopersicum*) comprising the mutant Solyc05g053850 gene, or homolog thereof, (e.g., a hypomorphic, knock-out or null allele disclosed) is homozygous for the mutant Solyc05g053850 gene.

In some embodiments, the mutant *S. lycopersicum* cv. M82 sp5g gene comprises, for example, a nucleic acid (e.g., DNA) having the sequence of SEQ ID NO: 55; a portion of SEQ ID NO: 55 that exhibits substantially the same activity (e.g., encodes the same polypeptide or substantially the same polypeptide that has the same activity) as a nucleic acid (e.g., DNA) having the nucleic acid sequence of SEQ ID NO: 55; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 55 or has 85%, 90%, 91%, 92%, 93%, 94%, 95%, 96%, 97%, 98%, 98.5%, 99%, 99.5% or 99.9% identity with the nucleic acid sequence of SEQ ID NO: 55, or any range or combination thereof; a homolog of the nucleic acid having the sequence of SEQ ID NO: 55.

In some embodiments, the mutant *S. lycopersicum* cv. M82 sp5g gene comprises a coding sequence that comprises, for example, a nucleic acid (e.g., DNA) having the sequence of SEQ ID NO: 56; a portion of SEQ ID NO: 56 that exhibits substantially the same activity (e.g., encodes the same polypeptide or substantially the same polypeptide that has the same activity) as a nucleic acid (e.g., DNA) having the nucleic acid sequence of SEQ ID NO: 56; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 56 or has 85%, 90%, 91%, 92%, 93%, 94%, 95%, 96%, 97%, 98%, 98.5%, 99%, 99.5% or 99.9% identity with the nucleic acid sequence of SEQ ID NO: 56, or any range or combination thereof; a homolog of the nucleic acid having the sequence of SEQ ID NO: 56.

In some embodiments, the mutant *S. lycopersicum* cv. M82 sp5g gene comprises a coding sequence that encodes a protein or polypeptide (e.g., amino acid sequence) having the sequence of SEQ ID NO: 57; a portion of SEQ ID NO: 57 that exhibits substantially the same activity as a protein or polypeptide having the amino acid sequence of SEQ ID NO: 57; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 57 or has 85%, 90%, 91%, 92%, 93%, 94%, 95%, 96%, 97%, 98%, 98.5%, 99%, 99.5% or 99.9% identity with the amino acid sequence of SEQ ID NO: 57, or any range or combination thereof; a homolog of the amino acid having the sequence of SEQ ID NO: 57.

In some embodiments, the mutant *S. lycopersicum* cv. Sweet100 sp5g comprises, for example, a nucleic acid (e.g., DNA) having the sequence of SEQ ID NO: 58; a portion of SEQ ID NO: 58 that exhibits substantially the same activity (e.g., encodes the same polypeptide or substantially the same polypeptide that has the same activity) as a nucleic acid (e.g., DNA) having the nucleic acid sequence of SEQ ID NO: 58; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 58 or has 85%, 90%, 91%, 92%, 93%, 94%, 95%, 96%, 97%, 98%, 98.5%, 99%, 99.5% or 99.9% identity with the nucleic acid sequence of SEQ ID NO: 58, or any range or combination thereof; a homolog of the nucleic acid having the sequence of SEQ ID NO: 58.

In some embodiments, the mutant *S. lycopersicum* cv. Sweet100 sp5g comprises a coding sequence that comprises, for example, a nucleic acid (e.g., DNA) having the sequence of SEQ ID NO: 59; a portion of SEQ ID NO: 59 that exhibits substantially the same activity (e.g., encodes the same polypeptide or substantially the same polypeptide that has the same activity) as a nucleic acid (e.g., DNA) having the nucleic acid sequence of SEQ ID NO: 59; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 59 or has 85%, 90%, 91%, 92%, 93%, 94%, 95%, 96%, 97%, 98%, 98.5%, 99%, 99.5% or 99.9% identity with the nucleic acid sequence of SEQ ID NO: 59, or any range or combination thereof; a homolog of the nucleic acid having the sequence of SEQ ID NO: 59.

In some embodiments, the mutant *S. lycopersicum* cv. Sweet100 sp5g comprises a coding sequence that encodes a protein or polypeptide (e.g., amino acid sequence) having the sequence of SEQ ID NO: 60; a portion of SEQ ID NO: 60 that exhibits substantially the same activity as a protein or polypeptide having the amino acid sequence of SEQ ID NO: 60; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 60 or has 85%, 90%, 91%, 92%, 93%, 94%, 95%, 96%, 97%, 98%, 98.5%, 99%, 99.5% or 99.9% identity with the amino acid sequence of SEQ ID NO: 60, or any range or combination thereof; a homolog of the amino acid having the sequence of SEQ ID NO: 60.

In some embodiments, the mutant sp5g-cocktail gene comprises, for example, a nucleic acid (e.g., DNA) having the sequence of SEQ ID NO: 61; a portion of SEQ ID NO: 61 that exhibits substantially the same activity (e.g., encodes the same polypeptide or substantially the same polypeptide that has the same activity) as a nucleic acid (e.g., DNA) having the nucleic acid sequence of SEQ ID NO: 61; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 61 or has 85%, 90%, 91%, 92%, 93%, 94%, 95%, 96%, 97%, 98%, 98.5%, 99%, 99.5% or 99.9% identity with the nucleic acid sequence of SEQ ID NO: 61, or any range or combination thereof; a homolog of the nucleic acid having the sequence of SEQ ID NO: 61.

In some embodiments, the mutant sp5g-cocktail gene comprises a coding sequence that comprises, for example, a nucleic acid (e.g., DNA) having the sequence of SEQ ID NO: 62; a portion of SEQ ID NO: 62 that exhibits substantially the same activity (e.g., encodes the same polypeptide or substantially the same polypeptide that has the same activity) as a nucleic acid (e.g., DNA) having the nucleic acid sequence of SEQ ID NO: 62; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 62 or has 85%, 90%, 91%, 92%, 93%, 94%, 95%, 96%, 97%, 98%, 98.5%, 99%, 99.5% or 99.9% identity with the nucleic acid sequence of SEQ ID NO: 62, or any range or combination thereof; a homolog of the nucleic acid having the sequence of SEQ ID NO: 62.

In some embodiments, the mutant sp5g-cocktail gene comprises a coding sequence that encodes a protein or polypeptide (e.g., amino acid sequence) having the sequence of SEQ ID NO: 63; a portion of SEQ ID NO: 63 that exhibits substantially the same activity as a protein or polypeptide having the amino acid sequence of SEQ ID NO: 63; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 63 or has 85%, 90%, 91%, 92%, 93%, 94%, 95%, 96%, 97%, 98%, 98.5%, 99%, 99.5% or 99.9% identity with the amino acid sequence of SEQ ID NO: 63, or any range or combination thereof; a homolog of the amino acid having the sequence of SEQ ID NO: 63.

In some embodiments, the mutant sp5g-grape gene comprises, for example, a nucleic acid (e.g., DNA) having the sequence of SEQ ID NO: 64; a portion of SEQ ID NO: 64 that exhibits substantially the same activity (e.g., encodes the same polypeptide or substantially the same polypeptide that has the same activity) as a nucleic acid (e.g., DNA) having the nucleic acid sequence of SEQ ID NO: 64; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 64 or has 85%, 90%, 91%, 92%, 93%, 94%, 95%, 96%, 97%, 98%, 98.5%, 99%, 99.5% or 99.9% identity with the nucleic acid sequence of SEQ ID NO: 64, or any range or combination thereof; a homolog of the nucleic acid having the sequence of SEQ ID NO: 64.

In some embodiments, the mutant sp5g-grape gene comprises a coding sequence that comprises, for example, a nucleic acid (e.g., DNA) having the sequence of SEQ ID NO: 65; a portion of SEQ ID NO: 65 that exhibits substantially the same activity (e.g., encodes the same polypeptide or substantially the same polypeptide that has the same activity) as a nucleic acid (e.g., DNA) having the nucleic acid sequence of SEQ ID NO: 65; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 65 or has 85%, 90%, 91%, 92%, 93%, 94%, 95%, 96%, 97%, 98%, 98.5%, 99%, 99.5% or 99.9% identity with the nucleic acid sequence of SEQ ID NO: 65, or any range or combination thereof; a homolog of the nucleic acid having the sequence of SEQ ID NO: 65.

In some embodiments, the mutant sp5g-grape gene comprises a coding sequence that encodes a protein or polypeptide (e.g., amino acid sequence) having the sequence of SEQ ID NO: 66; a portion of SEQ ID NO: 66 that exhibits substantially the same activity as a protein or polypeptide having the amino acid sequence of SEQ ID NO: 66; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 66 or has 85%, 90%, 91%, 92%, 93%, 94%, 95%, 96%, 97%, 98%, 98.5%, 99%, 99.5% or 99.9% identity with the amino acid sequence of SEQ ID NO: 66, or any range or combination thereof; a homolog of the amino acid having the sequence of SEQ ID NO: 66.

Mutant Solyc06g074350 (SP) Gene

Other aspects of the disclosure relate to mutants of the Solyc06g074350 gene (or a homolog thereof) as well as plants, plant cells, and seeds comprising such mutant genes, and nucleic acids comprising such mutant genes. The Solyc06g074350 gene is also referred to herein as self-pruning or SP. Homologs of Solyc06g074350 can be readily identified using tools, such as BLAST, available to one of ordinary skill in the art. In some embodiments, a Solyc06g074350 gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 67 or SEQ ID NO: 68 or has 85%, 90%, 91%, 92%, 93%, 94%, 95%, 96%, 97%, 98%, 98.5%, 99%, 99.5% or 99.9% identity with the nucleic acid sequence of SEQ ID NO: 79 or SEQ ID NO: 68. In some embodiments, the homolog of the Solyc06g074350 gene is not a *Solanum lycopersicum* gene.

In some embodiments, the mutant Solyc06g074350 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (See e.g., Riethoven et al., Methods Mol Biol (2010) 674:33-42). In some embodiments, the promoter is a region upstream of the start codon (e.g., ATG).

In some embodiments, the mutant Solyc06g074350 gene (or homolog thereof) comprises one or more mutations in the promoter of the Solyc06g074350 gene. In some embodiments, the promoter of the Solyc06g074350 gene comprises or consists of the nucleic acid sequence of SEQ ID NO: 149. In some embodiments, the promoter of the Solyc06g074350 gene comprising one or more mutations comprises a nucleic acid sequence with at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 149. In some embodiments, the promoter of the Solyc06g074350 gene comprises one or more of a missense, frameshift, nonsense, insertion, deletion, duplication, inversion or indel mutation. In some embodiments, the promoter of the Solyc06g074350 gene comprises a deletion of or at least 10, 20, 30, 40, 50, 60, 70, 80, 90, 100, 150, 200, 250, 300, 250, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000, or any range or combination thereof, of the nucleotides from the nucleic acid sequence comprising the promoter. In some embodiments, one continuous nucleic acid sequence is deleted from the promoter. In some embodiments, two or more nucleic acid sequences are deleted from the promoter, wherein the sequences are not contiguous.

In some embodiments, the mutant Solyc06g074350 gene (or homolog thereof) contains a mutation in an exon. In some embodiments, the mutant Solyc06g074350 gene (or homolog thereof) contains a mutation in an intron. In some embodiments, the mutant Solyc06g074350 gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant Solyc06g074350 gene (or homolog thereof) is a hypomorphic allele or a null allele. In some embodiments, a hypomorphic allele is an allele that results in an mRNA or protein expression level of the gene of interest that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than an mRNA or protein expression level that results from an allele of the gene of interest that does not contain the mutation (e.g., a wild-type allele or an allele with a mutation in a gene other than a Solyc06g074350 gene (or homolog thereof)).

In some embodiments, a Solanaceae plant (e.g., *Solanum lycopersicum*) comprising the mutant Solyc06g074350 gene, or homolog thereof, (e.g., a hypomorphic, knock-out or null allele disclosed) is heterozygous for the mutant Solyc06g074350 gene. In some embodiments, a Solanaceae plant (e.g., *Solanum lycopersicum*) comprising the mutant Solyc06g074350 gene, or homolog thereof, (e.g., a hypomorphic, knock-out or null allele disclosed) is homozygous for the mutant Solyc06g074350 gene.

In some embodiments, the mutant *S. lycopersicum* cv. M82 sp gene comprises, for example, a nucleic acid (e.g., DNA) having the sequence of SEQ ID NO: 70; a portion of SEQ ID NO: 70 that exhibits substantially the same activity (e.g., encodes the same polypeptide or substantially the same polypeptide that has the same activity) as a nucleic acid (e.g., DNA) having the nucleic acid sequence of SEQ ID NO: 70; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 70 or has 85%, 90%, 91%, 92%, 93%, 94%, 95%, 96%, 97%, 98%, 98.5%, 99%, 99.5% or 99.9% identity with the nucleic acid sequence of SEQ ID NO: 70, or any range or combination thereof; a homolog of the nucleic acid having the sequence of SEQ ID NO: 70.

In some embodiments, the mutant *S. lycopersicum* cv. M82 sp gene comprises a coding sequence that comprises, for example, a nucleic acid (e.g., DNA) having the sequence of SEQ ID NO: 71; a portion of SEQ ID NO: 71 that exhibits substantially the same activity (e.g., encodes the same polypeptide or substantially the same polypeptide that has the same activity) as a nucleic acid (e.g., DNA) having the nucleic acid sequence of SEQ ID NO: 71; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 71 or has 85%, 90%, 91%, 92%, 93%, 94%, 95%, 96%, 97%, 98%, 98.5%, 99%, 99.5% or 99.9% identity with the nucleic acid sequence of SEQ ID NO: 71, or any range or combination thereof; a homolog of the nucleic acid having the sequence of SEQ ID NO: 71.

In some embodiments, the mutant *S. lycopersicum* cv. M82 sp gene comprises a coding sequence that encodes a protein or polypeptide (e.g., amino acid sequence) having the sequence of SEQ ID NO: 72; a portion of SEQ ID NO: 72 that exhibits substantially the same activity as a protein or polypeptide having the amino acid sequence of SEQ ID NO: 72; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 72 or has 85%, 90%, 91%, 92%, 93%, 94%, 95%, 96%, 97%, 98%, 98.5%, 99%, 99.5% or 99.9% identity with the amino acid sequence of SEQ ID NO: 72, or any range or combination thereof; a homolog of the amino acid having the sequence of SEQ ID NO: 72.

In some embodiments, the mutant $sp^{CR}$ gene comprises, for example, a nucleic acid (e.g., DNA) having the sequence of SEQ ID NO: 73; a portion of SEQ ID NO: 73 that exhibits substantially the same activity (e.g., encodes the same polypeptide or substantially the same polypeptide that has the same activity) as a nucleic acid (e.g., DNA) having the nucleic acid sequence of SEQ ID NO: 73; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 73 or has 85%, 90%, 91%, 92%, 93%, 94%, 95%, 96%, 97%, 98%, 98.5%, 99%, 99.5% or 99.9% identity with the nucleic acid sequence of SEQ ID NO: 73, or any range or combination thereof; a homolog of the nucleic acid having the sequence of SEQ ID NO: 73.

In some embodiments, the mutant $sp^{CR}$ gene comprises a coding sequence that comprises, for example, a nucleic acid (e.g., DNA) having the sequence of SEQ ID NO: 74; a portion of SEQ ID NO: 74 that exhibits substantially the same activity (e.g., encodes the same polypeptide or substantially the same polypeptide that has the same activity) as a nucleic acid (e.g., DNA) having the nucleic acid sequence of SEQ ID NO: 74; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 74 or has 85%, 90%, 91%, 92%, 93%, 94%, 95%, 96%, 97%, 98%, 98.5%, 99%, 99.5% or 99.9% identity with the nucleic acid sequence of SEQ ID NO: 74, or any range or combination thereof; a homolog of the nucleic acid having the sequence of SEQ ID NO: 74.

In some embodiments, the mutant $sp^{CR}$ gene comprises a coding sequence that encodes a protein or polypeptide (e.g., amino acid sequence) having the sequence of SEQ ID NO: 75; a portion of SEQ ID NO: 75 that exhibits substantially the same activity as a protein or polypeptide having the amino acid sequence of SEQ ID NO: 75; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 75 or has 85%, 90%, 91%, 92%, 93%, 94%, 95%, 96%, 97%, 98%, 98.5%, 99%, 99.5% or 99.9% identity with the amino acid sequence of SEQ ID NO: 75, or any range or combination thereof; a homolog of the amino acid having the sequence of SEQ ID NO: 75.

In some embodiments, the mutant *S. lycopersicum* cv. Sweet100 sp gene comprises, for example, a nucleic acid (e.g., DNA) having the sequence of SEQ ID NO: 76; a portion of SEQ ID NO: 76 that exhibits substantially the same activity (e.g., encodes the same polypeptide or substantially the same polypeptide that has the same activity) as a nucleic acid (e.g., DNA) having the nucleic acid sequence of SEQ ID NO: 76; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 76 or has 85%, 90%, 91%, 92%, 93%, 94%, 95%, 96%, 97%, 98%, 98.5%, 99%, 99.5% or 99.9% identity with the nucleic acid sequence of SEQ ID NO: 76, or any range or combination thereof; a homolog of the nucleic acid having the sequence of SEQ ID NO: 76.

In some embodiments, the mutant *S. lycopersicum* cv. Sweet100 sp gene comprises a coding sequence that comprises, for example, a nucleic acid (e.g., DNA) having the sequence of SEQ ID NO: 77; a portion of SEQ ID NO: 77 that exhibits substantially the same activity (e.g., encodes the same polypeptide or substantially the same polypeptide that has the same activity) as a nucleic acid (e.g., DNA) having the nucleic acid sequence of SEQ ID NO: 77; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 77 or has 85%, 90%, 91%, 92%, 93%, 94%, 95%, 96%, 97%, 98%, 98.5%, 99%, 99.5% or 99.9% identity with the nucleic acid sequence of SEQ ID NO: 77, or any range or combination thereof; a homolog of the nucleic acid having the sequence of SEQ ID NO: 77.

In some embodiments, the mutant *S. lycopersicum* cv. Sweet100 sp gene comprises a coding sequence that encodes a protein or polypeptide (e.g., amino acid sequence) having the sequence of SEQ ID NO: 78; a portion of SEQ ID NO: 78 that exhibits substantially the same activity as a protein or polypeptide having the amino acid sequence of SEQ ID NO: 78; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 78 or has 85%, 90%, 91%, 92%, 93%, 94%, 95%, 96%, 97%, 98%, 98.5%, 99%, 99.5% or 99.9% identity with the amino acid sequence of SEQ ID NO: 78, or any range or combination thereof; a homolog of the amino acid having the sequence of SEQ ID NO: 78.

In some embodiments, the mutant sp-cocktail gene comprises, for example, a nucleic acid (e.g., DNA) having the sequence of SEQ ID NO: 79; a portion of SEQ ID NO: 79 that exhibits substantially the same activity (e.g., encodes the same polypeptide or substantially the same polypeptide that has the same activity) as a nucleic acid (e.g., DNA) having the nucleic acid sequence of SEQ ID NO: 79; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 79 or has 85%, 90%, 91%, 92%, 93%, 94%, 95%, 96%, 97%, 98%, 98.5%, 99%, 99.5% or 99.9% identity with the nucleic acid sequence of SEQ ID NO: 79, or any range or combination thereof; a homolog of the nucleic acid having the sequence of SEQ ID NO: 79.

In some embodiments, the mutant sp-cocktail gene comprises a coding sequence that comprises, for example, a nucleic acid (e.g., DNA) having the sequence of SEQ ID NO: 80; a portion of SEQ ID NO: 80 that exhibits substantially the same activity (e.g., encodes the same polypeptide or substantially the same polypeptide that has the same activity) as a nucleic acid (e.g., DNA) having the nucleic acid sequence of SEQ ID NO: 80; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 80 or has 85%, 90%, 91%, 92%, 93%, 94%, 95%, 96%, 97%, 98%, 98.5%, 99%, 99.5% or 99.9% identity with the nucleic acid sequence of SEQ ID NO: 80, or any range or combination thereof; a homolog of the nucleic acid having the sequence of SEQ ID NO: 80.

In some embodiments, the mutant sp-cocktail gene comprises a coding sequence that encodes a protein or polypeptide (e.g., amino acid sequence) having the sequence of SEQ ID NO: 81; a portion of SEQ ID NO: 81 that exhibits substantially the same activity as a protein or polypeptide having the amino acid sequence of SEQ ID NO: 81; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 81 or has 85%, 90%, 91%, 92%, 93%, 94%, 95%, 96%, 97%, 98%, 98.5%, 99%, 99.5% or 99.9% identity with the amino acid sequence of SEQ ID NO: 81, or any range or combination thereof; a homolog of the amino acid having the sequence of SEQ ID NO: 81.

In some embodiments, the mutant sp-grape gene comprises, for example, a nucleic acid (e.g., DNA) having the sequence of SEQ ID NO: 82; a portion of SEQ ID NO: 82 that exhibits substantially the same activity (e.g., encodes the same polypeptide or substantially the same polypeptide that has the same activity) as a nucleic acid (e.g., DNA) having the nucleic acid sequence of SEQ ID NO: 82; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 82 or has 85%, 90%, 91%, 92%, 93%, 94%, 95%, 96%, 97%, 98%, 98.5%, 99%, 99.5% or 99.9% identity with the nucleic acid sequence of SEQ ID NO: 82, or any range or combination thereof; a homolog of the nucleic acid having the sequence of SEQ ID NO: 82.

In some embodiments, the mutant sp-grape gene comprises a coding sequence that comprises, for example, a nucleic acid (e.g., DNA) having the sequence of SEQ ID NO: 83; a portion of SEQ ID NO: 83 that exhibits substantially the same activity (e.g., encodes the same polypeptide or substantially the same polypeptide that has the same activity) as a nucleic acid (e.g., DNA) having the nucleic acid sequence of SEQ ID NO: 83; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 83 or has 85%, 90%, 91%, 92%, 93%, 94%, 95%, 96%, 97%, 98%, 98.5%, 99%, 99.5% or 99.9% identity with the nucleic acid sequence of SEQ ID NO: 83, or any range or combination thereof; a homolog of the nucleic acid having the sequence of SEQ ID NO: 83.

In some embodiments, the mutant sp-grape gene comprises a coding sequence that encodes a protein or polypeptide (e.g., amino acid sequence) having the sequence of SEQ ID NO: 84; a portion of SEQ ID NO: 84 that exhibits substantially the same activity as a protein or polypeptide having the amino acid sequence of SEQ ID NO: 84; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 84 or has 85%, 90%, 91%, 92%, 93%, 94%, 95%, 96%, 97%, 98%, 98.5%, 99%, 99.5% or 99.9% identity with the amino acid sequence of SEQ ID NO: 84, or any range or combination thereof; a homolog of the amino acid having the sequence of SEQ ID NO: 84.

Mutant Solyc04g072570 (SlSERK1) Gene

Other aspects of the disclosure relate to mutants of the Solyc04g072570 gene (or a homolog thereof) as well as plants, plant cells, and seeds comprising such mutant genes, and nucleic acids comprising such mutant genes. The Solyc04g072570 gene is also referred to herein as somatic embryogenesis receptor kinase 1 or SlSERK1. Homologs of Solyc04g072570 can be readily identified using tools, such as BLAST, available to one of ordinary skill in the art. In some embodiments, a Solyc04g072570 gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of SEQ ID NO: 85 or SEQ ID NO: 86 or has 85%, 90%, 91%, 92%, 93%, 94%, 95%, 96%, 97%, 98%, 98.5%, 99%, 99.5% or 99.9% identity with the nucleic acid sequence of SEQ ID NO: 85 or SEQ ID NO: 86. In some embodiments, the homolog of the Solyc04g072570 gene is not a *Solanum lycopersicum* gene.

In some embodiments, the mutant Solyc04g072570 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (see, e.g., Riethoven et al., Methods Mol Biol (2010) 674:33-42). In some embodiments, the mutant Solyc04g072570 gene (or homolog thereof) contains a mutation in an exon. In some embodiments, the mutant Solyc04g072570 gene (or homolog thereof) contains a mutation in an intron. In some embodiments, the mutant Solyc04g072570 gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant Solyc04g072570 gene (or homolog thereof) is a hypomorphic allele or a null allele. In some embodiments, a hypomorphic allele of the mutant Solyc04g072570 gene (or homolog thereof) is an allele that encodes a mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a Solanaceae plant (e.g., *Solanum lycopersicum*) comprising the mutant Solyc04g072570 gene, or homolog thereof, (e.g., a hypomorphic, knock-out or null allele disclosed) is heterozygous for the mutant Solyc04g072570 gene. In some embodiments, a Solanaceae plant (e.g., *Solanum lycopersicum*) comprising the mutant Solyc04g072570 gene, or homolog thereof, (e.g., a hypomorphic, knock-out or null allele disclosed) is homozygous for the mutant Solyc04g072570 gene.

In some embodiments, the mutant slserk1' gene comprises, for example, a nucleic acid (e.g., DNA) having the sequence of SEQ ID NO: 88; a portion of SEQ ID NO: 88 that exhibits substantially the same activity (e.g., encodes the same polypeptide or substantially the same polypeptide that has the same activity) as a nucleic acid (e.g., DNA) having the nucleic acid sequence of SEQ ID NO: 88; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 88 or has 85%, 90%, 91%, 92%, 93%, 94%, 95%, 96%, 97%, 98%, 98.5%, 99%, 99.5% or 99.9% identity with the nucleic acid sequence of SEQ ID NO: 88, or any range or combination thereof; a homolog of the nucleic acid having the sequence of SEQ ID NO: 88.

In some embodiments, the mutant slserk1$^{W}$ gene comprises a coding sequence that comprises, for example, a nucleic acid (e.g., DNA) having the sequence of SEQ ID NO: 89; a portion of SEQ ID NO: 89 that exhibits substantially the same activity (e.g., encodes the same polypeptide or substantially the same polypeptide that has the same activity) as a nucleic acid (e.g., DNA) having the nucleic acid sequence of SEQ ID NO: 89; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 89 or has 85%, 90%, 91%, 92%, 93%, 94%, 95%, 96%, 97%, 98%, 98.5%, 99%, 99.5% or 99.9% identity with the nucleic acid sequence of SEQ ID NO: 89, or any range or combination thereof; a homolog of the nucleic acid having the sequence of SEQ ID NO: 89.

In some embodiments, the mutant slserk1$^{W}$ gene comprises a coding sequence that encodes a protein or polypeptide (e.g., amino acid sequence) having the sequence of SEQ ID NO: 90; a portion of SEQ ID NO: 90 that exhibits substantially the same activity as a protein or polypeptide having the amino acid sequence of SEQ ID NO: 90; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 90 or has 85%, 90%, 91%, 92%, 93%, 94%, 95%, 96%, 97%, 98%, 98.5%, 99%, 99.5% or 99.9% identity with the amino acid sequence of SEQ ID NO: 90, or any range or combination thereof; a homolog of the amino acid having the sequence of SEQ ID NO: 90.

In some embodiments, the mutant slserk1$^{S1}$ gene comprises, for example, a nucleic acid (e.g., DNA) having the sequence of SEQ ID NO: 91; a portion of SEQ ID NO: 91 that exhibits substantially the same activity (e.g., encodes the same polypeptide or substantially the same polypeptide that has the same activity) as a nucleic acid (e.g., DNA) having the nucleic acid sequence of SEQ ID NO: 91; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 91 or has 85%, 90%, 91%, 92%, 93%, 94%, 95%, 96%, 97%, 98%, 98.5%, 99%, 99.5% or 99.9% identity with the nucleic acid sequence of SEQ ID NO: 91, or any range or combination thereof; a homolog of the nucleic acid having the sequence of SEQ ID NO: 91.

In some embodiments, the mutant slserk1$^{S1}$ gene comprises a coding sequence that comprises, for example, a nucleic acid (e.g., DNA) having the sequence of SEQ ID NO: 92; a portion of SEQ ID NO: 92 that exhibits substantially the same activity (e.g., encodes the same polypeptide or substantially the same polypeptide that has the same activity) as a nucleic acid (e.g., DNA) having the nucleic acid sequence of SEQ ID NO: 92; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 92 or has 85%, 90%, 91%, 92%, 93%, 94%, 95%, 96%, 97%, 98%, 98.5%, 99%, 99.5% or 99.9% identity with the nucleic acid sequence of SEQ ID NO: 92, or any range or combination thereof; a homolog of the nucleic acid having the sequence of SEQ ID NO: 92.

In some embodiments, the mutant slserk1$^{S1}$ gene comprises a coding sequence that encodes a protein or polypeptide (e.g., amino acid sequence) having the sequence of SEQ ID NO: 93; a portion of SEQ ID NO: 93 that exhibits substantially the same activity as a protein or polypeptide having the amino acid sequence of SEQ ID NO: 93; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 93 or has 85%, 90%, 91%, 92%, 93%, 94%, 95%, 96%, 97%, 98%, 98.5%, 99%, 99.5% or 99.9% identity with the amino acid sequence of SEQ ID NO: 93, or any range or combination thereof; a homolog of the amino acid having the sequence of SEQ ID NO: 93.

In some embodiments, the mutant slserk1$^{S2}$ gene comprises, for example, a nucleic acid (e.g., DNA) having the sequence of SEQ ID NO: 94; a portion of SEQ ID NO: 94 that exhibits substantially the same activity (e.g., encodes the same polypeptide or substantially the same polypeptide that has the same activity) as a nucleic acid (e.g., DNA) having the nucleic acid sequence of SEQ ID NO: 94; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 94 or has 85%, 90%, 91%, 92%, 93%, 94%, 95%, 96%, 97%, 98%, 98.5%, 99%, 99.5% or 99.9% identity with the nucleic acid sequence of SEQ ID NO: 94, or any range or combination thereof; a homolog of the nucleic acid having the sequence of SEQ ID NO: 94.

In some embodiments, the mutant slserk1$^{S2}$ gene comprises a coding sequence that comprises, for example, a nucleic acid (e.g., DNA) having the sequence of SEQ ID NO: 95; a portion of SEQ ID NO: 95 that exhibits substantially the same activity (e.g., encodes the same polypeptide or substantially the same polypeptide that has the same activity) as a nucleic acid (e.g., DNA) having the nucleic acid sequence of SEQ ID NO: 95; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 95 or has 85%, 90%, 91%, 92%, 93%, 94%, 95%, 96%, 97%, 98%, 98.5%, 99%, 99.5% or 99.9% identity with the nucleic acid sequence of SEQ ID NO: 95, or any range or combination thereof; a homolog of the nucleic acid having the sequence of SEQ ID NO: 95.

In some embodiments, the mutant slserk1$^{S2}$ gene comprises a coding sequence that encodes a protein or polypeptide (e.g., amino acid sequence) having the sequence of SEQ ID NO: 96; a portion of SEQ ID NO: 96 that exhibits substantially the same activity as a protein or polypeptide having the amino acid sequence of SEQ ID NO: 96; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 96 or has 85%, 90%, 91%, 92%, 93%, 94%, 95%, 96%, 97%, 98%, 98.5%, 99%, 99.5% or 99.9% identity with the amino acid sequence of SEQ ID NO: 96, or any range or combination thereof; a homolog of the amino acid having the sequence of SEQ ID NO: 96.

In some embodiments, the mutant slserk1$^{CR\text{-}5\text{-}a1}$ gene comprises, for example, a nucleic acid (e.g., DNA) having the sequence of SEQ ID NO: 97; a portion of SEQ ID NO: 97 that exhibits substantially the same activity (e.g., encodes the same polypeptide or substantially the same polypeptide that has the same activity) as a nucleic acid (e.g., DNA) having the nucleic acid sequence of SEQ ID NO: 97; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 97 or has 85%, 90%, 91%, 92%, 93%, 94%, 95%, 96%, 97%, 98%, 98.5%, 99%, 99.5% or 99.9% identity with the nucleic acid sequence of SEQ ID NO: 97, or any range or combination thereof; a homolog of the nucleic acid having the sequence of SEQ ID NO: 97.

In some embodiments, the mutant slserk1$^{CR\text{-}5\text{-}a1}$ gene comprises a coding sequence that comprises, for example, a nucleic acid (e.g., DNA) having the sequence of SEQ ID NO: 98; a portion of SEQ ID NO: 98 that exhibits substantially the same activity (e.g., encodes the same polypeptide or substantially the same polypeptide that has the same activity) as a nucleic acid (e.g., DNA) having the nucleic acid sequence of SEQ ID NO: 98; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 98 or has 85%, 90%, 91%, 92%, 93%, 94%, 95%, 96%, 97%, 98%, 98.5%, 99%, 99.5% or 99.9% identity with the nucleic acid sequence of SEQ ID NO: 98, or any range or combination thereof; a homolog of the nucleic acid having the sequence of SEQ ID NO: 98.

In some embodiments, the mutant slserk1$^{CR\text{-}5\text{-}a1}$ gene comprises a coding sequence that encodes a protein or polypeptide (e.g., amino acid sequence) having the sequence of SEQ ID NO: 99; a portion of SEQ ID NO: 99 that exhibits substantially the same activity as a protein or polypeptide having the amino acid sequence of SEQ ID NO: 99; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 99 or has 85%, 90%, 91%, 92%, 93%, 94%, 95%, 96%, 97%, 98%, 98.5%, 99%, 99.5% or 99.9% identity with the amino acid sequence of SEQ ID NO: 99, or any range or combination thereof; a homolog of the amino acid having the sequence of SEQ ID NO: 99.

In some embodiments, the mutant slserk1$^{CR\text{-}5\text{-}a2}$ gene comprises, for example, a nucleic acid (e.g., DNA) having the sequence of SEQ ID NO: 100; a portion of SEQ ID NO: 100 that exhibits substantially the same activity (e.g., encodes the same polypeptide or substantially the same polypeptide that has the same activity) as a nucleic acid (e.g., DNA) having the nucleic acid sequence of SEQ ID NO: 100; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 100 or has 85%, 90%, 91%, 92%, 93%, 94%, 95%, 96%, 97%, 98%, 98.5%, 99%, 99.5% or 99.9% identity with the nucleic acid sequence of SEQ ID NO: 100, or any range or combination thereof; a homolog of the nucleic acid having the sequence of SEQ ID NO: 100.

In some embodiments, the mutant slserk1$^{CR\text{-}5\text{-}a2}$ gene comprises a coding sequence that comprises, for example, a nucleic acid (e.g., DNA) having the sequence of SEQ ID NO: 101; a portion of SEQ ID NO: 101 that exhibits substantially the same activity (e.g., encodes the same polypeptide or substantially the same polypeptide that has the same activity) as a nucleic acid (e.g., DNA) having the nucleic acid sequence of SEQ ID NO: 101; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 101 or has 85%, 90%, 91%, 92%, 93%, 94%, 95%, 96%, 97%, 98%, 98.5%, 99%, 99.5% or 99.9% identity with the nucleic acid sequence of SEQ ID NO: 101, or any range or combination thereof; a homolog of the nucleic acid having the sequence of SEQ ID NO: 101.

In some embodiments, the mutant slserk1$^{CR\text{-}5\text{-}a2}$ gene comprises a coding sequence that encodes a protein or polypeptide (e.g., amino acid sequence) having the sequence of SEQ ID NO: 102; a portion of SEQ ID NO: 102 that exhibits substantially the same activity as a protein or polypeptide having the amino acid sequence of SEQ ID NO: 102; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 102 or has 85%, 90%, 91%, 92%, 93%, 94%, 95%, 96%, 97%, 98%, 98.5%, 99%, 99.5% or 99.9% identity with the amino acid sequence of SEQ ID NO: 102, or any range or combination thereof; a homolog of the amino acid having the sequence of SEQ ID NO: 102.

In some embodiments, the mutant slserk1$^{CR\text{-}5\text{-}a3}$ gene comprises, for example, a nucleic acid (e.g., DNA) having the sequence of SEQ ID NO: 103; a portion of SEQ ID NO: 103 that exhibits substantially the same activity (e.g., encodes the same polypeptide or substantially the same polypeptide that has the same activity) as a nucleic acid (e.g., DNA) having the nucleic acid sequence of SEQ ID NO: 103; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 103 or has 85%, 90%, 91%, 92%, 93%, 94%, 95%, 96%, 97%, 98%, 98.5%, 99%, 99.5% or 99.9% identity with the nucleic acid sequence of SEQ ID NO: 103, or any range or combination thereof; a homolog of the nucleic acid having the sequence of SEQ ID NO: 103.

In some embodiments, the mutant slserk1$^{CR\text{-}5\text{-}a3}$ gene comprises a coding sequence that comprises, for example, a nucleic acid (e.g., DNA) having the sequence of SEQ ID NO: 104; a portion of SEQ ID NO: 104 that exhibits substantially the same activity (e.g., encodes the same polypeptide or substantially the same polypeptide that has the same activity) as a nucleic acid (e.g., DNA) having the nucleic acid sequence of SEQ ID NO: 104; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 104 or has 85%, 90%, 91%, 92%, 93%, 94%, 95%, 96%, 97%, 98%, 98.5%, 99%, 99.5% or 99.9% identity with the nucleic acid sequence of SEQ ID NO: 104, or any range or combination thereof; a homolog of the nucleic acid having the sequence of SEQ ID NO: 104.

In some embodiments, the mutant slserk1$^{CR\text{-}5\text{-}a3}$ gene comprises a coding sequence that encodes a protein or polypeptide (e.g., amino acid sequence) having the sequence of SEQ ID NO: 105; a portion of SEQ ID NO: 105 that exhibits substantially the same activity as a protein or polypeptide having the amino acid sequence of SEQ ID NO: 105; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 105 or has 85%, 90%, 91%, 92%, 93%, 94%, 95%, 96%, 97%, 98%, 98.5%, 99%, 99.5% or 99.9% identity with the amino acid sequence of SEQ ID NO: 105, or any range or combination thereof; a homolog of the amino acid having the sequence of SEQ ID NO: 105.

In some embodiments, the mutant slserk1$^{CR\text{-}7\text{-}a1}$ gene comprises, for example, a nucleic acid (e.g., DNA) having the sequence of SEQ ID NO: 106; a portion of SEQ ID NO: 106 that exhibits substantially the same activity (e.g., encodes the same polypeptide or substantially the same polypeptide that has the same activity) as a nucleic acid (e.g., DNA) having the nucleic acid sequence of SEQ ID NO: 106; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 106 or has 85%, 90%, 91%, 92%, 93%, 94%, 95%, 96%, 97%, 98%, 98.5%, 99%, 99.5% or 99.9% identity with the nucleic acid sequence of SEQ ID NO: 106, or any range or combination thereof; a homolog of the nucleic acid having the sequence of SEQ ID NO: 106.

In some embodiments, the mutant slserk1$^{CR\text{-}7\text{-}a1}$ gene comprises a coding sequence that comprises, for example, a nucleic acid (e.g., DNA) having the sequence of SEQ ID NO: 107; a portion of SEQ ID NO: 107 that exhibits substantially the same activity (e.g., encodes the same polypeptide or substantially the same polypeptide that has the same activity) as a nucleic acid (e.g., DNA) having the nucleic acid sequence of SEQ ID NO: 107; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 107 or has 85%, 90%, 91%, 92%, 93%, 94%, 95%, 96%, 97%, 98%, 98.5%, 99%, 99.5% or 99.9% identity with the nucleic acid sequence of SEQ ID NO: 107, or any range or combination thereof; a homolog of the nucleic acid having the sequence of SEQ ID NO: 107.

In some embodiments, the mutant slserk1$^{CR\text{-}7\text{-}a1}$ gene comprises a coding sequence that encodes a protein or polypeptide (e.g., amino acid sequence) having the sequence of SEQ ID NO: 108; a portion of SEQ ID NO: 108 that exhibits substantially the same activity as a protein or polypeptide having the amino acid sequence of SEQ ID NO: 108; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 108 or has 85%, 90%, 91%, 92%, 93%, 94%, 95%, 96%, 97%, 98%, 98.5%, 99%, 99.5% or 99.9% identity with the amino acid sequence of SEQ ID NO: 108, or any range or combination thereof; a homolog of the amino acid having the sequence of SEQ ID NO: 108.

In some embodiments, the mutant slserk1$^{CR\text{-}7\text{-}a2}$ gene comprises, for example, a nucleic acid (e.g., DNA) having the sequence of SEQ ID NO: 109; a portion of SEQ ID NO: 109 that exhibits substantially the same activity (e.g., encodes the same polypeptide or substantially the same polypeptide that has the same activity) as a nucleic acid (e.g., DNA) having the nucleic acid sequence of SEQ ID NO: 109; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 109 or has 85%, 90%, 91%, 92%, 93%, 94%, 95%, 96%, 97%, 98%, 98.5%, 99%, 99.5% or 99.9% identity with the nucleic acid sequence of SEQ ID NO: 109, or any range or combination thereof; a homolog of the nucleic acid having the sequence of SEQ ID NO: 109.

In some embodiments, the mutant slserk1$^{CR\text{-}7\text{-}a2}$ gene comprises a coding sequence that comprises, for example, a nucleic acid (e.g., DNA) having the sequence of SEQ ID NO: 110; a portion of SEQ ID NO: 110 that exhibits substantially the same activity (e.g., encodes the same polypeptide or substantially the same polypeptide that has the same activity) as a nucleic acid (e.g., DNA) having the nucleic acid sequence of SEQ ID NO: 110; a nucleic acid (e.g., DNA) having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the sequence of SEQ ID NO: 110 or has 85%, 90%, 91%, 92%, 93%, 94%, 95%, 96%, 97%, 98%, 98.5%, 99%, 99.5% or 99.9% identity with the nucleic acid sequence of SEQ ID NO: 110, or any range or combination thereof; a homolog of the nucleic acid having the sequence of SEQ ID NO: 110.

In some embodiments, the mutant slserk1$^{CR\text{-}7\text{-}a2}$ gene comprises a coding sequence that encodes a protein or polypeptide (e.g., amino acid sequence) having the sequence of SEQ ID NO: 111; a portion of SEQ ID NO: 111 that exhibits substantially the same activity as a protein or polypeptide having the amino acid sequence of SEQ ID NO: 111; a protein or polypeptide having at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the amino acid sequence of SEQ ID NO: 111 or has 85%, 90%, 91%, 92%, 93%, 94%, 95%, 96%, 97%, 98%, 98.5%, 99%, 99.5% or 99.9% identity with the amino acid sequence of SEQ ID NO: 111, or any range or combination thereof; a homolog of the amino acid having the sequence of SEQ ID NO: 111.

Mutant SlCLAVATA Gene

Other aspects of the disclosure relate to mutants of the SlCLAVATA gene (or a homolog thereof) as well as plants, plant cells, and seeds comprising such mutant genes, and nucleic acids comprising such mutant genes. The SlCLAVATA gene is a homolog of CLAVATA in *A. thaliana*. Homologs of SlCLAVATA can be readily identified using tools, such as a BLAST, known to those of ordinary skill in the art. In some embodiments, the SlCLAVATA gene is SlCLAVATA1, SlCLAVATA2, or SlCLAVATA3. In some embodiments, the SlCLAVATA gene encodes a CLV1, a CLV2, or a CLV3 protein isoform (See e.g., Xu et al., *Nat Genet* (2015) 47, 784-792). In some embodiments, a SlCLAVATA gene homolog has a sequence that has at least 85%, at least 90%, at least 91%, at least 92%, at least 93%, at least 94%, at least 95%, at least 96%, at least 97%, at least 98%, at least 98.5%, at least 99%, at least 99.5%, or at least 99.9% identity with the nucleic acid sequence of the SlCLAVATA gene or has 85%, 90%, 91%, 92%, 93%, 94%, 95%, 96%, 97%, 98%, 98.5%, 99%, 99.5% or 99.9% identity with the nucleic acid sequence of the SlCLAVATA gene. In some embodiments, the homolog of the SlCLAVATA gene is not a *Solanum lycopersicum* gene.

In some embodiments, the mutant the SlCLAVATA gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter, a cis-regulatory element, a proximal promoter region, an enhancer region, a silencer region, or insulator region (see, e.g., Riethoven et al., *Methods Mol Biol* (2010) 674:33-42). In some embodiments, the mutant SlCLAVATA gene (or homolog thereof) contains a mutation in an exon. In some embodiments, the mutant SlCLAVATA gene (or homolog thereof) contains a mutation in an intron. In some embodiments, the mutant SlCLAVATA gene (or homolog thereof) contains a nonsense mutation that results in the introduction of an early stop codon or in a truncated protein. In some embodiments, the mutation is a null mutation in which the coding sequence has been deleted, or in which the coding sequence is not translated into a functional protein.

In some embodiments, the mutant SlCLAVATA gene (or homolog thereof) is a hypomorphic allele or a null allele. In some embodiments, a hypomorphic allele of the mutant SlCLAVATA gene (or homolog thereof) is an allele that encodes a mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a Solanaceae plant (e.g., *Solanum lycopersicum*) comprising the mutant SlCLAVATA gene, or homolog thereof, (e.g., a hypomorphic, knock-out or null allele disclosed) is heterozygous for the mutant SlCLAVATA gene. In some embodiments, a Solanaceae plant (e.g., *Solanum lycopersicum*) comprising the mutant SlCLAVATA gene, or homolog thereof, (e.g., a hypomorphic, knock-out or null allele disclosed) is homozygous for the mutant SlCLAVATA gene.

Plants Comprising Mutant Genes

Plant compactness and timing for yield can be manipulated in a wide variety of types of plants (e.g., Solanaceae plants, such as *Solanum lycopersicum*) that comprise a mutant gene, such as a mutant Solyc08g061560 gene (or homolog thereof), a mutant Solyc05g053850 gene (or homolog thereof), or a mutant Solyc06g074350 gene (or homolog thereof); two mutant genes, such as both a mutant Solyc08g061560 gene (or homolog thereof) and a mutant Solyc05g053850 gene (or homolog thereof), both a mutant Solyc08gO61560 gene (or homolog thereof) and a mutant Solyc06g074350 gene (or homolog thereof), or both a mutant Solyc05g053850 gene (or homolog thereof) and a mutant Solyc06g074350 gene (or homolog thereof); or three mutant genes, such as a mutant SolycO8gO61560 gene (or homolog thereof), a mutant Solyc05g053850 gene (or homolog thereof), and a mutant Solyc06g074350 gene (or homolog thereof). In some embodiments, the plant, such as the Solanaceae plant, is a genetically-altered plant.

In some embodiments, a "genetically-altered" plant is a plant that comprises (e.g., has been altered to comprise/has introduced into it, or has been introduced into a plant that is used to produce the plant, such as a parental line) at least one mutation by any means, such as any gene-editing system or gene-editing technique (e.g., using an RNA-guided endonuclease, such as clustered regularly interspaced short palindromic repeats (CRISPR)/Cas9 and prime editing), chemical mutagenesis, radiatn, Agrobacterium-mediated recombination, viral-vector mediated recombination, or transposon mutagenesis.

CRISPR/Cas is a prokaryotic antiviral system that has been modified for conducting genomic engineering in many cell types (see, e.g., Sander et al. *Nature Biotech* (2014) 32: 347-55 and Hsu et al. *Cell* (2014) 157(6):1262-78), including plants and plant cells (see, e.g., Brooks et al. *Plant Phys* (2014) 166(3):1292-7; Zhou et al. *Nucleic Acids Res* (2014) 42(17):10903-14; Feng et al. PNAS (2014) 111(12):4632-7 and Samanta et al. *Transgenic Res* (2016) 25:561). In some embodiments, the RNA-guided endonuclease is a Cas endonuclease (e.g., Cas9, Cpf1, or Csm1 or a functional variant thereof). CRISPR/Cas9, CRISPR/Cpf1(see, e.g., Zetsche et al. *Cell* (2015) 163(3):759-71), CRISPR/Csm1 (see, e.g., U.S. Pat. No. 9,896,696) are systems that may be used for genomic engineering.

In some embodiments, CRISPR or CRISPR system is class 1 (e.g., pre-CRISPR RNA (pre-crRNA) processing and interference stages are not accomplished by one single multifunctional protein) or class 2 (e.g., pre-CRISPR RNA (pre-crRNA) processing and interference stages are accomplished by one single multifunctional protein). In some embodiments, each class is divided into different types. In some embodiments, class 1 includes a type I (e.g., Cas3), type III (e.g., Cas10), or a type IV (e.g., Csf1) signature protein. In some embodiments, class 2 includes a type II (Cas9), a type V (Cas12a-e (Casl2d and Casl2e are also known as CasY and CasX, respectively), Cas12g-i and Cas14a-c) or type VI (Cas13a-d) signature protein. (See e.g., Makarova, et al. *Nat Rev Microbiol* 13, 722-736 (2015); Burstein, et al. *Nature* 542, 237-241 (2017); Harrington, et al. *Science* 362, 839-842 (2018); Liu, et al. *Nature* 566, 218 (2019); Shmakov, et al. Mol. Cell 60, 385-397 (2015); Shmakov, et al. *Nat Rev Microbiol* 15, 169-182 (2017); and Yan, et al. *Science* 363, 88-91 (2019)).

CRISPR/Cas nucleases from different bacterial species have different properties (e.g., specificity, activity, binding affinity). In some embodiments, orthogonal catalytically-active RNA-guided nuclease species are used. Orthogonal species are distinct species (e.g., two or more bacterial species). For example, a first catalytically-active Cas9 nuclease as used herein may be a *Neisseria meningitidis* Cas9 and a second catalytically-active Cas9 nuclease as used herein may be a *Streptococcus thermophilus* Cas9. A “Cas9 nuclease” herein includes any of the recombinant or naturally-occurring forms of the CRISPR-associated protein 9 (Cas9) or variants or homologs thereof that maintain Cas9 enzyme activity (e.g. within at least 50%, 80%, 90%, 95%, 96%, 97%, 98%, 99% or 100% activity compared to Cas9). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Cas9 nuclease. In some embodiments, a Cas9 nuclease is substantially identical to the protein identified by the UniProt reference number Q99ZW2 or a variant or homolog having substantial identity thereto.

Non-limiting examples of bacterial CRISPR/endonucleases for use herein include *Streptococcus thermophilus* Cas9, *Streptococcus thermophilus* Cas10, Streptococus *thermophilus* Cas3, *Staphylococcus aureus* Cas9, *Staphylococcus aureus* Cas10, *Staphylococcus aureus* Cas3, *Neisseria meningitidis* Cas9, *Neisseria meningitidis* Cas10, *Neisseria meningitidis* Cas3, *Streptococcus pyogenes* Cas9, *Streptococcus pyogenes* Cas10, and *Streptococcus pyogenes* Cas3.

In some embodiments, a Cas9, Cas9 nickase (nCas9) or a catalytically inactive or dead Cas9 (dCas9) is used. *Streptococcus pyogenes* Cas9 (SpCas9) recognizes a simple PAM sequence (NGG). In some embodiments, SpCas9 is codon-optimized. In some embodiments, SpCas9 is codon optimized for human (e.g., *Homo sapiens*; hCas9), plant (e.g., pcoCas9 and Cas9p), *Arabidopsis thaliana* (e.g., AteCas9), maize (e.g., *Zea mays*; zCas9) or soybean (e.g., *Glycine max*; GmCas9). In some embodiments, Cas9 includes a D10A point-mutation in the RuvCI domain or a H840A point-mutation in the HNH domain, which generates a nCas9 that only cleaves the targeting or non-targeting strand, respectively. In some embodiments, as many plumes both a D10A point-mutation in the RuvCI domain and a H840A point-mutation in the HNH domain to abolish nuclease activity resulting in a dCas9.

In some embodiments, the endonuclease is a Cas9 or a variant thereof or a homolog thereof or the endonuclease is a Cas12a or a variant thereof or a homolog thereof. Non-limiting examples of a Cas9 or a variant thereofor a homolog thereofor the endonuclease is a Cas2a or a variant thereof or a homolog thereof are in Table 1 (Zhang et al., Nature Plants (2019) 5, pp. 778-94):

TABLE 1

Examples of variants and homologs or orthologs of Cas9 and Cas12a

| Cas | Size (amino acids) | PAM | Mutations | Plants | Features |
|---|---|---|---|---|---|
| SpCas9 | 1,368-1,424 | NGG | — | Many plant species | — |
| SpCas9 VQR | 1,372 | NGA | D1135V/R1335Q/T1337R | Rice | Altered PAM |
| SpCas9 EQR | 1,372 | NGAG | D1135E/R1335Q/T1337R | — | Altered PAM |
| SpCas9 VRER | 1,372 | NGCG | D1135V/G1218R/R1335E/T1337R | Rice | Altered PAM |
| SpCas9 D1135E | 1,372 | NAG and NGA | D1135E | — | Altered PAM |
| SpCas9 QQR1 | 1,372 | NAAG | G1218R/N1286Q/I1331F/D1332K/R1333Q/R1335Q/T1337R | — | Altered PAM |
| SpCas9-NG | 1,372 | NG | R1335V/L1111R/D1135V/G1218R/E1219F/A1322R/T1337R | Rice and *Arabidopsis* | Altered PAM |
| iSpy-macCas9 | 1,359 | NAA | R221K/N394K | — | Altered PAM |
| SpCas9-HF1 | 1,368 | NGG | N497A/R661A/Q695A/Q926A | Rice and *Arabidopsis* | Enhanced specificity |
| SpCas9 (K855A) | 1,424 | NGG | K855A | — | Enhanced specificity |
| eSpCas9 (1.0) | 1,424 | NGG | K810A/K1003A/R1060A | Rice and *Arabidopsis* | Enhanced specificity |
| eSpCas9 (1.1) | 1,424 | NGG | K848A/K1003A/R1060A | Rice and *Arabidopsis* | Enhanced specificity |
| HypaCas9 | 1,368 | NGG | N692A/M694A/Q695A/H698A | Rice | Enhanced specificity |
| eHF1-Cas9 | 1,368 | NGG | N497A/R661A/Q695A/K848A/Q926A/K1003A/R1060A | Rice | Enhanced specificity |

TABLE 1-continued

| Examples of variants and homologs or orthologs of Cas9 and Cas12a | | | | | |
|---|---|---|---|---|---|
| Cas | Size (amino acids) | PAM | Mutations | Plants | Features |
| eHypa-Cas9 | 1,368 | NGG | N692A/M694A/Q695A/H698A/K848A/K1003A/R1060A | Rice | Enhanced specificity |
| EvoCas9 | 1,368 | NGG | M495V/Y515N/K526E/R661Q | — | Enhanced specificity |
| Sniper-Cas9 | 1,372 | NGG | F539S/M763I/K890N | — | Enhanced specificity |
| HiFi Cas9 | 1,368 | NGG | R691A | — | Enhanced specificity |
| xCas9 3.7 | 1,368 | NG, GAA and GAT | A262T/R324L/S409I/E480K/E543D/M694I/E1219V | Rice | Enhanced specificity and altered PAM |
| SaCas9 | 1,053 | NNGRRT | — | *N. benthamiana*, *Arabidopsis*, rice and citrus | — |
| SaCas9 KKH | 1,053 | NNNRRT | E782K/N968K/R1015H | — | — |
| St1Cas9 | 1,122 | NNAGAAW | — | *Arabidopsis* | — |
| St3Cas9 | 1,393 | NGGNG | — | — | — |
| NmCas9 | 1,109 | NNNNGATT | — | — | — |
| FnCas9 | 1,629 | NGG | — | — | — |
| FnCas9 RHA | 1,632 | YG | E1369R/E1449H/R1556A | — | — |
| TdCas9 | 1,423 | NAAAAN | — | — | — |
| CjCas9 | 984 | NNNNACAC or NNNNRYAC | — | — | — |
| ScCas9 | 1,379 | NNG | — | — | — |
| SmacCas9 | 1,338 | NAA | — | — | — |
| BlatCas9 | 1,092 | NNNNCND | — | Maize | — |
| AsCas12a | 1,307 | TTTV | — | Rice, *N. benthamiana* and tomato, soybean and wild tobacco | — |
| AsCas12a RR | 1,307 | TYCV and CCCC | S542R/K607R | — | Altered PAM |
| AsCas12a RVR | 1,307 | TATV | S542R/K548V/N552R | — | Altered PAM |
| enAsCas12a | 1,307 | VTTV, TTTT, TTCN and TATV | E174R/S542R/K548R | | Altered PAM and enhanced activity at low temperature |
| LbCas12a | 1,228 | TTTV | — | Rice, *Arabidopsis*, *N. benthamiana* and tomato, soybean and wild | — |

TABLE 1-continued

Examples of variants and homologs or orthologs of Cas9 and Cas12a

| Cas | Size (amino acids) | PAM | Mutations | Plants | Features |
|---|---|---|---|---|---|
| | | | | tobacco, cotton, citrus and maize | |
| LbCas12a RR | 1,228 | TYCV and CCCC | G532R/K595R | Rice | Altered PAM |
| LbCas12a RVR | 1,228 | TATV | G532R/K538V/Y542R | Rice | Altered PAM |
| FnCas12a | 1,300 | TTV, TTTV and KYTV | — | Rice | — |
| FnCas12a RR | 1,300 | TYCV and TCTV | N607R/K671R | Rice | — |
| FnCas12a RVR | 1,300 | TWTV | N607R/K613V/N617R | Rice | — |
| MbCas12a | 1,373 | TTV and TTTV | — | — | — |
| MbCas12a RR | 1,373 | TY CV and TC TV | N576R/K637R | — | Altered PAM |
| MbCas12a RVR | 1,373 | TWTV | N576R/K582V/N586R | — | Altered PAM |

Variants of RNA-guided endonucleases such as variants of Cas endonucleases may also be used, such as SpCas9-HF1 and eSpCas9 (see, e.g., Kleinstiver et al. Nature (2016) 529, 490-5 and Slaymaker et al. Science (2016) 351(6268): 84-8). Other example variants of RNA-guided endonucleases that may be used include, but are not limited to, variants of Cpf1 endonucleases, including variants to reduce or inactivate nuclease activity, variants which further comprise at least one nuclear localization sequence, variants which further comprise at least one plastid targeting signal peptide or a signal peptide targeting Cpf1 to both plastids and mitochondria, and/or variants of Cpf1 which further comprise at least one marker domain (see, e.g., Zetsche et al. Cell (2015) 163(3):759-71; U.S. Pat. No. 9,896,696); variants of Csm1 endonucleases, including variants to reduce or inactivate nuclease activity, variants which further comprise at least one nuclear localization sequence, variants which further comprise at least one plastid targeting signal peptide or a signal peptide targeting Cpf1 to both plastids and mitochondria, and/or variants of Cpf1 which further comprise at least one marker domain (see, e.g., U.S. Pat. No. 9,896,696). Further example RNA-guided endonucleases that may be used include, but are not limited to, SpCas9, SpCas9 VQR, SpCas9 EQR, SPCas9 VRER, SpCas9 D1135E, SpCas9 QQR1, SpCas9-NG, SpCas9-cytidine deaminase, iSpy-macCas9, SpCas9-HF1, SpCas9 (K855A), eSpCas9 (1.0), eSpCas9 (1.1), HypaCas9, eHF1-Cas9, eHypa-Cas9, EvoCas9, Sniper-Cas9, HiFi Cas9, xCas9 3.7, SaCas9 KKH, St3Cas9, FnCas9 RHA, TdCas9, CjCas9, ScCas9, SmacCas9, BlatCas9, Cas12a, Cas12b, AsCas12a, AsCas12a RR, AsCas12a RVR, enAsCas12a, LbCas12a, LbCas12a RR, LbCas12a RVR, FnCas12a, FnCas12a RR, FnCas12a RVR, MbCas12a, MbCas12a RR, MbCas12a RVR, LshC2c2, FnCas9, SaCas9, St1Cas9, Nmcas9, FnCpf1, AsCpf1, SpCas9-nickase, eSpcas9, Split-SpCas9, dSpCas9FokI, and SpCas9-cytidine deaminase (see, e.g., Zhang et al., *Nature Plants* (2019) 5, pp. 778-94; Murovec et al. *Plant Biotechnol J* (2017) 15, pp. 917-26).

Other RNA-guided nucleases may be used as provided herein. In some embodiments, the endonuclease is a Prevotella and Francisella 1 (Cpf1) endonuclease. Cpf1 is a bacterial endonuclease similar to Cas9 nuclease in terms of activity. However, Cpf1 is typically used with a short (~42 nucleotide) gRNA, while Cas9 is typically used with a longer (~100 nucleotide) gRNA. Additionally, Cpf1 cuts the DNA 5' to the target sequence and leaves blunted ends, while Cas9 leaves sticky ends with DNA overhangs. Cpf1 proteins from Acidaminococcus and Lachnospiraceae bacteria efficiently cut DNA in human cells in vitro. In some embodiments, a RNA-guided nuclease is Acidaminococcus Cpf1 or Lachnospiraceae Cpf1, which require shorter gRNAs than Cas nucleases. The Cpf1 endonuclease may be any Cpf1 endonuclease known in the art or disclosed (e.g., FnCpf1, AsCpf1, Lb2Cpf1, CMtCpf1, MbCpf1, LbCpf1, PcCpf1, or PdCpf1, see, e.g., U.S. Pat. No. 9,896,696). In some embodiments, the CRISPR expression cassette disclosed encodes a Csm1 endonuclease. The Csm1 endonuclease may be any Csm1 endonuclease known in the art or disclosed (e.g., SsCsm1, SmCsm1, ObCsm1, Sm2Csm1, or MbCsm1, see, e.g., U.S. Pat. No. 9,896,696).

In some embodiments, the Cas9 endonuclease may be any Cas9 endonuclease known in the art or disclosed. In some embodiments, the Cas9 endonuclease is a rice optimized Cas9 (see, e.g., Jiang et al. *Nucleic Acids Res* (2013) 41(20):e188). In some embodiments, the Cas9 endonuclease has an amino acid sequence that is at least 90%, 95%, 98%, 99% or 100% identical to the following amino acid sequence:

(SEQ ID NO: 147)

```
MDKKYSIGLDIGTNSVGWAVITDEYKVPSKKFKVLGNTDRHSIKKNLIGALLFDSGETAEATRLKRTARRRYTRRKN
RICYLQEIFSNEMAKVDDSFFHRLEESFLVEEDKKHERHPIFGNIVDEVAYHEKYPTIYHLRKKLVDSTDKADLRLI
YLALAHMIKFRGHFLIEGDLNPDNSDVDKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKILTFRIPYYVGPLARGNSRF
AWMTRKSEETITPWNFEEVVDKGASAQSFIERMTNFDKNLPNEKVLPKHSLLYEYFTVYNELTKVKYVTEGMRKPAF
LSGEQKKAIVDLLFKTNRKVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDKQSGKTILDFLKSDGFANRNE
MQLIHDDSLTFKEDIQKAQVSGQGDSLHEHIANLAGSPAIKKGILQTVKVVDELVKVMGRHKPENIVIEMARENQTT
QKGQKNSRERMKRIEEGIKELGSQILKEHPVENTQLQNEKLYLYYLQNGRDMYVDQELDINRLSDYDVDHIVPQSFL
KDDSIDNKVLTRSDKNRGKSDNVPSEEVVKKMKNYWRQLLNAKLITQRKFDNLTKAERGGLSELDKAGFIKRQLVET
RQITKHVAQILDSRMNTKYDENDKLIREVKVITLKSKLVSDFRKDFQFYKVREINNYHHAHDAYLNAVVGTALIKKY
PKLESEFVYGDYKVYDVRKMIAKSEQEIGKATAKYFFYSNIMNFFKTEITLANGEIRKRPLIETNGETGEIVWDKGR
DFATVRKVLSMPQVNIVKKTEVQTGGFSKESILPKRNSDKLIARKKDWDPKKYGGFDSPTVAYSVLVVAKVEKGKSK
KLKSVKELLGITIMERSSFEKNPIDFLEAKGYKEVKKDLIIKLPKYSLFELENGRKRMLASAGELQKGNELALPSKY
VNFLYLASHYEKLKGSPEDNEQKQLFVEQHKHYLDEIIEQISEFSKRVILADANLDKVLSAYNKHRDKPIREQAENI
IHLFTLTNLGAPAAFKYFDTTIDRKRYTSTKEVLDATLIHQSITGLYETRIDLSQLGGDSRADPKKKRKV.
```

In some embodiments, the endonuclease is any one of a cytidine base editor (CBE) or an adenine base editor (ABE). The CBE may be any CBE known in the art or disclosed (e.g., BE1, BE2, BE3, HF-BE3, BE4, BE4max, BE4-GAM, YE1-BE3, EE-BE3, YEE-BE3, YE2-BE3, VQR-BE3, VRER-BE3, SaBE3, Sa(KKH)BE3, SaBE4, SaBE4-Gam, Cas12a-BE, eBE-S3, dCpf1-eBE, dCpf1-eBE-YE, Target-AID, Target-AID-NG, xBE3, hA3A-eBE3, hA3A-eBE-Y130F, hA3A-eBE-Y132D, eA3A-BE3, A3A-BE3, BE-PLUS, TAM, CRISPR-X, BE3-R33A, or BE3-R33A/K34A, see, e.g., Wang, et al. *Genome Biology* (2019) 20, article number: 218; Rees & Liu, *Nat Rev Genetics* (2018) 19(12), pp. 770-88). The ABE may be any ABE known in the art or disclosed (e.g., TAM, CRISPR-X, ABE7.9, ABE7.10, ABE7.10*, eABE7.10, HFABE7.10, Hypa-ABE7.10, evo-ABE7.10, xABE, ABESa, VQR-ABE, VRER-ABE, SaKKH-ABE, see, e.g., Rees & Liu, *Nat Rev Genetics* (2018) 19(12), pp. 770-88).

In some embodiments, a CRISPR expression cassette encodes a RNA-guided endonuclease (e.g., a CRISPR/Cas9 expression cassette or a CRISPR/Cpf1 expression cassette), which is introduced into a plant (e.g., tomato, a Solanaceae plant) using any method known in the art or disclosed (e.g., by such as Agrobacterium-mediated recombination, viral-vector mediated recombination, microinjection, gene gun bombardment/biolistic particle delivery, or electroporation of plant protoplasts). In some embodiments, the CRISPR expression cassette (e.g., CRISPR/RNA-guided endonuclease expression cassette such as a CRISPR/Cas9 expression cassette or a CRISPR/Cpf1 expression cassette) is integrated into the same chromosome or a different chromosome of a gene (e.g., a mutant gene) disclosed. In some embodiments, the CRISPR expression cassette can later be removed through a self-cross or through a cross with another plant.

In some embodiments, a "genetically-altered" plant is a plant that comprises (e.g., has been altered to comprise/has introduced into it, or has been introduced into a plant that is used to produce the plant, such as a parental line) at least one mutation by using a site-specific nuclease, a meganuclease, or a programmable nuclease.

Site-specific nuclease cleavage sites, as disclosed, are cleaved by cognate site-specific nucleases. A nuclease, generally, is an enzyme that cleaves a nucleic acid into smaller units. Without wishing to be bound by theory, it is thought that a chemical modification at (or near) a site-specific nuclease cleavage site of a donor nucleic acid renders the nucleic acid resistant to site-specific nuclease activity (e.g., exonuclease or endonuclease activity). A nucleic acid is considered to be resistant to cleavage by a nuclease if the nucleic acid cannot be cleaved by the nuclease, or the frequency at which the nucleic acid is cleaved by the nuclease is reduced, for example, by least 50% (e.g., at least 55%, at least 60%, at least 65%, at least 70%, at least 75%, at least 80%, at least 85%, at least 90%, or at least 95%). Therefore, in some embodiments, a site-specific nuclease is used to cleave a target site, for example, in genomic DNA (e.g., of a host cell), but does not cleave the corresponding chemically-modified target site in the internal region of the donor nucleic acid. Non-limiting examples of site-specific nucleases that may be used as provided herein include meganucleases and programmable nucleases.

Meganucleases, also referred to as homing endonucleases, recognize a double-stranded DNA sequence of 12 to 40 base pairs. There are five families of meganucleases: LAGLIDADG, GIY-YIG, HNH, His-Cys box, and PD-(D/E)XK. The families are delineated by sequence and structure motifs. Non-limiting examples of meganucleases include I-Sce I, I-Ceu I, I-Chu I, I-Cre I, i-Csm I, I-Dir I, I-Dmo I, I-Hmu I, I-Hmu II, I-Ppo I, I-Sce II, I-Sce III, I-Sce IV, I-Tev I, I-Tev II, I-Tev III, PI-Mle I, PI-Mtu I, PI-Pfu I, PI-Psp I, PI-Tli I, PI-Tli II, and PI-Sce V. Other meganucleases are known in the art and may be accessed, for example from databases such as homingendonuclease.net (see e.g., Taylor et al., Nucleic Acids Res. 40(W1):W110-W116). Engineered meganucleases are also contemplated herein. See, e.g., Silva et al. Curr Gene Ther. 2011 February; 11(1): 11-27, incorporated herein by reference).

Programmable nucleases (also known as targeted nucleases; see, e.g., Porter et al. Compr Physiol. 2019 Mar. 14; 9(2):665-714); Kim et al. Nat Rev Genet. 2014 May; 15(5): 321-34; and Gaj et al. Trends Biotechnol. 2013 July;31(7): 397-405) include, for example, zinc finger nucleases (ZFNs), transcription activator-like effector nucleases (TALENs), RNA-guided nucleases, such as Cas9 and Cpf1 nucleases, and prime editing using an endonuclease and a reverse-transcriptase (Anzalone et al. Nature (576):149-157 (2019)). It should be understood that the aspects and embodiments provided herein that encompass "nucleases" also encompass "nickases." A nickase is a type of nuclease. Thus, a Cas9 nickase is a type of Cas9 nuclease. In some embodiments, a programmable nuclease is a ZFN. In some embodiments, a programmable nuclease is a TALEN. In some embodiments, a programmable nuclease is a Cas9 nuclease (e.g., that introduces a double-strand break in DNA; cleaves the sense strand and the antisense strand). For example, the Cas9 nuclease may be a Cas9 nickase (introduces a single-strand break in DNA; cleaves the sense strand or the antisense strand).

In some embodiments, programmable nucleases are guided to a target sequence by protein DNA binding domains (e.g., zinc finger domains, transcription activator-like effector domains) or by guide RNAs (gRNAs).

For specific nucleases described herein, the named protein includes any of the protein's naturally occurring forms, or variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference or functional fragment or homolog thereof.

In some embodiments, a site-specific nuclease cleavage site is a zinc finger nuclease (ZFN) cleavage site. ZFNs are composed of a zinc-finger DNA-binding domain and a nuclease domain. The DNA-binding domains of individual ZFNs generally contain 3-6 individual zinc finger repeats that recognize 9-18 nucleotides. For example, if the zinc finger domain perfectly recognizes a 3 base pair sequence, then a 3 zinc finger array can be generated to recognize a 9 base pair target DNA sequence. Because individual zinc fingers recognize relatively short (e.g., 3 base pairs) target DNA sequences, ZFNs with 4, 5, or 6 zinc finger domains are typically used to minimize off-target DNA cutting. Non-limiting examples of zinc finger DNA-binding domains that may be used with methods of the present disclosure include Zif268, Gal4, HIV nucleocapsid protein, MYST family histone acetyltransferases, myelin transcription factor Mytl, and suppressor of tumurigenicity protein 18 (ST18). A ZFN may contain homogeneous DNA binding domains (all from the same source molecule) or a ZFN may contain heterogeneous DNA binding domains (at least one DNA binding domain is from a different source molecule).

Zinc finger DNA-binding domains work in concert with a nuclease domain to form ZFNs that cut target DNA. The nuclease cuts the DNA in a non-sequence specific manner after being recruited to the target DNA by the zinc fingers DNA-binding domains. In some embodiments, a type II restriction enzyme FokI, which forms a heterodimer before producing a double-stranded break in the DNA, is disclosed. Thus, two ZFN proteins bind to opposite strands of DNA to create the FokI heterodimer and form a double-stranded break, reducing off-target DNA cleavage events (Kim, et al., Proc Natl Acad Sci USA, 1996, 93(3): 1156-1160). Additionally, ZFNs may be nickases that only cleave one strand of the double-stranded DNA. By cleaving only one strand, the DNA is more likely to be repaired by error-free HR as opposed to error-prone NHEJ (Ramirez, et al., Nucleic Acids Research, 40(7): 5560-5568). Non-limiting examples of nucleases that may be used as provided herein include FokI and DNaseI.

It should be understood that a ZFN may be expressed as a fusion protein, with the DNA-binding domain and the nuclease domain expressed in the same polypeptide. This fusion may include a linker of amino acids (e.g., 1, 2, 3, 4, 5, 6, or more) between the DNA-binding domain and the nuclease domain.

Methods described herein, in some embodiments, include the use of transcription activator-like effector nucleases (TALENs) to genetically modify genomic DNA. A TALEN is an endonuclease that can be programmed to cut specific sequences of DNA. TALENs are composed of transcription activator-like effector (TALE) DNA-binding domains, which recognize single target nucleotides in the DNA, and transcription activator-like effector nucleases (TALENs) which cut the DNA at or near a target nucleotide.

Transcription activator-like effectors (TALEs) found in bacteria are modular DNA binding domains that include central repeat domains made up of repetitive sequences of residues (Boch J. et al. Annual Review of Phytopathology 2010; 48: 419-36; Boch J Biotechnology 2011; 29(2): 135-136). The central repeat domains, in some embodiments, contain between 1.5 and 33.5 repeat regions, and each repeat region may be made of 34 amino acids; amino acids 12 and 13 of the repeat region, in some embodiments, determines the nucleotide specificity of the TALE and are known as the repeat variable diresidue (RVD) (Moscou M J et al. Science 2009; 326 (5959): 1501; Juillerat A et al. Scientific Reports 2015; 5: 8150). Unlike ZF DNA sensors, TALE-based sequence detectors can recognize single nucleotides. In some embodiments, combining multiple repeat regions produces sequence-specific synthetic TALEs (Cermak T et al. Nucleic Acids Research 2011; 39 (12): e82). Non-limiting examples of TALEs that may be utilized in the present disclosure include IL2RG, AvrBs, dHax3, and thXoI.

A transcription activator-like effector nuclease (TALEN) cleaves the DNA non-specifically after being recruited to a target sequence by the TALE. This non-specific cleavage can lead to off-target DNA cleavage events. The most widely-used TALEN is the type II restriction enzyme FokI, which forms a heterodimer to produce a double-stranded break in DNA. Thus, two TALEN proteins must bind to opposite strands of DNA to create the FokI heterodimer and form a double-stranded break, reducing off-target DNA cleavage events (Christian M et al. Genetics 2010; 186: 757-761). Additionally, TALEN nucleases may be nickases, which cut only a single-strand of the DNA, thus promoting repair of the break by HR (Gabsalilow L. et al. Nucleic Acids Res. 41, e83). Non-limiting examples of TALENs that may be utilized in the present disclosure include Fok1, RNAseH, and MutH.

It should be understood that the TALEN may be expressed as a fusion protein, with the DNA-binding domain and the nuclease domain expressed in the same polypeptide. This fusion may include a linker of amino acids (e.g., 1, 2, 3, 4, 5, 6, or more) between the DNA-binding domain and the nuclease domain.

In some embodiments, a genetically-altered plant disclosed comprises a mutation in the first allele. In some embodiments, a genetically-altered plant disclosed comprises a mutation in the second allele. In some embodiments, the first allele contains the region, such as a target region, against which one or more than one different gRNAs (e.g., sgRNAs) are designed such that mutations can be introduced into a target region of the first allele using the RNA-guided endonuclease (e.g., Cas9, Cpf1, or Csm1 endonuclease). In some embodiments, the second allele contains the region, such as a target region, against which one or more than one different gRNAs (e.g., sgRNAs) are designed such that mutations can be introduced into a target region of the second allele using the RNA-guided endonuclease (e.g., Cas9, Cpf1, or Csm1 endonuclease). In some embodiments, the target region or a portion thereof, is absent from the first allele. In some embodiments, the target region or a portion thereof, is present in the first allele and the second allele. In some embodiments, the first allele is a null allele in which most or the entire coding sequence is deleted such that further mutations induced by the RNA-guided endonuclease (e.g., Cas9, Cpf1, or Csm1 endonuclease) generally have no further effect on the first allele. In some embodiments, the second allele that contains the target region against which the multiple guide RNAS (gRNAs), such as single-guide RNAs (sgRNAs), are designed is a naturally-occurring allele (e.g., an allele naturally present in a plant). In some embodiments, the second allele is not a hypomorphic allele or a null allele. In some embodiments, the gRNA/RNA-guided endonuclease-induced mutation (e.g., a Cas9-induced mutation or a Cp1-inducted mutation) is a deletion, insertion, inversion, or translocation, or a combination of structural variations thereof, such as an indel.

One non-limiting approach to creating knock-out mutations is to use CRISPR/RNA-guided endonuclease mutagenesis (e.g., CRISPR/Cas9 mutagenesis or CRISPR/Cpf1 mutagenesis) to target exons that encode functional protein domains or to target a large portion (e.g., at least 80%) or the entirety of the coding sequence (see, e.g., Shi et al. *Nat Biotech* (2015) 33(6): 661-7 and Online Methods). Other mutagenesis techniques may also be used to produce a hypomorphic or null first allele, for example, by introducing mutations in the first allele through transposon insertions, EMS mutagenesis, fast neutron mutagenesis, or other applicable mutagenesis methods. In some embodiments, a hypomorphic or null first allele may be produced using a method as disclosed for producing gRNA/endonuclease-induced mutations (e.g., using a CRISPR/RNA-guided endonuclease expression construct (e.g., a CRISPR/Cas9 expression construct or a CRISPR/Cpf1 expression construct) as disclosed to induce gRNA/RNA-guided endonuclease mutations (such as Cas9 mutations or Cpf1 mutations) and selecting a mutated first allele that is a hypomorphic or null allele).

In some embodiments, the mutant Solyc08g061560 gene (or homolog thereof) contains a mutation in a regulatory region, a coding region or both (e.g., a missense, frameshift, nonsense, insertion, deletion, duplication, inversion, indel, introduction of an early stop codon, splicing or translocation mutation in such a region). In some embodiments, the regulatory region is a promoter or promoter region (e.g., a core promoter or core promoter region, a proximal promoter of proximal promoter region, a distal promoter or distal promoter region), a cis-regulatory element, an enhancer region, a silencer region, or insulator region (see, e.g., Riethoven et al., *Methods Mol Biol* (2010) 674:33-42).

In some embodiments, one or more of the gRNA (e.g., sgRNA; 2, 3, 4, 5, 6, 7, 8, 9, 10, 11, 12, 13, 14, 15, or 16) contains a sequence that is complementary to a target sequence within a target region. Guide RNA sequences, such as sgRNA sequences, can be designed using methods known in the art or disclosed (see, e.g., the CRISPR tool available from crispr.mit.edu). In some embodiments, a target sequence is located next to a Protospacer Adjacent Motif (PAM) sequence, such as NGG, NAA, NNNNGATT, NNAGAA, or NAAAAC. In some embodiments, the PAM sequence is a Cpf1 or Csm1 PAM sequence, such as TTN, CTA, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, or CCGN. In some embodiments, the gRNA is a single guide RNA (sgRNA) containing a trans-activating CRISPR RNA (tracrRNA) and a CRISPR RNA (crRNA) designed to cleave the target site of interest. In some embodiments, the gRNA is a sgRNA containing a crRNA. In some embodiments, when two or more gRNAs are used which target two different target sequences in a target region, each target sequence in the target region is located 50 to 500 base pairs (e.g., 50 to 500, 50 to 400, 50 to 300, 50 to 200, 50 to 100, 100 to 500, 100 to 400, 100 to 300, 100 to 200, 200 to 500, 200 to 400, or 200 to 300 base pairs) away from at least one other different target sequence.

In some embodiments, the target region is 0 to 5000 base pairs (e.g., 0 to 5000, 0 to 4000, 0 to 3000, 0 to 2000, 0 to 1000, 100 to 5000, 100 to 4000, 100 to 3000, 100 to 2000, 100 to 1000, 500 to 5000, 500 to 4000, 500 to 3000, 500 to 2000, 500 to 1000, 1000 to 5000, 1000 to 4000, 1000 to 3000, or 1000 to 2000 base pairs) upstream of the 5' end of the coding sequence of a gene disclosed, such as a SlER (Solyc08g061560) gene or a homolog thereof. In some embodiments, the target region is 0 to 5000 base pairs (e.g., 0 to 5000, 0 to 4000, 0 to 3000, 0 to 2000, 0 to 1000, 100 to 5000, 100 to 4000, 100 to 3000, 100 to 2000, 100 to 1000, 500 to 5000, 500 to 4000, 500 to 3000, 500 to 2000, 500 to 1000, 1000 to 5000, 1000 to 4000, 1000 to 3000, or 1000 to 2000 base pairs) downstream of the 3' end of the coding sequence of a gene disclosed, such as a SlER (Solyc08g061560) gene or a homolog thereof. In some embodiments, the target region is in the first allele of the gene, in the second allele of the gene, or both in the first allele and in the second allele of the gene.

In some embodiments, the target region comprises a regulatory region of a gene disclosed, such as a SlER (Solyc08g061560) gene or a homolog thereof. As used herein, a "regulatory region" of a gene of interest contains one or more nucleotide sequences that, alone or in combination, are capable of modulating expression of the gene. Regulatory regions include, for example, promoters, enhancers, and introns. In some embodiments, the regulatory region comprises a transcription factor binding site, an RNA polymerase binding site, a TATA box, or a combination thereof.

In some embodiments, the regulatory region is within a certain distance of a gene disclosed, such as 0 to 5000 base pairs (e.g., 0 to 5000, 0 to 4000, 0 to 3000, 0 to 2000, 0 to 1000, 100 to 5000, 100 to 4000, 100 to 3000, 100 to 2000, 100 to 1000, 500 to 5000, 500 to 4000, 500 to 3000, 500 to 2000, 500 to 1000, 1000 to 5000, 1000 to 4000, 1000 to 3000, or 1000 to 2000 base pairs) upstream of the 5' end of the coding sequence of the gene of interest or 0 to 5000 base pairs (e.g., 0 to 5000, 0 to 4000, 0 to 3000, 0 to 2000, 0 to 1000, 100 to 5000, 100 to 4000, 100 to 3000, 100 to 2000, 100 to 1000, 500 to 5000, 500 to 4000, 500 to 3000, 500 to 2000, 500 to 1000, 1000 to 5000, 1000 to 4000, 1000 to 3000, or 1000 to 2000 base pairs) downstream of the 3' end of the coding sequence of the gene of interest. In some embodiments, the target region may be larger, e.g., 0 to 100 kilobases (e.g., 0 to 100, 0 to 90, 0 to 80, 0 to 70, 0 to 60, 0 to 50, 0 to 40, 0 to 30, 0 to 20 or 0 to 10 kilobases) upstream of the 5' end of the coding sequence of a gene disclosed or 0 to 60 kilobases (e.g., 0 to 60, 0 to 50, 0 to 40, 0 to 30, 0 to 20 or 0 to 10 kilobases) base pairs downstream of the 3' end of the coding sequence of a gene disclosed. Such larger regions may include both proximal promoter regions (e.g., within 1 to 3 Kb of the 5' end of the coding sequence) and distal enhancer regions.

In some embodiments, a regulatory region can be identified, e.g., by analyzing the sequences within a certain distance of the gene of interest (e.g., within 5 kilobases) for one or more of transcription factor binding sites, RNA polymerase binding sites, TATA boxes, reduced SNP density or conserved non-coding sequences.

In some embodiments, the CRISPR expression cassette (e.g., CRISPR/RNA-guided endonuclease expression cassette such as a CRISPR/Cas9 expression cassette or a CRISPR/Cpf1 expression cassette) contains a constitutive promoter, e.g., a CaMV 35s promoter, a maize U6 promoter, a rice U6 promoter, a maize Ubiquitin promoter, a CMV promoter, a EFla promoter, a CAG promoter, a PGK promoter or a U6 promoter. In some embodiments, the promoter is an inducible promoter, e.g., TRE.

In some embodiments, the CRISPR expression cassette (e.g., CRISPR/RNA-guided endonuclease expression cassette such as a CRISPR/Cas9 expression cassette or a CRISPR/Cpf1 expression cassette) contains a tissue-specific promoter, such as an anther-specific promoter or a pollen-specific promoter. In some embodiments, the CRISPR expression cassette (e.g., CRISPR/RNA-guided endonuclease expression cassette such as a CRISPR/Cas9 expression cassette or a CRISPR/Cpf1 expression cassette) contains an inducible promoter, such as an ethanol inducible promoter, a dexamethasone inducible promoter, a beta-estradioal inducible promoter, or a heat shock inducible promoter. In some embodiments, the same promoter is used to drive expression of both the RNA-guided endonuclease (e.g., Cas9, Cpf1, or Csm1) sequence and the gRNA, such as sgRNA, sequences. In some embodiments, different promoters are used to drive the expression of the RNA-guided endonuclease (e.g., Cas9, Cpf1, or Csm1) sequence and the gRNA sequences. In some embodiments, expression of the gRNAs is driven a using a polycistronic tRNA system.

In some embodiments, the nucleic acid is a vector, such as a plasmid. In some embodiments, a suitable vector, such as a plasmid, contains an origin of replication functional in at least one organism, convenient restriction endonuclease or other cloning sites, and one or more selectable markers. In some embodiments, the nucleic acid is contained within a cell. In some embodiments, the cell is plant cell (e.g., a crop plant cell). In some embodiments, the plant cell is isolated. In some embodiments, the plant cell is a non-replicating plant cell.

In some embodiments, a noncoding DNA and noncoding region of a gene disclosed (e.g., a sler gene or mutant or homolog thereof) is used interchangeably to refer to one or more sequences of DNA or regions of a gene that does not encode a mRNA or protein. In some embodiments, the noncoding DNA or noncoding region of a gene disclosed regulates gene activity. For example, noncoding DNA or noncoding region of a gene may contain sequences that act as regulatory elements, determining when and where genes are turned on and off. In some embodiments, the regulatory element (e.g., promoter, enhancer, silencer, insulator, etc.) regulates binding of a transcription factor to either activate or repress transcription). In some embodiments, the noncoding DNA or noncoding region of a gene regulates production of tRNAs, rRNAs, miRNAs, lncRNAs, etc. In some embodiments, a structural element of a chromosome is also part of noncoding DNA (e.g., telomeres, satellite DNA, etc.). In some embodiments, the noncoding DNA or noncoding region of a gene is an intron or an intergenic region.

As disclosed, a promoter is a region of DNA where transcription of a gene is initiated. In some embodiments, the promoter controls the binding of an RNA polymerase to DNA, which transcribes DNA to mRNA. mRNA is ultimately translated into a functional protein. In some embodiments, RNA polymerase is RNA polymerase I, RNA polymerase II, or RNA polymerase III. Thus, a promoter disclosed controls one or more of the location or the time a gene disclosed (e.g., a SlER gene or a mutant thereof or a homolog thereof, a SP gene or a mutant thereof or a homolog thereof, or a SP5G gene or a mutant thereof or a homolog thereof) is expressed. In some embodiments, the promoter has one or more mutations. In some embodiments, the promoter or a mutant thereof is about 100-10000 base pairs long. In some embodiments, the promoter is 100, 200, 300, 400, 500, 600, 700, 800, 900, 1000, 1500, 2000, 3500, 3000, 3500, 4000, 4500, 5000, 5500, 6000, 6500, 7000, 7500, 8000, 8500, 9000, 9500, 10000 base pairs long, or any range or combination thereof. In some embodiments, the promoter is at least 100, at least 200, at least 300, at least 400, at least 500, at least 600, at least 700, at least 800, at least 900, at least 1000, at least 1500, at least 2000, at least 3500, at least 3000, at least 3500, at least 4000, at least 4500, at least 5000, at least 5500, at least 6000, at least 6500, at least 7000, at least 7500, at least 8000, at least 8500, at least 9000, at least 9500, at least 10000 base pairs long. In some embodiments, the promoter is more than 100, more than 200, more than 300, more than 400, more than 500, more than 600, more than 700, more than 800, more than 900, more than 1000, more than 1500, more than 2000, more than 3500, more than 3000, more than 3500, more than 4000, more than 4500, more than 5000, more than 5500, more than 6000, more than 6500, more than 7000, more than 7500, more than 8000, more than 8500, more than 9000, more than 9500, or more than 10000 base pairs long. In some embodiments, the promoter is adjacent and upstream (5') of the sense or coding strand of the transcribed gene disclosed, such as a mutant gene disclosed. The coding strand is the DNA strand that includes codons and whose sequence produces a mRNA transcript.

In some embodiments, a promoter comprises a core promoter or core promoter region, a proximal promoter or proximal promoter region, and a distal promoter or distal promoter region. The core promoter or core promoter region is located most proximal to the start codon and contains the RNA polymerase binding site, TATA box, and transcription start site (TSS). RNA polymerase will bind to this core promoter region stably and transcription of the template strand can initiate. The TATA box is a DNA sequence (5'-TATAAA-3') within the core promoter region where general transcription factor proteins and histones can bind. The proximal promoter or proximal promoter region, which contains many primary regulatory elements, is upstream from the core promoter or core promoter region. In some embodiments, the proximal promoter is found upstream from the TSS and it is the site where general transcription factors bind. The distal promoter, which is upstream of the proximal promoter, contains transcription factor binding sites, but mostly contains regulatory elements.

In some embodiments, a gene disclosed (e.g., a SlER gene or a mutant thereof or a homolog thereof, a SP gene or a mutant thereof or a homolog thereof, or a SP5G gene or a mutant thereof or a homolog thereof) comprises one or more mutations in one, two or three of the core promoter or core promoter region, proximal promoter or proximal promoter region and distal promoter or distal promoter region.

In some embodiments, a gene disclosed comprises a mutation in a core promoter or core promoter region. In some embodiments, a mutation in a core promoter or core promoter region of a gene disclosed disrupts or reduces the binding of RNA polymerase, one or more transcription factors, or both RNA polymerase and one or more transcription factors. In some embodiments, a mutation in a core promoter or core promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a proximal promoter or proximal promoter region. In some embodiments, a mutation in a proximal promoter or proximal promoter region of a gene disclosed, disrupts or reduces the binding of RNA polymerase, one or more transcription factors, or both RNA polymerase and one or more transcription factors. In some embodiments, a mutation in a proximal promoter or proximal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a distal promoter or distal promoter region. In some embodiments, a mutation in a distal promoter or distal promoter region of a gene disclosed, disrupts or reduces the binding of RNA polymerase, one or more transcription factors, or both RNA polymerase and one or more transcription factors. In some embodiments, a mutation in a distal promoter or distal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a core promoter or core promoter region and in a distal promoter or distal promoter region. In some embodiments, a mutation in a core promoter or core promoter region and in a distal promoter or distal promoter region of a gene disclosed disrupts or reduces the binding of RNA polymerase, one or more transcription factors, or both RNA polymerase and one or more transcription factors. In some embodiments, a mutation in a core promoter or core promoter region and in a distal promoter or distal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a core promoter or core promoter region and in a proximal promoter or proximal promoter region. In some embodiments, a mutation in a core promoter or core promoter region and in a proximal promoter or proximal promoter region of a gene disclosed disrupts or reduces the binding of RNA polymerase, one or more transcription factors, or both RNA polymerase and one or more transcription factors. In some embodiments, a mutation in a core promoter or core promoter region and in a proximal promoter or proximal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a proximal promoter or proximal promoter region and in a distal promoter or distal promoter region. In some embodiments, a mutation in a proximal promoter or proximal promoter region and in a distal promoter or distal promoter region of a gene disclosed disrupts or reduces the binding of RNA polymerase, one or more transcription factors, or both RNA polymerase and one or more transcription factors. In some embodiments, a mutation in a proximal promoter or proximal promoter region and in a distal promoter or distal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

In some embodiments, a gene disclosed comprises a mutation in a proximal promoter or proximal promoter region, in a core promoter or core promoter region, and in a distal promoter or distal promoter region. In some embodiments, a mutation in a proximal promoter or proximal promoter region, in a core promoter or core promoter region, and in a distal promoter or distal promoter region of a gene disclosed disrupts or reduces the binding of RNA polymerase, one or more transcription factors, or both RNA polymerase and one or more transcription factors. In some embodiments, a mutation in a proximal promoter or proximal promoter region, in a core promoter or core promoter region, and in a distal promoter or distal promoter region in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

Response elements are DNA sequences that provide a stable binding site for RNA polymerase and transcription factors in a promoter. In some embodiments, the promoter includes one or more response elements. In some embodiments, a gene disclosed (e.g., a SlER gene or a mutant thereof or a homolog thereof, a SP gene or a mutant thereof or a homolog thereof, or a SP5G gene or a mutant thereof or a homolog thereof) comprises one or more mutations in one or more response elements. In some embodiments, a mutation in a response element of a gene disclosed disrupts or reduces the binding of RNA polymerase, one or more transcription factors, or both RNA polymerase and one or more transcription factors. In some embodiments, a mutation in one or more response elements in an allele of a gene disclosed encodes mRNA or protein at a level of expression that is at least 30% lower (e.g., at least 30%, at least 40%, at least 50%, at least 60%, at least 70%, at least 80% or at least 90%) or 30%, 40%, 50%, 60%, 70%, 80%, 90%, 95%, 99%, or any range or combination thereof, than a mRNA or protein level of expression encoded by a corresponding reference allele.

The mutant Solyc08g061560 gene (or homolog thereof) can be any of the mutant Solyc08g061560 genes (or homologs thereof) disclosed. The mutant Solyc05g053850 gene (or homolog thereof) can be any of the mutant Solyc05g053850 genes (or homologs thereof) disclosed. The mutant Solyc06g074350 gene (or homolog thereof) can be any of the mutant Solyc06g074350 genes (or homologs thereof) disclosed.

The genetically-altered plant (e.g., a Solanaceae plant) can be, for example, inbred, isogenic or hybrid, as long as the plant comprises a mutant gene, such as a mutant Solyc08g061560 gene (or homolog thereof), a mutant Solyc05g053850 gene (or homolog thereof), or a mutant Solyc06g074350 gene (or homolog thereof); or two mutant genes, such as both a mutant Solyc08g061560 gene (or homolog thereof) and a mutant Solyc05g053850 gene (or homolog thereof), both a mutant Solyc08g061560 gene (or homolog thereof) and a mutant Solyc06g074350 gene (or homolog thereof), or both a mutant Solyc05g053850 gene (or homolog thereof) and a mutant Solyc06g074350 gene (or homolog thereof); or three mutant genes, such as a mutant Solyc08g061560 gene (or homolog thereof), a mutant Solyc05g053850 gene (or homolog thereof), and a mutant SolycO6gO74350 gene (or homolog thereof).

In some embodiments, the genetically-altered plant (e.g., a Solanaceae plant) comprises one WT copy of the Solyc08GO61560 gene (or homolog thereof) and one mutant copy of the Solyc08g061560 gene (or homolog thereof) as disclosed (is heterozygous for the mutant Solyc08g061560 gene or homolog thereof). In some embodiments, the Solanaceae plant comprises two copies of a mutant Solyc08g061560 gene (or homolog thereof) as disclosed (is homozygous for the mutant Solyc08g061560 gene or homolog thereof). In some embodiments, the Solanaceae plant comprises a first mutant Solyc08g061560 gene (or homolog thereof) as disclosed and a second mutant Solyc08g061560 gene (or homolog thereof) as disclosed, wherein the first mutant Solyc08g061560 gene (or homolog thereof) and the second mutant Solyc08g061560 gene (or homolog thereof) are different. In some embodiments, the plant (e.g., a Solanaceae plant) comprises one copy of a mutant Solyc08g061560 gene (or homolog thereof) as disclosed and one copy of a mutant Solyc05g053850 gene (or homolog thereof) as disclosed (is heterozygous for the mutant Solyc08g061560 gene, or homolog thereof, and heterozygous for the mutant Solyc05g053850 gene, or homolog thereof). In some embodiments, the plant (e.g., a Solanaceae plant) comprises one copy of a mutant Solyc08g061560 gene (or homolog thereof) as disclosed and two copies of a mutant Solyc05g053850 gene (or homolog thereof) as disclosed (is heterozygous for the mutant Solyc08g061560 gene, or homolog thereof and homozygous for the mutant Solyc05g053850 gene, or homolog thereof). In some embodiments, the Solanaceae plant comprises two copies of a mutant Solyc08g061560 gene (or homolog thereof) as disclosed and two copies of a mutant Solyc05g053850 gene (or homolog thereof) as disclosed (is homozygous for the mutant Solyc08g061560 gene, or homolog thereof, and homozygous for the mutant Solyc05g053850 gene, or homolog thereof).

In some embodiments, the plant, such as a genetically-altered plant (e.g., a Solanaceae plant), comprises one WT copy of a SOLYC06G074350 gene (or homolog thereof) and one mutant copy of a Solyc06g074350 gene (or homolog thereof) as disclosed (is heterozygous for the mutant Solyc06g074350 gene, or homolog thereof). In some embodiments, the plant (e.g., a Solanaceae plant) comprises two copies of a mutant Solyc06g074350 gene (or homolog thereof) as disclosed (is homozygous for the mutant Solyc06g074350 gene or homolog thereof). In some embodiments, the plant (e.g., a Solanaceae plant) comprises one copy of a mutant Solyc06g074350 gene (or homolog thereof) as disclosed and one copy of a mutant Solyc08g061560 gene (or homolog thereof) as disclosed (is heterozygous for the mutant Solyc06g074350 gene, or homolog thereof, and heterozygous for the mutant Solyc08g061560 gene, or homolog thereof). In some embodiments, the plant (e.g., a Solanaceae plant) comprises one copy of a mutant Solyc06g074350 gene (or homolog thereof) as disclosed and two copies of a mutant Solyc08g061560 gene (or homolog thereof) as disclosed (is heterozygous for the mutant Solyc06g074350 gene, or homolog thereof, and homozygous for the mutant Solyc08g061560 gene, or homolog thereof). In some embodiments, the plant (e.g., a Solanaceae plant) comprises two copies of a mutant Solyc06g074350 gene (or homolog thereof) as disclosed and two copies of a mutant Solyc08g061560 gene (or homolog thereof) as disclosed (is homozygous for the mutant Solyc06g074350 gene, or homolog thereof, and homozygous for the mutant Solyc08g061560 gene, or homolog thereof).

In some embodiments, the genetically-altered plant (e.g., a Solanaceae plant) comprises one WT copy of a SOLYC06G074350 gene and one mutant copy of a Solyc06g074350 gene as disclosed (is heterozygous for the mutant Solyc06g074350 gene) and comprises one WT copy of the SOLYC05G053850 gene and one mutant copy of the Solyc05g053850 gene as disclosed (is heterozygous for the mutant Solyc05g053850 gene). In some embodiments, the plant (e.g., a Solanaceae plant) comprises two copies of a mutant Solyc06g074350 gene as disclosed (is homozygous for the mutant Solyc06g074350 gene) and comprises two copies of a mutant Solyc05g053850 gene as disclosed (is homozygous for the mutant Solyc05g053850 gene). In some embodiments, the plant (e.g., a Solanaceae plant) comprising a mutant Solyc06g074350 gene (one or two copies) as disclosed and a mutant Solyc05g053850 gene (one or two copies) further comprises one copy of a mutant Solyc08g061560 gene as disclosed (is heterozygous or homozygous for the mutant Solyc06g074350 gene and the mutant Solyc05g053850 gene and heterozygous for the mutant Solyc08g061560 gene). In some embodiments, the plant (e.g., a Solanaceae plant) further comprises two copies of a mutant Solyc08g061560 gene as disclosed (is homozygous for the mutant Solyc08g061560 gene).

Other, non-limiting exemplary genotype combinations which a Solanaceae (e.g., *Solanum lycopersicum*) plant may comprise are displayed in Table 2. The combinations in Table 2 may also be with homologs of the genes.

TABLE 2

Examples of genotype combinations of genetically-altered plants (e.g., a *Solanaceae* plant, such as tomato).

| SlER or homolog thereof Genotype | SP5G or homolog thereof Genotype | SP or homolog thereof Genotype |
|---|---|---|
| sler$^{EMS-1}$/sler$^{EMS-1}$ | sp5g/sp5g | sp/sp |
| sler$^{EMS-1}$/sler$^{EMS-1}$ | sp5g/sp5g | sp/+ |
| sler$^{EMS-1}$/sler$^{EMS-1}$ | sp5g/sp5g | sp$^{CR}$/sp$^{CR}$ |
| sler$^{EMS-1}$/sler$^{EMS-1}$ | sp5g/sp5g | sp$^{CR}$/+ |
| sler$^{EMS-1}$/sler$^{EMS-1}$ | sp5g/sp5g | +/+ |
| sler$^{EMS-1}$/sler$^{EMS-1}$ | sp5g/+ | sp/sp |
| sler$^{EMS-1}$/sler$^{EMS-1}$ | sp5g/+ | sp/+ |
| sler$^{EMS-1}$/sler$^{EMS-1}$ | sp5g/+ | sp$^{CR}$/sp$^{CR}$ |
| sler$^{EMS-1}$/sler$^{EMS-1}$ | sp5g/+ | sp$^{CR}$/+ |
| sler$^{EMS-1}$/sler$^{EMS-1}$ | sp5g/+ | +/+ |
| sler$^{EMS-1}$/sler$^{EMS-1}$ | +/+ | sp/sp |
| sler$^{EMS-1}$/sler$^{EMS-1}$ | +/+ | sp/+ |
| sler$^{EMS-1}$/sler$^{EMS-1}$ | +/+ | sp$^{CR}$/sp$^{CR}$ |
| sler$^{EMS-1}$/sler$^{EMS-1}$ | +/+ | sp$^{CR}$/+ |
| sler$^{EMS-1}$/sler$^{EMS-1}$ | +/+ | +/+ |
| sler$^{EMS-1}$/+ | sp5g/sp5g | sp/sp |
| sler$^{EMS-1}$/+ | sp5g/sp5g | sp/+ |
| sler$^{EMS-1}$/+ | sp5g/sp5g | sp$^{CR}$/sp$^{CR}$ |
| sler$^{EMS-1}$/+ | sp5g/sp5g | sp$^{CR}$/+ |
| sler$^{EMS-1}$/+ | sp5g/sp5g | +/+ |
| sler$^{EMS-1}$/+ | sp5g/+ | sp/sp |
| sler$^{EMS-1}$/+ | sp5g/+ | sp/+ |
| sler$^{EMS-1}$/+ | sp5g/+ | sp$^{CR}$/sp$^{CR}$ |
| sler$^{EMS-1}$/+ | sp5g/+ | sp$^{CR}$/+ |
| sler$^{EMS-1}$/+ | sp5g/+ | +/+ |
| sler$^{EMS-1}$/+ | +/+ | sp/sp |
| sler$^{EMS-1}$/+ | +/+ | sp/+ |
| sler$^{EMS-1}$/+ | +/+ | sp$^{CR}$/sp$^{CR}$ |
| sler$^{EMS-1}$/+ | +/+ | sp$^{CR}$/+ |
| sler$^{EMS-1}$/+ | +/+ | +/+ |
| +/+ | sp5g/sp5g | sp/sp |
| +/+ | sp5g/sp5g | sp/+ |
| +/+ | sp5g/sp5g | sp$^{CR}$/sp$^{CR}$ |
| +/+ | sp5g/sp5g | sp$^{CR}$/+ |
| +/+ | sp5g/sp5g | +/+ |
| +/+ | sp5g/+ | sp/sp |
| +/+ | sp5g/+ | sp/+ |
| +/+ | sp5g/+ | sp$^{CR}$/sp$^{CR}$ |
| +/+ | sp5g/+ | sp$^{CR}$/+ |
| +/+ | sp5g/+ | +/+ |
| +/+ | +/+ | sp/sp |
| +/+ | +/+ | sp/+ |
| +/+ | +/+ | sp$^{CR}$/sp$^{CR}$ |
| +/+ | +/+ | sp$^{CR}$/+ |
| +/+ | +/+ | +/+ |
| sler$^{EMS-2}$/sler$^{EMS-2}$ | sp5g/sp5g | sp/sp |
| sler$^{EMS-2}$/sler$^{EMS-2}$ | sp5g/sp5g | sp/+ |
| sler$^{EMS-2}$/sler$^{EMS-2}$ | sp5g/sp5g | sp$^{CR}$/sp$^{CR}$ |
| sler$^{EMS-2}$/sler$^{EMS-2}$ | sp5g/sp5g | sp$^{CR}$/+ |
| sler$^{EMS-2}$/sler$^{EMS-2}$ | sp5g/sp5g | +/+ |
| sler$^{EMS-2}$/sler$^{EMS-2}$ | sp5g/+ | sp/sp |
| sler$^{EMS-2}$/sler$^{EMS-2}$ | sp5g/+ | sp/+ |
| sler$^{EMS-2}$/sler$^{EMS-2}$ | sp5g/+ | sp$^{CR}$/sp$^{CR}$ |
| sler$^{EMS-2}$/sler$^{EMS-2}$ | sp5g/+ | sp$^{CR}$/+ |
| sler$^{EMS-2}$/sler$^{EMS-2}$ | sp5g/+ | +/+ |
| sler$^{EMS-2}$/sler$^{EMS-2}$ | +/+ | sp/sp |
| sler$^{EMS-2}$/sler$^{EMS-2}$ | +/+ | sp/+ |
| sler$^{EMS-2}$/sler$^{EMS-2}$ | +/+ | sp$^{CR}$/sp$^{CR}$ |
| sler$^{EMS-2}$/sler$^{EMS-2}$ | +/+ | sp$^{CR}$/+ |
| sler$^{EMS-2}$/sler$^{EMS-2}$ | +/+ | +/+ |
| sler$^{EMS-2}$/+ | sp5g/sp5g | sp/sp |
| sler$^{EMS-2}$/+ | sp5g/sp5g | sp/+ |
| sler$^{EMS-2}$/+ | sp5g/sp5g | sp$^{CR}$/sp$^{CR}$ |
| sler$^{EMS-2}$/+ | sp5g/sp5g | sp$^{CR}$/+ |
| sler$^{EMS-2}$/+ | sp5g/sp5g | +/+ |

TABLE 2-continued

Examples of genotype combinations of genetically-altered plants (e.g., a *Solanaceae* plant, such as tomato).

| SlER or homolog thereof Genotype | SP5G or homolog thereof Genotype | SP or homolog thereof Genotype |
|---|---|---|
| sler$^{EMS-2}$/+ | sp5g/+ | sp/sp |
| sler$^{EMS-2}$/+ | sp5g/+ | sp/+ |
| sler$^{EMS-2}$/+ | sp5g/+ | sp$^{CR}$/sp$^{CR}$ |
| sler$^{EMS-2}$/+ | sp5g/+ | sp$^{CR}$/+ |
| sler$^{EMS-2}$/+ | sp5g/+ | +/+ |
| sler$^{EMS-2}$/+ | +/+ | sp/sp |
| sler$^{EMS-2}$/+ | +/+ | sp/+ |
| sler$^{EMS-2}$/+ | +/+ | sp$^{CR}$/sp$^{CR}$ |
| sler$^{EMS-2}$/+ | +/+ | sp$^{CR}$/+ |
| sler$^{EMS-2}$/+ | +/+ | +/+ |
| M82 sler$^{CR-1}$/M82 sler$^{CR-1}$ | sp5g/sp5g | sp/sp |
| M82 sler$^{CR-1}$/M82 sler$^{CR-1}$ | sp5g/sp5g | sp/+ |
| M82 sler$^{CR-1}$/M82 sler$^{CR-1}$ | sp5g/sp5g | sp$^{CR}$/sp$^{CR}$ |
| M82 sler$^{CR-1}$/M82 sler$^{CR-1}$ | sp5g/sp5g | sp$^{CR}$/+ |
| M82 sler$^{CR-1}$/M82 sler$^{CR-1}$ | sp5g/sp5g | +/+ |
| M82 sler$^{CR-1}$/M82 sler$^{CR-1}$ | sp5g/+ | sp/sp |
| M82 sler$^{CR-1}$/M82 sler$^{CR-1}$ | sp5g/+ | sp/+ |
| M82 sler$^{CR-1}$/M82 sler$^{CR-1}$ | sp5g/+ | sp$^{CR}$/sp$^{CR}$ |
| M82 sler$^{CR-1}$/M82 sler$^{CR-1}$ | sp5g/+ | sp$^{CR}$/+ |
| M82 sler$^{CR-1}$/M82 sler$^{CR-1}$ | sp5g/+ | +/+ |
| M82 sler$^{CR-1}$/M82 sler$^{CR-1}$ | +/+ | sp/sp |
| M82 sler$^{CR-1}$/M82 sler$^{CR-1}$ | +/+ | sp/+ |
| M82 sler$^{CR-1}$/M82 sler$^{CR-1}$ | +/+ | sp$^{CR}$/sp$^{CR}$ |
| M82 sler$^{CR-1}$/M82 sler$^{CR-1}$ | +/+ | sp$^{CR}$/+ |
| M82 sler$^{CR-1}$/M82 sler$^{CR-1}$ | +/+ | +/+ |
| M82 sler$^{CR-1}$/+ | sp5g/sp5g | sp/sp |
| M82 sler$^{CR-1}$/+ | sp5g/sp5g | sp/+ |
| M82 sler$^{CR-1}$/+ | sp5g/sp5g | sp$^{CR}$/sp$^{CR}$ |
| M82 sler$^{CR-1}$/+ | sp5g/sp5g | sp$^{CR}$/+ |
| M82 sler$^{CR-1}$/+ | sp5g/sp5g | +/+ |
| M82 sler$^{CR-1}$/+ | sp5g/+ | sp/sp |
| M82 sler$^{CR-1}$/+ | sp5g/+ | sp/+ |
| M82 sler$^{CR-1}$/+ | sp5g/+ | sp$^{CR}$/sp$^{CR}$ |
| M82 sler$^{CR-1}$/+ | sp5g/+ | sp$^{CR}$/+ |
| M82 sler$^{CR-1}$/+ | sp5g/+ | +/+ |
| M82 sler$^{CR-1}$/+ | +/+ | sp/sp |
| M82 sler$^{CR-1}$/+ | +/+ | sp/+ |
| M82 sler$^{CR-1}$/+ | +/+ | sp$^{CR}$/sp$^{CR}$ |
| M82 sler$^{CR-1}$/+ | +/+ | sp$^{CR}$/+ |
| M82 sler$^{CR-1}$/+ | +/+ | +/+ |
| M82 sler$^{CR-2}$M82 sler$^{CR-2}$ | sp5g/sp5g | sp/sp |
| M82 sler$^{CR-2}$M82 sler$^{CR-2}$ | sp5g/sp5g | sp/+ |
| M82 sler$^{CR-2}$M82 sler$^{CR-2}$ | sp5g/sp5g | sp$^{CR}$/sp$^{CR}$ |
| M82 sler$^{CR-2}$M82 sler$^{CR-2}$ | sp5g/sp5g | sp$^{CR}$/+ |
| M82 sler$^{CR-2}$M82 sler$^{CR-2}$ | sp5g/sp5g | +/+ |
| M82 sler$^{CR-2}$M82 sler$^{CR-2}$ | sp5g/+ | sp/sp |
| M82 sler$^{CR-2}$M82 sler$^{CR-2}$ | sp5g/+ | sp/+ |
| M82 sler$^{CR-2}$M82 sler$^{CR-2}$ | sp5g/+ | sp$^{CR}$/sp$^{CR}$ |
| M82 sler$^{CR-2}$M82 sler$^{CR-2}$ | sp5g/+ | sp$^{CR}$/+ |

TABLE 2-continued

Examples of genotype combinations of genetically-altered plants (e.g., a *Solanaceae* plant, such as tomato).

| SlER or homolog thereof Genotype | SP5G or homolog thereof Genotype | SP or homolog thereof Genotype |
|---|---|---|
| M82 sler$^{CR-2}$M82 sler$^{CR-2}$ | sp5g/+ | +/+ |
| M82 sler$^{CR-2}$M82 sler$^{CR-2}$ | +/+ | sp/sp |
| M82 sler$^{CR-2}$M82 sler$^{CR-2}$ | +/+ | sp/+ |
| M82 sler$^{CR-2}$M82 sler$^{CR-2}$ | +/+ | sp$^{CR}$/sp$^{CR}$ |
| M82 sler$^{CR-2}$M82 sler$^{CR-2}$ | +/+ | sp$^{CR}$/+ |
| M82 sler$^{CR-2}$M82 sler$^{CR-2}$ | +/+ | +/+ |
| M82 sler$^{CR-2}$/+ | sp5g/sp5g | sp/sp |
| M82 sler$^{CR-2}$/+ | sp5g/sp5g | sp/+ |
| M82 sler$^{CR-2}$/+ | sp5g/sp5g | sp$^{CR}$/sp$^{CR}$ |
| M82 sler$^{CR-2}$/+ | sp5g/sp5g | sp$^{CR}$/+ |
| M82 sler$^{CR-2}$/+ | sp5g/sp5g | +/+ |
| M82 sler$^{CR-2}$/+ | sp5g/+ | sp/sp |
| M82 sler$^{CR-2}$/+ | sp5g/+ | sp/+ |
| M82 sler$^{CR-2}$/+ | sp5g/+ | sp$^{CR}$/sp$^{CR}$ |
| M82 sler$^{CR-2}$/+ | sp5g/+ | sp$^{CR}$/+ |
| M82 sler$^{CR-2}$/+ | sp5g/+ | +/+ |
| M82 sler$^{CR-2}$/+ | +/+ | sp/sp |
| M82 sler$^{CR-2}$/+ | +/+ | sp/+ |
| M82 sler$^{CR-2}$/+ | +/+ | sp$^{CR}$/sp$^{CR}$ |
| M82 sler$^{CR-2}$/+ | +/+ | sp$^{CR}$/+ |
| M82 sler$^{CR-2}$/+ | +/+ | +/+ |
| sler$^{MT}$/sler$^{MT}$ | sp5g/sp5g | sp/sp |
| sler$^{MT}$/sler$^{MT}$ | sp5g/sp5g | sp/+ |
| sler$^{MT}$/sler$^{MT}$ | sp5g/sp5g | sp$^{CR}$/sp$^{CR}$ |
| sler$^{MT}$/sler$^{MT}$ | sp5g/sp5g | sp$^{CR}$/+ |
| sler$^{MT}$/sler$^{MT}$ | sp5g/sp5g | +/+ |
| sler$^{MT}$/sler$^{MT}$ | sp5g/+ | sp/sp |
| sler$^{MT}$/sler$^{MT}$ | sp5g/+ | sp/+ |
| sler$^{MT}$/sler$^{MT}$ | sp5g/+ | sp$^{CR}$/sp$^{CR}$ |
| sler$^{MT}$/sler$^{MT}$ | sp5g/+ | sp$^{CR}$/+ |
| sler$^{MT}$/sler$^{MT}$ | sp5g/+ | +/+ |
| sler$^{MT}$/sler$^{MT}$ | +/+ | sp/sp |
| sler$^{MT}$/sler$^{MT}$ | +/+ | sp/+ |
| sler$^{MT}$/sler$^{MT}$ | +/+ | sp$^{CR}$/sp$^{CR}$ |
| sler$^{MT}$/sler$^{MT}$ | +/+ | sp$^{CR}$/+ |
| sler$^{MT}$/sler$^{MT}$ | +/+ | +/+ |
| sler$^{MT}$/+ | sp5g/sp5g | sp/sp |
| sler$^{MT}$/+ | sp5g/sp5g | sp/+ |
| sler$^{MT}$/+ | sp5g/sp5g | sp$^{CR}$/sp$^{CR}$ |
| sler$^{MT}$/+ | sp5g/sp5g | sp$^{CR}$/+ |
| sler$^{MT}$/+ | sp5g/sp5g | +/+ |
| sler$^{MT}$/+ | sp5g/+ | sp/sp |
| sler$^{MT}$/+ | sp5g/+ | sp/+ |
| sler$^{MT}$/+ | sp5g/+ | sp$^{CR}$/sp$^{CR}$ |
| sler$^{MT}$/+ | sp5g/+ | sp$^{CR}$l+ |
| sler$^{MT}$/+ | sp5g/+ | +/+ |
| sler$^{MT}$/+ | +/+ | sp/sp |
| sler$^{MT}$/+ | +/+ | sp/+ |
| sler$^{MT}$/+ | +/+ | sp$^{CR}$/sp$^{CR}$ |
| sler$^{MT}$/+ | +/+ | sp$^{CR}$l+ |
| sler$^{MT}$/+ | +/+ | +/+ |
| sler$^{CR-pro-4}$/sler$^{CR-pro-4}$ | sp5g/sp5g | sp/sp |
| sler$^{CR-pro-4}$/sler$^{CR-pro-4}$ | sp5g/sp5g | sp/+ |
| sler$^{CR-pro-4}$/sler$^{CR-pro-4}$ | sp5g/sp5g | sp$^{CR}$/sp$^{CR}$ |
| sler$^{CR-pro-4}$/sler$^{CR-pro-4}$ | sp5g/sp5g | sp$^{CR}$/+ |
| sler$^{CR-pro-4}$/sler$^{CR-pro-4}$ | sp5g/sp5g | +/+ |
| sler$^{CR-pro-4}$/sler$^{CR-pro-4}$ | sp5g/+ | sp/sp |
| sler$^{CR-pro-4}$/sler$^{CR-pro-4}$ | sp5g/+ | sp/+ |
| sler$^{CR-pro-4}$/sler$^{CR-pro-4}$ | sp5g/+ | sp$^{CR}$/sp$^{CR}$ |
| sler$^{CR-pro-4}$/sler$^{CR-pro-4}$ | sp5g/+ | sp$^{CR}$/+ |
| sler$^{CR-pro-4}$/sler$^{CR-pro-4}$ | sp5g/+ | +/+ |
| sler$^{CR-pro-4}$/sler$^{CR-pro-4}$ | +/+ | sp/sp |
| sler$^{CR-pro-4}$/sler$^{CR-pro-4}$ | +/+ | sp/+ |
| sler$^{CR-pro-4}$/sler$^{CR-pro-4}$ | +/+ | sp$^{CR}$/sp$^{CR}$ |
| sler$^{CR-pro-4}$/sler$^{CR-pro-4}$ | +/+ | sp$^{CR}$/+ |
| sler$^{CR-pro-4}$/sler$^{CR-pro-4}$ | +/+ | +/+ |
| sler$^{CR-pro-4}$/+ | sp5g/sp5g | sp/sp |
| sler$^{CR-pro-4}$/+ | sp5g/sp5g | sp/+ |
| sler$^{CR-pro-4}$/+ | sp5g/sp5g | sp$^{CR}$/sp$^{CR}$ |
| sler$^{CR-pro-4}$/+ | sp5g/sp5g | sp$^{CR}$/+ |
| sler$^{CR-pro-4}$/+ | sp5g/sp5g | +/+ |
| sler$^{CR-pro-4}$/+ | sp5g/+ | sp/sp |
| sler$^{CR-pro-4}$/+ | sp5g/+ | sp/+ |
| sler$^{CR-pro-4}$/+ | sp5g/+ | sp$^{CR}$/sp$^{CR}$ |
| sler$^{CR-pro-4}$/+ | sp5g/+ | sp$^{CR}$/+ |
| sler$^{CR-pro-4}$/+ | sp5g/+ | +/+ |
| sler$^{CR-pro-4}$/+ | +/+ | sp/sp |
| sler$^{CR-pro-4}$/+ | +/+ | sp/+ |
| sler$^{CR-pro-4}$/+ | +/+ | sp$^{CR}$/sp$^{CR}$ |
| sler$^{CR-pro-4}$/+ | +/+ | sp$^{CR}$/+ |
| sler$^{CR-pro-4}$/+ | +/+ | +/+ |
| sler$^{CR-pro-14}$/sler$^{CR-pro-14}$ | sp5g/sp5g | sp/sp |
| sler$^{CR-pro-14}$/sler$^{CR-pro-14}$ | sp5g/sp5g | sp/+ |
| sler$^{CR-pro-14}$/sler$^{CR-pro-14}$ | sp5g/sp5g | sp$^{CR}$/sp$^{CR}$ |
| sler$^{CR-pro-14}$/sler$^{CR-pro-14}$ | sp5g/sp5g | sp$^{CR}$/+ |
| sler$^{CR-pro-14}$/sler$^{CR-pro-14}$ | sp5g/sp5g | +/+ |
| sler$^{CR-pro-14}$/sler$^{CR-pro-14}$ | sp5g/+ | sp/sp |
| sler$^{CR-pro-14}$/sler$^{CR-pro-14}$ | sp5g/+ | sp/+ |
| sler$^{CR-pro-14}$/sler$^{CR-pro-14}$ | sp5g/+ | sp$^{CR}$/sp$^{CR}$ |
| sler$^{CR-pro-14}$/sler$^{CR-pro-14}$ | sp5g/+ | sp$^{CR}$/+ |
| sler$^{CR-pro-14}$/sler$^{CR-pro-14}$ | sp5g/+ | +/+ |
| sler$^{CR-pro-14}$/sler$^{CR-pro-14}$ | +/+ | sp/sp |
| sler$^{CR-pro-14}$/sler$^{CR-pro-14}$ | +/+ | sp/+ |
| sler$^{CR-pro-14}$/sler$^{CR-pro-14}$ | +/+ | sp$^{CR}$/sp$^{CR}$ |
| sler$^{CR-pro-14}$/sler$^{CR-pro-14}$ | +/+ | sp$^{CR}$/+ |
| sler$^{CR-pro-14}$/sler$^{CR-pro-14}$ | +/+ | +/+ |
| sler$^{CR-pro-14}$/+ | sp5g/sp5g | sp/sp |
| sler$^{CR-pro-14}$/+ | sp5g/sp5g | sp/+ |
| sler$^{CR-pro-14}$/+ | sp5g/sp5g | sp$^{CR}$/sp$^{CR}$ |
| sler$^{CR-pro-14}$/+ | sp5g/sp5g | sp$^{CR}$/+ |
| sler$^{CR-pro-14}$/+ | sp5g/sp5g | +/+ |
| sler$^{CR-pro-14}$/+ | sp5g/+ | sp/sp |
| sler$^{CR-pro-14}$/+ | sp5g/+ | sp/+ |
| sler$^{CR-pro-14}$/+ | sp5g/+ | sp$^{CR}$/sp$^{CR}$ |
| sler$^{CR-pro-14}$/+ | sp5g/+ | sp$^{CR}$/+ |
| sler$^{CR-pro-14}$/+ | sp5g/+ | +/+ |
| sler$^{CR-pro-14}$/+ | +/+ | sp/sp |
| sler$^{CR-pro-14}$/+ | +/+ | sp/+ |
| sler$^{CR-pro-14}$/+ | +/+ | sp$^{CR}$/sp$^{CR}$ |
| sler$^{CR-pro-14}$/+ | +/+ | sp$^{CR}$/+ |
| sler$^{CR-pro-14}$/+ | +/+ | +/+ |
| Sweet100 sler$^{CR-1}$/ Sweet100 sler$^{CR-1}$ | sp5g/sp5g | sp/sp |
| Sweet100 sler$^{CR-1}$/ Sweet100 sler$^{CR-1}$ | sp5g/sp5g | sp/+ |
| Sweet100 sler$^{CR-1}$/ Sweet100 sler$^{CR-1}$ | sp5g/sp5g | sp$^{CR}$/sp$^{CR}$ |
| Sweet100 sler$^{CR-1}$/ Sweet100 sler$^{CR-1}$ | sp5g/sp5g | sp$^{CR}$/+ |
| Sweet100 sler$^{CR-1}$/ Sweet100 sler$^{CR-1}$ | sp5g/sp5g | +/+ |
| Sweet100 sler$^{CR-1}$/ Sweet100 sler$^{CR-1}$ | sp5g/+ | sp/sp |
| Sweet100 sler$^{CR-1}$/ Sweet100 sler$^{CR-1}$ | sp5g/+ | sp/+ |
| Sweet100 sler$^{CR-1}$/ Sweet100 sler$^{CR-1}$ | sp5g/+ | sp$^{CR}$/sp$^{CR}$ |
| Sweet100 sler$^{CR-1}$/ Sweet100 sler$^{CR-1}$ | sp5g/+ | sp$^{CR}$/+ |
| Sweet100 sler$^{CR-1}$/ Sweet100 sler$^{CR-1}$ | sp5g/+ | +/+ |
| Sweet100 sler$^{CR-1}$/ Sweet100 sler$^{CR-1}$ | +/+ | sp/sp |
| Sweet100 sler$^{CR-1}$/ Sweet100 sler$^{CR-1}$ | +/+ | sp/+ |
| Sweet100 sler$^{CR-1}$/ Sweet100 sler$^{CR-1}$ | +/+ | sp$^{CR}$/sp$^{CR}$ |
| Sweet100 sler$^{CR-1}$/ Sweet100 sler$^{CR-1}$ | +/+ | sp$^{CR}$/+ |
| Sweet100 sler$^{CR-1}$/ Sweet100 sler$^{CR-1}$ | +/+ | +/+ |
| Sweet100 sler$^{CR-1}$/ | sp5g/sp5g | sp/sp |

TABLE 2-continued

Examples of genotype combinations of genetically-altered plants (e.g., a *Solanaceae* plant, such as tomato).

| SlER or homolog thereof Genotype | SP5G or homolog thereof Genotype | SP or homolog thereof Genotype |
|---|---|---|
| Sweet100 sler$^{CR-1}$ | sp5g/sp5g | sp/+ |
| Sweet100 sler$^{CR-1}$/ | sp5g/sp5g | sp$^{CR}$/sp$^{CR}$ |
| Sweet100 sler$^{CR-1}$ | sp5g/sp5g | sp$^{CR}$/+ |
| Sweet100 sler$^{CR-1}$/ | sp5g/sp5g | +/+ |
| Sweet100 sler$^{CR-1}$ | sp5g/+ | sp/sp |
| Sweet100 sler$^{CR-1}$/ | sp5g/+ | sp/+ |
| Sweet100 sler$^{CR-1}$ | sp5g/+ | sp$^{CR}$/sp$^{CR}$ |
| Sweet100 sler$^{CR-1}$/ | sp5g/+ | sp$^{CR}$/+ |
| Sweet100 sler$^{CR-1}$ | sp5g/+ | +/+ |
| Sweet100 sler$^{CR-1}$/ | +/+ | sp/sp |
| Sweet100 sler$^{CR-1}$ | +/+ | sp/+ |
| Sweet100 sler$^{CR-1}$/ | +/+ | sp$^{CR}$/sp$^{CR}$ |
| Sweet100 sler$^{CR-1}$ | +/+ | sp$^{CR}$/+ |
| Sweet100 sler$^{CR-1}$/ | +/+ | +/+ |
| Sweet100 sler$^{CR-2}$/Sweet100 sler$^{CR-2}$ | sp5g/sp5g | sp/sp |
| Sweet100 sler$^{CR-2}$/Sweet100 sler$^{CR-2}$ | sp5g/sp5g | sp/+ |
| Sweet100 sler$^{CR-2}$/Sweet100 sler$^{CR-2}$ | sp5g/sp5g | sp$^{CR}$/sp$^{CR}$ |
| Sweet100 sler$^{CR-2}$/Sweet100 sler$^{CR-2}$ | sp5g/sp5g | sp$^{CR}$/+ |
| Sweet100 sler$^{CR-2}$/Sweet100 sler$^{CR-2}$ | sp5g/sp5g | +/+ |
| Sweet100 sler$^{CR-2}$/Sweet100 sler$^{CR-2}$ | sp5g/+ | sp/sp |
| Sweet100 sler$^{CR-2}$/Sweet100 sler$^{CR-2}$ | sp5g/+ | sp/+ |
| Sweet100 sler$^{CR-2}$/Sweet100 sler$^{CR-2}$ | sp5g/+ | sp$^{CR}$/sp$^{CR}$ |
| Sweet100 sler$^{CR-2}$/Sweet100 sler$^{CR-2}$ | sp5g/+ | sp$^{CR}$/+ |
| Sweet100 sler$^{CR-2}$/Sweet100 sler$^{CR-2}$ | sp5g/+ | +/+ |
| Sweet100 sler$^{CR-2}$/Sweet100 sler$^{CR-2}$ | +/+ | sp/sp |
| Sweet100 sler$^{CR-2}$/Sweet100 sler$^{CR-2}$ | +/+ | sp/+ |
| Sweet100 sler$^{CR-2}$/Sweet100 sler$^{CR-2}$ | +/+ | sp$^{CR}$/sp$^{CR}$ |
| Sweet100 sler$^{CR-2}$/Sweet100 sler$^{CR-2}$ | +/+ | sp$^{CR}$/+ |
| Sweet100 sler$^{CR-2}$/Sweet100 sler$^{CR-2}$ | +/+ | +/+ |
| Sweet100 sler$^{CR-2}$/+ | sp5g/sp5g | sp/sp |
| Sweet100 sler$^{CR-2}$/+ | sp5g/sp5g | sp/+ |
| Sweet100 sler$^{CR-2}$/+ | sp5g/sp5g | sp$^{CR}$/sp$^{CR}$ |
| Sweet100 sler$^{CR-2}$/+ | sp5g/sp5g | sp$^{CR}$/+ |
| Sweet100 sler$^{CR-2}$/+ | sp5g/sp5g | +/+ |
| Sweet100 sler$^{CR-2}$/+ | sp5g/+ | sp/sp |
| Sweet100 sler$^{CR-2}$/+ | sp5g/+ | sp/+ |
| Sweet100 sler$^{CR-2}$/+ | sp5g/+ | sp$^{CR}$/sp$^{CR}$ |
| Sweet100 sler$^{CR-2}$/+ | sp5g/+ | sp$^{CR}$/+ |
| Sweet100 sler$^{CR-2}$/+ | sp5g/+ | +/+ |
| Sweet100 sler$^{CR-2}$/+ | +/+ | sp/sp |
| Sweet100 sler$^{CR-2}$/+ | +/+ | sp/+ |
| Sweet100 sler$^{CR-2}$/+ | +/+ | sp$^{CR}$/sp$^{CR}$ |
| Sweet100 sler$^{CR-2}$/+ | +/+ | sp$^{CR}$/+ |
| Sweet100 sler$^{CR-2}$/+ | +/+ | +/+ |
| Sweet100 sler$^{CR-3}$/Sweet100 sler$^{CR-3}$ | sp5g/sp5g | sp/sp |
| Sweet100 sler$^{CR-3}$/Sweet100 sler$^{CR-3}$ | sp5g/sp5g | sp/+ |
| Sweet100 sler$^{CR-3}$/Sweet100 sler$^{CR-3}$ | sp5g/sp5g | sp$^{CR}$/sp$^{CR}$ |
| Sweet100 sler$^{CR-3}$/Sweet100 sler$^{CR-3}$ | sp5g/sp5g | sp$^{CR}$/+ |
| Sweet100 sler$^{CR-3}$/Sweet100 sler$^{CR-3}$ | sp5g/sp5g | +/+ |
| Sweet100 sler$^{CR-3}$/Sweet100 sler$^{CR-3}$ | sp5g/+ | sp/sp |
| Sweet100 sler$^{CR-3}$/Sweet100 sler$^{CR-3}$ | sp5g/+ | sp/+ |
| Sweet100 sler$^{CR-3}$/Sweet100 sler$^{CR-3}$ | sp5g/+ | sp$^{CR}$/sp$^{CR}$ |
| Sweet100 sler$^{CR-3}$/Sweet100 sler$^{CR-3}$ | sp5g/+ | sp$^{CR}$/+ |
| Sweet100 sler$^{CR-3}$/Sweet100 sler$^{CR-3}$ | sp5g/+ | +/+ |
| Sweet100 sler$^{CR-3}$/Sweet100 sler$^{CR-3}$ | +/+ | sp/sp |
| Sweet100 sler$^{CR-3}$/Sweet100 sler$^{CR-3}$ | +/+ | sp/+ |
| Sweet100 sler$^{CR-3}$/Sweet100 sler$^{CR-3}$ | +/+ | sp$^{CR}$/sp$^{CR}$ |
| Sweet100 sler$^{CR-3}$/Sweet100 sler$^{CR-3}$ | +/+ | sp$^{CR}$/+ |
| Sweet100 sler$^{CR-3}$/Sweet100 sler$^{CR-3}$ | +/+ | +/+ |
| Sweet100 sler$^{CR-3}$/+ | sp5g/sp5g | sp/sp |
| Sweet100 sler$^{CR-3}$/+ | sp5g/sp5g | sp/+ |
| Sweet100 sler$^{CR-3}$/+ | sp5g/sp5g | sp$^{CR}$/sp$^{CR}$ |
| Sweet100 sler$^{CR-3}$/+ | sp5g/sp5g | sp$^{CR}$/+ |
| Sweet100 sler$^{CR-3}$/+ | sp5g/sp5g | +/+ |
| Sweet100 sler$^{CR-3}$/+ | sp5g/+ | sp/sp |
| Sweet100 sler$^{CR-3}$/+ | sp5g/+ | sp/+ |
| Sweet100 sler$^{CR-3}$/+ | sp5g/+ | sp$^{CR}$/sp$^{CR}$ |
| Sweet100 sler$^{CR-3}$/+ | sp5g/+ | sp$^{CR}$/+ |
| Sweet100 sler$^{CR-3}$/+ | sp5g/+ | +/+ |
| Sweet100 sler$^{CR-3}$/+ | +/+ | sp/sp |
| Sweet100 sler$^{CR-3}$/+ | +/+ | sp/+ |
| Sweet100 sler$^{CR-3}$/+ | +/+ | sp$^{CR}$/sp$^{CR}$ |
| Sweet100 sler$^{CR-3}$/+ | +/+ | sp$^{CR}$/+ |
| Sweet100 sler$^{CR-3}$/+ | +/+ | +/+ |
| Sweet100 +/+ | sp5g/sp5g | sp/sp |
| Sweet100 +/+ | sp5g/sp5g | sp/+ |
| Sweet100 +/+ | sp5g/sp5g | sp$^{CR}$/sp$^{CR}$ |
| Sweet100 +/+ | sp5g/sp5g | sp$^{CR}$/+ |
| Sweet100 +/+ | sp5g/sp5g | +/+ |
| Sweet100 +/+ | sp5g/+ | sp/sp |
| Sweet100 +/+ | sp5g/+ | sp/+ |
| Sweet100 +/+ | sp5g/+ | sp$^{CR}$/sp$^{CR}$ |
| Sweet100 +/+ | sp5g/+ | sp$^{CR}$/+ |
| Sweet100 +/+ | sp5g/+ | +/+ |
| Sweet100 +/+ | +/+ | sp/sp |
| Sweet100 +/+ | +/+ | sp/+ |
| Sweet100 +/+ | +/+ | sp$^{CR}$/sp$^{CR}$ |
| Sweet100 +/+ | +/+ | sp$^{CR}$/+ |
| Sweet100 +/+ | +/+ | +/+ |

In some embodiments, the plant is a Solanaceae plant. In some embodiments, the Solanaceae plant is belladonna (*Atropa belladonna*) bell pepper (*Capsicum annuum*), cayenne pepper (*Capsicum annuum*), tabasco pepper (*Capsicum frutescens*), jimsonweed (*Datura stramonium*), henbane (*Hyoscyamus niger*), potato (*Solanum tuberosum*), woody nightshade (*Solanum dulcamara*), eggplant (*Solanum melongena*), tomato (*Solanum lycopersicum*), or buffalo bur (*Solanum rostratum*). In some embodiments, the Solanaceae plant belongs to the genus Browallia, Brugmansia, Brunfelsia, Capsicum, Cestrum, Datura, Lycium, Mandragora, Nierembergia, Petunia, Salpiglossis, Schizanthus, Solandra, Solanum, or Streptosolen. In some embodiments, the Solanaceae plant, e.g. tomato plant, is not a variety.

In some embodiments, the plant cell, such as from a plant, such as a genetically-altered plant, is contemplated herein. In some embodiments, the plant cell is a Solanaceae plant cell. A plant cell may comprise any genotype disclosed, e.g., as shown without limitation in Table 2, e.g., in the context of the Solanaceae plant. In some embodiments, the plant cell is isolated. In some embodiments, the Solanaceae plant cell is a non-replicating Solanaceae plant cell.

In some embodiments, a plant disclosed (e.g., any of the Solanaceae plants disclosed) may have an altered phenotype relative to a reference plant. In some embodiments, any of the plants (e.g., Solanaceae plants) disclosed have a shorter internode or stem length than a corresponding WT plant (e.g., Solanaceae plants). In some embodiments, any of the plants (e.g., Solanaceae plants) disclosed have one or more of the following characteristics that are appealing to consumers (e.g., mutant plants are more compact than the corresponding WT plant and/or can be grown indoors) and are advantageous for growers (e.g., mutant plants are more compact than the corresponding WT plant and occupy less room so that growers can have more plants and increase production without requiring additional land and/or space).

The characteristics include, but are not limited to, one or more of the following: modified stem or pedicel length and/or number of leaves to first inflorescence, which, according to some aspects, yields a compact plant architecture and/or early-yielding forms.

Food products are also contemplated herein. Such food products comprise a plant part, such as a Solanaceae plant part, such as a fruit (e.g., a tomato fruit). Non-limiting examples of food products include sauces (e.g., tomato sauce or ketchup), purees, pastes, juices, canned fruits, and soups. Food products may be produced or producible by using methods known in the art.

Isolated polynucleotides are also disclosed, including WT and mutant alleles of the Solyc08g061560 gene (or a homolog thereof). Isolated polynucleotides including WT and mutant alleles of the Solyc05g053850 gene (or a homolog thereof) are also contemplated. Isolated polynucleotides including WT and mutant alleles of the Solyc06g074350 gene (or a homolog thereof) are also contemplated.

Isolated polynucleotides can comprise, for example, a nucleic acid (e.g., DNA) having the sequence of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, or SEQ ID NO: 110; a portion of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 147, SEQ ID NO: 148, or SEQ ID NO: 149 that exhibits substantially the same activity as a nucleic acid (e.g., DNA) having the sequence of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 49, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, or SEQ ID NO: 110; a nucleic acid (e.g., DNA) having at least 85%, at least 90%, at least 95%, at least 96%, at least 97%, at least 98%, or at least 99% identity with the sequence of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 49, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 147, SEQ ID NO: 148, or SEQ ID NO: 149; an ortholog or homolog of the nucleic acid having the sequence of SEQ ID NO: 2, SEQ ID NO: 5, SEQ ID NO: 8, SEQ ID NO: 11, SEQ ID NO: 14, SEQ ID NO: 17, SEQ ID NO: 20, SEQ ID NO: 23, SEQ ID NO: 26, SEQ ID NO: 29, SEQ ID NO: 32, SEQ ID NO: 35, SEQ ID NO: 38, SEQ ID NO: 41, SEQ ID NO: 44, SEQ ID NO: 47, SEQ ID NO: 50, SEQ ID NO: 53, SEQ ID NO: 56, SEQ ID NO: 59, SEQ ID NO: 62, SEQ ID NO: 65, SEQ ID NO: 68, SEQ ID NO: 71, SEQ ID NO: 74, SEQ ID NO: 77, SEQ ID NO: 80, SEQ ID NO: 83, SEQ ID NO: 86, SEQ ID NO: 89, SEQ ID NO: 92, SEQ ID NO: 95, SEQ ID NO: 98, SEQ ID NO: 101, SEQ ID NO: 104, SEQ ID NO: 107, SEQ ID NO: 110, SEQ ID NO: 147, SEQ ID NO: 148, or SEQ ID NO: 149.

In some embodiments, the isolated polynucleotide is a cDNA. Such isolated polynucleotides can be used, for example, in methods of producing genetically-altered plants.

Other aspects of the disclosure relate to seeds for producing a plant (e.g., a Solanaceae plant) as disclosed, e.g., a mutant Solyc08g061560 gene (or a homolog thereof), a mutant Solyc05g053850 gene (or a homolog thereof), or a mutant Solyc06g074350 gene (or a homolog thereof).

Methods of Producing Plants

In other aspects, the disclosure provides methods for producing a genetically-altered plant (e.g., a Solanaceae plant). In some embodiments, the method comprises introducing a mutation into a Solyc08g061560 gene (or a homolog thereof), into a Solyc05g053850 gene (or a homolog thereof), or into a Solyc06g074350 gene (or a homolog thereof) in the plant (e.g., a Solanaceae plant), thereby producing a genetically-altered plant (e.g., a Solanaceae plant) containing a mutant version of the gene. In some embodiments, the method comprises introducing a mutation into a Solyc08g061560 gene (or a homolog thereof), into a Solyc05g053850 gene (or a homolog thereof), or into a Solyc06g074350 gene (or a homolog thereof) in the plant (e.g., a Solanaceae plant) part, maintaining the plant part under conditions and for sufficient time for production of a genetically-altered plant (e.g., a Solanaceae plant), thereby producing a genetically-altered plant (or a homolog thereof) containing a mutant version of the gene. In some embodiments, mutations are introduced into two or all three of a Solyc08g061560 gene (or a homolog thereof), a Solyc05g053850 gene (or a homolog thereof), and a Solyc06g074350 gene (or a homolog thereof).

In any of the methods disclosed, the mutant gene can be introduced into a plant (e.g., a Solanaceae plant) or a plant part or produced in a plant (e.g., a Solanaceae plant) or plant part by any method disclosed or known to those of skill in the art, such as *Agrobacterium*-mediated recombination, viral-vector mediated recombination, microinjection, gene gun bombardment/biolistic particle delivery, electroporation, mutagenesis (e.g., by ethyl methanesulfonate or fast neutron irradiation), TILLING (Targeting Induced Local Lesions in Genomes), conventional marker-assisted introgression, and nuclease mediated recombination (e.g., use of custom-made restriction enzymes for targeting mutagenesis by gene replacement, see, e.g., Ran et al., *Nat Protoc* (2013) 8(11):2281-308; Cermak et al., *Nucleic Acids Res* (2011) 39(12):e82; Tzfira et al., *Plant Biotechnol J* (2012) 10(4): 373-89). Genetically-altered plants (e.g., a Solanaceae plants) produced by or producible by a method disclosed are also claimed.

In some embodiments, the mutation produces a null allele, a hypomorphic allele, or a hypermorphic allele of a Solyc08g061560 gene (or a homolog thereof), a Solyc05g053850 gene (or a homolog thereof), or a Solyc06g074350 gene (or a homolog thereof) as disclosed. In some embodiments, the mutation is a null mutation of a Solyc08g061560 gene (or a homolog thereof), a Solyc05g053850 gene (or a homolog thereof), or a Solyc06g074350 gene (or a homolog thereof) that is introduced using genome editing (e.g., CRISPR/Cas9).

Alternatively, a method of producing a genetically-altered plant (e.g., a Solanaceae plant) comprises a reducing (partially or completely) function of a wild-type Solyc08g061560 gene (or a homolog thereof), a wild-type Solyc05g053850 gene (or a homolog thereof), or a wild-type Solyc06g074350 gene (or a homolog thereof) in the plant or plant part. In some embodiments, reducing the function comprises performing any of the following methods of RNA-interference (e.g., administering to the plant a micro-RNA or a small interfering (si)-RNA or hairpin RNA) or translational blocking (e.g., administering to the plant a morpholino). Methods of RNA-interference and translational blocking are well-known in the art. Methods of producing micro-RNAs, si-RNAs, and morpholinos are well-known in the art and can involve use of the nucleotides sequences provided herein.

In some embodiments, the method comprises crossing a produced genetically-altered plant (e.g., a Solanaceae plant) containing a mutant Solyc08g061560 gene (or a homolog thereof) to another genetically-altered plant (e.g., a Solanaceae plant) comprising a mutant Solyc05g053850 gene (or a homolog thereof), a mutant Solyc06g074350 gene (or a homolog thereof), or both a mutant Solyc05g053850 gene (or a homolog thereof) and a mutant Solyc06g074350 gene (or a homolog thereof). In some embodiments, the method comprises crossing a produced genetically-altered plant (e.g., a Solanaceae plant) containing a mutant Solyc05g053850 gene (or a homolog thereof) to another genetically-altered plant (e.g., a Solanaceae plant) a mutant Solyc08g061560 gene (or a homolog thereof), a mutant Solyc06g074350 gene (or a homolog thereof), or both a mutant Solyc08g061560 gene (or a homolog thereof) and a mutant Solyc06g074350 gene (or a homolog thereof). In some embodiments, the method comprises crossing a produced genetically-altered plant (e.g., a Solanaceae plant) containing a mutant Solyc06g074350 gene (or a homolog thereof) to another genetically-altered plant (e.g., a Solanaceae plant) comprising a mutant Solyc05g053850 gene (or a homolog thereof), a mutant Solyc08g061560 gene (or a homolog thereof), or both a mutant Solyc05g053850 gene (or a homolog thereof) and a mutant Solyc08g061560 gene (or a homolog thereof).

According to some aspects, disclosed are mutations, such as mutations of interest, in plants (e.g., Solanaceae plants, such as *Solanum lycopersicum*) that shorten one or more of the primary shoot length, axial shoot length and/or primordial shoot length in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of a shoot internode (e.g., a first, second, third, fourth, fifth, sixth, seventh, eighth, ninth, or tenth shoot internode) in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of a distal pedicel (e.g., a first, second, third, fourth, fifth, sixth, seventh, eighth, ninth, or tenth distal pedicel) in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of a proximal pedicel (e.g., a first, second, third, fourth, fifth, sixth, seventh, eighth, ninth, or tenth proximal pedicel) in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of a peduncle in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of an inflorescence internode (e.g., a first, second, third, fourth, fifth, sixth, seventh, eighth, ninth, or tenth inflorescence internode) in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that shorten the length of a stem in a genetically-altered plant disclosed (e.g., a genetically-altered Solanaceae plant, such as a mutant genetically-altered *Solanum lycopersicum*) by 1 mm, 1.5 mm, 2 mm, 2.5 mm, 3 mm, 3.5 mm, 14 mm, 4.5 mm, 5 mm, 5.5 mm, 6 mm, 6.5 mm, 7 mm, 7.5 mm, 8 mm, 8.5 mm, 9 mm, 9.5 mm, 10 mm, 12 mm, 14 mm, 16 mm, 18 mm, 20 mm, 25 mm, 30 mm, 35 mm, 40 mm, 45 mm, 50 mm, more than 50 mm, 1 cm, 1.5 cm, 2 cm, 2.5 cm, 3 cm, 3.5 cm, 14 cm, 4.5 cm, 5 cm, 5.5 cm, 6 cm, 6.5 cm, 7 cm, 7.5 cm, 8 cm, 8.5 cm, 9 cm, 9.5 cm, 10 cm, 12 cm, 14 cm, 16 cm, 18 cm, 20 cm, 25 cm, 30 cm, 35 cm, 40 cm, 45 cm, 50 cm, or more than 50 cm, or any range or combination thereof, relative to a reference plant.

According to some aspects, disclosed are mutations of interest in plants (e.g., Solanaceae plants, such as *Solanum lycopersicum*) that decrease the number of leaves to a first inflorescence in a mutant plant disclosed (e.g., a mutant Solanaceae plant, such as a mutant *Solanum lycopersicum*) to one leaf, two leaves, three leaves, four leaves, five leaves, six leaves, seven leaves, eight leaves, nine leaves, or 10 leaves, or any range or combination thereof.

In some embodiments, the total plant weight, fruit weight, total yield and/or harvest index (e.g., as measured in the Examples and/or through other methods known to one of ordinary skill in the art) is not significantly different in the mutated (e.g., mutant) plant relative to a reference plant.

Compositions and methods for producing and obtaining the genetically-altered plants (e.g., tomato, a Solanaceae plant) and methods of producing such mutant plants disclosed can be obtained using the compositions and methods described, for instance, in one or more of PCT/US2013/070825 (incorporated by reference herein in its entirety), PCT/US2017/026635 (incorporated by reference herein in its entirety), PCT/US2018/033143 (incorporated by reference herein in its entirety), PCT/US2018/033126 (incorporated by reference herein in its entirety), which are also contemplated herein. All references, including patent documents, disclosed herein are incorporated by reference in their entirety.

It is noted here that, as used in this specification and the appended claims, the singular forms "a," "an," and "the" include plural reference unless the context clearly dictates otherwise.

Example Nucleic Acid Sequences of the Disclosure

Solyc08-061560 (SlER)

```
Wild-type Solyc08g061560
Nucleic acid sequence of wild-type Solyc08g061560 gene
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAGATTGGTGACTGTTCAGCACTGAAAAATTTGTAAGTATGAAAT
GCTTCTGAATCTTGTGTTATTGTTTGGAAAAATAAGTAACCATTTTTTCCCTTAGGGACCTTTCCTTCAATGAGCTT
TATGGTGATATTCCCTTCTCCATATCTAAACTCAAGCAACTGGAATATCTGTAAGTTTTGATACTCTCCTTCTTCTA
AATGTTGTATTATTTGCTTTCCGAGATTGTTAGTTGATTATGCTCGTCTTATTCAACTTAGGATTTTGAAGAATAAT
CAATTGATTGGACCAATTCCATCTACATTGTCACAGATCCCTAACTTGAAGGTCTTGTAAGTATATTCTCTCTGCTT
TGTCATGATATTGGTAGATTATGAATAATTTTAGTTTGATCCAAGAACTTCCTCCAGGGACCTGGCTCAAAATAGGT
TAAGTGGAGAAATTCCTAGGCTGATATACTGGAACGAAGTCCTGCAGTATCTGTGAGTGTTTTAATCCGGTGTTCCT
CTTCTTCCTGTTTGTTTTAACCTTAGGACACTTTCATTTCGTATATGGATATGATTACATCTGTTGTATGTTTTTAT
TCATATAGGGGACTGCGTGGTAACAACTTGGGTGGATCCCTTTCTCCTGATATGTGTCAGCTCACCGGCCTGTGGTA
CTTGTAAGTTTGTAATCCTGTTGCTCTTAAGATCTTACTTTAGTTCCTCTAGGTGATGACATTAACCATTGTTCATT
GTGTTGTACAGTGATGTTCGGAACAATAGTTTGACTGGTTCCATTCCTCAAAATATTGGCAACTGTACTGCCTTCCA
GGTTCTGTAAGTATCTAAATCAATTGAATGAAGTTTGACTATATTCTGTATGTTTGGTTGGCATAACACCTTGTTTT
GTTCTGTCAGAGATTTGTCTTATAATGATTTGACCGGAGAGATTCCTTTCAATATTGGTTTCCTGCAAGTAGCGACC
TTGTAAGTTTATGCTGCTTCTCTTCATTACAAACTATTCAATATATGGTTGTTTGAAGTGTACTTTCATCATTCCAG
GTCTTTGCAAGGTAATCGTCTTTCAGGGCAGATCCCTTCTGTAATTGGATTGATGCAAGCTCTTGCAGTTTTGTGAG
TGTTTTGTGTCTTGATATCTCAATCTAATGCTACTGAATCTAATTCTTGGAAACCATTATAATGCATCTGTTATTTA
AGTTTTCTGACCCTTTTACTGTCAGGGACTTGAGCTGCAATATGTTGAGTGGAACAATTCCTTCAATTCTTGGGAAT
TTGACTTACACAGAGAAATTGTTAGTACTTCAACATTATTAAAAGCAATTTGGATCATTTTGTGCTTCCTAAATTGT
```

-continued

GTAGTGGATCAATTACTGTAAGTTCGCATTGTATTGCAGGTATCTACACGGGAACAAGCTATCTGGTTCCATTCCTC
CAGAGCTGGGAAATATGACAAAGCTCCACTACTTGTATGAATGCCTTCTATCAATCATTTTTTGTTAGCTTTGTTTT
GTTCTTCCTGTTCAAACCCTTTTAAATGAATGCTTACCATTTAGAAGCATTTGTTTGATTATTTAGCCTTTGGGCAA
CCACGGATTTGAATGATAGAAAGCTGTTATGAGAATTTTTATTAAGAGACTTTCTTCAACCTTAAGGCTCAAAGATG
GTAATTTGCAGGGAATTGAATGATAACCAACTTACTGGACGCATACCACCAGAACTTGGAAAGCTGACAGAATTGTT
TGACTTGTAAATCCCGTTTCTCTTCATCTTCTACTTTGGACTTGTTAACATCATTATTTATTTACTCATGTTGTATG
TTTCAGAAATGTTGCAAACAACCACCTAGATGGGCCCATACCTTCCAATATTAGCTCATGTACCAATTTGAATAGTC
TGTGAGTGTTTTTAATGTCCGAAGTGTTTCAATTATGCACGACCATGCTTGTTTGGTAGTTATTGACACCTGATTTT
GTTGCAGCAACGTTCATGGAAACAAATTGAATGGTACTATTCCACCTGCTTTTCAGAAGCTGGAAAGTATGACCTAT
CTGTAAGTTCTTACTTTCTGATCTTTTTCTTTTGAAGAATTATGTTTAAGGTTATCGAAGTTACCGTCCATGCTGTT
GAGCAAGATTGTAAACTTACTGTGCCTTGTATATAAATTTTACTGGCGTTGTATTATTGAAAAAATCATTTTATTTA
TATTGCTCTCAAATCATACTGGCTTATATCCATTCATGAAGAATCATTTCTACTGTCTGAAGTTTTCAGCTATATGT
ATCGAAAAAATTTAGTTATTATATAGTTTATTTTGAGCCTCTGCATCATCTATTTGTGAATTTCATTTGCTTATTCT
GCATACTCTCAGCATTAACCGTCTCTTCTTTTGTTAATTGCTTTAGTAATCTCTCCTCCAACAATCTCAAAGGCCCA
ATTCCAATTGAGCTATCTCGTATTGGGAATGTAGATACACTGTAAGTGCAAACTTTCTCATCTACTTTCATTTCTCT
CATTGCAATTATGGTTGCGGGGAAAGCACTTTTTGTCAGTCTTAAGAATCTTCAACATTTTTTGGCTTAGGGACTTA
TCAAACAACAGGATCAGTGGTCCTATACCTATGTCCCTTGGTGATTTGGAACATCTTCTTAAACTGTGAGCATAACC
GTCAAGTTGTTATGTTAGCATCATATATCTGTTGTACTTACATCCCTTTTGTCAATGCTGTAGGAACTTAAGCAAGA
ATGAAATAAATGGAAACTTACCAGCTGAATTTGGCAATTTAAGGAGCATCATGGAGATGTATGGAACCTTGCTAAAT
TCAGTTACTTTGAATTTATGGTTTGCTTGATTTTCAGCTTTTTGACTGCACTCCTAATTGTAGTGATCTGTCAAGCA
ATCACCTCTCTGGTCCCTTACCTCAGGAACTTGGTCAGCTTCCAAACCTGTACTTGCTGTAAGTACTTCAGATTTAC
TTTGAGACTCTCATCCTCTTAGCTATTGGTAATAATCTGTAGAGTGAATAAGTATGAACTTCTAAACTCGGTAAGTA
GATTTTAAAATTATTTTGGATGCCATTTTCAAAAAAGTAGAGATGAAGTTGGTTGTGTTGCTATTGTTTTATATGAT
CTGGCTTCATATGTTCATTACTTTGGTGTTCTCAGTTTTGCTTTATATTGCATTATTGCACGGGGCTCAAATGCAGC
ATATCTCTATCTTCTTTTTCTTGTGGCCTTAATTATTTTACAAATTAATGAACAGGAAGGTGGAAAACAACAATTTA
TCAGGCGATGTGATGTCCTTAGCCAGTTGCCTCAGTCTAAATATCTTGTGAGTTTTCAAGTCCATAGTAAGACACCA
GTACAAACAAATGTTTTGTTAATCTAATCAACCTCATGTTAGCAGAAATGTCTCATACAATAATCTGGGAGGGAATA
TTCCAACCGGCAATAATTTCTCTAGATTTTCACCAGACAGGTAAGTGGAGCTATTAAGATTTTACACAAGTCACAAG
CATTTATTGGTTTTTAATTCTTTGCTTCTAATTTCTTCCTTTTGCTATGTCTCCGAAAAAGCTTCATAGGAAATCCA
GATCTGTGTGGGTATTGGCTCACTTCTCCTTGTCATGCATCTCATCCGGCAGAGCGAGGTCTGATCAAACTGTAACA
ATCATTTGGCCTTTACTCTATTGCTTTTTGAAGTTCCATTTCACTTTAGACATCTGCAACATTTATTAAGTGTGAT
GGACAGATATATTGATTAATGAGGAATTATCCCTTGGTTGAGCAAACTTAATTCTGTGTTAGCCTGGTAGTAGGGTG
TACCACAAGGTTTGTCGTCATGGTTTCCTATGTTCACAATCCCTGATTGTAACATTTAGATGTGTACACATATCTAA
TTAACATGAAATAATCTTCATTTGCTGGAGTTACATTGACGTAAAGATGCGTTAGCTGTCAAATGAAACTGCATTTG
TTTTATTTCCATCATCAGTACATTAATTAAGTGCATAAATATTTTAACAGTTGTTGAATGATATAAGATGAATTTAT
TGGACAATTGCAGTTTCAATTTCTAAAGCAGCAATACTTGGTATTGCTCTGGGTGGCTTGGTGATTCTTCTGATGAT
ACTAGTAGCAGCATGCCGGCCACAGAAACCTGCACCTTTCATGGAAGGATCTATTGATAAACCAGGTACAATATTTT
CCGGACGGTTGGATAGTGTTTGGAGATGTTCATGTCAGAAGGACAGTCGTCAGAGTTTATTGAAGTTGCCATGTATT
GATTGTTTAACGTTTTTGATGAACAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTTAGTAAATC
CAAAATGGTTAAGGTGATTGATGCATTGATTTTGTGTTAAAGCATCAAGTAATCAGTCCTCTTGTATCTTTTTTTGC
AGGTCCTACAACAAAGAAGAAAAAGCTTGATTGGGTTACTCGCCTTCGAATTGCATTGGGATCAGCTCAAGGGCTTG
CATATCTTCATCATGATTGTAGCCCTCGAATAATCCACCGTGATGTTAAATCATCTAATATCTTGTTGGACAAAGAC
TTTGAGGCTCATCTGACTGATTTTGGCATAGCTAAAAGCTTATGCATATCAAAGACCTATACGTCCACGTACATTAT
GGGAACCATTGGTTACATTGATCCAGAGTATGCTCGCACTTCTCGCTTGACAGAGAAGTCTGATGTTTACAGCTATG
GTATTGTTCTATTGGAATTGCTCACTGGAAGGAAAGCTGTAGATAATGAATCTAATCTACATCATTTGGTAAGCTCT
TGCAATTTAGTTAATATGAACTTGTCCTATGATGTTTATTCATATAATTATATTAAGATTCAATTCAATTGATCATA
ACAGTTTTGCATATATGTTACAGATTCTAACTAAGGCAGCAAACGATGCTGTAATGGAAACAGTGGATCCTGAGATA
ACATGCACATGCAAAGATCTTGCAGATGTGAAGAAGGTTTTTCAGCTTGCCCTTCTATGTTCCAAAAGACAGCCTGC
TGAGAGACCAACAATGCATGAAGTGGCAAGAGTACTTGAAAGCCTAATACCCGTCGCTGAAACGAAACAGCCAAATC
CAACCCCCTCACTTGCATTACTCCCATCTGCTAAGGTACCTTGTTACATGGATGAATATGTCAACCTCAAGACACCC
CACCTAGTGAACTGTTCATCCATGAGCACTTCAGATGCCCAACTTTTCCTCAAGTTTGGAGAGGTCATATCCCAGAA
TAGTGGCTGA (SEQ ID NO: 1)

Nucleic acid sequence of wild-type Solyc08g061560 coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACAAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC -continued AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGTTTCAATTTCTAAAGCAGCAA
TACTTGGTATTGCTCTGGGTGGCTTGGTGATTCTTCTGATGATACTAGTAGCAGCATGCCGGCCACAGAAACCTGCA
CCTTTCATGGAAGGATCTATTGATAAACCAGTTTATTACTCATCTCCAAAACTTGTGATCCTTCATATGAACATGGC
ACTTCATGTTTACGAGGACATTATGAGGATGACTGAGAACTTGAGTGAGAAGTATATAATTGGTTGTGGAGCATCAA
GTACTGTATATAAATGTGTTTTGAAAAATTGCAAGCCTGTAGCTATCAAGAAGTTGTACTCTCACAACCCGCAATAC
TTGAAGGAATTTGAGACTGAACTTGAGACAGTTGGGAGTATTAAGCATCGTAATCTTGTCTGTCTCCAAGGATATTC
TCTTTCTCCATCTGGCCATCTTCTTTTCTATGACTACATGGAAAATGGTAGCCTTTGGGATTTGCTTCATGGTCCTA
CAACAAAGAAGAAAAAGCTTGATTGGGTTACTCGCCTTCGAATTGCATTGGGATCAGCTCAAGGGCTTGCATATCTT
CATCATGATTGTAGCCCTCGAATAATCCACCGTGATGTTAAATCATCTAATATCTTGTTGGACAAAGACTTTGAGGC
TCATCTGACTGATTTTGGCATAGCTAAAAGCTTATGCATATCAAAGACCTATACGTCCACGTACATTATGGGAACCA
TTGGTTACATTGATCCAGAGTATGCTCGCACTTCTCGCTTGACAGAGAAGTCTGATGTTTACAGCTATGGTATTGTT
CTATTGGAATTGCTCACTGGAAGGAAAGCTGTAGATAATGAATCTAATCTACATCATTTGATTCTAACTAAGGCAGC
AAACGATGCTGTAATGGAAACAGTGGATCCTGAGATAACATGCACATGCAAAGATCTTGCAGATGTGAAGAAGGTTT
TTCAGCTTGCCCTTCTATGTTCCAAAAGACAGCCTGCTGAGAGACCAACAATGCATGAAGTGGCAAGAGTACTTGAA
AGCCTAATACCCGTCGCTGAAACGAAACAGCCAAATCCAACCCCCTCACTTGCATTACTCCCATCTGCTAAGGTACC
TTGTTACATGGATGAATATGTCAACCTCAAGACACCCCACCTAGTGAACTGTTCATCCATGAGCACTTCAGATGCCC
AACTTTTCCTCAAGTTTGGAGAGGTCATATCCCAGAATAGTGGCTGA (SEQ ID NO: 2)

Amino acid sequence for polypeptide encoded by wild-type Solyc08g061560 coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGNKLNGTIPPAFQKLESMTYLNLSSNNLKGPIPIELSRIGNVDTLDLSNNRISGPIPMSLGDLEHLL
KLNLSKNEINGNLPAEFGNLRSIMEIDLSSNHLSGPLPQELGQLPNLYLLKVENNNLSGDVMSLASCLSLNILNVSY
NNLGGNIPTGNNFSRFSPDSFIGNPDLCGYWLTSPCHASHPAERVSISKAAILGIALGGLVILLMILVAACRPQKPA
PFMEGSIDKPVYYSSPKLVILHMNMALHVYEDIMRMTENLSEKYIIGCGASSTVYKCVLKNCKPVAIKKLYSHNPQY
LKEFETELETVGSIKHRNLVCLQGYSLSPSGHLLFYDYMENGSLWDLLHGPTTKKKKLDWVTRLRIALGSAQGLAYL
HHDCSPRIIHRDVKSSNILLDKDFEAHLTDFGIAKSLCISKTYTSTYIMGTIGYIDPEYARTSRLTEKSDVYSYGIV
LLELLTGRKAVDNESNLHHLILTKAANDAVMETVDPEITCTCKDLADVKKVFQLALLCSKRQPAERPTMHEVARVLE
SLIPVAETKQPNPTPSLALLPSAKVPCYMDEYVNLKTPHLVNCSSMSTSDAQLFLKFGEVISQNSG* (SEQ ID
NO: 3)

Mutant Solyc08g061560 gene allele sler$^{EMS-1}$
Nucleic acid sequence for a mutant Solyc08g061560 gene allele sler$^{EMS-1}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAGATTGGTGACTGTTCAGCACTGAAAAATTTGTAAGTATGAAAT
GCTTCTGAATCTTGTGTTATTGTTTGGAAAAATAAGTAACCATTTTTTCCCTTAGGGACCTTTCCTTCAATGAGCTT
TATGGTGATATTCCCTTCTCCATATCTAAACTCAAGCAACTGGAATATCTGTAAGTTTTGATACTCTCCTTCTTCTA
AATGTTGTATTATTTGCTTTCCGAGATTGTTAGTTGATTATGCTCGTCTTATTCAACTTAGGATTTTGAAGAATAAT
CAATTGATTGGACCAATTCCATCTACATTGTCACAGATCCCTAACTTGAAGGTCTTGTAAGTATATTCTCTCTGCTT
TGTCATGATATTGGTAGATTATGAATAATTTTAGTTTGATCCAAGAACTTCCTCCAGGGACCTGGCTCAAAATAGGT
TAAGTGGAGAAATTCCTAGGCTGATATACTGGAACGAAGTCCTGCAGTATCTGTGAGTGTTTTAATCCGGTGTTCCT
CTTCTTCCTGTTTGTTTTAACCTTAGGACACTTTCATTTCGTATATGGATATGATTACATCTGTTGTATGTTTTTAT
TCATATAGGGGACTGCGTGGTAACAACTTGGGTGGATCCCTTTCTCCTGATATGTGTCAGCTCACCGGCCTGTGGTA
CTTGTAAGTTTGTAATCCTGTTGCTCTTAAGATCTTACTTTAGTTCCTCTAGGTGATGACATTAACCATTGTTCATT
GTGTTGTACAGTGATGTTCGGAACAATAGTTTGACTGGTTCCATTCCTCAAAATATTGGCAACTGTACTGCCTTCCA
GGTTCTGTAAGTATCTAAATCAATTGAATGAAGTTTGACTATATTCTGTATGTTTGGTTGGCATAACACCTTGTTTT
GTTCTGTCAGAGATTTGTCTTATAATGATTTGACCGGAGAGATTCCTTTCAATATTGGTTTCCTGCAAGTAGCGACC
TTGTAAGTTTATGCTGCTTCTCTTCATTACAAACTATTCAATATATGGTTGTTTGAAGTGTACTTTCATCATTCCAG
GTCTTTGCAAGGTAATCGTCTTTCAGGGCAGATCCCTTCTGTAATTGGATTGATGCAAGCTCTTGCAGTTTTGTGAG
TGTTTTGTGTCTTGATATCTCAATCTAATGCTACTGAATCTAATTCTTGGAAACCATTATAATGCATCTGTTATTTA
AGTTTTCTGACCCTTTTACTGTCAGGGACTTGAGCTGCAATATGTTGAGTGGAACAATTCCTTCAATTCTTGGGAAT
TTGACTTACACAGAGAAATTGTTAGTACTTCAACATTATTAAAAGCAATTTGGATCATTTTGTGCTTCCTAAATTGT
GTAGTGGATCAATTACTGTAAGTTCGCATTGTATTGCAGGTATCTACACGGGAACAAGCTATCTGGTTCCATTCCTC
CAGAGCTGGGAAATATGACAAAGCTCCACTACTTGTATGAATGCCTTCTATCAATCATTTTTTGTTAGCTTTGTTTT
GTTCTTCCTGTTCAAACCCTTTTAAATGAATGCTTACCATTTAGAAGCATTTGTTTGATTATTTAGCCTTTGGGCAA
CCACGGATTTGAATGATAGAAAGCTGTTATGAGAATTTTTATTAAGAGACTTTCTTCAACCTTAAGGCTCAAAGATG
GTAATTTGCAGGGAATTGAATGATAACCAACTTACTGGACGCATACCACCAGAACTTGGAAAGCTGACAGAATTGTT
TGACTTGTAAATCCCGTTTCTCTTCATCTTCTACTTTGGACTTGTTAACATCATTATTTATTTACTCATGTTGTATG
TTTCAGAAATGTTGCAAACAACCACCTAGATGGGCCCATACCTTCCAATATTAGCTCATGTACCAATTTGAATAGTC
TGTGAGTGTTTTTAATGTCCGAAGTGTTTCAATTATGCACGACCATGCTTGTTTGGTAGTTATTGACACCTGATTTT
GTTGCAGCAACGTTCATGGAAACAAATTGAATGGTACTATTCCACCTGCTTTTCAGAAGCTGGAAAGTATGACCTAT
CTGTAAGTTCTTACTTTCTGATCTTTTTCTTTTGAAGAATTATGTTTAAGGTTATCGAAGTTACCGTCCATGCTGTT
GAGCAAGATTGTAAACTTACTGTGCCTTGTATATAAATTTTACTGGCGTTGTATTATTGAAAAAATCATTTTATTTA
TATTGCTCTCAAATCATACTGGCTTATATCCATTCATGAAGAATCATTTCTACTGTCTGAAGTTTTCAGCTATATGT
ATCGAAAAAATTTAGTTATTATATAGTTTATTTTGAGCCTCTGCATCATCTATTTGTGAATTTCATTTGCTTATTCT
GCATACTCTCAGCATTAACCGTCTCTTCTTTTGTTAATTGCTTTAGTAATCTCTCCTCCAACAATCTCAAAGGCCCA
ATTCCAATTGAGCTATCTCGTATTGGGAATGTAGATACACTGTAAGTGCAAACTTTCTCATCTACTTTCATTTCTCT -continued CATTGCAATTATGGTTGCGGGGAAAGCACTTTTTGTCAGTCTTAAGAATCTTCAACATTTTTTGGCTTAGGGACTTA
TCAAACAACAGGATCAGTGGTCCTATACCTATGTCCCTTGGTGATTTGGAACATCTTCTTAAACTGTGAGCATAACC
GTCAAGTTGTTATGTTAGCATCATATATCTGTTGTACTTACATCCCTTTTGTCAATGCTGTAGGAACTTAAGCAAGA
ATGAAATAAATGGAAACTTACCAGCTGAATTTGGCAATTTAAGGAGCATCATGGAGATGTATGGAACCTTGCTAAAT
TCAGTTACTTTGAATTTATGGTTTGCTTGATTTTCAGCTTTTTGACTGCACTCCTAATTGTAGTGATCTGTCAAGCA
ATCACCTCTCTGGTCCCTTACCTCAGGAACTTGGTCAGCTTCCAAACCTGTACTTGCTGTAAGTACTTCAGATTTAC
TTTGAGACTCTCATCCTCTTAGCTATTGGTAATAATCTGTAGAGTGAATAAGTATGAACTTCTAAACTCGGTAAGTA
GATTTTAAAATTATTTTGGATGCCATTTTCAAAAAAGTAGAGATGAAGTTGGTTGTGTTGCTATTGTTTTATATGAT
CTGGCTTCATATGTTCATTACTTTGGTGTTCTCAGTTTTGCTTTATATTGCATTATTGCACGGGGCTCAAATGCAGC
ATATCTCTATCTTCTTTTTCTTGTGGCCTTAATTATTTTACAAATTAATGAACAGGAAGGTGGAAAACAACAATTTA
TCAGGCGATGTGATGTCCTTAGCCAGTTGCCTCAGTCTAAATATCTTGTGAGTTTTCAAGTCCATAGTAAGACACCA
GTACAAACAAATGTTTTGTTAATCTAATCAACCTCATGTTAGCAGAAATGTCTCATACAATAATCTGGGAGGGAATA
TTCCAACCGGCAATAATTTCTCTAGATTTTCACCAGACAGGTAAGTGGAGCTATTAAGATTTTACACAAGTCACAAG
CATTTATTGGTTTTTAATTCTTTGCTTCTAATTTCTTCCTTTTGCTATGTCTCCGAAAAAGCTTCATAGGAAATCCA
GATCTGTGTGGGTATTGGCTCACTTCTCCTTGTCATGCATCTCATCCGGCAGAGCGAGATCTGATCAAACTGTAACA
ATCATTTGGCCTTTACTCTATTGCATTTTTGAAGTTCCATTTCACTTTAGACATCTGCAACATTTATTAAGTGTGAT
GGACAGATATATTGATTAATGAGGAATTATCCCTTGGTTGAGCAAACTTAATTCTGTGTTAGCCTGGTAGTAGGGTG
TACCACAAGGTTTGTCGTCATGGTTTCCTATGTTCACAATCCCTGATTGTAACATTTAGATGTGTACACATATCTAA
TTAACATGAAATAATCTTCATTTGCTGGAGTTACATTGACGTAAAGATGCGTTAGCTGTCAAATGAAACTGCATTTG
TTTTATTTCCATCATCAGTACATTAATTAAGTGCATAAATATTTTAACAGTTGTTGAATGATATAAGATGAATTTAT
TGGACAATTGCAGTTTCAATTTCTAAAGCAGCAATACTTGGTATTGCTCTGGGTGGCTTGGTGATTCTTCTGATGAT
ACTAGTAGCAGCATGCCGGCCACAGAAACCTGCACCTTTCATGGAAGGATCTATTGATAAACCAGGTACAATATTTT
CCGGACGGTTGGATAGTGTTTGGAGATGTTCATGTCAGAAGGACAGTCGTCAGAGTTTATTGAAGTTGCCATGTATT
GATTGTTTAACGTTTTTGATGAACAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTTAGTAAATC
CAAAATGGTTAAGGTGATTGATGCATTGATTTTGTGTTAAAGCATCAAGTAATCAGTCCTCTTGTATCTTTTTTTGC
AGGTCCTACAACAAAGAAGAAAAAGCTTGATTGGGTTACTCGCCTTCGAATTGCATTGGGATCAGCTCAAGGGCTTG
CATATCTTCATCATGATTGTAGCCCTCGAATAATCCACCGTGATGTTAAATCATCTAATATCTTGTTGGACAAAGAC
TTTGAGGCTCATCTGACTGATTTTGGCATAGCTAAAAGCTTATGCATATCAAAGACCTATACGTCCACGTACATTAT
GGGAACCATTGGTTACATTGATCCAGAGTATGCTCGCACTTCTCGCTTGACAGAGAAGTCTGATGTTTACAGCTATG
GTATTGTTCTATTGGAATTGCTCACTGGAAGGAAAGCTGTAGATAATGAATCTAATCTACATCATTTGGTAAGCTCT
TGCAATTTAGTTAATATGAACTTGTCCTATGATGTTTATTCATATAATTATATTAAGATTCAATTCAATTGATCATA
ACAGTTTTGCATATATGTTACAGATTCTAACTAAGGCAGCAAACGATGCTGTAATGGAAACAGTGGATCCTGAGATA
ACATGCACATGCAAAGATCTTGCAGATGTGAAGAAGGTTTTTCAGCTTGCCCTTCTATGTTCCAAAAGACAGCCTGC
TGAGAGACCAACAATGCATGAAGTGGCAAGAGTACTTGAAAGCCTAATACCCGTCGCTGAAACGAAACAGCCAAATC
CAACCCCCTCACTTGCATTACTCCCATCTGCTAAGGTACCTTGTTACATGGATGAATATGTCAACCTCAAGACACCC
CACCTAGTGAACTGTTCATCCATGAGCACTTCAGATGCCCAACTTTTCCTCAAGTTTGGAGAGGTCATATCCCAGAA
TAGTGGCTGA (SEQ ID NO: 4)

Nucleic acid sequence for a mutant Solyc08g061560 gene allele sler$^{EMS-1}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACAAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC
AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGATCTGATCAAACTTTTCAATT
TCTAAAGCAGCAATACTTGGTATTGCTCTGGGTGGCTTGGTGATTCTTCTGATGATACTAGTAGCAGCATGCCGGCC
ACAGAAACCTGCACCTTTCATGGAAGGATCTATTGATAAACCAGTTTATTACTCATCTCCAAAACTTGTGATCCTTC
ATATGAACATGGCACTTCATGTTTACGAGGACATTATGAGGATGACTGAGAACTTGAGTGAGAAGTATATAATTGGT
TGTGGAGCATCAAGTACTGTATATAAATGTGTTTTGAAAAATTGCAAGCCTGTAGCTATCAAGAAGTTGTACTCTCA
CAACCCGCAATACTTGAAGGAATTTGAGACTGAACTTGAGACAGTTGGGAGTATTAAGCATCGTAATCTTGTCTGTC
TCCAAGGATATTCTCTTTCTCCATCTGGCCATCTTCTTTTCTATGACTACATGGAAAATGGTAGCCTTTGGGATTTG
CTTCATGGTCCTACAACAAAGAAGAAAAAGCTTGATTGGGTTACTCGCCTTCGAATTGCATTGGGATCAGCTCAAGG
GCTTGCATATCTTCATCATGATTGTAGCCCTCGAATAATCCACCGTGATGTTAAATCATCTAATATCTTGTTGGACA
AAGACTTTGAGGCTCATCTGACTGATTTTGGCATAGCTAAAAGCTTATGCATATCAAAGACCTATACGTCCACGTAC
ATTATGGGAACCATTGGTTACATTGATCCAGAGTATGCTCGCACTTCTCGCTTGACAGAGAAGTCTGATGTTTACAG
CTATGGTATTGTTCTATTGGAATTGCTCACTGGAAGGAAAGCTGTAGATAATGAATCTAATCTACATCATTTGATTC
TAACTAAGGCAGCAAACGATGCTGTAATGGAAACAGTGGATCCTGAGATAACATGCACATGCAAAGATCTTGCAGAT
GTGAAGAAGGTTTTTCAGCTTGCCCTTCTATGTTCCAAAAGACAGCCTGCTGAGAGACCAACAATGCATGAAGTGGC -continued AAGAGTACTTGAAAGCCTAATACCCGTCGCTGAAACGAAACAGCCAAATCCAACCCCCTCACTTGCATTACTCCCAT
CTGCTAAGGTACCTTGTTACATGGATGAATATGTCAACCTCAAGACACCCCACCTAGTGAACTGTTCATCCATGAGC
ACTTCAGATGCCCAACTTTTCCTCAAGTTTGGAGAGGTCATATCCCAGAATAGTGGCTGA (SEQ ID NO: 5)

Amino acid sequence for a mutant polypeptide encoded by a mutant Solyc08g061560 gene allele sler$^{EMS-1}$ coding sequence MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGNKLNGTIPPAFQKLESMTYLNLSSNNLKGPIPIELSRIGNVDTLDLSNNRISGPIPMSLGDLEHLL
KLNLSKNEINGNLPAEFGNLRSIMEIDLSSNHLSGPLPQELGQLPNLYLLKVENNNLSGDVMSLASCLSLNILNVSY
NNLGGNIPTGNNFSRFSPDSFIGNPDLCGYWLTSPCHASHPAERDLIKLFNF* (SEQ ID NO: 6)

Mutant Solyc08g061560 gene allele sler$^{EMS-2}$

Nucleic acid sequence for a mutant Solyc08g061560 gene allele sler$^{EMS-2}$

ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAGATTGGTGACTGTTCAGCACTGAAAAATTTGTAAGTATGAAAT
GCTTCTGAATCTTGTGTTATTGTTTGGAAAAATAAGTAACCATTTTTTCCCTTAGGGACCTTTCCTTCAATGAGCTT
TATGGTGATATTCCCTTCTCCATATCTAAACTCAAGCAACTGGAATATCTGTAAGTTTTGATACTCTCCTTCTTCTA
AATGTTGTATTATTTGCTTTCCGAGATTGTTAGTTGATTATGCTCGTCTTATTCAACTTAGGATTTTGAAGAATAAT
CAATTGATTGGACCAATTCCATCTACATTGTCACAGATCCCTAACTTGAAGGTCTTGTAAGTATATTCTCTCTGCTT
TGTCATGATATTGGTAGATTATGAATAATTTTAGTTTGATCCAAGAACTTCCTCCAGGGACCTGGCTCAAAATAGGT
TAAGTGGAGAAATTCCTAGGCTGATATACTGGAACGAAGTCCTGCAGTATCTGTGAGTGTTTTAATCCGGTGTTCCT
CTTCTTCCTGTTTGTTTTAACCTTAGGACACTTTCATTTCGTATATGGATATGATTACATCTGTTGTATGTTTTTAT
TCATATAGGGGACTGCGTGGTAACAACTTGGGTGGATCCCTTTCTCCTGATATGTGTCAGCTCACCGGCCTGTGGTA
CTTGTAAGTTTGTAATCCTGTTGCTCTTAAGATCTTACTTTAGTTCCTCTAGGTGATGACATTAACCATTGTTCATT
GTGTTGTACAGTGATGTTCGGAACAATAGTTTGACTGGTTCCATTCCTCAAAATATTGGCAACTGTACTGCCTTCCA
GGTTCTGTAAGTATCTAAATCAATTGAATGAAGTTTGACTATATTCTGTATGTTTGGTTGGCATAACACCTTGTTTT
GTTCTGTCAGAGATTTGTCTTATAATGATTTGACCGGAGAGATTCCTTTCAATATTGGTTTCCTGCAAGTAGCGACC
TTGTAAGTTTATGCTGCTTCTCTTCATTACAAACTATTCAATATATGGTTGTTTGAAGTGTACTTTCATCATTCCAG
GTCTTTGCAAGGTAATCGTCTTTCAGGGCAGATCCCTTCTGTAATTGGATTGATGCAAGCTCTTGCAGTTTTGTGAG
TGTTTTGTGTCTTGATATCTCAATCTAATGCTACTGAATCTAATTCTTGGAAACCATTATAATGCATCTGTTATTTA
AGTTTTCTGACCCTTTTACTGTCAGGGACTTGAGCTGCAATATGTTGAGTGGAACAATTCCTTCAATTCTTGGGAAT
TTGACTTACACAGAGAAATTGTTAGTACTTCAACATTATTAAAAGCAATTTGGATCATTTTGTGCTTCCTAAATTGT
GTAGTGGATCAATTACTGTAAGTTCGCATTGTATTGCAGGTATCTACACGGGAACAAGCTATCTGGTTCCATTCCTC
CAGAGCTGGGAAATATGACAAAGCTCCACTACTTGTATGAATGCCTTCTATCAATCATTTTTTGTTAGCTTTGTTTT
GTTCTTCCTGTTCAAACCCTTTTAAATGAATGCTTACCATTTAGAAGCATTGTTTGATTATTTAGCCTTTGGGCAA
CCACGGATTTGAATGATAGAAAGCTGTTATGAGAATTTTTATTAAGAGACTTTCTTCAACCTTAAGGCTCAAAGATG
GTAATTTGCAGGGAATTGAATGATAACCAACTTACTGGACGCATACCACCAGAACTTGGAAAGCTGACAGAATTGTT
TGACTTGTAAATCCCGTTTCTCTTCATCTTCTACTTTGGACTTGTTAACATCATTATTTATTTACTCATGTTGTATG
TTTCTGAAATGTTGCAAACAACCACCTAGATGGGCCCATACCTTCCAATATTAGCTCATGTACCAATTTGAATAGTC
TGTGAGTGTTTTTAATGTCCGAAGTGTTTCAATTATGCACGACCATGCTTGTTTGGTAGTTATTGACACCTGATTTT
GTTGCAGCAACGTTCATGGAAACAAATTGAATGGTACTATTCCACCTGCTTTTCAGAAGCTGGAAAGTATGACCTAT
CTGTAAGTTCTTACTTTCTGATCTTTTTCTTTTGAAGAATTATGTTTAAGGTTATCGAAGTTACCGTCCATGCTGTT
GAGCAAGATTGTAAACTTACTGTGCCTTGTATATAAATTTTACTGGCGTTGTATTATTGAAAAAATCATTTTATTTA
TATTGCTCTCAAATCATACTGGCTTATATCCATTCATGAAGAATCATTTCTACTGTCTGAAGTTTTCAGCTATATGT
ATCGAAAAAATTTAGTTATTATATAGTTTATTTTGAGCCTCTGCATCATCTATTTGTGAATTTCATTTGCTTATTCT
GCATACTCTCAGCATTAACCGTCTCTTCTTTTGTTAATTGCTTTAGTAATCTCTCCTCCAACAATCTCAAAGGCCCA
ATTCCAATTGAGCTATCTCGTATTGGGAATGTAGATACACTGTAAGTGCAAACTTTCTCATCTACTTTCATTTCTCT
CATTGCAATTATGGTTGCGGGGAAAGCACTTTTTGTCAGTCTTAAGAATCTTCAACATTTTTGGCTTAGGGACTTA
TCAAACAACAGGATCAGTGGTCCTATACCTATGTCCCTTGGTGATTTGGAACATCTTCTTAAACTGTGAGCATAACC
GTCAAGTTGTTATGTTAGCATCATATATCTGTTGTACTTACATCCCTTTTGTCAATGCTGTAGGAACTTAAGCAAGA
ATGAAATAAATGGAAACTTACCAGCTGAATTTGGCAATTTAAGGAGCATCATGGAGATGTATGGAACCTTGCTAAAT
TCAGTTACTTTGAATTTATGGTTTGCTTGATTTTCAGCTTTTTGACTGCACTCCTAATTGTAGTGATCTGTCAAGCA
ATCACCTCTCTGGTCCCTTACCTCAGGAACTTGGTCAGCTTCCAAACCTGTACTTGCTGTAAGTACTTCAGATTTAC
TTTGAGACTCTCATCCTCTTAGCTATTGGTAATAATCTGTAGAGTGAATAAGTATGAACTTCTAAACTCGGTAAGTA
GATTTTAAAATTATTTTGGATGCCATTTTCAAAAAAGTAGAGATGAAGTTGGTTGTGTTGCTATTGTTTTATATGAT
CTGGCTTCATATGTTCATTACTTTGGTGTTCTCAGTTTTGCTTTATATTGCATTATTGCACGGGGCTCAAATGCAGC
ATATCTCTATCTTCTTTTTCTTGTGGCCTTAATTATTTTACAAATTAATGAACAGGAAGGTGGAAAACAACAATTTA
TCAGGCGATGTGATGTCCTTAGCCAGTTGCCTCAGTCTAAATATCTTGTGAGTTTTCAAGTCCATAGTAAGACACCA
GTACAAACAAATGTTTTGTTAATCTAATCAACCTCATGTTAGCAGAAATGTCTCATACAATAATCTGGGAGGGAATA
TTCCAACCGGCAATAATTTCTCTAGATTTTCACCAGACAGGTAAGTGGAGCTATTAAGATTTTACACAAGTCACAAG
CATTTATTGGTTTTTAATTCTTTGCTTCTAATTTCTTCCTTTTGCTATGTCTCCGAAAAAGCTTCATAGGAAATCCA
GATCTGTGTGGGTATTGGCTCACTTCTCCTTGTCATGCATCTCATCCGGCAGAGCGAGGTCTGATCAAACTGTAACA
ATCATTTGGCCTTTACTCTATTGCATTTTTGAAGTTCCATTTCACTTTAGACATCTGCAACATTTATTAAGTGTGAT
GGACAGATATATTGATTAATGAGGAATTATCCCTTGGTTGAGCAAACTTAATTCTGTGTTAGCCTGGTAGTAGGGTG
TACCACAAGGTTTGTCGTCATGGTTTCCTATGTTCACAATCCCTGATTGTAACATTTAGATGTGTACACATATCTAA
TTAACATGAAATAATCTTCATTTGCTGGAGTTACATTGACGTAAAGATGCGTTAGCTGTCAAATGAAACTGCATTTG
TTTTATTTCCATCATCAGTACATTAATTAAGTGCATAAATATTTTAACAGTTGTTGAATGATATAAGATGAATTTAT

-continued

TGGACAATTGCAGTTTCAATTTCTAAAGCAGCAATACTTGGTATTGCTCTGGGTGGCTTGGTGATTCTTCTGATGAT
ACTAGTAGCAGCATGCCGGCCACAGAAACCTGCACCTTTCATGGAAGGATCTATTGATAAACCAGGTACAATATTTT
CCGGACGGTTGGATAGTGTTTGGAGATGTTCATGTCAGAAGGACAGTCGTCAGAGTTTATTGAAGTTGCCATGTATT
GATTGTTTAACGTTTTTGATGAACAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTTAGTAAATC
CAAAATGGTTAAGGTGATTGATGCATTGATTTTGTGTTAAAGCATCAAGTAATCAGTCCTCTTGTATCTTTTTTTGC
AGGTCCTACAACAAAGAAGAAAAAGCTTGATTGGGTTACTCGCCTTCGAATTGCATTGGGATCAGCTCAAGGGCTTG
CATATCTTCATCATGATTGTAGCCCTCGAATAATCCACCGTGATGTTAAATCATCTAATATCTTGTTGGACAAAGAC
TTTGAGGCTCATCTGACTGATTTTGGCATAGCTAAAAGCTTATGCATATCAAAGACCTATACGTCCACGTACATTAT
GGGAACCATTGGTTACATTGATCCAGAGTATGCTCGCACTTCTCGCTTGACAGAGAAGTCTGATGTTTACAGCTATG
GTATTGTTCTATTGGAATTGCTCACTGGAAGGAAAGCTGTAGATAATGAATCTAATCTACATCATTTGGTAAGCTCT
TGCAATTTAGTTAATATGAACTTGTCCTATGATGTTTATTCATATAATTATATTAAGATTCAATTCAATTGATCATA
ACAGTTTTGCATATATGTTACAGATTCTAACTAAGGCAGCAAACGATGCTGTAATGGAAACAGTGGATCCTGAGATA
ACATGCACATGCAAAGATCTTGCAGATGTGAAGAAGGTTTTTCAGCTTGCCCTTCTATGTTCCAAAAGACAGCCTGC
TGAGAGACCAACAATGCATGAAGTGGCAAGAGTACTTGAAAGCCTAATACCCGTCGCTGAAACGAAACAGCCAAATC
CAACCCCCTCACTTGCATTACTCCCATCTGCTAAGGTACCTTGTTACATGGATGAATATGTCAACCTCAAGACACCC
CACCTAGTGAACTGTTCATCCATGAGCACTTCAGATGCCCAACTTTTCCTCAAGTTTGGAGAGGTCATATCCCAGAA
TAGTGGCTGA (SEQ ID NO: 7)

Nucleic acid sequence for a mutant Solyc08g061560 gene allele sle+5’2 coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTCAACGTTCATGGAAACAAATTGAATGGTACTATTCCACCTGCTTTTCAGAAG
CTGGAAAGTATGACCTATCTTAATCTCTCCTCCAACAATCTCAAAGGCCCAATTCCAATTGAGCTATCTCGTATTGG
GAATGTAGATACACTGGACTTATCAAACAACAGGATCAGTGGTCCTATACCTATGTCCCTTGGTGATTTGGAACATC
TTCTTAAACTGAACTTAAGCAAGAATGAAATAAATGGAAACTTACCAGCTGAATTTGGCAATTTAAGGAGCATCATG
GAGATTGATCTGTCAAGCAATCACCTCTCTGGTCCCTTACCTCAGGAACTTGGTCAGCTTCCAAACCTGTACTTGCT
GAAGGTGGAAAACAACAATTTATCAGGCGATGTGATGTCCTTAGCCAGTTGCCTCAGTCTAAATATCTTAAATGTCT
CATACAATAATCTGGGAGGGAATATTCCAACCGGCAATAATTTCTCTAGATTTTCACCAGACAGCTTCATAGGAAAT
CCAGATCTGTGTGGGTATTGGCTCACTTCTCCTTGTCATGCATCTCATCCGGCAGAGCGAGTTTCAATTTCTAAAGC
AGCAATACTTGGTATTGCTCTGGGTGGCTTGGTGATTCTTCTGATGATACTAGTAGCAGCATGCCGGCCACAGAAAC
CTGCACCTTTCATGGAAGGATCTATTGATAAACCAGTTTATTACTCATCTCCAAAACTTGTGATCCTTCATATGAAC
ATGGCACTTCATGTTTACGAGGACATTATGAGGATGACTGAGAACTTGAGTGAGAAGTATATAATTGGTTGTGGAGC
ATCAAGTACTGTATATAAATGTGTTTTGAAAAATTGCAAGCCTGTAGCTATCAAGAAGTTGTACTCTCACAACCCGC
AATACTTGAAGGAATTTGAGACTGAACTTGAGACAGTTGGGAGTATTAAGCATCGTAATCTTGTCTGTCTCCAAGGA
TATTCTCTTTCTCCATCTGGCCATCTTCTTTTCTATGACTACATGGAAAATGGTAGCCTTTGGGATTTGCTTCATGG
TCCTACAACAAAGAAGAAAAAGCTTGATTGGGTTACTCGCCTTCGAATTGCATTGGGATCAGCTCAAGGGCTTGCAT
ATCTTCATCATGATTGTAGCCCTCGAATAATCCACCGTGATGTTAAATCATCTAATATCTTGTTGGACAAAGACTTT
GAGGCTCATCTGACTGATTTTGGCATAGCTAAAAGCTTATGCATATCAAAGACCTATACGTCCACGTACATTATGGG
AACCATTGGTTACATTGATCCAGAGTATGCTCGCACTTCTCGCTTGACAGAGAAGTCTGATGTTTACAGCTATGGTA
TTGTTCTATTGGAATTGCTCACTGGAAGGAAAGCTGTAGATAATGAATCTAATCTACATCATTTGATTCTAACTAAG
GCAGCAAACGATGCTGTAATGGAAACAGTGGATCCTGAGATAACATGCACATGCAAAGATCTTGCAGATGTGAAGAA
GGTTTTTCAGCTTGCCCTTCTATGTTCCAAAAGACAGCCTGCTGAGAGACCAACAATGCATGAAGTGGCAAGAGTAC
TTGAAAGCCTAATACCCGTCGCTGAAACGAAACAGCCAAATCCAACCCCCTCACTTGCATTACTCCCATCTGCTAAG
GTACCTTGTTACATGGATGAATATGTCAACCTCAAGACACCCCACCTAGTGAACTGTTCATCCATGAGCACTTCAGA
TGCCCAACTTTTCCTCAAGTTTGGAGAGGTCATATCCCAGAATAGTGGCTGA (SEQ ID NO: 8)

Amino acid sequence for a mutant polypeptide encoded by a mutant Solyc08g061560 gene allele sle+5’2 coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDFNVHGNKLNGTIPPAFQK
LESMTYLNLSSNNLKGPIPIELSRIGNVDTLDLSNNRISGPIPMSLGDLEHLLKLNLSKNEINGNLPAEFGNLRSIM
EIDLSSNHLSGPLPQELGQLPNLYLLKVENNNLSGDVMSLASCLSLNILNVSYNNLGGNIPTGNNFSRFSPDSFIGN
PDLCGYWLTSPCHASHPAERVSISKAAILGIALGGLVILLMILVAACRPQKPAPFMEGSIDKPVYYSSPKLVILHMN
MALHVYEDIMRMTENLSEKYIIGCGASSTVYKCVLKNCKPVAIKKLYSHNPQYLKEFETELETVGSIKHRNLVCLQG
YSLSPSGHLLFYDYMENGSLWDLLHGPTTKKKKLDWVTRLRIALGSAQGLAYLHHDCSPRIIHRDVKSSNILLDKDF
EAHLTDFGIAKSLCISKTYTSTYIMGTIGYIDPEYARTSRLTEKSDVYSYGIVLLELLTGRKAVDNESNLHHLILTK
AANDAVMETVDPEITCTCKDLADVKKVFQLALLCSKRQPAERPTMHEVARVLESLIPVAETKQPNPTPSLALLPSAK
VPCYMDEYVNLKTPHLVNCSSMSTSDAQLFLKFGEVISQNSG* (SEQ ID NO: 9)

-continued

Mutant Solyc08g061560 gene allele sler$^{CR-1}$
Nucleic acid sequence for a mutant Solyc08g061560 gene allele sler$^{CR-1}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAAGATTGGTGACTGTTCAGCACTGAAAAATTTGTAAGTATGAAA
TGCTTCTGAATCTTGTGTTATTGTTTGGAAAAATAAGTAACCATTTTTTCCCTTAGGGACCTTTCCTTCAATGAGCT
TTATGGTGATATTCCCTTCTCCATATCTAAACTCAAGCAACTGGAATATCTGTAAGTTTTGATACTCTCCTTCTTCT
AAATGTTGTATTATTTGCTTTCCGAGATTGTTAGTTGATTATGCTCGTCTTATTCAACTTAGGATTTTGAAGAATAA
TCAATTGATTGGACCAATTCCATCTACATTGTCACAGATCCCTAACTTGAAGGTCTTGTAAGTATATTCTCTCTGCT
TTGTCATGATATTGGTAGATTATGAATAATTTTAGTTTGATCCAAGAACTTCCTCCAGGGACCTGGCTCAAAATAGG
TTAAGTGGAGAAATTCCTAGGCTGATATACTGGAACGAAGTCCTGCAGTATCTGTGAGTGTTTTAATCCGGTGTTCC
TCTTCTTCCTGTTTGTTTTAACCTTAGGACACTTTCATTTCGTATATGGATATGATTACATCTGTTGTATGTTTTTA
TTCATATAGGGGACTGCGTGGTAACAACTTGGGTGGATCCCTTTCTCCTGATATGTGTCAGCTCACCGGCCTGTGGT
ACTTGTAAGTTTGTAATCCTGTTGCTCTTAAGATCTTACTTTAGTTCCTCTAGGTGATGACATTAACCATTGTTCAT
TGTGTTGTACAGTGATGTTCGGAACAATAGTTTGACTGGTTCCATTCCTCAAAATATTGGCAACTGTACTGCCTTCC
AGGTTCTGTAAGTATCTAAATCAATTGAATGAAGTTTGACTATATTCTGTATGTTTGGTTGGCATAACACCTTGTTT
TGTTCTGTCAGAGATTTGTCTTATAATGATTTGACCGGAGAGATTCCTTTCAATATTGGTTTCCTGCAAGTAGCGAC
CTTGTAAGTTTATGCTGCTTCTCTTCATTACAAACTATTCAATATATGGTTGTTTGAAGTGTACTTTCATCATTCCA
GGTCTTTGCAAGGTAATCGTCTTTCAGGGCAGATCCCTTCTGTAATTGGATTGATGCAAGCTCTTGCAGTTTTGTGA
GTGTTTTGTGTCTTGATATCTCAATCTAATGCTACTGAATCTAATTCTTGGAAACCATTATAATGCATCTGTTATTT
AAGTTTTCTGACCCTTTTACTGTCAGGGACTTGAGCTGCAATATGTTGAGTGGAACAATTCCTTCAATTCTTGGGAA
TTTGACTTACACAGAGAAATTGTTAGTACTTCAACATTATTAAAAGCAATTTGGATCATTTTGTGCTTCCTAAATTG
TGTAGTGGATCAATTACTGTAAGTTCGCATTGTATTGCAGGTATCTACACGGGAACAAGCTATCTGGTTCCATTCCT
CCAGAGCTGGGAAATATGACAAAGCTCCACTACTTGTATGAATGCCTTCTATCAATCATTTTTTGTTAGCTTTGTTT
TGTTCTTCCTGTTCAAACCCTTTTAAATGAATGCTTACCATTTAGAAGCATTTGTTTGATTATTTAGCCTTTGGGCA
ACCACGGATTTGAATGATAGAAAGCTGTTATGAGAATTTTTATTAAGAGACTTTCTTCAACCTTAAGGCTCAAAGAT
GGTAATTTGCAGGGAATTGAATGATAACCAACTTACTGGACGCATACCACCAGAACTTGGAAAGCTGACAGAATTGT
TTGACTTGTAAATCCCGTTTCTCTTCATCTTCTACTTTGGACTTGTTAACATCATTATTTATTTACTCATGTTGTAT
GTTTCAGAAATGTTGCAAACAACCACCTAGATGGGCCCATACCTTCCAATATTAGCTCATGTACCAATTTGAATAGT
CTGTGAGTGTTTTTAATGTCCGAAGTGTTTCAATTATGCACGACCATGCTTGTTTGGTAGTTATTGACACCTGATTT
TGTTGCAGCAACGTTCATGGAAACAAATTGAATGGTACTATTCCACCTGCTTTTCAGAAGCTGGAAAGTATGACCTA
TCTGTAAGTTCTTACTTTCTGATCTTTTTCTTTTGAAGAATTATGTTTAAGGTTATCGAAGTTACCGTCCATGCTGT
TGAGCAAGATTGTAAACTTACTGTGCCTTGTATATAAATTTTACTGGCGTTGTATTATTGAAAAAATCATTTTATTT
ATATTGCTCTCAAATCATACTGGCTTATATCCATTCATGAAGAATCATTTCTACTGTCTGAAGTTTTCAGCTATATG
TATCGAAAAAATTTAGTTATTATATAGTTTATTTTGAGCCTCTGCATCATCTATTTGTGAATTTCATTTGCTTATTC
TGCATACTCTCAGCATTAACCGTCTCTTCTTTTGTTAATTGCTTTAGTAATCTCTCCTCCAACAATCTCAAAGGCCC
AATTCCAATTGAGCTATCTCGTATTGGGAATGTAGATACACTGTAAGTGCAAACTTTCTCATCTACTTTCATTTCTC
TCATTGCAATTATGGTTGCGGGGAAAGCACTTTTTGTCAGTCTTAAGAATCTTCAACATTTTTTGGCTTAGGGACTT
ATCAAACAACAGGATCAGTGGTCCTATACCTATGTCCCTTGGTGATTTGGAACATCTTCTTAAACTGTGAGCATAAC
CGTCAAGTTGTTATGTTAGCATCATATATCTGTTGTACTTACATCCCTTTTGTCAATGCTGTAGGAACTTAAGCAAG
AATGAAATAAATGGAAACTTACCAGCTGAATTTGGCAATTTAAGGAGCATCATGGAGATGTATGGAACCTTGCTAAA
TTCAGTTACTTTGAATTTATGGTTTGCTTGATTTTCAGCTTTTTGACTGCACTCCTAATTGTAGTGATCTGTCAAGC
AATCACCTCTCTGGTCCCTTACCTCAGGAACTTGGTCAGCTTCCAAACCTGTACTTGCTGTAAGTACTTCAGATTTA
CTTTGAGACTCTCATCCTCTTAGCTATTGGTAATAATCTGTAGAGTGAATAAGTATGAACTTCTAAACTCGGTAAGT
AGATTTTAAAATTATTTTGGATGCCATTTTCAAAAAAGTAGAGATGAAGTTGGTTGTGTTGCTATTGTTTTATATGA
TCTGGCTTCATATGTTCATTACTTTGGTGTTCTCAGTTTTGCTTTATATTGCATTATTGCACGGGGCTCAAATGCAG
CATATCTCTATCTTCTTTTTCTTGTGGCCTTAATTATTTTACAAATTAATGAACAGGAAGGTGGAAAACAACAATTT
ATCAGGCGATGTGATGTCCTTAGCCAGTTGCCTCAGTCTAAATATCTTGTGAGTTTTCAAGTCCATAGTAAGACACC
AGTACAAACAAATGTTTTGTTAATCTAATCAACCTCATGTTAGCAGAAATGTCTCATACAATAATCTGGGAGGGAAT
ATTCCAACCGGCAATAATTTCTCTAGATTTTCACCAGACAGGTAAGTGGAGCTATTAAGATTTTACACAAGTCACAA
GCATTTATTGGTTTTTAATTCTTTGCTTCTAATTTCTTCCTTTTGCTATGTCTCCGAAAAAGCTTCATAGGAAATCC
AGATCTGTGTGGGTATTGGCTCACTTCTCCTTGTCATGCATCTCATCCGGCAGAGCGAGGTCTGATCAAACTGTAAC
AATCATTTGGCCTTTACTCTATTGCATTTTTGAAGTTCCATTTCACTTTAGACATCTGCAACATTTATTAAGTGTGA
TGGACAGATATATTGATTAATGAGGAATTATCCCTTGGTTGAGCAAACTTAATTCTGTGTTAGCCTGGTAGTAGGGT
GTACCACAAGGTTTGTCGTCATGGTTTCCTATGTTCACAATCCCTGATTGTAACATTTAGATGTGTACACATATCTA
ATTAACATGAAATAATCTTCATTTGCTGGAGTTACATTGACGTAAAGATGCGTTAGCTGTCAAATGAAACTGCATTT
GTTTTATTTCCATCATCAGTACATTAATTAAGTGCATAAATATTTTAACAGTTGTTGAATGATATAAGATGAATTTA
TTGGACAATTGCAGTTTCAATTTCTAAAGCAGCAATACTTGGTATTGCTCTGGGTGGCTTGGTGATTCTTCTGATGA
TACTAGTAGCAGCATGCCGGCCACAGAAACCTGCACCTTTCATGGAAGGATCTATTGATAAACCAGGTACAATATTT
TCCGGACGGTTGGATAGTGTTTGGAGATGTTCATGTCAGAAGGACAGTCGTCAGAGTTTATTGAAGTTGCCATGTAT
TGATTGTTTAACGTTTTTGATGAACAGTTTATTACTCATCTCCAAAACTTGTGATCCTTCATATGAACATGGCACTT
CATGTTTACGAGGACATTATGAGGATGACTGAGAACTTGAGTGAGAAGTATATAATTGGTTGTGGAGCATCAAGTAC
TGTATATAAATGTGTTTTGAAAAATTGCAAGCCTGTAGCTATCAAGAAGTTGTACTCTCACAACCCGCAATACTTGA
AGGAATTTGAGACTGAACTTGAGACAGTTGGGAGTATTAAGCATCGTAATCTTGTCTGTCTCCAAGGATATTCTCTT
TCTCCATCTGGCCATCTTCTTTTCTATGACTACATGGAAAATGGTAGCCTTTGGGATTTGCTTCATGGTTAGTAAAT
CCAAAATGGTTAAGGTGATTGATGCATTGATTTTGTGTTAAAGCATCAAGTAATCAGTCCTCTTGTATCTTTTTTTG
CAGGTCCTACAACAAAGAAGAAAAAGCTTGATTGGGTTACTCGCCTTCGAATTGCATTGGGATCAGCTCAAGGGCTT
GCATATCTTCATCATGATTGTAGCCCTCGAATAATCCACCGTGATGTTAAATCATCTAATATCTTGTTGGACAAAGA
CTTTGAGGCTCATCTGACTGATTTTGGCATAGCTAAAAGCTTATGCATATCAAAGACCTATACGTCCACGTACATTA
TGGGAACCATTGGTTACATTGATCCAGAGTATGCTCGCACTTCTCGCTTGACAGAGAAGTCTGATGTTTACAGCTAT
GGTATTGTTCTATTGGAATTGCTCACTGGAAGGAAAGCTGTAGATAATGAATCTAATCTACATCATTTGGTAAGCTC -continued TTGCAATTTAGTTAATATGAACTTGTCCTATGATGTTTATTCATATAATTATATTAAGATTCAATTCAATTGATCAT
AACAGTTTTGCATATATGTTACAGATTCTAACTAAGGCAGCAAACGATGCTGTAATGGAAACAGTGGATCCTGAGAT
AACATGCACATGCAAAGATCTTGCAGATGTGAAGAAGGTTTTTCAGCTTGCCCTTCTATGTTCCAAAAGACAGCCTG
CTGAGAGACCAACAATGCATGAAGTGGCAAGAGTACTTGAAAGCCTAATACCCGTCGCTGAAACGAAACAGCCAAAT
CCAACCCCCTCACTTGCATTACTCCCATCTGCTAAGGTACCTTGTTACATGGATGAATATGTCAACCTCAAGACACC
CCACCTAGTGAACTGTTCATCCATGAGCACTTCAGATGCCCAACTTTTCCTCAAGTTTGGAGAGGTCATATCCCAGA
ATAGTGGCTGA (SEQ ID NO: 10)

Nucleic acid sequence for a mutant Solyc08g061560 gene allele sler$^{CR-1}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAAGATTGGTGACTGTTCAGCACTGAAAAAT
TTGGACCTTTCCTTCAATGAGCTTTATGGTGATATTCCCTTCTCCATATCTAAACTCAAGCAACTGGAATATCTGAT
TTTGAAGAATAATCAATTGATTGGACCAATTCCATCTACATTGTCACAGATCCCTAACTTGAAGGTCTTGGACCTGG
CTCAAAATAGGTTAAGTGGAGAAATTCCTAGGCTGATATACTGGAACGAAGTCCTGCAGTATCTGGGACTGCGTGGT
AACAACTTGGGTGGATCCCTTTCTCCTGATATGTGTCAGCTCACCGGCCTGTGGTACTTTGATGTTCGGAACAATAG
TTTGACTGGTTCCATTCCTCAAAATATTGGCAACTGTACTGCCTTCCAGGTTCTAGATTTGTCTTATAATGATTTGA
CCGGAGAGATTCCTTTCAATATTGGTTTCCTGCAAGTAGCGACCTTGTCTTTGCAAGGTAATCGTCTTTCAGGGCAG
ATCCCTTCTGTAATTGGATTGATGCAAGCTCTTGCAGTTTTGGACTTGAGCTGCAATATGTTGAGTGGAACAATTCC
TTCAATTCTTGGGAATTTGACTTACACAGAGAAATTGTATCTACACGGGAACAAGCTATCTGGTTCCATTCCTCCAG
AGCTGGGAAATATGACAAAGCTCCACTACTTGGAATTGAATGATAACCAACTTACTGGACGCATACCACCAGAACTT
GGAAAGCTGACAGAATTGTTTGACTTAAATGTTGCAAACAACCACCTAGATGGGCCCATACCTTCCAATATTAGCTC
ATGTACCAATTTGAATAGTCTCAACGTTCATGGAAACAAATTGAATGGTACTATTCCACCTGCTTTTCAGAAGCTGG
AAAGTATGACCTATCTTAATCTCTCCTCCAACAATCTCAAAGGCCCAATTCCAATTGAGCTATCTCGTATTGGGAAT
GTAGATACACTGGACTTATCAAACAACAGGATCAGTGGTCCTATACCTATGTCCCTTGGTGATTTGGAACATCTTCT
TAAACTGAACTTAAGCAAGAATGAAATAAATGGAAACTTACCAGCTGAATTTGGCAATTTAAGGAGCATCATGGAGA
TTGATCTGTCAAGCAATCACCTCTCTGGTCCCTTACCTCAGGAACTTGGTCAGCTTCCAAACCTGTACTTGCTGAAG
GTGGAAAACAACAATTTATCAGGCGATGTGATGTCCTTAGCCAGTTGCCTCAGTCTAAATATCTTAAATGTCTCATA
CAATAATCTGGGAGGGAATATTCCAACCGGCAATAATTTCTCTAGATTTTCACCAGACAGCTTCATAGGAAATCCAG
ATCTGTGTGGGTATTGGCTCACTTCTCCTTGTCATGCATCTCATCCGGCAGAGCGAGTTTCAATTTCTAAAGCAGCA
ATACTTGGTATTGCTCTGGGTGGCTTGGTGATTCTTCTGATGATACTAGTAGCAGCATGCCGGCCACAGAAACCTGC
ACCTTTCATGGAAGGATCTATTGATAAACCAGTTTATTACTCATCTCCAAAACTTGTGATCCTTCATATGAACATGG
CACTTCATGTTTACGAGGACATTATGAGGATGACTGAGAACTTGAGTGAGAAGTATATAATTGGTTGTGGAGCATCA
AGTACTGTATATAAATGTGTTTTGAAAAATTGCAAGCCTGTAGCTATCAAGAAGTTGTACTCTCACAACCCGCAATA
CTTGAAGGAATTTGAGACTGAACTTGAGACAGTTGGGAGTATTAAGCATCGTAATCTTGTCTGTCTCCAAGGATATT
CTCTTTCTCCATCTGGCCATCTTCTTTTCTATGACTACATGGAAAATGGTAGCCTTTGGGATTTGCTTCATGGTCCT
ACAACAAAGAAGAAAAAGCTTGATTGGGTTACTCGCCTTCGAATTGCATTGGGATCAGCTCAAGGGCTTGCATATCT
TCATCATGATTGTAGCCCTCGAATAATCCACCGTGATGTTAAATCATCTAATATCTTGTTGGACAAAGACTTTGAGG
CTCATCTGACTGATTTTGGCATAGCTAAAAGCTTATGCATATCAAAGACCTATACGTCCACGTACATTATGGGAACC
ATTGGTTACATTGATCCAGAGTATGCTCGCACTTCTCGCTTGACAGAGAAGTCTGATGTTTACAGCTATGGTATTGT
TCTATTGGAATTGCTCACTGGAAGGAAAGCTGTAGATAATGAATCTAATCTACATCATTTGATTCTAACTAAGGCAG
CAAACGATGCTGTAATGGAAACAGTGGATCCTGAGATAACATGCACATGCAAAGATCTTGCAGATGTGAAGAAGGTT
TTTCAGCTTGCCCTTCTATGTTCCAAAAGACAGCCTGCTGAGAGACCAACAATGCATGAAGTGGCAAGAGTACTTGA
AAGCCTAATACCCGTCGCTGAAACGAAACAGCCAAATCCAACCCCCTCACTTGCATTACTCCCATCTGCTAAGGTAC
CTTGTTACATGGATGAATATGTCAACCTCAAGACACCCCACCTAGTGAACTGTTCATCCATGAGCACTTCAGATGCC
CAACTTTTCCTCAAGTTTGGAGAGGTCATATCCCAGAATAGTGGCTGA (SEQ ID NO: 11)

Amino acid sequence of the mutant polypeptide encoded by a mutant Solyc08g061560 gene allele sler$^{CR-1}$ coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEDW* (SEQ ID NO: 12)

Mutant Solyc08g061560 gene allele sler$^{CR-2}$
Nucleic acid sequence for a mutant Solyc08g061560 gene allele sler$^{CR-2}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCTATTGGACAGCTCAAAGGCCTTGTATCTATGTAATATCTCCTCCCATTATCTCACAATTAC
CCTTTTTGTTTGATCTTTTGACTTAGTGCACATTATAGACTATGCCTGTTAATTTTTTTTTGAAGTGATATGAGGGG
AAATCGCCTTTCTGGCCAGATACCAGATGAGATTGGTGACTGTTCAGCACTGAAAAATTTGTAAGTATGAAATGCTT
CTGAATCTTGTGTTATTGTTTGGAAAAATAAGTAACCATTTTTTCCCTTAGGGACCTTTCCTTCAATGAGCTTTATG
GTGATATTCCCTTCTCCATATCTAAACTCAAGCAACTGGAATATCTGTAAGTTTTGATACTCTCCTTCTTCTAAATG
TTGTATTATTTGCTTTCCGAGATTGTTAGTTGATTATGCTCGTCTTATTCAACTTAGGATTTTGAAGAATAATCAAT
TGATTGGACCAATTCCATCTACATTGTCACAGATCCCTAACTTGAAGGTCTTGTAAGTATATTCTCTCTGCTTTGTC
ATGATATTGGTAGATTATGAATAATTTTAGTTTGATCCAAGAACTTCCTCCAGGGACCTGGCTCAAAATAGGTTAAG
TGGAGAAATTCCTAGGCTGATATACTGGAACGAAGTCCTGCAGTATCTGTGAGTGTTTTAATCCGGTGTTCCTCTTC
TTCCTGTTTGTTTTAACCTTAGGACACTTTCATTTCGTATATGGATATGATTACATCTGTTGTATGTTTTTATTCAT
ATAGGGGACTGCGTGGTAACAACTTGGGTGGATCCCTTTCTCCTGATATGTGTCAGCTCACCGGCCTGTGGTACTTG
TAAGTTTGTAATCCTGTTGCTCTTAAGATCTTACTTTAGTTCCTCTAGGTGATGACATTAACCATTGTTCATTGTGT
TGTACAGTGATGTTCGGAACAATAGTTTGACTGGTTCCATTCCTCAAAATATTGGCAACTGTACTGCCTTCCAGGTT
CTGTAAGTATCTAAATCAATTGAATGAAGTTTGACTATATTCTGTATGTTTGGTTGGCATAACACCTTGTTTTGTTC
TGTCAGAGATTTGTCTTATAATGATTTGACCGGAGAGATTCCTTTCAATATTGGTTTCCTGCAAGTAGCGACCTTGT
AAGTTTATGCTGCTTCTCTTCATTACAACTATTCAATATATGGTTGTTTGAAGTGTACTTTCATCATTCCAGGTCT -continued TTGCAAGGTAATCGTCTTTCAGGGCAGATCCCTTCTGTAATTGGATTGATGCAAGCTCTTGCAGTTTTGTGAGTGTT
TTGTGTCTTGATATCTCAATCTAATGCTACTGAATCTAATTCTTGGAAACCATTATAATGCATCTGTTATTTAAGTT
TTCTGACCCTTTTACTGTCAGGGACTTGAGCTGCAATATGTTGAGTGGAACAATTCCTTCAATTCTTGGGAATTTGA
CTTACACAGAGAAATTGTTAGTACTTCAACATTATTAAAAGCAATTTGGATCATTTTGTGCTTCCTAAATTGTGTAG
TGGATCAATTACTGTAAGTTCGCATTGTATTGCAGGTATCTACACGGGAACAAGCTATCTGGTTCCATTCCTCCAGA
GCTGGGAAATATGACAAAGCTCCACTACTTGTATGAATGCCTTCTATCAATCATTTTTTGTTAGCTTTGTTTTGTTC
TTCCTGTTCAAACCCTTTTAAATGAATGCTTACCATTTAGAAGCATTTGTTTGATTATTTAGCCTTTGGGCAACCAC
GGATTTGAATGATAGAAAGCTGTTATGAGAATTTTTATTAAGAGACTTTCTTCAACCTTAAGGCTCAAAGATGGTAA
TTTGCAGGGAATTGAATGATAACCAACTTACTGGACGCATACCACCAGAACTTGGAAAGCTGACAGAATTGTTTGAC
TTGTAAATCCCGTTTCTCTTCATCTTCTACTTTGGACTTGTTAACATCATTATTTATTTACTCATGTTGTATGTTTC
AGAAATGTTGCAAACAACCACCTAGATGGGCCCATACCTTCCAATATTAGCTCATGTACCAATTTGAATAGTCTGTG
AGTGTTTTTAATGTCCGAAGTGTTTCAATTATGCACGACCATGCTTGTTTGGTAGTTATTGACACCTGATTTTGTTG
CAGCAACGTTCATGGAAACAAATTGAATGGTACTATTCCACCTGCTTTTCAGAAGCTGGAAAGTATGACCTATCTGT
AAGTTCTTACTTTCTGATCTTTTTCTTTTGAAGAATTATGTTTAAGGTTATCGAAGTTACCGTCCATGCTGTTGAGC
AAGATTGTAAACTTACTGTGCCTTGTATATAAATTTTACTGGCGTTGTATTATTGAAAAAATCATTTTATTTATATT
GCTCTCAAATCATACTGGCTTATATCCATTCATGAAGAATCATTTCTACTGTCTGAAGTTTTCAGCTATATGTATCG
AAAAAATTTAGTTATTATATAGTTTATTTTGAGCCTCTGCATCATCTATTTGTGAATTTCATTTGCTTATTCTGCAT
ACTCTCAGCATTAACCGTCTCTTCTTTTGTTAATTGCTTTAGTAATCTCTCCTCCAACAATCTCAAAGGCCCAATTC
CAATTGAGCTATCTCGTATTGGGAATGTAGATACACTGTAAGTGCAAACTTTCTCATCTACTTTCATTTCTCTCATT
GCAATTATGGTTGCGGGGAAAGCACTTTTTGTCAGTCTTAAGAATCTTCAACATTTTTTGGCTTAGGGACTTATCAA
ACAACAGGATCAGTGGTCCTATACCTATGTCCCTTGGTGATTTGGAACATCTTCTTAAACTGTGAGCATAACCGTCA
AGTTGTTATGTTAGCATCATATATCTGTTGTACTTACATCCCTTTTGTCAATGCTGTAGGAACTTAAGCAAGAATGA
AATAAATGGAAACTTACCAGCTGAATTTGGCAATTTAAGGAGCATCATGGAGATGTATGGAACCTTGCTAAATTCAG
TTACTTTGAATTTATGGTTTGCTTGATTTTCAGCTTTTTGACTGCACTCCTAATTGTAGTGATCTGTCAAGCAATCA
CCTCTCTGGTCCCTTACCTCAGGAACTTGGTCAGCTTCCAAACCTGTACTTGCTGTAAGTACTTCAGATTTACTTTG
AGACTCTCATCCTCTTAGCTATTGGTAATAATCTGTAGAGTGAATAAGTATGAACTTCTAAACTCGGTAAGTAGATT
TTAAAATTATTTTGGATGCCATTTTCAAAAAAGTAGAGATGAAGTTGGTTGTGTTGCTATTGTTTTATATGATCTGG
CTTCATATGTTCATTACTTTGGTGTTCTCAGTTTTGCTTTATATTGCATTATTGCACGGGGCTCAAATGCAGCATAT
CTCTATCTTCTTTTTCTTGTGGCCTTAATTATTTTACAAATTAATGAACAGGAAGGTGGAAAACAACAATTTATCAG
GCGATGTGATGTCCTTAGCCAGTTGCCTCAGTCTAAATATCTTGTGAGTTTTCAAGTCCATAGTAAGACACCAGTAC
AAACAAATGTTTTGTTAATCTAATCAACCTCATGTTAGCAGAAATGTCTCATACAATAATCTGGGAGGGAATATTCC
AACCGGCAATAATTTCTCTAGATTTTCACCAGACAGGTAAGTGGAGCTATTAAGATTTTACACAAGTCACAAGCATT
TATTGGTTTTTAATTCTTTGCTTCTAATTTCTTCCTTTTGCTATGTCTCCGAAAAAGCTTCATAGGAAATCCAGATC
TGTGTGGGTATTGGCTCACTTCTCCTTGTCATGCATCTCATCCGGCAGAGCGAGGTCTGATCAAACTGTAACAATCA
TTTGGCCTTTACTCTATTGCATTTTTGAAGTTCCATTTCACTTTAGACATCTGCAACATTTATTAAGTGTGATGGAC
AGATATATTGATTAATGAGGAATTATCCCTTGGTTGAGCAAACTTAATTCTGTGTTAGCCTGGTAGTAGGGTGTACC
ACAAGGTTTGTCGTCATGGTTTCCTATGTTCACAATCCCTGATTGTAACATTTAGATGTGTACACATATCTAATTAA
CATGAAATAATCTTCATTTGCTGGAGTTACATTGACGTAAAGATGCGTTAGCTGTCAAATGAAACTGCATTTGTTTT
ATTTCCATCATCAGTACATTAATTAAGTGCATAAATATTTTAACAGTTGTTGAATGATATAAGATGAATTTATTGGA
CAATTGCAGTTTCAATTTCTAAAGCAGCAATACTTGGTATTGCTCTGGGTGGCTTGGTGATTCTTCTGATGATACTA
GTAGCAGCATGCCGGCCACAGAAACCTGCACCTTTCATGGAAGGATCTATTGATAAACCAGGTACAATATTTTCCGG
ACGGTTGGATAGTGTTTGGAGATGTTCATGTCAGAAGGACAGTCGTCAGAGTTTATTGAAGTTGCCATGTATTGATT
GTTTAACGTTTTTGATGAACAGTTTATTACTCATCTCCAAAACTTGTGATCCTTCATATGAACATGGCACTTCATGT
TTACGAGGACATTATGAGGATGACTGAGAACTTGAGTGAGAAGTATATAATTGGTTGTGGAGCATCAAGTACTGTAT
ATAAATGTGTTTTGAAAAATTGCAAGCCTGTAGCTATCAAGAAGTTGTACTCTCACAACCCGCAATACTTGAAGGAA
TTTGAGACTGAACTTGAGACAGTTGGGAGTATTAAGCATCGTAATCTTGTCTGTCTCCAAGGATATTCTCTTTCTCC
ATCTGGCCATCTTCTTTTCTATGACTACATGGAAAATGGTAGCCTTTGGGATTTGCTTCATGGTTAGTAAATCCAAA
ATGGTTAAGGTGATTGATGCATTGATTTTGTGTTAAAGCATCAAGTAATCAGTCCTCTTGTATCTTTTTTTGCAGGT
CCTACAACAAAGAAGAAAAAGCTTGATTGGGTTACTCGCCTTCGAATTGCATTGGGATCAGCTCAAGGGCTTGCATA
TCTTCATCATGATTGTAGCCCTCGAATAATCCACCGTGATGTTAAATCATCTAATATCTTGTTGGACAAAGACTTTG
AGGCTCATCTGACTGATTTTGGCATAGCTAAAAGCTTATGCATATCAAAGACCTATACGTCCACGTACATTATGGGA
ACCATTGGTTACATTGATCCAGAGTATGCTCGCACTTCTCGCTTGACAGAGAAGTCTGATGTTTACAGCTATGGTAT
TGTTCTATTGGAATTGCTCACTGGAAGGAAAGCTGTAGATAATGAATCTAATCTACATCATTTGGTAAGCTCTTGCA
ATTTAGTTAATATGAACTTGTCCTATGATGTTTATTCATATAATTATATTAAGATTCAATTCAATTGATCATAACAG
TTTTGCATATATGTTACAGATTCTAACTAAGGCAGCAAACGATGCTGTAATGGAAACAGTGGATCCTGAGATAACAT
GCACATGCAAAGATCTTGCAGATGTGAAGAAGGTTTTTCAGCTTGCCCTTCTATGTTCCAAAAGACAGCCTGCTGAG
AGACCAACAATGCATGAAGTGGCAAGAGTACTTGAAAGCCTAATACCCGTCGCTGAAACGAAACAGCCAAATCCAAC
CCCCTCACTTGCATTACTCCCATCTGCTAAGGTACCTTGTTACATGGATGAATATGTCAACCTCAAGACACCCCACC
TAGTGAACTGTTCATCCATGAGCACTTCAGATGCCCAACTTTTCCTCAAGTTTGGAGAGGTCATATCCCAGAATAGT
GGCTGA (SEQ ID NO: 13)

Nucleic acid sequence for a mutant Solyc08g061560 gene allele sler$^{CR-2}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCTATTGGACAGCTCAAAGGCCTTGTATCT
ATTGATATGAGGGGAAATCGCCTTTCTGGCCAGATACCAGATGAGATTGGTGACTGTTCAGCACTGAAAAATTTGGA
CCTTTCCTTCAATGAGCTTTATGGTGATATTCCCTTCTCCATATCTAAACTCAAGCAACTGGAATATCTGATTTTGA
AGAATAATCAATTGATTGGACCAATTCCATCTACATTGTCACAGATCCCTAACTTGAAGGTCTTGGACCTGGCTCAA
AATAGGTTAAGTGGAGAAATTCCTAGGCTGATATACTGGAACGAAGTCCTGCAGTATCTGGGACTGCGTGGTAACAA
CTTGGGTGGATCCCTTTCTCCTGATATGTGTCAGCTCACCGGCCTGTGGTACTTTGATGTTCGGAACAATAGTTTGA
CTGGTTCCATTCCTCAAAATATTGGCAACTGTACTGCCTTCCAGGTTCTAGATTTGTCTTATAATGATTTGACCGGA
GAGATTCCTTTCAATATTGGTTTCCTGCAAGTAGCGACCTTGTCTTTGCAAGGTAATCGTCTTTCAGGGCAGATCCC
TTCTGTAATTGGATTGATGCAAGCTCTTGCAGTTTTGGACTTGAGCTGCAATATGTTGAGTGGAACAATTCCTTCAA
TTCTTGGGAATTTGACTTACACAGAGAAATTGTATCTACACGGGAACAAGCTATCTGGTTCCATTCCTCCAGAGCTG
GGAAATATGACAAAGCTCCACTACTTGGAATTGAATGATAACCAACTTACTGGACGCATACCACCAGAACTTGGAAA
GCTGACAGAATTGTTTGACTTAAATGTTGCAAACAACCACCTAGATGGGCCCATACCTTCCAATATTAGCTCATGTA
CCAATTTGAATAGTCTCAACGTTCATGGAAACAAATTGAATGGTACTATTCCACCTGCTTTTCAGAAGCTGGAAAGT
ATGACCTATCTTAATCTCTCCTCCAACAATCTCAAAGGCCCAATTCCAATTGAGCTATCTCGTATTGGGAATGTAGA -continued TACACTGGACTTATCAAACAACAGGATCAGTGGTCCTATACCTATGTCCCTTGGTGATTTGGAACATCTTCTTAAAC
TGAACTTAAGCAAGAATGAAATAAATGGAAACTTACCAGCTGAATTTGGCAATTTAAGGAGCATCATGGAGATTGAT
CTGTCAAGCAATCACCTCTCTGGTCCCTTACCTCAGGAACTTGGTCAGCTTCCAAACCTGTACTTGCTGAAGGTGGA
AAACAACAATTTATCAGGCGATGTGATGTCCTTAGCCAGTTGCCTCAGTCTAAATATCTTAAATGTCTCATACAATA
ATCTGGGAGGGAATATTCCAACCGGCAATAATTTCTCTAGATTTTCACCAGACAGCTTCATAGGAAATCCAGATCTG
TGTGGGTATTGGCTCACTTCTCCTTGTCATGCATCTCATCCGGCAGAGCGAGTTTCAATTTCTAAAGCAGCAATACT
TGGTATTGCTCTGGGTGGCTTGGTGATTCTTCTGATGATACTAGTAGCAGCATGCCGGCCACAGAAACCTGCACCTT
TCATGGAAGGATCTATTGATAAACCAGTTTATTACTCATCTCCAAAACTTGTGATCCTTCATATGAACATGGCACTT
CATGTTTACGAGGACATTATGAGGATGACTGAGAACTTGAGTGAGAAGTATATAATTGGTTGTGGAGCATCAAGTAC
TGTATATAAATGTGTTTTGAAAAATTGCAAGCCTGTAGCTATCAAGAAGTTGTACTCTCACAACCCGCAATACTTGA
AGGAATTTGAGACTGAACTTGAGACAGTTGGGAGTATTAAGCATCGTAATCTTGTCTGTCTCCAAGGATATTCTCTT
TCTCCATCTGGCCATCTTCTTTTCTATGACTACATGGAAAATGGTAGCCTTTGGGATTTGCTTCATGGTCCTACAAC
AAAGAAGAAAAAGCTTGATTGGGTTACTCGCCTTCGAATTGCATTGGGATCAGCTCAAGGGCTTGCATATCTTCATC
ATGATTGTAGCCCTCGAATAATCCACCGTGATGTTAAATCATCTAATATCTTGTTGGACAAAGACTTTGAGGCTCAT
CTGACTGATTTTGGCATAGCTAAAAGCTTATGCATATCAAAGACCTATACGTCCACGTACATTATGGGAACCATTGG
TTACATTGATCCAGAGTATGCTCGCACTTCTCGCTTGACAGAGAAGTCTGATGTTTACAGCTATGGTATTGTTCTAT
TGGAATTGCTCACTGGAAGGAAAGCTGTAGATAATGAATCTAATCTACATCATTTGATTCTAACTAAGGCAGCAAAC
GATGCTGTAATGGAAACAGTGGATCCTGAGATAACATGCACATGCAAAGATCTTGCAGATGTGAAGAAGGTTTTTCA
GCTTGCCCTTCTATGTTCCAAAAGACAGCCTGCTGAGAGACCAACAATGCATGAAGTGGCAAGAGTACTTGAAAGCC
TAATACCCGTCGCTGAAACGAAACAGCCAAATCCAACCCCCTCACTTGCATTACTCCCATCTGCTAAGGTACCTTGT
TACATGGATGAATATGTCAACCTCAAGACACCCCACCTAGTGAACTGTTCATCCATGAGCACTTCAGATGCCCAACT
TTTCCTCAAGTTTGGAGAGGTCATATCCCAGAATAGTGGCTGA (SEQ ID NO: 14)

Amino acid sequence for a mutant polypeptide encoded by a mutant Solyc08g061560 gene allele sler$^{CR-2}$ coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSLLDSSKALYLLI* (SEQ ID NO: 15)

Mutant Solyc08g061560 gene allele sler$^{MT}$
Nucleic acid sequence for a mutant Solyc08g061560 gene allele sler$^{MT}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAGATTGGTGACTGTTCAGCACTGAAAAATTTGTAAGTATGAAAT
GCTTCTGAATCTTGTGTTATTGTTTGGAAAAATAAGTAACCATTTTTTCCCTTAGGGACCTTTCCTTCAATGAGCTT
TATGGTGATATTCCCTTCTCCATATCTAAACTCAAGCAACTGGAATATCTGTAAGTTTTGATACTCTCCTTCTTCTA
AATGTTGTATTATTTGCTTTCCGAGATTGTTAGTTGATTATGCTCGTCTTATTCAACTTAGGATTTTGAAGAATAAT
CAATTGATTGGACCAATTCCATCTACATTGTCACAGATCCCTAACTTGAAGGTCTTGTAAGTATATTCTCTCTGCTT
TGTCATGATATTGGTAGATTATGAATAATTTAGTTTGATCCAAGAACTTCCTCCAGGGACCTGGCTCAAAATAGGT
TAAGTGGAGAAATTCCTAGGCTGATATACTGGAACGAAGTCCTGCAGTATCTGTGAGTGTTTTAATCCGGTGTTCCT
CTTCTTCCTGTTTGTTTTAACCTTAGGACACTTTCATTTCGTATATGGATATGATTACATCTGTTGTATGTTTTTAT
TCATATAGGGGACTGCGTGGTAACAACTTGGGTGGATCCCTTTCTCCTGATATGTGTCAGCTCACCGGCCTGTGGTA
CTTGTAAGTTTGTAATCCTGTTGCTCTTAAGATCTTACTTTAGTTCCTCTAGGTGATGACATTAACCATTGTTCATT
GTGTTGTACAGTGATGTTCGGAACAATAGTTTGACTGGTTCCATTCCTCAAAATATTGGCAACTGTACTGCCTTCCA
GGTTCTGTAAGTATCTAAATCAATTGAATGAAGTTTGACTATATTCTGTATGTTTGGTTGGCATAACACCTTGTTTT
GTTCTGTCAGAGATTTGTCTTATAATGATTTGACCGGAGAGATTCCTTTCAATATTGGTTTCCTGCAAGTAGCGACC
TTGTAAGTTTATGCTGCTTCTCTTCATTACAAACTATTCAATATATGGTTGTTTGAAGTGTACTTTCATCATTCCAG
GTCTTTGCAAGGTAATCGTCTTTCAGGGCAGATCCCTTCTGTAATTGGATTGATGCAAGCTCTTGCAGTTTTGTGAG
TGTTTTGTGTCTTGATATCTCAATCTAATGCTACTGAATCTAATTCTTGGAAACCATTATAATGCATCTGTTATTTA
AGTTTTCTGACCCTTTTACTGTCAGGGACTTGAGCTGCAATATGTTGAGTGGAACAATTCCTTCAATTCTTGGGAAT
TTGACTTACACAGAGAAATTGTTAGTACTTCAACATTATTAAAAGCAATTTGGATCATTTTGTGCTTCCTAAATTGT
GTAGTGGATCAATTACTGTAAGTTCGCATTGTATTGCAGGTATCTACACGGGAACAAGCTATCTGGTTCCATTCCTC
CAGAGCTGGGAAATATGACAAAGCTCCACTACTTGTATGAATGCCTTCTATCAATCATTTTTTGTTAGCTTTGTTTT
GTTCTTCCTGTTCAAACCCTTTTAAATGAATGCTTACCATTTAGAAGCATTTGTTTGATTATTTAGCCTTTGGGCAA
CCACGGATTTGAATGATAGAAAGCTGTTATGAGAATTTTTATTAAGAGACTTTCTTCAACCTTAAGGCTCAAAGATG
GTAATTTGCAGGGAATTGAATGATAACCAACTTACTGGACGCATACCACCAGAACTTGGAAAGCTGACAGAATTGTT
TGACTTGTAAATCCCGTTTCTCTTCATCTTCTACTTTGGACTTGTTAACATCATTATTTATTTACTCATGTTGTATG
TTTCAGAAATGTTGCAAACAACCACCTAGATGGGCCCATACCTTCCAATATTAGCTCATGTACCAATTTGAATAGTC
TGTGAGTGTTTTTAATGTCCGAAGTGTTTCAATTATGCACGACCATGCTTGTTTGGTAGTTATTGACACCTGATTTT
GTTGCAGCAACGTTCATGGAAACTAATTGAATGGTACTATTCCACCTGCTTTTCAGAAGCTGGAAAGTATGACCTAT
CTGTAAGTTCTTACTTTCTGATCTTTTTCTTTTGAAGAATTATGTTTAAGGTTATCGAAGTTACCGTCCATGCTGTT
GAGCAAGATTGTAAACTTACTGTGCCTTGTATATAAATTTTACTGGCGTTGTATTATTGAAAAAATCATTTTATTTA
TATTGCTCTCAAATCATACTGGCTTATATCCATTCATGAAGAATCATTTCTACTGTCTGAAGTTTTCAGCTATATGT
ATCGAAAAAATTTAGTTATTATATAGTTTATTTTGAGCCTCTGCATCATCTATTTGTGAATTTCATTTGCTTATTCT
GCATACTCTCAGCATTAACCGTCTCTTCTTTTGTTAATTGCTTTAGTAATCTCTCCTCCAACAATCTCAAAGGCCCA
ATTCCAATTGAGCTATCTCGTATTGGGAATGTAGATACACTGTAAGTGCAAACTTTCTCATCTACTTTCATTTCTCT
CATTGCAATTATGGTTGCGGGGAAAGCACTTTTTGTCAGTCTTAAGAATCTTCAACATTTTTTGGCTTAGGGACTTA
TCAAACAACAGGATCAGTGGTCCTATACCTATGTCCCTTGGTGATTTGGAACATCTTCTTAAACTGTGAGCATAACC
GTCAAGTTGTTATGTTAGCATCATATATCTGTTGTACTTACATCCCTTTTGTCAATGCTGTAGGAACTTAAGCAAGA
ATGAAATAAATGGAAACTTACCAGCTGAATTTGGCAATTTAAGGAGCATCATGGAGATGTATGGAACCTTGCTAAAT
TCAGTTACTTTGAATTTATGGTTTGCTTGATTTTCAGCTTTTTGACTGCACTCCTAATTGTAGTGATCTGTCAAGCA
ATCACCTCTCTGGTCCCTTACCTCAGGAACTTGGTCAGCTTCCAAACCTGTACTTGCTGTAAGTACTTCAGATTTAC
TTTGAGACTCTCATCCTCTTAGCTATTGGTAATAATCTGTAGAGTGAATAAGTATGAACTTCTAAACTCGGTAAGTA -continued GATTTTAAAATTATTTTGGATGCCATTTTCAAAAAAGTAGAGATGAAGTTGGTTGTGTTGCTATTGTTTTATATGAT
CTGGCTTCATATGTTCATTACTTTGGTGTTCTCAGTTTTGCTTTATATTGCATTATTGCACGGGGCTCAAATGCAGC
ATATCTCTATCTTCTTTTTCTTGTGGCCTTAATTATTTTACAAATTAATGAACAGGAAGGTGGAAAACAACAATTTA
TCAGGCGATGTGATGTCCTTAGCCAGTTGCCTCAGTCTAAATATCTTGTGAGTTTTCAAGTCCATAGTAAGACACCA
GTACAAACAAATGTTTTGTTAATCTAATCAACCTCATGTTAGCAGAAATGTCTCATACAATAATCTGGGAGGGAATA
TTCCAACCGGCAATAATTTCTCTAGATTTTCACCAGACAGGTAAGTGGAGCTATTAAGATTTTACACAAGTCACAAG
CATTTATTGGTTTTTAATTCTTTGCTTCTAATTTCTTCCTTTTGCTATGTCTCCGAAAAAGCTTCATAGGAAATCCA
GATCTGTGTGGGTATTGGCTCACTTCTCCTTGTCATGCATCTCATCCGGCAGAGCGAGGTCTGATCAAACTGTAACA
ATCATTTGGCCTTTACTCTATTGCATTTTTGAAGTTCCATTTCACTTTAGACATCTGCAACATTTATTAAGTGTGAT
GGACAGATATATTGATTAATGAGGAATTATCCCTTGGTTGAGCAAACTTAATTCTGTGTTAGCCTGGTAGTAGGGTG
TACCACAAGGTTTGTCGTCATGGTTTCCTATGTTCACAATCCCTGATTGTAACATTTAGATGTGTACACATATCTAA
TTAACATGAAATAATCTTCATTTGCTGGAGTTACATTGACGTAAAGATGCGTTAGCTGTCAAATGAAACTGCATTTG
TTTTATTTCCATCATCAGTACATTAATTAAGTGCATAAATATTTTAACAGTTGTTGAATGATATAAGATGAATTTAT
TGGACAATTGCAGTTTCAATTTCTAAAGCAGCAATACTTGGTATTGCTCTGGGTGGCTTGGTGATTCTTCTGATGAT
ACTAGTAGCAGCATGCCGGCCACAGAAACCTGCACCTTTCATGGAAGGATCTATTGATAAACCAGGTACAATATTTT
CCGGACGGTTGGATAGTGTTTGGAGATGTTCATGTCAGAAGGACAGTCGTCAGAGTTTATTGAAGTTGCCATGTATT
GATTGTTTAACGTTTTTGATGAACAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTTAGTAAATC
CAAAATGGTTAAGGTGATTGATGCATTGATTTTGTGTTAAAGCATCAAGTAATCAGTCCTCTTGTATCTTTTTTTGC
AGGTCCTACAACAAAGAAGAAAAAGCTTGATTGGGTTACTCGCCTTCGAATTGCATTGGGATCAGCTCAAGGGCTTG
CATATCTTCATCATGATTGTAGCCCTCGAATAATCCACCGTGATGTTAAATCATCTAATATCTTGTTGGACAAAGAC
TTTGAGGCTCATCTGACTGATTTTGGCATAGCTAAAAGCTTATGCATATCAAAGACCTATACGTCCACGTACATTAT
GGGAACCATTGGTTACATTGATCCAGAGTATGCTCGCACTTCTCGCTTGACAGAGAAGTCTGATGTTTACAGCTATG
GTATTGTTCTATTGGAATTGCTCACTGGAAGGAAAGCTGTAGATAATGAATCTAATCTACATCATTTGGTAAGCTCT
TGCAATTTAGTTAATATGAACTTGTCCTATGATGTTTATTCATATAATTATATTAAGATTCAATTCAATTGATCATA
ACAGTTTTGCATATATGTTACAGATTCTAACTAAGGCAGCAAACGATGCTGTAATGGAAACAGTGGATCCTGAGATA
ACATGCACATGCAAAGATCTTGCAGATGTGAAGAAGGTTTTTCAGCTTGCCCTTCTATGTTCCAAAAGACAGCCTGC
TGAGAGACCAACAATGCATGAAGTGGCAAGAGTACTTGAAAGCCTAATACCCGTCGCTGAAACGAAACAGCCAAATC
CAACCCCCTCACTTGCATTACTCCCATCTGCTAAGGTACCTTGTTACATGGATGAATATGTCAACCTCAAGACACCC
CACCTAGTGAACTGTTCATCCATGAGCACTTCAGATGCCCAACTTTTCCTCAAGTTTGGAGAGGTCATATCCCAGAA
TAGTGGCTGA (SEQ ID NO: 16)

Nucleic acid sequence for a mutant Solyc08g061560 gene allele sler$^{MT}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACTAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC
AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGTTTCAATTTCTAAAGCAGCAA
TACTTGGTATTGCTCTGGGTGGCTTGGTGATTCTTCTGATGATACTAGTAGCAGCATGCCGGCCACAGAAACCTGCA
CCTTTCATGGAAGGATCTATTGATAAACCAGTTTATTACTCATCTCCAAAACTTGTGATCCTTCATATGAACATGGC
ACTTCATGTTTACGAGGACATTATGAGGATGACTGAGAACTTGAGTGAGAAGTATATAATTGGTTGTGGAGCATCAA
GTACTGTATATAAATGTGTTTTGAAAAATTGCAAGCCTGTAGCTATCAAGAAGTTGTACTCTCACAACCCGCAATAC
TTGAAGGAATTTGAGACTGAACTTGAGACAGTTGGGAGTATTAAGCATCGTAATCTTGTCTGTCTCCAAGGATATTC
TCTTTCTCCATCTGGCCATCTTCTTTTCTATGACTACATGGAAAATGGTAGCCTTTGGGATTTGCTTCATGGTCCTA
CAACAAAGAAGAAAAAGCTTGATTGGGTTACTCGCCTTCGAATTGCATTGGGATCAGCTCAAGGGCTTGCATATCTT
CATCATGATTGTAGCCCTCGAATAATCCACCGTGATGTTAAATCATCTAATATCTTGTTGGACAAAGACTTTGAGGC
TCATCTGACTGATTTTGGCATAGCTAAAAGCTTATGCATATCAAAGACCTATACGTCCACGTACATTATGGGAACCA
TTGGTTACATTGATCCAGAGTATGCTCGCACTTCTCGCTTGACAGAGAAGTCTGATGTTTACAGCTATGGTATTGTT
CTATTGGAATTGCTCACTGGAAGGAAAGCTGTAGATAATGAATCTAATCTACATCATTTGATTCTAACTAAGGCAGC
AAACGATGCTGTAATGGAAACAGTGGATCCTGAGATAACATGCACATGCAAAGATCTTGCAGATGTGAAGAAGGTTT
TTCAGCTTGCCCTTCTATGTTCCAAAAGACAGCCTGCTGAGAGACCAACAATGCATGAAGTGGCAAGAGTACTTGAA
AGCCTAATACCCGTCGCTGAAACGAAACAGCCAAATCCAACCCCCTCACTTGCATTACTCCCATCTGCTAAGGTACC
TTGTTACATGGATGAATATGTCAACCTCAAGACACCCCACCTAGTGAACTGTTCATCCATGAGCACTTCAGATGCCC
AACTTTTCCTCAAGTTTGGAGAGGTCATATCCCAGAATAGTGGCTGA (SEQ ID NO: 17)

-continued

Amino acid sequence for a mutant polypeptide encoded by a mutant Solyc08g061560 gene allele sler$^{MT}$ coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGN* (SEQ ID NO: 18)

Mutant Solyc08g061560 gene allele sler-cocktail
Nucleic acid sequence for a mutant Solyc08g061560 gene allele sler-cocktail
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTTATTGGACAGCTCAAAGGCCTTGTATCTATGTAATATCTCCTCCCATTATCTCACAATTACC
CTTTTTGTTTGATCTTTTGACTTAGTGCACATTATAGACTATGCCTGTTAATTTTTTTTGAAGTGATATGAGGGGA
AATCGCCTTTCTGGCCAGATACCAGATGAGATTGGTGACTGTTCAGCACTGAAAAATTTGTAAGTATGAAATGCTTC
TGAATCTTGTGTTATTGTTTGGAAAAATAAGTAACCATTTTTTCCCTTAGGGACCTTTCCTTCAATGAGCTTTATGG
TGATATTCCCTTCTCCATATCTAAACTCAAGCAACTGGAATATCTGTAAGTTTTGATACTCTCCTTCTTCTAAATGT
TGTATTATTTGCTTTCCGAGATTGTTAGTTGATTATGCTCGTCTTATTCAACTTAGGATTTTGAAGAATAATCAATT
GATTGGACCAATTCCATCTACATTGTCACAGATCCCTAACTTGAAGGTCTTGTAAGTATATTCTCTCTGCTTTGTCA
TGATATTGGTAGATTATGAATAATTTTAGTTTGATCCAAGAACTTCCTCCAGGGACCTGGCTCAAAATAGGTTAAGT
GGAGAAATTCCTAGGCTGATATACTGGAACGAAGTCCTGCAGTATCTGTGAGTGTTTTAATCCGGTGTTCCTCTTCT
TCCTGTTTGTTTTAACCTTAGGACACTTTCATTTCGTATATGGATATGATTACATCTGTTGTATGTTTTTATTCATA
TAGGGGACTGCGTGGTAACAACTTGGGTGGATCCCTTTCTCCTGATATGTGTCAGCTCACCGGCCTGTGGTACTTGT
AAGTTTGTAATCCTGTTGCTCTTAAGATCTTACTTTAGTTCCTCTAGGTGATGACATTAACCATTGTTCATTGTGTT
GTACAGTGATGTTCGGAACAATAGTTTGACTGGTTCCATTCCTCAAAATATTGGCAACTGTACTGCCTTCCAGGTTC
TGTAAGTATCTAAATCAATTGAATGAAGTTTGACTATATTCTGTATGTTTGGTTGGCATAACACCTTGTTTTGTTCT
GTCAGAGATTTGTCTTATAATGATTTGACCGGAGAGATTCCTTTCAATATTGGTTTCCTGCAAGTAGCGACCTTGTA
AGTTTATGCTGCTTCTCTTCATTACAAACTATTCAATATATGGTTGTTTGAAGTGTACTTTCATCATTCCAGGTCTT
TGCAAGGTAATCGTCTTTCAGGGCAGATCCCTTCTGTAATTGGATTGATGCAAGCTCTTGCAGTTTTGTGAGTGTTT
TGTGTCTTGATATCTCAATCTAATGCTACTGAATCTAATTCTTGGAAACCATTATAATGCATCTGTTATTTAAGTTT
TCTGACCCTTTTACTGTCAGGGACTTGAGCTGCAATATGTTGAGTGGAACAATTCCTTCAATTCTTGGGAATTTGAC
TTACACAGAGAAATTGTTAGTACTTCAACATTATTAAAAGCAATTTGGATCATTTTGTGCTTCCTAAATTGTGTAGT
GGATCAATTACTGTAAGTTCGCATTGTATTGCAGGTATCTACACGGGAACAAGCTATCTGGTTCCATTCCTCCAGAG
CTGGGAAATATGACAAAGCTCCACTACTTGTATGAATGCCTTCTATCAATCATTTTTTGTTAGCTTTGTTTTGTTCT
TCCTGTTCAAACCCTTTTAAATGAATGCTTACCATTTAGAAGCATTTGTTTGATTATTTAGCCTTTGGGCAACCACG
GATTTGAATGATAGAAAGCTGTTATGAGAATTTTTATTAAGAGACTTTCTTCAACCTTAAGGCTCAAAGATGGTAAT
TTGCAGGGAATTGAATGATAACCAACTTACTGGACGCATACCACCAGAACTTGGAAAGCTGACAGAATTGTTTGACT
TGTAAATCCCGTTTCTCTTCATCTTCTACTTTGGACTTGTTAACATCATTATTTATTTACTCATGTTGTATGTTTCA
GAAATGTTGCAAACAACCACCTAGATGGGCCCATACCTTCCAATATTAGCTCATGTACCAATTTGAATAGTCTGTGA
GTGTTTTTAATGTCCGAAGTGTTTCAATTATGCACGACCATGCTTGTTTGGTAGTTATTGACACCTGATTTTGTTGC
AGCAACGTTCATGGAAACAAATTGAATGGTACTATTCCACCTGCTTTTCAGAAGCTGGAAAGTATGACCTATCTGTA
AGTTCTTACTTTCTGATCTTTTTCTTTTGAAGAATTATGTTTAAGGTTATCGAAGTTACCGTCCATGCTGTTGAGCA
AGATTGTAAACTTACTGTGCCTTGTATATAAATTTTACTGGCGTTGTATTATTGAAAAAATCATTTTATTTATATTG
CTCTCAAATCATACTGGCTTATATCCATTCATGAAGAATCATTTCTACTGTCTGAAGTTTTCAGCTATATGTATCGA
AAAAATTTAGTTATTATATAGTTTATTTTGAGCCTCTGCATCATCTATTTGTGAATTTCATTTGCTTATTCTGCATA
CTCTCAGCATTAACCGTCTCTTCTTTTGTTAATTGCTTTAGTAATCTCTCCTCCAACAATCTCAAAGGCCCAATTCC
AATTGAGCTATCTCGTATTGGGAATGTAGATACACTGTAAGTGCAAACTTTCTCATCTACTTTCATTTCTCTCATTG
CAATTATGGTTGCGGGGAAAGCACTTTTTGTCAGTCTTAAGAATCTTCAACATTTTTTGGCTTAGGGACTTATCAAA
CAACAGGATCAGTGGTCCTATACCTATGTCCCTTGGTGATTTGGAACATCTTCTTAAACTGTGAGCATAACCGTCAA
GTTGTTATGTTAGCATCATATATCTGTTGTACTTACATCCCTTTTGTCAATGCTGTAGGAACTTAAGCAAGAATGAA
ATAAATGGAAACTTACCAGCTGAATTTGGCAATTTAAGGAGCATCATGGAGATGTATGGAACCTTGCTAAATTCAGT
TACTTTGAATTTATGGTTTGCTTGATTTTCAGCTTTTTGACTGCACTCCTAATTGTAGTGATCTGTCAAGCAATCAC
CTCTCTGGTCCCTTACCTCAGGAACTTGGTCAGCTTCCAAACCTGTACTTGCTGTAAGTACTTCAGATTTACTTTGA
GACTCTCATCCTCTTAGCTATTGGTAATAATCTGTAGAGTGAATAAGTATGAACTTCTAAACTCGGTAAGTAGATTT
TAAAATTATTTTGGATGCCATTTTCAAAAAAGTAGAGATGAAGTTGGTTGTGTTGCTATTGTTTTATATGATCTGGC
TTCATATGTTCATTACTTTGGTGTTCTCAGTTTTGCTTTATATTGCATTATTGCACGGGGCTCAAATGCAGCATATC
TCTATCTTCTTTTTCTTGTGGCCTTAATTATTTTACAAATTAATGAACAGGAAGGTGGAAAACAACAATTTATCAGG
CGATGTGATGTCCTTAGCCAGTTGCCTCAGTCTAAATATCTTGTGAGTTTTCAAGTCCATAGTAAGACACCAGTACA
AACAAATGTTTTGTTAATCTAATCAACCTCATGTTAGCAGAAATGTCTCATACAATAATCTGGGAGGGAATATTCCA
ACCGGCAATAATTTCTCTAGATTTTCACCAGACAGGTAAGTGGAGCTATTAAGATTTTACACAAGTCACAAGCATTT
ATTGGTTTTTAATTCTTTGCTTCTAATTTCTTCCTTTTGCTATGTCTCCGAAAAAGCTTCATAGGAAATCCAGATCT
GTGTGGGTATTGGCTCACTTCTCCTTGTCATGCATCTCATCCGGCAGAGCGAGGTCTGATCAAACTGTAACAATCAT
TTGGCCTTTACTCTATTGCATTTTTGAAGTTCCATTTCACTTTAGACATCTGCAACATTTATTAAGTGTGATGGACA
GATATATTGATTAATGAGGAATTATCCCTTGGTTGAGCAAACTTAATTCTGTGTTAGCCTGGTAGTAGGGTGTACCA
CAAGGTTTGTCGTCATGGTTTCCTATGTTCACAATCCCTGATTGTAACATTTAGATGTGTACACATATCTAATTAAC
ATGAAATAATCTTCATTTGCTGGAGTTACATTGACGTAAAGATGCGTTAGCTGTCAAATGAAACTGCATTTGTTTTA
TTTCCATCATCAGTACATTAATTAAGTGCATAAATATTTTAACAGTTGTTGAATGATATAAGATGAATTTATTGGAC
AATTGCAGTTTCAATTTCTAAAGCAGCAATACTTGGTATTGCTCTGGGTGGCTTGGTGATTCTTCTGATGATACTAG
TAGCAGCATGCCGGCCACAGAAACCTGCACCTTTCATGGAAGGATCTATTGATAAACCAGGTACAATATTTTCCGGA
CGGTTGGATAGTGTTTGGAGATGTTCATGTCAGAAGGACAGTCGTCAGAGTTTATTGAAGTTGCCATGTATTGATTG
TTTAACGTTTTTGATGAACAGTTTATTACTCATCTCCAAAACTTGTGATCCTTCATATGAACATGGCACTTCATGTT
TACGAGGACATTATGAGGATGACTGAGAACTTGAGTGAGAAGTATATAATTGGTTGTGGAGCATCAAGTACTGTATA -continued TAAATGTGTTTTGAAAAATTGCAAGCCTGTAGCTATCAAGAAGTTGTACTCTCACAACCCGCAATACTTGAAGGAAT
TTGAGACTGAACTTGAGACAGTTGGGAGTATTAAGCATCGTAATCTTGTCTGTCTCCAAGGATATTCTCTTTCTCCA
TCTGGCCATCTTCTTTTCTATGACTACATGGAAAATGGTAGCCTTTGGGATTTGCTTCATGGTTAGTAAATCCAAAA
TGGTTAAGGTGATTGATGCATTGATTTTGTGTTAAAGCATCAAGTAATCAGTCCTCTTGTATCTTTTTTTGCAGGTC
CTACAACAAAGAAGAAAAAGCTTGATTGGGTTACTCGCCTTCGAATTGCATTGGGATCAGCTCAAGGGCTTGCATAT
CTTCATCATGATTGTAGCCCTCGAATAATCCACCGTGATGTTAAATCATCTAATATCTTGTTGGACAAAGACTTTGA
GGCTCATCTGACTGATTTTGGCATAGCTAAAAGCTTATGCATATCAAAGACCTATACGTCCACGTACATTATGGGAA
CCATTGGTTACATTGATCCAGAGTATGCTCGCACTTCTCGCTTGACAGAGAAGTCTGATGTTTACAGCTATGGTATT
GTTCTATTGGAATTGCTCACTGGAAGGAAAGCTGTAGATAATGAATCTAATCTACATCATTTGGTAAGCTCTTGCAA
TTTAGTTAATATGAACTTGTCCTATGATGTTTATTCATATAATTATATTAAGATTCAATTCAATTGATCATAACAGT
TTTGCATATATGTTACAGATTCTAACTAAGGCAGCAAACGATGCTGTAATGGAAACAGTGGATCCTGAGATAACATG
CACATGCAAAGATCTTGCAGATGTGAAGAAGGTTTTTCAGCTTGCCCTTCTATGTTCCAAAAGACAGCCTGCTGAGA
GACCAACAATGCATGAAGTGGCAAGAGTACTTGAAAGCCTAATACCCGTCGCTGAAACGAAACAGCCAAATCCAACC
CCCTCACTTGCATTACTCCCATCTGCTAAGGTACCTTGTTACATGGATGAATATGTCAACCTCAAGACACCCCACCT
AGTGAACTGTTCATCCATGAGCACTTCAGATGCCCAACTTTTCCTCAAGTTTGGAGAGGTCATATCCCAGAATAGTG
GCTGA (SEQ ID NO: 19)

Nucleic acid sequence for a mutant Solyc08g061560 gene allele sler-cocktail coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTTATTGGACAGCTCAAAGGCCTTGTATCTA
TTGATATGAGGGGAAATCGCCTTTCTGGCCAGATACCAGATGAGATTGGTGACTGTTCAGCACTGAAAAAATTTGGAC
CTTTCCTTCAATGAGCTTTATGGTGATATTCCCTTCTCCATATCTAAACTCAAGCAACTGGAATATCTGATTTTGAA
GAATAATCAATTGATTGGACCAATTCCATCTACATTGTCACAGATCCCTAACTTGAAGGTCTTGGACCTGGCTCAAA
ATAGGTTAAGTGGAGAAATTCCTAGGCTGATATACTGGAACGAAGTCCTGCAGTATCTGGGACTGCGTGGTAACAAC
TTGGGTGGATCCCTTTCTCCTGATATGTGTCAGCTCACCGGCCTGTGGTACTTTGATGTTCGGAACAATAGTTTGAC
TGGTTCCATTCCTCAAAATATTGGCAACTGTACTGCCTTCCAGGTTCTAGATTTGTCTTATAATGATTTGACCGGAG
AGATTCCTTTCAATATTGGTTTCCTGCAAGTAGCGACCTTGTCTTTGCAAGGTAATCGTCTTTCAGGGCAGATCCCT
TCTGTAATTGGATTGATGCAAGCTCTTGCAGTTTTGGACTTGAGCTGCAATATGTTGAGTGGAACAATTCCTTCAAT
TCTTGGGAATTTGACTTACACAGAGAAATTGTATCTACACGGGAACAAGCTATCTGGTTCCATTCCTCCAGAGCTGG
GAAATATGACAAAGCTCCACTACTTGGAATTGAATGATAACCAACTTACTGGACGCATACCACCAGAACTTGGAAAG
CTGACAGAATTGTTTGACTTAAATGTTGCAAACAACCACCTAGATGGGCCCATACCTTCCAATATTAGCTCATGTAC
CAATTTGAATAGTCTCAACGTTCATGGAAACAAATTGAATGGTACTATTCCACCTGCTTTTCAGAAGCTGGAAAGTA
TGACCTATCTTAATCTCTCCTCCAACAATCTCAAAGGCCCAATTCCAATTGAGCTATCTCGTATTGGGAATGTAGAT
ACACTGGACTTATCAAACAACAGGATCAGTGGTCCTATACCTATGTCCCTTGGTGATTTGGAACATCTTCTTAAACT
GAACTTAAGCAAGAATGAAATAAATGGAAACTTACCAGCTGAATTTGGCAATTTAAGGAGCATCATGGAGATTGATC
TGTCAAGCAATCACCTCTCTGGTCCCTTACCTCAGGAACTTGGTCAGCTTCCAAACCTGTACTTGCTGAAGGTGGAA
AACAACAATTTATCAGGCGATGTGATGTCCTTAGCCAGTTGCCTCAGTCTAAATATCTTAAATGTCTCATACAATAA
TCTGGGAGGGAATATTCCAACCGGCAATAATTTCTCTAGATTTTCACCAGACAGCTTCATAGGAAATCCAGATCTGT
GTGGGTATTGGCTCACTTCTCCTTGTCATGCATCTCATCCGGCAGAGCGAGTTTCAATTTCTAAAGCAGCAATACTT
GGTATTGCTCTGGGTGGCTTGGTGATTCTTCTGATGATACTAGTAGCAGCATGCCGGCCACAGAAACCTGCACCTTT
CATGGAAGGATCTATTGATAAACCAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTCCTACAACA
AAGAAGAAAAAGCTTGATTGGGTTACTCGCCTTCGAATTGCATTGGGATCAGCTCAAGGGCTTGCATATCTTCATCA
TGATTGTAGCCCTCGAATAATCCACCGTGATGTTAAATCATCTAATATCTTGTTGGACAAAGACTTTGAGGCTCATC
TGACTGATTTTGGCATAGCTAAAAGCTTATGCATATCAAAGACCTATACGTCCACGTACATTATGGGAACCATTGGT
TACATTGATCCAGAGTATGCTCGCACTTCTCGCTTGACAGAGAAGTCTGATGTTTACAGCTATGGTATTGTTCTATT
GGAATTGCTCACTGGAAGGAAAGCTGTAGATAATGAATCTAATCTACATCATTTGATTCTAACTAAGGCAGCAAACG
ATGCTGTAATGGAAACAGTGGATCCTGAGATAACATGCACATGCAAAGATCTTGCAGATGTGAAGAAGGTTTTTCAG
CTTGCCCTTCTATGTTCCAAAAGACAGCCTGCTGAGAGACCAACAATGCATGAAGTGGCAAGAGTACTTGAAAGCCT
AATACCCGTCGCTGAAACGAAACAGCCAAATCCAACCCCCTCACTTGCATTACTCCCATCTGCTAAGGTACCTTGTT
ACATGGATGAATATGTCAACCTCAAGACACCCCACCTAGTGAACTGTTCATCCATGAGCACTTCAGATGCCCAACTT
TTCCTCAAGTTTGGAGAGGTCATATCCCAGAATAGTGGCTGA (SEQ ID NO: 20)

Amino acid sequence for a mutant polypeptide encoded by a mutant Solyc08g061560 gene allele sler-cocktail coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSYWTAQRPCIY* (SEQ ID NO: 21)

Mutant Solyc08g061560 gene allele sler-grape
Nucleic acid sequence for a mutant Solyc08g061560 gene allele sler-grape
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTTATTGGACAGCTCAAAGGCCTTGTATCTATGTAATATCTCCTCCCATTATCTCACAATTACC
CTTTTTGTTTGATCTTTTGACTTAGTGCACATTATAGACTATGCCTGTTAATTTTTTTTTGAAGTGATATGAGGGGA
AATCGCCTTTCTGGCCAGATACCAGATGAGATTGGTGACTGTTCAGCACTGAAAAAATTTGTAAGTATGAAATGCTTC
TGAATCTTGTGTTATTGTTTGGAAAAAATAAGTAACCATTTTTTCCCTTAGGGACCTTTCCTTCAATGAGCTTTATGG
TGATATTCCCTTCTCCATATCTAAACTCAAGCAACTGGAATATCTGTAAGTTTTGATACTCTCCTTCTTCTAAATGT
TGTATTATTTGCTTTCCGAGATTGTTAGTTGATTATGCTCGTCTTATTCAACTTAGGATTTTGAAGAATAATCAATT
GATTGGACCAATTCCATCTACATTGTCACAGATCCCTAACTTGAAGGTCTTGTAAGTATATTCTCTCTGCTTTGTCA -continued TGATATTGGTAGATTATGAATAATTTTAGTTTGATCCAAGAACTTCCTCCAGGGACCTGGCTCAAAATAGGTTAAGT
GGAGAAATTCCTAGGCTGATATACTGGAACGAAGTCCTGCAGTATCTGTGAGTGTTTTAATCCGGTGTTCCTCTTCT
TCCTGTTTGTTTTAACCTTAGGACACTTTCATTTCGTATATGGATATGATTACATCTGTTGTATGTTTTTATTCATA
TAGGGGACTGCGTGGTAACAACTTGGGTGGATCCCTTTCTCCTGATATGTGTCAGCTCACCGGCCTGTGGTACTTGT
AAGTTTGTAATCCTGTTGCTCTTAAGATCTTACTTTAGTTCCTCTAGGTGATGACATTAACCATTGTTCATTGTGTT
GTACAGTGATGTTCGGAACAATAGTTTGACTGGTTCCATTCCTCAAAATATTGGCAACTGTACTGCCTTCCAGGTTC
TGTAAGTATCTAAATCAATTGAATGAAGTTTGACTATATTCTGTATGTTTGGTTGGCATAACACCTTGTTTTGTTCT
GTCAGAGATTTGTCTTATAATGATTTGACCGGAGAGATTCCTTTCAATATTGGTTTCCTGCAAGTAGCGACCTTGTA
AGTTTATGCTGCTTCTCTTCATTACAAACTATTCAATATATGGTTGTTTGAAGTGTACTTTCATCATTCCAGGTCTT
TGCAAGGTAATCGTCTTTCAGGGCAGATCCCTTCTGTAATTGGATTGATGCAAGCTCTTGCAGTTTTGTGAGTGTTT
TGTGTCTTGATATCTCAATCTAATGCTACTGAATCTAATTCTTGGAAACCATTATAATGCATCTGTTATTTAAGTTT
TCTGACCCTTTTACTGTCAGGGACTTGAGCTGCAATATGTTGAGTGGAACAATTCCTTCAATTCTTGGGAATTTGAC
TTACACAGAGAAATTGTTAGTACTTCAACATTATTAAAAGCAATTTGGATCATTTTGTGCTTCCTAAATTGTGTAGT
GGATCAATTACTGTAAGTTCGCATTGTATTGCAGGTATCTACACGGGAACAAGCTATCTGGTTCCATTCCTCCAGAG
CTGGGAAATATGACAAAGCTCCACTACTTGTATGAATGCCTTCTATCAATCATTTTTTGTTAGCTTTGTTTTGTTCT
TCCTGTTCAAACCCTTTTAAATGAATGCTTACCATTTAGAAGCATTTGTTTGATTATTTAGCCTTTGGGCAACCACG
GATTTGAATGATAGAAAGCTGTTATGAGAATTTTTATTAAGAGACTTTCTTCAACCTTAAGGCTCAAAGATGGTAAT
TTGCAGGGAATTGAATGATAACCAACTTACTGGACGCATACCACCAGAACTTGGAAAGCTGACAGAATTGTTTGACT
TGTAAATCCCGTTTCTCTTCATCTTCTACTTTGGACTTGTTAACATCATTATTTATTTACTCATGTTGTATGTTTCA
GAAATGTTGCAAACAACCACCTAGATGGGCCCATACCTTCCAATATTAGCTCATGTACCAATTTGAATAGTCTGTGA
GTGTTTTTAATGTCCGAAGTGTTTCAATTATGCACGACCATGCTTGTTTGGTAGTTATTGACACCTGATTTTGTTGC
AGCAACGTTCATGGAAACAAATTGAATGGTACTATTCCACCTGCTTTTCAGAAGCTGGAAAGTATGACCTATCTGTA
AGTTCTTACTTTCTGATCTTTTTCTTTTGAAGAATTATGTTTAAGGTTATCGAAGTTACCGTCCATGCTGTTGAGCA
AGATTGTAAACTTACTGTGCCTTGTATATAAATTTTACTGGCGTTGTATTATTGAAAAAATCATTTTATTTATATTG
CTCTCAAATCATACTGGCTTATATCCATTCATGAAGAATCATTTCTACTGTCTGAAGTTTTCAGCTATATGTATCGA
AAAAATTTAGTTATTATATAGTTTATTTTGAGCCTCTGCATCATCTATTTGTGAATTTCATTTGCTTATTCTGCATA
CTCTCAGCATTAACCGTCTCTTCTTTTGTTAATTGCTTTAGTAATCTCTCCTCCAACAATCTCAAAGGCCCAATTCC
AATTGAGCTATCTCGTATTGGGAATGTAGATACACTGTAAGTGCAAACTTTCTCATCTACTTTCATTTCTCTCATTG
CAATTATGGTTGCGGGGAAAGCACTTTTTGTCAGTCTTAAGAATCTTCAACATTTTTTGGCTTAGGGACTTATCAAA
CAACAGGATCAGTGGTCCTATACCTATGTCCCTTGGTGATTTGGAACATCTTCTTAAACTGTGAGCATAACCGTCAA
GTTGTTATGTTAGCATCATATATCTGTTGTACTTACATCCCTTTTGTCAATGCTGTAGGAACTTAAGCAAGAATGAA
ATAAATGGAAACTTACCAGCTGAATTTGGCAATTTAAGGAGCATCATGGAGATGTATGGAACCTTGCTAAATTCAGT
TACTTTGAATTTATGGTTTGCTTGATTTTCAGCTTTTTGACTGCACTCCTAATTGTAGTGATCTGTCAAGCAATCAC
CTCTCTGGTCCCTTACCTCAGGAACTTGGTCAGCTTCCAAACCTGTACTTGCTGTAAGTACTTCAGATTTACTTTGA
GACTCTCATCCTCTTAGCTATTGGTAATAATCTGTAGAGTGAATAAGTATGAACTTCTAAACTCGGTAAGTAGATTT
TAAAATTATTTTGGATGCCATTTTCAAAAAAGTAGAGATGAAGTTGGTTGTGTTGCTATTGTTTTATATGATCTGGC
TTCATATGTTCATTACTTTGGTGTTCTCAGTTTTGCTTTATATTGCATTATTGCACGGGGCTCAAATGCAGCATATC
TCTATCTTCTTTTTCTTGTGGCCTTAATTATTTTACAAATTAATGAACAGGAAGGTGGAAAACAACAATTTATCAGG
CGATGTGATGTCCTTAGCCAGTTGCCTCAGTCTAAATATCTTGTGAGTTTTCAAGTCCATAGTAAGACACCAGTACA
AACAAATGTTTTGTTAATCTAATCAACCTCATGTTAGCAGAAATGTCTCATACAATAATCTGGGAGGGAATATTCCA
ACCGGCAATAATTTCTCTAGATTTTCACCAGACAGGTAAGTGGAGCTATTAAGATTTTACACAAGTCACAAGCATTT
ATTGGTTTTTAATTCTTTGCTTCTAATTTCTTCCTTTTGCTATGTCTCCGAAAAAGCTTCATAGGAAATCCAGATCT
GTGTGGGTATTGGCTCACTTCTCCTTGTCATGCATCTCATCCGGCAGAGCGAGGTCTGATCAAACTGTAACAATCAT
TTGGCCTTTACTCTATTGCATTTTTGAAGTTCCATTTCACTTTAGACATCTGCAACATTTATTAAGTGTGATGGACA
GATATATTGATTAATGAGGAATTATCCCTTGGTTGAGCAAACTTAATTCTGTGTTAGCCTGGTAGTAGGGTGTACCA
CAAGGTTTGTCGTCATGGTTTCCTATGTTCACAATCCCTGATTGTAACATTTAGATGTGTACACATATCTAATTAAC
ATGAAATAATCTTCATTTGCTGGAGTTACATTGACGTAAAGATGCGTTAGCTGTCAAATGAAACTGCATTTGTTTTA
TTTCCATCATCAGTACATTAATTAAGTGCATAAATATTTTAACAGTTGTTGAATGATATAAGATGAATTTATTGGAC
AATTGCAGTTTCAATTTCTAAAGCAGCAATACTTGGTATTGCTCTGGGTGGCTTGGTGATTCTTCTGATGATACTAG
TAGCAGCATGCCGGCCACAGAAACCTGCACCTTTCATGGAAGGATCTATTGATAAACCAGGTACAATATTTTCCGGA
CGGTTGGATAGTGTTTGGAGATGTTCATGTCAGAAGGACAGTCGTCAGAGTTTATTGAAGTTGCCATGTATTGATTG
TTTAACGTTTTTGATGAACAGTTTATTACTCATCTCCAAAACTTGTGATCCTTCATATGAACATGGCACTTCATGTT
TACGAGGACATTATGAGGATGACTGAGAACTTGAGTGAGAAGTATATAATTGGTTGTGGAGCATCAAGTACTGTATA
TAAATGTGTTTTGAAAAATTGCAAGCCTGTAGCTATCAAGAAGTTGTACTCTCACAACCCGCAATACTTGAAGGAAT
TTGAGACTGAACTTGAGACAGTTGGGAGTATTAAGCATCGTAATCTTGTCTGTCTCCAAGGATATTCTCTTTCTCCA
TCTGGCCATCTTCTTTTCTATGACTACATGGAAAATGGTAGCCTTTGGGATTTGCTTCATGGTTAGTAAATCCAAAA
TGGTTAAGGTGATTGATGCATTGATTTTGTGTTAAAGCATCAAGTAATCAGTCCTCTTGTATCTTTTTTTGCAGGTC
CTACAACAAAGAAGAAAAAGCTTGATTGGGTTACTCGCCTTCGAATTGCATTGGGATCAGCTCAAGGGCTTGCATAT
CTTCATCATGATTGTAGCCCTCGAATAATCCACCGTGATGTTAAATCATCTAATATCTTGTTGGACAAAGACTTTGA
GGCTCATCTGACTGATTTTGGCATAGCTAAAAGCTTATGCATATCAAAGACCTATACGTCCACGTACATTATGGGAA
CCATTGGTTACATTGATCCAGAGTATGCTCGCACTTCTCGCTTGACAGAGAAGTCTGATGTTTACAGCTATGGTATT
GTTCTATTGGAATTGCTCACTGGAAGGAAAGCTGTAGATAATGAATCTAATCTACATCATTTGGTAAGCTCTTGCAA
TTTAGTTAATATGAACTTGTCCTATGATGTTTATTCATATAATTATATTAAGATTCAATTCAATTGATCATAACAGT
TTTGCATATATGTTACAGATTCTAACTAAGGCAGCAAACGATGCTGTAATGGAAACAGTGGATCCTGAGATAACATG
CACATGCAAAGATCTTGCAGATGTGAAGAAGGTTTTTCAGCTTGCCCTTCTATGTTCCAAAAGACAGCCTGCTGAGA
GACCAACAATGCATGAAGTGGCAAGAGTACTTGAAAGCCTAATACCCGTCGCTGAAACGAAACAGCCAAATCCAACC
CCCTCACTTGCATTACTCCCATCTGCTAAGGTACCTTGTTACATGGATGAATATGTCAACCTCAAGACACCCCACCT
AGTGAACTGTTCATCCATGAGCACTTCAGATGCCCAACTTTTCCTCAAGTTTGGAGAGGTCATATCCCAGAATAGTG
GCTGA (SEQ ID NO: 22)

Nucleic acid sequence for a mutant Solyc08g061560 gene allele sler-grape coding sequence
ATGGCATCATTTTTACTCCAAAGATGTAATCTTCTCTTTGAGGTTCTTCTTATTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTTATTGGACAGCTCAAAGGCCTTGTATCTA
TTGATATGAGGGGAAATCGCCTTTCTGGCCAGATACCAGATGAGATTGGTGACTGTTCAGCACTGAAAAATTTGGAC
CTTTCCTTCAATGAGCTTTATGGTGATATTCCCTTCTCCATATCTAAACTCAAGCAACTGGAATATCTGATTTTGAA
GAATAATCAATTGATTGGACCAATTCCATCTACATTGTCACAGATCCCTAACTTGAAGGTCTTGGACCTGGCTCAAA
ATAGGTTAAGTGGAGAAATTCCTAGGCTGATATACTGGAACGAAGTCCTGCAGTATCTGGGACTGCGTGGTAACAAC -continued TTGGGTGGATCCCTTTCTCCTGATATGTGTCAGCTCACCGGCCTGTGGTACTTTGATGTTCGGAACAATAGTTTGAC
TGGTTCCATTCCTCAAAATATTGGCAACTGTACTGCCTTCCAGGTTCTAGATTTGTCTTATAATGATTTGACCGGAG
AGATTCCTTTCAATATTGGTTTCCTGCAAGTAGCGACCTTGTCTTTGCAAGGTAATCGTCTTTCAGGGCAGATCCCT
TCTGTAATTGGATTGATGCAAGCTCTTGCAGTTTTGGACTTGAGCTGCAATATGTTGAGTGGAACAATTCCTTCAAT
TCTTGGGAATTTGACTTACACAGAGAAATTGTATCTACACGGGAACAAGCTATCTGGTTCCATTCCTCCAGAGCTGG
GAAATATGACAAAGCTCCACTACTTGGAATTGAATGATAACCAACTTACTGGACGCATACCACCAGAACTTGGAAAG
CTGACAGAATTGTTTGACTTAAATGTTGCAAACAACCACCTAGATGGGCCCATACCTTCCAATATTAGCTCATGTAC
CAATTTGAATAGTCTCAACGTTCATGGAAACAAATTGAATGGTACTATTCCACCTGCTTTTCAGAAGCTGGAAAGTA
TGACCTATCTTAATCTCTCCTCCAACAATCTCAAAGGCCCAATTCCAATTGAGCTATCTCGTATTGGGAATGTAGAT
ACACTGGACTTATCAAACAACAGGATCAGTGGTCCTATACCTATGTCCCTTGGTGATTTGGAACATCTTCTTAAACT
GAACTTAAGCAAGAATGAAATAAATGGAAACTTACCAGCTGAATTTGGCAATTTAAGGAGCATCATGGAGATTGATC
TGTCAAGCAATCACCTCTCTGGTCCCTTACCTCAGGAACTTGGTCAGCTTCCAAACCTGTACTTGCTGAAGGTGGAA
AACAACAATTTATCAGGCGATGTGATGTCCTTAGCCAGTTGCCTCAGTCTAAATATCTTAAATGTCTCATACAATAA
TCTGGGAGGGAATATTCCAACCGGCAATAATTTCTCTAGATTTTCACCAGACAGCTTCATAGGAAATCCAGATCTGT
GTGGGTATTGGCTCACTTCTCCTTGTCATGCATCTCATCCGGCAGAGCGAGTTTCAATTTCTAAAGCAGCAATACTT
GGTATTGCTCTGGGTGGCTTGGTGATTCTTCTGATGATACTAGTAGCAGCATGCCGGCCACAGAAACCTGCACCTTT
CATGGAAGGATCTATTGATAAACCAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTCCTACAACA
AAGAAGAAAAAGCTTGATTGGGTTACTCGCCTTCGAATTGCATTGGGATCAGCTCAAGGGCTTGCATATCTTCATCA
TGATTGTAGCCCTCGAATAATCCACCGTGATGTTAAATCATCTAATATCTTGTTGGACAAAGACTTTGAGGCTCATC
TGACTGATTTTGGCATAGCTAAAAGCTTATGCATATCAAAGACCTATACGTCCACGTACATTATGGGAACCATTGGT
TACATTGATCCAGAGTATGCTCGCACTTCTCGCTTGACAGAGAAGTCTGATGTTTACAGCTATGGTATTGTTCTATT
GGAATTGCTCACTGGAAGGAAAGCTGTAGATAATGAATCTAATCTACATCATTTGATTCTAACTAAGGCAGCAAACG
ATGCTGTAATGGAAACAGTGGATCCTGAGATAACATGCACATGCAAAGATCTTGCAGATGTGAAGAAGGTTTTTCAG
CTTGCCCTTCTATGTTCCAAAAGACAGCCTGCTGAGAGACCAACAATGCATGAAGTGGCAAGAGTACTTGAAAGCCT
AATACCCGTCGCTGAAACGAAACAGCCAAATCCAACCCCCTCACTTGCATTACTCCCATCTGCTAAGGTACCTTGTT
ACATGGATGAATATGTCAACCTCAAGACACCCCACCTAGTGAACTGTTCATCCATGAGCACTTCAGATGCCCAACTT
TTCCTCAAGTTTGGAGAGGTCATATCCCAGAATAGTGGCTGA (SEQ ID NO: 23)

Amino acid sequence for a mutant polypeptide encoded by a mutant Solyc08g061560 gene allele sler-grape coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSYWTAQRPCIY* (SEQ ID NO: 24)

Mutant Solyc08g061560 allele SlER$^{CR\text{-}pro\text{-}4}$
Nucleic acid sequence for a mutant Solyc08g061560 promoter allele SlER$^{CR\text{-}pro\text{-}4}$
TTTTCGAGTTGACATAGTACCTTCGCAGTTGAAGAAGAAATTGATTAAGAAGATAAATTCGACATTGGAACTTG
ATAATTAAGAAGAAATCAATGAAAAAGAGATATAATATAATGAGGTAAAGAAAATAAATAATGATGAAGAGAAACAA
AAGAGGAGAAATAATGGAAGAATGGGAGAAATTAGGGTTAAAAGGGGGAAGAAGATCGTTGGTGGGTGGTTCAAGAT
CCACATGTGCGCTTTTAAAGAGTTTGCACGCGCTTAAAGGACGTGAGATCACGTTTGGCTCCACATCAGCCAAGAAT
ATTTAAAAGGATCAAATTATAGGGGGTTAAAGGATTTAATAGGAATCTTGGTTAGTTAAGGTATCTGGGGGAAAAGC
GCGAACAACTTTAGGGACCTGCATATGTATTTGGCCAAGAAAAAATAAACAAATAATGAGAGAAAGAGTGAATATAT
GTGTATGGACTAGCAATAAAAGTGGCACTAGTAATTGAAAAGCAAGTGTATAGAGAGAGATAATGAGAGAGAAAGAG
TAAGTACACTACTACTGCTACTATCCCATATACCTGTAATGTTGCAGGTCTGAATTTTGCAGTTGCAGACCCCCTTC
TCTTGGCACAAGCTCTTTTAACTTTTATCTTCTCAAATAATTCTCTCTCTCTCTCTTTTCTATCATTTTTTTTTACA
TTGAGAGTAAACTTAATATCCGTTGTATGTATTAGTGTGAGGCCTATCTGCCACAAGGATGTGATGGAACACTATGC
TTCCTCTGCTAAAACCCCACAACCCCAAAACTCTCTTTCACTTCACATTTAAGCACAATTCCTCAGTAAAATTATCC
TTTTGATCTCTCTAACATCAATGTTGGTTAGTTCAAGAATTGGTTTTTCCATTTCAAAGGAGCTGAGTTAGTGAGGT
TTTGAGTTTTGACTGAGACTTGAGTCTACCATGGCATCATTTTTACTCCAAAGATGTAATCTTCTCTTTGAGGTTCT
TCTTATTTTGGGGTTCTTGATTTTCTTCAGCTTTGGTTCTGTGGTGTCTGATGATGGTGAGTAGAGTAGAGTAGTAG
AACTTTCTGCTTCTTATGTTTTAGTTTAATGTTTTGTTTAAGATGTTAAAAAGACAAAGTGTGCTTTTTTTAATCAT
TTTTTAAATGGTGGTTTTTGATTAATCCCACGTTTTGTAGTTGTTATTTGTTAAAGGTTTATTTTTTTGTCTCATTA
TTATAATAATAATTGGGAAATAGGTTCTGCATTGTTGGAAATTAAGAAGTCAATTAGGGACGTGGAGAATGTGTTGT
ATGACTGGACTGATTCTCCTTCATCTGATTACTGTGCCTGGAGAGGTGTTACCTGTGATAATGTCACCTTCAATGTT
GTTCAACTGTAAGACATAACTCAAAAACACTATCATTTGGGATTCTTTAGTTATAAAGTTGTAATCTTTTGACATTA
TCTTGTAGTAATCTTTCGAGTTTAAATCTTGATGGGGAGTTGTCTCCTGCTATTGGACAGCTCAAAGGCCTTGTATC
TATGTAATATCTCCTCCCATTATCTCACAATTACCCTTTTTGTTTGATCTTTTGACTTAGTGCACATTATAGACTAT
GCCTGTTAATTTTTTTTTGAAGTGATATGAGGGGAAATCGCCTTTCTGGCCAGATACCAGATGAGATTGGTGACTGT
TCAGCACTGAAAAATTTGTAAGTATGAAATGCTTCTGAATCTTGTGTTATTGTTTGGAAAAATAAGTAACCATTTTT
TCCCTTAGGGACCTTTCCTTCAATGAGCTTTATGGTGATATTCCCTTCTCCATATCTAAACTCAAGCAACTGGAATA
TCTGTAAGTTTTGATACTCTCCTTCTTCTAAATGTTGTATTATTTGCTTTCCGAGATTGTTAGTTGATTATGCTCGT
CTTATTCAACTTAGGATTTTGAAGAATAATCAATTGATTGGACCAATTCCATCTACATTGTCACAGATCCCTAACTT
GAAGGTCTTGTAAGTATATTCTCTCTGCTTTGTCATGATATTGGTAGATTATGAATAATTTTAGTTTGATCCAAGAA
CTTCCTCCAGGGACCTGGCTCAAAATAGGTTAAGTGGAGAAATTCCTAGGCTGATATACTGGAACGAAGTCCTGCAG
TATCTGTGAGTGTTTTAATCCGGTGTTCCTCTTCTTCCTGTTTGTTTTAACCTTAGGACACTTTCATTTCGTATATG
GATATGATTACATCTGTTGTATGTTTTTATTCATATAGGGGACTGCGTGGTAACAACTTGGGTGGATCCCTTTCTCC
TGATATGTGTCAGCTCACCGGCCTGTGGTACTTGTAAGTTTGTAATCCTGTTGCTCTTAAGATCTTACTTTAGTTCC
TCTAGGTGATGACATTAACCATTGTTCATTGTGTTGTACAGTGATGTTCGGAACAATAGTTTGACTGGTTCCATTCC
TCAAAATATTGGCAACTGTACTGCCTTCCAGGTTCTGTAAGTATCTAAATCAATTGAATGAAGTTTGACTATATTCT
GTATGTTTGGTTGGCATAACACCTTGTTTTGTTCTGTCAGAGATTTGTCTTATAATGATTTGACCGGAGAGATTCCT
TTCAATATTGGTTTCCTGCAAGTAGCGACCTTGTAAGTTTATGCTGCTTCTCTTCATTACAAACTATTCAATATATG
GTTGTTTGAAGTGTACTTTCATCATTCCAGGTCTTTGCAAGGTAATCGTCTTTCAGGGCAGATCCCTTCTGTAATTG
GATTGATGCAAGCTCTTGCAGTTTTGTGAGTGTTTTGTGTCTTGATATCTCAATCTAATGCTACTGAATCTAATTCT
TGGAAACCATTATAATGCATCTGTTATTTAAGTTTTCTGACCCTTTTACTGTCAGGGACTTGAGCTGCAATATGTTG
AGTGGAACAATTCCTTCAATTCTTGGGAATTTGACTTACACAGAGAAATTGTTAGTACTTCAACATTATTAAAAGCA
ATTTGGATCATTTTGTGCTTCCTAAATTGTGTAGTGGATCAATTACTGTAAGTTCGCATTGTATTGCAGGTATCTAC -continued ACGGGAACAAGCTATCTGGTTCCATTCCTCCAGAGCTGGGAAATATGACAAAGCTCCACTACTTGTATGAATGCCTT
CTATCAATCATTTTTGTTAGCTTTGTTTTGTTCTTCCTGTTCAAACCCTTTTAAATGAATGCTTACCATTTAGAAG
CATTTGTTTGATTATTTAGCCTTTGGGCAACCACGGATTTGAATGATAGAAAGCTGTTATGAGAATTTTTATTAAGA
GACTTTCTTCAACCTTAAGGCTCAAAGATGGTAATTTGCAGGGAATTGAATGATAACCAACTTACTGGACGCATACC
ACCAGAACTTGGAAAGCTGACAGAATTGTTTGACTTGTAAATCCCGTTTCTCTTCATCTTCTACTTTGGACTTGTTA
ACATCATTATTTATTTACTCATGTTGTATGTTTCAGAAATGTTGCAAACAACCACCTAGATGGGCCCATACCTTCCA
ATATTAGCTCATGTACCAATTTGAATAGTCTGTGAGTGTTTTTAATGTCCGAAGTGTTTCAATTATGCACGACCATG
CTTGTTTGGTAGTTATTGACACCTGATTTTGTTGCAGCAACGTTCATGGAAACAAATTGAATGGTACTATTCCACCT
GCTTTTCAGAAGCTGGAAAGTATGACCTATCTGTAAGTTCTTACTTTCTGATCTTTTTCTTTTGAAGAATTATGTTT
AAGGTTATCGAAGTTACCGTCCATGCTGTTGAGCAAGATTGTAAACTTACTGTGCCTTGTATATAAATTTTACTGGC
GTTGTATTATTGAAAAAATCATTTTATTTATATTGCTCTCAAATCATACTGGCTTATATCCATTCATGAAGAATCAT
TTCTACTGTCTGAAGTTTTCAGCTATATGTATCGAAAAAATTTAGTTATTATATAGTTTATTTTGAGCCTCTGCATC
ATCTATTTGTGAATTTCATTTGCTTATTCTGCATACTCTCAGCATTAACCGTCTCTTCTTTTGTTAATTGCTTTAGT
AATCTCTCCTCCAACAATCTCAAAGGCCCAATTCCAATTGAGCTATCTCGTATTGGGAATGTAGATACACTGTAAGT
GCAAACTTTCTCATCTACTTTCATTTCTCTCATTGCAATTATGGTTGCGGGGAAAGCACTTTTTGTCAGTCTTAAGA
ATCTTCAACATTTTTTGGCTTAGGGACTTATCAAACAACAGGATCAGTGGTCCTATACCTATGTCCCTTGGTGATTT
GGAACATCTTCTTAAACTGTGAGCATAACCGTCAAGTTGTTATGTTAGCATCATATATCTGTTGTACTTACATCCCT
TTTGTCAATGCTGTAGGAACTTAAGCAAGAATGAAATAAATGGAAACTTACCAGCTGAATTTGGCAATTTAAGGAGC
ATCATGGAGATGTATGGAACCTTGCTAAATTCAGTTACTTTGAATTTATGGTTTGCTTGATTTTCAGCTTTTTGACT
GCACTCCTAATTGTAGTGATCTGTCAAGCAATCACCTCTCTGGTCCCTTACCTCAGGAACTTGGTCAGCTTCCAAAC
CTGTACTTGCTGTAAGTACTTCAGATTTACTTTGAGACTCTCATCCTCTTAGCTATTGGTAATAATCTGTAGAGTGA
ATAAGTATGAACTTCTAAACTCGGTAAGTAGATTTTAAAATTATTTTGGATGCCATTTTCAAAAAAGTAGAGATGAA
GTTGGTTGTGTTGCTATTGTTTTATATGATCTGGCTTCATATGTTCATTACTTTGGTGTTCTCAGTTTTGCTTTATA
TTGCATTATTGCACGGGGCTCAAATGCAGCATATCTCTATCTTCTTTTTCTTGTGGCCTTAATTATTTTACAAATTA
ATGAACAGGAAGGTGGAAAACAACAATTTATCAGGCGATGTGATGTCCTTAGCCAGTTGCCTCAGTCTAAATATCTT
GTGAGTTTTCAAGTCCATAGTAAGACACCAGTACAAACAAATGTTTTGTTAATCTAATCAACCTCATGTTAGCAGAA
ATGTCTCATACAATAATCTGGGAGGGAATATTCCAACCGGCAATAATTTCTCTAGATTTTCACCAGACAGGTAAGTG
GAGCTATTAAGATTTTACACAAGTCACAAGCATTTATTGGTTTTTAATTCTTTGCTTCTAATTTCTTCCTTTTGCTA
TGTCTCCGAAAAAGCTTCATAGGAAATCCAGATCTGTGTGGGTATTGGCTCACTTCTCCTTGTCATGCATCTCATCC
GGCAGAGCGAGGTCTGATCAAACTGTAACAATCATTTGGCCTTTACTCTATTGCATTTTTGAAGTTCCATTTCACTT
TAGACATCTGCAACATTTATTAAGTGTGATGGACAGATATATTGATTAATGAGGAATTATCCCTTGGTTGAGCAAAC
TTAATTCTGTGTTAGCCTGGTAGTAGGGTGTACCACAAGGTTTGTCGTCATGGTTTCCTATGTTCACAATCCCTGAT
TGTAACATTTAGATGTGTACACATATCTAATTAACATGAAATAATCTTCATTTGCTGGAGTTACATTGACGTAAAGA
TGCGTTAGCTGTCAAATGAAACTGCATTTGTTTTATTTCCATCATCAGTACATTAATTAAGTGCATAAATATTTTAA
CAGTTGTTGAATGATATAAGATGAATTTATTGGACAATTGCAGTTTCAATTTCTAAAGCAGCAATACTTGGTATTGC
TCTGGGTGGCTTGGTGATTCTTCTGATGATACTAGTAGCAGCATGCCGGCCACAGAAACCTGCACCTTTCATGGAAG
GATCTATTGATAAACCAGGTACAATATTTTCCGGACGGTTGGATAGTGTTTGGAGATGTTCATGTCAGAAGGACAGT
CGTCAGAGTTTATTGAAGTTGCCATGTATTGATTGTTTAACGTTTTTGATGAACAGTTTATTACTCATCTCCAAAAC
TTGTGATCCTTCATATGAACATGGCACTTCATGTTTACGAGGACATTATGAGGATGACTGAGAACTTGAGTGAGAAG
TATATAATTGGTTGTGGAGCATCAAGTACTGTATATAAATGTGTTTTGAAAAATTGCAAGCCTGTAGCTATCAAGAA
GTTGTACTCTCACAACCCGCAATACTTGAAGGAATTTGAGACTGAACTTGAGACAGTTGGGAGTATTAAGCATCGTA
ATCTTGTCTGTCTCCAAGGATATTCTCTTTCTCCATCTGGCCATCTTCTTTTCTATGACTACATGGAAAATGGTAGC
CTTTGGGATTTGCTTCATGGTTAGTAAATCCAAAATGGTTAAGGTGATTGATGCATTGATTTTGTGTTAAAGCATCA
AGTAATCAGTCCTCTTGTATCTTTTTTTGCAGGTCCTACAACAAAGAAGAAAAAGCTTGATTGGGTTACTCGCCTTC
GAATTGCATTGGGATCAGCTCAAGGGCTTGCATATCTTCATCATGATTGTAGCCCTCGAATAATCCACCGTGATGTT
AAATCATCTAATATCTTGTTGGACAAAGACTTTGAGGCTCATCTGACTGATTTTGGCATAGCTAAAAGCTTATGCAT
ATCAAAGACCTATACGTCCACGTACATTATGGGAACCATTGGTTACATTGATCCAGAGTATGCTCGCACTTCTCGCT
TGACAGAGAAGTCTGATGTTTACAGCTATGGTATTGTTCTATTGGAATTGCTCACTGGAAGGAAAGCTGTAGATAAT
GAATCTAATCTACATCATTTGGTAAGCTCTTGCAATTTAGTTAATATGAACTTGTCCTATGATGTTTATTCATATAA
TTATATTAAGATTCAATTCAATTGATCATAACAGTTTTGCATATATGTTACAGATTCTAACTAAGGCAGCAAACGAT
GCTGTAATGGAAACAGTGGATCCTGAGATAACATGCACATGCAAAGATCTTGCAGATGTGAAGAAGGTTTTTCAGCT
TGCCCTTCTATGTTCCAAAAGACAGCCTGCTGAGAGACCAACAATGCATGAAGTGGCAAGAGTACTTGAAAGCCTAA
TACCCGTCGCTGAAACGAAACAGCCAAATCCAACCCCCTCACTTGCATTACTCCCATCTGCTAAGGTACCTTGTTAC
ATGGATGAATATGTCAACCTCAAGACACCCCACCTAGTGAACTGTTCATCCATGAGCACTTCAGATGCCCAACTTTT
CCTCAAGTTTGGAGAGGTCATATCCCAGAATAGTGGCTGA (SEQ ID NO: 25)

Nucleic acid sequence for a mutant Solyc08g061560 promoter allele SlER$^{CR\text{-}pro\text{-}4}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACAAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC -continued AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGTTTCAATTTCTAAAGCAGCAA
TACTTGGTATTGCTCTGGGTGGCTTGGTGATTCTTCTGATGATACTAGTAGCAGCATGCCGGCCACAGAAACCTGCA
CCTTTCATGGAAGGATCTATTGATAAACCAGTTTATTACTCATCTCCAAAACTTGTGATCCTTCATATGAACATGGC
ACTTCATGTTTACGAGGACATTATGAGGATGACTGAGAACTTGAGTGAGAAGTATATAATTGGTTGTGGAGCATCAA
GTACTGTATATAAATGTGTTTTGAAAAATTGCAAGCCTGTAGCTATCAAGAAGTTGTACTCTCACAACCCGCAATAC
TTGAAGGAATTTGAGACTGAACTTGAGACAGTTGGGAGTATTAAGCATCGTAATCTTGTCTGTCTCCAAGGATATTC
TCTTTCTCCATCTGGCCATCTTCTTTTCTATGACTACATGGAAAATGGTAGCCTTTGGGATTTGCTTCATGGTCCTA
CAACAAAGAAGAAAAAGCTTGATTGGGTTACTCGCCTTCGAATTGCATTGGGATCAGCTCAAGGGCTTGCATATCTT
CATCATGATTGTAGCCCTCGAATAATCCACCGTGATGTTAAATCATCTAATATCTTGTTGGACAAAGACTTTGAGGC
TCATCTGACTGATTTTGGCATAGCTAAAAGCTTATGCATATCAAAGACCTATACGTCCACGTACATTATGGGAACCA
TTGGTTACATTGATCCAGAGTATGCTCGCACTTCTCGCTTGACAGAGAAGTCTGATGTTTACAGCTATGGTATTGTT
CTATTGGAATTGCTCACTGGAAGGAAAGCTGTAGATAATGAATCTAATCTACATCATTTGATTCTAACTAAGGCAGC
AAACGATGCTGTAATGGAAACAGTGGATCCTGAGATAACATGCACATGCAAAGATCTTGCAGATGTGAAGAAGGTTT
TTCAGCTTGCCCTTCTATGTTCCAAAAGACAGCCTGCTGAGAGACCAACAATGCATGAAGTGGCAAGAGTACTTGAA
AGCCTAATACCCGTCGCTGAAACGAAACAGCCAAATCCAACCCCCTCACTTGCATTACTCCCATCTGCTAAGGTACC
TTGTTACATGGATGAATATGTCAACCTCAAGACACCCCACCTAGTGAACTGTTCATCCATGAGCACTTCAGATGCCC
AACTTTTCCTCAAGTTTGGAGAGGTCATATCCCAGAATAGTGGCTGA (SEQ ID NO: 26)

Amino acid sequence for a mutant polypeptide encoded by a mutant Solyc08g061560 promoter allele SlER$^{CR-pro-4}$ coding sequence MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGNKLNGTIPPAFQKLESMTYLNLSSNNLKGPIPIELSRIGNVDTLDLSNNRISGPIPMSLGDLEHLL
KLNLSKNEINGNLPAEFGNLRSIMEIDLSSNHLSGPLPQELGQLPNLYLLKVENNNLSGDVMSLASCLSLNILNVSY
NNLGGNIPTGNNFSRFSPDSFIGNPDLCGYWLTSPCHASHPAERVSISKAAILGIALGGLVILLMILVAACRPQKPA
PFMEGSIDKPVYYSSPKLVILHMNMALHVYEDIMRMTENLSEKYIIGCGASSTVYKCVLKNCKPVAIKKLYSHNPQY
LKEFETELETVGSIKHRNLVCLQGYSLSPSGHLLFYDYMENGSLWDLLHGPTTKKKKLDWVTRLRIALGSAQGLAYL
HHDCSPRIIHRDVKSSNILLDKDFEAHLTDFGIAKSLCISKTYTSTYIMGTIGYIDPEYARTSRLTEKSDVYSYGIV
LLELLTGRKAVDNESNLHHLILTKAANDAVMETVDPEITCTCKDLADVKKVFQLALLCSKRQPAERPTMHEVARVLE
SLIPVAETKQPNPTPSLALLPSAKVPCYMDEYVNLKTPHLVNCSSMSTSDAQLFLKFGEVISQNSG* (SEQ ID NO: 27)

Mutant Solyc08g061560 allele SlER$^{CR-pro-4}$

Nucleic acid sequence for a mutant Solyc08g061560 promoter allele SlER$^{CR-pro-14}$ TTTTCGAGTTGACATAGTACCTTCGCAGTTGAAGAAGAAGAAATTGATTAAGAAGATAAATTCGACATTGGAACTTG
ATAATTAAGAAGAAATCAATGAAAAAGAGATATAATATAATGAGGTAAAGAAAATAAATAATGATGAAGAGAAACAA
AAGAGGAGAAATAATGGAAGAATGGGAGAAATTAGGGTTAAAAGGGGGAAGAAGATCGTTGGTGGGTGGTTCAAGAT
CCACATGTGCGCTTTTAAAGAGTTTGCACGCGCTTAAAGGACGTGAGATCACGTTTGGCTCCACATCAGCCAAGAAT
ATTTAAAAGGATCAAATTATAGGGGGTTAAAGGATTTAATAGGAATCTTGGTTAGTTAAGGTATCTGGGGGAAAAGC
GCGAACAACTTTAGGGACCTGCATATGTATTTGGCCAAGAAAAAATAAACAAATAATGAGAGAAAGAGTGAATATAT
ATAAACAATGGTATAGTCCCTCTGTCACTTTAACACTCACACGTCAAGATTGTTGTAGTTAAATCTTGAAGAGCCCG
TGAAAGGTGTTTCATTTTTACTCAAATATATTGATGAAATAATTACTTAAGTGGAGAACAAATAACTTTATAATAAT
TTATCATATGATTTTACAGTTTTTTTTATTTGATAAATTTGAATAAACAATTGAGGTTATTTTAATAGTTTTAGAA
CTTATGAGATTTTTATGTTTATGAGAAAATATACATTACCAAAATTTCATATCGCATGTCCAAACAAAACATCAATT
TTAGTATGATTCCATATCATAATACCATATCGAATGACCAAACGGACCGTTAGAATAACTTTATAATAGTTATTATA
CTTTCATTATGAATTTTTGCTTATTTAGTAAGATTGTATGAATAAAGTTAGGACAATATTTGGTGAGATTTTGATTT
ATGAGCTAACAATAGAATTTCAAAATCATAATTTCTATATGGCTAAGCAAAACTTCAATTTCATGTTAAACGAATGA
AAAGTAAGTAGGCGTTTGGTCATGTGATATCATATCACGATATGAAATCGTGAGAAGGAATCAGCGTTTGAACATGC
GATTATACATTGATTCTATATCATGAGATGTAATTCCATATTCTTCAAAAACCATGATATGGAAATTTCATATCATG
ATTTGATATATTTTTAATACAAAAATTGATCCACATATTTGTATTTTGTTAAAACAACCCATATTTAATTTTTTGGG
TAAGCCATCGACGTTTTGTATTTATATTAAAATCTGATTAAATTTGAAGCTGATTTATATTTAGAATGAAACTTCAG
CTTAAAAATAAGAAAATAGTTTATGATTTCATTAGAATTAAGGCGTAGTCACTGTCAAACTTGAGAAAGGATTACCC
CTTTAAGCTTTGCCCTTGTTTGCAGAGACAGTGACTTGTGATGAAATGAAGCCAGAGAAGGCACTCTGTTATCACAC
TTAAATGATAATACATGTGTATGGACTAGCAATAAAAGTGGCACTAGTAATTGAAAAGCAAGTGTATAGAGAGAGAT
AATGAGAGAGAAAGAGTAAGTACACTACTACTGCTACTATCCCATATACCTGTAATGTTGCAGGTCTGAATTTTGCA
GTTGCAGACCCCCTTCTCTTGGCACAAGCTCTTTTAACTTTTATCTTCTCAAATAATTCTCTCTCTCTCTCTTTTCT
ATCATTTTTTTTTACATTGAGAGTAAACTTAATATCCGTTGTATGTATTAGTGTGAGGCCTATCTGCCACAAGGATG
TGATGGAACACTATGCTTCCTCTGCTAAAACCCCACAACCCCAAAACTCTCTTTCACTTCACATTTAAGCACAATTC
CTCAGTAAAATTATCCTTTTGATCTCTCTAACATCAATGTTGGTTAGTTCAAGAATTGGTTTTTCCATTTCAAAGGA
GCTGAGTTAGTGAGGTTTTGAGTTTTGACTGAGACTTGAGTCTACCATGGCATCATTTTTACTCCAAAGATGTAATC
TTCTCTTTGAGGTTCTTCTTATTTTGGGGTTCTTGATTTTCTTCAGCTTTGGTTCTGTGGTGTCTGATGATGGTGAG
TAGAGTAGAGTAGTAGAACTTTCTGCTTCTTATGTTTTAGTTTAATGTTTTGTTTAAGATGTTAAAAAGACAAAGTG
TGCTTTTTTTAATCATTTTTTAAATGGTGGTTTTTGATTAATCCCACGTTTTGTAGTTGTTATTTGTTAAAGGTTTA
TTTTTTTGTCTCATTATTATAATAATAATTGGGAAATAGGTTCTGCATTGTTGGAAATTAAGAAGTCAATTAGGGAC
GTGGAGAATGTGTTGTATGACTGGACTGATTCTCCTTCATCTGATTACTGTGCCTGGAGAGGTGTTACCTGTGATAA
TGTCACCTTCAATGTTGTTCAACTGTAAGACATAACTCAAAAACACTATCATTTGGGATTCTTTAGTTATAAAGTTG
TAATCTTTTGACATTATCTTGTAGTAATCTTTCGAGTTTAAATCTTGATGGGGAGTTGTCTCCTGCTATTGGACAGC
TCAAAGGCCTTGTATCTATGTAATATCTCCTCCCATTATCTCACAATTACCCTTTTTGTTTGATCTTTTGACTTAGT
GCACATTATAGACTATGCCTGTTAATTTTTTTTTGAAGTGATATGAGGGGAAATCGCCTTTCTGGCCAGATACCAGA
TGAGATTGGTGACTGTTCAGCACTGAAAAATTTGTAAGTATGAAATGCTTCTGAATCTTGTGTTATTGTTTGGAAAA
ATAAGTAACCATTTTTTCCCTTAGGGACCTTTCCTTCAATGAGCTTTATGGTGATATTCCCTTCTCCATATCTAAAC
TCAAGCAACTGGAATATCTGTAAGTTTTGATACTCTCCTTCTTCTAAATGTTGTATTATTTGCTTTCCGAGATTGTT
AGTTGATTATGCTCGTCTTATTCAACTTAGGATTTTGAAGAATAATCAATTGATTGGACCAATTCCATCTACATTGT
CACAGATCCCTAACTTGAAGGTCTTGTAAGTATATTCTCTCTGCTTTGTCATGATATTGGTAGATTATGAATAATTT
TAGTTTGATCCAAGAACTTCCTCCAGGGACCTGGCTCAAAATAGGTTAAGTGGAGAAATTCCTAGGCTGATATACTG -continued GAACGAAGTCCTGCAGTATCTGTGAGTGTTTTAATCCGGTGTTCCTCTTCTTCCTGTTTGTTTTAACCTTAGGACAC
TTTCATTTCGTATATGGATATGATTACATCTGTTGTATGTTTTTATTCATATAGGGGACTGCGTGGTAACAACTTGG
GTGGATCCCTTTCTCCTGATATGTGTCAGCTCACCGGCCTGTGGTACTTGTAAGTTTGTAATCCTGTTGCTCTTAAG
ATCTTACTTTAGTTCCTCTAGGTGATGACATTAACCATTGTTCATTGTGTTGTACAGTGATGTTCGGAACAATAGTT
TGACTGGTTCCATTCCTCAAAATATTGGCAACTGTACTGCCTTCCAGGTTCTGTAAGTATCTAAATCAATTGAATGA
AGTTTGACTATATTCTGTATGTTTGGTTGGCATAACACCTTGTTTTGTTCTGTCAGAGATTTGTCTTATAATGATTT
GACCGGAGAGATTCCTTTCAATATTGGTTTCCTGCAAGTAGCGACCTTGTAAGTTTATGCTGCTTCTCTTCATTACA
AACTATTCAATATATGGTTGTTTGAAGTGTACTTTCATCATTCCAGGTCTTTGCAAGGTAATCGTCTTTCAGGGCAG
ATCCCTTCTGTAATTGGATTGATGCAAGCTCTTGCAGTTTTGTGAGTGTTTTGTGTCTTGATATCTCAATCTAATGC
TACTGAATCTAATTCTTGGAAACCATTATAATGCATCTGTTATTTAAGTTTTCTGACCCTTTTACTGTCAGGGACTT
GAGCTGCAATATGTTGAGTGGAACAATTCCTTCAATTCTTGGGAATTTGACTTACACAGAGAAATTGTTAGTACTTC
AACATTATTAAAAGCAATTTGGATCATTTTGTGCTTCCTAAATTGTGTAGTGGATCAATTACTGTAAGTTCGCATTG
TATTGCAGGTATCTACACGGGAACAAGCTATCTGGTTCCATTCCTCCAGAGCTGGGAAATATGACAAAGCTCCACTA
CTTGTATGAATGCCTTCTATCAATCATTTTTTGTTAGCTTTGTTTTGTTCTTCCTGTTCAAACCCTTTTAAATGAAT
GCTTACCATTTAGAAGCATTTGTTTGATTATTTAGCCTTTGGGCAACCACGGATTTGAATGATAGAAAGCTGTTATG
AGAATTTTTATTAAGAGACTTTCTTCAACCTTAAGGCTCAAAGATGGTAATTTGCAGGGAATTGAATGATAACCAAC
TTACTGGACGCATACCACCAGAACTTGGAAAGCTGACAGAATTGTTTGACTTGTAAATCCCGTTTCTCTTCATCTTC
TACTTTGGACTTGTTAACATCATTATTTATTTACTCATGTTGTATGTTTCAGAAATGTTGCAAACAACCACCTAGAT
GGGCCCATACCTTCCAATATTAGCTCATGTACCAATTTGAATAGTCTGTGAGTGTTTTTAATGTCCGAAGTGTTTCA
ATTATGCACGACCATGCTTGTTTGGTAGTTATTGACACCTGATTTTGTTGCAGCAACGTTCATGGAAACAAATTGAA
TGGTACTATTCCACCTGCTTTTCAGAAGCTGGAAAGTATGACCTATCTGTAAGTTCTTACTTTCTGATCTTTTTCTT
TTGAAGAATTATGTTTAAGGTTATCGAAGTTACCGTCCATGCTGTTGAGCAAGATTGTAAACTTACTGTGCCTTGTA
TATAAATTTTACTGGCGTTGTATTATTGAAAAAATCATTTTATTTATATTGCTCTCAAATCATACTGGCTTATATCC
ATTCATGAAGAATCATTTCTACTGTCTGAAGTTTTCAGCTATATGTATCGAAAAAATTTAGTTATTATATAGTTTAT
TTTGAGCCTCTGCATCATCTATTTGTGAATTTCATTTGCTTATTCTGCATACTCTCAGCATTAACCGTCTCTTCTTT
TGTTAATTGCTTTAGTAATCTCTCCTCCAACAATCTCAAAGGCCCAATTCCAATTGAGCTATCTCGTATTGGGAATG
TAGATACACTGTAAGTGCAAACTTTCTCATCTACTTTCATTTCTCTCATTGCAATTATGGTTGCGGGGAAAGCACTT
TTTGTCAGTCTTAAGAATCTTCAACATTTTTTGGCTTAGGGACTTATCAAACAACAGGATCAGTGGTCCTATACCTA
TGTCCCTTGGTGATTTGGAACATCTTCTTAAACTGTGAGCATAACCGTCAAGTTGTTATGTTAGCATCATATATCTG
TTGTACTTACATCCCTTTTGTCAATGCTGTAGGAACTTAAGCAAGAATGAAATAAATGGAAACTTACCAGCTGAATT
TGGCAATTTAAGGAGCATCATGGAGATGTATGGAACCTTGCTAAATTCAGTTACTTTGAATTTATGGTTTGCTTGAT
TTTCAGCTTTTTGACTGCACTCCTAATTGTAGTGATCTGTCAAGCAATCACCTCTCTGGTCCCTTACCTCAGGAACT
TGGTCAGCTTCCAAACCTGTACTTGCTGTAAGTACTTCAGATTTACTTTGAGACTCTCATCCTCTTAGCTATTGGTA
ATAATCTGTAGAGTGAATAAGTATGAACTTCTAAACTCGGTAAGTAGATTTTAAAATTATTTGGATGCCATTTTCA
AAAAAGTAGAGATGAAGTTGGTTGTGTTGCTATTGTTTTATATGATCTGGCTTCATATGTTCATTACTTTGGTGTTC
TCAGTTTTGCTTTATATTGCATTATTGCACGGGGCTCAAATGCAGCATATCTCTATCTTCTTTTTCTTGTGGCCTTA
ATTATTTTACAAATTAATGAACAGGAAGGTGGAAAACAACAATTTATCAGGCGATGTGATGTCCTTAGCCAGTTGCC
TCAGTCTAAATATCTTGTGAGTTTTCAAGTCCATAGTAAGACACCAGTACAAACAAATGTTTTGTTAATCTAATCAA
CCTCATGTTAGCAGAAATGTCTCATACAATAATCTGGGAGGGAATATTCCAACCGGCAATAATTTCTCTAGATTTTC
ACCAGACAGGTAAGTGGAGCTATTAAGATTTTACACAAGTCACAAGCATTTATTGGTTTTTAATTCTTTGCTTCTAA
TTTCTTCCTTTTGCTATGTCTCCGAAAAAGCTTCATAGGAAATCCAGATCTGTGTGGGTATTGGCTCACTTCTCCTT
GTCATGCATCTCATCCGGCAGAGCGAGGTCTGATCAAACTGTAACAATCATTTGGCCTTTACTCTATTGCATTTTTG
AAGTTCCATTTCACTTTAGACATCTGCAACATTTATTAAGTGTGATGGACAGATATATTGATTAATGAGGAATTATC
CCTTGGTTGAGCAAACTTAATTCTGTGTTAGCCTGGTAGTAGGGTGTACCACAAGGTTTGTCGTCATGGTTTCCTAT
GTTCACAATCCCTGATTGTAACATTTAGATGTGTACACATATCTAATTAACATGAAATAATCTTCATTTGCTGGAGT
TACATTGACGTAAAGATGCGTTAGCTGTCAAATGAAACTGCATTTGTTTTATTTCCATCATCAGTACATTAATTAAG
TGCATAAATATTTTAACAGTTGTTGAATGATATAAGATGAATTTATTGGACAATTGCAGTTTCAATTTCTAAAGCAG
CAATACTTGGTATTGCTCTGGGTGGCTTGGTGATTCTTCTGATGATACTAGTAGCAGCATGCCGGCCACAGAAACCT
GCACCTTTCATGGAAGGATCTATTGATAAACCAGGTACAATATTTTCCGGACGGTTGGATAGTGTTTGGAGATGTTC
ATGTCAGAAGGACAGTCGTCAGAGTTTATTGAAGTTGCCATGTATTGATTGTTTAACGTTTTTGATGAACAGTTTAT
TACTCATCTCCAAAACTTGTGATCCTTCATATGAACATGGCACTTCATGTTTACGAGGACATTATGAGGATGACTGA
GAACTTGAGTGAGAAGTATATAATTGGTTGTGGAGCATCAAGTACTGTATATAAATGTGTTTTGAAAAATTGCAAGC
CTGTAGCTATCAAGAAGTTGTACTCTCACAACCCGCAATACTTGAAGGAATTTGAGACTGAACTTGAGACAGTTGGG
AGTATTAAGCATCGTAATCTTGTCTGTCTCCAAGGATATTCTCTTTCTCCATCTGGCCATCTTCTTTTCTATGACTA
CATGGAAAATGGTAGCCTTTGGGATTTGCTTCATGGTTAGTAAATCCAAAATGGTTAAGGTGATTGATGCATTGATT
TTGTGTTAAAGCATCAAGTAATCAGTCCTCTTGTATCTTTTTTTGCAGGTCCTACAACAAAGAAGAAAAAGCTTGAT
TGGGTTACTCGCCTTCGAATTGCATTGGGATCAGCTCAAGGGCTTGCATATCTTCATCATGATTGTAGCCCTCGAAT
AATCCACCGTGATGTTAAATCATCTAATATCTTGTTGGACAAAGACTTTGAGGCTCATCTGACTGATTTTGGCATAG
CTAAAAGCTTATGCATATCAAAGACCTATACGTCCACGTACATTATGGGAACCATTGGTTACATTGATCCAGAGTAT
GCTCGCACTTCTCGCTTGACAGAGAAGTCTGATGTTTACAGCTATGGTATTGTTCTATTGGAATTGCTCACTGGAAG
GAAAGCTGTAGATAATGAATCTAATCTACATCATTTGGTAAGCTCTTGCAATTTAGTTAATATGAACTTGTCCTATG
ATGTTTATTCATATAATTATATTAAGATTCAATTCAATTGATCATAACAGTTTTGCATATATGTTACAGATTCTAAC
TAAGGCAGCAAACGATGCTGTAATGGAAACAGTGGATCCTGAGATAACATGCACATGCAAAGATCTTGCAGATGTGA
AGAAGGTTTTTCAGCTTGCCCTTCTATGTTCCAAAAGACAGCCTGCTGAGAGACCAACAATGCATGAAGTGGCAAGA
GTACTTGAAAGCCTAATACCCGTCGCTGAAACGAAACAGCCAAATCCAACCCCCTCACTTGCATTACTCCCATCTGC
TAAGGTACCTTGTTACATGGATGAATATGTCAACCTCAAGACACCCCACCTAGTGAACTGTTCATCCATGAGCACTT
CAGATGCCCAACTTTTCCTCAAGTTTGGAGAGGTCATATCCCAGAATAGTGGCTGA (SEQ ID NO: 28)

Nucleic acid sequence for a mutant Solyc08g061560 promoter allele SlER$^{CR-pro-14}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT -continued TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGAACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACAAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC
AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGTTTCAATTTCTAAAGCAGCAA
TACTTGGTATTGCTCTGGGTGGCTTGGTGATTCTTCTGATGATACTAGTAGCAGCATGCCGGCCACAGAAACCTGCA
CCTTTCATGGAAGGATCTATTGATAAACCAGTTTATTACTCATCTCCAAAACTTGTGATCCTTCATATGAACATGGC
ACTTCATGTTTACGAGGACATTATGAGGATGACTGAGAACTTGAGTGAGAAGTATATAATTGGTTGTGGAGCATCAA
GTACTGTATATAAATGTGTTTTGAAAAATTGCAAGCCTGTAGCTATCAAGAAGTTGTACTCTCACAACCCGCAATAC
TTGAAGGAATTTGAGACTGAACTTGAGACAGTTGGGAGTATTAAGCATCGTAATCTTGTCTGTCTCCAAGGATATTC
TCTTTCTCCATCTGGCCATCTTCTTTTCTATGACTACATGGAAAATGGTAGCCTTTGGGATTTGCTTCATGGTCCTA
CAACAAAGAAGAAAAAGCTTGATTGGGTTACTCGCCTTCGAATTGCATTGGGATCAGCTCAAGGGCTTGCATATCTT
CATCATGATTGTAGCCCTCGAATAATCCACCGTGATGTTAAATCATCTAATATCTTGTTGGACAAAGACTTTGAGGC
TCATCTGACTGATTTTGGCATAGCTAAAAGCTTATGCATATCAAAGACCTATACGTCCACGTACATTATGGGAACCA
TTGGTTACATTGATCCAGAGTATGCTCGCACTTCTCGCTTGACAGAGAAGTCTGATGTTTACAGCTATGGTATTGTT
CTATTGGAATTGCTCACTGGAAGGAAAGCTGTAGATAATGAATCTAATCTACATCATTTGATTCTAACTAAGGCAGC
AAACGATGCTGTAATGGAAACAGTGGATCCTGAGATAACATGCACATGCAAAGATCTTGCAGATGTGAAGAAGGTTT
TTCAGCTTGCCCTTCTATGTTCCAAAAGACAGCCTGCTGAGAGACCAACAATGCATGAAGTGGCAAGAGTACTTGAA
AGCCTAATACCCGTCGCTGAAACGAAACAGCCAAATCCAACCCCCTCACTTGCATTACTCCCATCTGCTAAGGTACC
TTGTTACATGGATGAATATGTCAACCTCAAGACACCCCACCTAGTGAACTGTTCATCCATGAGCACTTCAGATGCCC
AACTTTTCCTCAAGTTTGGAGAGGTCATATCCCAGAATAGTGGCTGA (SEQ ID NO: 29)

Amino acid sequence for a mutant polypeptide encoded by a mutant Solyc08g061560 promoter allele SlER$^{CR\text{-}pro\text{-}14}$ coding sequence MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGNKLNGTIPPAFQKLESMTYLNLSSNNLKGPIPIELSRIGNVDTLDLSNNRISGPIPMSLGDLEHLL
KLNLSKNEINGNLPAEFGNLRSIMEIDLSSNHLSGPLPQELGQLPNLYLLKVENNNLSGDVMSLASCLSLNILNVSY
NNLGGNIPTGNNFSRFSPDSFIGNPDLCGYWLTSPCHASHPAERVSISKAAILGIALGGLVILLMILVAACRPQKPA
PFMEGSIDKPVYYSSPKLVILHMNMALHVYEDIMRMTENLSEKYIIGCGASSTVYKCVLKNCKPVAIKKLYSHNPQY
LKEFETELETVGSIKHRNLVCLQGYSLSPSGHLLFYDYMENGSLWDLLHGPTTKKKKLDWVTRLRIALGSAQGLAYL
HHDCSPRIIHRDVKSSNILLDKDFEAHLTDFGIAKSLCISKTYTSTYIMGTIGYIDPEYARTSRLTEKSDVYSYGIV
LLELLTGRKAVDNESNLHHLILTKAANDAVMETVDPEITCTCKDLADVKKVFQLALLCSKRQPAERPTMHEVARVLE
SLIPVAETKQPNPTPSLALLPSAKVPCYMDEYVNLKTPHLVNCSSMSTSDAQLFLKFGEVISQNSG* (SEQ ID NO: 30)

*S. lycopersicum* cv. Sweet100 SlER gene

Nucleic acid sequence of a *S. lycopersicum* cv. Sweet100 SlER gene

ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGCTATTGGACAGCTCAAAGGCCTTGTATCTATGTAATATCTCCTCCCATTATCTCACAA
TTACCCTTTTTGTTTGATCTTTTGACTTAGTGCACATTATAGACTATGCCTGTTAATTTTTTTTTGAAGTGATATGA
GGGGAAATCGCCTTTCTGGCCAGATACCAGATGAGATTGGTGACTGTTCAGCACTGAAAAAATTTGTAAGTATGAAAT
GCTTCTGAATCTTGTGTTATTGTTTGGAAAAATAAGTAACCATTTTTTCCCTTAGGGACCTTTCCTTCAATGAGCTT
TATGGTGATATTCCCTTCTCCATATCTAAACTCAAGCAACTGGAATATCTGTAAGTTTTGATACTCTCCTTCTTCTA
AATGTTGTATTATTTGCTTTCCGAGATTGTTAGTTGATTATGCTCGTCTTATTCAACTTAGGATTTTGAAGAATAAT
CAATTGATTGGACCAATTCCATCTACATTGTCACAGATCCCTAACTTGAAGGTCTTGTAAGTATATTCTCTCTGCTT
TGTCATGATATTGGTAGATTATGAATAATTTAGTTTGATCCAAGAACTTCCTCCAGGGACCTGGCTCAAAATAGGT
TAAGTGGAGAAATTCCTAGGCTGATATACTGGAACGAAGTCCTGCAGTATCTGTGAGTGTTTTAATCCGGTGTTCCT
CTTCTTCCTGTTTGTTTTAACCTTAGGACACTTTCATTTCGTATATGGATATGATTACATCTGTTGTATGTTTTTAT
TCATATAGGGGACTGCGTGGTAACAACTTGGGTGGATCCCTTTCTCCTGATATGTGTCAGCTCACCGGCCTGTGGTA
CTTGTAAGTTTGTAATCCTGTTGCTCTTAAGATCTTACTTTAGTTCCTCTAGGTGATGACATTAACCATTGTTCATT
GTGTTGTACAGTGATGTTCGGAACAATAGTTTGACTGGTTCCATTCCTCAAAATATTGGCAACTGTACTGCCTTCCA
GGTTCTGTAAGTATCTAAATCAATTGAATGAAGTTTGACTATATTCTGTATGTTTGGTTGGCATAACACCTTGTTTT
GTTCTGTCAGAGATTTGTCTTATAATGATTTGACCGGAGAGATTCCTTTCAATATTGGTTTCCTGCAAGTAGCGACC
TTGTAAGTTTATGCTGCTTCTCTTCATTACAAACTATTCAATATATGGTTGTTTGAAGTGTACTTTCATCATTCCAG
GTCTTTGCAAGGTAATCGTCTTTCAGGGCAGATCCCTTCTGTAATTGGATTGATGCAAGCTCTTGCAGTTTTGTGAG
TGTTTTGTGTCTTGATATCTCAATCTAATGCTACTGAATCTAATTCTTGGAAACCATTATAATGCATCTGTTATTTA
AGTTTTCTGACCCTTTTACTGTCAGGGACTTGAGCTGCAATATGTTGAGTGGAACAATTCCTTCAATTCTTGGGAAT
TTGACTTACACAGAGAAATTGTTAGTACTTCAACATTATTAAAAGCAATTTGGATCATTTTGTGCTTCCTAAATTGT
GTAGTGGATCAATTACTGTAAGTTCGCATTGTATTGCAGGTATCTACACGGGAACAAGCTATCTGGTTCCATTCCTC
CAGAGCTGGGAAATATGACAAAGCTCCACTACTTGTATGAATGCCTTCTATCAATCATTTTTTGTTAGCTTTGTTTT

-continued

GTTCTTCCTGTTCAAACCCTTTTAAATGAATGCTTACCATTTAGAAGCATTTGTTTGATTATTTAGCCTTTGGGCAA
CCACGGATTTGAATGATAGAAAGCTGTTATGAGAATTTTTATTAAGAGACTTTCTTCAACCTTAAGGCTCAAAGATG
GTAATTTGCAGGGAATTGAATGATAACCAACTTACTGGACGCATACCACCAGAACTTGGAAAGCTGACAGAATTGTT
TGACTTGTAAATCCCGTTTCTCTTCATCTTCTACTTTGGACTTGTTAACATCATTATTTATTTACTCATGTTGTATG
TTTCAGAAATGTTGCAAACAACCACCTAGATGGGCCCATACCTTCCAATATTAGCTCATGTACCAATTTGAATAGTC
TGTGAGTGTTTTTAATGTCCGAAGTGTTTCAATTATGCACGACCATGCTTGTTTGGTAGTTATTGACACCTGATTTT
GTTGCAGCAACGTTCATGGAAACAAATTGAATGGTACTATTCCACCTGCTTTTCAGAAGCTGGAAAGTATGACCTAT
CTGTAAGTTCTTACTTTCTGATCTTTTTCTTTTGAAGAATTATGTTTAAGGTTATCGAAGTTACCGTCCATGCTGTT
GAGCAAGATTGTAAACTTACTGTGCCTTGTATATAAATTTTACTGGCGTTGTATTATTGAAAAAATCATTTTATTTA
TATTGCTCTCAAATCATACTGGCTTATATCCATTCATGAAGAATCATTTCTACTGTCTGAAGTTTTCAGCTATATGT
ATCGAAAAAATTTAGTTATTATATAGTTTATTTTGAGCCTCTGCATCATCTATTTGTGAATTTCATTTGCTTATTCT
GCATACTCTCAGCATTAACCGTCTCTTCTTTTGTTAATTGCTTTAGTAATCTCTCCTCCAACAATCTCAAAGGCCCA
ATTCCAATTGAGCTATCTCGTATTGGGAATGTAGATACACTGTAAGTGCAAACTTTCTCATCTACTTTCATTTCTCT
CATTGCAATTATGGTTGCGGGGAAAGCACTTTTTGTCAGTCTTAAGAATCTTCAACATTTTTTGGCTTAGGGACTTA
TCAAACAACAGGATCAGTGGTCCTATACCTATGTCCCTTGGTGATTTGGAACATCTTCTTAAACTGTGAGCATAACC
GTCAAGTTGTTATGTTAGCATCATATATCTGTTGTACTTACATCCCTTTTGTCAATGCTGTAGGAACTTAAGCAAGA
ATGAAATAAATGGAAACTTACCAGCTGAATTTGGCAATTTAAGGAGCATCATGGAGATGTATGGAACCTTGCTAAAT
TCAGTTACTTTGAATTTATGGTTTGCTTGATTTTCAGCTTTTTGACTGCACTCCTAATTGTAGTGATCTGTCAAGCA
ATCACCTCTCTGGTCCCTTACCTCAGGAACTTGGTCAGCTTCCAAACCTGTACTTGCTGTAAGTACTTCAGATTTAC
TTTGAGACTCTCATCCTCTTAGCTATTGGTAATAATCTGTAGAGTGAATAAGTATGAACTTCTAAACTCGGTAAGTA
GATTTTAAAATTATTTTGGATGCCATTTTCAAAAAAGTAGAGATGAAGTTGGTTGTGTTGCTATTGTTTTATATGAT
CTGGCTTCATATGTTCATTACTTTGGTGTTCTCAGTTTTGCTTTATATTGCATTATTGCACGGGGCTCAAATGCAGC
ATATCTCTATCTTCTTTTTCTTGTGGCCTTAATTATTTTACAAATTAATGAACAGGAAGGTGGAAAACAACAATTTA
TCAGGCGATGTGATGTCCTTAGCCAGTTGCCTCAGTCTAAATATCTTGTGAGTTTTCAAGTCCATAGTAAGACACCA
GTACAAACAAATGTTTTGTTAATCTAATCAACCTCATGTTAGCAGAAATGTCTCATACAATAATCTGGGAGGGAATA
TTCCAACCGGCAATAATTTCTCTAGATTTTCACCAGACAGGTAAGTGGAGCTATTAAGATTTTACACAAGTCACAAG
CATTTATTGGTTTTTAATTCTTTGCTTCTAATTTCTTCCTTTTGCTATGTCTCCGAAAAAGCTTCATAGGAAATCCA
GATCTGTGTGGGTATTGGCTCACTTCTCCTTGTCATGCATCTCATCCGGCAGAGCGAGGTCTGATCAAACTGTAACA
ATCATTTGGCCTTTACTCTATTGCATTTTTGAAGTTCCATTTCACTTTAGACATCTGCAACATTTATTAAGTGTGAT
GGACAGATATATTGATTAATGAGGAATTATCCCTTGGTTGAGCAAACTTAATTCTGTGTTAGCCTGGTAGTAGGGTG
TACCACAAGGTTTGTCGTCATGGTTTCCTATGTTCACAATCCCTGATTTGTAACATTTAGATGTGTACACATATCTAA
TTAACATGAAATAATCTTCATTTGCTGGAGTTACATTGACGTAAAGATGCGTTAGCTGTCAAATGAAACTGCATTTG
TTTTATTTCCATCATCAGTACATTAATTAAGTGCATAAATATTTTAACAGTTGTTGAATGATATAAGATGAATTTAT
TGGACAATTGCAGTTTCAATTTCTAAAGCAGCAATACTTGGTATTGCTCTGGGTGGCTTGGTGATTCTTCTGATGAT
ACTAGTAGCAGCATGCCGGCCACAGAAACCTGCACCTTTCATGGAAGGATCTATTGATAAACCAGGTACAATATTTT
CCGGACGGTTGGATAGTGTTTGGAGATGTTCATGTCAGAAGGACAGTCGTCAGAGTTTATTGAAGTTGCCATGTATT
GATTGTTTAACGTTTTTGATGAACAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTTAGTAAATC
CAAAATGGTTAAGGTGATTGATGCATTGATTTTGTGTTAAAGCATCAAGTAATCAGTCCTCTTGTATCTTTTTTTGC
AGGTCCTACAACAAAGAAGAAAAAGCTTGATTGGGTTACTCGCCTTCGAATTGCATTGGGATCAGCTCAAGGGCTTG
CATATCTTCATCATGATTGTAGCCCTCGAATAATCCACCGTGATGTTAAATCATCTAATATCTTGTTGGACAAAGAC
TTTGAGGCTCATCTGACTGATTTTGGCATAGCTAAAAGCTTATGCATATCAAAGACCTATACGTCCACGTACATTAT
GGGAACCATTGGTTACATTGATCCAGAGTATGCTCGCACTTCTCGCTTGACAGAGAAGTCTGATGTTTACAGCTATG
GTATTGTTCTATTGGAATTGCTCACTGGAAGGAAAGCTGTAGATAATGAATCTAATCTACATCATTTGGTAAGCTCT
TGCAATTTAGTTAATATGAACTTGTCCTATGATGTTTATTCATATAATTATATTAAGATTCAATTCAATTGATCATA
ACAGTTTTGCATATATGTTACAGATTCTAACTAAGGCAGCAAACGATGCTGTAATGGAAACAGTGGATCCTGAGATA
ACATGCACATGCAAAGATCTTGCAGATGTGAAGAAGGTTTTTCAGCTTGCCCTTCTATGTTCCAAAAGACAGCCTGC
TGAGAGACCAACAATGCATGAAGTGGCAAGAGTACTTGAAAGCCTAATACCCGTCGCTGAAACGAAACAGCCAAATC
CAACCCCCTCACTTGCATTACTCCCATCTGCTAAGGTACCTTGTTACATGGATGAATATGTCAACCTCAAGACACCC
CACCTAGTGAACTGTTCATCCATGAGCACTTCAGATGCCCAACTTTTCCTCAAGTTTGGAGAGGTCATATCCCAGAA
TAGTGGCTGA (SEQ ID NO: 31)

Nucleic acid sequence of a *S. lycopersicum* cv. Sweet100 SlER coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGCTATTGGACAGCTCAAAGGCCTTGT
ATCTATTGATATGAGGGGAAATCGCCTTTCTGGCCAGATACCAGATGAGATTGGTGACTGTTCAGCACTGAAAAATT
TGGACCTTTCCTTCAATGAGCTTTATGGTGATATTCCCTTCTCCATATCTAAACTCAAGCAACTGGAATATCTGATT
TTGAAGAATAATCAATTGATTGGACCAATTCCATCTACATTGTCACAGATCCCTAACTTGAAGGTCTTGGACCTGGC
TCAAAATAGGTTAAGTGGAGAAATTCCTAGGCTGATATACTGGAACGAAGTCCTGCAGTATCTGGGACTGCGTGGTA
ACAACTTGGGTGGATCCCTTTCTCCTGATATGTGTCAGCTCACCGGCCTGTGGTACTTTGATGTTCGGAACAATAGT
TTGACTGGTTCCATTCCTCAAAATATTGGCAACTGTACTGCCTTCCAGGTTCTAGATTTGTCTTATAATGATTTGAC
CGGAGAGATTCCTTTCAATATTGGTTTCCTGCAAGTAGCGACCTTGTCTTTGCAAGGTAATCGTCTTTCAGGGCAGA
TCCCTTCTGTAATTGGATTGATGCAAGCTCTTGCAGTTTTGGACTTGAGCTGCAATATGTTGAGTGGACAATTCCT
TCAATTCTTGGGAATTTGACTTACACAGAGAAATTGTATCTACACGGGAACAAGCTATCTGGTTCCATTCCTCCAGA
GCTGGGAAATATGACAAAGCTCCACTACTTGGAATTGAATGATAACCAACTTACTGGACGCATACCACCAGAACTTG
GAAAGCTGACAGAATTGTTTGACTTAAATGTTGCAAACAACCACCTAGATGGGCCCATACCTTCCAATATTAGCTCA
TGTACCAATTTGAATAGTCTCAACGTTCATGGAAACAAATTGAATGGTACTATTCCACCTGCTTTTCAGAAGCTGGA
AAGTATGACCTATCTTAATCTCTCCTCCAACAATCTCAAAGGCCCAATTCCAATTGAGCTATCTCGTATTGGGAATG
TAGATACACTGGACTTATCAAACAACAGGATCAGTGGTCCTATACCTATGTCCCTTGGTGATTTGGAACATCTTCTT
AAACTGAACTTAAGCAAGAATGAAATAAATGGAAACTTACCAGCTGAATTTGGCAATTTAAGGAGCATCATGGAGAT
TGATCTGTCAAGCAATCACCTCTCTGGTCCCTTACCTCAGGAACTTGGTCAGCTTCCAAACCTGTACTTGCTGAAGG
TGGAAAACAACAATTTATCAGGCGATGTGATGTCCTTAGCCAGTTGCCTCAGTCTAAATATCTTAAATGTCTCATAC
AATAATCTGGGAGGGAATATTCCAACCGGCAATAATTTCTCTAGATTTTCACCAGACAGCTTCATAGGAAATCCAGA
TCTGTGTGGGTATTGGCTCACTTCTCCTTGTCATGCATCTCATCCGGCAGAGCGAGTTTCAATTTCTAAAGCAGCAA -continued TACTTGGTATTGCTCTGGGTGGCTTGGTGATTCTTCTGATGATACTAGTAGCAGCATGCCGGCCACAGAAACCTGCA
CCTTTCATGGAAGGATCTATTGATAAACCAGTTTATTACTCATCTCCAAAACTTGTGATCCTTCATATGAACATGGC
ACTTCATGTTTACGAGGACATTATGAGGATGACTGAGAACTTGAGTGAGAAGTATATAATTGGTTGTGGAGCATCAA
GTACTGTATATAAATGTGTTTTGAAAAATTGCAAGCCTGTAGCTATCAAGAAGTTGTACTCTCACAACCCGCAATAC
TTGAAGGAATTTGAGACTGAACTTGAGACAGTTGGGAGTATTAAGCATCGTAATCTTGTCTGTCTCCAAGGATATTC
TCTTTCTCCATCTGGCCATCTTCTTTTCTATGACTACATGGAAAATGGTAGCCTTTGGGATTTGCTTCATGGTCCTA
CAACAAAGAAGAAAAAGCTTGATTGGGTTACTCGCCTTCGAATTGCATTGGGATCAGCTCAAGGGCTTGCATATCTT
CATCATGATTGTAGCCCTCGAATAATCCACCGTGATGTTAAATCATCTAATATCTTGTTGGACAAAGACTTTGAGGC
TCATCTGACTGATTTTGGCATAGCTAAAAGCTTATGCATATCAAAGACCTATACGTCCACGTACATTATGGGAACCA
TTGGTTACATTGATCCAGAGTATGCTCGCACTTCTCGCTTGACAGAGAAGTCTGATGTTTACAGCTATGGTATTGTT
CTATTGGAATTGCTCACTGGAAGGAAAGCTGTAGATAATGAATCTAATCTACATCATTTGATTCTAACTAAGGCAGC
AAACGATGCTGTAATGGAAACAGTGGATCCTGAGATAACATGCACATGCAAAGATCTTGCAGATGTGAAGAAGGTTT
TTCAGCTTGCCCTTCTATGTTCCAAAAGACAGCCTGCTGAGAGACCAACAATGCATGAAGTGGCAAGAGTACTTGAA
AGCCTAATACCCGTCGCTGAAACGAAACAGCCAAATCCAACCCCCTCACTTGCATTACTCCCATCTGCTAAGGTACC
TTGTTACATGGATGAATATGTCAACCTCAAGACACCCCACCTAGTGAACTGTTCATCCATGAGCACTTCAGATGCCC
AACTTTTCCTCAAGTTTGGAGAGGTCATATCCCAGAATAGTGGCTGA (SEQ ID NO: 32)

Amino acid sequence for a polypeptide encoded by a *S. lycopersicum* cv. Sweet100 SlER coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPAIGQLKGLVSIDMRGNRLSGQIPDEIGDCSALKNLDLSFNELYGDIPFSISKLKQLEYLI
LKNNQLIGPIPSTLSQIPNLKVLDLAQNRLSGEIPRLIYWNEVLQYLGLRGNNLGGSLSPDMCQLTGLWYFDVRNNS
LTGSIPQNIGNCTAFQVLDLSYNDLTGEIPFNIGFLQVATLSLQGNRLSGQIPSVIGLMQALAVLDLSCNMLSGTIP
SILGNLTYTEKLYLHGNKLSGSIPPELGNMTKLHYLELNDNQLTGRIPPELGKLTELFDLNVANNHLDGPIPSNISS
CTNLNSLNVHGNKLNGTIPPAFQKLESMTYLNLSSNNLKGPIPIELSRIGNVDTLDLSNNRISGPIPMSLGDLEHLL
KLNLSKNEINGNLPAEFGNLRSIMEIDLSSNHLSGPLPQELGQLPNLYLLKVENNNLSGDVMSLASCLSLNILNVSY
NNLGGNIPTGNNFSRFSPDSFIGNPDLCGYWLTSPCHASHPAERVSISKAAILGIALGGLVILLMILVAACRPQKPA
PFMEGSIDKPVYYSSPKLVILHMNMALHVYEDIMRMTENLSEKYIIGCGASSTVYKCVLKNCKPVAIKKLYSHNPQY
LKEFETELETVGSIKHRNLVCLQGYSLSPSGHLLFYDYMENGSLWDLLHGPTTKKKKLDWVTRLRIALGSAQGLAYL
HHDCSPRIIHRDVKSSNILLDKDFEAHLTDFGIAKSLCISKTYTSTYIMGTIGYIDPEYARTSRLTEKSDVYSYGIV
LLELLTGRKAVDNESNLHHLILTKAANDAVMETVDPEITCTCKDLADVKKVFQLALLCSKRQPAERPTMHEVARVLE
SLIPVAETKQPNPTPSLALLPSAKVPCYMDEYVNLKTPHLVNCSSMSTSDAQLFLKFGEVISQNSG* (SEQ ID NO: 33)

*S. lycopersicum* cv. Sweet100 gene allele sler$^{CR-1}$
Nucleic acid sequence of a *S. lycopersicum* cv. Sweet100 gene allele sler$^{CR-1}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTCCTGTATTGGACAGCTCAAAGGCCTTGTATCTATGTAATATCTCCTCCCATTATCTCACAAT
TACCCTTTTTGTTTGATCTTTTGACTTAGTGCACATTATAGACTATGCCTGTTAATTTTTTTTTGAAGTGATATGAG
GGGAAATCGCCTTTCTGGCCAGATACCAGATTTGGTGACTGTTCAGCACTGAAAAAATTTGTAAGTATGAAATGCTTC
TGAATCTTGTGTTATTGTTTGGAAAAATAAGTAACCATTTTTTCCCTTAGGGACCTTTCCTTCAATGAGCTTTATGG
TGATATTCCCTTCTCCATATCTAAACTCAAGCAACTGGAATATCTGTAAGTTTTGATACTCTCCTTCTTCTAAATGT
TGTATTATTTGCTTTCCGAGATTGTTAGTTGATTATGCTCGTCTTATTCAACTTAGGATTTTGAAGAATAATCAATT
GATTGGACCAATTCCATCTACATTGTCACAGATCCCTAACTTGAAGGTCTTGTAAGTATATTCTCTCTGCTTTGTCA
TGATATTGGTAGATTATGAATAATTTTAGTTTGATCCAAGAACTTCCTCCAGGGACCTGGCTCAAAATAGGTTAAGT
GGAGAAATTCCTAGGCTGATATACTGGAACGAAGTCCTGCAGTATCTGTGAGTGTTTTAATCCGGTGTTCCTCTTCT
TCCTGTTTGTTTTAACCTTAGGACACTTTCATTTCGTATATGGATATGATTACATCTGTTGTATGTTTTTATTCATA
TAGGGGACTGCGTGGTAACAACTTGGGTGGATCCCTTTCTCCTGATATGTGTCAGCTCACCGGCCTGTGGTACTTGT
AAGTTTGTAATCCTGTTGCTCTTAAGATCTTACTTTAGTTCCTCTAGGTGATGACATTAACCATTGTTCATTGTGTT
GTACAGTGATGTTCGGAACAATAGTTTGACTGGTTCCATTCCTCAAAATATTGGCAACTGTACTGCCTTCCAGGTTC
TGTAAGTATCTAAATCAATTGAATGAAGTTTGACTATATTCTGTATGTTTGGTTGGCATAACACCTTGTTTTGTTCT
GTCAGAGATTTGTCTTATAATGATTTGACCGGAGAGATTCCTTTCAATATTGGTTTCCTGCAAGTAGCGACCTTGTA
AGTTTATGCTGCTTCTCTTCATTACAAACTATTCAATATATGGTTGTTTGAAGTGTACTTTCATCATTCCAGGTCTT
TGCAAGGTAATCGTCTTTCAGGGCAGATCCCTTCTGTAATTGGATTGATGCAAGCTCTTGCAGTTTTGTGAGTGTTT
TGTGTCTTGATATCTCAATCTAATGCTACTGAATCTAATTCTTGGAAACCATTATAATGCATCTGTTATTTAAGTTT
TCTGACCCTTTTACTGTCAGGGACTTGAGCTGCAATATGTTGAGTGGAACAATTCCTTCAATTCTTGGGAATTTGAC
TTACACAGAGAAATTGTTAGTACTTCAACATTATTAAAAGCAATTTGGATCATTTTGTGCTTCCTAAATTGTGTAGT
GGATCAATTACTGTAAGTTCGCATTGTATTGCAGGTATCTACACGGGAACAAGCTATCTGGTTCCATTCCTCCAGAG
CTGGGAAATATGACAAAGCTCCACTACTTGTATGAATGCCTTCTATCAATCATTTTTTGTTAGCTTTGTTTTGTTCT
TCCTGTTCAAACCCTTTTAAATGAATGCTTACCATTTAGAAGCATTTGTTTGATTATTTAGCCTTTGGGCAACCACG
GATTTGAATGATAGAAAGCTGTTATGAGAATTTTTATTAAGAGACTTTCTTCAACCTTAAGGCTCAAAGATGGTAAT
TTGCAGGGAATTGAATGATAACCAACTTACTGGACGCATACCACCAGAACTTGGAAAGCTGACAGAATTGTTTGACT
TGTAAATCCCGTTTCTCTTCATCTTCTACTTTGGACTTGTTAACATCATTATTTATTTACTCATGTTGTATGTTTCA
GAAATGTTGCAAACAACCACCTAGATGGGCCCATACCTTCCAATATTAGCTCATGTACCAATTTGAATAGTCTGTGA
GTGTTTTTAATGTCCGAAGTGTTTCAATTATGCACGACCATGCTTGTTTGGTAGTTATTGACACCTGATTTTGTTGC
AGCAACGTTCATGGAAACAAATTGAATGGTACTATTCCACCTGCTTTTCAGAAGCTGGAAAGTATGACCTATCTGTA
AGTTCTTACTTTCTGATCTTTTTCTTTTGAAGAATTATGTTTAAGGTTATCGAAGTTACCGTCCATGCTGTTGAGCA
AGATTGTAAACTTACTGTGCCTTGTATATAAATTTTACTGGCGTTGTATTATTGAAAAAATCATTTTATTTATATTG
CTCTCAAATCATACTGGCTTATATCCATTCATGAAGAATCATTTCTACTGTCTGAAGTTTTCAGCTATATGTATCGA
AAAAATTTAGTTATTATATAGTTTATTTTGAGCCTCTGCATCATCTATTTGTGAATTTCATTTGCTTATTCTGCATA
CTCTCAGCATTAACCGTCTCTTCTTTTGTTAATTGCTTTAGTAATCTCTCCTCCAACAATCTCAAAGGCCCAATTCC
AATTGAGCTATCTCGTATTGGGAATGTAGATACACTGTAAGTGCAAACTTTCTCATCTACTTTCATTTCTCTCATTG
CAATTATGGTTGCGGGGAAAGCACTTTTTGTCAGTCTTAAGAATCTTCAACATTTTTTGGCTTAGGGACTTATCAAA -continued CAACAGGATCAGTGGTCCTATACCTATGTCCCTTGGTGATTTGGAACATCTTCTTAAACTGTGAGCATAACCGTCAA
GTTGTTATGTTAGCATCATATATCTGTTGTACTTACATCCCTTTTGTCAATGCTGTAGGAACTTAAGCAAGAATGAA
ATAAATGGAAACTTACCAGCTGAATTTGGCAATTTAAGGAGCATCATGGAGATGTATGGAACCTTGCTAAATTCAGT
TACTTTGAATTTATGGTTTGCTTGATTTTCAGCTTTTTGACTGCACTCCTAATTGTAGTGATCTGTCAAGCAATCAC
CTCTCTGGTCCCTTACCTCAGGAACTTGGTCAGCTTCCAAACCTGTACTTGCTGTAAGTACTTCAGATTTACTTTGA
GACTCTCATCCTCTTAGCTATTGGTAATAATCTGTAGAGTGAATAAGTATGAACTTCTAAACTCGGTAAGTAGATTT
TAAAATTATTTTGGATGCCATTTTCAAAAAGTAGAGATGAAGTTGGTTGTGTTGCTATTGTTTTATATGATCTGGC
TTCATATGTTCATTACTTTGGTGTTCTCAGTTTTGCTTTATATTGCATTATTGCACGGGGCTCAAATGCAGCATATC
TCTATCTTCTTTTTCTTGTGGCCTTAATTATTTTACAAATTAATGAACAGGAAGGTGGAAAACAACAATTTATCAGG
CGATGTGATGTCCTTAGCCAGTTGCCTCAGTCTAAATATCTTGTGAGTTTTCAAGTCCATAGTAAGACACCAGTACA
AACAAATGTTTTGTTAATCTAATCAACCTCATGTTAGCAGAAATGTCTCATACAATAATCTGGGAGGGAATATTCCA
ACCGGCAATAATTTCTCTAGATTTTCACCAGACAGGTAAGTGGAGCTATTAAGATTTTACACAAGTCACAAGCATTT
ATTGGTTTTTAATTCTTTGCTTCTAATTTCTTCCTTTTGCTATGTCTCCGAAAAAGCTTCATAGGAAATCCAGATCT
GTGTGGGTATTGGCTCACTTCTCCTTGTCATGCATCTCATCCGGCAGAGCGAGGTCTGATCAAACTGTAACAATCAT
TTGGCCTTTACTCTATTGCATTTTTGAAGTTCCATTTCACTTTAGACATCTGCAACATTTATTAAGTGTGATGGACA
GATATATTGATTAATGAGGAATTATCCCTTGGTTGAGCAAACTTAATTCTGTGTTAGCCTGGTAGTAGGGTGTACCA
CAAGGTTTGTCGTCATGGTTTCCTATGTTCACAATCCCTGATTGTAACATTTAGATGTGTACACATATCTAATTAAC
ATGAAATAATCTTCATTTGCTGGAGTTACATTGACGTAAAGATGCGTTAGCTGTCAAATGAAACTGCATTTGTTTTA
TTTCCATCATCAGTACATTAATTAAGTGCATAAATATTTTAACAGTTGTTGAATGATATAAGATGAATTTATTGGAC
AATTGCAGTTTCAATTTCTAAAGCAGCAATACTTGGTATTGCTCTGGGTGGCTTGGTGATTCTTCTGATGATACTAG
TAGCAGCATGCCGGCCACAGAAACCTGCACCTTTCATGGAAGGATCTATTGATAAACCAGGTACAATATTTTCCGGA
CGGTTGGATAGTGTTTGGAGATGTTCATGTCAGAAGGACAGTCGTCAGAGTTTATTGAAGTTGCCATGTATTGATTG
TTTAACGTTTTTGATGAACAGTTTATTACTCATCTCCAAAACTTGTGATCCTTCATATGAACATGGCACTTCATGTT
TACGAGGACATTATGAGGATGACTGAGAACTTGAGTGAGAAGTATATAATTGGTTGTGGAGCATCAAGTACTGTATA
TAAATGTGTTTTGAAAAATTGCAAGCCTGTAGCTATCAAGAAGTTGTACTCTCACAACCCGCAATACTTGAAGGAAT
TTGAGACTGAACTTGAGACAGTTGGGAGTATTAAGCATCGTAATCTTGTCTGTCTCCAAGGATATTCTCTTTCTCCA
TCTGGCCATCTTCTTTTCTATGACTACATGGAAAATGGTAGCCTTTGGGATTTGCTTCATGGTTAGTAAATCCAAAA
TGGTTAAGGTGATTGATGCATTGATTTTGTGTTAAAGCATCAAGTAATCAGTCCTCTTGTATCTTTTTTTGCAGGTC
CTACAACAAAGAAGAAAAAGCTTGATTGGGTTACTCGCCTTCGAATTGCATTGGGATCAGCTCAAGGGCTTGCATAT
CTTCATCATGATTGTAGCCCTCGAATAATCCACCGTGATGTTAAATCATCTAATATCTTGTTGGACAAAGACTTTGA
GGCTCATCTGACTGATTTTGGCATAGCTAAAAGCTTATGCATATCAAAGACCTATACGTCCACGTACATTATGGGAA
CCATTGGTTACATTGATCCAGAGTATGCTCGCACTTCTCGCTTGACAGAGAAGTCTGATGTTTACAGCTATGGTATT
GTTCTATTGGAATTGCTCACTGGAAGGAAAGCTGTAGATAATGAATCTAATCTACATCATTTGGTAAGCTCTTGCAA
TTTAGTTAATATGAACTTGTCCTATGATGTTTATTCATATAATTATATTAAGATTCAATTCAATTGATCATAACAGT
TTTGCATATATGTTACAGATTCTAACTAAGGCAGCAAACGATGCTGTAATGGAAACAGTGGATCCTGAGATAACATG
CACATGCAAAGATCTTGCAGATGTGAAGAAGGTTTTTCAGCTTGCCCTTCTATGTTCCAAAAGACAGCCTGCTGAGA
GACCAACAATGCATGAAGTGGCAAGAGTACTTGAAAGCCTAATACCCGTCGCTGAAACGAAACAGCCAAATCCAACC
CCCTCACTTGCATTACTCCCATCTGCTAAGGTACCTTGTTACATGGATGAATATGTCAACCTCAAGACACCCCACCT
AGTGAACTGTTCATCCATGAGCACTTCAGATGCCCAACTTTTCCTCAAGTTTGGAGAGGTCATATCCCAGAATAGTG
GCTGA (SEQ ID NO: 34)

Nucleic acid sequence of a *S. lycopersicum* cv. Sweet100 gene allele sler$^{CR-1}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTCCTGTATTGGACAGCTCAAAGGCCTTGTA
TCTATTGATATGAGGGGAAATCGCCTTTCTGGCCAGATACCAGATTTGGTGACTGTTCAGCACTGAAAAATTTGGAC
CTTTCCTTCAATGAGCTTTATGGTGATATTCCCTTCTCCATATCTAAACTCAAGCAACTGGAATATCTGATTTTGAA
GAATAATCAATTGATTGGACCAATTCCATCTACATTGTCACAGATCCCTAACTTGAAGGTCTTGGACCTGGCTCAAA
ATAGGTTAAGTGGAGAAATTCCTAGGCTGATATACTGGAACGAAGTCCTGCAGTATCTGGGACTGCGTGGTAACAAC
TTGGGTGGATCCCTTTCTCCTGATATGTGTCAGCTCACCGGCCTGTGGTACTTTGATGTTCGGAACAATAGTTTGAC
TGGTTCCATTCCTCAAAATATTGGCAACTGTACTGCCTTCCAGGTTCTAGATTTGTCTTATAATGATTTGACCGGAG
AGATTCCTTTCAATATTGGTTTCCTGCAAGTAGCGACCTTGTCTTTGCAAGGTAATCGTCTTTCAGGGCAGATCCCT
TCTGTAATTGGATTGATGCAAGCTCTTGCAGTTTTGGACTTGAGCTGCAATATGTTGAGTGGAACAATTCCTTCAAT
TCTTGGGAATTTGACTTACACAGAGAAATTGTATCTACACGGGAACAAGCTATCTGGTTCCATTCCTCCAGAGCTGG
GAAATATGACAAAGCTCCACTACTTGGAATTGAATGATAACCAACTTACTGGACGCATACCACCAGAACTTGGAAAG
CTGACAGAATTGTTTGACTTAAATGTTGCAAACAACCACCTAGATGGGCCCATACCTTCCAATATTAGCTCATGTAC
CAATTTGAATAGTCTCAACGTTCATGGAAACAAATTGAATGGTACTATTCCACCTGCTTTTCAGAAGCTGGAAAGTA
TGACCTATCTTAATCTCTCCTCCAACAATCTCAAAGGCCCAATTCCAATTGAGCTATCTCGTATTGGGAATGTAGAT
ACACTGGACTTATCAAACAACAGGATCAGTGGTCCTATACCTATGTCCCTTGGTGATTTGGAACATCTTCTTAAACT
GAACTTAAGCAAGAATGAAATAAATGGAAACTTACCAGCTGAATTTGGCAATTTAAGGAGCATCATGGAGATTGATC
TGTCAAGCAATCACCTCTCTGGTCCCTTACCTCAGGAACTTGGTCAGCTTCCAAACCTGTACTTGCTGAAGGTGGAA
AACAACAATTTATCAGGCGATGTGATGTCCTTAGCCAGTTGCCTCAGTCTAAATATCTTAAATGTCTCATACAATAA
TCTGGGAGGGAATATTCCAACCGGCAATAATTTCTCTAGATTTTCACCAGACAGCTTCATAGGAAATCCAGATCTGT
GTGGGTATTGGCTCACTTCTCCTTGTCATGCATCTCATCCGGCAGAGCGAGTTTCAATTTCTAAAGCAGCAATACTT
GGTATTGCTCTGGGTGGCTTGGTGATTCTTCTGATGATACTAGTAGCAGCATGCCGGCCACAGAAACCTGCACCTTT
CATGGAAGGATCTATTGATAAACCAGTTTATTACTCATCTCCAAAACTTGTGATCCTTCATATGAACATGGCACTTC
ATGTTTACGAGGACATTATGAGGATGACTGAGAACTTGAGTGAGAAGTATATAATTGGTTGTGGAGCATCAAGTACT
GTATATAAATGTGTTTTGAAAAATTGCAAGCCTGTAGCTATCAAGAAGTTGTACTCTCACAACCCGCAATACTTGAA
GGAATTTGAGACTGAACTTGAGACAGTTGGGAGTATTAAGCATCGTAATCTTGTCTGTCTCCAAGGATATTCTCTTT
CTCCATCTGGCCATCTTCTTTTCTATGACTACATGGAAAATGGTAGCCTTTGGGATTTGCTTCATGGTCCTACAACA
AAGAAGAAAAAGCTTGATTGGGTTACTCGCCTTCGAATTGCATTGGGATCAGCTCAAGGGCTTGCATATCTTCATCA
TGATTGTAGCCCTCGAATAATCCACCGTGATGTTAAATCATCTAATATCTTGTTGGACAAAGACTTTGAGGCTCATC
TGACTGATTTTGGCATAGCTAAAAGCTTATGCATATCAAAGACCTATACGTCCACGTACATTATGGGAACCATTGGT
TACATTGATCCAGAGTATGCTCGCACTTCTCGCTTGACAGAGAAGTCTGATGTTTACAGCTATGGTATTGTTCTATT
GGAATTGCTCACTGGAAGGAAAGCTGTAGATAATGAATCTAATCTACATCATTTGATTCTAACTAAGGCAGCAAACG
ATGCTGTAATGGAAACAGTGGATCCTGAGATAACATGCACATGCAAAGATCTTGCAGATGTGAAGAAGGTTTTTCAG
CTTGCCCTTCTATGTTCCAAAAGACAGCCTGCTGAGAGACCAACAATGCATGAAGTGGCAAGAGTACTTGAAAGCCT
AATACCCGTCGCTGAAACGAAACAGCCAAATCCAACCCCCTCACTTGCATTACTCCCATCTGCTAAGGTACCTTGTT -continued ACATGGATGAATATGTCAACCTCAAGACACCCCACCTAGTGAACTGTTCATCCATGAGCACTTCAGATGCCCAACTT
TTCCTCAAGTTTGGAGAGGTCATATCCCAGAATAGTGGCTGA (SEQ ID NO: 35)

Amino acid sequence for a polypeptide encoded by a *S. lycopersicum* cv. Sweet100 gene allele sler$^{CR-1}$ coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSPVLDSSKALYLLI* (SEQ ID NO: 36)

*S. lycopersicum* cv. Sweet100 gene allele sler$^{CR-2}$
Nucleic acid sequence of a *S. lycopersicum* cv. Sweet100 gene allele sler$^{CR-2}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTTATTGGACAGCTCAAAGGCCTTGTATCTATGTAATATCTCCTCCCATTATCTCACAATTACC
CTTTTTGTTTGATCTTTTGACTTAGTGCACATTATAGACTATGCCTGTTAATTTTTTTTTGAAGTGATATGAGGGGA
AATCGCCTTTCTGGCCAGATACCAGATTTGGTGACTGTTCAGCACTGAAAAATTTGTAAGTATGAAATGCTTCTGAA
TCTTGTGTTATTGTTTGGAAAAATAAGTAACCATTTTTTCCCTTAGGGACCTTTCCTTCAATGAGCTTTATGGTGAT
ATTCCCTTCTCCATATCTAAACTCAAGCAACTGGAATATCTGTAAGTTTTGATACTCTCCTTCTTCTAAATGTTGTA
TTATTTGCTTTCCGAGATTGTTAGTTGATTATGCTCGTCTTATTCAACTTAGGATTTTGAAGAATAATCAATTGATT
GGACCAATTCCATCTACATTGTCACAGATCCCTAACTTGAAGGTCTTGTAAGTATATTCTCTCTGCTTTGTCATGAT
ATTGGTAGATTATGAATAATTTTAGTTTGATCCAAGAACTTCCTCCAGGGACCTGGCTCAAAATAGGTTAAGTGGAG
AAATTCCTAGGCTGATATACTGGAACGAAGTCCTGCAGTATCTGTGAGTGTTTTAATCCGGTGTTCCTCTTCTTCCT
GTTTGTTTTAACCTTAGGACACTTTCATTTCGTATATGGATATGATTACATCTGTTGTATGTTTTTATTCATATAGG
GGACTGCGTGGTAACAACTTGGGTGGATCCCTTTCTCCTGATATGTGTCAGCTCACCGGCCTGTGGTACTTGTAAGT
TTGTAATCCTGTTGCTCTTAAGATCTTACTTTAGTTCCTCTAGGTGATGACATTAACCATTGTTCATTGTGTTGTAC
AGTGATGTTCGGAACAATAGTTTGACTGGTTCCATTCCTCAAAATATTGGCAACTGTACTGCCTTCCAGGTTCTGTA
AGTATCTAAATCAATTGAATGAAGTTTGACTATATTCTGTATGTTTGGTTGGCATAACACCTTGTTTTGTTCTGTCA
GAGATTTGTCTTATAATGATTTGACCGGAGAGATTCCTTTCAATATTGGTTTCCTGCAAGTAGCGACCTTGTAAGTT
TATGCTGCTTCTCTTCATTACAAACTATTCAATATATGGTTGTTTGAAGTGTACTTTCATCATTCCAGGTCTTTGCA
AGGTAATCGTCTTTCAGGGCAGATCCCTTCTGTAATTGGATTGATGCAAGCTCTTGCAGTTTTGTGAGTGTTTTGTG
TCTTGATATCTCAATCTAATGCTACTGAATCTAATTCTTGGAAACCATTATAATGCATCTGTTATTTAAGTTTTCTG
ACCCTTTTACTGTCAGGGACTTGAGCTGCAATATGTTGAGTGGAACAATTCCTTCAATTCTTGGGAATTTGACTTAC
ACAGAGAAATTGTTAGTACTTCAACATTATTAAAAGCAATTTGGATCATTTTGTGCTTCCTAAATTGTGTAGTGGAT
CAATTACTGTAAGTTCGCATTGTATTGCAGGTATCTACACGGGAACAAGCTATCTGGTTCCATTCCTCCAGAGCTGG
GAAATATGACAAAGCTCCACTACTTGTATGAATGCCTTCTATCAATCATTTTTTGTTAGCTTTGTTTTGTTCTTCCT
GTTCAAACCCTTTTAAATGAATGCTTACCATTTAGAAGCATTTGTTTGATTATTTAGCCTTTGGGCAACCACGGATT
TGAATGATAGAAAGCTGTTATGAGAATTTTTATTAAGAGACTTTCTTCAACCTTAAGGCTCAAAGATGGTAATTTGC
AGGGAATTGAATGATAACCAACTTACTGGACGCATACCACCAGAACTTGGAAAGCTGACAGAATTGTTTGACTTGTA
AATCCCGTTTCTCTTCATCTTCTACTTTGGACTTGTTAACATCATTATTTATTTACTCATGTTGTATGTTTCAGAAA
TGTTGCAAACAACCACCTAGATGGGCCCATACCTTCCAATATTAGCTCATGTACCAATTTGAATAGTCTGTGAGTGT
TTTTAATGTCCGAAGTGTTTCAATTATGCACGACCATGCTTGTTTGGTAGTTATTGACACCTGATTTTGTTGCAGCA
ACGTTCATGGAAACAAATTGAATGGTACTATTCCACCTGCTTTTCAGAAGCTGGAAAGTATGACCTATCTGTAAGTT
CTTACTTTCTGATCTTTTTCTTTTGAAGAATTATGTTTAAGGTTATCGAAGTTACCGTCCATGCTGTTGAGCAAGAT
TGTAAACTTACTGTGCCTTGTATATAAATTTTACTGGCGTTGTATTATTGAAAAAATCATTTTATTTATATTGCTCT
CAAATCATACTGGCTTATATCCATTCATGAAGAATCATTTCTACTGTCTGAAGTTTTCAGCTATATGTATCGAAAAA
ATTTAGTTATTATATAGTTTATTTTGAGCCTCTGCATCATCTATTTGTGAATTTCATTTGCTTATTCTGCATACTCT
CAGCATTAACCGTCTCTTCTTTTGTTAATTGCTTTAGTAATCTCTCCTCCAACAATCTCAAAGGCCCAATTCCAATT
GAGCTATCTCGTATTGGGAATGTAGATACACTGTAAGTGCAAACTTTCTCATCTACTTTCATTTCTCTCATTGCAAT
TATGGTTGCGGGGAAAGCACTTTTTGTCAGTCTTAAGAATCTTCAACATTTTTTGGCTTAGGGACTTATCAAACAAC
AGGATCAGTGGTCCTATACCTATGTCCCTTGGTGATTTGGAACATCTTCTTAAACTGTGAGCATAACCGTCAAGTTG
TTATGTTAGCATCATATATCTGTTGTACTTACATCCCTTTTGTCAATGCTGTAGGAACTTAAGCAAGAATGAAATAA
ATGGAAACTTACCAGCTGAATTTGGCAATTTAAGGAGCATCATGGAGATGTATGGAACCTTGCTAAATTCAGTTACT
TTGAATTTATGGTTTGCTTGATTTTCAGCTTTTTGACTGCACTCCTAATTGTAGTGATCTGTCAAGCAATCACCTCT
CTGGTCCCTTACCTCAGGAACTTGGTCAGCTTCCAAACCTGTACTTGCTGTAAGTACTTCAGATTTACTTTGAGACT
CTCATCCTCTTAGCTATTGGTAATAATCTGTAGAGTGAATAAGTATGAACTTCTAAACTCGGTAAGTAGATTTTAAA
ATTATTTTGGATGCCATTTTCAAAAAAGTAGAGATGAAGTTGGTTGTGTTGCTATTGTTTTATATGATCTGGCTTCA
TATGTTCATTACTTTGGTGTTCTCAGTTTTGCTTTATATTGCATTATTGCACGGGGCTCAAATGCAGCATATCTCTA
TCTTCTTTTTCTTGTGGCCTTAATTATTTTACAAATTAATGAACAGGAAGGTGGAAAACAACAATTTATCAGGCGAT
GTGATGTCCTTAGCCAGTTGCCTCAGTCTAAATATCTTGTGAGTTTTCAAGTCCATAGTAAGACACCAGTACAAACA
AATGTTTTGTTAATCTAATCAACCTCATGTTAGCAGAAATGTCTCATACAATAATCTGGGAGGGAATATTCCAACCG
GCAATAATTTCTCTAGATTTTCACCAGACAGGTAAGTGGAGCTATTAAGATTTTACACAAGTCACAAGCATTTATTG
GTTTTTAATTCTTTGCTTCTAATTTCTTCCTTTTGCTATGTCTCCGAAAAAGCTTCATAGGAAATCCAGATCTGTGT
GGGTATTGGCTCACTTCTCCTTGTCATGCATCTCATCCGGCAGAGCGAGGTCTGATCAAACTGTAACAATCATTTGG
CCTTTACTCTATTGCATTTTTGAAGTTCCATTTCACTTTAGACATCTGCAACATTTATTAAGTGTGATGGACAGATA
TATTGATTAATGAGGAATTATCCCTTGGTTGAGCAAACTTAATTCTGTGTTAGCCTGGTAGTAGGGTGTACCACAAG
GTTTGTCGTCATGGTTTCCTATGTTCACAATCCCTGATTGTAACATTTAGATGTGTACACATATCTAATTAACATGA
AATAATCTTCATTTGCTGGAGTTACATTGACGTAAAGATGCGTTAGCTGTCAAATGAAACTGCATTTGTTTTATTTC
CATCATCAGTACATTAATTAAGTGCATAAATATTTTAACAGTTGTTGAATGATATAAGATGAATTTATTGGACAATT
GCAGTTTCAATTTCTAAAGCAGCAATACTTGGTATTGCTCTGGGTGGCTTGGTGATTCTTCTGATGATACTAGTAGC
AGCATGCCGGCCACAGAAACCTGCACCTTTCATGGAAGGATCTATTGATAAACCAGGTACAATATTTTCCGGACGGT
TGGATAGTGTTTGGAGATGTTCATGTCAGAAGGACAGTCGTCAGAGTTTATTGAAGTTGCCATGTATTGATTGTTTA
ACGTTTTTGATGAACAGTTTATTACTCATCTCCAAAACTTGTGATCCTTCATATGAACATGGCACTTCATGTTTACG
AGGACATTATGAGGATGACTGAGAACTTGAGTGAGAAGTATATAATTGGTTGTGGAGCATCAAGTACTGTATATAAA
TGTGTTTTGAAAAATTGCAAGCCTGTAGCTATCAAGAAGTTGTACTCTCACAACCCGCAATACTTGAAGGAATTTGA
GACTGAACTTGAGACAGTTGGGAGTATTAAGCATCGTAATCTTGTCTGTCTCCAAGGATATTCTCTTTCTCCATCTG -continued GCCATCTTCTTTTCTATGACTACATGGAAAATGGTAGCCTTTGGGATTTGCTTCATGGTTAGTAAATCCAAAATGGT
TAAGGTGATTGATGCATTGATTTTGTGTTAAAGCATCAAGTAATCAGTCCTCTTGTATCTTTTTTTGCAGGTCCTAC
AACAAAGAAGAAAAAGCTTGATTGGGTTACTCGCCTTCGAATTGCATTGGGATCAGCTCAAGGGCTTGCATATCTTC
ATCATGATTGTAGCCCTCGAATAATCCACCGTGATGTTAAATCATCTAATATCTTGTTGGACAAAGACTTTGAGGCT
CATCTGACTGATTTTGGCATAGCTAAAAGCTTATGCATATCAAAGACCTATACGTCCACGTACATTATGGGAACCAT
TGGTTACATTGATCCAGAGTATGCTCGCACTTCTCGCTTGACAGAGAAGTCTGATGTTTACAGCTATGGTATTGTTC
TATTGGAATTGCTCACTGGAAGGAAAGCTGTAGATAATGAATCTAATCTACATCATTTGGTAAGCTCTTGCAATTTA
GTTAATATGAACTTGTCCTATGATGTTTATTCATATAATTATATTAAGATTCAATTCAATTGATCATAACAGTTTTG
CATATATGTTACAGATTCTAACTAAGGCAGCAAACGATGCTGTAATGGAAACAGTGGATCCTGAGATAACATGCACA
TGCAAAGATCTTGCAGATGTGAAGAAGGTTTTTCAGCTTGCCCTTCTATGTTCCAAAAGACAGCCTGCTGAGAGACC
AACAATGCATGAAGTGGCAAGAGTACTTGAAAGCCTAATACCCGTCGCTGAAACGAAACAGCCAAATCCAACCCCCT
CACTTGCATTACTCCCATCTGCTAAGGTACCTTGTTACATGGATGAATATGTCAACCTCAAGACACCCCCACCTAGTG
AACTGTTCATCCATGAGCACTTCAGATGCCCAACTTTTCCTCAAGTTTGGAGAGGTCATATCCCAGAATAGTGGCTG
A (SEQ ID NO: 37)

Nucleic acid sequence of a *S. lycopersicum* cv. Sweet100 gene allele sler$^{CR-2}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTTATTGGACAGCTCAAAGGCCTTGTATCTA
TTGATATGAGGGGAAATCGCCTTTCTGGCCAGATACCAGATTTGGTGACTGTTCAGCACTGAAAAATTTGGACCTTT
CCTTCAATGAGCTTTATGGTGATATTCCCTTCTCCATATCTAAACTCAAGCAACTGGAATATCTGATTTTGAAGAAT
AATCAATTGATTGGACCAATTCCATCTACATTGTCACAGATCCCTAACTTGAAGGTCTTGGACCTGGCTCAAAATAG
GTTAAGTGGAGAAATTCCTAGGCTGATATACTGGAACGAAGTCCTGCAGTATCTGGGACTGCGTGGTAACAACTTGG
GTGGATCCCTTTCTCCTGATATGTGTCAGCTCACCGGCCTGTGGTACTTTGATGTTCGGAACAATAGTTTGACTGGT
TCCATTCCTCAAAATATTGGCAACTGTACTGCCTTCCAGGTTCTAGATTTGTCTTATAATGATTTGACCGGAGAGAT
TCCTTTCAATATTGGTTTCCTGCAAGTAGCGACCTTGTCTTTGCAAGGTAATCGTCTTTCAGGGCAGATCCCTTCTG
TAATTGGATTGATGCAAGCTCTTGCAGTTTTGGACTTGAGCTGCAATATGTTGAGTGGAACAATTCCTTCAATTCTT
GGGAATTTGACTTACACAGAGAAATTGTATCTACACGGGAACAAGCTATCTGGTTCCATTCCTCCAGAGCTGGGAAA
TATGACAAAGCTCCACTACTTGGAATTGAATGATAACCAACTTACTGGACGCATACCACCAGAACTTGGAAAGCTGA
CAGAATTGTTTGACTTAAATGTTGCAAACAACCACCTAGATGGGCCCATACCTTCCAATATTAGCTCATGTACCAAT
TTGAATAGTCTCAACGTTCATGGAAACAAATTGAATGGTACTATTCCACCTGCTTTTCAGAAGCTGGAAAGTATGAC
CTATCTTAATCTCTCCTCCAACAATCTCAAAGGCCCAATTCCAATTGAGCTATCTCGTATTGGGAATGTAGATACAC
TGGACTTATCAAACAACAGGATCAGTGGTCCTATACCTATGTCCCTTGGTGATTTGGAACATCTTCTTAAACTGAAC
TTAAGCAAGAATGAAATAAATGGAAACTTACCAGCTGAATTTGGCAATTTAAGGAGCATCATGGAGATTGATCTGTC
AAGCAATCACCTCTCTGGTCCCTTACCTCAGGAACTTGGTCAGCTTCCAAACCTGTACTTGCTGAAGGTGGAAAACA
ACAATTTATCAGGCGATGTGATGTCCTTAGCCAGTTGCCTCAGTCTAAATATCTTAAATGTCTCATACAATAATCTG
GGAGGGAATATTCCAACCGGCAATAATTTCTCTAGATTTTCACCAGACAGCTTCATAGGAAATCCAGATCTGTGTGG
GTATTGGCTCACTTCTCCTTGTCATGCATCTCATCCGGCAGAGCGAGTTTCAATTTCTAAAGCAGCAATACTTGGTA
TTGCTCTGGGTGGCTTGGTGATTCTTCTGATGATACTAGTAGCAGCATGCCGGCCACAGAAACCTGCACCTTTCATG
GAAGGATCTATTGATAAACCAGTTTATTACTCATCTCCAAAACTTGTGATCCTTCATATGAACATGGCACTTCATGT
TTACGAGGACATTATGAGGATGACTGAGAACTTGAGTGAGAAGTATATAATTGGTTGTGGAGCATCAAGTACTGTAT
ATAAATGTGTTTTGAAAAATTGCAAGCCTGTAGCTATCAAGAAGTTGTACTCTCACAACCCGCAATACTTGAAGGAA
TTTGAGACTGAACTTGAGACAGTTGGGAGTATTAAGCATCGTAATCTTGTCTGTCTCCAAGGATATTCTCTTTCTCC
ATCTGGCCATCTTCTTTTCTATGACTACATGGAAAATGGTAGCCTTTGGGATTTGCTTCATGGTCCTACAACAAAGA
AGAAAAAGCTTGATTGGGTTACTCGCCTTCGAATTGCATTGGGATCAGCTCAAGGGCTTGCATATCTTCATCATGAT
TGTAGCCCTCGAATAATCCACCGTGATGTTAAATCATCTAATATCTTGTTGGACAAAGACTTTGAGGCTCATCTGAC
TGATTTTGGCATAGCTAAAAGCTTATGCATATCAAAGACCTATACGTCCACGTACATTATGGGAACCATTGGTTACA
TTGATCCAGAGTATGCTCGCACTTCTCGCTTGACAGAGAAGTCTGATGTTTACAGCTATGGTATTGTTCTATTGGAA
TTGCTCACTGGAAGGAAAGCTGTAGATAATGAATCTAATCTACATCATTTGATTCTAACTAAGGCAGCAAACGATGC
TGTAATGGAAACAGTGGATCCTGAGATAACATGCACATGCAAAGATCTTGCAGATGTGAAGAAGGTTTTTCAGCTTG
CCCTTCTATGTTCCAAAAGACAGCCTGCTGAGAGACCAACAATGCATGAAGTGGCAAGAGTACTTGAAAGCCTAATA
CCCGTCGCTGAAACGAAACAGCCAAATCCAACCCCCTCACTTGCATTACTCCCATCTGCTAAGGTACCTTGTTACAT
GGATGAATATGTCAACCTCAAGACACCCCCACCTAGTGAACTGTTCATCCATGAGCACTTCAGATGCCCAACTTTTCC
TCAAGTTTGGAGAGGTCATATCCCAGAATAGTGGCTGA (SEQ ID NO: 38)

Amino acid sequence for a polypeptide encoded by a *S. lycopersicum* cv. Sweet100 gene allele sler$^{CR-2}$ coding sequence
MASFLLQRCNLLFEVLLILGFLIFFSFGSVVSDDGSALLEIKKSIRDVENVLYDWTDSPSSDYCAWRGVTCDNVTFN
VVQLNLSSLNLDGELSYWTAQRPCIY* (SEQ ID NO: 39)

*S. lycopersicum* cv. Sweet100 gene allele sler$^{CR-3}$
Nucleic acid sequence of a *S. lycopersicum* cv. Sweet100 gene allele sler$^{CR-3}$
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTGAGTAGAGTAGAGTAGTAGAACTTTCTGCTTCTTATGTTTTAGTTTAAT
GTTTTGTTTAAGATGTTAAAAAGACAAAGTGTGCTTTTTTTAATCATTTTTTAAATGGTGGTTTTTGATTAATCCCA
CGTTTTGTAGTTGTTATTTGTTAAAGGTTTATTTTTTTGTCTCATTATTATAATAATAATTGGGAAATAGGTTCTGC
ATTGTTGGAAATTAAGAAGTCAATTAGGGACGTGGAGAATGTGTTGTATGACTGGACTGATTCTCCTTCATCTGATT
ACTGTGCCTGGAGAGGTGTTACCTGTGATAATGTCACCTTCAATGTTGTTCAACTGTAAGACATAACTCAAAAACAC
TATCATTTGGGATTCTTTAGTTATAAAGTTGTAATCTTTTGACATTATCTTGTAGTAATCTTTCGAGTTTAAATCTT
GATGGGGAGTTGTCTATTGGACAGCTCAAAGGCCTTGTATCTATGTAATATCTCCTCCCATTATCTCACAATTACCC
TTTTTGTTTGATCTTTTGACTTAGTGCACATTATAGACTATGCCTGTTAATTTTTTTTTGAAGTGATATGAGGGGAA
ATCGCCTTTCTGGCCAGATACCAGATGAGATTGGTGACTGTTCAGCACTGAAAAATTTGTAAGTATGAAATGCTTCT
GAATCTTGTGTTATTGTTTGGAAAAATAAGTAACCATTTTTTCCCTTAGGGACCTTTCCTTCAATGAGCTTTATGGT
GATATTCCCTTCTCCATATCTAAACTCAAGCAACTGGAATATCTGTAAGTTTTGATACTCTCCTTCTTCTAAATGTT
GTATTATTTGCTTTCCGAGATTGTTAGTTGATTATGCTCGTCTTATTCAACTTAGGATTTTGAAGAATAATCAATTG
ATTGGACCAATTCCATCTACATTGTCACAGATCCCTAACTTGAAGGTCTTGTAAGTATATTCTCTCTGCTTTGTCAT
GATATTGGTAGATTATGAATAATTTTAGTTTGATCCAAGAACTTCCTCCAGGGACCTGGCTCAAAATAGGTTAAGTG
GAGAAATTCCTAGGCTGATATACTGGAACGAAGTCCTGCAGTATCTGTGAGTGTTTTAATCCGGTGTTCCTCTTCTT -continued CCTGTTTGTTTTAACCTTAGGACACTTTCATTTCGTATATGGATATGATTACATCTGTTGTATGTTTTTATTCATAT
AGGGGACTGCGTGGTAACAACTTGGGTGGATCCCTTTCTCCTGATATGTGTCAGCTCACCGGCCTGTGGTACTTGTA
AGTTTGTAATCCTGTTGCTCTTAAGATCTTACTTTAGTTCCTCTAGGTGATGACATTAACCATTGTTCATTGTGTTG
TACAGTGATGTTCGGAACAATAGTTTGACTGGTTCCATTCCTCAAAATATTGGCAACTGTACTGCCTTCCAGGTTCT
GTAAGTATCTAAATCAATTGAATGAAGTTTGACTATATTCTGTATGTTTGGTTGGCATAACACCTTGTTTTGTTCTG
TCAGAGATTTGTCTTATAATGATTTGACCGGAGAGATTCCTTTCAATATTGGTTTCCTGCAAGTAGCGACCTTGTAA
GTTTATGCTGCTTCTCTTCATTACAAACTATTCAATATATGGTTGTTTGAAGTGTACTTTCATCATTCCAGGTCTTT
GCAAGGTAATCGTCTTTCAGGGCAGATCCCTTCTGTAATTGGATTGATGCAAGCTCTTGCAGTTTTGTGAGTGTTTT
GTGTCTTGATATCTCAATCTAATGCTACTGAATCTAATTCTTGGAAACCATTATAATGCATCTGTTATTTAAGTTTT
CTGACCCTTTTACTGTCAGGGACTTGAGCTGCAATATGTTGAGTGGAACAATTCCTTCAATTCTTGGGAATTTGACT
TACACAGAGAAATTGTTAGTACTTCAACATTATTAAAAGCAATTTGGATCATTTTGTGCTTCCTAAATTGTGTAGTG
GATCAATTACTGTAAGTTCGCATTGTATTGCAGGTATCTACACGGGAACAAGCTATCTGGTTCCATTCCTCCAGAGC
TGGGAAATATGACAAAGCTCCACTACTTGTATGAATGCCTTCTATCAATCATTTTTTGTTAGCTTTGTTTTGTTCTT
CCTGTTCAAACCCTTTTAAATGAATGCTTACCATTTAGAAGCATTTGTTTGATTATTTAGCCTTTGGGCAACCACGG
ATTTGAATGATAGAAAGCTGTTATGAGAATTTTTATTAAGAGACTTTCTTCAACCTTAAGGCTCAAAGATGGTAATT
TGCAGGGAATTGAATGATAACCAACTTACTGGACGCATACCACCAGAACTTGGAAAGCTGACAGAATTGTTTGACTT
GTAAATCCCGTTTCTCTTCATCTTCTACTTTGGACTTGTTAACATCATTATTTATTTACTCATGTTGTATGTTTCAG
AAATGTTGCAAACAACCACCTAGATGGGCCCATACCTTCCAATATTAGCTCATGTACCAATTTGAATAGTCTGTGAG
TGTTTTTAATGTCCGAAGTGTTTCAATTATGCACGACCATGCTTGTTTGGTAGTTATTGACACCTGATTTTGTTGCA
GCAACGTTCATGGAAACAAATTGAATGGTACTATTCCACCTGCTTTTCAGAAGCTGGAAAGTATGACCTATCTGTAA
GTTCTTACTTTCTGATCTTTTTCTTTTGAAGAATTATGTTTAAGGTTATCGAAGTTACCGTCCATGCTGTTGAGCAA
GATTGTAAACTTACTGTGCCTTGTATATAAATTTTACTGGCGTTGTATTATTGAAAAAATCATTTTATTTATATTGC
TCTCAAATCATACTGGCTTATATCCATTCATGAAGAATCATTTCTACTGTCTGAAGTTTTCAGCTATATGTATCGAA
AAAATTTAGTTATTATATAGTTTATTTTGAGCCTCTGCATCATCTATTTGTGAATTTCATTTGCTTATTCTGCATAC
TCTCAGCATTAACCGTCTCTTCTTTTGTTAATTGCTTTAGTAATCTCTCCTCCAACAATCTCAAAGGCCCAATTCCA
ATTGAGCTATCTCGTATTGGGAATGTAGATACACTGTAAGTGCAAACTTTCTCATCTACTTTCATTTCTCTCATTGC
AATTATGGTTGCGGGGAAAGCACTTTTTGTCAGTCTTAAGAATCTTCAACATTTTTTGGCTTAGGGACTTATCAAAC
AACAGGATCAGTGGTCCTATACCTATGTCCCTTGGTGATTTGGAACATCTTCTTAAACTGTGAGCATAACCGTCAAG
TTGTTATGTTAGCATCATATATCTGTTGTACTTACATCCCTTTTGTCAATGCTGTAGGAACTTAAGCAAGAATGAAA
TAAATGGAAACTTACCAGCTGAATTTGGCAATTTAAGGAGCATCATGGAGATGTATGGAACCTTGCTAAATTCAGTT
ACTTTGAATTTATGGTTTGCTTGATTTTCAGCTTTTTGACTGCACTCCTAATTGTAGTGATCTGTCAAGCAATCACC
TCTCTGGTCCCTTACCTCAGGAACTTGGTCAGCTTCCAAACCTGTACTTGCTGTAAGTACTTCAGATTTACTTTGAG
ACTCTCATCCTCTTAGCTATTGGTAATAATCTGTAGAGTGAATAAGTATGAACTTCTAAACTCGGTAAGTAGATTTT
AAAATTATTTTGGATGCCATTTTCAAAAAAGTAGAGATGAAGTTGGTTGTGTTGCTATTGTTTTATATGATCTGGCT
TCATATGTTCATTACTTTGGTGTTCTCAGTTTTGCTTTATATTGCATTATTGCACGGGGCTCAAATGCAGCATATCT
CTATCTTCTTTTTCTTGTGGCCTTAATTATTTTACAAATTAATGAACAGGAAGGTGGAAAACAACAATTTATCAGGC
GATGTGATGTCCTTAGCCAGTTGCCTCAGTCTAAATATCTTGTGAGTTTTCAAGTCCATAGTAAGACACCAGTACAA
ACAAATGTTTTGTTAATCTAATCAACCTCATGTTAGCAGAAATGTCTCATACAATAATCTGGGAGGGAATATTCCAA
CCGGCAATAATTTCTCTAGATTTTCACCAGACAGGTAAGTGGAGCTATTAAGATTTTACACAAGTCACAAGCATTTA
TTGGTTTTTAATTCTTTGCTTCTAATTTCTTCCTTTTGCTATGTCTCCGAAAAAGCTTCATAGGAAATCCAGATCTG
TGTGGGTATTGGCTCACTTCTCCTTGTCATGCATCTCATCCGGCAGAGCGAGGTCTGATCAAACTGTAACAATCATT
TGGCCTTTACTCTATTGCATTTTTGAAGTTCCATTTCACTTTAGACATCTGCAACATTTATTAAGTGTGATGGACAG
ATATATTGATTAATGAGGAATTATCCCTTGGTTGAGCAAACTTAATTCTGTGTTAGCCTGGTAGTAGGGTGTACCAC
AAGGTTTGTCGTCATGGTTTCCTATGTTCACAATCCCTGATTGTAACATTTAGATGTGTACACATATCTAATTAACA
TGAAATAATCTTCATTTGCTGGAGTTACATTGACGTAAAGATGCGTTAGCTGTCAAATGAAACTGCATTTGTTTTAT
TTCCATCATCAGTACATTAATTAAGTGCATAAATATTTTAACAGTTGTTGAATGATATAAGATGAATTTATTGGACA
ATTGCAGTTTCAATTTCTAAAGCAGCAATACTTGGTATTGCTCTGGGTGGCTTGGTGATTCTTCTGATGATACTAGT
AGCAGCATGCCGGCCACAGAAACCTGCACCTTTCATGGAAGGATCTATTGATAAACCAGGTACAATATTTTCCGGAC
GGTTGGATAGTGTTTGGAGATGTTCATGTCAGAAGGACAGTCGTCAGAGTTTATTGAAGTTGCCATGTATTGATTGT
TTAACGTTTTTGATGAACAGTTTATTACTCATCTCCAAAACTTGTGATCCTTCATATGAACATGGCACTTCATGTTT
ACGAGGACATTATGAGGATGACTGAGAACTTGAGTGAGAAGTATATAATTGGTTGTGGAGCATCAAGTACTGTATAT
AAATGTGTTTTGAAAAATTGCAAGCCTGTAGCTATCAAGAAGTTGTACTCTCACAACCCGCAATACTTGAAGGAATT
TGAGACTGAACTTGAGACAGTTGGGAGTATTAAGCATCGTAATCTTGTCTGTCTCCAAGGATATTCTCTTTCTCCAT
CTGGCCATCTTCTTTTCTATGACTACATGGAAAATGGTAGCCTTTGGGATTTGCTTCATGGTTAGTAAATCCAAAAT
GGTTAAGGTGATTGATGCATTGATTTTGTGTTAAAGCATCAAGTAATCAGTCCTCTTGTATCTTTTTTTGCAGGTCC
TACAACAAAGAAGAAAAAGCTTGATTGGGTTACTCGCCTTCGAATTGCATTGGGATCAGCTCAAGGGCTTGCATATC
TTCATCATGATTGTAGCCCTCGAATAATCCACCGTGATGTTAAATCATCTAATATCTTGTTGGACAAAGACTTTGAG
GCTCATCTGACTGATTTTGGCATAGCTAAAAGCTTATGCATATCAAAGACCTATACGTCCACGTACATTATGGGAAC
CATTGGTTACATTGATCCAGAGTATGCTCGCACTTCTCGCTTGACAGAGAAGTCTGATGTTTACAGCTATGGTATTG
TTCTATTGGAATTGCTCACTGGAAGGAAAGCTGTAGATAATGAATCTAATCTACATCATTTGGTAAGCTCTTGCAAT
TTAGTTAATATGAACTTGTCCTATGATGTTTATTCATATAATTATATTAAGATTCAATTCAATTGATCATAACAGTT
TTGCATATATGTTACAGATTCTAACTAAGGCAGCAAACGATGCTGTAATGGAAACAGTGGATCCTGAGATAACATGC
ACATGCAAAGATCTTGCAGATGTGAAGAAGGTTTTTCAGCTTGCCCTTCTATGTTCCAAAAGACAGCCTGCTGAGAG
ACCAACAATGCATGAAGTGGCAAGAGTACTTGAAAGCCTAATACCCGTCGCTGAAACGAAACAGCCAAATCCAACCC
CCTCACTTGCATTACTCCCATCTGCTAAGGTACCTTGTTACATGGATGAATATGTCAACCTCAAGACACCCCACCTA
GTGAACTGTTCATCCATGAGCACTTCAGATGCCCAACTTTTCCTCAAGTTTGGAGAGGTCATATCCCAGAATAGTGG
CTGA (SEQ ID NO: 40)

Nucleic acid sequence of a *S. lycopersicum* cv. Sweet100 gene allele sler$^{CR-3}$ coding sequence
ATGGCATCATTTTTACTCCAAAGATGTAATCTTCTCTTTGAGGTTCTTCTTATTTTGGGGTTCTTGATTTTCTTCAG
CTTTGGTTCTGTGGTGTCTGATGATGGTTCTGCATTGTTGGAAATTAAGAAGTCAATTAGGGACGTGGAGAATGTGT
TGTATGACTGGACTGATTCTCCTTCATCTGATTACTGTGCCTGGAGAGGTGTTACCTGTGATAATGTCACCTTCAAT
GTTGTTCAACTTAATCTTTCGAGTTTAAATCTTGATGGGGAGTTGTCTATTGGACAGCTCAAAGGCCTTGTATCTAT
TGATATGAGGGGAAATCGCCTTTCTGGCCAGATACCAGATGAGATTGGTGACTGTTCAGCACTGAAAAATTTGGACC
TTTCCTTCAATGAGCTTTATGGTGATATTCCCTTCTCCATATCTAAACTCAAGCAACTGGAATATCTGATTTTGAAG
AATAATCAATTGATTGGACCAATTCCATCTACATTGTCACAGATCCCTAACTTGAAGGTCTTGGACCTGGCTCAAAA
TAGGTTAAGTGGAGAAATTCCTAGGCTGATATACTGGAACGAAGTCCTGCAGTATCTGGGACTGCGTGGTAACAACT
TGGGTGGATCCCTTTCTCCTGATATGTGTCAGCTCACCGGCCTGTGGTACTTTGATGTTCGGAACAATAGTTTGACT
GGTTCCATTCCTCAAAATATTGGCAACTGTACTGCCTTCCAGGTTCTAGATTTGTCTTATAATGATTTGACCGGAGA -continued GATTCCTTTCAATATTGGTTTCCTGCAAGTAGCGACCTTGTCTTTGCAAGGTAATCGTCTTTCAGGGCAGATCCCTT
CTGTAATTGGATTGATGCAAGCTCTTGCAGTTTTGGACTTGAGCTGCAATATGTTGAGTGGAACAATTCCTTCAATT
CTTGGGAATTTGACTTACACAGAGAAATTGTATCTACACGGGAACAAGCTATCTGGTTCCATTCCTCCAGAGCTGGG
AAATATGACAAAGCTCCACTACTTGGAATTGAATGATAACCAACTTACTGGACGCATACCACCAGAACTTGGAAAGC
TGACAGAATTGTTTGACTTAAATGTTGCAAACAACCACCTAGATGGGCCCATACCTTCCAATATTAGCTCATGTACC
AATTTGAATAGTCTCAACGTTCATGGAAACAAATTGAATGGTACTATTCCACCTGCTTTTCAGAAGCTGGAAAGTAT
GACCTATCTTAATCTCTCCTCCAACAATCTCAAAGGCCCAATTCCAATTGAGCTATCTCGTATTGGGAATGTAGATA
CACTGGACTTATCAAACAACAGGATCAGTGGTCCTATACCTATGTCCCTTGGTGATTTGGAACATCTTCTTAAACTG
AACTTAAGCAAGAATGAAATAAATGGAAACTTACCAGCTGAATTTGGCAATTTAAGGAGCATCATGGAGATTGATCT
GTCAAGCAATCACCTCTCTGGTCCCTTACCTCAGGAACTTGGTCAGCTTCCAAACCTGTACTTGCTGAAGGTGGAAA
ACAACAATTTATCAGGCGATGTGATGTCCTTAGCCAGTTGCCTCAGTCTAAATATCTTAAATGTCTCATACAATAAT
CTGGGAGGGAATATTCCAACCGGCAATAATTTCTCTAGATTTTCACCAGACAGCTTCATAGGAAATCCAGATCTGTG
TGGGTATTGGCTCACTTCTCCTTGTCATGCATCTCATCCGGCAGAGCGAGTTTCAATTTCTAAAGCAGCAATACTTG
GTATTGCTCTGGGTGGCTTGGTGATTCTTCTGATGATACTAGTAGCAGCATGCCGGCCACAGAAACCTGCACCTTTC
ATGGAAGGATCTATTGATAAACCAGTTTATTACTCATCTCCAAAACTTGTGATCCTTCATATGAACATGGCACTTCA
TGTTTACGAGGACATTATGAGGATGACTGAGAACTTGAGTGAGAAGTATATAATTGGTTGTGGAGCATCAAGTACTG
TATATAAATGTGTTTTGAAAAATTGCAAGCCTGTAGCTATCAAGAAGTTGTACTCTCACAACCCGCAATACTTGAAG
GAATTTGAGACTGAACTTGAGACAGTTGGGAGTATTAAGCATCGTAATCTTGTCTGTCTCCAAGGATATTCTCTTTC
TCCATCTGGCCATCTTCTTTTCTATGACTACATGGAAAATGGTAGCCTTTGGGATTTGCTTCATGGTCCTACAACAA
AGAAGAAAAAGCTTGATTGGGTTACTCGCCTTCGAATTGCATTGGGATCAGCTCAAGGGCTTGCATATCTTCATCAT
GATTGTAGCCCTCGAATAATCCACCGTGATGTTAAATCATCTAATATCTTGTTGGACAAAGACTTTGAGGCTCATCT
GACTGATTTTGGCATAGCTAAAAGCTTATGCATATCAAAGACCTATACGTCCACGTACATTATGGGAACCATTGGTT
ACATTGATCCAGAGTATGCTCGCACTTCTCGCTTGACAGAGAAGTCTGATGTTTACAGCTATGGTATTGTTCTATTG
GAATTGCTCACTGGAAGGAAAGCTGTAGATAATGAATCTAATCTACATCATTTGATTCTAACTAAGGCAGCAAACGA
TGCTGTAATGGAAACAGTGGATCCTGAGATAACATGCACATGCAAAGATCTTGCAGATGTGAAGAAGGTTTTTCAGC
TTGCCCTTCTATGTTCCAAAAGACAGCCTGCTGAGAGACCAACAATGCATGAAGTGGCAAGAGTACTTGAAAGCCTA
ATACCCGTCGCTGAAACGAAACAGCCAAATCCAACCCCCTCACTTGCATTACTCCCATCTGCTAAGGTACCTTGTTA
CATGGATGAATATGTCAACCTCAAGACACCCCACCTAGTGAACTGTTCATCCATGAGCACTTCAGATGCCCAACTTT
TCCTCAAGTTTGGAGAGGTCATATCCCAGAATAGTGGCTGA (SEQ ID NO: 41)

Amino acid sequence for a polypeptide encoded by a *S. lycopersicum* cv. Sweet100 gene allele sler$^{CR-3}$ coding sequence MASFLLQRCNLLFEVLLILGFLIFFSFGSVVSDDGSALLEIKKSIRDVENVLYDWTDSPSSDYCAWRGVTCDNVTFN
VVQLNLSSLNLDGELSIGQLKGLVSIDMRGNRLSGQIPDEIGDCSALKNLDLSFNELYGDIPFSISKLKQLEYLILK
NNQLIGPIPSTLSQIPNLKVLDLAQNRLSGEIPRLIYWNEVLQYLGLRGNNLGGSLSPDMCQLTGLWYFDVRNNSLT
GSIPQNIGNCTAFQVLDLSYNDLTGEIPFNIGFLQVATLSLQGNRLSGQIPSVIGLMQALAVLDLSCNMLSGTIPSI
LGNLTYTEKLYLHGNKLSGSIPPELGNMTKLHYLELNDNQLTGRIPPELGKLTELFDLNVANNHLDGPIPSNISSCT
NLNSLNVHGNKLNGTIPPAFQKLESMTYLNLSSNNLKGPIPIELSRIGNVDTLDLSNNRISGPIPMSLGDLEHLLKL
NLSKNEINGNLPAEFGNLRSIMEIDLSSNHLSGPLPQELGQLPNLYLLKVENNNLSGDVMSLASCLSLNILNVSYNN
LGGNIPTGNNFSRFSPDSFIGNPDLCGYWLTSPCHASHPAERVSISKAAILGIALGGLVILLMILVAACRPQKPAPF
MEGSIDKPVYYSSPKLVILHMNMALHVYEDIMRMTENLSEKYIIGCGASSTVYKCVLKNCKPVAIKKLYSHNPQYLK
EFETELETVGSIKHRNLVCLQGYSLSPSGHLLFYDYMENGSLWDLLHGPTTKKKKLDWVTRLRIALGSAQGLAYLHH
DCSPRIIHRDVKSSNILLDKDFEAHLTDFGIAKSLCISKTYTSTYIMGTIGYIDPEYARTSRLTEKSDVYSYGIVLL
ELLTGRKAVDNESNLHHLILTKAANDAVMETVDPEITCTCKDLADVKKVFQLALLCSKRQPAERPTMHEVARVLESL
IPVAETKQPNPTPSLALLPSAKVPCYMDEYVNLKTPHLVNCSSMSTSDAQLFLKFGEVISQNSG* (SEQ ID NO: 42)

Solyc03g007050 (SlER1)

Wild-type Solyc03g007050 gene
Nucleic acid sequence of a wild-type Solyc03g007050 gene (SEQ ID NO: 43)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGTAACTATTTTTTTCAACACCTAATAGCTGTTTCGGTATTGCGTTGTGTGCTATTTAGGA

AATAAGGAAGTTATTGTTCGAATTTAGTTTTGTATTTTCAGTTTCTGGAGCTGCATTCCATGCTGTTTTAACTTTGA

TTACGAAAAATCCGTGTTATTTGAGATATATTTAGGCTTCAGTTTATGGCTTAACCACCGGAATACTACTTGATAAA

TACTAAAAATGGTTATGACTGCTTGCGCAGGCAAAGCATTAATGTCGATCAAGGCATCGTTTAGCAACGTAGCAAAC

GTGTTGCTGGATTGGGATGATATCCACGACGAGGATTTTTGCTCATGGAGAGGCGTGTTGTGTGGAAATTTCTCCAT

GTCCGTCGTTGCACTGTAGGTGTTTCATCCTTTGTTTCCTAACTTTCACTGATACACCAGGAAAAAAGCAGTAGCTG

AATTCTGATGACCTGCTAGCTATTGTATAGCACTTTGTTAGTTTAGCTAATAGTTATACGTCTTTTATATAAATTTA

CCTTCTCTGCTTGTGAAGGAATCTGTCTAATCTGAACTTGGGCGGGGAAATTTCACCAGACATTGGAGAGTTGAAGA

ATCTGGAGACATTGTATGGTGCAGTTTCTCTTTTACTGTTCTTGGTCCATTGACTGTCATTTTACCTCTCTGATATT

ACATTCCAATGTTAATGACAGAGACCTTCAGGGAAATAAATTAACTGGTCAAGTCCCAGATGAAATTGGCAACTGCA

TTTCACTGATCTATCTGTAAGTAAAATAGTTTTTAACCTATGATTTTAATATTTTTTTCTTGCATGTCAGTAAATTT

-continued

CAAGTGCTCACACTAATTGATTTGCTATTGTCTGCAGTGATTTGTCTGATAACTTGTTCTATGGAGATATACCATTC

TCAATTTCTAAGCTCAAGCAGCTAGAGTTGTTGTGAGTTATTTAATCACATGACATTGATGTTTTCTGATAACTAGT

TGATATGGTTATGATGAATTAATTCATTATGTGGTGCAGAAACTTTAAAAACAACCAGTTGTCCGGCCCAATCCCGT

CCACATTAACTCAAATTCCTAATCTAAAGACGCTGTGAGTTCCATGACTTTCGTTTTATCTCCCTCAAAATTTAGTC

CAATATACATGCTTAACAAATGGTTGTTTGAATGGTGAAGTGATCTGGCTCGAAACCAGCTCATTGGTGAGATACCA

AGGTTGATCTATTGGAATGAAGTTCTACAATATCTGTGAGTGCATTTTCCTGGTGTTTTGGAGGTTTTCATTTTTTG

TTTGAGAAATTTAAGATGTTTCTTTACCTTCTGTATTGCAGAGGATTAAGAGGCAACATGTTGACAGGAACATTGTC

CCCTGATATGTGCCAGTTGACTGGCTTGTGGTATTTGTATGTGCTCTGCTACATGATATCTATACGGGATGCTCTGT

TGTCTGTTTGGTGTAATATTTATGTATATTCTAACATTAGAAGTTTCATATTATTTCAGTGATGTGCGGGGCAATAA

CCTCAGCGGAATAATTCCAGATAATATTGGGAATTGTACAAGCTTTGAGATACTGTCAGTGTTGTCTTCTTGCTCTG

ATTATGTTAAGCTACAGTTCTTCTCCTACTGCTGCCCAATTCTAACAAAATCTATTTTTTCGTGATTTCAGGGATAT

CTCATACAATCAGATAACTGGAGAAATTCCCTACAATATTGGGTTTTTACAAGTGGCTACCTTGTTAGTAAATTCAA

CTTTGTCAGTTCTACCTTGTCTGTTCTGTTATGGGGTTCGTTTCTGTAAATGGTAAATGGAGATTATGGTCCTTTCA

ACAGGTCTTTGCAAGGAAATAGGCTAACTGGCAGGATCCCAGAAGTGATTGGTCTTATGCAAGCTCTTGCTGTTCTG

TGAGTATTCATACTAGTACAAGAATTGTTTATTTTTTCCAACTCCATTCTTACTAGTTACTGCTTGCAAGTAAGAAG

GTTCATGATGTCCGTCTCCTCTGTAGGGACTTGAGTGAAAATGAGTTGGTGGGACCAATCCCTCCAATCTTTGGCAA

TTTATCTTACACAGGGAAGCTGTAAGTTTTCACTCCTATTTTAATGCATATACCTTTCTATGTGAGGCTCGTTTATC

TGATTCATTTGTACATTCAACAGGTACCTGCACGGCAACAAACTTACAGGGCCAGTTCCACCGGAGCTAGGAAATAT

GTCTAAACTTAGTTACTTGTAAGAGCCTAAGAGGATTAATTCACAGTTTCAGATACATGATGTGGTCACCTTGTTTT

GCTTCATGCATTGAGCTATCTTATTTACAGGCAATTAAATGACAATCAGCTAATGGGTCGAATTCCCCCTGAACTTG

GCAAACTGGACCAGTTATTTGAATTGTGAGCCTTTTATTTTTGTAGTAAATATTTCTGGTTCCACTTCCTCTTGGAA

TATTGAGGTCTTAGCTATCCTCTACCAGGAATCTTGCAAATAACAAGTTGGAGGGACCAATTCCTGAAAATATCAGC

TCCTGTTCTGCATTGAATCAGCTGTAAGATTGTTCTGTTTCCTTTTGAAACTTCATTTTTTTTCTCTTTCTCTTTTGC

TAGTCTATTCATTCTGAGTCTCAACATATTTGTTTTTTTCTTTCAGTAATGTTCATGGCAACAACTTAAACGAGTCC

ATTCCTTCAGGGTTTAAGAATCTGGAGAGCTTGACGTATCTGTATGTTATAGTCTTCTGTTTTGGCTAGTGGTCATG

ATAATGATTTTGAATTTCTTTCATATGGTACTAACTTATTAGTGATATTTGTTGATATTTACCTGGCAGAAATCTTT

CAGCTAATAAATTTAAGGGTCACATACCTTCTCAACTTGGGCGAATCATCAACCTTGATACATTGTGAGTTCTTGAT

TGTCAAGGCCGATAAAATTTATTAGTTCACGTGATTCCTTGTACTAAAACTTTTATTCTTTAGGGATCTCTCTGGCA

ACAATTTTTCTGGGTCTATCCCTGGTTCTATTGGAGATTTGGAGCATCTCCTCACATTGTAAGATATTAAACATTTC

GATGTACAAGATGTTTGTATCATATTGAGACTGGAACATAATCACAATATCATTGCACATTGTAGGAATCTGAGCAG

CAATCATCTTGATGGACAAATTCCTGTAGAATTTGGCAATCTAAAAAGTATACAGACCATGTAAGTTTCTGCTGAGA

GCTTTGGTTACACTGCCTTCAAAATGTGTACTTTTTGTATACTGATTTTCATGTGCTGAGATTGGCTTCTATACTGC

CTTCAACATGTGTATTTTTATACTGATCTTCTTGCGCTGAGACTGGCTTCTATTCTTTCAGTGATATGTCAAGCAAC

AAGATCTCTGGTGGCATCCCAAAAGAGCTGGGACAGCTGCAGACCATGATAACTCTGTAAGTACATTAGTTTTTGTC

AAGTAAATTGATGTAGTGTTTAATCAGTTTTCCTTAATATCACAATCAATTCTAATAAAATTTTGATTGACTTTGTT

TCTTTTTGTAGTACTTTGACAGGTAACTATCTTACTGGAGCAATCCCTGACCAATTGACCAATTGTTTCAGCCTAAC

TAGTTTGTGAGTTCATCTATCTTTGCCTTTAACATCATAGACAGTCTAATTCTTTGTACAGTTACTGATCTTATGTC

ATTCTCCTTCAGGAATATATCCTACAACAATTTTAGTGGTGTTGTTCCTCTTTCACGGAATTTCTCGCGGTTTGCAC

CTGACAGGTATTTTCCGAATAGAATGAAGCTTTATCATTATATTTGTGCTTTAGTACTCTAGCTAATGACCACCTTA

TTATGGTCATCAGCTTTTTAGGGAACCCATTTCTTTGTGGCAACTGGAAAGGTTCAATATGTGACCCCTATGCACCA

AGGTCTAACGGTATGACTTCATTTTTGTGCATTGGTTAGCGAATCTCTTGGTATGCAGAGTCATGTGCATCAAAATG

-continued

ACTTGTTACTTTTGCAGCCTTGTTCTCCAGAACAGCTGTTGTTTGCACAGCACTGGGTTTCATTGCACTCTTATCCA

TGGTTGTAGTGGCTGTGTATAAGTCCAACCAACCACACCAGTTTTTGAAGGGGCCTAAGACCAATCAAGGTAAAAAT

TAGTACATGTACACTCTGTTCTTTTGTTTTTCAGTACTTTCAGGTATTTATGTTTGCTTTTTGTCTTGTTTCCCTCT

AATTCCATAGGCTCCCCCAAACTTGTGGTTCTTCACATGGATATGGCCATCCATACATATGATGACATTATGAGGAT

TACCGAGAACTTCAATGAGAAATTCATAATAGGATATGGTGCGTCCAGCACTGTATATAAATGTGATTTGAAAGATT

CCCGACCAATTGCAGTTAAGCGACTTTACACCGCACATCCGCACAGCTTGCGAGAGTTTGAGACTGAACTGGAGACA

ATTGGAAGCATTAGGCATAGAAACCTTGTTAGCTTGCATGGTTACTCCCTTTCCCCTCATGGGAATCTCCTTTGTTA

CGACTACATGGAGAATGGTTCACTCTGGGATCTACTTCATGGTTAGTAACCCACCTTTCCTTGTAATCTTTTATGAA

GTTTCTTCATGTAAGACAGTGTTGACTATTGGTTGATGTTAATTACTAGTTTCTCTGTCGGAGAACAGTTCTATTAG

CCAAGATTTTTGTGAAAATGGCTAATTATCAACTGAATACATGTCAATAGGGCCTTCCAAAAAGGTGAAGCTTGACT

GGGAAACACGTCTGAAGATTGCTGTTGGTGCTGCTCAGGGTCTTGCTTATCTTCACCACGATTGCAACCCAAGAATA

ATACACAGAGATGTAAAATCTTCAAACATCCTTGTTGATGAAAATTTTGAGGCTCATCTATCTGATTTTGGGGTTGC

AAAATGCATCCCTACTGCAAAAACTCATGCATCAACTTTGGTGTTGGGCACCATAGGTTACATTGACCCTGAGTATG

CCAGGACTTCCAGGTTAACTGAAAAGTCAGACGTCTACAGCTTTGGCATTGTTCTCCTAGAGCTTTTGACAGGAAAG

AAACCGGTTGATAATGACTTGAACCTGCATCAGCTGGTATTATTCTCCACTTATACTCTACGTTGTTACTTGTAAAA

AAGATTTAACTCAGACTGGATATAGAAAAGAACAACTTAGCTCAAATTATCCCATCTTCCTATAGCATTTGCAATAA

TGTCTTTTGTCTATTAACTCCTGTATTACATTTGTCTTTGAAGTAATTCGATTTGTGTTACAGATAATGTCAAAGGC

GGATGATAACACCGTGATGGATGCTGTTGATCCTGAGGTATCTGTTACATGTATGGATTTAATGCATGTTAGGAAAA

CTTTTCAGCTTGCGTTGCTGTGTGCAAAAAGATTCCCATGTGAGAGGCCAACAATGCATGAGGTTGCTAGGGTACTT

GTTTCCTTGCTTCCTCCCCCACCAACCAAACCTTGTTTAGACCCACCTCCCAAATCCATTGATTATACAAAATTTGT

GATTGGTAAAGGACTACCGCAAGTCCAGCAGGGTGACAATTCCTCCGAAGCTCAGTGGCTTGTTAGATTTCAAGAAG

CTATATCCAAAAACTCCCTTTGA

Nucleic acid sequence of a wild-type Solyc03g007050 coding sequence (SEQ ID NO: 44)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGCAAAGCATTAATGTCGATCAAGGCATCGTTTAGCAACGTAGCAAACGTGTTGCTGGATT

GGGATGATATCCACGACGAGGATTTTTGCTCATGGAGAGGCGTGTTGTGTGGAAATTTCTCCATGTCCGTCGTTGCA

CTGAATCTGTCTAATCTGAACTTGGGCGGGGAAATTTCACCAGACATTGGAGAGTTGAAGAATCTGGAGACATTAGA

CCTTCAGGGAAATAAATTAACTGGTCAAGTCCCAGATGAAATTGGCAACTGCATTTCACTGATCTATCTTGATTTGT

CTGATAACTTGTTCTATGGAGATATACCATTCTCAATTTCTAAGCTCAAGCAGCTAGAGTTGTTAAACTTTAAAAAC

AACCAGTTGTCCGGCCCAATCCCGTCCACATTAACTCAAATTCCTAATCTAAAGACGCTTGATCTGGCTCGAAACCA

GCTCATTGGTGAGATACCAAGGTTGATCTATTGGAATGAAGTTCTACAATATCTAGGATTAAGAGGCAACATGTTGA

CAGGAACATTGTCCCCTGATATGTGCCAGTTGACTGGCTTGTGGTATTTTGATGTGCGGGGCAATAACCTCAGCGGA

ATAATTCCAGATAATATTGGGAATTGTACAAGCTTTGAGATACTGGATATCTCATACAATCAGATAACTGGAGAAAT

TCCCTACAATATTGGGTTTTTACAAGTGGCTACCTTGTCTTTGCAAGGAAATAGGCTAACTGGCAGGATCCCAGAAG

TGATTGGTCTTATGCAAGCTCTTGCTGTTCTGGACTTGAGTGAAAATGAGTTGGTGGGACCAATCCCTCCAATCTTT

GGCAATTTATCTTACACAGGGAAGCTGTACCTGCACGGCAACAAACTTACAGGGCCAGTTCCACCGGAGCTAGGAAA

TATGTCTAAACTTAGTTACTTGCAATTAAATGACAATCAGCTAATGGGTCGAATTCCCCCTGAACTTGGCAAACTGG

ACCAGTTATTTGAATTGAATCTTGCAAATAACAAGTTGGAGGGACCAATTCCTGAAAATATCAGCTCCTGTTCTGCA

TTGAATCAGCTTAATGTTCATGGCAACAACTTAAACGAGTCCATTCCTTCAGGGTTTAAGAATCTGGAGAGCTTGAC

GTATCTAAATCTTTCAGCTAATAAATTTAAGGGTCACATACCTTCTCAACTTGGGCGAATCATCAACCTTGATACAT

-continued

TGGATCTCTCTGGCAACAATTTTTCTGGGTCTATCCCTGGTTCTATTGGAGATTTGGAGCATCTCCTCACATTGAAT

CTGAGCAGCAATCATCTTGATGGACAAATTCCTGTAGAATTTGGCAATCTAAAAAGTATACAGACCATTGATATGTC

AAGCAACAAGATCTCTGGTGGCATCCCAAAAGAGCTGGGACAGCTGCAGACCATGATAACTCTTACTTTGACAGGTA

ACTATCTTACTGGAGCAATCCCTGACCAATTGACCAATTGTTTCAGCCTAACTAGTTTGAATATATCCTACAACAAT

TTTAGTGGTGTTGTTCCTCTTTCACGGAATTTCTCGCGGTTTGCACCTGACAGCTTTTTAGGGAACCCATTTCTTTG

TGGCAACTGGAAAGGTTCAATATGTGACCCCTATGCACCAAGGTCTAACGCCTTGTTCTCCAGAACAGCTGTTGTTT

GCACAGCACTGGGTTTCATTGCACTCTTATCCATGGTTGTAGTGGCTGTGTATAAGTCCAACCAACCACACCAGTTT

TTGAAGGGGCCTAAGACCAATCAAGGCTCCCCCAAACTTGTGGTTCTTCACATGGATATGGCCATCCATACATATGA

TGACATTATGAGGATTACCGAGAACTTCAATGAGAAATTCATAATAGGATATGGTGCGTCCAGCACTGTATATAAAT

GTGATTTGAAAGATTCCCGACCAATTGCAGTTAAGCGACTTTACACCGCACATCCGCACAGCTTGCGAGAGTTTGAG

ACTGAACTGGAGACAATTGGAAGCATTAGGCATAGAAACCTTGTTAGCTTGCATGGTTACTCCCTTTCCCCTCATGG

GAATCTCCTTTGTTACGACTACATGGAGAATGGTTCACTCTGGGATCTACTTCATGGGCCTTCCAAAAAGGTGAAGC

TTGACTGGGAAACACGTCTGAAGATTGCTGTTGGTGCTGCTCAGGGTCTTGCTTATCTTCACCACGATTGCAACCCA

AGAATAATACACAGAGATGTAAAATCTTCAAACATCCTTGTTGATGAAAATTTTGAGGCTCATCTATCTGATTTTGG

GGTTGCAAAATGCATCCCTACTGCAAAAACTCATGCATCAACTTTGGTGTTGGGCACCATAGGTTACATTGACCCTG

AGTATGCCAGGACTTCCAGGTTAACTGAAAAGTCAGACGTCTACAGCTTTGGCATTGTTCTCCTAGAGCTTTTGACA

GGAAAGAAACCGGTTGATAATGACTTGAACCTGCATCAGCTGATAATGTCAAAGGCGGATGATAACACCGTGATGGA

TGCTGTTGATCCTGAGGTATCTGTTACATGTATGGATTTAATGCATGTTAGGAAAACTTTTCAGCTTGCGTTGCTGT

GTGCAAAAAGATTCCCATGTGAGAGGCCAACAATGCATGAGGTTGCTAGGGTACTTGTTTCCTTGCTTCCTCCCCCA

CCAACCAAACCTTGTTTAGACCCACCTCCCAAATCCATTGATTATACAAAATTTGTGATTGGTAAAGGACTACCGCA

AGTCCAGCAGGGTGACAATTCCTCCGAAGCTCAGTGGCTTGTTAGATTTCAAGAAGCTATATCCAAAAACTCCCTTT

GA

Amino acid sequence for a polypeptide encoded by a wild-type Solyc03g007050 coding sequence (SEQ ID NO: 45)

MEVSLKMKFRSQALLLVLLLVFPIVLALTEEGKALMSIKASFSNVANVLLDWDDIHDEDFCSWRGVLCGNFSMSVVA

LNLSNLNLGGEISPDIGELKNLETLDLQGNKLTGQVPDEIGNCISLIYLDLSDNLFYGDIPFSISKLKQLELLNFKN

NQLSGPIPSTLTQIPNLKTLDLARNQLIGEIPRLIYWNEVLQYLGLRGNMLTGTLSPDMCQLTGLWYFDVRGNNLSG

IIPDNIGNCTSFEILDISYNQITGEIPYNIGFLQVATLSLQGNRLTGRIPEVIGLMQALAVLDLSENELVGPIPPIF

GNLSYTGKLYLHGNKLTGPVPPELGNMSKLSYLQLNDNQLMGRIPPELGKLDQLFELNLANNKLEGPIPENISSCSA

LNQLNVHGNNLNESIPSGFKNLESLTYLNLSANKFKGHIPSQLGRIINLDTLDLSGNNFSGSIPGSIGDLEHLLTLN

LSSNHLDGQIPVEFGNLKSIQTIDMSSNKISGGIPKELGQLQTMITLTLTGNYLTGAIPDQLTNCFSLTSLNISYNN

FSGVVPLSRNFSRFAPDSFLGNPFLCGNWKGSICDPYAPRSNALFSRTAVVCTALGFIALLSMVVVAVYKSNQPHQF

LKGPKTNQGSPKLVVLHMDMAIHTYDDIMRITENFNEKFIIGYGASSTVYKCDLKDSRPIAVKRLYTAHPHSLREFE

TELETIGSIRHRNLVSLHGYSLSPHGNLLCYDYMENGSLWDLLHGPSKKVKLDWETRLKIAVGAAQGLAYLHHDCNP

RIIHRDVKSSNILVDENFEAHLSDFGVAKCIPTAKTHASTLVLGTIGYIDPEYARTSRLTEKSDVYSFGIVLLELLT

GKKPVDNDLNLHQLIMSKADDNTVMDAVDPEVSVTCMDLMHVRKTFQLALLCAKRFPCERPTMHEVARVLVSLLPPP

PTKPCLDPPPKSIDYTKFVIGKGLPQVQQGDNSSEAQWLVRFQEAISKNSL*

Mutant Solyc03g007050 gene allele slerl1$^{CR-1}$

Nucleic acid sequence for a mutant Solyc03g007050 gene allele slerl1$^{CR-1}$ (SEQ ID NO: 46)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGTAACTATTTTTTTCAACACCTAATAGCTGTTTCGGTATTGCGTTGTGTGCTATTTAGGA

AATAAGGAAGTTATTGTTCGAATTTAGTTTTGTATTTTCAGTTTCTGGAGCTGCATTCCATGCTGTTTTAACTTTGA

-continued

```
TTACGAAAAATCCGTGTTATTTGAGATATATTTAGGCTTCAGTTTATGGCTTAACCACCGGAATACTACTTGATAAA

TACTAAAAATGGTTATGACTGCTTGCGCAGGCAAAGCATTAATGTCGATCAAGGCATCGTTTAGCAACGTAGCAAAC

GTGTTGCTGGATTGGGATGATATCCACGACGAGGATTTTTGCTCATGGAGAGGCGTGTTGTGTGGAAATTTCTCCAT

GTCCGTCGTTGCACTGTAGGTGTTTCATCCTTTGTTTCCTAACTTTCACTGATACACCAGGAAAAAAGCAGTAGCTG

AATTCTGATGACCTGCTAGCTATTGTATAGCACTTTGTTAGTTTAGCTAATAGTTATACGTCTTTTATATAAATTTA

CCTTCTCTGCTTGTGAAGGAATCTGTCTAATCTGAACTTGGGCGGGGAAATTTCACCAGACATTGGAGAGTTGAAGA

ATCTGGAGACATTGTATGGTGCAGTTTCTCTTTTACTGTTCTTGGTCCATTGACTGTCATTTTACCTCTCTGATATT

ACATTCCAATGTTAATGACAGAGACCTCAGGGAAATAAATTAACTGGTCAAGTCCCAGATGAAATTGGCAACTGCAT

TTCACTGATCTATCTGTAAGTAAAATAGTTTTTAACCTATGATTTTAATATTTTTTTCTTGCATGTCAGTAAATTTC

AAGTGCTCACACTAATTGATTTGCTATTGTCTGCAGTGATTTGTCTGATAACTTGTTCTATGGAGATATACCATTCT

CAATTTCTAAGCTCAAGCAGCTAGAGTTGTTGTGAGTTATTTAATCACATGACATTGATGTTTTCTGATAACTAGTT

GATATGGTTATGATGAATTAATTCATTATGTGGTGCAGAAACTTTAAAAACAACCAGTTGTCCGGCCCAATCCCGTC

CACATTAACTCAAATTCCTAATCTAAAGACGCTGTGAGTTCCATGACTTTCGTTTTATCTCCCTCAAAATTTAGTCC

AATATACATGCTTAACAAATGGTTGTTTGAATGGTGAAGTGATCTGGCTCGAAACCAGCTCATTGGTGAGATACCAA

GGTTGATCTATTGGAATGAAGTTCTACAATATCTGTGAGTGCATTTTCCTGGTGTTTTGGAGGTTTTCATTTTTTGT

TTGAGAAATTTAAGATGTTTCTTTACCTTCTGTATTGCAGAGGATTAAGAGGCAACATGTTGACAGGAACATTGTCC

CCTGATATGTGCCAGTTGACTGGCTTGTGGTATTTGTATGTGCTCTGCTACATGATATCTATACGGGATGCTCTGTT

GTCTGTTTGGTGTAATATTTATGTATATTCTAACATTAGAAGTTTCATATTATTTCAGTGATGTGCGGGGCAATAAC

CTCAGCGGAATAATTCCAGATAATATTGGGAATTGTACAAGCTTTGAGATACTGTCAGTGTTGTCTTCTTGCTCTGA

TTATGTTAAGCTACAGTTCTTCTCCTACTGCTGCCCAATTCTAACAAAATCTATTTTTTCGTGATTTCAGGGATATC

TCATACAATCAGATAACTGGAGAAATTCCCTACAATATTGGGTTTTTACAAGTGGCTACCTTGTTAGTAAATTCAAC

TTTGTCAGTTCTACCTTGTCTGTTCTGTTATGGGGTTCGTTTCTGTAAATGGTAAATGGAGATTATGGTCCTTTCAA

CAGGTCTTTGCAAGGAAATAGGCTAACTGGCAGGATCCCAGAAGTGATTGGTCTTATGCAAGCTCTTGCTGTTCTGT

GAGTATTCATACTAGTACAAGAATTGTTTATTTTTTCCAACTCCATTCTTACTAGTTACTGCTTGCAAGTAAGAAGG

TTCATGATGTCCGTCTCCTCTGTAGGGACTTGAGTGAAAATGAGTTGGTGGGACCAATCCCTCCAATCTTTGGCAAT

TTATCTTACACAGGGAAGCTGTAAGTTTTCACTCCTATTTTAATGCATATACCTTTCTATGTGAGGCTCGTTTATCT

GATTCATTTGTACATTCAACAGGTACCTGCACGGCAACAAACTTACAGGGCCAGTTCCACCGGAGCTAGGAAATATG

TCTAAACTTAGTTACTTGTAAGAGCCTAAGAGGATTAATTCACAGTTTCAGATACATGATGTGGTCACCTTGTTTTG

CTTCATGCATTGAGCTATCTTATTTACAGGCAATTAAATGACAATCAGCTAATGGGTCGAATTCCCCCTGAACTTGG

CAAACTGGACCAGTTATTTGAATTGTGAGCCTTTTATTTTTGTAGTAAATATTTCTGGTTCCACTTCCTCTTGGAAT

ATTGAGGTCTTAGCTATCCTCTACCAGGAATCTTGCAAATAACAAGTTGGAGGGACCAATTCCTGAAAATATCAGCT

CCTGTTCTGCATTGAATCAGCTGTAAGATTGTTCTGTTTCCTTTTGAAACTTCATTTTTTTCTCTTTCTCTTTTGCT

AGTCTATTCATTCTGAGTCTCAACATATTTGTTTTTTTCTTTCAGTAATGTTCATGGCAACAACTTAAACGAGTCCA

TTCCTTCAGGGTTTAAGAATCTGGAGAGCTTGACGTATCTGTATGTTATAGTCTTCTGTTTTGGCTAGTGGTCATGA

TAATGATTTTGAATTTCTTTCATATGGTACTAACTTATTAGTGATATTTGTTGATATTTACCTGGCAGAAATCTTTC

AGCTAATAAATTTAAGGGTCACATACCTTCTCAACTTGGGCGAATCATCAACCTTGATACATTGTGAGTTCTTGATT

GTCAAGGCCGATAAAATTTATTAGTTCACGTGATTCCTTGTACTAAAACTTTTATTCTTTAGGGATCTCTCTGGCAA

CAATTTTTCTGGGTCTATCCCTGGTTCTATTGGAGATTTGGAGCATCTCCTCACATTGTAAGATATTAAACATTTCG

ATGTACAAGATGTTTGTATCATATTGAGACTGGAACATAATCACAATATCATTGCACATTGTAGGAATCTGAGCAGC

AATCATCTTGATGGACAAATTCCTGTAGAATTTGGCAATCTAAAAAGTATACAGACCATGTAAGTTTCTGCTGAGAG
```

-continued

CTTTGGTTACACTGCCTTCAAAATGTGTACTTTTTGTATACTGATTTTCATGTGCTGAGATTGGCTTCTATACTGCC

TTCAACATGTGTATTTTTATACTGATCTTCTTGCGCTGAGACTGGCTTCTATTCTTTCAGTGATATGTCAAGCAACA

AGATCTCTGGTGGCATCCCAAAAGAGCTGGGACAGCTGCAGACCATGATAACTCTGTAAGTACATTAGTTTTTGTCA

AGTAAATTGATGTAGTGTTTAATCAGTTTTCCTTAATATCACAATCAATTCTAATAAAATTTTGATTGACTTTGTTT

CTTTTTGTAGTACTTTGACAGGTAACTATCTTACTGGAGCAATCCCTGACCAATTGACCAATTGTTTCAGCCTAACT

AGTTTGTGAGTTCATCTATCTTTGCCTTTAACATCATAGACAGTCTAATTCTTTGTACAGTTACTGATCTTATGTCA

TTCTCCTTCAGGAATATATCCTACAACAATTTTAGTGGTGTTGTTCCTCTTTCACGGAATTTCTCGCGGTTTGCACC

TGACAGGTATTTTCCGAATAGAATGAAGCTTTATCATTATATTTGTGCTTTAGTACTCTAGCTAATGACCACCTTAT

TATGGTCATCAGCTTTTTAGGGAACCCATTTCTTTGTGGCAACTGGAAAGGTTCAATATGTGACCCCTATGCACCAA

GGTCTAACGGTATGACTTCATTTTTGTGCATTGGTTAGCGAATCTCTTGGTATGCAGAGTCATGTGCATCAAAATGA

CTTGTTACTTTTGCAGCCTTGTTCTCCAGAACAGCTGTTGTTTGCACAGCACTGGGTTTCATTGCACTCTTATCCAT

GGTTGTAGTGGCTGTGTATAAGTCCAACCAACCACACCAGTTTTTGAAGGGGCCTAAGACCAATCAAGGTAAAAATT

AGTACATGTACACTCTGTTCTTTTGTTTTTCAGTACTTTCAGGTATTTATGTTTGCTTTTTGTCTTGTTTCCCTCTA

ATTCCATAGGCTCCCCCAAACTTGTGGTTCTTCACATGGATATGGCCATCCATACATATGATGACATTATGAGGATT

ACCGAGAACTTCAATGAGAAATTCATAATAGGATATGGTGCGTCCAGCACTGTATATAAATGTGATTTGAAAGATTC

CCGACCAATTGCAGTTAAGCGACTTTACACCGCACATCCGCACAGCTTGCGAGAGTTTGAGACTGAACTGGAGACAA

TTGGAAGCATTAGGCATAGAAACCTTGTTAGCTTGCATGGTTACTCCCTTTCCCCTCATGGGAATCTCCTTTGTTAC

GACTACATGGAGAATGGTTCACTCTGGGATCTACTTCATGGTTAGTAACCCACCTTTCCTTGTAATCTTTTATGAAG

TTTCTTCATGTAAGACAGTGTTGACTATTGGTTGATGTTAATTACTAGTTTCTCTGTCGGAGAACAGTTCTATTAGC

CAAGATTTTTGTGAAAATGGCTAATTATCAACTGAATACATGTCAATAGGGCCTTCCAAAAAGGTGAAGCTTGACTG

GGAAACACGTCTGAAGATTGCTGTTGGTGCTGCTCAGGGTCTTGCTTATCTTCACCACGATTGCAACCCAAGAATAA

TACACAGAGATGTAAAATCTTCAAACATCCTTGTTGATGAAAATTTTGAGGCTCATCTATCTGATTTTGGGGTTGCA

AAATGCATCCCTACTGCAAAAACTCATGCATCAACTTTGGTGTTGGGCACCATAGGTTACATTGACCCTGAGTATGC

CAGGACTTCCAGGTTAACTGAAAAGTCAGACGTCTACAGCTTTGGCATTGTTCTCCTAGAGCTTTTGACAGGAAAGA

AACCGGTTGATAATGACTTGAACCTGCATCAGCTGGTATTATTCTCCACTTATACTCTACGTTGTTACTTGTAAAAA

AGATTTAACTCAGACTGGATATAGAAAAGAACAACTTAGCTCAAATTATCCCATCTTCCTATAGCATTTGCAATAAT

GTCTTTTGTCTATTAACTCCTGTATTACATTTGTCTTTGAAGTAATTCGATTTGTGTTACAGATAATGTCAAAGGCG

GATGATAACACCGTGATGGATGCTGTTGATCCTGAGGTATCTGTTACATGTATGGATTTAATGCATGTTAGGAAAAC

TTTTCAGCTTGCGTTGCTGTGTGCAAAAAGATTCCCATGTGAGAGGCCAACAATGCATGAGGTTGCTAGGGTACTTG

TTTCCTTGCTTCCTCCCCCACCAACCAAACCTTGTTTAGACCCACCTCCCAAATCCATTGATTATACAAAATTTGTG

ATTGGTAAAGGACTACCGCAAGTCCAGCAGGGTGACAATTCCTCCGAAGCTCAGTGGCTTGTTAGATTTCAAGAAGC

TATATCCAAAAACTCCCTTTGA

Nucleic acid sequence for a mutant Solyc03g007050 gene allele
slerl1$^{CR-1}$ coding sequence (SEQ ID NO: 47)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGCAAAGCATTAATGTCGATCAAGGCATCGTTTAGCAACGTAGCAAACGTGTTGCTGGATT

GGGATGATATCCACGACGAGGATTTTTGCTCATGGAGAGGCGTGTTGTGTGGAAATTTCTCCATGTCCGTCGTTGCA

CTGAATCTGTCTAATCTGAACTTGGGCGGGGAAATTTCACCAGACATTGGAGAGTTGAAGAATCTGGAGACATTAGA

CCTCAGGGAAATAAATTAACTGGTCAAGTCCCAGATGAAATTGGCAACTGCATTTCACTGATCTATCTTGATTTGTC

TGATAACTTGTTCTATGGAGATATACCATTCTCAATTTCTAAGCTCAAGCAGCTAGAGTTGTTAAACTTTAAAAACA

ACCAGTTGTCCGGCCCAATCCCGTCCACATTAACTCAAATTCCTAATCTAAAGACGCTTGATCTGGCTCGAAACCAG

-continued

CTCATTGGTGAGATACCAAGGTTGATCTATTGGAATGAAGTTCTACAATATCTAGGATTAAGAGGCAACATGTTGAC

AGGAACATTGTCCCCTGATATGTGCCAGTTGACTGGCTTGTGGTATTTTGATGTGCGGGGCAATAACCTCAGCGGAA

TAATTCCAGATAATATTGGGAATTGTACAAGCTTTGAGATACTGGATATCTCATACAATCAGATAACTGGAGAAATT

CCCTACAATATTGGGTTTTTACAAGTGGCTACCTTGTCTTTGCAAGGAAATAGGCTAACTGGCAGGATCCCAGAAGT

GATTGGTCTTATGCAAGCTCTTGCTGTTCTGGACTTGAGTGAAAATGAGTTGGTGGGACCAATCCCTCCAATCTTTG

GCAATTTATCTTACACAGGGAAGCTGTACCTGCACGGCAACAAACTTACAGGGCCAGTTCCACCGGAGCTAGGAAAT

ATGTCTAAACTTAGTTACTTGCAATTAAATGACAATCAGCTAATGGGTCGAATTCCCCCTGAACTTGGCAAACTGGA

CCAGTTATTTGAATTGAATCTTGCAAATAACAAGTTGGAGGGACCAATTCCTGAAAATATCAGCTCCTGTTCTGCAT

TGAATCAGCTTAATGTTCATGGCAACAACTTAAACGAGTCCATTCCTTCAGGGTTTAAGAATCTGGAGAGCTTGACG

TATCTAAATCTTTCAGCTAATAAATTTAAGGGTCACATACCTTCTCAACTTGGGCGAATCATCAACCTTGATACATT

GGATCTCTCTGGCAACAATTTTTCTGGGTCTATCCCTGGTTCTATTGGAGATTTGGAGCATCTCCTCACATTGAATC

TGAGCAGCAATCATCTTGATGGACAAATTCCTGTAGAATTTGGCAATCTAAAAAGTATACAGACCATTGATATGTCA

AGCAACAAGATCTCTGGTGGCATCCCAAAAGAGCTGGGACAGCTGCAGACCATGATAACTCTTACTTTGACAGGTAA

CTATCTTACTGGAGCAATCCCTGACCAATTGACCAATTGTTTCAGCCTAACTAGTTTGAATATATCCTACAACAATT

TTAGTGGTGTTGTTCCTCTTTCACGGAATTTCTCGCGGTTTGCACCTGACAGCTTTTTAGGGAACCCATTTCTTTGT

GGCAACTGGAAAGGTTCAATATGTGACCCCTATGCACCAAGGTCTAACGCCTTGTTCTCCAGAACAGCTGTTGTTTG

CACAGCACTGGGTTTCATTGCACTCTTATCCATGGTTGTAGTGGCTGTGTATAAGTCCAACCAACCACACCAGTTTT

TGAAGGGGCCTAAGACCAATCAAGGCTCCCCCAAACTTGTGGTTCTTCACATGGATATGGCCATCCATACATATGAT

GACATTATGAGGATTACCGAGAACTTCAATGAGAAATTCATAATAGGATATGGTGCGTCCAGCACTGTATATAAATG

TGATTTGAAAGATTCCCGACCAATTGCAGTTAAGCGACTTTACACCGCACATCCGCACAGCTTGCGAGAGTTTGAGA

CTGAACTGGAGACAATTGGAAGCATTAGGCATAGAAACCTTGTTAGCTTGCATGGTTACTCCCTTTCCCCTCATGGG

AATCTCCTTTGTTACGACTACATGGAGAATGGTTCACTCTGGGATCTACTTCATGGGCCTTCCAAAAAGGTGAAGCT

TGACTGGGAAACACGTCTGAAGATTGCTGTTGGTGCTGCTCAGGGTCTTGCTTATCTTCACCACGATTGCAACCCAA

GAATAATACACAGAGATGTAAAATCTTCAAACATCCTTGTTGATGAAAATTTTGAGGCTCATCTATCTGATTTTGGG

GTTGCAAAATGCATCCCTACTGCAAAAACTCATGCATCAACTTTGGTGTTGGGCACCATAGGTTACATTGACCCTGA

GTATGCCAGGACTTCCAGGTTAACTGAAAAGTCAGACGTCTACAGCTTTGGCATTGTTCTCCTAGAGCTTTTGACAG

GAAAGAAACCGGTTGATAATGACTTGAACCTGCATCAGCTGATAATGTCAAAGGCGGATGATAACACCGTGATGGAT

GCTGTTGATCCTGAGGTATCTGTTACATGTATGGATTTAATGCATGTTAGGAAAACTTTTCAGCTTGCGTTGCTGTG

TGCAAAAAGATTCCCATGTGAGAGGCCAACAATGCATGAGGTTGCTAGGGTACTTGTTTCCTTGCTTCCTCCCCCAC

CAACCAAACCTTGTTTAGACCCACCTCCCAAATCCATTGATTATACAAAATTTGTGATTGGTAAAGGACTACCGCAA

GTCCAGCAGGGTGACAATTCCTCCGAAGCTCAGTGGCTTGTTAGATTTCAAGAAGCTATATCCAAAAACTCCCTTTG

A

Amino acid sequence for a mutant polypeptide encoded by a mutant Solyc03g007050 gene allele slerl1$^{CR-1}$ coding sequence (SEQ ID NO: 48)

MEVSLKMKFRSQALLLVLLLVFPIVLALTEEGKALMSIKASFSNVANVLLDWDDIHDEDFCSWRGVLCGNFSMSVVA

LNLSNLNLGGEISPDIGELKNLETLDLREIN*

Mutant Solyc03g007050 gene allele slerl1$^{CR-2}$

Nucleic acid sequence for a mutant Solyc03g007050 gene allele slerl1$^{CR-2}$ (SEQ ID NO: 49)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGTAACTATTTTTTTCAACACCTAATAGCTGTTTCGGTATTGCGTTGTGTGCTATTTAGGA

AATAAGGAAGTTATTGTTCGAATTTAGTTTTGTATTTTCAGTTTCTGGAGCTGCATTCCATGCTGTTTTAACTTTGA

TTACGAAAAATCCGTGTTATTTGAGATATATTTAGGCTTCAGTTTATGGCTTAACCACCGGAATACTACTTGATAAA

-continued

TACTAAAAATGGTTATGACTGCTTGCGCAGGCAAAGCATTAATGTCGATCAAGGCATCGTTTAGCAACGTAGCAAAC

GTGTTTGCTGGATTGGGATGATATCCACGACGAGGATTTTTGCTCATGGAGAGGCGTGTTGTGTGGAAATTTCTCCA

TGTCCGTCGTTGCACTGTAGGTGTTTCATCCTTTGTTTCCTAACTTTCACTGATACACCAGGAAAAAAGCAGTAGCT

GAATTCTGATGACCTGCTAGCTATTGTATAGCACTTTGTTAGTTTAGCTAATAGTTATACGTCTTTTATATAAATTT

ACCTTCTCTGCTTGTGAAGGAATCTGTCTAATCTGAACTTGGGCGGGGAAATTTCACCAGACATTGGAGAGTTGAAG

AATCTGGAGACATTGTATGGTGCAGTTTCTCTTTTACTGTTCTTGGTCCATTGACTGTCATTTTACCTCTCTGATAT

TACATTCCAATGTTAATGACAGAGACCTTCAGGGAAATAAATTAACTGGTCAAGTCCCAGATGAAATTGGCAACTGC

ATTTCACTGATCTATCTGTAAGTAAAATAGTTTTTAACCTATGATTTTAATATTTTTTTCTTGCATGTCAGTAAATT

TCAAGTGCTCACACTAATTGATTTGCTATTGTCTGCAGTGATTTGTCTGATAACTTGTTCTATGGAGATATACCATT

CTCAATTTCTAAGCTCAAGCAGCTAGAGTTGTTGTGAGTTATTTAATCACATGACATTGATGTTTTCTGATAACTAG

TTGATATGGTTATGATGAATTAATTCATTATGTGGTGCAGAAACTTTAAAAACAACCAGTTGTCCGGCCCAATCCCG

TCCACATTAACTCAAATTCCTAATCTAAAGACGCTGTGAGTTCCATGACTTTCGTTTTATCTCCCTCAAAATTTAGT

CCAATATACATGCTTAACAAATGGTTGTTTGAATGGTGAAGTGATCTGGCTCGAAACCAGCTCATTGGTGAGATACC

AAGGTTGATCTATTGGAATGAAGTTCTACAATATCTGTGAGTGCATTTTCCTGGTGTTTTGGAGGTTTTCATTTTTT

GTTTGAGAAATTTAAGATGTTTCTTTACCTTCTGTATTGCAGAGGATTAAGAGGCAACATGTTGACAGGAACATTGT

CCCCTGATATGTGCCAGTTGACTGGCTTGTGGTATTTGTATGTGCTCTGCTACATGATATCTATACGGGATGCTCTG

TTGTCTGTTTGGTGTAATATTTATGTATATTCTAACATTAGAAGTTTCATATTATTTCAGTGATGTGCGGGGCAATA

ACCTCAGCGGAATAATTCCAGATAATATTGGGAATTGTACAAGCTTTGAGATACTGTCAGTGTTGTCTTCTTGCTCT

GATTATGTTAAGCTACAGTTCTTCTCCTACTGCTGCCCAATTCTAACAAAATCTATTTTTTCGTGATTTCAGGGATA

TCTCATACAATCAGATAACTGGAGAAATTCCCTACAATATTGGGTTTTTACAAGTGGCTACCTTGTTAGTAAATTCA

ACTTTGTCAGTTCTACCTTGTCTGTTCTGTTATGGGGTTCGTTTCTGTAAATGGTAAATGGAGATTATGGTCCTTTC

AACAGGTCTTTGCAAGGAAATAGGCTAACTGGCAGGATCCCAGAAGTGATTGGTCTTATGCAAGCTCTTGCTGTTCT

GTGAGTATTCATACTAGTACAAGAATTGTTTATTTTTTCCAACTCCATTCTTACTAGTTACTGCTTGCAAGTAAGAA

GGTTCATGATGTCCGTCTCCTCTGTAGGGACTTGAGTGAAAATGAGTTGGTGGGACCAATCCCTCCAATCTTTGGCA

ATTTATCTTACACAGGGAAGCTGTAAGTTTTCACTCCTATTTTAATGCATATACCTTTCTATGTGAGGCTCGTTTAT

CTGATTCATTTGTACATTCAACAGGTACCTGCACGGCAACAAACTTACAGGGCCAGTTCCACCGGAGCTAGGAAATA

TGTCTAAACTTAGTTACTTGTAAGAGCCTAAGAGGATTAATTCACAGTTTCAGATACATGATGTGGTCACCTTGTTT

TGCTTCATGCATTGAGCTATCTTATTTACAGGCAATTAAATGACAATCAGCTAATGGGTCGAATTCCCCCTGAACTT

GGCAAACTGGACCAGTTATTTGAATTGTGAGCCTTTTATTTTTGTAGTAAATATTTCTGGTTCCACTTCCTCTTGGA

ATATTGAGGTCTTAGCTATCCTCTACCAGGAATCTTGCAAATAACAAGTTGGAGGGACCAATTCCTGAAAATATCAG

CTCCTGTTCTGCATTGAATCAGCTGTAAGATTGTTCTGTTTCCTTTTGAAACTTCATTTTTTTCTCTTTCTCTTTTG

CTAGTCTATTCATTCTGAGTCTCAACATATTTGTTTTTTTCTTTCAGTAATGTTCATGGCAACAACTTAAACGAGTC

CATTCCTTCAGGGTTTAAGAATCTGGAGAGCTTGACGTATCTGTATGTTATAGTCTTCTGTTTTGGCTAGTGGTCAT

GATAATGATTTTGAATTTCTTTCATATGGTACTAACTTATTAGTGATATTTGTTGATATTTACCTGGCAGAAATCTT

TCAGCTAATAAATTTAAGGGTCACATACCTTCTCAACTTGGGCGAATCATCAACCTTGATACATTGTGAGTTCTTGA

TTGTCAAGGCCGATAAAATTTATTAGTTCACGTGATTCCTTGTACTAAAACTTTTATTCTTTAGGGATCTCTCTGGC

AACAATTTTTCTGGGTCTATCCCTGGTTCTATTGGAGATTTGGAGCATCTCCTCACATTGTAAGATATTAAACATTT

CGATGTACAAGATGTTTGTATCATATTGAGACTGGAACATAATCACAATATCATTGCACATTGTAGGAATCTGAGCA

GCAATCATCTTGATGGACAAATTCCTGTAGAATTTGGCAATCTAAAAAGTATACAGACCATGTAAGTTTCTGCTGAG

AGCTTTGGTTACACTGCCTTCAAAATGTGTACTTTTTGTATACTGATTTTCATGTGCTGAGATTGGCTTCTATACTG

-continued

CCTTCAACATGTGTATTTTTATACTGATCTTCTTGCGCTGAGACTGGCTTCTATTCTTTCAGTGATATGTCAAGCAA

CAAGATCTCTGGTGGCATCCCAAAAGAGCTGGGACAGCTGCAGACCATGATAACTCTGTAAGTACATTAGTTTTTGT

CAAGTAAATTGATGTAGTGTTTAATCAGTTTTCCTTAATATCACAATCAATTCTAATAAAATTTTGATTGACTTTGT

TTCTTTTTGTAGTACTTTGACAGGTAACTATCTTACTGGAGCAATCCCTGACCAATTGACCAATTGTTTCAGCCTAA

CTAGTTTGTGAGTTCATCTATCTTTGCCTTTAACATCATAGACAGTCTAATTCTTTGTACAGTTACTGATCTTATGT

CATTCTCCTTCAGGAATATATCCTACAACAATTTTAGTGGTGTTGTTCCTCTTTCACGGAATTTCTCGCGGTTTGCA

CCTGACAGGTATTTTCCGAATAGAATGAAGCTTTATCATTATATTTGTGCTTTAGTACTCTAGCTAATGACCACCTT

ATTATGGTCATCAGCTTTTTAGGGAACCCATTTCTTTGTGGCAACTGGAAAGGTTCAATATGTGACCCCTATGCACC

AAGGTCTAACGGTATGACTTCATTTTTGTGCATTGGTTAGCGAATCTCTTGGTATGCAGAGTCATGTGCATCAAAAT

GACTTGTTACTTTTGCAGCCTTGTTCTCCAGAACAGCTGTTGTTTGCACAGCACTGGGTTTCATTGCACTCTTATCC

ATGGTTGTAGTGGCTGTGTATAAGTCCAACCAACCACACCAGTTTTTGAAGGGGCCTAAGACCAATCAAGGTAAAAA

TTAGTACATGTACACTCTGTTCTTTTGTTTTTCAGTACTTTCAGGTATTTATGTTTGCTTTTTGTCTTGTTTCCCTC

TAATTCCATAGGCTCCCCCAAACTTGTGGTTCTTCACATGGATATGGCCATCCATACATATGATGACATTATGAGGA

TTACCGAGAACTTCAATGAGAAATTCATAATAGGATATGGTGCGTCCAGCACTGTATATAAATGTGATTTGAAAGAT

TCCCGACCAATTGCAGTTAAGCGACTTTACACCGCACATCCGCACAGCTTGCGAGAGTTTGAGACTGAACTGGAGAC

AATTGGAAGCATTAGGCATAGAAACCTTGTTAGCTTGCATGGTTACTCCCTTTCCCCTCATGGGAATCTCCTTTGTT

ACGACTACATGGAGAATGGTTCACTCTGGGATCTACTTCATGGTTAGTAACCCACCTTTCCTTGTAATCTTTTATGA

AGTTTCTTCATGTAAGACAGTGTTGACTATTGGTTGATGTTAATTACTAGTTTCTCTGTCGGAGAACAGTTCTATTA

GCCAAGATTTTTGTGAAAATGGCTAATTATCAACTGAATACATGTCAATAGGGCCTTCCAAAAAGGTGAAGCTTGAC

TGGGAAACACGTCTGAAGATTGCTGTTGGTGCTGCTCAGGGTCTTGCTTATCTTCACCACGATTGCAACCCAAGAAT

AATACACAGAGATGTAAAATCTTCAAACATCCTTGTTGATGAAAATTTTGAGGCTCATCTATCTGATTTTGGGGTTG

CAAAATGCATCCCTACTGCAAAAACTCATGCATCAACTTTGGTGTTGGGCACCATAGGTTACATTGACCCTGAGTAT

GCCAGGACTTCCAGGTTAACTGAAAAGTCAGACGTCTACAGCTTTGGCATTGTTCTCCTAGAGCTTTTGACAGGAAA

GAAACCGGTTGATAATGACTTGAACCTGCATCAGCTGGTATTATTCTCCACTTATACTCTACGTTGTTACTTGTAAA

AAAGATTTAACTCAGACTGGATATAGAAAAGAACAACTTAGCTCAAATTATCCCATCTTCCTATAGCATTTGCAATA

ATGTCTTTTGTCTATTAACTCCTGTATTACATTTGTCTTTGAAGTAATTCGATTTGTGTTACAGATAATGTCAAAGG

CGGATGATAACACCGTGATGGATGCTGTTGATCCTGAGGTATCTGTTACATGTATGGATTTAATGCATGTTAGGAAA

ACTTTTCAGCTTGCGTTGCTGTGTGCAAAAAGATTCCCATGTGAGAGGCCAACAATGCATGAGGTTGCTAGGGTACT

TGTTTCCTTGCTTCCTCCCCCACCAACCAAACCTTGTTTAGACCCACCTCCCAAATCCATTGATTATACAAAATTTG

TGATTGGTAAAGGACTACCGCAAGTCCAGCAGGGTGACAATTCCTCCGAAGCTCAGTGGCTTGTTAGATTTCAAGAA

GCTATATCCAAAAACTCCCTTTGA

Nucleic acid sequence for a mutant Solyc03g007050 gene allele slerl1$^{CR-2}$ coding sequence (SEQ ID NO: 50)

ATGGAAGTGAGCCTGAAAATGAAATTCCGCTCGCAAGCGCTACTGTTGGTTCTATTGCTTGTTTTCCCGATCGTTTT

GGCTCTCACCGAAGAAGGCAAAGCATTAATGTCGATCAAGGCATCGTTTAGCAACGTAGCAAACGTGT TGCTGGAT

TGGGATGATATCCACGACGAGGATTTTTGCTCATGGAGAGGCGTGTTGTGTGGAAATTTCTCCATGTCCGTCGTTGC

ACTGAATCTGTCTAATCTGAACTTGGGCGGGGAAATTTCACCAGACATTGGAGAGTTGAAGAATCTGGAGACATTAG

ACCTTCAGGGAAATAAATTAACTGGTCAAGTCCCAGATGAAATTGGCAACTGCATTTCACTGATCTATCTTGATTTG

TCTGATAACTTGTTCTATGGAGATATACCATTCTCAATTTCTAAGCTCAAGCAGCTAGAGTTGTTAAACTTTAAAAA

CAACCAGTTGTCCGGCCCAATCCCGTCCACATTAACTCAAATTCCTAATCTAAAGACGCTTGATCTGGCTCGAAACC

AGCTCATTGGTGAGATACCAAGGTTGATCTATTGGAATGAAGTTCTACAATATCTAGGATTAAGAGGCAACATGTTG

-continued

ACAGGAACATTGTCCCCTGATATGTGCCAGTTGACTGGCTTGTGGTATTTTGATGTGCGGGGCAATAACCTCAGCGG

AATAATTCCAGATAATATTGGGAATTGTACAAGCTTTGAGATACTGGATATCTCATACAATCAGATAACTGGAGAAA

TTCCCTACAATATTGGGTTTTTACAAGTGGCTACCTTGTCTTTGCAAGGAAATAGGCTAACTGGCAGGATCCCAGAA

GTGATTGGTCTTATGCAAGCTCTTGCTGTTCTGGACTTGAGTGAAAATGAGTTGGTGGGACCAATCCCTCCAATCTT

TGGCAATTTATCTTACACAGGGAAGCTGTACCTGCACGGCAACAAACTTACAGGGCCAGTTCCACCGGAGCTAGGAA

ATATGTCTAAACTTAGTTACTTGCAATTAAATGACAATCAGCTAATGGGTCGAATTCCCCCTGAACTTGGCAAACTG

GACCAGTTATTTGAATTGAATCTTGCAAATAACAAGTTGGAGGGACCAATTCCTGAAAATATCAGCTCCTGTTCTGC

ATTGAATCAGCTTAATGTTCATGGCAACAACTTAAACGAGTCCATTCCTTCAGGGTTTAAGAATCTGGAGAGCTTGA

CGTATCTAAATCTTTCAGCTAATAAATTTAAGGGTCACATACCTTCTCAACTTGGGCGAATCATCAACCTTGATACA

TTGGATCTCTCTGGCAACAATTTTTCTGGGTCTATCCCTGGTTCTATTGGAGATTTGGAGCATCTCCTCACATTGAA

TCTGAGCAGCAATCATCTTGATGGACAAATTCCTGTAGAATTTGGCAATCTAAAAAGTATACAGACCATTGATATGT

CAAGCAACAAGATCTCTGGTGGCATCCCAAAAGAGCTGGGACAGCTGCAGACCATGATAACTCTTACTTTGACAGGT

AACTATCTTACTGGAGCAATCCCTGACCAATTGACCAATTGTTTCAGCCTAACTAGTTTGAATATATCCTACAACAA

TTTTAGTGGTGTTGTTCCTCTTTCACGGAATTTCTCGCGGTTTGCACCTGACAGCTTTTTAGGGAACCCATTTCTTT

GTGGCAACTGGAAAGGTTCAATATGTGACCCCTATGCACCAAGGTCTAACGCCTTGTTCTCCAGAACAGCTGTTGTT

TGCACAGCACTGGGTTTCATTGCACTCTTATCCATGGTTGTAGTGGCTGTGTATAAGTCCAACCAACCACACCAGTT

TTTGAAGGGGCCTAAGACCAATCAAGGCTCCCCCAAACTTGTGGTTCTTCACATGGATATGGCCATCCATACATATG

ATGACATTATGAGGATTACCGAGAACTTCAATGAGAAATTCATAATAGGATATGGTGCGTCCAGCACTGTATATAAA

TGTGATTTGAAAGATTCCCGACCAATTGCAGTTAAGCGACTTTACACCGCACATCCGCACAGCTTGCGAGAGTTTGA

GACTGAACTGGAGACAATTGGAAGCATTAGGCATAGAAACCTTGTTAGCTTGCATGGTTACTCCCTTTCCCCTCATG

GGAATCTCCTTTGTTACGACTACATGGAGAATGGTTCACTCTGGGATCTACTTCATGGGCCTTCCAAAAAGGTGAAG

CTTGACTGGGAAACACGTCTGAAGATTGCTGTTGGTGCTGCTCAGGGTCTTGCTTATCTTCACCACGATTGCAACCC

AAGAATAATACACAGAGATGTAAAATCTTCAAACATCCTTGTTGATGAAAATTTTGAGGCTCATCTATCTGATTTTG

GGGTTGCAAAATGCATCCCTACTGCAAAAACTCATGCATCAACTTTGGTGTTGGGCACCATAGGTTACATTGACCCT

GAGTATGCCAGGACTTCCAGGTTAACTGAAAAGTCAGACGTCTACAGCTTTGGCATTGTTCTCCTAGAGCTTTTGAC

AGGAAAGAAACCGGTTGATAATGACTTGAACCTGCATCAGCTGATAATGTCAAAGGCGGATGATAACACCGTGATGG

ATGCTGTTGATCCTGAGGTATCTGTTACATGTATGGATTTAATGCATGTTAGGAAAACTTTTCAGCTTGCGTTGCTG

TGTGCAAAAAGATTCCCATGTGAGAGGCCAACAATGCATGAGGTTGCTAGGGTACTTGTTTCCTTGCTTCCTCCCCC

ACCAACCAAACCTTGTTTAGACCCACCTCCCAAATCCATTGATTATACAAAATTTGTGATTGGTAAAGGACTACCGC

AAGTCCAGCAGGGTGACAATTCCTCCGAAGCTCAGTGGCTTGTTAGATTTCAAGAAGCTATATCCAAAAACTCCCTT

TGA

Amino acid sequence for a mutant polypeptide encoded by a mutant Solyc03g007050 gene allele slerl1$^{CR-2}$ coding sequence (SEQ ID NO: 51)

MEVSLKMKFRSQALLLVLLLVFPIVLALTEEGKALMSIKASFSNVANVFAGLG*

SolycO5s053850 (SP5G)

Wild-type Solyc05g053850 gene

Nucleic acid sequence of a wild-type Solyc05g053850 gene (SEQ ID NO: 52)

ATGCCTAGAGATCCTTTAATAGTTTCTGGAGTTGTTGGAGATGTTGTTGATCCATTCACAAGATGTGTAGACTTTGG

TGTGGTTTACAACAATAGGGTGGTCTATAATGGATGTTCCTTGAGGCCTTCACAAGTTGTCAATCAACCTAGGGTTG

ACATTGATGGAGACGATCTTCGTACTTTTTACACTCTGGTATAAACTCATCGTTTTATTTCATATGATATACATATA

TATATATATATATATATATATATATATATATATTTTCTTTCTATTTATACATTTTAATATCTCTAAATTATTAACCT

-continued

TTTGTCAATTGATTATGAGTAGAAGATCAAAAGGACAATATGTGCAAAGGCTTCTAATTATGTGAATTTGTGTTAGT

TTTAATTTTGATTCACCATCTAAGTACTTGTTTTGTGGTTTTTATTTGAATTTGAGAACTCATAACATACTATTTAT

GATAATAAAAAATGTTAGTAACATGTATGTTTAATATTGCAAGCTTGAAAATATACAATATTTTTAAATTACTAATA

ATGTCATGTAATACATTTGGATATACAATATGGAAAATTATTTTTCCTAATTTTCAAAATATTTGAAATGTTTCTTT

TCTTTTTGGAAGATTATGGTGGATCCTGATGCTCCAAACCCTAGCAACCCAAACCTGAGGGAATATTTGCACTGGTA

AGTCATCTAGCTTATATTATATATATATATATATATATATATATATATTATATAAATAGATAAAAATATTCATTTTG

TTATATACTTCTTATTTCTCTTAAATCAATCGTCGATAGCGAAGACAAAATGTATGTGAGATTATATAAGAACCTA

AGGAAAGTATTATTTCATAAAATGATAACTTTCTGATACACAAATTAATCAATATTTCAAATAAATACCAAATATCG

AATAACAACGTAAAAAAATAATAACTATTATCGATTGCTTAATCCCCTTACAATTAATGTACCTAAACCTCTTTTTT

TTTTTAAAAAAAAAATAATAATAATAATGTTTAACACATTATTTTTTTAATAGGTTGGTCACAGATATCCCAGCAGC

CACAGGAGCAACCTTTGGTAAGTTTTTCTTACATTATTACCTAATGGCTCGTAATTACGCAGTGACGAAGCAAGAAA

TTTAAATATACTTTATATTTACGATACATTGTATCCGTATCACTACATTTTTAATATAAGACGGTTAGTAATATACA

AAATACAACTTGTATCATCATCACCTTAGTAGTACATTATTAGTACTATAGGCCCAATTATGACTACTAATAAAATA

AGACTTAAAAAGAAACATAAAATCAAAATGAAGTATATACTATGTATATAAATGTTTTTGAAACAAGGAAAATACGC

GTATTGAATGTCTTTGTTACTAAACTCAAACTCTCGTTATACAGGCAATGAAGTCGTGGGCTACGAGAGCCCACGAC

CCTCAATGGGAATCCATCGTTATATTTTCGTGTTGTATCGACAATTGGGCTGCGATGCCATCGATGCACCGGACATA

ATCGATTCTAGACAAAATTTCAACACAAGAGACTTTGCTAGGTTTCACAATCTAGGTTTGCCTGTTGCTGCTGTTTA

CTTCAATTGCAATAGGGAAGGTGGTACCGGTGGTCGTCGCCTATAA

Nucleic acid sequence of a wild-type Solyc05g053850 coding sequence
                                                            (SEQ ID NO: 53)
ATGCCTAGAGATCCTTTAATAGTTTCTGGAGTTGTTGGAGATGTTGTTGATCCATTCACAAGATGTGTAGACTTTGG

TGTGGTTTACAACAATAGGGTGGTCTATAATGGATGTTCCTTGAGGCCTTCACAAGTTGTCAATCAACCTAGGGTTG

ACATTGATGGAGACGATCTTCGTACTTTTTACACTCTGATTATGGTGGATCCTGATGCTCCAAACCCTAGCAACCCA

AACCTGAGGGAATATTTGCACTGGTTGGTCACAGATATCCCAGCAGCCACAGGAGCAACCTTTGGCAATGAAGTCGT

GGGCTACGAGAGCCCACGACCCTCAATGGGAATCCATCGTTATATTTTCGTGTTGTATCGACAATTGGGCTGCGATG

CCATCGATGCACCGGACATAATCGATTCTAGACAAAATTTCAACACAAGAGACTTTGCTAGGTTTCACAATCTAGGT

TTGCCTGTTGCTGCTGTTTACTTCAATTGCAATAGGGAAGGTGGTACCGGTGGTCGTCGCCTATAA

Amino acid sequence for a polypeptide encoded by a wild-type
Solyc05g053850 coding sequence
                                                            (SEQ ID NO: 54)
MPRDPLIVSGVVGDVVDPFTRCVDFGVVYNNRVVYNGCSLRPSQVVNQPRVDIDGDDLRTFYTLIMVDPDAPNPSNP

NLREYLHWLVTDIPAATGATFGNEVVGYESPRPSMGIHRYIFVLYRQLGCDAIDAPDIIDSRQNFNTRDFARFHNLG

LPVAAVYFNCNREGGTGGRRL*

Mutant Solyc05g053850 gene allele sp5g (M82 background)
Nucleic acid sequence for a mutant Solyc05g053850 gene allele
sp5g (M82 background)
                                                            (SEQ ID NO: 55)
ATGCCTAGAGATCCTTTAATGGATGTTCCTTGAGGCCTTCACAAGTTGTCAATCAACCTAGGGTTGACATTGATGGA

GACGATCTTCGTACTTTTTACACTCTGGTATAAACTCATCGTTTTATTTCATATGATATACATATATATATATATAT

ATATATATATATATATATATTTTTCTTTCTATTTATACATTTTAATATCTCTAAATTATTAACCTTTTGTCAATTG

ATTATGAGTAGAAGATCAAAAGGACAATATGTGCAAAGGCTTCTAATTATGTGAATTTGTGTTAGTTTTAATTTTGA

TTCACCATCTAAGTACTTGTTTTGTGGTTTTTATTTGAATTTGAGAACTCATAACATACTATTTATGATAATAAAAA

ATGTTAGTAACATGTATGTTTAATATTGCAAGCTTGAAAATATACAATATTTTTAAATTACTAATAATGTCATGTAA

TACATTTGGATATACAATATGGAAAATTATTTTTCCTAATTTTCAAAATATTTGAAATGTTTCTTTTCTTTTTGGAA

GATTATGGTGGATCCTGATGCTCCAAACCCTAGCAACCCAAACCTGAGGGAATATTTGCACTGGTAAGTCATCTAGC

-continued

TTATATTATATATATATATATATATATATATATATATATTATATAAATAGATAAAAATATTCATTTTGTTATATACTTC

TTATTTCTCTTAAATCAATCGTCGATAGCGAAGACAAAAATGTATGTGAGATTATATAAGAACCTAAGGAAAGTATT

ATTTCATAAAATGATAACTTTCTGATACACAAATTAATCAATATTTCAAATAAATACCAAATATCGAATAACAACGT

AAAAAAATAATAACTATTATCGATTGCTTAATCCCCTTACAATTAATGTACCTAAACCTCTTTTTTTTTTTAAAAAA

AAAATAATAATAATAATGTTTAACACATTATTTTTTTAATAGGTTGGTCACAGATATCCCAGCAGCCACAGGAGCAA

CCTTTGGTAAGTTTTTCTTACATTATTACCTAATGGCTCGTAATTACGCAGTGACGAAGCAAGAAATTTAAATATAC

TTTATATTTACGATACATTGTATCCGTATCACTACATTTTTAATATAAGACGGTTAGTAATATACAAAATACAACTT

GTATCATCATCACCTTAGTAGTACATTATTAGTACTATAGGCCCAATTATGACTACTAATAAAATAAGACTTAAAAA

GAAACATAAAATCAAAATGAAGTATATACTATGTATATAAATGTTTTTGAAACAAGGAAAATACGCGTATTGAATGT

CTTTGTTACTAAACTCAAACTCTCGTTATACAGGCAATGAAGTCGTGGGCTACGAGAGCCCACGACCCTCAATGGGA

ATCCATCGTTATATTTTCGTGTTGTATCGACAATTGGGCTGCGATGCCATCGATGCACCGGACATAATCGATTCTAG

ACAAAATTTCAACACAAGAGACTTTGCTAGGTTTCACAATCTAGGTTTGCCTGTTGCTGCTGTTTACTTCAATTGCA

ATAGGGAAGGTGGTACCGGTGGTCGTCGCCTATAA

Nucleic acid sequence for a mutant Solyc05g053850 gene allele sp5g
coding sequence (M82 background)

(SEQ ID NO: 56)

ATGCCTAGAGATCCTTTAATGGATGTTCCTTGAGGCCTTCACAAGTTGTCAATCAACCTAGGGTTGACATTGATGGA

GACGATCTTCGTACTTTTTACACTCTGATTATGGTGGATCCTGATGCTCCAAACCCTAGCAACCCAAACCTGAGGGA

ATATTTGCACTGGTTGGTCACAGATATCCCAGCAGCCACAGGAGCAACCTTTGGCAATGAAGTCGTGGGCTACGAGA

GCCCACGACCCTCAATGGGAATCCATCGTTATATTTTCGTGTTGTATCGACAATTGGGCTGCGATGCCATCGATGCA

CCGGACATAATCGATTCTAGACAAAATTTCAACACAAGAGACTTTGCTAGGTTTCACAATCTAGGTTTGCCTGTTGC

TGCTGTTTACTTCAATTGCAATAGGGAAGGTGGTACCGGTGGTCGTCGCCTATAA

Amino acid sequence for a mutant polypeptide encoded by a mutant
Solyc05g053850 gene allele sp5g coding sequence (M82 background)

(SEQ ID NO: 57)

MPRDPLMDVP*

Mutant Solyc05g053850 gene allele sp5g (Sweet100 background)
Nucleic acid sequence for a mutant Solyc05g053850 gene allele
sp5g (Sweet100 background)

(SEQ ID NO: 58)

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

TGATGGAGACGATCTTCGTACTTTTTACACTCTGGTATAAACTCATCGTTTTATTTCATATGATATACATATATATA

TATATATATATATATATATATATATATATTTTCTTTCTATTTATACATTTTAATATCTCTAAATTATTAACCTTTTG

TCAATTGATTATGAGTAGAAGATCAAAAGGACAATATGTGCAAAGGCTTCTAATTATGTGAATTTGTGTTAGTTTTA

ATTTTGATTCACCATCTAAGTACTTGTTTTGTGGTTTTTATTTGAATTTGAGAACTCATAACATACTATTTATGATA

ATAAAAAATGTTAGTAACATGTATGTTTAATATTGCAAGCTTGAAAATATACAATATTTTTAAATTACTAATAATGT

CATGTAATACATTTGGATATACAATATGGAAAATTATTTTTCCTAATTTTCAAAATATTTGAAATGTTTCTTTTCTT

TTTGGAAGATTATGGTGGATCCTGATGCTCCAAACCCTAGCAACCCAAACCTGAGGGAATATTTGCACTGGTAAGTC

ATCTAGCTTATATTATATATATATATATATATATATATATATATATTATATAAATAGATAAAAATATTCATTTTGTTAT

ATACTTCTTATTTCTCTTAAATCAATCGTCGATAGCGAAGACAAAAATGTATGTGAGATTATATAAGAACCTAAGGA

AAGTATTATTTCATAAAATGATAACTTTCTGATACACAAATTAATCAATATTTCAAATAAATACCAAATATCGAATA

ACAACGTAAAAAAATAATAACTATTATCGATTGCTTAATCCCCTTACAATTAATGTACCTAAACCTCTTTTTTTTTT

TAAAAAAAAAATAATAATAATAATGTTTAACACATTATTTTTTTAATAGGTTGGTCACAGATATCCCAGCAGCCACA

GGAGCAACCTTTGGTAAGTTTTTCTTACATTATTACCTAATGGCTCGTAATTACGCAGTGACGAAGCAAGAAATTTA

-continued

AATATACTTTATATTTACGATACATTGTATCCGTATCACTACATTTTTAATATAAGACGGTTAGTAATATACAAAAT

ACAACTTGTATCATCATCACCTTAGTAGTACATTATTAGTACTATAGGCCCAATTATGACTACTAATAAAATAAGAC

TTAAAAAGAAACATAAAATCAAAATGAAGTATATACTATGTATATAAATGTTTTTGAAACAAGGAAAATACGCGTAT

TGAATGTCTTTGTTACTAAACTCAAACTCTCGTTATACAGGCAATGAAGTCGTGGGCTACGAGAGCCCACGACCCTC

AATGGGAATCCATCGTTATATTTTCGTGTTGTATCGACAATTGGGCTGCGATGCCATCGATGCACCGGACATAATCG

ATTCTAGACAAAATTTCAACACAAGAGACTTTGCTAGGTTTCACAATCTAGGTTTGCCTGTTGCTGCTGTTTACTTC

AATTGCAATAGGGAAGGTGGTACCGGTGGTCGTCGCCTATAA

Nucleic acid sequence for a mutant Solyc05g053850 gene allele
sp5g coding sequence (Sweet100 background)

(SEQ ID NO: 59)

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

TGATGGAGACGATCTTCGTACTTTTTACACTCTGATTATGGTGGATCCTGATGCTCCAAACCCTAGCAACCCAAACC

TGAGGGAATATTTGCACTGGTTGGTCACAGATATCCCAGCAGCCACAGGAGCAACCTTTGGCAATGAAGTCGTGGGC

TACGAGAGCCCACGACCCTCAATGGGAATCCATCGTTATATTTTCGTGTTGTATCGACAATTGGGCTGCGATGCCAT

CGATGCACCGGACATAATCGATTCTAGACAAAATTTCAACACAAGAGACTTTGCTAGGTTTCACAATCTAGGTTTGC

CTGTTGCTGCTGTTTACTTCAATTGCAATAGGGAAGGTGGTACCGGTGGTCGTCGCCTATAA

Amino acid sequence for a mutant polypeptide encoded by a mutant
Solyc05g053850 gene allele
sp5g coding sequence (Sweet 100 background)

(SEQ ID NO: 60)

MPRDPLIVWSCWRCC*

Mutant Solyc05g053850 gene allele sp5g-cocktail (SEQ ID NO: 61)

Nucleic acid sequence for a mutant Solyc05g053850 gene allele sp5g-cocktail

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

TGATGGAGACGATCTTCGTACTTTTTACACTCTGGTATAAACTCATCGTTTTATTTCATATGATATACATATATATA

TATATATATATATATATATATATATATATTTTCTTTCTATTTATACATTTTAATATCTCTAAATTATTAACCTTTTG

TCAATTGATTATGAGTAGAAGATCAAAAGGACAATATGTGCAAAGGCTTCTAATTATGTGAATTTGTGTTAGTTTTA

ATTTTGATTCACCATCTAAGTACTTGTTTTGTGGTTTTTATTTGAATTTGAGAACTCATAACATACTATTTATGATA

ATAAAAAATGTTAGTAACATGTATGTTTAATATTGCAAGCTTGAAAATATACAATATTTTTAAATTACTAATAATGT

CATGTAATACATTTGGATATACAATATGGAAAATTATTTTTCCTAATTTTCAAAATATTTGAAATGTTTCTTTTCTT

TTTGGAAGATTATGGTGGATCCTGATGCTCCAAACCCTAGCAACCCAAACCTGAGGGAATATTTGCACTGGTAAGTC

ATCTAGCTTATATTATATATATATATATATATATATATATATATATTATATAAATAGATAAAAATATTCATTTTGTTAT

ATACTTCTTATTTCTCTTAAATCAATCGTCGATAGCGAAGACAAAAATGTATGTGAGATTATATAAGAACCTAAGGA

AAGTATTATTTCATAAAATGATAACTTTCTGATACACAAATTAATCAATATTTCAAATAAATACCAAATATCGAATA

ACAACGTAAAAAAATAATAACTATTATCGATTGCTTAATCCCCTTACAATTAATGTACCTAAACCTCTTTTTTTTT

TAAAAAAAAAATAATAATAATAATGTTTAACACATTATTTTTTTAATAGGTTGGTCACAGATATCCCAGCAGCCACA

GGAGCAACCTTTGGTAAGTTTTTCTTACATTATTACCTAATGGCTCGTAATTACGCAGTGACGAAGCAAGAAATTTA

AATATACTTTATATTTACGATACATTGTATCCGTATCACTACATTTTTAATATAAGACGGTTAGTAATATACAAAAT

ACAACTTGTATCATCATCACCTTAGTAGTACATTATTAGTACTATAGGCCCAATTATGACTACTAATAAAATAAGAC

TTAAAAAGAAACATAAAATCAAAATGAAGTATATACTATGTATATAAATGTTTTTGAAACAAGGAAAATACGCGTAT

TGAATGTCTTTGTTACTAAACTCAAACTCTCGTTATACAGGCAATGAAGTCGTGGGCTACGAGAGCCCACGACCCTC

AATGGGAATCCATCGTTATATTTTCGTGTTGTATCGACAATTGGGCTGCGATGCCATCGATGCACCGGACATAATCG

-continued

ATTCTAGACAAAATTTCAACACAAGAGACTTTGCTAGGTTTCACAATCTAGGTTTGCCTGTTGCTGCTGTTTACTTC

AATTGCAATAGGGAAGGTGGTACCGGTGGTCGTCGCCTATAA

Nucleic acid sequence for a mutant Solyc05g053850 gene allele sp5g-cocktail coding sequence (SEQ ID NO: 62)

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

TGATGGAGACGATCTTCGTACTTTTTACACTCTGATTATGGTGGATCCTGATGCTCCAAACCCTAGCAACCCAAACC

TGAGGGAATATTTGCACTGGTTGGTCACAGATATCCCAGCAGCCACAGGAGCAACCTTTGGCAATGAAGTCGTGGGC

TACGAGAGCCCACGACCCTCAATGGGAATCCATCGTTATATTTTCGTGTTGTATCGACAATTGGGCTGCGATGCCAT

CGATGCACCGGACATAATCGATTCTAGACAAAATTTCAACACAAGAGACTTTGCTAGGTTTCACAATCTAGGTTTGC

CTGTTGCTGCTGTTTACTTCAATTGCAATAGGGAAGGTGGTACCGGTGGTCGTCGCCTATAA

Amino acid sequence for a mutant polypeptide encoded by a mutant Solyc05g053850 gene allele sp5g-cocktail coding sequence (SEQ ID NO: 63)

MPRDPLIVWSCWRCC*

Mutant Solyc05g053850 gene allele sp5g-grape (SEQ ID NO: 64)

Nucleic acid sequence for a mutant Solyc05g053850 gene allele sp5g-grape

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

TGATGGAGACGATCTTCGTACTTTTTACACTCTGGTATAAACTCATCGTTTTATTTCATATGATATACATATATATA

TATATATATATATATATATATATATATATTTTCTTTCTATTTATACATTTTAATATCTCTAAATTATTAACCTTTTG

TCAATTGATTATGAGTAGAAGATCAAAAGGACAATATGTGCAAAGGCTTCTAATTATGTGAATTTGTGTTAGTTTTA

ATTTTGATTCACCATCTAAGTACTTGTTTTGTGGTTTTTATTTGAATTTGAGAACTCATAACATACTATTTATGATA

ATAAAAAATGTTAGTAACATGTATGTTTAATATTGCAAGCTTGAAAATATACAATATTTTTAAATTACTAATAATGT

CATGTAATACATTTGGATATACAATATGGAAAATTATTTTTCCTAATTTTCAAAATATTTGAAATGTTTCTTTTCTT

TTTGGAAGATTATGGTGGATCCTGATGCTCCAAACCCTAGCAACCCAAACCTGAGGGAATATTTGCACTGGTAAGTC

ATCTAGCTTATATTATATATATATATATATATATATATATATATATATTATATAAATAGATAAAAATATTCATTTTGTTAT

ATACTTCTTATTTCTCTTAAATCAATCGTCGATAGCGAAGACAAAAATGTATGTGAGATTATATAAGAACCTAAGGA

AAGTATTATTTCATAAAATGATAACTTTCTGATACACAAATTAATCAATATTTCAAATAAATACCAAATATCGAATA

ACAACGTAAAAAAATAATAACTATTATCGATTGCTTAATCCCCTTACAATTAATGTACCTAAACCTCTTTTTTTTTT

TAAAAAAAAAATAATAATAATAATGTTTAACACATTATTTTTTTAATAGGTTGGTCACAGATATCCCAGCAGCCACA

GGAGCAACCTTTGGTAAGTTTTTCTTACATTATTACCTAATGGCTCGTAATTACGCAGTGACGAAGCAAGAAATTTA

AATATACTTTATATTTACGATACATTGTATCCGTATCACTACATTTTTAATATAAGACGGTTAGTAATATACAAAAT

ACAACTTGTATCATCATCACCTTAGTAGTACATTATTAGTACTATAGGCCCAATTATGACTACTAATAAAATAAGAC

TTAAAAAGAAACATAAAATCAAAATGAAGTATATACTATGTATATAAATGTTTTTGAAACAAGGAAAATACGCGTAT

TGAATGTCTTTGTTACTAAACTCAAACTCTCGTTATACAGGCAATGAAGTCGTGGGCTACGAGAGCCCACGACCCTC

AATGGGAATCCATCGTTATATTTTCGTGTTGTATCGACAATTGGGCTGCGATGCCATCGATGCACCGGACATAATCG

ATTCTAGACAAAATTTCAACACAAGAGACTTTGCTAGGTTTCACAATCTAGGTTTGCCTGTTGCTGCTGTTTACTTC

AATTGCAATAGGGAAGGTGGTACCGGTGGTCGTCGCCTATAA

Nucleic acid sequence for a mutant Solyc05g053850 gene allele sp5g-grape coding sequence (SEQ ID NO: 65)

ATGCCTAGAGATCCTTTAATAGTCTGGAGTTGTTGGAGATGTTGTTGATCCATTCACAAGATGTGTAGACTTTGGTG

TGGTTTACAACAATAGGGTGGTCTAATGGATGTTCCTTGAGGCCTTCACAAGTTGTCAATCAACCTAGGGTTGACAT

-continued

TGATGGAGACGATCTTCGTACTTTTTACACTCTGATTATGGTGGATCCTGATGCTCCAAACCCTAGCAACCCAAACC

TGAGGGAATATTTGCACTGGTTGGTCACAGATATCCCAGCAGCCACAGGAGCAACCTTTGGCAATGAAGTCGTGGGC

TACGAGAGCCCACGACCCTCAATGGGAATCCATCGTTATATTTTCGTGTTGTATCGACAATTGGGCTGCGATGCCAT

CGATGCACCGGACATAATCGATTCTAGACAAAATTTCAACACAAGAGACTTTGCTAGGTTTCACAATCTAGGTTTGC

CTGTTGCTGCTGTTTACTTCAATTGCAATAGGGAAGGTGGTACCGGTGGTCGTCGCCTATAA

Amino acid sequence for a mutant polypeptide encoded by a mutant Solyc05g053850 gene allele sp5g-grape coding sequence (SEQ ID NO: 66)

MPRDPLIVWSCWRCC*

Solyc06g074350 (SP) (Tomato)
Wild-type Solyc06g074350 Gene

Nucleic acid sequence of a wild-type Solyc06g074350 gene (SEQ ID NO: 67)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTCAGTAACTTCTA

AACCTAGGGTTGAAGTTCATGGTGGTGATCTCAGATCCTTCTTCACACTGGTATATATTAATCTTCAACACTTCCAA

TTTACTCCGTCTGTCTGTCCTAATTTATGTCACACATTTTCTATGATATATAGTTTTAGAAATTATTCAAGACCATA

ACTTTTTAAAGAAAAAATCATAGACTTTCTTAGTCAACGTCAAATAAATTGAGACGGACAAGATGACATGATTAGTA

CATTTATCTTCTATTATTGACCTCTCATTTTCTTTTATACATTATTTGACAGATCATGATAGATCCAGATGTTCCTG

GTCCTAGTGATCCATATCTCAGGGAACATCTACACTGGTATAGACAACATATGCCTTAAAACTAACTCAGTCAATTT

TATCTTCAATTGTTTACTTTGGAAGGGGAAATGACATGATCATTATATCATAGTACAAATTATTATGTAATTTCTGT

TCGTCTAAAAAATGTCACTTTAGAAAAAACTGATAATCATATACAATACCACAATAAAGATAGAAGAACATGTACTA

ATATTGAACTTAAATAATGAGTACTAGGAGTATTATTAATTAACTTTAAAAATGCTAGTCAATATACCTATGTTTAT

ATGTTAAAAAATCCTTTATATTTGGAAACATGAGTACTCCTATACCATACAATGTTGTCGTACAGTTGATTAGACGG

GCAAATTAAACAAATGTCCAATAATTGTACTAATTAATAACTACTTGTTCTCTTCATCTATTATTAGTTATTACCAA

AAAAAGAGGACTGCAAAATGGTGATATTATTATGTGTAACGGAAAAAAACGTACTCTATTTAATATGATAGAATCAA

AGTGACATATTTTGTTCTAGTTAGACAAATAAGTAACTGAAAAGAGGATTTGACCATCTTTACAGGATTGTCACAGA

CATTCCAGGCACTACAGATTGCTCTTTTGGTATGTATCCTTAACCCATAAATCAAAATAATGTACTTTCTTTTTATT

TGCCATTAATATCTCTAGTACAAAAAAGAAATATTATAAAAAAAATTAATTTCAATTTTTATATTATAGGTTTAAGA

TAATAATATTAAACGATATTTTAGTCTCTACCAAATAGACGAGCAAATTAAAACTAAGAAAGCACTACATGTTTTCT

TTATATTATTAGTATAAAAATATATTATAATTTGCCTGGTGGTAATAGGATCAAAGTATTGATTCTTAATTATTATT

ATATAATTAATAATAATGGTAAACAAAAAGATATAAAGTGCTTACCTCCTAATTCCCTATATGAAAAAATATACTTA

CTTAATTACTCTTTTTACACGTAAGCATGCATTTAAAAAAATATTAAAAAATTATTCCAGAGGTTATATATAATATG

TATGGATAAAAAAAAAATTCACCTATATACATAATAATATAATTTTCGAGTGAATTGACCGCCCTTCAGCATCATTA

TATAATGTTATCGATCTAGGTCTTTGTGTGAAATTAAAAGTTATTTATACGGTTAGTACGATCGCGTAATAACGAAG

GTAAAAATATTTCAGGAAGAGAAGTGGTTGGGTATGAAATGCCAAGGCCAAATATTGGAATCCACAGGTTTGTATTT

TTGCTGTTTAAGCAGAAGAAAAGGCAAACAATATCGAGTGCACCAGTGTCCAGAGATCAATTTAGTAGTAGAAAATT

TTCAGAAGAAAATGAACTTGGCTCACCAGTTGCTGCTGTTTTCTTCAATTGTCAGAGGGAAACTGCCGCTAGAAGGC

GTTGA

Nucleic acid sequence of a wild-type Solyc06g074350 coding sequence (SEQ ID NO: 68)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTCAGTAACTTCTA

-continued

AACCTAGGGTTGAAGTTCATGGTGGTGATCTCAGATCCTTCTTCACACTGATCATGATAGATCCAGATGTTCCTGGT

CCTAGTGATCCATATCTCAGGGAACATCTACACTGGATTGTCACAGACATTCCAGGCACTACAGATTGCTCTTTTGG

AAGAGAAGTGGTTGGGTATGAAATGCCAAGGCCAAATATTGGAATCCACAGGTTTGTATTTTTGCTGTTTAAGCAGA

AGAAAAGGCAAACAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

Amino acid sequence for a polypeptide encoded by a wild-type
Solyc06g074350 coding sequence (SEQ ID NO: 69)

MASKMCEPLVIGRVIGEVVDYFCPSVKMSVVYNNNKHVYNGHEFFPSSVTSKPRVEVHGGDLRSFFTLIMIDPDVPG

PSDPYLREHLHWIVTDIPGTTDCSFGREVVGYEMPRPNIGIHRFVFLLFKQKKRQTISSAPVSRDQFSSRKFSEENE

LGSPVAAVFFNCQRETAARRR*

Mutant Solyc06g074350 gene allele sp (M82 background)
Nucleic acid sequence for a mutant Solyc06g074350 gene
allele sp (M82 background)

(SEQ ID NO: 70)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTCAGTAACTTCTA

AACCTAGGGTTGAAGTTCATGGTGGTGATCTCAGATCCTTCTTCACACTGGTATATATTAATCTTCAACACTTCCAA

TTTACTCCGTCTGTCTGTCCTAATTTATGTCACACATTTTCTATGATATATAGTTTTAGAAATTATTCAAGACCATA

ACTTTTTAAAGAAAAAATCATAGACTTTCTTAGTCAACGTCAAATAAATTGAGACGGACAAGATGACATGATTAGTA

CATTTATCTTCTATTATTGACCTCTCATTTTCTTTTATACATTATTTGACAGATCATGATAGATCCAGATGTTC TG

GTCCTAGTGATCCATATCTCAGGGAACATCTACACTGGTATAGACAACATATGCCTTAAAACTAACTCAGTCAATTT

TATCTTCAATTGTTTACTTTGGAAGGGGAAATGACATGATCATTATATCATAGTACAAATTATTATGTAATTTCTGT

TCGTCTAAAAAATGTCACTTTAGAAAAAACTGATAATCATATACAATACCACAATAAAGATAGAAGAACATGTACTA

ATATTGAACTTAAATAATGAGTACTAGGAGTATTATTAATTAACTTTAAAAATGCTAGTCAATATACCTATGTTTAT

ATGTTAAAAAATCCTTTATATTTGGAAACATGAGTACTCCTATACCATACAATGTTGTCGTACAGTTGATTAGACGG

GCAAATTAAACAAATGTCCAATAATTGTACTAATTAATAACTACTTGTTCTCTTCATCTATTATTAGTTATTACCAA

AAAAAGAGGACTGCAAAATGGTGATATTATTATGTGTAACGGAAAAAAACGTACTCTATTTAATATGATAGAATCAA

AGTGACATATTTTGTTCTAGTTAGACAAATAAGTAACTGAAAAGAGGATTTGACCATCTTTACAGGATTGTCACAGA

CATTCCAGGCACTACAGATTGCTCTTTTGGTATGTATCCTTAACCCATAAATCAAAATAATGTACTTTCTTTTTTATT

TGCCATTAATATCTCTAGTACAAAAAAGAAATATTATAAAAAAAAATTAATTTCAATTTTTATATTATAGGTTTAAGA

TAATAATATTAAACGATATTTTAGTCTCTACCAAATAGACGAGCAAATTAAAACTAAGAAAGCACTACATGTTTTCT

TTATATTATTAGTATAAAAATATATTATAATTTGCCTGGTGGTAATAGGATCAAAGTATTGATTCTTAATTATTATT

ATATAATTAATAATAATGGTAAACAAAAAGATATAAAGTGCTTACCTCCTAATTCCCTATATGAAAAAATATACTTA

CTTAATTACTCTTTTTACACGTAAGCATGCATTTAAAAAAATATTAAAAAATTATTCCAGAGGTTATATATAATATG

TATGGATAAAAAAAAAATTCACCTATATACATAATAATATAATTTTCGAGTGAATTGACCGCCCTTCAGCATCATTA

TATAATGTTATCGATCTAGGTCTTTGTGTGAAATTAAAAGTTATTTATACGGTTAGTACGATCGCGTAATAACGAAG

GTAAAAATATTTCAGGAAGAGAAGTGGTTGGGTATGAAATGCCAAGGCCAAATATTGGAATCCACAGGTTTGTATTT

TTGCTGTTTAAGCAGAAGAAAAGGCAAACAATATCGAGTGCACCAGTGTCCAGAGATCAATTTAGTAGTAGAAAATT

TTCAGAAGAAAATGAACTTGGCTCACCAGTTGCTGCTGTTTTCTTCAATTGTCAGAGGGAAACTGCCGCTAGAAGGC

GTTGA

Nucleic acid sequence for a mutant Solyc06g074350 gene allele sp
coding sequence (M82 background)

(SEQ ID NO: 71)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTCAGTAACTTCTA

-continued

AACCTAGGGTTGAAGTTCATGGTGGTGATCTCAGATCCTTCTTCACACTGATCATGATAGATCCAGATGTTC TGGT

CCTAGTGATCCATATCTCAGGGAACATCTACACTGGATTGTCACAGACATTCCAGGCACTACAGATTGCTCTTTTGG

AAGAGAAGTGGTTGGGTATGAAATGCCAAGGCCAAATATTGGAATCCACAGGTTTGTATTTTTGCTGTTTAAGCAGA

AGAAAAGGCAAACAATATCGAGTGCACCAGTGTCCAGAGATCAATTTAGTAGTAGAAAATTTTCAGAAGAAAATGAA

CTTGGCTCACCAGTTGCTGCTGTTTTCTTCAATTGTCAGAGGGAAACTGCCGCTAGAAGGCGTTGA

Amino acid sequence for a mutant polypeptide encoded by a mutant Solyc06g074350 gene allele sp coding sequence (M82 background)

(SEQ ID NO: 72)

MASKMCEPLVIGRVIGEVVDYFCPSVKMSVVYNNNKHVYNGHEFFPSSVTSKPRVEVHGGDLRSFFTLIMIDPDV G

PSDPYLREHLHWIVTDIPGTTDCSFGREVVGYEMPRPNIGIHRFVFLLFKQKKRQTISSAPVSRDQFSSRKFSEENE

LGSPVAAVFFNCQRETAARRR*

Mutant Solyc06g074350 gene allele $sp^{CR}$ (M82 background)
Nucleic acid sequence for a mutant Solyc06g074350 gene allele $sp^{CR}$ (M82 background)

(SEQ ID NO: 73)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTAACTTCTAAACC

TAGGGTTGAAGTTCATGGTGGTGATCTCAGATCCTTCTTCACACTGGTATATATTAATCTTCAACACTTCCAATTTA

CTCCGTCTGTCTGTCCTAATTTATGTCACACATTTTCTATGATATATAGTTTTAGAAATTATTCAAGACCATAACTT

TTTAAAGAAAAAATCATAGACTTTCTTAGTCAACGTCAAATAAATTGAGACGGACAAGATGACATGATTAGTACATT

TATCTTCTATTATTGACCTCTCATTTTCTTTTATACATTATTTGACAGATCATGATAGATCCAGATGTTCCTGGTCC

TAGTGATCCATATCTCAGGGAACATCTACACTGGTATAGACAACATATGCCTTAAAACTAACTCAGTCAATTTTATC

TTCAATTGTTTACTTTGGAAGGGGAAATGACATGATCATTATATCATAGTACAAATTATTATGTAATTTCTGTTCGT

CTAAAAAATGTCACTTTAGAAAAAACTGATAATCATATACAATACCACAATAAAGATAGAAGAACATGTACTAATAT

TGAACTTAAATAATGAGTACTAGGAGTATTATTAATTAACTTTAAAAATGCTAGTCAATATACCTATGTTTATATGT

TAAAAAATCCTTTATATTTGGAAACATGAGTACTCCTATACCATACAATGTTGTCGTACAGTTGATTAGACGGGCAA

ATTAAACAAATGTCCAATAATTGTACTAATTAATAACTACTTGTTCTCTTCATCTATTATTAGTTATTACCAAAAAA

AGAGGACTGCAAAATGGTGATATTATTATGTGTAACGGAAAAAAACGTACTCTATTTAATATGATAGAATCAAAGTG

ACATATTTTGTTCTAGTTAGACAAATAAGTAACTGAAAAGAGGATTTGACCATCTTTACAGGATTGTCACAGACATT

CCAGGCACTACAGATTGCTCTTTTGGTATGTATCCTTAACCCATAAATCAAAATAATGTACTTTCTTTTTATTTGCC

ATTAATATCTCTAGTACAAAAAAGAAATATTATAAAAAAAATTAATTTCAATTTTTATATTATAGGTTTAAGATAAT

AATATTAAACGATATTTTAGTCTCTACCAAATAGACGAGCAAATTAAAACTAAGAAAGCACTACATGTTTTCTTTAT

ATTATTAGTATAAAAATATATTATAATTTGCCTGGTGGTAATAGGATCAAAGTATTGATTCTTAATTATTATTATAT

AATTAATAATAATGGTAAACAAAAAGATATAAAGTGCTTACCTCCTAATTCCCTATATGAAAAAATATACTTACTTA

ATTACTCTTTTTACACGTAAGCATGCATTTAAAAAAATATTAAAAAATTATTCCAGAGGTTATATATAATATGTATG

GATAAAAAAAAAATTCACCTATATACATAATAATATAATTTTCGAGTGAATTGACCGCCCTTCAGCATCATTATATA

ATGTTATCGATCTAGGTCTTTGTGTGAAATTAAAAGTTATTTATACGGTTAGTACGATCGCGTAATAACGAAGGTAA

AAATATTTCAGGAAGAGAAGTGGTTGGGTATGAAATGCCAAGGCCAAATATTGGAATCCACAGGTTTGTATTTTTGC

TGTTTAAGCAGAAGAAAAGGCAAACAATATCGAGTGCACCAGTGTCCAGAGATCAATTTAGTAGTAGAAAATTTTCA

GAAGAAAATGAACTTGGCTCACCAGTTGCTGCTGTTTTCTTCAATTGTCAGAGGGAAACTGCCGCTAGAAGGCGTTG

A

-continued

Nucleic acid sequence for a mutant Solyc06g074350 gene allele
$sp^{CR}$ coding sequence (M82 background)

(SEQ ID NO: 74)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCCTAACTTCTAAACC

TAGGGTTGAAGTTCATGGTGGTGATCTCAGATCCTTCTTCACACTGATCATGATAGATCCAGATGTTCCTGGTCCTA

GTGATCCATATCTCAGGGAACATCTACACTGGATTGTCACAGACATTCCAGGCACTACAGATTGCTCTTTTGGAAGA

GAAGTGGTTGGGTATGAAATGCCAAGGCCAAATATTGGAATCCACAGGTTTGTATTTTTGCTGTTTAAGCAGAAGAA

AAGGCAAACAATATCGAGTGCACCAGTGTCCAGAGATCAATTTAGTAGTAGAAAATTTTCAGAAGAAAATGAACTTG

GCTCACCAGTTGCTGCTGTTTTCTTCAATTGTCAGAGGGAAACTGCCGCTAGAAGGCGTTGA

Amino acid sequence for a mutant polypeptide encoded by a mutant
Solyc06g074350 gene allele
$sp^{CR}$ coding sequence (M82 background)

(SEQ ID NO: 75)

MASKMCEPLVIGRVIGEVVDYFCPSVKMSVVYNNNKHVYNGHEFFPS*

Mutant Solyc06g074350 gene allele sp (Sweet100 background)
Nucleic acid sequence for a mutant Solyc06g074350 gene allele sp
(Sweet100 background)

(SEQ ID NO: 76)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGGTATATATTAATCTTCAACACTTCCA

ATTTACTCCGTCTGTCTGTCCTAATTTATGTCACACATTTTCTATGATATATAGTTTTAGAAATTATTCAAGACCAT

AACTTTTTAAAGAAAAAATCATAGACTTTCTTAGTCAACGTCAAATAAATTGAGACGGACAAGATGACATGATTAGT

ACATTTATCTTCTATTATTGACCTCTCATTTTCTTTTATACATTATTTGACAGATCATGATAGATCCAGATGTTCCT

GGTCCTAGTGATCCATATCTCAGGGAACATCTACACTGGTATAGACAACATATGCCTTAAAACTAACTCAGTCAATT

TTATCTTCAATTGTTTACTTTGGAAGGGGAAATGACATGATCATTATATCATAGTACAAATTATTATGTAATTTCTG

TTCGTCTAAAAAATGTCACTTTAGAAAAAACTGATAATCATATACAATACCACAATAAAGATAGAAGAACATGTACT

AATATTGAACTTAAATAATGAGTACTAGGAGTATTATTAATTAACTTTAAAAATGCTAGTCAATATACCTATGTTTA

TATGTTAAAAAATCCTTTATATTTGGAAACATGAGTACTCCTATACCATACAATGTTGTCGTACAGTTGATTAGACG

GGCAAATTAAACAAATGTCCAATAATTGTACTAATTAATAACTACTTGTTCTCTTCATCTATTATTAGTTATTACCA

AAAAAAGAGGACTGCAAAATGGTGATATTATTATGTGTAACGGAAAAAAACGTACTCTATTTAATATGATAGAATCA

AAGTGACATATTTTGTTCTAGTTAGACAAATAAGTAACTGAAAAGAGGATTTGACCATCTTTACAGGATTGTCACAG

ACATTCCAGGCACTACAGATTGCTCTTTTGGTATGTATCCTTAACCCATAAATCAAAATAATGTACTTTCTTTTTAT

TTGCCATTAATATCTCTAGTACAAAAAAGAAATATTATAAAAAAAATTAATTTCAATTTTTATATTATAGGTTTAAG

ATAATAATATTAAACGATATTTTAGTCTCTACCAAATAGACGAGCAAATTAAAACTAAGAAAGCACTACATGTTTTC

TTTATATTATTAGTATAAAAATATATTATAATTTGCCTGGTGGTAATAGGATCAAAGTATTGATTCTTAATTATTAT

TATATAATTAATAATAATGGTAAACAAAAAGATATAAAGTGCTTACCTCCTAATTCCCTATATGAAAAAATATACTT

ACTTAATTACTCTTTTTACACGTAAGCATGCATTTAAAAAAATATTAAAAAATTATTCCAGAGGTTATATATAATAT

GTATGGATAAAAAAAAAATTCACCTATATACATAATAATATAATTTTCGAGTGAATTGACCGCCCTTCAGCATCATT

ATATAATGTTATCGATCTAGGTCTTTGTGTGAAATTAAAAGTTATTTATACGGTTAGTACGATCGCGTAATAACGAA

GGTAAAAATATTTCAGGAAGAGAAGTGGTTGGGTATGAAATGCCAAGGCCAAATATTGGAATCCACAGGTTTGTATT

TTTGCTGTTTAAGCAGAAGAAAAGGCAAACAATATCGAGTGCACCAGTGTCCAGAGATCAATTTAGTAGTAGAAAAT

TTTCAGAAGAAAATGAACTTGGCTCACCAGTTGCTGCTGTTTTCTTCAATTGTCAGAGGGAAACTGCCGCTAGAAGG

CGTTGA

-continued

Nucleic acid sequence for a mutant Solyc06g074350 gene allele sp coding sequence (Sweet100 background)

(SEQ ID NO: 77)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGATCATGATAGATCCAGATGTTCCTGG

TCCTAGTGATCCATATCTCAGGGAACATCTACACTGGATTGTCACAGACATTCCAGGCACTACAGATTGCTCTTTTG

GAAGAGAAGTGGTTGGGTATGAAATGCCAAGGCCAAATATTGGAATCCACAGGTTTGTATTTTTGCTGTTTAAGCAG

AAGAAAAGGCAAACAATATCGAGTGCACCAGTGTCCAGAGATCAATTTAGTAGTAGAAAATTTTCAGAAGAAAATGA

ACTTGGCTCACCAGTTGCTGCTGTTTTCTTCAATTGTCAGAGGGAAACTGCCGCTAGAAGGCGTTGA

Amino acid sequence for a mutant polypeptide encoded by a mutant Solyc06g074350 gene allele sp coding sequence (Sweet100 background)

(SEQ ID NO: 78)

MASKMCEPLVIGRVIGEVVDYFCPSVKMSVVYNNNKHVYNGHEFFPSISNF*

Mutant Solyc06g074350 gene allele sp-cocktail

Nucleic acid sequence for a mutant Solyc06g074350 gene allele sp-cocktail (SEQ ID NO: 79)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGGTATATATTAATCTTCAACACTTCCA

ATTTACTCCGTCTGTCTGTCCTAATTTATGTCACACATTTTCTATGATATATAGTTTTAGAAATTATTCAAGACCAT

AACTTTTTAAAGAAAAAATCATAGACTTTCTTAGTCAACGTCAAATAAATTGAGACGGACAAGATGACATGATTAGT

ACATTTATCTTCTATTATTGACCTCTCATTTTCTTTTATACATTATTTGACAGATCATGATAGATCCAGATGTTCCT

GGTCCTAGTGATCCATATCTCAGGGAACATCTACACTGGTATAGACAACATATGCCTTAAAACTAACTCAGTCAATT

TTATCTTCAATTGTTTACTTTGGAAGGGGAAATGACATGATCATTATATCATAGTACAAATTATTATGTAATTTCTG

TTCGTCTAAAAAATGTCACTTTAGAAAAAACTGATAATCATATACAATACCACAATAAAGATAGAAGAACATGTACT

AATATTGAACTTAAATAATGAGTACTAGGAGTATTATTAATTAACTTTAAAAATGCTAGTCAATATACCTATGTTTA

TATGTTAAAAAATCCTTTATATTTGGAAACATGAGTACTCCTATACCATACAATGTTGTCGTACAGTTGATTAGACG

GGCAAATTAAACAAATGTCCAATAATTGTACTAATTAATAACTACTTGTTCTCTTCATCTATTATTAGTTATTACCA

AAAAAAGAGGACTGCAAAATGGTGATATTATTATGTGTAACGGAAAAAAACGTACTCTATTTAATATGATAGAATCA

AAGTGACATATTTTGTTCTAGTTAGACAAATAAGTAACTGAAAAGAGGATTTGACCATCTTTACAGGATTGTCACAG

ACATTCCAGGCACTACAGATTGCTCTTTTGGTATGTATCCTTAACCCATAAATCAAAATAATGTACTTTCTTTTTAT

TTGCCATTAATATCTCTAGTACAAAAAAGAAATATTATAAAAAAAATTAATTTCAATTTTTATATTATAGGTTTAAG

ATAATAATATTAAACGATATTTTAGTCTCTACCAAATAGACGAGCAAATTAAAACTAAGAAAGCACTACATGTTTTC

TTTATATTATTAGTATAAAAATATATTATAATTTGCCTGGTGGTAATAGGATCAAAGTATTGATTCTTAATTATTAT

TATATAATTAATAATAATGGTAAACAAAAAGATATAAAGTGCTTACCTCCTAATTCCCTATATGAAAAAATATACTT

ACTTAATTACTCTTTTTACACGTAAGCATGCATTTAAAAAAATATTAAAAAATTATTCCAGAGGTTATATATAATAT

GTATGGATAAAAAAAAAATTCACCTATATACATAATAATATAATTTTCGAGTGAATTGACCGCCCTTCAGCATCATT

ATATAATGTTATCGATCTAGGTCTTTGTGTGAAATTAAAAGTTATTTATACGGTTAGTACGATCGCGTAATAACGAA

GGTAAAAATATTTCAGGAAGAGAAGTGGTTGGGTATGAAATGCCAAGGCCAAATATTGGAATCCACAGGTTTGTATT

TTTGCTGTTTAAGCAGAAGAAAAGGCAAACAATATCGAGTGCACCAGTGTCCAGAGATCAATTTAGTAGTAGAAAAT

TTTCAGAAGAAAATGAACTTGGCTCACCAGTTGCTGCTGTTTTCTTCAATTGTCAGAGGGAAACTGCCGCTAGAAGG

CGTTGA

-continued

Nucleic acid sequence for a mutant Solyc06g074350 gene allele
sp-cocktail coding sequence (SEQ ID NO: 80)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGATCATGATAGATCCAGATGTTCCTGG

TCCTAGTGATCCATATCTCAGGGAACATCTACACTGGATTGTCACAGACATTCCAGGCACTACAGATTGCTCTTTTG

GAAGAGAAGTGGTTGGGTATGAAATGCCAAGGCCAAATATTGGAATCCACAGGTTTGTATTTTTGCTGTTTAAGCAG

AAGAAAAGGCAAACAATATCGAGTGCACCAGTGTCCAGAGATCAATTTAGTAGTAGAAAATTTTCAGAAGAAAATGA

ACTTGGCTCACCAGTTGCTGCTGTTTTCTTCAATTGTCAGAGGGAAACTGCCGCTAGAAGGCGTTGA

Amino acid sequence for a mutant polypeptide encoded by a mutant
Solyc06g074350 gene allele sp-cocktail coding sequence (SEQ ID NO: 81)

MASKMCEPLVIGRVIGEVVDYFCPSVKMSVVYNNNKHVYNGHEFFPSISNF*

Mutant Solyc06g074350 gene allele sp-grape
Nucleic acid sequence for a mutant Solyc06g074350 gene allele sp-grape (SEQ ID NO: 82)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGGTATATATTAATCTTCAACACTTCCA

ATTTACTCCGTCTGTCTGTCCTAATTTATGTCACACATTTTCTATGATATATAGTTTTAGAAATTATTCAAGACCAT

AACTTTTTAAAGAAAAAATCATAGACTTTCTTAGTCAACGTCAAATAAATTGAGACGGACAAGATGACATGATTAGT

ACATTTATCTTCTATTATTGACCTCTCATTTTCTTTTATACATTATTTGACAGATCATGATAGATCCAGATGTTCCT

GGTCCTAGTGATCCATATCTCAGGGAACATCTACACTGGTATAGACAACATATGCCTTAAAACTAACTCAGTCAATT

TTATCTTCAATTGTTTACTTTGGAAGGGGAAATGACATGATCATTATATCATAGTACAAATTATTATGTAATTTCTG

TTCGTCTAAAAAATGTCACTTTAGAAAAAACTGATAATCATATACAATACCACAATAAAGATAGAAGAACATGTACT

AATATTGAACTTAAATAATGAGTACTAGGAGTATTATTAATTAACTTTAAAAATGCTAGTCAATATACCTATGTTTA

TATGTTAAAAAATCCTTTATATTTGGAAACATGAGTACTCCTATACCATACAATGTTGTCGTACAGTTGATTAGACG

GGCAAATTAAACAAATGTCCAATAATTGTACTAATTAATAACTACTTGTTCTCTTCATCTATTATTAGTTATTACCA

AAAAAAGAGGACTGCAAAATGGTGATATTATTATGTGTAACGGAAAAAAACGTACTCTATTTAATATGATAGAATCA

AAGTGACATATTTTGTTCTAGTTAGACAAATAAGTAACTGAAAAGAGGATTTGACCATCTTTACAGGATTGTCACAG

ACATTCCAGGCACTACAGATTGCTCTTTTGGTATGTATCCTTAACCCATAAATCAAAATAATGTACTTTCTTTTTAT

TTGCCATTAATATCTCTAGTACAAAAAAGAAATATTATAAAAAAAATTAATTTCAATTTTTATATTATAGGTTTAAG

ATAATAATATTAAACGATATTTTAGTCTCTACCAAATAGACGAGCAAATTAAAACTAAGAAAGCACTACATGTTTTC

TTTATATTATTAGTATAAAAATATATTATAATTTGCCTGGTGGTAATAGGATCAAAGTATTGATTCTTAATTATTAT

TATATAATTAATAATAATGGTAAACAAAAAGATATAAAGTGCTTACCTCCTAATTCCCTATATGAAAAAATATACTT

ACTTAATTACTCTTTTTACACGTAAGCATGCATTTAAAAAAATATTAAAAAATTATTCCAGAGGTTATATATAATAT

GTATGGATAAAAAAAAAATTCACCTATATACATAATAATATAATTTTCGAGTGAATTGACCGCCCTTCAGCATCATT

ATATAATGTTATCGATCTAGGTCTTTGTGTGAAATTAAAAGTTATTTATACGGTTAGTACGATCGCGTAATAACGAA

GGTAAAAATATTTCAGGAAGAGAAGTGGTTGGGTATGAAATGCCAAGGCCAAATATTGGAATCCACAGGTTTGTATT

-continued

TTTGCTGTTTAAGCAGAAGAAAAGGCAAACAATATCGAGTGCACCAGTGTCCAGAGATCAATTTAGTAGTAGAAAAT

TTTCAGAAGAAAATGAACTTGGCTCACCAGTTGCTGCTGTTTTCTTCAATTGTCAGAGGGAAACTGCCGCTAGAAGG

CGTTGA

Nucleic acid sequence for a mutant Solyc06g074350 gene allele
sp-grape coding sequence (SEQ ID NO: 83)

ATGGCTTCCAAAATGTGTGAACCCCTTGTGATTGGTAGAGTGATTGGTGAAGTTGTTGATTATTTCTGTCCAAGTGT

TAAGATGTCTGTTGTTTATAACAACAACAAACATGTCTATAATGGACATGAATTCTTTCCTTCC TCAGTAACTTCT

AAACCTAGGGTTGAAGTTCATGGTGGTGATCTCAGATCCTTCTTCACACTGATCATGATAGATCCAGATGTTCCTGG

TCCTAGTGATCCATATCTCAGGGAACATCTACACTGGATTGTCACAGACATTCCAGGCACTACAGATTGCTCTTTTG

GAAGAGAAGTGGTTGGGTATGAAATGCCAAGGCCAAATATTGGAATCCACAGGTTTGTATTTTTGCTGTTTAAGCAG

AAGAAAAGGCAAACAATATCGAGTGCACCAGTGTCCAGAGATCAATTTAGTAGTAGAAAATTTTCAGAAGAAAATGA

ACTTGGCTCACCAGTTGCTGCTGTTTTCTTCAATTGTCAGAGGGAAACTGCCGCTAGAAGGCGTTGA

Amino acid sequence for a mutant polypeptide encoded by a mutant
Solyc06g074350 gene allele sp-grape coding sequence (SEQ ID NO: 84)

MASKMCEPLVIGRVIGEVVDYFCPSVKMSVVYNNNKHVYNGHEFFPSISNF*

Solyc04s072570 (SlSERK1)

Wild-type Solyc04g072570 gene
Nucleic acid sequence of a wild-type Solyc04g072570 gene (SEQ ID NO: 85)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCCTTGTTAATCCTTGCACATGGTTTCACGTTACCTGCAACAATGACAACAGTGTTATAAGAGT

GTAAGAATCTGTTTTCTGGTCTACCTCCATTTGAATGGATTTGCAATTCCACTCTCTTGTGGTGGTGAGCAATCTAA

TTGCAGTTTGTGCTCCCATAACACTTGTTATATGATCAACCTTTCCAGTGATTTAGGAAATGCAGCTTTATCTGGTT

TGTTAGTTCCACAGCTTGGCCTTTTGAAGAATTTGCAGTACTTGTAAGTCTCACTTCATGAACTATGTTTGGAATTA

TTTTACAAATTTAGAGTTGGAAAACTGGCATTGAGTGTATTGGTTTTTCCAGCTGTTGAAGATTTTCATATTACCTC

TAGAATTCGCTGCATGAAAATAATGTAGGTGGCTTGCATATTAACTTTTGCATAAAAACAAAGCTGTTGTAAGTGGC

AAAAATGAGCAGAGAACACTTTCTCCTCTCCATCTCTTGTTTCACTTGATGTTGTAGTCGATGGCATAGTTGTTGAT

GTGTTCCCTGAACAACACAAATTTGAATGTGTACTTCATAAAAAAAGATTTAAATATTTGTTTCACATTACATACTA

GTAAATTAAGTAACTCAGATACTTGGATGAGACTAGCAATGAAGTAACTTATGTGGCAAAGTAGTGTCTGTAATTGC

TTGTGAAAACATTGTAGTTGAACTTAAATTTTTGTCATACACTCCCTTATATAAAGATAAGCAGAGTAATCGTTAAC

TTTTTTATGAACTCTTAAACAGAGTATTATTCTAAATATTATTACTAATGCCAGTACCCTAAGCACTCTTAATTTGG

AATGACAAACTTCAACTCATATCAAATCCTTTATTCCCTCTTTCCTTGTTCCATGTAGACTCTAATCACGATTTAGG

ATGATGGAATAGGATAAAACAAACAAGAGAAACAAGTCCATTGTAAAAGTAAAGCAAAATCTAGACTTAAAAAGAGG

AAATATGGCATGAGGGTAGGTTGATGTCTTGGAGGAGAAGATCTGAAGTTTTCTGGTCATATAACAGATGCTATTCT

GGTTTTCACCAAGAGTTCGAATCATGATTCAATTAAGCATAGATTTTGTACAAGTGTTAAGCTTAGTTTGGAGTTCA

-continued

ATATACCGTTCACTTAAATTACATCTCAAATTTCATTGTTCTTATTGTAACCCATGCTCTTTTGAAGCTGCAACTGT

ATGGAAGTTCACAGAGACAGTATGTGCATGTGCACCTGGTGAAGCAGGGCATTACATGATGTATAACCATGCATCAG

ACAATGTTATAATGATGGGTATAATTATTACCTAGTGACTGCTTCATCCTGCTCACACATTAATATATTCCTATGGA

TGCCTAGATTTGCTTGAGGCTTGTGTAGTACGCGTGCTAAGTATTTTCCTAGTGTATGCAAGTGACAATCACATCAA

GAATGAAACAATATAAAAAGAACATCAAAAGTATAACATTATCTTTGTCAAAAAAAAAAAGAAAGAACATCAAGAGT

GCTGATGGAATTTAACAATCACCGGGCATACACACTGTTTAGATGAAGTTCGAAATTAACATAATGACAGACGTTAA

ATTTTTATTGATGAGTTATATAGATTGTATAAAATGTTTGACGAGCTGATTCTTTGCAGCACATGGGACGACAGGTT

TTTATATAGAAAAGTGCTTGTAACCAAATATAAGAAAATACCTCCATGAAATAGACATCGGTAACTAGTTATAATTG

CTATCTTGGAACTCCTAGACCTTTCTCATTTGTTGACTTTTAATTGTCGCTTGATGCCAGTATTGATGGATGTGAGA

ATTCTCCTTCATTATCTTGGTTGTCCCATTATCCTAGGGATGTCATTGGTATGATATGTGGAATTGACTCATTCTCT

GGTTTTCTTGTCACAGGGAGCTTTACAGTAATAATATAAGTGGTCTGATACCGAGTGATCTTGGGAATTTGACTAAT

CTGGTCAGCTTGGATCTCTACTTGAACAACTTCGTCGGTCCCATCCCAGATTCCTTGGGCAAGCTGTCGAAATTGAG

ATTCCTGTATGTATTTTTGTTCTATATTAGATTTATGTGGATATTGTGATGCCAAATGTATATTTCATCAACCAAGA

TGGACCTACTCTTACTGGCATGTTGAGAAAGGAAAGGAAGCCTGAATTCTTTTCTAGGTTTCACATAAGATGACCTC

TATTAGTATTATGTTTCACTCTTAAGTTTTGATGGTAGAAGGTATTTGAGGACTTCATGGGTCTGATATCATTCATA

AAACCGATCTTACATAAGTCTTTTAATTTTCTCCCTTTGTTCTAATCCTTGTATAAAGGAAAAGAATAGAAGCCTAT

GCTTTGTCTGATACTGATATTGTAAAATTAATCAGAGTTTAGTAATGGGTGTTGGGATCCTTTTCTAGAAGAGAGAA

GAAGTTTAGAATCCCATGCTTCATCTTGCATTTTTCACTGCTGAAGTTTCTCTTGCTTAATGCTCCACAAACTTCTT

TCTTTTGGCTTGACTGTCTAAGAAGTGTGCCAAATTGTTCTATCATGCAGACTCAGCATGAAACCTCATTAACTGCA

TCTTGGGACTTACTATAGAACTATTGCAGTACTGCAACGTTGACTAACATGATTTAGTCCAAAAGGTGTTTCAAGTC

TGTTTATCGGGGGGGGGGGATGTTTTGAGGCTCTTTATCGTGGTTCTGAACTGACGCCTTCATTTCCAGCTGAAGTG

CCGGTTCTGGCTCGAAGTTGAATATGTTTTACATCCACATATTAATAATTTATTAAGATGATTCTCCTTGTCAAATA

ATAAATAAATTAAGATGATTCAATTAGTAGCCTTTTCTTCTGTTTTATTCTCCATTATTTACTTGTACCAAAGATGA

AGCTCATTCCTGTAAACCTTTGTGTTTTCTTGCAAGGATAGTCGGCTCAACAATAATAGCTTGACTGGTAACATCCC

AATGTCACTGACTAATATCTCATCACTGCAAGTGTTGTAAGTACACTGATTATTTTGTGACTTGATTTAGATAATTC

TTTCTGTCTTCCATATCTTCTCATGCATTTCCTTTTCCTTCTAATGCATATACAGATTTACTTATGCTCAATTCTTG

TCTCACCTGTATGTAGGGATCTGTCAAACAACCGTCTCTCAGGTGCTGTTCCAGATAATGGTTCATTTTCTCTATTC

ACGCCTATCAGGTATATTTCATTTAAGGCGGTGCACCATCTAACTGGCTGGTGGTTTTAGCATGCTACTATTTGCTA

ATATATTTTTCTTGTTTACAGTTTTGCGAATAATTTAGATCTTTGCGGGCCTGTAACTGGACGCCCTTGCCCTGGAT

CTCCTCCATTCTCCCCTCCGCCTCCATTTGTTCCACCACCACCAATTTCTGCTCCAGGTGGTTCTCTAAATTGGTGT

GGATAAATTGTTCTCCTTTCTTTTTTCTTTTGTTTTTTTTGCTTTTTTGCGGTTAGTGATTTTAGTTTGTCCATCCA

ACGTAAGTGAGAATTTGTGCTATAGAAGCTAAAGTACTGACAAGAAAGGGGGCAGAAGAGGAAAACCCATCTTAACT

AGTCAGGCATTAGTTCTGATGGGAAACTGGTATGCACGAGACTACATTTAGTCTCTAAGCATTCTGGTCTTTATACA

AATTTAATTCAGCATTGTGGACATCTTTTCTTTGGTCCCCTTGTAAATTATTATCTGTGGTATTTGAAGTCATGTGT

CTGAATGAAATTAATCATATTTATGCCAGAACTTGTGAAGATTTTCTTTTCTTTGTAAAAACTGTCCTGGAAATTAG

ATCTGATGATAGATACAAATTTGTCTACTAATTTCTTTTTGAAGTGATTTAATTAATGAAGGGCCGGCCAAAATTAT

GTGTTAAATATAGTCTAGATCATATGAAGGAAATTAATCAAATTTATGGGAACTTCAGGAGGAAATGGTGCAACTGG

AGCAATTGCTGGAGGTGTAGCTGCTGGTGCTGCTCTACTATTTGCTGCTCCTGCCATTGCATTTGCCTGGTGGCGCC

GTAGAAAGCCACAAGAATATTTCTTTGACGTACCAGGTTAGCAGTATTCAAATACCCAACCATAAGTCCATAACTCC

TACTTACTCTCTCACGTGTTTATGGTTTCTCTTGCATGTTTTATTTTTTGGCTCCATAATTAACGTCTTTGCTTAAA

-continued

CTTATTGCAGCCGAAGAAGATCCTGAAGTTCACTTAGGTCAACTGAAAAGGTTCTCCCTCCGAGAGCTACAAGTTGC

AACTGACAGTTTTAGCAATAAAAATATACTGGGTCGAGGTGGATTTGGTAAGGTATACAAAGGACGCTTAGCAGATG

GATCATTGGTGGCTGTTAAGCGGCTAAAGGAAGAGCGTACTCCTGGAGGGGAGTTGCAATTTCAAACAGAAGTTGAG

ATGATTAGCATGGCAGTGCATAGGAATCTTCTACGATTGCGTGGTTTCTGTATGACACCAACTGAAAGACTGCTTGT

CTACCCCTACATGGCGAATGGAAGTGTTGCATCATGCCTGAGAGGTGACACTTTCTGAAATCTATCACTCCATAAAT

GTTCTCACCTTTAATTTGGAGGGTATTATTGCATAATGCAAGAATGTCTTTCGCTGGTTAACATTCTATCTTGGCAT

AACTTACTCTTTATAACAAAACATATTCTTGTTAGTTATTTTCCTGTAACTTTTTAAAAGGTAGAAGTATAATTTGT

ATTGTATTCTCTTGACAACATAATTTATTTTATCAGAACGACCGCCTTCTGAACCACCACTTGATTGGCCAACGCGA

AAACGTATTGCTTTGGGGTCTGCCAGGGGATTATCGTATTTGCATGATCATTGTGACCCTAAGATTATCCATCGTGA

TGTGAAGGCTGCAAATATATTGCTAGATGAAGAATTTGAGGCTGTTGTTGGAGACTTTGGTTTGGCTAAACTTATGG

ACTACAAGGATACACATGTTACAACTGCTGTGCGTGGTACAATCGGGCATATAGCTCCAGAATACCTTTCCACAGGG

AAGTCTTCAGAAAAGACTGATGTTTTTGGGTATGGGATCATGCTTCTGGAGCTAATCACCGGCCAACGTGCTTTTGA

TCTTGCTCGGCTGGCAAATGATGACGATGTCATGTTGCTTGACTGGGTATGTTGTCATACCTGCTTTACATGTGAAC

ATGACACGAGTACCATAATGTGTTCATTTTTTAATCTGTACATCACAACACTAGCTGACTAATAAGTATTTGTGCCT

TTAGCAGGAATATTTAAGTCTATGACTAAACTTGTTGAGGTTCTTGTTTCAGGTGAAAGGACTCCTCAAAGAGAAGA

AACTGGAAATGCTGGTTGACCCTGATCTTCAGAACAAATATGTGGAGGCTGAGGTGGAGCAACTGATCCAGGTAGCA

TTGCTTTGTACACAAAGCAACCCAATGGATCGGCCTAAGATGTCGGAAGTGGTGAGAATGCTTGAAGGTGATGGTTT

GGCTGAAAGATGGGATGAGTGGCAGAAGGTAGAAGTTCTCCGGCAGGAAGTGGAACTTGCACCACATCCTGGTTCTG

ATTGGCTTGTTGACTCGACAGAGAATTTACATGCAGTTGAATTATCGGGTCCAAGGTGA

Nucleic acid sequence of a wild-type Solyc04g072570 coding sequence
                                                                    (SEQ ID NO: 86)
ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCCTTGTTAATCCTTGCACATGGTTTCACGTTACCTGCAACAATGACAACAGTGTTATAAGA

GTTGATTTAGGAAATGCAGCTTTATCTGGTTTGTTAGTTCCACAGCTTGGCCTTTTGAAGAATTTGCAGTACTTGGA

GCTTTACAGTAATAATATAAGTGGTCTGATACCGAGTGATCTTGGGAATTTGACTAATCTGGTCAGCTTGGATCTCT

ACTTGAACAACTTCGTCGGTCCCATCCCAGATTCCTTGGGCAAGCTGTCGAAATTGAGATTCCTTCGGCTCAACAAT

AATAGCTTGACTGGTAACATCCCAATGTCACTGACTAATATCTCATCACTGCAAGTGTTGGATCTGTCAAACAACCG

TCTCTCAGGTGCTGTTCCAGATAATGGTTCATTTTCTCTATTCACGCCTATCAGTTTTGCGAATAATTTAGATCTTT

GCGGGCCTGTAACTGGACGCCCTTGCCCTGGATCTCCTCCATTCTCCCCTCCGCCTCCATTTGTTCCACCACCACCA

ATTTCTGCTCCAGGAGGAAATGGTGCAACTGGAGCAATTGCTGGAGGTGTAGCTGCTGGTGCTGCTCTACTATTTGC

TGCTCCTGCCATTGCATTTGCCTGGTGGCGCCGTAGAAAGCCACAAGAATATTTCTTTGACGTACCAGCCGAAGAAG

ATCCTGAAGTTCACTTAGGTCAACTGAAAAGGTTCTCCCTCCGAGAGCTACAAGTTGCAACTGACAGTTTTAGCAAT

AAAAATATACTGGGTCGAGGTGGATTTGGTAAGGTATACAAAGGACGCTTAGCAGATGGATCATTGGTGGCTGTTAA

GCGGCTAAAGGAAGAGCGTACTCCTGGAGGGGAGTTGCAATTTCAAACAGAAGTTGAGATGATTAGCATGGCAGTGC

ATAGGAATCTTCTACGATTGCGTGGTTTCTGTATGACACCAACTGAAAGACTGCTTGTCTACCCCTACATGGCGAAT

GGAAGTGTTGCATCATGCCTGAGAGAACGACCGCCTTCTGAACCACCACTTGATTGGCCAACGCGAAAACGTATTGC

TTTGGGGTCTGCCAGGGGATTATCGTATTTGCATGATCATTGTGACCCTAAGATTATCCATCGTGATGTGAAGGCTG

CAAATATATTGCTAGATGAAGAATTTGAGGCTGTTGTTGGAGACTTTGGTTTGGCTAAACTTATGGACTACAAGGAT

ACACATGTTACAACTGCTGTGCGTGGTACAATCGGGCATATAGCTCCAGAATACCTTTCCACAGGGAAGTCTTCAGA

AAAGACTGATGTTTTTGGGTATGGGATCATGCTTCTGGAGCTAATCACCGGCCAACGTGCTTTTGATCTTGCTCGGC

TGGCAAATGATGACGATGTCATGTTGCTTGACTGGGTGAAAGGACTCCTCAAAGAGAAGAAACTGGAAATGCTGGTT

-continued

GACCCTGATCTTCAGAACAAATATGTGGAGGCTGAGGTGGAGCAACTGATCCAGGTAGCATTGCTTTGTACACAAAG

CAACCCAATGGATCGGCCTAAGATGTCGGAAGTGGTGAGAATGCTTGAAGGTGATGGTTTGGCTGAAAGATGGGATG

AGTGGCAGAAGGTAGAAGTTCTCCGGCAGGAAGTGGAACTTGCACCACATCCTGGTTCTGATTGGCTTGTTGACTCG

ACAGAGAATTTACATGCAGTTGAATTATCGGGTCCAAGGTGA

Amino acid sequence for a polypeptide encoded by the wild-type Solyc04g072570 coding sequence (SEQ ID NO: 87)

MVKVMEKDTVVVSLVVWLILVVYHLKLIYANMEGDALHSLRVNLQDPNNVLQSWDPTLVNPCTWFHVTCNNDNSVIR

VDLGNAALSGLLVPQLGLLKNLQYLELYSNNISGLIPSDLGNLTNLVSLDLYLNNFVGPIPDSLGKLSKLRFLRLNN

NSLTGNIPMSLTNISSLQVLDLSNNRLSGAVPDNGSFSLFTPISFANNLDLCGPVTGRPCPGSPPFSPPPPFVPPPP

ISAPGGNGATGAIAGGVAAGAALLFAAPAIAFAWWRRRKPQEYFFDVPAEEDPEVHLGQLKRFSLRELQVATDSFSN

KNILGRGGFGKVYKGRLADGSLVAVKRLKEERTPGGELQFQTEVEMISMAVHRNLLRLRGFCMTPTERLLVYPYMAN

GSVASCLRERPPSEPPLDWPTRKRIALGSARGLSYLHDHCDPKIIHRDVKAANILLDEEFEAVVGDFGLAKLMDYKD

THVTTAVRGTIGHIAPEYLSTGKSSEKTDVFGYGIMLLELITGQRAFDLARLANDDDVMLLDWVKGLLKEKKLEMLV

DPDLQNKYVEAEVEQLIQVALLCTQSNPMDRPKMSEVVRMLEGDGLAERWDEWQKVEVLRQEVELAPHPGSDWLVDS

TENLHAVELSGPR*

Mutant Solyc04g072570 gene allele slserk1[w]
Nucleic acid sequence for a mutant Solyc04g072570 gene allele slserk1[w]

(SEQ ID NO: 88)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCCTTGTTAATCCTTGCACATGGTTTCACGTTACCTGCAACAATGACAACAGTGTTATAAGAGT

GTAAGAATCTGTTTTCTGGTCTACCTCCATTTGAATGGATTTGCAATTCCACTCTCTTGTGGTGGTGAGCAATCTAA

TTGCAGTTTGTGCTCCCATAACACTTGTTATATGATCAACCTTTCCAGTGATTTAGGAAATGCAGCTTTATCTGGTT

TGTTAGTTCCACAGCTTGGCCTTTTGAAGAATTTGCAGTACTTGTAAGTCTCACTTCATGAACTATGTTTGGAATTA

TTTTACAAATTTAGAGTTGGAAAACTGGCATTGAGTGTATTGGTTTTTCCAGCTGTTGAAGATTTTCATATTACCTC

TAGAATTCGCTGCATGAAAATAATGTAGGTGGCTTGCATATTAACTTTTGCATAAAAACAAAGCTGTTGTAAGTGGC

AAAAATGAGCAGAGAACACTTTCTCCTCTCCATCTCTTGTTTCACTTGATGTTGTAGTCGATGGCATAGTTGTTGAT

GTGTTCCCTGAACAACACAAATTTGAATGTGTACTTCATAAAAAAAGATTTAAATATTTGTTTCACATTACATACTA

GTAAATTAAGTAACTCAGATACTTGGATGAGACTAGCAATGAAGTAACTTATGTGGCAAAGTAGTGTCTGTAATTGC

TTGTGAAAACATTGTAGTTGAACTTAAATTTTTGTCATACACTCCCTTATATAAAGATAAGCAGAGTAATCGTTAAC

TTTTTTATGAACTCTTAAACAGAGTATTATTCTAAATATTATTACTAATGCCAGTACCCTAAGCACTCTTAATTTGG

AATGACAAACTTCAACTCATATCAAATCCTTTATTCCCTCTTTCCTTGTTCCATGTAGACTCTAATCACGATTTAGG

ATGATGGAATAGGATAAAACAAACAAGAGAAACAAGTCCATTGTAAAAGTAAAGCAAAATCTAGACTTAAAAAGAGG

AAATATGGCATGAGGGTAGGTTGATGTCTTGGAGGAGAAGATCTGAAGTTTTCTGGTCATATAACAGATGCTATTCT

GGTTTTCACCAAGAGTTCGAATCATGATTCAATTAAGCATAGATTTTGTACAAGTGTTAAGCTTAGTTTGGAGTTCA

ATATACCGTTCACTTAAATTACATCTCAAATTTCATTGTTCTTATTGTAACCCATGCTCTTTTGAAGCTGCAACTGT

-continued

ATGGAAGTTCACAGAGACAGTATGTGCATGTGCACCTGGTGAAGCAGGGCATTACATGATGTATAACCATGCATCAG

ACAATGTTATAATGATGGGTATAATTATTACCTAGTGACTGCTTCATCCTGCTCACACATTAATATATTCCTATGGA

TGCCTAGATTTGCTTGAGGCTTGTGTAGTACGCGTGCTAAGTATTTTCCTAGTGTATGCAAGTGACAATCACATCAA

GAATGAAACAATATAAAAAGAACATCAAAAGTATAACATTATCTTTGTCAAAAAAAAAAAGAAAGAACATCAAGAGT

GCTGATGGAATTTAACAATCACCGGGCATACACACTGTTTAGATGAAGTTCGAAATTAACATAATGACAGACGTTAA

AYYYYYAYYGAYGAGYYAYAYAGAYYGYAYAAAAYGYYYGACGAGCYGAYYCYYYGCAGCACAYGGGACGACAGGYY

TTTATATAGAAAAGTGCTTGTAACCAAATATAAGAAAATACCTCCATGAAATAGACATCGGTAACTAGTTATAATTG

CTATCTTGGAACTCCTAGACCTTTCTCATTTGTTGACTTTTAATTGTCGCTTGATGCCAGTATTGATGGATGTGAGA

ATTCTCCTTCATTATCTTGGTTGTCCCATTATCCTAGGGATGTCATTGGTATGATATGTGGAATTGACTCATTCTCT

GGTTTTCTTGTCACAGGGAGCTTTACAGTAATAATATAAGTGGTCTGATACCGAGTGATCTTGGGAATTTGACTAAT

CTGGTCAGCTTGGATCTCTACTTGAACAACTTCGTCGGTCCCATCCCAGATTCCTTGGGCAAGCTGTCGAAATTGAG

ATTCCTGTATGTATTTTTGTTCTATATTAGATTTATGTGGATATTGTGATGCCAAATGTATATTTCATCAACCAAGA

TGGACCTACTCTTACTGGCATGTTGAGAAAGGAAAGGAAGCCTGAATTCTTTTCTAGGTTTCACATAAGATGACCTC

TATTAGTATTATGTTTCACTCTTAAGTTTTGATGGTAGAAGGTATTTGAGGACTTCATGGGTCTGATATCATTCATA

AAACCGATCTTACATAAGTCTTTTAATTTTCTCCCTTTGTTCTAATCCTTGTATAAAGGAAAAGAATAGAAGCCTAT

GCTTTGTCTGATACTGATATTGTAAAATTAATCAGAGTTTAGTAATGGGTGTTGGGATCCTTTTCTAGAAGAGAGAA

GAAGTTTAGAATCCCATGCTTCATCTTGCATTTTTCACTGCTGAAGTTTCTCTTGCTTAATGCTCCACAAACTTCTT

TCTTTTGGCTTGACTGTCTAAGAAGTGTGCCAAATTGTTCTATCATGCAGACTCAGCATGAAACCTCATTAACTGCA

TCTTGGGACTTACTATAGAACTATTGCAGTACTGCAACGTTGACTAACATGATTTAGTCCAAAAGGTGTTTCAAGTC

TGTTTATCGGGGGGGGGGGATGTTTTGAGGCTCTTTATCGTGGTTCTGAACTGACGCCTTCATTTCCAGCTGAAGTG

CCGGTTCTGGCTCGAAGTTGAATATGTTTTACATCCACATATTAATAATTTATTAAGATGATTCTCCTTGTCAAATA

ATAAATAAATTAAGATGATTCAATTAGTAGCCTTTTCTTCTGTTTTATTCTCCATTATTTACTTGTACCAAAGATGA

AGCTCATTCCTGTAAACCTTTGTGTTTTCTTGCAAGGATAGTCGGCTCAACAATAATAGCTTGACTGGTAACATCCC

AATGTCACTGACTAATATCTCATCACTGCAAGTGTTGTAAGTACACTGATTATTTTGTGACTTGATTTAGATAATTC

TTTCTGTCTTCCATATCTTCTCATGCATTTCCTTTTCCTTCTAATGCATATACAGATTTACTTATGCTCAATTCTTG

TCTCACCTGTATGTAGGGATCTGTCAAACAACCGTCTCTCAGGTGCTGTTCCAGATAATGGTTCATTTTCTCTATTC

ACGCCTATCAGGTATATTTCATTTAAGGCGGTGCACCATCTAACTGGCTGGTGGTTTTAGCATGCTACTATTTGCTA

ATATATTTTTCTTGTTTACAGTTTTGCGAATAATTTAGATCTTTGCGGGCCTGTAACTGGACGCCCTTGCCCTGGAT

CTCCTCCATTCTCCCCTCCGCCTCCATTTGTTCCACCACCACCAATTTCTGCTCCAGGTGGTTCTCTAAATTGGTGT

GGATAAATTGTTCTCCTTTCTTTTTTCTTTTGTTTTTTTTGCTTTTTTGCGGTTAGTGATTTTAGTTTGTCCATCCA

ACGTAAGTGAGAATTTGTGCTATAGAAGCTAAAGTACTGACAAGAAAGGGGGCAGAAGAGGAAAACCCATCTTAACT

AGTCAGGCATTAGTTCTGATGGGAAACTGGTATGCACGAGACTACATTTAGTCTCTAAGCATTCTGGTCTTTATACA

AATTTAATTCAGCATTGTGGACATCTTTTCTTTGGTCCCCTTGTAAATTATTATCTGTGGTATTTGAAGTCATGTGT

CTGAATGAAATTAATCATATTTATGCCAGAACTTGTGAAGATTTTCTTTTCTTTGTAAAAACTGTCCTGGAAATTAG

ATCTGATGATAGATACAAATTTGTCTACTAATTTCTTTTTGAAGTGATTTAATTAATGAAGGGCCGGCCAAAATTAT

GTGTTAAATATAGTCTAGATCATATGAAGGAAATTAATCAAATTTATGGGAACTTCAGGAGGAAATGGTGCAACTGG

AGCAATTGCTGGAGGTGTAGCTGCTGGTGCTGCTCTACTATTTGCTGCTCCTGCCATTGCATTTGCCTGGTGGCGCC

GTAGAAAGCCACAAGAATATTTCTTTGACGTACCAGGTTAGCAGTATTCAAATACCCAACCATAAGTCCATAACTCC

TACTTACTCTCTCACGTGTTTATGGTTTCTCTTGCATGTTTTATTTTTTGGCTCCATAATTAACGTCTTTGCTTAAA

CTTATTGCAGCCGAAGAAGATCCTGAAGTTCACTTAGGTCAACTGAAAAGGTTCTCCCTCCGAGAGCTACAAGTTGC

AACTGACAGTT TAGCAATAAAAATATACTGGGTCGAGGTGGATTTGGTAAGGTATACAAAGGACGCTTAGCAGATG

-continued

GATCATTGGTGGCTGTTAAGCGGCTAAAGGAAGAGCGTACTCCTGGAGGGGAGTTGCAATTTCAAACAGAAGTTGAG
ATGATTAGCATGGCAGTGCATAGGAATCTTCTACGATTGCGTGGTTTCTGTATGACACCAACTGAAAGACTGCTTGT
CTACCCCTACATGGCGAATGGAAGTGTTGCATCATGCCTGAGAGGTGACACTTTCTGAAATCTATCACTCCATAAAT
GTTCTCACCTTTAATTTGGAGGGTATTATTGCATAATGCAAGAATGTCTTTCGCTGGTTAACATTCTATCTTGGCAT
AACTTACTCTTTATAACAAAACATATTCTTGTTAGTTATTTTCCTGTAACTTTTTAAAAGGTAGAAGTATAATTTGT
ATTGTATTCTCTTGACAACATAATTTATTTTATCAGAACGACCGCCTTCTGAACCACCACTTGATTGGCCAACGCGA
AAACGTATTGCTTTGGGGTCTGCCAGGGGATTATCGTATTTGCATGATCATTGTGACCCTAAGATTATCCATCGTGA
TGTGAAGGCTGCAAATATATTGCTAGATGAAGAATTTGAGGCTGTTGTTGGAGACTTTGGTTTGGCTAAACTTATGG
ACTACAAGGATACACATGTTACAACTGCTGTGCGTGGTACAATCGGGCATATAGCTCCAGAATACCTTTCCACAGGG
AAGTCTTCAGAAAAGACTGATGTTTTTGGGTATGGGATCATGCTTCTGGAGCTAATCACCGGCCAACGTGCTTTTGA
TCTTGCTCGGCTGGCAAATGATGACGATGTCATGTTGCTTGACTGGGTATGTTGTCATACCTGCTTTACATGTGAAC
ATGACACGAGTACCATAATGTGTTCATTTTTTAATCTGTACATCACAACACTAGCTGACTAATAAGTATTTGTGCCT
TTAGCAGGAATATTTAAGTCTATGACTAAACTTGTTGAGGTTCTTGTTTCAGGTGAAAGGACTCCTCAAAGAGAAGA
AACTGGAAATGCTGGTTGACCCTGATCTTCAGAACAAATATGTGGAGGCTGAGGTGGAGCAACTGATCCAGGTAGCA
TTGCTTTGTACACAAAGCAACCCAATGGATCGGCCTAAGATGTCGGAAGTGGTGAGAATGCTTGAAGGTGATGGTTT
GGCTGAAAGATGGGATGAGTGGCAGAAGGTAGAAGTTCTCCGGCAGGAAGTGGAACTTGCACCACATCCTGGTTCTG
ATTGGCTTGTTGACTCGACAGAGAATTTACATGCAGTTGAATTATCGGGTCCAAGGTGA

Nucleic acid sequence for a mutant Solyc04g072570 gene allele slserk1$^{w}$ coding sequence (SEQ ID NO: 89)

ATGGTGAAGGTGATGGAGAAGGATACTGTGGTGGTATCACTGGTGGTATGGCTAATCTTGGTTGTATATCATCTTAA
GCTCATTTATGCTAATATGGAAGGTGATGCATTGCACAGTCTACGCGTCAATTTACAAGATCCTAACAATGTGCTAC
AGAGCTGGGACCCAACCCTTGTTAATCCTTGCACATGGTTTCACGTTACCTGCAACAATGACAACAGTGTTATAAGA
GTTGATTTAGGAAATGCAGCTTTATCTGGTTTGTTAGTTCCACAGCTTGGCCTTTTGAAGAATTTGCAGTACTTGGA
GCTTTACAGTAATAATATAAGTGGTCTGATACCGAGTGATCTTGGGAATTTGACTAATCTGGTCAGCTTGGATCTCT
ACTTGAACAACTTCGTCGGTCCCATCCCAGATTCCTTGGGCAAGCTGTCGAAATTGAGATTCCTTCGGCTCAACAAT
AATAGCTTGACTGGTAACATCCCAATGTCACTGACTAATATCTCATCACTGCAAGTGTTGGATCTGTCAAACAACCG
TCTCTCAGGTGCTGTTCCAGATAATGGTTCATTTTCTCTATTCACGCCTATCAGTTTTGCGAATAATTTAGATCTTT
GCGGGCCTGTAACTGGACGCCCTTGCCCTGGATCTCCTCCATTCTCCCCTCCGCCTCCATTTGTTCCACCACCACCA
ATTTCTGCTCCAGGAGGAAATGGTGCAACTGGAGCAATTGCTGGAGGTGTAGCTGCTGGTGCTGCTCTACTATTTGC
TGCTCCTGCCATTGCATTTGCCTGGTGGCGCCGTAGAAAGCCACAAGAATATTTCTTTGACGTACCAGCCGAAGAAG
ATCCTGAAGTTCACTTAGGTCAACTGAAAAGGTTCTCCCTCCGAGAGCTACAAGTTGCAACTGACAGTT TAGCAAT
AAAAATATACTGGGTCGAGGTGGATTTGGTAAGGTATACAAAGGACGCTTAGCAGATGGATCATTGGTGGCTGTTAA
GCGGCTAAAGGAAGAGCGTACTCCTGGAGGGGAGTTGCAATTTCAAACAGAAGTTGAGATGATTAGCATGGCAGTGC
ATAGGAATCTTCTACGATTGCGTGGTTTCTGTATGACACCAACTGAAAGACTGCTTGTCTACCCCTACATGGCGAAT
GGAAGTGTTGCATCATGCCTGAGAGAACGACCGCCTTCTGAACCACCACTTGATTGGCCAACGCGAAAACGTATTGC
TTTGGGGTCTGCCAGGGGATTATCGTATTTGCATGATCATTGTGACCCTAAGATTATCCATCGTGATGTGAAGGCTG
CAAATATATTGCTAGATGAAGAATTTGAGGCTGTTGTTGGAGACTTTGGTTTGGCTAAACTTATGGACTACAAGGAT
ACACATGTTACAACTGCTGTGCGTGGTACAATCGGGCATATAGCTCCAGAATACCTTTCCACAGGGAAGTCTTCAGA
AAAGACTGATGTTTTTGGGTATGGGATCATGCTTCTGGAGCTAATCACCGGCCAACGTGCTTTTGATCTTGCTCGGC
TGGCAAATGATGACGATGTCATGTTGCTTGACTGGGTGAAAGGACTCCTCAAAGAGAAGAAACTGGAAATGCTGGTT
GACCCTGATCTTCAGAACAAATATGTGGAGGCTGAGGTGGAGCAACTGATCCAGGTAGCATTGCTTTGTACACAAAG

-continued

CAACCCAATGGATCGGCCTAAGATGTCGGAAGTGGTGAGAATGCTTGAAGGTGATGGTTTGGCTGAAAGATGGGATG

AGTGGCAGAAGGTAGAAGTTCTCCGGCAGGAAGTGGAACTTGCACCACATCCTGGTTCTGATTGGCTTGTTGACTCG

ACAGAGAATTTACATGCAGTTGAATTATCGGGTCCAAGGTGA

Amino acid sequence for a mutant polypeptide encoded by a mutant Solyc04g072570 gene allele slserk1$^{w}$ coding sequence (SEQ ID NO: 90)

MVKVMEKDTVVVSLVVWLILVVYHLKLIYANMEGDALHSLRVNLQDPNNVLQSWDPTLVNPCTWFHVTCNNDNSVIR

VDLGNAALSGLLVPQLGLLKNLQYLELYSNNISGLIPSDLGNLTNLVSLDLYLNNFVGPIPDSLGKLSKLRFLRLNN

NSLTGNIPMSLTNISSLQVLDLSNNRLSGAVPDNGSFSLFTPISFANNLDLCGPVTGRPCPGSPPFSPPPPFVPPPP

ISAPGGNGATGAIAGGVAAGAALLFAAPAIAFAWWRRRKPQEYFFDVPAEEDPEVHLGQLKRFSLRELQVATDS SN

KNILGRGGFGKVYKGRLADGSLVAVKRLKEERTPGGELQFQTEVEMISMAVHRNLLRLRGFCMTPTERLLVYPYMAN

GSVASCLRERPPSEPPLDWPTRKRIALGSARGLSYLHDHCDPKIIHRDVKAANILLDEEFEAVVGDFGLAKLMDYKD

THVTTAVRGTIGHIAPEYLSTGKSSEKTDVFGYGIMLLELITGQRAFDLARLANDDDVMLLDWVKGLLKEKKLEMLV

DPDLQNKYVEAEVEQLIQVALLCTQSNPMDRPKMSEVVRMLEGDGLAERWDEWQKVEVLRQEVELAPHPGSDWLVDS

TENLHAVELSGPR*

Mutant Solyc04g072570 gene allele slserk1$^{S1}$

Nucleic acid sequence for a mutant Solyc04g072570 gene allele slserk1$^{S1}$ (SEQ ID NO: 91)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCCTTGTTAATCCTTGCACATGGTTTCACGTTACCTGCAACAATGACAACAGTGTTATAAGAGT

GTAAGAATCTGTTTTCTGGTCTACCTCCATTTGAATGGATTTGCAATTCCACTCTCTTGTGGTGGTGAGCAATCTAA

TTGCAGTTTGTGCTCCCATAACACTTGTTATATGATCAACCTTTCCAGTGATTTAGGAAATGCAGCTTTATCTGGTT

TGTTAGTTCCACAGCTTGGCCTTTTGAAGAATTTGCAGTACTTGTAAGTCTCACTTCATGAACTATGTTTGGAATTA

TTTTACAAATTTAGAGTTGGAAAACTGGCATTGAGTGTATTGGTTTTTCCAGCTGTTGAAGATTTTCATATTACCTC

TAGAATTCGCTGCATGAAAATAATGTAGGTGGCTTGCATATTAACTTTTGCATAAAAACAAAGCTGTTGTAAGTGGC

AAAAATGAGCAGAGAACACTTTCTCCTCTCCATCTCTTGTTTCACTTGATGTTGTAGTCGATGGCATAGTTGTTGAT

GTGTTCCCTGAACAACACAAATTTGAATGTGTACTTCATAAAAAAAGATTTAAATATTTGTTTCACATTACATACTA

GTAAATTAAGTAACTCAGATACTTGGATGAGACTAGCAATGAAGTAACTTATGTGGCAAAGTAGTGTCTGTAATTGC

TTGTGAAAACATTGTAGTTGAACTTAAATTTTTGTCATACACTCCCTTATATAAAGATAAGCAGAGTAATCGTTAAC

YYYYYYAYGAACYCYYAAACAGAGYAYYAYYCYAAAYAYYAYYACYAAYGCCAGYACCCYAAGCACYCYYAAYYYGG

AATGACAAACTTCAACTCATATCAAATCCTTTATTCCCTCTTTCCTTGTTCCATGTAGACTCTAATCACGATTTAGG

ATGATGGAATAGGATAAAACAAACAAGAGAAACAAGTCCATTGTAAAAGTAAAGCAAAATCTAGACTTAAAAAGAGG

AAATATGGCATGAGGGTAGGTTGATGTCTTGGAGGAGAAGATCTGAAGTTTTCTGGTCATATAACAGATGCTATTCT

GGTTTTCACCAAGAGTTCGAATCATGATTCAATTAAGCATAGATTTTGTACAAGTGTTAAGCTTAGTTTGGAGTTCA

ATATACCGTTCACTTAAATTACATCTCAAATTTCATTGTTCTTATTGTAACCCATGCTCTTTTGAAGCTGCAACTGT

ATGGAAGTTCACAGAGACAGTATGTGCATGTGCACCTGGTGAAGCAGGGCATTACATGATGTATAACCATGCATCAG

-continued

ACAATGTTATAATGATGGGTATAATTATTACCTAGTGACTGCTTCATCCTGCTCACACATTAATATATTCCTATGGA

TGCCTAGATTTGCTTGAGGCTTGTGTAGTACGCGTGCTAAGTATTTTCCTAGTGTATGCAAGTGACAATCACATCAA

GAATGAAACAATATAAAAAGAACATCAAAAGTATAACATTATCTTTGTCAAAAAAAAAAAGAAAGAACATCAAGAGT

GCTGATGGAATTTAACAATCACCGGGCATACACACTGTTTAGATGAAGTTCGAAATTAACATAATGACAGACGTTAA

ATTTTTATTGATGAGTTATATAGATTGTATAAAATGTTTGACGAGCTGATTCTTTGCAGCACATGGGACGACAGGTT

TTTATATAGAAAAGTGCTTGTAACCAAATATAAGAAAATACCTCCATGAAATAGACATCGGTAACTAGTTATAATTG

CTATCTTGGAACTCCTAGACCTTTCTCATTTGTTGACTTTTAATTGTCGCTTGATGCCAGTATTGATGGATGTGAGA

ATTCTCCTTCATTATCTTGGTTGTCCCATTATCCTAGGGATGTCATTGGTATGATATGTGGAATTGACTCATTCTCT

GGTTTTCTTGTCACAGGGAGCTTTACAGTAATAATATAAGTGGTCTGATACCGAGTGATCTTGGGAATTTGACTAAT

CTGGTCAGCTTGGATCTCTACTTGAACAACTTCGTCGGTCCCATCCCAGATTCCTTGGGCAAGCTGTCGAAATTGAG

ATTCCTGTATGTATTTTTGTTCTATATTAGATTTATGTGGATATTGTGATGCCAAATGTATATTTCATCAACCAAGA

TGGACCTACTCTTACTGGCATGTTGAGAAAGGAAAGGAAGCCTGAATTCTTTTCTAGGTTTCACATAAGATGACCTC

TATTAGTATTATGTTTCACTCTTAAGTTTTGATGGTAGAAGGTATTTGAGGACTTCATGGGTCTGATATCATTCATA

AAACCGATCTTACATAAGTCTTTTAATTTTCTCCCTTTGTTCTAATCCTTGTATAAAGGAAAAGAATAGAAGCCTAT

GCTTTGTCTGATACTGATATTGTAAAATTAATCAGAGTTTAGTAATGGGTGTTGGGATCCTTTTCTAGAAGAGAGAA

GAAGTTTAGAATCCCATGCTTCATCTTGCATTTTTCACTGCTGAAGTTTCTCTTGCTTAATGCTCCACAAACTTCTT

TCTTTTGGCTTGACTGTCTAAGAAGTGTGCCAAATTGTTCTATCATGCAGACTCAGCATGAAACCTCATTAACTGCA

TCTTGGGACTTACTATAGAACTATTGCAGTACTGCAACGTTGACTAACATGATTTAGTCCAAAAGGTGTTTCAAGTC

TGTTTATCGGGGGGGGGGGATGTTTTGAGGCTCTTTATCGTGGTTCTGAACTGACGCCTTCATTTCCAGCTGAAGTG

CCGGTTCTGGCTCGAAGTTGAATATGTTTTACATCCACATATTAATAATTTATTAAGATGATTCTCCTTGTCAAATA

ATAAATAAATTAAGATGATTCAATTAGTAGCCTTTTCTTCTGTTTTATTCTCCATTATTTACTTGTACCAAAGATGA

AGCTCATTCCTGTAAACCTTTGTGTTTTCTTGCAAGGATAGTCGGCTCAACAATAATAGCTTGACTGGTAACATCCC

AATGTCACTGACTAATATCTCATCACTGCAAGTGTTGTAAGTACACTGATTATTTTGTGACTTGATTTAGATAATTC

TTTCTGTCTTCCATATCTTCTCATGCATTTCCTTTTCCTTCTAATGCATATACAGATTTACTTATGCTCAATTCTTG

TCTCACCTGTATGTAGGGATCTGTCAAACAACCGTCTCTCAGGTGCTGTTCCAGATAATGGTTCATTTTCTCTATTC

ACGCCTATCAGGTATATTTCATTTAAGGCGGTGCACCATCTAACTGGCTGGTGGTTTTAGCATGCTACTATTTGCTA

ATATATTTTTCTTGTTTACAGTTTTGCGAATAATTTAGATCTTTGCGGGCCTGTAACTGGACGCCCTTGCCCTGGAT

CTCCTCCATTCTCCCCTCCGCCTCCATTTGTTCCACCACCACCAATTTCTGCTCCAGGTGGTTCTCTAAATTGGTGT

GGATAAATTGTTCTCCTTTCTTTTTTCTTTTGTTTTTTTTGCTTTTTTGCGGTTAGTGATTTTAGTTTGTCCATCCA

ACGTAAGTGAGAATTTGTGCTATAGAAGCTAAAGTACTGACAAGAAAGGGGGCAGAAGAGGAAAACCCATCTTAACT

AGTCAGGCATTAGTTCTGATGGGAAACTGGTATGCACGAGACTACATTTAGTCTCTAAGCATTCTGGTCTTTATACA

AATTTAATTCAGCATTGTGGACATCTTTTCTTTGGTCCCCTTGTAAATTATTATCTGTGGTATTTGAAGTCATGTGT

CTGAATGAAATTAATCATATTTATGCCAGAACTTGTGAAGATTTTCTTTTCTTTGTAAAAACTGTCCTGGAAATTAG

ATCTGATGATAGATACAAATTTGTCTACTAATTTCTTTTTGAAGTGATTTAATTAATGAAGGGCCGGCCAAAATTAT

GTGTTAAATATAGTCTAGATCATATGAAGGAAATTAATCAAATTTATGGGAACTTCAGGAGGAAATGGTGCAACTGG

AGCAATTGCTGGAGGTGTAGCTGCTGGTGCTGCTCTACTATTTGCTGCTCCTGCCATTGCATTTGCCTGGTGGCGCC

GTAGAAAGCCACAAGAATATTTCTTTGACGTACCAGGTTAGCAGTATTCAAATACCCAACCATAAGTCCATAACTCC

TACTTACTCTCTCACGTGTTTATGGTTTCTCTTGCATGTTTTATTTTTTGGCTCCATAATTAACGTCTTTGCTTAAA

CTTATTGCAGCCGAAGAAGATCCTGAAGTTCACTTAGGTCAACTGAAAAGGTTCTCCCTCCGAGAGCTACAAGTTGC

AACTGACAGTTTTAGCAATAAAAATATACTGGGTCGAGGTGGATTTGGTAAGGTATACAAAGGACGCTTAGCAGATG

GATCATTGGTGGCTGTTAAGCGGCTAAAGGAAGAGCGTACTCCTGGAGGGGAGTTGCAATTTCAAACAAAAGTTGAG

-continued

ATGATTAGCATGGCAGTGCATAGGAATCTTCTACGATTGCGTGGTTTCTGTATGACACCAACTGAAAGACTGCTTGT

CTACCCCTACATGGCGAATGGAAGTGTTGCATCATGCCTGAGAGGTGACACTTTCTGAAATCTATCACTCCATAAAT

GTTCTCACCTTTAATTTGGAGGGTATTATTGCATAATGCAAGAATGTCTTTCGCTGGTTAACATTCTATCTTGGCAT

AACTTACTCTTTATAACAAAACATATTCTTGTTAGTTATTTTCCTGTAACTTTTTAAAAGGTAGAAGTATAATTTGT

ATTGTATTCTCTTGACAACATAATTTATTTTATCAGAACGACCGCCTTCTGAACCACCACTTGATTGGCCAACGCGA

AAACGTATTGCTTTGGGGTCTGCCAGGGGATTATCGTATTTGCATGATCATTGTGACCCTAAGATTATCCATCGTGA

TGTGAAGGCTGCAAATATATTGCTAGATGAAGAATTTGAGGCTGTTGTTGGAGACTTTGGTTTGGCTAAACTTATGG

ACTACAAGGATACACATGTTACAACTGCTGTGCGTGGTACAATCGGGCATATAGCTCCAGAATACCTTTCCACAGGG

AAGTCTTCAGAAAAGACTGATGTTTTTGGGTATGGGATCATGCTTCTGGAGCTAATCACCGGCCAACGTGCTTTTGA

TCTTGCTCGGCTGGCAAATGATGACGATGTCATGTTGCTTGACTGGGTATGTTGTCATACCTGCTTTACATGTGAAC

ATGACACGAGTACCATAATGTGTTCATTTTTTAATCTGTACATCACAACACTAGCTGACTAATAAGTATTTGTGCCT

TTAGCAGGAATATTTAAGTCTATGACTAAACTTGTTGAGGTTCTTGTTTCAGGTGAAAGGACTCCTCAAAGAGAAGA

AACTGGAAATGCTGGTTGACCCTGATCTTCAGAACAAATATGTGGAGGCTGAGGTGGAGCAACTGATCCAGGTAGCA

TTGCTTTGTACACAAAGCAACCCAATGGATCGGCCTAAGATGTCGGAAGTGGTGAGAATGCTTGAAGGTGATGGTTT

GGCTGAAAGATGGGATGAGTGGCAGAAGGTAGAAGTTCTCCGGCAGGAAGTGGAACTTGCACCACATCCTGGTTCTG

ATTGGCTTGTTGACTCGACAGAGAATTTACATGCAGTTGAATTATCGGGTCCAAGGTGA

Nucleic acid sequence for a mutant Solyc04g072570 gene allele
slserk1$^{S1}$ coding sequence (SEQ ID NO: 92)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCCTTGTTAATCCTTGCACATGGTTTCACGTTACCTGCAACAATGACAACAGTGTTATAAGA

GTTGATTTAGGAAATGCAGCTTTATCTGGTTTGTTAGTTCCACAGCTTGGCCTTTTGAAGAATTTGCAGTACTTGGA

GCTTTACAGTAATAATATAAGTGGTCTGATACCGAGTGATCTTGGGAATTTGACTAATCTGGTCAGCTTGGATCTCT

ACTTGAACAACTTCGTCGGTCCCATCCCAGATTCCTTGGGCAAGCTGTCGAAATTGAGATTCCTTCGGCTCAACAAT

AATAGCTTGACTGGTAACATCCCAATGTCACTGACTAATATCTCATCACTGCAAGTGTTGGATCTGTCAAACAACCG

TCTCTCAGGTGCTGTTCCAGATAATGGTTCATTTTCTCTATTCACGCCTATCAGTTTTGCGAATAATTTAGATCTTT

GCGGGCCTGTAACTGGACGCCCTTGCCCTGGATCTCCTCCATTCTCCCCTCCGCCTCCATTTGTTCCACCACCACCA

ATTTCTGCTCCAGGAGGAAATGGTGCAACTGGAGCAATTGCTGGAGGTGTAGCTGCTGGTGCTGCTCTACTATTTGC

TGCTCCTGCCATTGCATTTGCCTGGTGGCGCCGTAGAAAGCCACAAGAATATTTCTTTGACGTACCAGCCGAAGAAG

ATCCTGAAGTTCACTTAGGTCAACTGAAAAGGTTCTCCCTCCGAGAGCTACAAGTTGCAACTGACAGTTTTAGCAAT

AAAAATATACTGGGTCGAGGTGGATTTGGTAAGGTATACAAAGGACGCTTAGCAGATGGATCATTGGTGGCTGTTAA

GCGGCTAAAGGAAGAGCGTACTCCTGGAGGGGAGTTGCAATTTCAAACA AAGTTGAGATGATTAGCATGGCAGTGC

ATAGGAATCTTCTACGATTGCGTGGTTTCTGTATGACACCAACTGAAAGACTGCTTGTCTACCCCTACATGGCGAAT

GGAAGTGTTGCATCATGCCTGAGAGAACGACCGCCTTCTGAACCACCACTTGATTGGCCAACGCGAAAACGTATTGC

TTTGGGGTCTGCCAGGGGATTATCGTATTTGCATGATCATTGTGACCCTAAGATTATCCATCGTGATGTGAAGGCTG

CAAATATATTGCTAGATGAAGAATTTGAGGCTGTTGTTGGAGACTTTGGTTTGGCTAAACTTATGGACTACAAGGAT

ACACATGTTACAACTGCTGTGCGTGGTACAATCGGGCATATAGCTCCAGAATACCTTTCCACAGGGAAGTCTTCAGA

AAAGACTGATGTTTTTGGGTATGGGATCATGCTTCTGGAGCTAATCACCGGCCAACGTGCTTTTGATCTTGCTCGGC

TGGCAAATGATGACGATGTCATGTTGCTTGACTGGGTGAAAGGACTCCTCAAAGAGAAGAAACTGGAAATGCTGGTT

GACCCTGATCTTCAGAACAAATATGTGGAGGCTGAGGTGGAGCAACTGATCCAGGTAGCATTGCTTTGTACACAAAG

CAACCCAATGGATCGGCCTAAGATGTCGGAAGTGGTGAGAATGCTTGAAGGTGATGGTTTGGCTGAAAGATGGGATG

-continued

AGTGGCAGAAGGTAGAAGTTCTCCGGCAGGAAGTGGAACTTGCACCACATCCTGGTTCTGATTGGCTTGTTGACTCG

ACAGAGAATTTACATGCAGTTGAATTATCGGGTCCAAGGTGA

Amino acid sequence for a mutant polypeptide encoded by a mutant Solyc04g072570 gene allele slserk1$^{S1}$ coding sequence (SEQ ID NO: 93)

MVKVMEKDTVVVSLVVWLILVVYHLKLIYANMEGDALHSLRVNLQDPNNVLQSWDPTLVNPCTWFHVTCNNDNSVIR

VDLGNAALSGLLVPQLGLLKNLQYLELYSNNISGLIPSDLGNLTNLVSLDLYLNNFVGPIPDSLGKLSKLRFLRLNN

NSLTGNIPMSLTNISSLQVLDLSNNRLSGAVPDNGSFSLFTPISFANNLDLCGPVTGRPCPGSPPFSPPPPFVPPPP

ISAPGGNGATGAIAGGVAAGAALLFAAPAIAFAWWRRRKPQEYFFDVPAEEDPEVHLGQLKRFSLRELQVATDSFSN

KNILGRGGFGKVYKGRLADGSLVAVKRLKEERTPGGELQFQT VEMISMAVHRNLLRLRGFCMTPTERLLVYPYMAN

GSVASCLRERPPSEPPLDWPTRKRIALGSARGLSYLHDHCDPKIIHRDVKAANILLDEEFEAVVGDFGLAKLMDYKD

THVTTAVRGTIGHIAPEYLSTGKSSEKTDVFGYGIMLLELITGQRAFDLARLANDDDVMLLDWVKGLLKEKKLEMLV

DPDLQNKYVEAEVEQLIQVALLCTQSNPMDRPKMSEVVRMLEGDGLAERWDEWQKVEVLRQEVELAPHPGSDWLVDS

TENLHAVELSGPR*

Mutant Solyc04g072570 gene allele slserk1$^{S2}$
Nucleic acid sequence for a mutant Solyc04g072570 gene allele slserk1$^{S2}$ (SEQ ID NO: 94)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCCTTGTTAATCCTTGCACATGGTTTCACGTTACCTGCAACAATGACAACAGTGTTATAAGAGT

GTAAGAATCTGTTTTCTGGTCTACCTCCATTTGAATGGATTTGCAATTCCACTCTCTTGTGGTGGTGAGCAATCTAA

TTGCAGTTTGTGCTCCCATAACACTTGTTATATGATCAACCTTTCCAGTGATTTAGGAAATGCAGCTTTATCTGGTT

TGTTAGTTCCACAGCTTGGCCTTTTGAAGAATTTGCAGTACTTGTAAGTCTCACTTCATGAACTATGTTTGGAATTA

TTTTACAAATTTAGAGTTGGAAAACTGGCATTGAGTGTATTGGTTTTTCCAGCTGTTGAAGATTTTCATATTACCTC

TAGAATTCGCTGCATGAAAATAATGTAGGTGGCTTGCATATTAACTTTTGCATAAAAACAAAGCTGTTGTAAGTGGC

AAAAATGAGCAGAGAACACTTTCTCCTCTCCATCTCTTGTTTCACTTGATGTTGTAGTCGATGGCATAGTTGTTGAT

GTGTTCCCTGAACAACACAAATTTGAATGTGTACTTCATAAAAAAAGATTTAAATATTTGTTTCACATTACATACTA

GTAAATTAAGTAACTCAGATACTTGGATGAGACTAGCAATGAAGTAACTTATGTGGCAAAGTAGTGTCTGTAATTGC

TTGTGAAAACATTGTAGTTGAACTTAAATTTTTGTCATACACTCCCTTATATAAAGATAAGCAGAGTAATCGTTAAC

TTTTTTATGAACTCTTAAACAGAGTATTATTCTAAATATTATTACTAATGCCAGTACCCTAAGCACTCTTAATTTGG

AATGACAAACTTCAACTCATATCAAATCCTTTATTCCCTCTTTCCTTGTTCCATGTAGACTCTAATCACGATTTAGG

ATGATGGAATAGGATAAAACAAACAAGAGAAACAAGTCCATTGTAAAAGTAAAGCAAAATCTAGACTTAAAAAGAGG

AAATATGGCATGAGGGTAGGTTGATGTCTTGGAGGAGAAGATCTGAAGTTTTCTGGTCATATAACAGATGCTATTCT

GGTTTTCACCAAGAGTTCGAATCATGATTCAATTAAGCATAGATTTTGTACAAGTGTTAAGCTTAGTTTGGAGTTCA

ATATACCGTTCACTTAAATTACATCTCAAATTTCATTGTTCTTATTGTAACCCATGCTCTTTTGAAGCTGCAACTGT

ATGGAAGTTCACAGAGACAGTATGTGCATGTGCACCTGGTGAAGCAGGGCATTACATGATGTATAACCATGCATCAG

ACAATGTTATAATGATGGGTATAATTATTACCTAGTGACTGCTTCATCCTGCTCACACATTAATATATTCCTATGGA

-continued

TGCCTAGATTTGCTTGAGGCTTGTGTAGTACGCGTGCTAAGTATTTTCCTAGTGTATGCAAGTGACAATCACATCAA

GAATGAAACAATATAAAAAGAACATCAAAAGTATAACATTATCTTTGTCAAAAAAAAAAAGAAAGAACATCAAGAGT

GCTGATGGAATTTAACAATCACCGGGCATACACACTGTTTAGATGAAGTTCGAAATTAACATAATGACAGACGTTAA

ATTTTTATTGATGAGTTATATAGATTGTATAAAATGTTTGACGAGCTGATTCTTTGCAGCACATGGGACGACAGGTT

TTTATATAGAAAAGTGCTTGTAACCAAATATAAGAAAATACCTCCATGAAATAGACATCGGTAACTAGTTATAATTG

CTATCTTGGAACTCCTAGACCTTTCTCATTTGTTGACTTTTAATTGTCGCTTGATGCCAGTATTGATGGATGTGAGA

ATTCTCCTTCATTATCTTGGTTGTCCCATTATCCTAGGGATGTCATTGGTATGATATGTGGAATTGACTCATTCTCT

GGTTTTCTTGTCACAGGGAGCTTTACAGTAATAATATAAGTGGTCTGATACCGAGTGATCTTGGGAATTTGACTAAT

CTGGTCAGCTTGGATCTCTACTTGAACAACTTCGTCGGTCCCATCCCAGATTCCTTGGGCAAGCTGTCGAAATTGAG

ATTCCTGTATGTATTTTTGTTCTATATTAGATTTATGTGGATATTGTGATGCCAAATGTATATTTCATCAACCAAGA

TGGACCTACTCTTACTGGCATGTTGAGAAAGGAAAGGAAGCCTGAATTCTTTTCTAGGTTTCACATAAGATGACCTC

TATTAGTATTATGTTTCACTCTTAAGTTTTGATGGTAGAAGGTATTTGAGGACTTCATGGGTCTGATATCATTCATA

AAACCGATCTTACATAAGTCTTTTAATTTTCTCCCTTTGTTCTAATCCTTGTATAAAGGAAAAGAATAGAAGCCTAT

GCTTTGTCTGATACTGATATTGTAAAATTAATCAGAGTTTAGTAATGGGTGTTGGGATCCTTTTCTAGAAGAGAGAA

GAAGTTTAGAATCCCATGCTTCATCTTGCATTTTTCACTGCTGAAGTTTCTCTTGCTTAATGCTCCACAAACTTCTT

TCTTTTGGCTTGACTGTCTAAGAAGTGTGCCAAATTGTTCTATCATGCAGACTCAGCATGAAACCTCATTAACTGCA

TCTTGGGACTTACTATAGAACTATTGCAGTACTGCAACGTTGACTAACATGATTTAGTCCAAAAGGTGTTTCAAGTC

TGTTTATCGGGGGGGGGGGATGTTTTGAGGCTCTTTATCGTGGTTCTGAACTGACGCCTTCATTTCCAGCTGAAGTG

CCGGTTCTGGCTCGAAGTTGAATATGTTTTACATCCACATATTAATAATTTATTAAGATGATTCTCCTTGTCAAATA

ATAAATAAATTAAGATGATTCAATTAGTAGCCTTTTCTTCTGTTTTATTCTCCATTATTTACTTGTACCAAAGATGA

AGCTCATTCCTGTAAACCTTTGTGTTTTCTTGCAAGGATAGTCGGCTCAACAATAATAGCTTGACTGGTAACATCCC

AATGTCACTGACTAATATCTCATCACTGCAAGTGTTGTAAGTACACTGATTATTTTGTGACTTGATTTAGATAATTC

TTTCTGTCTTCCATATCTTCTCATGCATTTCCTTTTCCTTCTAATGCATATACAGATTTACTTATGCTCAATTCTTG

TCTCACCTGTATGTAGGGATCTGTCAAACAACCGTCTCTCAGGTGCTGTTCCAGATAATGGTTCATTTTCTCTATTC

ACGCCTATCAGGTATATTTCATTTAAGGCGGTGCACCATCTAACTGGCTGGTGGTTTTAGCATGCTACTATTTGCTA

ATATATTTTTCTTGTTTACAGTTTTGCGAATAATTTAGATCTTTGCGGGCCTGTAACTGGACGCCCTTGCCCTGGAT

CTCCTCCATTCTCCCCTCCGCCTCCATTTGTTCCACCACCACCAATTTCTGCTCCAGGTGGTTCTCTAAATTGGTGT

GGATAAATTGTTCTCCTTTCTTTTTTCTTTTGTTTTTTTTGCTTTTTTGCGGTTAGTGATTTTAGTTTGTCCATCCA

ACGTAAGTGAGAATTTGTGCTATAGAAGCTAAAGTACTGACAAGAAAGGGGGCAGAAGAGGAAAACCCATCTTAACT

AGTCAGGCATTAGTTCTGATGGGAAACTGGTATGCACGAGACTACATTTAGTCTCTAAGCATTCTGGTCTTTATACA

AATTTAATTCAGCATTGTGGACATCTTTTCTTTGGTCCCCTTGTAAATTATTATCTGTGGTATTTGAAGTCATGTGT

CTGAATGAAATTAATCATATTTATGCCAGAACTTGTGAAGATTTTCTTTTCTTTGTAAAAACTGTCCTGGAAATTAG

ATCTGATGATAGATACAAATTTGTCTACTAATTTCTTTTTGAAGTGATTTAATTAATGAAGGGCCGGCCAAAATTAT

GTGTTAAATATAGTCTAGATCATATGAAGGAAATTAATCAAATTTATGGGAACTTCAGGAGGAAATGGTGCAACTGG

AGCAATTGCTGGAGGTGTAGCTGCTGGTGCTGCTCTACTATTTGCTGCTCCTGCCATTGCATTTGCCTGGTGGCGCC

GTAGAAAGCCACAAGAATATTTCTTTGACGTACCAGGTTAGCAGTATTCAAATACCCAACCATAAGTCCATAACTCC

TACTTACTCTCTCACGTGTTTATGGTTTCTCTTGCATGTTTTATTTTTTGGCTCCATAATTAACGTCTTTGCTTAAA

CTTATTGCAGCCGAAGAAGATCCTGAAGTTCACTTAGGTCAACTGAAAAGGTTCTCCCTCCGAGAGCTACAAGTTGC

AACTGACAGTTTTAGCAATAAAAATATACTGGATCGAGGTGGATTTGGTAAGGTATACAAAGGACGCTTAGCAGATG

GATCATTGGTGGCTGTTAAGCGGCTAAAGGAAGAGCGTACTCCTGGAGGGGAGTTGCAATTTCAAACAGAAGTTGAG

ATGATTAGCATGGCAGTGCATAGGAATCTTCTACGATTGCGTGGTTTCTGTATGACACCAACTGAAAGACTGCTTGT

-continued

CTACCCCTACATGGCGAATGGAAGTGTTGCATCATGCCTGAGAGGTGACACTTTCTGAAATCTATCACTCCATAAAT

GTTCTCACCTTTAATTTGGAGGGTATTATTGCATAATGCAAGAATGTCTTTCGCTGGTTAACATTCTATCTTGGCAT

AACTTACTCTTTATAACAAAACATATTCTTGTTAGTTATTTTCCTGTAACTTTTTAAAAGGTAGAAGTATAATTTGT

ATTGTATTCTCTTGACAACATAATTTATTTTATCAGAACGACCGCCTTCTGAACCACCACTTGATTGGCCAACGCGA

AAACGTATTGCTTTGGGGTCTGCCAGGGGATTATCGTATTTGCATGATCATTGTGACCCTAAGATTATCCATCGTGA

TGTGAAGGCTGCAAATATATTGCTAGATGAAGAATTTGAGGCTGTTGTTGGAGACTTTGGTTTGGCTAAACTTATGG

ACTACAAGGATACACATGTTACAACTGCTGTGCGTGGTACAATCGGGCATATAGCTCCAGAATACCTTTCCACAGGG

AAGTCTTCAGAAAAGACTGATGTTTTTGGGTATGGGATCATGCTTCTGGAGCTAATCACCGGCCAACGTGCTTTTGA

TCTTGCTCGGCTGGCAAATGATGACGATGTCATGTTGCTTGACTGGGTATGTTGTCATACCTGCTTTACATGTGAAC

ATGACACGAGTACCATAATGTGTTCATTTTTTAATCTGTACATCACAACACTAGCTGACTAATAAGTATTTGTGCCT

TTAGCAGGAATATTTAAGTCTATGACTAAACTTGTTGAGGTTCTTGTTTCAGGTGAAAGGACTCCTCAAAGAGAAGA

AACTGGAAATGCTGGTTGACCCTGATCTTCAGAACAAATATGTGGAGGCTGAGGTGGAGCAACTGATCCAGGTAGCA

TTGCTTTGTACACAAAGCAACCCAATGGATCGGCCTAAGATGTCGGAAGTGGTGAGAATGCTTGAAGGTGATGGTTT

GGCTGAAAGATGGGATGAGTGGCAGAAGGTAGAAGTTCTCCGGCAGGAAGTGGAACTTGCACCACATCCTGGTTCTG

ATTGGCTTGTTGACTCGACAGAGAATTTACATGCAGTTGAATTATCGGGTCCAAGGTGA

Nucleic acid sequence for a mutant Solyc04g072570 gene
allele slserk1$^{S2}$ coding sequence (SEQ ID NO: 95)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCCTTGTTAATCCTTGCACATGGTTTCACGTTACCTGCAACAATGACAACAGTGTTATAAGA

GTTGATTTAGGAAATGCAGCTTTATCTGGTTTGTTAGTTCCACAGCTTGGCCTTTTGAAGAATTTGCAGTACTTGGA

GCTTTACAGTAATAATATAAGTGGTCTGATACCGAGTGATCTTGGGAATTTGACTAATCTGGTCAGCTTGGATCTCT

ACTTGAACAACTTCGTCGGTCCCATCCCAGATTCCTTGGGCAAGCTGTCGAAATTGAGATTCCTTCGGCTCAACAAT

AATAGCTTGACTGGTAACATCCCAATGTCACTGACTAATATCTCATCACTGCAAGTGTTGGATCTGTCAAACAACCG

TCTCTCAGGTGCTGTTCCAGATAATGGTTCATTTTCTCTATTCACGCCTATCAGTTTTGCGAATAATTTAGATCTTT

GCGGGCCTGTAACTGGACGCCCTTGCCCTGGATCTCCTCCATTCTCCCCTCCGCCTCCATTTGTTCCACCACCACCA

ATTTCTGCTCCAGGAGGAAATGGTGCAACTGGAGCAATTGCTGGAGGTGTAGCTGCTGGTGCTGCTCTACTATTTGC

TGCTCCTGCCATTGCATTTGCCTGGTGGCGCCGTAGAAAGCCACAAGAATATTTCTTTGACGTACCAGCCGAAGAAG

ATCCTGAAGTTCACTTAGGTCAACTGAAAAGGTTCTCCCTCCGAGAGCTACAAGTTGCAACTGACAGTTTTAGCAAT

AAAAATATACTGG TCGAGGTGGATTTGGTAAGGTATACAAAGGACGCTTAGCAGATGGATCATTGGTGGCTGTTAA

GCGGCTAAAGGAAGAGCGTACTCCTGGAGGGGAGTTGCAATTTCAAACAGAAGTTGAGATGATTAGCATGGCAGTGC

ATAGGAATCTTCTACGATTGCGTGGTTTCTGTATGACACCAACTGAAAGACTGCTTGTCTACCCCTACATGGCGAAT

GGAAGTGTTGCATCATGCCTGAGAGAACGACCGCCTTCTGAACCACCACTTGATTGGCCAACGCGAAAACGTATTGC

TTTGGGGTCTGCCAGGGGATTATCGTATTTGCATGATCATTGTGACCCTAAGATTATCCATCGTGATGTGAAGGCTG

CAAATATATTGCTAGATGAAGAATTTGAGGCTGTTGTTGGAGACTTTGGTTTGGCTAAACTTATGGACTACAAGGAT

ACACATGTTACAACTGCTGTGCGTGGTACAATCGGGCATATAGCTCCAGAATACCTTTCCACAGGGAAGTCTTCAGA

AAAGACTGATGTTTTTGGGTATGGGATCATGCTTCTGGAGCTAATCACCGGCCAACGTGCTTTTGATCTTGCTCGGC

TGGCAAATGATGACGATGTCATGTTGCTTGACTGGGTGAAAGGACTCCTCAAAGAGAAGAAACTGGAAATGCTGGTT

GACCCTGATCTTCAGAACAAATATGTGGAGGCTGAGGTGGAGCAACTGATCCAGGTAGCATTGCTTTGTACACAAAG

-continued

CAACCCAATGGATCGGCCTAAGATGTCGGAAGTGGTGAGAATGCTTGAAGGTGATGGTTTGGCTGAAAGATGGGATG

AGTGGCAGAAGGTAGAAGTTCTCCGGCAGGAAGTGGAACTTGCACCACATCCTGGTTCTGATTGGCTTGTTGACTCG

ACAGAGAATTTACATGCAGTTGAATTATCGGGTCCAAGGTGA

Amino acid sequence for a mutant polypeptide encoded by a mutant Solyc04g072570 gene allele slserk1$^{S2}$ coding sequence (SEQ ID NO: 96)

MVKVMEKDTVVVSLVVWLILVVYHLKLIYANMEGDALHSLRVNLQDPNNVLQSWDPTLVNPCTWFHVTCNNDNSVIR

VDLGNAALSGLLVPQLGLLKNLQYLELYSNNISGLIPSDLGNLTNLVSLDLYLNNFVGPIPDSLGKLSKLRFLRLNN

NSLTGNIPMSLTNISSLQVLDLSNNRLSGAVPDNGSFSLFTPISFANNLDLCGPVTGRPCPGSPPFSPPPPFVPPPP

ISAPGGNGATGAIAGGVAAGAALLFAAPAIAFAWWRRRKPQEYFFDVPAEEDPEVHLGQLKRFSLRELQVATDSFSN

KNIL RGGFGKVYKGRLADGSLVAVKRLKEERTPGGELQFQTEVEMISMAVHRNLLRLRGFCMTPTERLLVYPYMAN

GSVASCLRERPPSEPPLDWPTRKRIALGSARGLSYLHDHCDPKIIHRDVKAANILLDEEFEAVVGDFGLAKLMDYKD

THVTTAVRGTIGHIAPEYLSTGKSSEKTDVFGYGIMLLELITGQRAFDLARLANDDDVMLLDWVKGLLKEKKLEMLV

DPDLQNKYVEAEVEQLIQVALLCTQSNPMDRPKMSEVVRMLEGDGLAERWDEWQKVEVLRQEVELAPHPGSDWLVDS

TENLHAVELSGPR*

Mutant Solyc04g072570 gene allele slserk1$^{CR\text{-}5\text{-}\alpha1}$
Nucleic acid sequence for a mutant Solyc04g072570 gene allele slserk1$^{CR\text{-}5\text{-}\alpha1}$ (SEQ ID NO: 97)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGTGTTATAAGAGTGTAAGAATCTGTTTTCTGGTCTACCTCCATTTGAATGGATT

TGCAATTCCACTCTCTTGTGGTGGTGAGCAATCTAATTGCAGTTTGTGCTCCCATAACACTTGTTATATGATCAACC

TTTCCAGTGATTTAGGAAATGCAGCTTTATCTGGTTTGTTAGTTCCACAGCTTGGCCTTTTGAAGAATTTGCAGTAC

TTGTAAGTCTCACTTCATGAACTATGTTTGGAATTATTTTACAAATTTAGAGTTGGAAAACTGGCATTGAGTGTATT

GGTTTTTCCAGCTGTTGAAGATTTTCATATTACCTCTAGAATTCGCTGCATGAAAATAATGTAGGTGGCTTGCATAT

TAACTTTTGCATAAAAACAAAGCTGTTGTAAGTGGCAAAAATGAGCAGAGAACACTTTCTCCTCTCCATCTCTTGTT

TCACTTGATGTTGTAGTCGATGGCATAGTTGTTGATGTGTTCCCTGAACAACACAAATTTGAATGTGTACTTCATAA

AAAAAGATTTAAATATTTGTTTCACATTACATACTAGTAAATTAAGTAACTCAGATACTTGGATGAGACTAGCAATG

AAGTAACTTATGTGGCAAAGTAGTGTCTGTAATTGCTTGTGAAAACATTGTAGTTGAACTTAAATTTTTGTCATACA

CTCCCTTATATAAAGATAAGCAGAGTAATCGTTAACTTTTTTATGAACTCTTAAACAGAGTATTATTCTAAATATTA

TTACTAATGCCAGTACCCTAAGCACTCTTAATTTGGAATGACAAACTTCAACTCATATCAAATCCTTTATTCCCTCT

TTCCTTGTTCCATGTAGACTCTAATCACGATTTAGGATGATGGAATAGGATAAAACAAACAAGAGAAACAAGTCCAT

TGTAAAAGTAAAGCAAAATCTAGACTTAAAAAGAGGAAATATGGCATGAGGGTAGGTTGATGTCTTGGAGGAGAAGA

TCTGAAGTTTTCTGGTCATATAACAGATGCTATTCTGGTTTTCACCAAGAGTTCGAATCATGATTCAATTAAGCATA

GATTTTGTACAAGTGTTAAGCTTAGTTTGGAGTTCAATATACCGTTCACTTAAATTACATCTCAAATTTCATTGTTC

TTATTGTAACCCATGCTCTTTTGAAGCTGCAACTGTATGGAAGTTCACAGAGACAGTATGTGCATGTGCACCTGGTG

AAGCAGGGCATTACATGATGTATAACCATGCATCAGACAATGTTATAATGATGGGTATAATTATTACCTAGTGACTG

CTTCATCCTGCTCACACATTAATATATTCCTATGGATGCCTAGATTTGCTTGAGGCTTGTGTAGTACGCGTGCTAAG

-continued

```
TATTTTCCTAGTGTATGCAAGTGACAATCACATCAAGAATGAAACAATATAAAAAGAACATCAAAAGTATAACATTA

TCTTTGTCAAAAAAAAAAAGAAAGAACATCAAGAGTGCTGATGGAATTTAACAATCACCGGGCATACACACTGTTTA

GATGAAGTTCGAAATTAACATAATGACAGACGTTAAATTTTTATTGATGAGTTATATAGATTGTATAAAATGTTTGA

CGAGCTGATTCTTTGCAGCACATGGGACGACAGGTTTTTATATAGAAAAGTGCTTGTAACCAAATATAAGAAAATAC

CTCCATGAAATAGACATCGGTAACTAGTTATAATTGCTATCTTGGAACTCCTAGACCTTTCTCATTTGTTGACTTTT

AATTGTCGCTTGATGCCAGTATTGATGGATGTGAGAATTCTCCTTCATTATCTTGGTTGTCCCATTATCCTAGGGAT

GTCATTGGTATGATATGTGGAATTGACTCATTCTCTGGTTTTCTTGTCACAGGGAGCTTTACAGTAATAATATAAGT

GGTCTGATACCGAGTGATCTTGGGAATTTGACTAATCTGGTCAGCTTGGATCTCTACTTGAACAACTTCGTCGGTCC

CATCCCAGATTCCTTGGGCAAGCTGTCGAAATTGAGATTCCTGTATGTATTTTTGTTCTATATTAGATTTATGTGGA

TATTGTGATGCCAAATGTATATTTCATCAACCAAGATGGACCTACTCTTACTGGCATGTTGAGAAAGGAAAGGAAGC

CTGAATTCTTTTCTAGGTTTCACATAAGATGACCTCTATTAGTATTATGTTTCACTCTTAAGTTTTGATGGTAGAAG

GTATTTGAGGACTTCATGGGTCTGATATCATTCATAAAACCGATCTTACATAAGTCTTTTAATTTTCTCCCTTTGTT

CTAATCCTTGTATAAAGGAAAAGAATAGAAGCCTATGCTTTGTCTGATACTGATATTGTAAAATTAATCAGAGTTTA

GTAATGGGTGTTGGGATCCTTTTCTAGAAGAGAGAAGAAGTTTAGAATCCCATGCTTCATCTTGCATTTTTCACTGC

TGAAGTTTCTCTTGCTTAATGCTCCACAAACTTCTTTCTTTTGGCTTGACTGTCTAAGAAGTGTGCCAAATTGTTCT

ATCATGCAGACTCAGCATGAAACCTCATTAACTGCATCTTGGGACTTACTATAGAACTATTGCAGTACTGCAACGTT

GACTAACATGATTTAGTCCAAAAGGTGTTTCAAGTCTGTTTATCGGGGGGGGGGGATGTTTTGAGGCTCTTTATCGT

GGTTCTGAACTGACGCCTTCATTTCCAGCTGAAGTGCCGGTTCTGGCTCGAAGTTGAATATGTTTTACATCCACATA

TTAATAATTTATTAAGATGATTCTCCTTGTCAAATAATAAATAAATTAAGATGATTCAATTAGTAGCCTTTTCTTCT

GTTTTATTCTCCATTATTTACTTGTACCAAAGATGAAGCTCATTCCTGTAAACCTTTGTGTTTTCTTGCAAGGATAG

TCGGCTCAACAATAATAGCTTGACTGGTAACATCCCAATGTCACTGACTAATATCTCATCACTGCAAGTGTTGTAAG

TACACTGATTATTTTGTGACTTGATTTAGATAATTCTTTCTGTCTTCCATATCTTCTCATGCATTTCCTTTTCCTTC

TAATGCATATACAGATTTACTTATGCTCAATTCTTGTCTCACCTGTATGTAGGGATCTGTCAAACAACCGTCTCTCA

GGTGCTGTTCCAGATAATGGTTCATTTTCTCTATTCACGCCTATCAGGTATATTTCATTTAAGGCGGTGCACCATCT

AACTGGCTGGTGGTTTTAGCATGCTACTATTTGCTAATATATTTTTCTTGTTTACAGTTTTGCGAATAATTTAGATC

TTTGCGGGCCTGTAACTGGACGCCCTTGCCCTGGATCTCCTCCATTCTCCCCTCCGCCTCCATTTGTTCCACCACCA

CCAATTTCTGCTCCAGGTGGTTCTCTAAATTGGTGTGGATAAATTGTTCTCCTTTCTTTTTTCTTTTGTTTTTTTTG

CTTTTTTGCGGTTAGTGATTTTAGTTTGTCCATCCAACGTAAGTGAGAATTTGTGCTATAGAAGCTAAAGTACTGAC

AAGAAAGGGGGCAGAAGAGGAAAACCCATCTTAACTAGTCAGGCATTAGTTCTGATGGGAAACTGGTATGCACGAGA

CTACATTTAGTCTCTAAGCATTCTGGTCTTTATACAAATTTAATTCAGCATTGTGGACATCTTTTCTTTGGTCCCCT

TGTAAATTATTATCTGTGGTATTTGAAGTCATGTGTCTGAATGAAATTAATCATATTTATGCCAGAACTTGTGAAGA

TTTTCTTTTCTTTGTAAAAACTGTCCTGGAAATTAGATCTGATGATAGATACAAATTTGTCTACTAATTTCTTTTTG

AAGTGATTTAATTAATGAAGGGCCGGCCAAAATTATGTGTTAAATATAGTCTAGATCATATGAAGGAAATTAATCAA

ATTTATGGGAACTTCAGGAGGAAATGGTGCAACTGGAGCAATTGCTGGAGGTGTAGCTGCTGGTGCTGCTCTACTAT

TTGCTGCTCCTGCCATTGCATTTGCCTGGTGGCGCCGTAGAAAGCCACAAGAATATTTCTTTGACGTACCAGGTTAG

CAGTATTCAAATACCCAACCATAAGTCCATAACTCCTACTTACTCTCTCACGTGTTTATGGTTTCTCTTGCATGTTT

TATTTTTTGGCTCCATAATTAACGTCTTTGCTTAAACTTATTGCAGCCGAAGAAGATCCTGAAGTTCACTTAGGTCA

ACTGAAAAGGTTCTCCCTCCGAGAGCTACAAGTTGCAACTGACAGTTTTAGCAATAAAAATATACTGGGTCGAGGTG

GATTTGGTAAGGTATACAAAGGACGCTTAGCAGATGGATCATTGGTGGCTGTTAAGCGGCTAAAGGAAGAGCGTACT

CCTGGAGGGGAGTTGCAATTTCAAACAGAAGTTGAGATGATTAGCATGGCAGTGCATAGGAATCTTCTACGATTGCG
```

-continued

TGGTTTCTGTATGACACCAACTGAAAGACTGCTTGTCTACCCCTACATGGCGAATGGAAGTGTTGCATCATGCCTGA

GAGGTGACACTTTCTGAAATCTATCACTCCATAAATGTTCTCACCTTTAATTTGGAGGGTATTATTGCATAATGCAA

GAATGTCTTTCGCTGGTTAACATTCTATCTTGGCATAACTTACTCTTTATAACAAAACATATTCTTGTTAGTTATTT

TCCTGTAACTTTTTAAAAGGTAGAAGTATAATTTGTATTGTATTCTCTTGACAACATAATTTATTTTATCAGAACGA

CCGCCTTCTGAACCACCACTTGATTGGCCAACGCGAAAACGTATTGCTTTGGGGTCTGCCAGGGGATTATCGTATTT

GCATGATCATTGTGACCCTAAGATTATCCATCGTGATGTGAAGGCTGCAAATATATTGCTAGATGAAGAATTTGAGG

CTGTTGTTGGAGACTTTGGTTTGGCTAAACTTATGGACTACAAGGATACACATGTTACAACTGCTGTGCGTGGTACA

ATCGGGCATATAGCTCCAGAATACCTTTCCACAGGGAAGTCTTCAGAAAAGACTGATGTTTTTGGGTATGGGATCAT

GCTTCTGGAGCTAATCACCGGCCAACGTGCTTTTGATCTTGCTCGGCTGGCAAATGATGACGATGTCATGTTGCTTG

ACTGGGTATGTTGTCATACCTGCTTTACATGTGAACATGACACGAGTACCATAATGTGTTCATTTTTTAATCTGTAC

ATCACAACACTAGCTGACTAATAAGTATTTGTGCCTTTAGCAGGAATATTTAAGTCTATGACTAAACTTGTTGAGGT

TCTTGTTTCAGGTGAAAGGACTCCTCAAAGAGAAGAAACTGGAAATGCTGGTTGACCCTGATCTTCAGAACAAATAT

GTGGAGGCTGAGGTGGAGCAACTGATCCAGGTAGCATTGCTTTGTACACAAAGCAACCCAATGGATCGGCCTAAGAT

GTCGGAAGTGGTGAGAATGCTTGAAGGTGATGGTTTGGCTGAAAGATGGGATGAGTGGCAGAAGGTAGAAGTTCTCC

GGCAGGAAGTGGAACTTGCACCACATCCTGGTTCTGATTGGCTTGTTGACTCGACAGAGAATTTACATGCAGTTGAA

TTATCGGGTCCAAGGTGA

Nucleic acid sequence for a mutant Solyc04g072570 gene allele slserk1$^{CR\text{-}5\text{-}\alpha1}$ coding sequence (SEQ ID NO: 98)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGTGTTATAAGAGTTGATTTAGGAAATGCAGCTTTATCTGGTTTGTTAGTTCC

ACAGCTTGGCCTTTTGAAGAATTTGCAGTACTTGGAGCTTTACAGTAATAATATAAGTGGTCTGATACCGAGTGATC

TTGGGAATTTGACTAATCTGGTCAGCTTGGATCTCTACTTGAACAACTTCGTCGGTCCCATCCCAGATTCCTTGGGC

AAGCTGTCGAAATTGAGATTCCTTCGGCTCAACAATAATAGCTTGACTGGTAACATCCCAATGTCACTGACTAATAT

CTCATCACTGCAAGTGTTGGATCTGTCAAACAACCGTCTCTCAGGTGCTGTTCCAGATAATGGTTCATTTTCTCTAT

TCACGCCTATCAGTTTTGCGAATAATTTAGATCTTTGCGGGCCTGTAACTGGACGCCCTTGCCCTGGATCTCCTCCA

TTCTCCCCTCCGCCTCCATTTGTTCCACCACCACCAATTTCTGCTCCAGGAGGAAATGGTGCAACTGGAGCAATTGC

TGGAGGTGTAGCTGCTGGTGCTGCTCTACTATTTGCTGCTCCTGCCATTGCATTTGCCTGGTGGCGCCGTAGAAAGC

CACAAGAATATTTCTTTGACGTACCAGCCGAAGAAGATCCTGAAGTTCACTTAGGTCAACTGAAAAGGTTCTCCCTC

CGAGAGCTACAAGTTGCAACTGACAGTTTTAGCAATAAAAATATACTGGGTCGAGGTGGATTTGGTAAGGTATACAA

AGGACGCTTAGCAGATGGATCATTGGTGGCTGTTAAGCGGCTAAAGGAAGAGCGTACTCCTGGAGGGGAGTTGCAAT

TTCAAACAGAAGTTGAGATGATTAGCATGGCAGTGCATAGGAATCTTCTACGATTGCGTGGTTTCTGTATGACACCA

ACTGAAAGACTGCTTGTCTACCCCTACATGGCGAATGGAAGTGTTGCATCATGCCTGAGAGAACGACCGCCTTCTGA

ACCACCACTTGATTGGCCAACGCGAAAACGTATTGCTTTGGGGTCTGCCAGGGGATTATCGTATTTGCATGATCATT

GTGACCCTAAGATTATCCATCGTGATGTGAAGGCTGCAAATATATTGCTAGATGAAGAATTTGAGGCTGTTGTTGGA

GACTTTGGTTTGGCTAAACTTATGGACTACAAGGATACACATGTTACAACTGCTGTGCGTGGTACAATCGGGCATAT

AGCTCCAGAATACCTTTCCACAGGGAAGTCTTCAGAAAAGACTGATGTTTTTGGGTATGGGATCATGCTTCTGGAGC

TAATCACCGGCCAACGTGCTTTTGATCTTGCTCGGCTGGCAAATGATGACGATGTCATGTTGCTTGACTGGGTGAAA

GGACTCCTCAAAGAGAAGAAACTGGAAATGCTGGTTGACCCTGATCTTCAGAACAAATATGTGGAGGCTGAGGTGGA

GCAACTGATCCAGGTAGCATTGCTTTGTACACAAAGCAACCCAATGGATCGGCCTAAGATGTCGGAAGTGGTGAGAA

-continued

TGCTTGAAGGTGATGGTTTGGCTGAAAGATGGGATGAGTGGCAGAAGGTAGAAGTTCTCCGGCAGGAAGTGGAACTT

GCACCACATCCTGGTTCTGATTGGCTTGTTGACTCGACAGAGAATTTACATGCAGTTGAATTATCGGGTCCAAGGTG

A

Amino acid sequence for a mutant polypeptide encoded by a mutant Solyc04g072570 gene allele (SEQ ID NO: 99)

slserk1$^{CR\text{-}5\text{-}\alpha1}$ coding sequence
MVKVMEKDTVVVSLVVWLILVVYHLKLIYANMEGVL*

Mutant Solyc04g072570 gene allele slserk1$^{CR\text{-}5\text{-}\alpha2}$
Nucleic acid sequence for a mutant Solyc04g072570 gene allele slserk1$^{CR\text{-}5\text{-}\alpha2}$ (SEQ ID NO: 100)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGTCCTTGCACATGGTTTCACGTTACCTGCAACAATGACAACAGTGTTATAAGAGTGTAAGAATCTGTTTTC

TGGTCTACCTCCATTTGAATGGATTTGCAATTCCACTCTCTTGTGGTGGTGAGCAATCTAATTGCAGTTTGTGCTCC

CATAACACTTGTTATATGATCAACCTTTCCAGTGATTTAGGAAATGCAGCTTTATCTGGTTTGTTAGTTCCACAGCT

TGGCCTTTTGAAGAATTTGCAGTACTTGTAAGTCTCACTTCATGAACTATGTTTGGAATTATTTTACAAATTTAGAG

TTGGAAAACTGGCATTGAGTGTATTGGTTTTTCCAGCTGTTGAAGATTTTCATATTACCTCTAGAATTCGCTGCATG

AAAATAATGTAGGTGGCTTGCATATTAACTTTTGCATAAAAACAAAGCTGTTGTAAGTGGCAAAAATGAGCAGAGAA

CACTTTCTCCTCTCCATCTCTTGTTTCACTTGATGTTGTAGTCGATGGCATAGTTGTTGATGTGTTCCCTGAACAAC

ACAAATTTGAATGTGTACTTCATAAAAAAAGATTTAAATATTTGTTTCACATTACATACTAGTAAATTAAGTAACTC

AGATACTTGGATGAGACTAGCAATGAAGTAACTTATGTGGCAAAGTAGTGTCTGTAATTGCTTGTGAAAACATTGTA

GTTGAACTTAAATTTTTGTCATACACTCCCTTATATAAAGATAAGCAGAGTAATCGTTAACTTTTTTATGAACTCTT

AAACAGAGTATTATTCTAAATATTATTACTAATGCCAGTACCCTAAGCACTCTTAATTTGGAATGACAAACTTCAAC

TCATATCAAATCCTTTATTCCCTCTTTCCTTGTTCCATGTAGACTCTAATCACGATTTAGGATGATGGAATAGGATA

AAACAAACAAGAGAAACAAGTCCATTGTAAAAGTAAAGCAAAATCTAGACTTAAAAAGAGGAAATATGGCATGAGGG

TAGGTTGATGTCTTGGAGGAGAAGATCTGAAGTTTTCTGGTCATATAACAGATGCTATTCTGGTTTTCACCAAGAGT

TCGAATCATGATTCAATTAAGCATAGATTTTGTACAAGTGTTAAGCTTAGTTTGGAGTTCAATATACCGTTCACTTA

AATTACATCTCAAATTTCATTGTTCTTATTGTAACCCATGCTCTTTTGAAGCTGCAACTGTATGGAAGTTCACAGAG

ACAGTATGTGCATGTGCACCTGGTGAAGCAGGGCATTACATGATGTATAACCATGCATCAGACAATGTTATAATGAT

GGGTATAATTATTACCTAGTGACTGCTTCATCCTGCTCACACATTAATATATTCCTATGGATGCCTAGATTTGCTTG

AGGCTTGTGTAGTACGCGTGCTAAGTATTTTCCTAGTGTATGCAAGTGACAATCACATCAAGAATGAAACAATATAA

AAAGAACATCAAAAGTATAACATTATCTTTGTCAAAAAAAAAAAGAAAGAACATCAAGAGTGCTGATGGAATTTAAC

AATCACCGGGCATACACACTGTTTAGATGAAGTTCGAAATTAACATAATGACAGACGTTAAATTTTTATTGATGAGT

TATATAGATTGTATAAAATGTTTGACGAGCTGATTCTTTGCAGCACATGGGACGACAGGTTTTTATATAGAAAAGTG

CTTGTAACCAAATATAAGAAAATACCTCCATGAAATAGACATCGGTAACTAGTTATAATTGCTATCTTGGAACTCCT

AGACCTTTCTCATTTGTTGACTTTTAATTGTCGCTTGATGCCAGTATTGATGGATGTGAGAATTCTCCTTCATTATC

TTGGTTGTCCCATTATCCTAGGGATGTCATTGGTATGATATGTGGAATTGACTCATTCTCTGGTTTTCTTGTCACAG

-continued

```
GGAGCTTTACAGTAATAATATAAGTGGTCTGATACCGAGTGATCTTGGGAATTTGACTAATCTGGTCAGCTTGGATC

TCTACTTGAACAACTTCGTCGGTCCCATCCCAGATTCCTTGGGCAAGCTGTCGAAATTGAGATTCCTGTATGTATTT

TTGTTCTATATTAGATTTATGTGGATATTGTGATGCCAAATGTATATTTCATCAACCAAGATGGACCTACTCTTACT

GGCATGTTGAGAAAGGAAAGGAAGCCTGAATTCTTTTCTAGGTTTCACATAAGATGACCTCTATTAGTATTATGTTT

CACTCTTAAGTTTTGATGGTAGAAGGTATTTGAGGACTTCATGGGTCTGATATCATTCATAAAACCGATCTTACATA

AGTCTTTTAATTTTCTCCCTTTGTTCTAATCCTTGTATAAAGGAAAAGAATAGAAGCCTATGCTTTGTCTGATACTG

ATATTGTAAAATTAATCAGAGTTTAGTAATGGGTGTTGGGATCCTTTTCTAGAAGAGAGAAGAAGTTTAGAATCCCA

TGCTTCATCTTGCATTTTTCACTGCTGAAGTTTCTCTTGCTTAATGCTCCACAAACTTCTTTCTTTTGGCTTGACTG

TCTAAGAAGTGTGCCAAATTGTTCTATCATGCAGACTCAGCATGAAACCTCATTAACTGCATCTTGGGACTTACTAT

AGAACTATTGCAGTACTGCAACGTTGACTAACATGATTTAGTCCAAAAGGTGTTTCAAGTCTGTTTATCGGGGGGGG

GGGATGTTTTGAGGCTCTTTATCGTGGTTCTGAACTGACGCCTTCATTTCCAGCTGAAGTGCCGGTTCTGGCTCGAA

GTTGAATATGTTTTACATCCACATATTAATAATTTATTAAGATGATTCTCCTTGTCAAATAATAAATAAATTAAGAT

GATTCAATTAGTAGCCTTTTCTTCTGTTTTATTCTCCATTATTTACTTGTACCAAAGATGAAGCTCATTCCTGTAAA

CCTTTGTGTTTTCTTGCAAGGATAGTCGGCTCAACAATAATAGCTTGACTGGTAACATCCCAATGTCACTGACTAAT

ATCTCATCACTGCAAGTGTTGTAAGTACACTGATTATTTTGTGACTTGATTTAGATAATTCTTTCTGTCTTCCATAT

CTTCTCATGCATTTCCTTTTCCTTCTAATGCATATACAGATTTACTTATGCTCAATTCTTGTCTCACCTGTATGTAG

GGATCTGTCAAACAACCGTCTCTCAGGTGCTGTTCCAGATAATGGTTCATTTTCTCTATTCACGCCTATCAGGTATA

TTTCATTTAAGGCGGTGCACCATCTAACTGGCTGGTGGTTTTAGCATGCTACTATTTGCTAATATATTTTTCTTGTT

TACAGTTTTGCGAATAATTTAGATCTTTGCGGGCCTGTAACTGGACGCCCTTGCCCTGGATCTCCTCCATTCTCCCC

TCCGCCTCCATTTGTTCCACCACCACCAATTTCTGCTCCAGGTGGTTCTCTAAATTGGTGTGGATAAATTGTTCTCC

TTTCTTTTTTCTTTTGTTTTTTTTGCTTTTTTGCGGTTAGTGATTTTAGTTTGTCCATCCAACGTAAGTGAGAATTT

GTGCTATAGAAGCTAAAGTACTGACAAGAAAGGGGGCAGAAGAGGAAAACCCATCTTAACTAGTCAGGCATTAGTTC

TGATGGGAAACTGGTATGCACGAGACTACATTTAGTCTCTAAGCATTCTGGTCTTTATACAAATTTAATTCAGCATT

GTGGACATCTTTTCTTTGGTCCCCTTGTAAATTATTATCTGTGGTATTTGAAGTCATGTGTCTGAATGAAATTAATC

ATATTTATGCCAGAACTTGTGAAGATTTTCTTTTCTTTGTAAAAACTGTCCTGGAAATTAGATCTGATGATAGATAC

AAATTTGTCTACTAATTTCTTTTTGAAGTGATTTAATTAATGAAGGGCCGGCCAAAATTATGTGTTAAATATAGTCT

AGATCATATGAAGGAAATTAATCAAATTTATGGGAACTTCAGGAGGAAATGGTGCAACTGGAGCAATTGCTGGAGGT

GTAGCTGCTGGTGCTGCTCTACTATTTGCTGCTCCTGCCATTGCATTTGCCTGGTGGCGCCGTAGAAAGCCACAAGA

ATATTTCTTTGACGTACCAGGTTAGCAGTATTCAAATACCCAACCATAAGTCCATAACTCCTACTTACTCTCTCACG

TGTTTATGGTTTCTCTTGCATGTTTTATTTTTTGGCTCCATAATTAACGTCTTTGCTTAAACTTATTGCAGCCGAAG

AAGATCCTGAAGTTCACTTAGGTCAACTGAAAAGGTTCTCCCTCCGAGAGCTACAAGTTGCAACTGACAGTTTTAGC

AATAAAAATATACTGGGTCGAGGTGGATTTGGTAAGGTATACAAAGGACGCTTAGCAGATGGATCATTGGTGGCTGT

TAAGCGGCTAAAGGAAGAGCGTACTCCTGGAGGGGAGTTGCAATTTCAAACAGAAGTTGAGATGATTAGCATGGCAG

TGCATAGGAATCTTCTACGATTGCGTGGTTTCTGTATGACACCAACTGAAAGACTGCTTGTCTACCCCTACATGGCG

AATGGAAGTGTTGCATCATGCCTGAGAGGTGACACTTTCTGAAATCTATCACTCCATAAATGTTCTCACCTTTAATT

TGGAGGGTATTATTGCATAATGCAAGAATGTCTTTCGCTGGTTAACATTCTATCTTGGCATAACTTACTCTTTATAA

CAAAACATATTCTTGTTAGTTATTTTCCTGTAACTTTTTAAAAGGTAGAAGTATAATTTGTATTGTATTCTCTTGAC

AACATAATTTATTTTATCAGAACGACCGCCTTCTGAACCACCACTTGATTGGCCAACGCGAAAACGTATTGCTTTGG

GGTCTGCCAGGGGATTATCGTATTTGCATGATCATTGTGACCCTAAGATTATCCATCGTGATGTGAAGGCTGCAAAT

ATATTGCTAGATGAAGAATTTGAGGCTGTTGTTGGAGACTTTGGTTTGGCTAAACTTATGGACTACAAGGATACACA
```

-continued

TGTTACAACTGCTGTGCGTGGTACAATCGGGCATATAGCTCCAGAATACCTTTCCACAGGGAAGTCTTCAGAAAAGA

CTGATGTTTTTGGGTATGGGATCATGCTTCTGGAGCTAATCACCGGCCAACGTGCTTTTGATCTTGCTCGGCTGGCA

AATGATGACGATGTCATGTTGCTTGACTGGGTATGTTGTCATACCTGCTTTACATGTGAACATGACACGAGTACCAT

AATGTGTTCATTTTTTAATCTGTACATCACAACACTAGCTGACTAATAAGTATTTGTGCCTTTAGCAGGAATATTTA

AGTCTATGACTAAACTTGTTGAGGTTCTTGTTTCAGGTGAAAGGACTCCTCAAAGAGAAGAAACTGGAAATGCTGGT

TGACCCTGATCTTCAGAACAAATATGTGGAGGCTGAGGTGGAGCAACTGATCCAGGTAGCATTGCTTTGTACACAAA

GCAACCCAATGGATCGGCCTAAGATGTCGGAAGTGGTGAGAATGCTTGAAGGTGATGGTTTGGCTGAAAGATGGGAT

GAGTGGCAGAAGGTAGAAGTTCTCCGGCAGGAAGTGGAACTTGCACCACATCCTGGTTCTGATTGGCTTGTTGACTC

GACAGAGAATTTACATGCAGTTGAATTATCGGGTCCAAGGTGA

Nucleic acid sequence for a mutant Solyc04g072570
gene allele slserk1$^{CR\text{-}5\text{-}\alpha 2}$ coding sequence (SEQ ID NO: 101)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGTCCTTGCACATGGTTTCACGTTACCTGCAACAATGACAACAGTGTTATAAGAGTTGATTTAGGAAATG

CAGCTTTATCTGGTTTGTTAGTTCCACAGCTTGGCCTTTTGAAGAATTTGCAGTACTTGGAGCTTTACAGTAATAAT

ATAAGTGGTCTGATACCGAGTGATCTTGGGAATTTGACTAATCTGGTCAGCTTGGATCTCTACTTGAACAACTTCGT

CGGTCCCATCCCAGATTCCTTGGGCAAGCTGTCGAAATTGAGATTCCTTCGGCTCAACAATAATAGCTTGACTGGTA

ACATCCCAATGTCACTGACTAATATCTCATCACTGCAAGTGTTGGATCTGTCAAACAACCGTCTCTCAGGTGCTGTT

CCAGATAATGGTTCATTTTCTCTATTCACGCCTATCAGTTTTGCGAATAATTTAGATCTTTGCGGGCCTGTAACTGG

ACGCCCTTGCCCTGGATCTCCTCCATTCTCCCCTCCGCCTCCATTTGTTCCACCACCACCAATTTCTGCTCCAGGAG

GAAATGGTGCAACTGGAGCAATTGCTGGAGGTGTAGCTGCTGGTGCTGCTCTACTATTTGCTGCTCCTGCCATTGCA

TTTGCCTGGTGGCGCCGTAGAAAGCCACAAGAATATTTCTTTGACGTACCAGCCGAAGAAGATCCTGAAGTTCACTT

AGGTCAACTGAAAAGGTTCTCCCTCCGAGAGCTACAAGTTGCAACTGACAGTTTTAGCAATAAAAATATACTGGGTC

GAGGTGGATTTGGTAAGGTATACAAAGGACGCTTAGCAGATGGATCATTGGTGGCTGTTAAGCGGCTAAAGGAAGAG

CGTACTCCTGGAGGGGAGTTGCAATTTCAAACAGAAGTTGAGATGATTAGCATGGCAGTGCATAGGAATCTTCTACG

ATTGCGTGGTTTCTGTATGACACCAACTGAAAGACTGCTTGTCTACCCCTACATGGCGAATGGAAGTGTTGCATCAT

GCCTGAGAGAACGACCGCCTTCTGAACCACCACTTGATTGGCCAACGCGAAAACGTATTGCTTTGGGGTCTGCCAGG

GGATTATCGTATTTGCATGATCATTGTGACCCTAAGATTATCCATCGTGATGTGAAGGCTGCAAATATATTGCTAGA

TGAAGAATTTGAGGCTGTTGTTGGAGACTTTGGTTTGGCTAAACTTATGGACTACAAGGATACACATGTTACAACTG

CTGTGCGTGGTACAATCGGGCATATAGCTCCAGAATACCTTTCCACAGGGAAGTCTTCAGAAAAGACTGATGTTTTT

GGGTATGGGATCATGCTTCTGGAGCTAATCACCGGCCAACGTGCTTTTGATCTTGCTCGGCTGGCAAATGATGACGA

TGTCATGTTGCTTGACTGGGTGAAAGGACTCCTCAAAGAGAAGAAACTGGAAATGCTGGTTGACCCTGATCTTCAGA

ACAAATATGTGGAGGCTGAGGTGGAGCAACTGATCCAGGTAGCATTGCTTTGTACACAAAGCAACCCAATGGATCGG

CCTAAGATGTCGGAAGTGGTGAGAATGCTTGAAGGTGATGGTTTGGCTGAAAGATGGGATGAGTGGCAGAAGGTAGA

AGTTCTCCGGCAGGAAGTGGAACTTGCACCACATCCTGGTTCTGATTGGCTTGTTGACTCGACAGAGAATTTACATG

CAGTTGAATTATCGGGTCCAAGGTGA

-continued

Amino acid sequence for a mutant polypeptide encoded by a mutant Solyc04g072570 gene allele slserk1$^{CR-5-\alpha 2}$ coding sequence (SEQ ID NO: 102)

MVKVMEKDTVVVSLVVWLILVVYHLKLIYANMEGDALHSLRVNLQDPNNVLQSWVLAHGFTLPATMTTVL*

Mutant Solyc04g072570 gene allele slserk1$^{CR-5-\alpha 3}$
Nucleic acid sequence for a mutant Solyc04g072570 gene allele slserk1$^{CR-5-\alpha 3}$ (SEQ ID NO: 103)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCGTTTCACGTTACCTGCAACAATGACAACAGTGTTATAAGAGTGTAAGAATCTGTTTTCTGGT

CTACCTCCATTTGAATGGATTTGCAATTCCACTCTCTTGTGGTGGTGAGCAATCTAATTGCAGTTTGTGCTCCCATA

ACACTTGTTATATGATCAACCTTTCCAGTGATTTAGGAAATGCAGCTTTATCTGGTTTGTTAGTTCCACAGCTTGGC

CTTTTGAAGAATTTGCAGTACTTGTAAGTCTCACTTCATGAACTATGTTTGGAATTATTTTACAAATTTAGAGTTGG

AAAACTGGCATTGAGTGTATTGGTTTTTCCAGCTGTTGAAGATTTTCATATTACCTCTAGAATTCGCTGCATGAAAA

TAATGTAGGTGGCTTGCATATTAACTTTTGCATAAAAACAAAGCTGTTGTAAGTGGCAAAAATGAGCAGAGAACACT

TTCTCCTCTCCATCTCTTGTTTCACTTGATGTTGTAGTCGATGGCATAGTTGTTGATGTGTTCCCTGAACAACACAA

ATTTGAATGTGTACTTCATAAAAAAAGATTTAAATATTTGTTTCACATTACATACTAGTAAATTAAGTAACTCAGAT

ACTTGGATGAGACTAGCAATGAAGTAACTTATGTGGCAAAGTAGTGTCTGTAATTGCTTGTGAAAACATTGTAGTTG

AACTTAAATTTTTGTCATACACTCCCTTATATAAAGATAAGCAGAGTAATCGTTAACTTTTTTATGAACTCTTAAAC

AGAGTATTATTCTAAATATTATTACTAATGCCAGTACCCTAAGCACTCTTAATTTGGAATGACAAACTTCAACTCAT

ATCAAATCCTTTATTCCCTCTTTCCTTGTTCCATGTAGACTCTAATCACGATTTAGGATGATGGAATAGGATAAAAC

AAACAAGAGAAACAAGTCCATTGTAAAAGTAAAGCAAAATCTAGACTTAAAAAGAGGAAATATGGCATGAGGGTAGG

TTGATGTCTTGGAGGAGAAGATCTGAAGTTTTCTGGTCATATAACAGATGCTATTCTGGTTTTCACCAAGAGTTCGA

ATCATGATTCAATTAAGCATAGATTTTGTACAAGTGTTAAGCTTAGTTTGGAGTTCAATATACCGTTCACTTAAATT

ACATCTCAAATTTCATTGTTCTTATTGTAACCCATGCTCTTTTGAAGCTGCAACTGTATGGAAGTTCACAGAGACAG

TATGTGCATGTGCACCTGGTGAAGCAGGGCATTACATGATGTATAACCATGCATCAGACAATGTTATAATGATGGGT

ATAATTATTACCTAGTGACTGCTTCATCCTGCTCACACATTAATATATTCCTATGGATGCCTAGATTTGCTTGAGGC

TTGTGTAGTACGCGTGCTAAGTATTTTCCTAGTGTATGCAAGTGACAATCACATCAAGAATGAAACAATATAAAAAG

AACATCAAAAGTATAACATTATCTTTGTCAAAAAAAAAAAGAAAGAACATCAAGAGTGCTGATGGAATTTAACAATC

ACCGGGCATACACACTGTTTAGATGAAGTTCGAAATTAACATAATGACAGACGTTAAATTTTTATTGATGAGTTATA

TAGATTGTATAAAATGTTTGACGAGCTGATTCTTTGCAGCACATGGGACGACAGGTTTTTATATAGAAAAGTGCTTG

TAACCAAATATAAGAAAATACCTCCATGAAATAGACATCGGTAACTAGTTATAATTGCTATCTTGGAACTCCTAGAC

CTTTCTCATTTGTTGACTTTTAATTGTCGCTTGATGCCAGTATTGATGGATGTGAGAATTCTCCTTCATTATCTTGG

TTGTCCCATTATCCTAGGGATGTCATTGGTATGATATGTGGAATTGACTCATTCTCTGGTTTTCTTGTCACAGGGAG

CTTTACAGTAATAATATAAGTGGTCTGATACCGAGTGATCTTGGGAATTTGACTAATCTGGTCAGCTTGGATCTCTA

CTTGAACAACTTCGTCGGTCCCATCCCAGATTCCTTGGGCAAGCTGTCGAAATTGAGATTCCTGTATGTATTTTTGT

TCTATATTAGATTTATGTGGATATTGTGATGCCAAATGTATATTTCATCAACCAAGATGGACCTACTCTTACTGGCA

-continued

TGTTGAGAAAGGAAAGGAAGCCTGAATTCTTTTCTAGGTTTCACATAAGATGACCTCTATTAGTATTATGTTTCACT

CTTAAGTTTTGATGGTAGAAGGTATTTGAGGACTTCATGGGTCTGATATCATTCATAAAACCGATCTTACATAAGTC

TTTTAATTTTCTCCCTTTGTTCTAATCCTTGTATAAAGGAAAAGAATAGAAGCCTATGCTTTGTCTGATACTGATAT

TGTAAAATTAATCAGAGTTTAGTAATGGGTGTTGGGATCCTTTTCTAGAAGAGAGAAGAAGTTTAGAATCCCATGCT

TCATCTTGCATTTTTCACTGCTGAAGTTTCTCTTGCTTAATGCTCCACAAACTTCTTTCTTTTGGCTTGACTGTCTA

AGAAGTGTGCCAAATTGTTCTATCATGCAGACTCAGCATGAAACCTCATTAACTGCATCTTGGGACTTACTATAGAA

CTATTGCAGTACTGCAACGTTGACTAACATGATTTAGTCCAAAAGGTGTTTCAAGTCTGTTTATCGGGGGGGGGGGA

TGTTTTGAGGCTCTTTATCGTGGTTCTGAACTGACGCCTTCATTTCCAGCTGAAGTGCCGGTTCTGGCTCGAAGTTG

AATATGTTTTACATCCACATATTAATAATTTATTAAGATGATTCTCCTTGTCAAATAATAAATAAATTAAGATGATT

CAATTAGTAGCCTTTTCTTCTGTTTTATTCTCCATTATTTACTTGTACCAAAGATGAAGCTCATTCCTGTAAACCTT

TGTGTTTTCTTGCAAGGATAGTCGGCTCAACAATAATAGCTTGACTGGTAACATCCCAATGTCACTGACTAATATCT

CATCACTGCAAGTGTTGTAAGTACACTGATTATTTTGTGACTTGATTTAGATAATTCTTTCTGTCTTCCATATCTTC

TCATGCATTTCCTTTTCCTTCTAATGCATATACAGATTTACTTATGCTCAATTCTTGTCTCACCTGTATGTAGGGAT

CTGTCAAACAACCGTCTCTCAGGTGCTGTTCCAGATAATGGTTCATTTTCTCTATTCACGCCTATCAGGTATATTTC

ATTTAAGGCGGTGCACCATCTAACTGGCTGGTGGTTTTAGCATGCTACTATTTGCTAATATATTTTTCTTGTTTACA

GTTTTGCGAATAATTTAGATCTTTGCGGGCCTGTAACTGGACGCCCTTGCCCTGGATCTCCTCCATTCTCCCCTCCG

CCTCCATTTGTTCCACCACCACCAATTTCTGCTCCAGGTGGTTCTCTAAATTGGTGTGGATAAATTGTTCTCCTTTC

TTTTTTCTTTTGTTTTTTTTGCTTTTTTGCGGTTAGTGATTTTAGTTTGTCCATCCAACGTAAGTGAGAATTTGTGC

TATAGAAGCTAAAGTACTGACAAGAAAGGGGGCAGAAGAGGAAAACCCATCTTAACTAGTCAGGCATTAGTTCTGAT

GGGAAACTGGTATGCACGAGACTACATTTAGTCTCTAAGCATTCTGGTCTTTATACAAATTTAATTCAGCATTGTGG

ACATCTTTTCTTTGGTCCCCTTGTAAATTATTATCTGTGGTATTTGAAGTCATGTGTCTGAATGAAATTAATCATAT

TTATGCCAGAACTTGTGAAGATTTTCTTTTCTTTGTAAAAACTGTCCTGGAAATTAGATCTGATGATAGATACAAAT

TTGTCTACTAATTTCTTTTTGAAGTGATTTAATTAATGAAGGGCCGGCCAAAATTATGTGTTAAATATAGTCTAGAT

CATATGAAGGAAATTAATCAAATTTATGGGAACTTCAGGAGGAAATGGTGCAACTGGAGCAATTGCTGGAGGTGTAG

CTGCTGGTGCTGCTCTACTATTTGCTGCTCCTGCCATTGCATTTGCCTGGTGGCGCCGTAGAAAGCCACAAGAATAT

TTCTTTGACGTACCAGGTTAGCAGTATTCAAATACCCAACCATAAGTCCATAACTCCTACTTACTCTCTCACGTGTT

TATGGTTTCTCTTGCATGTTTTATTTTTTGGCTCCATAATTAACGTCTTTGCTTAAACTTATTGCAGCCGAAGAAGA

TCCTGAAGTTCACTTAGGTCAACTGAAAAGGTTCTCCCTCCGAGAGCTACAAGTTGCAACTGACAGTTTTAGCAATA

AAAATATACTGGGTCGAGGTGGATTTGGTAAGGTATACAAAGGACGCTTAGCAGATGGATCATTGGTGGCTGTTAAG

CGGCTAAAGGAAGAGCGTACTCCTGGAGGGGAGTTGCAATTTCAAACAGAAGTTGAGATGATTAGCATGGCAGTGCA

TAGGAATCTTCTACGATTGCGTGGTTTCTGTATGACACCAACTGAAAGACTGCTTGTCTACCCCTACATGGCGAATG

GAAGTGTTGCATCATGCCTGAGAGGTGACACTTTCTGAAATCTATCACTCCATAAATGTTCTCACCTTTAATTTGGA

GGGTATTATTGCATAATGCAAGAATGTCTTTCGCTGGTTAACATTCTATCTTGGCATAACTTACTCTTTATAACAAA

ACATATTCTTGTTAGTTATTTTCCTGTAACTTTTTAAAAGGTAGAAGTATAATTTGTATTGTATTCTCTTGACAACA

TAATTTATTTTATCAGAACGACCGCCTTCTGAACCACCACTTGATTGGCCAACGCGAAAACGTATTGCTTTGGGGTC

TGCCAGGGGATTATCGTATTTGCATGATCATTGTGACCCTAAGATTATCCATCGTGATGTGAAGGCTGCAAATATAT

TGCTAGATGAAGAATTTGAGGCTGTTGTTGGAGACTTTGGTTTGGCTAAACTTATGGACTACAAGGATACACATGTT

ACAACTGCTGTGCGTGGTACAATCGGGCATATAGCTCCAGAATACCTTTCCACAGGGAAGTCTTCAGAAAAGACTGA

TGTTTTTGGGTATGGGATCATGCTTCTGGAGCTAATCACCGGCCAACGTGCTTTTGATCTTGCTCGGCTGGCAAATG

ATGACGATGTCATGTTGCTTGACTGGGTATGTTGTCATACCTGCTTTACATGTGAACATGACACGAGTACCATAATG

-continued

TGTTCATTTTTTAATCTGTACATCACAACACTAGCTGACTAATAAGTATTTGTGCCTTTAGCAGGAATATTTAAGTC

TATGACTAAACTTGTTGAGGTTCTTGTTTCAGGTGAAAGGACTCCTCAAAGAGAAGAAACTGGAAATGCTGGTTGAC

CCTGATCTTCAGAACAAATATGTGGAGGCTGAGGTGGAGCAACTGATCCAGGTAGCATTGCTTTGTACACAAAGCAA

CCCAATGGATCGGCCTAAGATGTCGGAAGTGGTGAGAATGCTTGAAGGTGATGGTTTGGCTGAAAGATGGGATGAGT

GGCAGAAGGTAGAAGTTCTCCGGCAGGAAGTGGAACTTGCACCACATCCTGGTTCTGATTGGCTTGTTGACTCGACA

GAGAATTTACATGCAGTTGAATTATCGGGTCCAAGGTGA

Nucleic acid sequence for a mutant Solyc04g072570 gene allele
slserk1$^{CR-5-\alpha3}$ coding sequence (SEQ ID NO: 104)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCGTTTCACGTTACCTGCAACAATGACAACAGTGTTATAAGAGTTGATTTAGGAAATGCAGC

TTTATCTGGTTTGTTAGTTCCACAGCTTGGCCTTTTGAAGAATTTGCAGTACTTGGAGCTTTACAGTAATAATATAA

GTGGTCTGATACCGAGTGATCTTGGGAATTTGACTAATCTGGTCAGCTTGGATCTCTACTTGAACAACTTCGTCGGT

CCCATCCCAGATTCCTTGGGCAAGCTGTCGAAATTGAGATTCCTTCGGCTCAACAATAATAGCTTGACTGGTAACAT

CCCAATGTCACTGACTAATATCTCATCACTGCAAGTGTTGGATCTGTCAAACAACCGTCTCTCAGGTGCTGTTCCAG

ATAATGGTTCATTTTCTCTATTCACGCCTATCAGTTTTGCGAATAATTTAGATCTTTGCGGGCCTGTAACTGGACGC

CCTTGCCCTGGATCTCCTCCATTCTCCCCTCCGCCTCCATTTGTTCCACCACCACCAATTTCTGCTCCAGGAGGAAA

TGGTGCAACTGGAGCAATTGCTGGAGGTGTAGCTGCTGGTGCTGCTCTACTATTTGCTGCTCCTGCCATTGCATTTG

CCTGGTGGCGCCGTAGAAAGCCACAAGAATATTTCTTTGACGTACCAGCCGAAGAAGATCCTGAAGTTCACTTAGGT

CAACTGAAAAGGTTCTCCCTCCGAGAGCTACAAGTTGCAACTGACAGTTTTAGCAATAAAAATATACTGGGTCGAGG

TGGATTTGGTAAGGTATACAAAGGACGCTTAGCAGATGGATCATTGGTGGCTGTTAAGCGGCTAAAGGAAGAGCGTA

CTCCTGGAGGGGAGTTGCAATTTCAAACAGAAGTTGAGATGATTAGCATGGCAGTGCATAGGAATCTTCTACGATTG

CGTGGTTTCTGTATGACACCAACTGAAAGACTGCTTGTCTACCCCTACATGGCGAATGGAAGTGTTGCATCATGCCT

GAGAGAACGACCGCCTTCTGAACCACCACTTGATTGGCCAACGCGAAAACGTATTGCTTTGGGGTCTGCCAGGGGAT

TATCGTATTTGCATGATCATTGTGACCCTAAGATTATCCATCGTGATGTGAAGGCTGCAAATATATTGCTAGATGAA

GAATTTGAGGCTGTTGTTGGAGACTTTGGTTTGGCTAAACTTATGGACTACAAGGATACACATGTTACAACTGCTGT

GCGTGGTACAATCGGGCATATAGCTCCAGAATACCTTTCCACAGGGAAGTCTTCAGAAAAGACTGATGTTTTTGGGT

ATGGGATCATGCTTCTGGAGCTAATCACCGGCCAACGTGCTTTTGATCTTGCTCGGCTGGCAAATGATGACGATGTC

ATGTTGCTTGACTGGGTGAAAGGACTCCTCAAAGAGAAGAAACTGGAAATGCTGGTTGACCCTGATCTTCAGAACAA

ATATGTGGAGGCTGAGGTGGAGCAACTGATCCAGGTAGCATTGCTTTGTACACAAAGCAACCCAATGGATCGGCCTA

AGATGTCGGAAGTGGTGAGAATGCTTGAAGGTGATGGTTTGGCTGAAAGATGGGATGAGTGGCAGAAGGTAGAAGTT

CTCCGGCAGGAAGTGGAACTTGCACCACATCCTGGTTCTGATTGGCTTGTTGACTCGACAGAGAATTTACATGCAGT

TGAATTATCGGGTCCAAGGTGA

Amino acid sequence for a mutant polypeptide encoded by a
mutant Solyc04g072570 gene allele slserk1$^{CR-5-\alpha3}$ coding sequence (SEQ ID NO: 105)

MVKVMEKDTVVVSLVVWLILVVYHLKLIYANMEGDALHSLRVNLQDPNNVLQSWDPTVSRYLQQ*

Mutant Solyc04g072570 gene allele slserk1$^{CR-5-\alpha1}$
Nucleic acid sequence for a mutant Solyc04g072570 gene allele slserk1$^{CR-5-\alpha1}$ (SEQ ID NO: 106)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

-continued

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCGCTTGGCCTTTTGAAGAATTTGCAGTACTTGTAAGTCTCACTTCATGAACTATGTTTGGAAT

TATTTTACAAATTTAGAGTTGGAAAACTGGCATTGAGTGTATTGGTTTTTCCAGCTGTTGAAGATTTTCATATTACC

TCTAGAATTCGCTGCATGAAAATAATGTAGGTGGCTTGCATATTAACTTTTGCATAAAAACAAAGCTGTTGTAAGTG

GCAAAAATGAGCAGAGAACACTTTCTCCTCTCCATCTCTTGTTTCACTTGATGTTGTAGTCGATGGCATAGTTGTTG

ATGTGTTCCCTGAACAACACAAATTTGAATGTGTACTTCATAAAAAAAGATTTAAATATTTGTTTCACATTACATAC

TAGTAAATTAAGTAACTCAGATACTTGGATGAGACTAGCAATGAAGTAACTTATGTGGCAAAGTAGTGTCTGTAATT

GCTTGTGAAAACATTGTAGTTGAACTTAAATTTTTGTCATACACTCCCTTATATAAAGATAAGCAGAGTAATCGTTA

ACTTTTTTATGAACTCTTAAACAGAGTATTATTCTAAATATTATTACTAATGCCAGTACCCTAAGCACTCTTAATTT

GGAATGACAAACTTCAACTCATATCAAATCCTTTATTCCCTCTTTCCTTGTTCCATGTAGACTCTAATCACGATTTA

GGATGATGGAATAGGATAAAACAAACAAGAGAAACAAGTCCATTGTAAAAGTAAAGCAAAATCTAGACTTAAAAAGA

GGAAATATGGCATGAGGGTAGGTTGATGTCTTGGAGGAGAAGATCTGAAGTTTTCTGGTCATATAACAGATGCTATT

CTGGTTTTCACCAAGAGTTCGAATCATGATTCAATTAAGCATAGATTTTGTACAAGTGTTAAGCTTAGTTTGGAGTT

CAATATACCGTTCACTTAAATTACATCTCAAATTTCATTGTTCTTATTGTAACCCATGCTCTTTTGAAGCTGCAACT

GTATGGAAGTTCACAGAGACAGTATGTGCATGTGCACCTGGTGAAGCAGGGCATTACATGATGTATAACCATGCATC

AGACAATGTTATAATGATGGGTATAATTATTACCTAGTGACTGCTTCATCCTGCTCACACATTAATATATTCCTATG

GATGCCTAGATTTGCTTGAGGCTTGTGTAGTACGCGTGCTAAGTATTTTCCTAGTGTATGCAAGTGACAATCACATC

AAGAATGAAACAATATAAAAAGAACATCAAAAGTATAACATTATCTTTGTCAAAAAAAAAAAGAAAGAACATCAAGA

GTGCTGATGGAATTTAACAATCACCGGGCATACACACTGTTTAGATGAAGTTCGAAATTAACATAATGACAGACGTT

AAATTTTTATTGATGAGTTATATAGATTGTATAAAATGTTTGACGAGCTGATTCTTTGCAGCACATGGGACGACAGG

TTTTTATATAGAAAAGTGCTTGTAACCAAATATAAGAAAATACCTCCATGAAATAGACATCGGTAACTAGTTATAAT

TGCTATCTTGGAACTCCTAGACCTTTCTCATTTGTTGACTTTTAATTGTCGCTTGATGCCAGTATTGATGGATGTGA

GAATTCTCCTTCATTATCTTGGTTGTCCCATTATCCTAGGGATGTCATTGGTATGATATGTGGAATTGACTCATTCT

CTGGTTTTCTTGTCACAGGGAGCTTTACAGTAATAATATAAGTGGTCTGATACCGAGTGATCTTGGGAATTTGACTA

ATCTGGTCAGCTTGGATCTCTACTTGAACAACTTCGTCGGTCCCATCCCAGATTCCTTGGGCAAGCTGTCGAAATTG

AGATTCCTGTATGTATTTTTGTTCTATATTAGATTTATGTGGATATTGTGATGCCAAATGTATATTTCATCAACCAA

GATGGACCTACTCTTACTGGCATGTTGAGAAAGGAAAGGAAGCCTGAATTCTTTTCTAGGTTTCACATAAGATGACC

TCTATTAGTATTATGTTTCACTCTTAAGTTTTGATGGTAGAAGGTATTTGAGGACTTCATGGGTCTGATATCATTCA

TAAAACCGATCTTACATAAGTCTTTTAATTTTCTCCCTTTGTTCTAATCCTTGTATAAAGGAAAAGAATAGAAGCCT

ATGCTTTGTCTGATACTGATATTGTAAAATTAATCAGAGTTTAGTAATGGGTGTTGGGATCCTTTTCTAGAAGAGAG

AAGAAGTTTAGAATCCCATGCTTCATCTTGCATTTTTCACTGCTGAAGTTTCTCTTGCTTAATGCTCCACAAACTTC

TTTCTTTTGGCTTGACTGTCTAAGAAGTGTGCCAAATTGTTCTATCATGCAGACTCAGCATGAAACCTCATTAACTG

CATCTTGGGACTTACTATAGAACTATTGCAGTACTGCAACGTTGACTAACATGATTTAGTCCAAAAGGTGTTTCAAG

TCTGTTTATCGGGGGGGGGGGATGTTTTGAGGCTCTTTATCGTGGTTCTGAACTGACGCCTTCATTTCCAGCTGAAG

TGCCGGTTCTGGCTCGAAGTTGAATATGTTTTACATCCACATATTAATAATTTATTAAGATGATTCTCCTTGTCAAA

TAATAAATAAATTAAGATGATTCAATTAGTAGCCTTTTCTTCTGTTTTATTCTCCATTATTTACTTGTACCAAAGAT

GAAGCTCATTCCTGTAAACCTTTGTGTTTTCTTGCAAGGATAGTCGGCTCAACAATAATAGCTTGACTGGTAACATC

CCAATGTCACTGACTAATATCTCATCACTGCAAGTGTTGTAAGTACACTGATTATTTTGTGACTTGATTTAGATAAT

-continued

TCTTTCTGTCTTCCATATCTTCTCATGCATTTCCTTTTCCTTCTAATGCATATACAGATTTACTTATGCTCAATTCT

TGTCTCACCTGTATGTAGGGATCTGTCAAACAACCGTCTCTCAGGTGCTGTTCCAGATAATGGTTCATTTTCTCTAT

TCACGCCTATCAGGTATATTTCATTTAAGGCGGTGCACCATCTAACTGGCTGGTGGTTTTAGCATGCTACTATTTGC

TAATATATTTTTCTTGTTTACAGTTTTGCGAATAATTTAGATCTTTGCGGGCCTGTAACTGGACGCCCTTGCCCTGG

ATCTCCTCCATTCTCCCCTCCGCCTCCATTTGTTCCACCACCACCAATTTCTGCTCCAGGTGGTTCTCTAAATTGGT

GTGGATAAATTGTTCTCCTTTCTTTTTTCTTTTGTTTTTTTTGCTTTTTTGCGGTTAGTGATTTTAGTTTGTCCATC

CAACGTAAGTGAGAATTTGTGCTATAGAAGCTAAAGTACTGACAAGAAAGGGGGCAGAAGAGGAAAACCCATCTTAA

CTAGTCAGGCATTAGTTCTGATGGGAAACTGGTATGCACGAGACTACATTTAGTCTCTAAGCATTCTGGTCTTTATA

CAAATTTAATTCAGCATTGTGGACATCTTTTCTTTGGTCCCCTTGTAAATTATTATCTGTGGTATTTGAAGTCATGT

GTCTGAATGAAATTAATCATATTTATGCCAGAACTTGTGAAGATTTTCTTTTCTTTGTAAAAACTGTCCTGGAAATT

AGATCTGATGATAGATACAAATTTGTCTACTAATTTCTTTTTGAAGTGATTTAATTAATGAAGGGCCGGCCAAAATT

ATGTGTTAAATATAGTCTAGATCATATGAAGGAAATTAATCAAATTTATGGGAACTTCAGGAGGAAATGGTGCAACT

GGAGCAATTGCTGGAGGTGTAGCTGCTGGTGCTGCTCTACTATTTGCTGCTCCTGCCATTGCATTTGCCTGGTGGCG

CCGTAGAAAGCCACAAGAATATTTCTTTGACGTACCAGGTTAGCAGTATTCAAATACCCAACCATAAGTCCATAACT

CCTACTTACTCTCTCACGTGTTTATGGTTTCTCTTGCATGTTTTATTTTTTGGCTCCATAATTAACGTCTTTGCTTA

AACTTATTGCAGCCGAAGAAGATCCTGAAGTTCACTTAGGTCAACTGAAAAGGTTCTCCCTCCGAGAGCTACAAGTT

GCAACTGACAGTTTTAGCAATAAAAATATACTGGGTCGAGGTGGATTTGGTAAGGTATACAAAGGACGCTTAGCAGA

TGGATCATTGGTGGCTGTTAAGCGGCTAAAGGAAGAGCGTACTCCTGGAGGGGAGTTGCAATTTCAAACAGAAGTTG

AGATGATTAGCATGGCAGTGCATAGGAATCTTCTACGATTGCGTGGTTTCTGTATGACACCAACTGAAAGACTGCTT

GTCTACCCCTACATGGCGAATGGAAGTGTTGCATCATGCCTGAGAGGTGACACTTTCTGAAATCTATCACTCCATAA

ATGTTCTCACCTTTAATTTGGAGGGTATTATTGCATAATGCAAGAATGTCTTTCGCTGGTTAACATTCTATCTTGGC

ATAACTTACTCTTTATAACAAAACATATTCTTGTTAGTTATTTTCCTGTAACTTTTTAAAAGGTAGAAGTATAATTT

GTATTGTATTCTCTTGACAACATAATTTATTTTATCAGAACGACCGCCTTCTGAACCACCACTTGATTGGCCAACGC

GAAAACGTATTGCTTTGGGGTCTGCCAGGGGATTATCGTATTTGCATGATCATTGTGACCCTAAGATTATCCATCGT

GATGTGAAGGCTGCAAATATATTGCTAGATGAAGAATTTGAGGCTGTTGTTGGAGACTTTGGTTTGGCTAAACTTAT

GGACTACAAGGATACACATGTTACAACTGCTGTGCGTGGTACAATCGGGCATATAGCTCCAGAATACCTTTCCACAG

GGAAGTCTTCAGAAAAGACTGATGTTTTTGGGTATGGGATCATGCTTCTGGAGCTAATCACCGGCCAACGTGCTTTT

GATCTTGCTCGGCTGGCAAATGATGACGATGTCATGTTGCTTGACTGGGTATGTTGTCATACCTGCTTTACATGTGA

ACATGACACGAGTACCATAATGTGTTCATTTTTTAATCTGTACATCACAACACTAGCTGACTAATAAGTATTTGTGC

CTTTAGCAGGAATATTTAAGTCTATGACTAAACTTGTTGAGGTTCTTGTTTCAGGTGAAAGGACTCCTCAAAGAGAA

GAAACTGGAAATGCTGGTTGACCCTGATCTTCAGAACAAATATGTGGAGGCTGAGGTGGAGCAACTGATCCAGGTAG

CATTGCTTTGTACACAAAGCAACCCAATGGATCGGCCTAAGATGTCGGAAGTGGTGAGAATGCTTGAAGGTGATGGT

TTGGCTGAAAGATGGGATGAGTGGCAGAAGGTAGAAGTTCTCCGGCAGGAAGTGGAACTTGCACCACATCCTGGTTC

TGATTGGCTTGTTGACTCGACAGAGAATTTACATGCAGTTGAATTATCGGGTCCAAGGTGA

Nucleic acid sequence for a mutant Solyc04g072570 gene allele
slserk1$^{CR\text{-}5\text{-}\alpha 1}$ coding sequence (SEQ ID NO: 107)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCGCTTGGCCTTTTGAAGAATTTGCAGTACTTGGAGCTTTACAGTAATAATATAAGTGGTCT

GATACCGAGTGATCTTGGGAATTTGACTAATCTGGTCAGCTTGGATCTCTACTTGAACAACTTCGTCGGTCCCATCC

CAGATTCCTTGGGCAAGCTGTCGAAATTGAGATTCCTTCGGCTCAACAATAATAGCTTGACTGGTAACATCCCAATG

-continued

TCACTGACTAATATCTCATCACTGCAAGTGTTGGATCTGTCAAACAACCGTCTCTCAGGTGCTGTTCCAGATAATGG

TTCATTTTCTCTATTCACGCCTATCAGTTTTGCGAATAATTTAGATCTTTGCGGGCCTGTAACTGGACGCCCTTGCC

CTGGATCTCCTCCATTCTCCCCTCCGCCTCCATTTGTTCCACCACCACCAATTTCTGCTCCAGGAGGAAATGGTGCA

ACTGGAGCAATTGCTGGAGGTGTAGCTGCTGGTGCTGCTCTACTATTTGCTGCTCCTGCCATTGCATTTGCCTGGTG

GCGCCGTAGAAAGCCACAAGAATATTTCTTTGACGTACCAGCCGAAGAAGATCCTGAAGTTCACTTAGGTCAACTGA

AAAGGTTCTCCCTCCGAGAGCTACAAGTTGCAACTGACAGTTTTAGCAATAAAAATATACTGGGTCGAGGTGGATTT

GGTAAGGTATACAAAGGACGCTTAGCAGATGGATCATTGGTGGCTGTTAAGCGGCTAAAGGAAGAGCGTACTCCTGG

AGGGGAGTTGCAATTTCAAACAGAAGTTGAGATGATTAGCATGGCAGTGCATAGGAATCTTCTACGATTGCGTGGTT

TCTGTATGACACCAACTGAAAGACTGCTTGTCTACCCCTACATGGCGAATGGAAGTGTTGCATCATGCCTGAGAGAA

CGACCGCCTTCTGAACCACCACTTGATTGGCCAACGCGAAAACGTATTGCTTTGGGGTCTGCCAGGGGATTATCGTA

TTTGCATGATCATTGTGACCCTAAGATTATCCATCGTGATGTGAAGGCTGCAAATATATTGCTAGATGAAGAATTTG

AGGCTGTTGTTGGAGACTTTGGTTTGGCTAAACTTATGGACTACAAGGATACACATGTTACAACTGCTGTGCGTGGT

ACAATCGGGCATATAGCTCCAGAATACCTTTCCACAGGGAAGTCTTCAGAAAAGACTGATGTTTTTGGGTATGGGAT

CATGCTTCTGGAGCTAATCACCGGCCAACGTGCTTTTGATCTTGCTCGGCTGGCAAATGATGACGATGTCATGTTGC

TTGACTGGGTGAAAGGACTCCTCAAAGAGAAGAAACTGGAAATGCTGGTTGACCCTGATCTTCAGAACAAATATGTG

GAGGCTGAGGTGGAGCAACTGATCCAGGTAGCATTGCTTTGTACACAAAGCAACCCAATGGATCGGCCTAAGATGTC

GGAAGTGGTGAGAATGCTTGAAGGTGATGGTTTGGCTGAAAGATGGGATGAGTGGCAGAAGGTAGAAGTTCTCCGGC

AGGAAGTGGAACTTGCACCACATCCTGGTTCTGATTGGCTTGTTGACTCGACAGAGAATTTACATGCAGTTGAATTA

TCGGGTCCAAGGTGA

Amino acid sequence for a mutant polypeptide encoded by a mutant Solyc04g072570 gene allele slserk1$^{CR-5-\alpha 1}$ coding sequence (SEQ ID NO: 108)

MVKVMEKDTVVVSLVVWLILVVYHLKLIYANMEGDALHSLRVNLQDPNNVLQSWDPTAWPFEEFAVLGALQ*

Mutant Solyc04g072570 gene allele slserk1$^{CR-5-\alpha 2}$
Nucleic acid sequence for a mutant Solyc04g072570 gene allele slserk1$^{CR-5-\alpha 2}$ (SEQ ID NO: 109)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTTTGTGGGCCCATCATCCTCATTTAGTTAATTTTAGGTCTATATTTGATGTTC

TATTTTGTGAGATGAGTTTCAAATGTCGAAACTTTTCGTACTAGAAATAAAATATATGCTAAAAGTGAAATTGGTAT

GTGCAAAATTGGATTTTGAATTTGACTAATGTGTGAGTTGTTGAATTTTCCCAAAAGGGTAAGCAAGATGTACAATG

AGTTCCCTGCACTGTTACAGTGACAAGCAGTTTAGTTTTAATGTCAGTTAAATGTGAAAGTTTTTAGTTATCATTGC

CATTCAACCTTAGTGCATTATGTTTCCTATACAAGCTTGAGTAATTTGATGTGATTTAATTTGGTTGTTTGCCAAAA

TCTTGATAAACTGTTTTGTTCAGTCAATAGATTAAATTTTTATGCGCATTTAGGTGGTTGAAAATTGTCTATGTTTT

CCTAAATGAATACACGAACAGGTGATGCATTGCACAGTCTACGCGTCAATTTACAAGATCCTAACAATGTGCTACAG

AGCTGGGACCCAACCTGTTAATCCTTGCACATGGTTTCACGTTACCTGCAACAATGACAACAGTGTTATAAGAGTGT

AAGAATCTGTTTTCTGGTCTACCTCCATTTGAATGGATTTGCAATTCCACTCTCTTGTGGTGGTGAGCAATCTAATT

GCAGTTTGTGCTCCCATAACACTTGTTATATGATCAACCTTTCCAGTGATTTAGGAAATGCAGCTTTATCTGGTTTG

TTAGTTCCACACTTGGCCTTTTGAAGAATTTGCAGTACTTGTAAGTCTCACTTCATGAACTATGTTTGGAATTATTT

TACAAATTTAGAGTTGGAAAACTGGCATTGAGTGTATTGGTTTTTCCAGCTGTTGAAGATTTTCATATTACCTCTAG

AATTCGCTGCATGAAAATAATGTAGGTGGCTTGCATATTAACTTTTGCATAAAAACAAAGCTGTTGTAAGTGGCAAA

AATGAGCAGAGAACACTTTCTCCTCTCCATCTCTTGTTTCACTTGATGTTGTAGTCGATGGCATAGTTGTTGATGTG

TTCCCTGAACAACACAAATTTGAATGTGTACTTCATAAAAAAAGATTTAAATATTTGTTTCACATTACATACTAGTA

AATTAAGTAACTCAGATACTTGGATGAGACTAGCAATGAAGTAACTTATGTGGCAAAGTAGTGTCTGTAATTGCTTG

-continued

```
TGAAAACATTGTAGTTGAACTTAAATTTTTGTCATACACTCCCTTATATAAAGATAAGCAGAGTAATCGTTAACTTT

TTTATGAACTCTTAAACAGAGTATTATTCTAAATATTATTACTAATGCCAGTACCCTAAGCACTCTTAATTTGGAAT

GACAAACTTCAACTCATATCAAATCCTTTATTCCCTCTTTCCTTGTTCCATGTAGACTCTAATCACGATTTAGGATG

ATGGAATAGGATAAAACAAACAAGAGAAACAAGTCCATTGTAAAAGTAAAGCAAAATCTAGACTTAAAAAGAGGAAA

TATGGCATGAGGGTAGGTTGATGTCTTGGAGGAGAAGATCTGAAGTTTTCTGGTCATATAACAGATGCTATTCTGGT

TTTCACCAAGAGTTCGAATCATGATTCAATTAAGCATAGATTTTGTACAAGTGTTAAGCTTAGTTTGGAGTTCAATA

TACCGTTCACTTAAATTACATCTCAAATTTCATTGTTCTTATTGTAACCCATGCTCTTTTGAAGCTGCAACTGTATG

GAAGTTCACAGAGACAGTATGTGCATGTGCACCTGGTGAAGCAGGGCATTACATGATGTATAACCATGCATCAGACA

ATGTTATAATGATGGGTATAATTATTACCTAGTGACTGCTTCATCCTGCTCACACATTAATATATTCCTATGGATGC

CTAGATTTGCTTGAGGCTTGTGTAGTACGCGTGCTAAGTATTTTCCTAGTGTATGCAAGTGACAATCACATCAAGAA

TGAAACAATATAAAAAGAACATCAAAAGTATAACATTATCTTTGTCAAAAAAAAAAAGAAAGAACATCAAGAGTGCT

GATGGAATTTAACAATCACCGGGCATACACACTGTTTAGATGAAGTTCGAAATTAACATAATGACAGACGTTAAATT

TTTATTGATGAGTTATATAGATTGTATAAAATGTTTGACGAGCTGATTCTTTGCAGCACATGGGACGACAGGTTTTT

ATATAGAAAAGTGCTTGTAACCAAATATAAGAAAATACCTCCATGAAATAGACATCGGTAACTAGTTATAATTGCTA

TCTTGGAACTCCTAGACCTTTCTCATTTGTTGACTTTTAATTGTCGCTTGATGCCAGTATTGATGGATGTGAGAATT

CTCCTTCATTATCTTGGTTGTCCCATTATCCTAGGGATGTCATTGGTATGATATGTGGAATTGACTCATTCTCTGGT

TTTCTTGTCACAGGGAGCTTTACAGTAATAATATAAGTGGTCTGATACCGAGTGATCTTGGGAATTTGACTAATCTG

GTCAGCTTGGATCTCTACTTGAACAACTTCGTCGGTCCCATCCCAGATTCCTTGGGCAAGCTGTCGAAATTGAGATT

CCTGTATGTATTTTTGTTCTATATTAGATTTATGTGGATATTGTGATGCCAAATGTATATTTCATCAACCAAGATGG

ACCTACTCTTACTGGCATGTTGAGAAAGGAAAGGAAGCCTGAATTCTTTTCTAGGTTTCACATAAGATGACCTCTAT

TAGTATTATGTTTCACTCTTAAGTTTTGATGGTAGAAGGTATTTGAGGACTTCATGGGTCTGATATCATTCATAAAA

CCGATCTTACATAAGTCTTTTAATTTTCTCCCTTTGTTCTAATCCTTGTATAAAGGAAAAGAATAGAAGCCTATGCT

TTGTCTGATACTGATATTGTAAAATTAATCAGAGTTTAGTAATGGGTGTTGGGATCCTTTTCTAGAAGAGAGAAGAA

GTTTAGAATCCCATGCTTCATCTTGCATTTTTCACTGCTGAAGTTTCTCTTGCTTAATGCTCCACAAACTTCTTTCT

TTTGGCTTGACTGTCTAAGAAGTGTGCCAAATTGTTCTATCATGCAGACTCAGCATGAAACCTCATTAACTGCATCT

TGGGACTTACTATAGAACTATTGCAGTACTGCAACGTTGACTAACATGATTTAGTCCAAAAGGTGTTTCAAGTCTGT

TTATCGGGGGGGGGGGATGTTTTGAGGCTCTTTATCGTGGTTCTGAACTGACGCCTTCATTTCCAGCTGAAGTGCCG

GTTCTGGCTCGAAGTTGAATATGTTTTACATCCACATATTAATAATTTATTAAGATGATTCTCCTTGTCAAATAATA

AATAAATTAAGATGATTCAATTAGTAGCCTTTTCTTCTGTTTTATTCTCCATTATTTACTTGTACCAAAGATGAAGC

TCATTCCTGTAAACCTTTGTGTTTTCTTGCAAGGATAGTCGGCTCAACAATAATAGCTTGACTGGTAACATCCCAAT

GTCACTGACTAATATCTCATCACTGCAAGTGTTGTAAGTACACTGATTATTTTGTGACTTGATTTAGATAATTCTTT

CTGTCTTCCATATCTTCTCATGCATTTCCTTTTCCTTCTAATGCATATACAGATTTACTTATGCTCAATTCTTGTCT

CACCTGTATGTAGGGATCTGTCAAACAACCGTCTCTCAGGTGCTGTTCCAGATAATGGTTCATTTTCTCTATTCACG

CCTATCAGGTATATTTCATTTAAGGCGGTGCACCATCTAACTGGCTGGTGGTTTTAGCATGCTACTATTTGCTAATA

TATTTTTCTTGTTTACAGTTTTGCGAATAATTTAGATCTTTGCGGGCCTGTAACTGGACGCCCTTGCCCTGGATCTC

CTCCATTCTCCCCTCCGCCTCCATTTGTTCCACCACCACCAATTTCTGCTCCAGGTGGTTCTCTAAATTGGTGTGGA

TAAATTGTTCTCCTTTCTTTTTTCTTTTGTTTTTTTTGCTTTTTTGCGGTTAGTGATTTTAGTTTGTCCATCCAACG

TAAGTGAGAATTTGTGCTATAGAAGCTAAAGTACTGACAAGAAAGGGGGCAGAAGAGGAAAACCCATCTTAACTAGT

CAGGCATTAGTTCTGATGGGAAACTGGTATGCACGAGACTACATTTAGTCTCTAAGCATTCTGGTCTTTATACAAAT

TTAATTCAGCATTGTGGACATCTTTTCTTTGGTCCCCTTGTAAATTATTATCTGTGGTATTTGAAGTCATGTGTCTG

AATGAAATTAATCATATTTATGCCAGAACTTGTGAAGATTTTCTTTTCTTTGTAAAAACTGTCCTGGAAATTAGATC
```

-continued

TGATGATAGATACAAATTTGTCTACTAATTTCTTTTTGAAGTGATTTAATTAATGAAGGGCCGGCCAAAATTATGTG

TTAAATATAGTCTAGATCATATGAAGGAAATTAATCAAATTTATGGGAACTTCAGGAGGAAATGGTGCAACTGGAGC

AATTGCTGGAGGTGTAGCTGCTGGTGCTGCTCTACTATTTGCTGCTCCTGCCATTGCATTTGCCTGGTGGCGCCGTA

GAAAGCCACAAGAATATTTCTTTGACGTACCAGGTTAGCAGTATTCAAATACCCAACCATAAGTCCATAACTCCTAC

TTACTCTCTCACGTGTTTATGGTTTCTCTTGCATGTTTTATTTTTTGGCTCCATAATTAACGTCTTTGCTTAAACTT

ATTGCAGCCGAAGAAGATCCTGAAGTTCACTTAGGTCAACTGAAAAGGTTCTCCCTCCGAGAGCTACAAGTTGCAAC

TGACAGTTTTAGCAATAAAAATATACTGGGTCGAGGTGGATTTGGTAAGGTATACAAAGGACGCTTAGCAGATGGAT

CATTGGTGGCTGTTAAGCGGCTAAAGGAAGAGCGTACTCCTGGAGGGGAGTTGCAATTTCAAACAGAAGTTGAGATG

ATTAGCATGGCAGTGCATAGGAATCTTCTACGATTGCGTGGTTTCTGTATGACACCAACTGAAAGACTGCTTGTCTA

CCCCTACATGGCGAATGGAAGTGTTGCATCATGCCTGAGAGGTGACACTTTCTGAAATCTATCACTCCATAAATGTT

CTCACCTTTAATTTGGAGGGTATTATTGCATAATGCAAGAATGTCTTTCGCTGGTTAACATTCTATCTTGGCATAAC

TTACTCTTTATAACAAAACATATTCTTGTTAGTTATTTTCCTGTAACTTTTTAAAAGGTAGAAGTATAATTTGTATT

GTATTCTCTTGACAACATAATTTATTTTATCAGAACGACCGCCTTCTGAACCACCACTTGATTGGCCAACGCGAAAA

CGTATTGCTTTGGGGTCTGCCAGGGGATTATCGTATTTGCATGATCATTGTGACCCTAAGATTATCCATCGTGATGT

GAAGGCTGCAAATATATTGCTAGATGAAGAATTTGAGGCTGTTGTTGGAGACTTTGGTTTGGCTAAACTTATGGACT

ACAAGGATACACATGTTACAACTGCTGTGCGTGGTACAATCGGGCATATAGCTCCAGAATACCTTTCCACAGGGAAG

TCTTCAGAAAAGACTGATGTTTTTGGGTATGGGATCATGCTTCTGGAGCTAATCACCGGCCAACGTGCTTTTGATCT

TGCTCGGCTGGCAAATGATGACGATGTCATGTTGCTTGACTGGGTATGTTGTCATACCTGCTTTACATGTGAACATG

ACACGAGTACCATAATGTGTTCATTTTTTAATCTGTACATCACAACACTAGCTGACTAATAAGTATTTGTGCCTTTA

GCAGGAATATTTAAGTCTATGACTAAACTTGTTGAGGTTCTTGTTTCAGGTGAAAGGACTCCTCAAAGAGAAGAAAC

TGGAAATGCTGGTTGACCCTGATCTTCAGAACAAATATGTGGAGGCTGAGGTGGAGCAACTGATCCAGGTAGCATTG

CTTTGTACACAAAGCAACCCAATGGATCGGCCTAAGATGTCGGAAGTGGTGAGAATGCTTGAAGGTGATGGTTTGGC

TGAAAGATGGGATGAGTGGCAGAAGGTAGAAGTTCTCCGGCAGGAAGTGGAACTTGCACCACATCCTGGTTCTGATT

GGCTTGTTGACTCGACAGAGAATTTACATGCAGTTGAATTATCGGGTCCAAGGTGA

Nucleic acid sequence for a mutant Solyc04g072570 gene allele slserk1$^{CR\text{-}5\text{-}\alpha 2}$ coding sequence (SEQ ID NO: 110)

ATGGTGAAGGTGATGGAGAAGGATACTGTGGTGGTATCACTGGTGGTATGGCTAATCTTGGTTGTATATCATCTTAA

GCTCATTTATGCTAATATGGAAGGTGATGCATTGCACAGTCTACGCGTCAATTTACAAGATCCTAACAATGTGCTAC

AGAGCTGGGACCCAACCTGTTAATCCTTGCACATGGTTTCACGTTACCTGCAACAATGACAACAGTGTTATAAGAGT

TGATTTAGGAAATGCAGCTTTATCTGGTTTGTTAGTTCCACACTTGGCCTTTTGAAGAATTTGCAGTACTTGGAGCT

TTACAGTAATAATATAAGTGGTCTGATACCGAGTGATCTTGGGAATTTGACTAATCTGGTCAGCTTGGATCTCTACT

TGAACAACTTCGTCGGTCCCATCCCAGATTCCTTGGGCAAGCTGTCGAAATTGAGATTCCTTCGGCTCAACAATAAT

AGCTTGACTGGTAACATCCCAATGTCACTGACTAATATCTCATCACTGCAAGTGTTGGATCTGTCAAACAACCGTCT

CTCAGGTGCTGTTCCAGATAATGGTTCATTTTCTCTATTCACGCCTATCAGTTTTGCGAATAATTTAGATCTTTGCG

GGCCTGTAACTGGACGCCCTTGCCCTGGATCTCCTCCATTCTCCCCTCCGCCTCCATTTGTTCCACCACCACCAATT

TCTGCTCCAGGAGGAAATGGTGCAACTGGAGCAATTGCTGGAGGTGTAGCTGCTGGTGCTGCTCTACTATTTGCTGC

TCCTGCCATTGCATTTGCCTGGTGGCGCCGTAGAAAGCCACAAGAATATTTCTTTGACGTACCAGCCGAAGAAGATC

CTGAAGTTCACTTAGGTCAACTGAAAAGGTTCTCCCTCCGAGAGCTACAAGTTGCAACTGACAGTTTTAGCAATAAA

AATATACTGGGTCGAGGTGGATTTGGTAAGGTATACAAAGGACGCTTAGCAGATGGATCATTGGTGGCTGTTAAGCG

GCTAAAGGAAGAGCGTACTCCTGGAGGGGAGTTGCAATTTCAAACAGAAGTTGAGATGATTAGCATGGCAGTGCATA

GGAATCTTCTACGATTGCGTGGTTTCTGTATGACACCAACTGAAAGACTGCTTGTCTACCCCTACATGGCGAATGGA

-continued

AGTGTTGCATCATGCCTGAGAGAACGACCGCCTTCTGAACCACCACTTGATTGGCCAACGCGAAAACGTATTGCTTT

GGGGTCTGCCAGGGGATTATCGTATTTGCATGATCATTGTGACCCTAAGATTATCCATCGTGATGTGAAGGCTGCAA

ATATATTGCTAGATGAAGAATTTGAGGCTGTTGTTGGAGACTTTGGTTTGGCTAAACTTATGGACTACAAGGATACA

CATGTTACAACTGCTGTGCGTGGTACAATCGGGCATATAGCTCCAGAATACCTTTCCACAGGGAAGTCTTCAGAAAA

GACTGATGTTTTTGGGTATGGGATCATGCTTCTGGAGCTAATCACCGGCCAACGTGCTTTTGATCTTGCTCGGCTGG

CAAATGATGACGATGTCATGTTGCTTGACTGGGTGAAAGGACTCCTCAAAGAGAAGAAACTGGAAATGCTGGTTGAC

CCTGATCTTCAGAACAAATATGTGGAGGCTGAGGTGGAGCAACTGATCCAGGTAGCATTGCTTTGTACACAAAGCAA

CCCAATGGATCGGCCTAAGATGTCGGAAGTGGTGAGAATGCTTGAAGGTGATGGTTTGGCTGAAAGATGGGATGAGT

GGCAGAAGGTAGAAGTTCTCCGGCAGGAAGTGGAACTTGCACCACATCCTGGTTCTGATTGGCTTGTTGACTCGACA

GAGAATTTACATGCAGTTGAATTATCGGGTCCAAGGTGA

Amino acid sequence for a mutant polypeptide encoded by a mutant Solyc04g072570 gene allele slserk1$^{CR\text{-}5\text{-}\alpha 2}$ coding sequence (SEQ ID NO: 111)

MVKVMEKDTVVVSLVVWLILVVYHLKLIYANMEGDALHSLRVNLQDPNNVLQSWDPTC*

| | | |
|---|---|---|
| SlERL1 | TAGCAACGTAGCAAACGTGTTGC ATT(239)TCTGTCTAATCTGA<br>ACTTGGGCC AAA(111)AATGTTAATGACAGAGACCTTCA AA | SEQ ID NO: 112 |
| slerl1$^{CR\text{-}1}$ | ATAGCAACGTAGCAAACGTGTTGCTGGATT(239)TCTGTCTAATCTGA<br>ACTTGGGCG AAA(111)AATGTTAATGACAGAGACC-<br>TCA AAA | SEQ ID NO: 113 |
| slerl1$^{CR\text{-}2}$ | TAGCAACGTAGCAAACGTGT**T**TGCTGGATT(239)TCTGTCTAATCTG<br>AACTTGGGCG AAA(111)AATGTTAATGACAGAGACCTTCA A<br>AA | SEQ ID NO: 114 |
| | 23$^{rd}$ exon 23$^{rd}$ intron | |
| WT gDNA | 5'-AGAGCGAGGTCTGATCAAACT-3' | SEQ ID NO: 115 |
| sler$^{EMS\text{-}1}$ gDNA | 5'-AGAGCGAGAGTCTGATCAAACT-3' | SEQ ID NO: 116 |
| | 23$^{rd}$ exon 24$^{th}$ exon | |
| WT cDNA | 5'-AGAGCGAGTTTCAATT-3' | SEQ ID NO: 117 |
| sler$^{EMS\text{-}1}$ cDNA | 5'-AGAGCGAGATCTGATCAAACTTTTCAATT-3'<br>11 bp insertion | SEQ ID NO: 118 |
| | 14$^{th}$ intron 15$^{th}$ exon | |
| WT gDNA | 5'-TGTTTCTGAAAT (64 bp) GTCT-3' | SEQ ID NO: 119 |
| sler$^{EMS\text{-}2}$ gDNA | 5'-TGTTTCTGAAAT(64 bp)GTCT-3' | SEQ ID NO: 120 |
| | 14th exon 15$^{th}$ exon 16th exon | |
| WT cDNA | 5'-TTTGACTTAAAT(64 bp)GTCTCAACGTTC-3' | SEQ ID NO: 121 |
| sler$^{EMS\text{-}2}$ cDNA | 5'-TTTGACTT----(64 bp)----CAACGTTC-3'<br>No 15th exon (72 bp) | SEQ ID NO: 122 |
| SlER | CTCCTTCATCTGATTACTGTGCC AGA(140)GATGGGGAGTTG<br>TCTCCTGCTAT ACA(139)TCTGGCCAGATACCAGATGAGAT<br>TGA | SEQ ID NO: 123 |
| sler$^{CR\text{-}1}$ | CTCCTTCATCTGATTACTGTGCC AGA(140)GATGGGGAGTTG<br>TCTCCTGCTAT ACA(139)TCTGGCCAGATACCAGATGA**A**GAT<br>TGA | SEQ ID NO: 124 |
| sler$^{CR\text{-}2}$ | CTCCTTCATCTGATTACTGTGCCAGA(140)GATGGGGAGTTG<br>TCT----<br>CTAT ACA(139)TCTGGCCAGATACCAGATGAGATTGA | SEQ ID NO: 125 |
| WT | GTG(59)GACAACCCTTGTTAATCCTTGCACATGGTTTCACGTTA<br>CCTGCAACAATGACAACAGTGT(156)TCTGGTTTGTTAGTTCCACA<br>GCTCCT | SEQ ID NO: 126 |
| #5<br>a1 | ---(59)--------------------------------------<br>-------------------<br>TGT(156)TCTGGTTTGTTAGTTCCACAGCTCCT | SEQ ID NO: 127 |

-continued

| | | |
|---|---|---|
| a2 | GTG(59)G-------------------------------------<br>TCCTTGCACATGGTTTCACGTTACCTGCAACAATGACAACAG<br>TGT(156)TCTGGTTTGTTAGTTCCACAGCTCCT | SEQ ID NO: 128 |
| a2 | GTG(59)GGAACC----------------------------<br>TCCTTGCACATGGTTTCACGTTACCTGCAACAATGACAACAG<br>TGT(156)TCTGGTTTGTTAGTTCCACAGCTCCT | SEQ ID NO: 129 |
| #7 | | |
| a1 | GTG(59)GACACC-------------------------------<br>---------------------(156)---------------------<br>GCTCCT | SEQ ID NO: 130 |
| a2 | GTG(59)GACACC--<br>TGTTAATCCTTGCACATGGTTTCACGTTACCTGCAACAATGACAACAG<br>TGT(156)TCTGGTTTGTTAGTTCCACA-CTCCT | SEQ ID NO: 131 |
| SP | TGTAGTGTTAAGATGTCTGTTGTTTA(37)TTTTCCTCAGTAA<br>CTTCTAAACCTAG | SEQ ID NO: 132 |
| sp$^{CR}$ | TGTAGTGTTAAGATGTCTGTTGTTTA(37)TTTTCCT----<br>AACTTCTAAACCTAG | SEQ ID NO: 133 |

Edited Sequences in *S. lycopersicum* cv. Sweet100

| | | |
|---|---|---|
| SlER | TTGATGGGGAGTTGTCTCCTGCTAT<br>ACAGC(135)TTTCTTGC<br>CAGATACCAGATGAGATTGACT | SEQ ID NO: 134 |
| sler$^{CR-1}$ | TTGATGGGGAGTTGTCTCCTG-TAT<br>ACAGC(135)TTTCTGGCCAGATAC<br>CAGATGAGA----TTGACT | SEQ ID NO: 135 |
| sler$^{CR-2}$ | TTGATGGGGAGTTGTCT-----TAT<br>ACAGC(135)TTTCTTGC<br>CAGATACCAGAT----TTGACT | SEQ ID NO: 136 |
| SP | TCTGTAGTGTTAAGATGTCTGTTGT<br>TTATA(33)TCTTT**CCT**TCCATCAGTAA<br>CTTCTAAACCTAGGG | SEQ ID NO: 137 |
| sp-cocktail | TCTGTAGTGTTAAGATGTCTGTTG<br>TTTATA(33)TCTTT**CCT**TCC**A**TCAGT<br>AACTTCTAAACCTAGGG | SEQ ID NO: 138 |
| sp-grape | TCTGTAGTGTTAAGATGTCTGTTG<br>TTTATA(33)TCTTT**CCT**TCC**A**TCAGT<br>AACTTCTAAACCTAGGG | SEQ ID NO: 139 |
| SP5G | TGCCTAGAGATCCTTTAATAGTTTC<br>AGTTG(48)TTTAC<br>AACAATAGGGTGGTCTATAAATGTT | SEQ ID NO: 140 |
| sp5g-cocktail | TGCCTAGAGATCCTTTAATAG--TC<br>AGTTG(48)TTTAC<br>AACAATAGGGTGGTCTATAAATGTT | SEQ ID NO: 141 |
| sp5g-grape | TGCCTAGAGATCCTTTAATAG--TC<br>AGTTG(48)TTTAC<br>AACAATAGGGTGG--TATAAATGTT | SEQ ID NO: 142 |
| SlER | TTGATGGGGAGTTGTCTCCTGCTAT<br>ACAGC(135)TTTCTGG<br>CCAGATACCAGATGAGATTGACT | SEQ ID NO: 143 |
| sler-cocktail | TTGATGGGGAGTTGTCT----TAT<br>ACAGC(135)TTTCTGG<br>CCAGATACCAGATGAGATTGACT | SEQ ID NO: 144 |
| sler-grape | TTGATGGGGAGTTGTCT----TAT<br>ACAGC(135)TTTCTGG<br>CCAGATACCAGATGAGATTGACT | SEQ ID NO: 145 |
| sler$^{CR-3}$ | TTGATGGGGAGTTGTC-------<br>TATACAGC(135)TTTCTGGCCA<br>GATACCAGATGAGATTGACT | SEQ ID NO: 146 |

Wild-type Solyc08g061560 SIER
Nucleic acid sequence of wild-type
Solyc08g061560 SIER promoter
(upstream region of start codon (ATG))
(SEQ ID NO: 147)

TTTTCGAGTTGACATAGTACCTTCGCAGTTGAAGA

AGAAGAAATTGATTAAGAAGATAAATTCGACATTG

GAACTTGATAATTAAGAAGAAATCAATGAAAAAG

AGATATAATATAATGAGGTAAAGAAAATAAATAAT

GATGAAGAGAAACAAAAGAGGAGAAATAATGGAA

GAATGGGAGAAATTAGGGTTAAAAGGGGGAAGAAG

ATCGTTGGTGGGTGGTTCAAGATCCACATGTGCG

CTTTTAAAGAGTTTGCACGCGCTTAAAGGACGTGA

GATCACGTTTGGCTCCACATCAGCCAAGAATATT

TAAAAGGATCAAATTATAGGGGGTTAAAGGATTTA

ATAGGAATCTTGGTTAGTTAAGGTATCTGGGGGAA

AAGCGCGAACAACTTTAGGGACCTGCATATGTAT

TTGGCCAAGAAAAAATAAACAAATAATGAGAGAAA

GAGTGAATATATATAAACAATGGTATAGTCCCTC

TATTTGAACTTTTTGGTCAAAATTCATAGTGGCAT

TACAATTGCACAATATGACTTTGGGTGCTTTGAC

TACGCTCCATGTTAGTTTCTTCTTTGCCATAATGT

TTCTTAGTAAAGAATCAAATAATTATAGAATCGC

CTTTAGTGTGATAATCACTATTCCTTTTGTACCAA

TTTAAGTATGTTTTTTTTTTAAATTAGTATATGTA

CCGGGAGTTTTGATATATAATATTATTTTTTAAT

CTAAAATTATTTTGGACATTTGATAATTTTGAATT

CTCTAACAAGTTTGATATATAAAATTTTGACCGA

TAACTTTATATTTTGTAAAAAAAAAATCCATCATT

ATGTATGACATTTGTTTTTACAAGAATATCAAAG

GAATGATGAAATATTTATGGAATATGAACATGATA

-continued

TATAATTACTAATGATATTGATTATGTTCGACTT
TTTTAAAGAAAAGTTCATTGTTTATAATCACGGTT
CAATTTATCTTTTTATTGAACTAAAGTTTTATCA
ATAAATGTTATCCTAGTCTGAGTAGGCATTTGACC
ATATGATAGCATATTACCAGAGGTGGATCTAGTAT
TTGAAGGTCCTGAGTGTCACATTGTCCAAATAAG
ATAAGTTGGTCAGTTGCTTTAATTTTGATTTACAA
TCGAATCATTTATCTTTTTTCGATCTTTATAAAC
AAATCGATCAAACATGCATGTTAGTAATTTTTCTT
TTAGATATCATGAGATTAGGGCTTAGTAACCATT
TAATTTTTATTTATTGTTAGGAATTAGTAGCCTTA
TTCGCTGAAACTTTGAGGAAAAAAAATTGACACT
AAAATTTGAGCTTGTATAAACTATCAAATAGTGTT
AACTCAATATATTCATATTCTATTGAGTTGTTGCA
AAATACAACAAAAGAGAATACAAATTTTAGTTCA
TTTAGTCATCTTACTTAACAAGAATATTGGTGAAG
ATCGAAGAACCTTCAAATTAAAAGAATTCTAATA
ATAATATTTATCATTTTTAAATTTATGTTTTTTAA
ATTTACTATTGAAATATAGTCTTAATAATATTTA
TGTCATGTTCATAATTTAATTGATAAAGTATAAAC
ACGTGACACTCATATCAAAAGATTAATAATTAGT
AAAAAAAGAAAGTAGAAGAACTTAAAAATTAATTA
TAGTGAATAGGAATCAATTTGAATTAACAAAAAAT
ACTTGTAAATAAATAAGAATGAATGGAAGGGGAA
AATAACTCACACATTTTAAAAAAAGAAAAGAAAAG
AAAAAGCTTCCAAAAATTAATGCTGCAAATGAGG
TTCGAATTGGTGTTGTCTGTGTGGTAGATTAACTA
TTTTGCCAATTGAACTATTAACCATTTTATTCAA
AGAGTGGAAAAGAAAATATATACTCATTTTCTTAA
ACATGTATACTATATATACAAAGTTTAGAGATCA
GTGGGTGCCGTGACATTACCACATAAATTCATAAA
TCCGCCCCTGCATATTACGATATAGTATCATGAG
ATGGAATCAGCGTTTGGACGTGCAATTTTACATTG
ATTCGATCTTATGATTCTATATCATGAGATATGAT
TGCATATTCTCCATAAACCATGATATGAAATCAT
ATGGGAATACCACTTCATGATTTGAGTTACTTTAA
TACAAAAATTGATCCACGAGTTTATATTTTGTTA
ACATAACCCCGCATTTATATCTACTAACAATTTAT
TTCACATGTAAATAAAATTTATAATCACATCATT
ACTTTTTAAATTTATTATTCTCACAGACATAAAGT

-continued

TTATTATTATTCTCACCAACCTATAGTCACTTTA
ACACTCACACGTCAAGATTGTTGTAGTTAAATCTT
GAAGAGCCCGTGAAAGGTGTTTCATTTTTACTCAA
ATATATTGATGAAATAATTACTTAAGTGGAGAAC
AAATAACTTTATAATAATTTATCATATGATTTTAC
AGTTTTTTTTTATTTGATAAATTTGAATAAACAA
TTGAGGTTATTTTAATAGTTTTAGAACTTATGAGA
TTTTTATGTTTATGAGAAAATATACATTACCAAA
ATTTCATATCGCATGTCCAAACAAAACATCAATTT
TAGTATGATTCCATATCATAATACCATATCGAAT
GACCAAACGGACCGTTAGAATAACTTTATAATAGT
TATTATACTTTCATTATGAATTTTTGCTTATTTA
GTAAGATTGTATGAATAAAGTTAGGACAATATTTG
GTGAGATTTTGATTTATGAGCTAACAATAGAATTT
CAAAATCATAATTTCTATATGGCTAAGCAAAACT
TCAATTTCATGTTAAACGAATGAAAAGTAAGTAGG
CGTTTGGTCATGTGATATCATATCACGATATGAA
ATCGTGAGAAGGAATCAGCGTTTGAACATGCGATT
ATACATTGATTCTATATCATGAGATGTAATTCCA
TATTCTTCAAAAACCATGATATGGAAATTTCATAT
CATGATTTGATATATTTTTAATACAAAAATTGAT
CCACATATTTGTATTTTGTTAAAACAACCCATATT
TATATCTACTAACCATTTATTTCATTTGTAAATAA
AATTTATAATCAGATCATTACTTTCAAAATTTAT
TATTCTCACGACATAAAATTTATTTTTCTTACCAA
CATATAATTACTTTAACTCACACCAATCGATTGT
TGAGTTAATAAATTTGTTCTCTTCATTTATTTCAA
CACCTAATTTATTATTTTTTACCGTTTTATATTT
ATTACAACTTAAAAGTAACAATATTGGTTCTTCTT
CTCAATCACATGATCGAGAAATACAAGTTCAACA
TGAGGAAATGTCCAGACGATGTGAGAAGATTATAT
TAAAAATTAGTACATTATAATTTATGTTCAATTTT
TTTATTGAACTAAAGTTAGATGAAACAGTTACCG
TAGTGGAAAACAAGTAACTTTGTGATAATTTAAAT
GCGATCTTATGATTTTTTTTATTTGATAAGACTG
AATAAAAAATTGAGATTATGTTAATAGTTTTACAA
TTTATGAGATTCATATACAAAACAATTTTTTTTA
TCATATATCTAAATAAAATTTTAATTTTATATTAT
GATTTCATATTATAATATCATATCAACAAACTAG
CTATTAAATTTTATAAATGATAAATTATAGCCAAA
ACACTTAAATTAAAACTGAGAGAAGTAGCATTTT

TACCTTAAATGATGATAGGACAGTTGCTAGCTAAA
TATGAAGAAAAGAAACAAATGTGTAGGTAAAACCC
TCCCATCATTACTTGTGATAATATCCTATGGCTT
CATAAATCATATAACACTGATCGAGACAAACAACG
CATTACCCCACTGAAAAGGTTGAAACCCCATTTC
TCGTGAGTACATAACTGCACATGTTGGGTAGTGAA
GAGTAGTCATTGTCAAACATTTTTTGGGTAAGCC
ATCGACGTTTTGTATTTATATTAAAATCTGATTAA
ATTTGAAGCTGATTTATATTTAGAATGAAACTTC
AGCTTAAAAATAAGAAAATAGTTTATGATTTCATT
AGAATTAAGGCGTAGTCACTGTCAAACTTGAGAAA
GGATTACCCCTTTAAGCTTTGCCCTTGTTTGCAG
AGACAGTGACTTGTGATGAAATGAAGCCAGAGAAG
GCACTCTGTTATCACACTTAAATGATAATACATG
TGTATGGACTAGCAATAAAAGTGGCACTAGTAATT
GAAAAGCAAGTGTATAGAGAGAGATAATGAGAGA
GAAAGAGTAAGTACACTACTACTGCTACTATCCCA
TATACCTGTAATGTTGCAGGTCTGAATTTTGCAGT
TGCAGACCCCCTTCTCTTGGCACAAGCTCTTTTAA
CTTTTATCTTCTCAAATAATTCTCTCTCTCTCTCT
TTTCTATCATTTTTTTTTACATTGAGAGTAAACTT
AATATCCGTTGTATGTATTAGTGTGAGGCCTATCT
GCCACAAGGATGTGATGGAACACTATGCTTCCTCT
GCTAAAACCCCACAACCCCAAAACTCTCTTTCACT
TCACATTTAAGCACAATTCCTCAGTAAAATTATCC
TTTTGATCTCTCTAACATCAATGTTGGTTAGTTCA
AGAATTGGTTTTTCCATTTCAAAGGAGCTGAGTTA
GTGAGGTTTTGAGTTTTGACTGAGACTTGAGTCTA
CC

Wild-type Solyc05g053850 SP5G
Nucleic acid sequence of wild-type Solyc05g053850 SP5G promoter (upstream region of start codon (ATG))
(SEQ ID NO: 148)

AATAAGACAAAGAGAATTGCGATATGGGGATAATT
TTTCTAGTTAGATTAGAGATAAAAGGGGATCGAAT
TTAGATTTGAAAGCAGATATGATTATTAGATAATT
TTAATAATTAGTTAGGGATTAATTAAGAATAAAAT
AAAGTTAGCAAAAGAAAAGTTAATTAATTTAAAAA
ATAAAAAAAATATAAAATTATAATTTCTAACGTGG
TGCTGATGTGACACTGATGTAGCAGTAAGTGTAAT
ACATCACATACATGTGATGGCGGTATTACATGTCT
CAAGGTGATATTAAATTCACTTTAACTAATAAAAG
TATGTTGTTATAAAATCATCATAATAATTAAAACG
TGTAATTAATTATTCGATATAATTTTTTAAGAGGA
AATTTATGTCTTTTCACTAAAAAAAAAACAAAAAA
AATCAAATATTGTGAATCAGGCTGTCCACTAAAAT
AGGTATTTATTTTATAGCCACATTAAACCTCAAGA
GGATATCTTTCAAATTCTTTATGGCCTAAAAAATA
ATAATTTTTTTTCCTGCAAACCGTTTAATTCATA
GGTTTCCAAAGGGAGAAAAGAAAAATAGAATTAAG
AAAAAAAAAACTAGCAATATTCTTTCTTTCACTCA
TCTTTACATCTCACAATCGGATCGCATAGCCGTTA
CTCTTTAGGTATGCATCGGATAATTTTGCTCTTAT
CCATTAACTTGTAAAATACATTAGATTATAGAATA
TGTTTAGTTGGACCAGCTACTCGATAGGAAGTCGA
CTTAAAATTCATTATTATTACAACAAAAGCAATTC
TAATGGTAATATATCATGCGCATCAACAAAGAACA
CTAGATCCTTTATCAACGTTAGTTAATTGTTATTA
GATCTAATGTTGCTATAAACTTTAGCGACATTTAC
AAAAAATGTTAATTGTCTCTAAAAAAAATATATTTA
ACTATAATTAGCTATTATCGCCAAAAAATTCCTTA
ATTTACAGTATAACACACCAGCTCCTGGTGTACCA
CCCAAAATCCACCTACATATAAATAAACTACACTT
AAAATAAGAAATTAACAACCGACAAAATTTTGCGA
TAAAAGTTCAAATAATTTAAAATTTATATAATTAT
ATATATTAGCTAGAGATTATCGATAAATTTCATAG
CTGATTATTACCAATCACTTTCCATGTCCCCACAC
TTGTAGTAACCCTACCCCCACTCTTACTGAACTTT
GATCACTATGAGGAGAAAGAAAAGGAATGTTGTTT
TGTGTGGAGAGGCTATCAAATGCTTCTGATATTAT
TGATTCTCTCTAGACACAATTTGAACACAAAGAAA
CTTGTGAAAATGGACAAAAGAGCTAATATTCTTTA
TTTCCTCATATGTACATCTTAATTAAAAAAAAGTC
ACATATATCTTTTTTTTTTGCCATTAGGAATATCA
ATTAATATTATATAGAATTGTAGTTGTTCGACGTA
AAAATAAGAGAGACAGAAATTTTATCAAGGAGTGT
TATGAAGTAAAAAAATAAATAAGAAGCGACACACA
AAGAAATCGGGAAGTATACATATATCGTATATATA
CATAAATTTAGTATCGTGACCTAGTTAAATAACGT
AATTTTCTGATGAAAAGGTGTCAAGAATATCAATT
AATATCATATAGATTTGTTGTTATTCGACATAAAA
TAAGAGAGATATAAATTTTATCAAAGAGTGTCATA

-continued

AAATAAAAAAATAAGAAGAGACACACAAAGAATTG
AGAAGTATACATATAGTATAGATACATAAATTTAA
TATCGTGACCTAATTAAATAATATAATTTTCTGGT
GAAAAGTCGTCAAGACATCCCTTACCATAAGGTGG
CTCGACCACTCGTCCAAATTAGTCTTCTTTTTGGA
GAGGCCGTAGATGTAAGCTGAAGAAGAATTTGGGA
TGATGGTTACATAAGATGTTATATATTTTCAACTT
ATCGAGGACATAACCTAGATAAAAAGATAGAAAAA
TCGAAGATTAAAATAATAGAGTAGTAGATAAATAT
TACCTTACTTTTACATGGGAGAGACTGGGTGCTAG
ACTCCTCTTCTCCTAATTTTGTATAATATCTTTAT
CTTCTATTTACATAATTAGTTGTTGCTTTATTTAC
TTTGTTTATTTTGCTATTTTATTGTTATTTTAATT
TCTTTTGCGCTCATGCTTTAATTTTTATTTCTTTT
AAGCTAAGGATCTATTGAAAAAAAACATCTTCATT
TCACAAAGACAAAAGTATTGTTCGTGTACATTCTA
TTCTCCTAGATCTCCTGTCATAAGGTTCATTGATT
TGTTATTATTTTTGTAAATTCAGTATAAATACAAA
TTCTAATCTCTCATCGAAGACGAGTCAATAATTTC
TGTAGGTCAACGGATTGTATGTAAAATATAACCGA
CTTCAATTTTTTTTTTAATTTTTCAAATAAAATTT
CTAATTTCGCTACTAAATAATATAAAGAGCGGCGG
GCCTCTCTAGAGGTGCATTCCTTCTTATAATTTTT
TCACCTTCATTATTATTAATTAAAAGTCCCAATAA
ACAAAGGAAAAAGTTCTATCACTTTTTTACAATTG
GAAAAAAGAGATTCTTTTAAGGAATGTGTGGTGAC
AAATAAGCATCCTATTTTCTTCTGTTACTAAAGCC
TCTAAAAAAAATAAAAAATAAAAATATATATACTTA
AACTCACAAGTTTAGGGCAATTTTGATGCATCTTT
ATTTTGTTTATCAAACTCTATATATAGTCATTCAT
AAAAATGATAGTACGACACATAAATCACTCCATAT
TTTATTATATTGTAATTATGATTCGAGAAAGGATT
TAATTTCTCAAAATATAATATAAATAGACTATCGT
AATATAAATATTAGTACTATCTAATGAAGTACGAT
TTGATGAAGTGTAAAGTTAACTTACATATGACCTA
GAGAAACCACTTAAGTAGCAATGAATAATCCAAGA
TATATATATACTTAAACTCACAAGTTACATTTTTG
ACGTATCTTTATTTGTTTATTAAACTCTATATAT
AGTCATTCATAAAAAATGATAATATGACGCATAAAT
CATTCCATATTTTATTAAATTATAATTAAGATTTG
AAAAAAGAATTTACTTCTTCAAAATATAATCTAAA

-continued

TAGTCTATCGTAATATAAATATTAATGTTATCTAG
TGAAGTATGATTTAATGAAGTGTAAAGTTAACTTA
CATATGACCTAGAGAAATCACTTAAGTAGCGATGA
ATAATCCAAGAATATGTTTGGTCCTTTATTCTTTC
TTGTCATGGCTCATGTATCCATGCACTTTATTATA
ACAATTCGAGAAGTGTTATAATTATGGTGATTCTC
TTATTTAAAATTTTTTCGAACTATTAATAAAGTAA
ATGAATAATAATAATAATAATATGAATTAGGAAAA
TATTTATGTATATAATTTTTATGTCAAAATTACTT
GATTCTCCACTTTACAGCTCAACAATTAACATATA
TGGTTTCCCCTTAAAGAAAAACTTCAAAAAGATTC
CTATGATGGTAAAGAAACGTTTGGCCATAAAAATT
AAATATTTTTCAATTTTCAAATCGAAATTTTTTTG
ATCACTATGGATCTGATATAAACAGTCTCCCTATT
ACGAAAAAGTAAGAGTAAGGTCTGCATACATCTTA
TCCTCTTTAAACCTCACAGTTTGAAGATGCGACTT
TGTTTGATTATACTTTTTCCAAAGGAGAGAATTAA
GAGATTATATTTGGAATTACGCAGACAAAATTTGA
AAGACATCTTATAAGTTTGAAATCCAATTACAAGT
GGAATTTAAAATTTTCACGACTTGTCAACCATTGA
TTCTCAAATAAAGTGAAAAATTATTCCAAAAACAA
ATAAATATTTTTTTTATGACCAAATATGTCCTCAA
GAACATATGAAAGCTCTCTAGTCATGAGTATAAAT
AACAAGGGCTAGCTAGCTCTTGTCTACTCATAAAA
TATCATCCATCCATCTCATGTAATAAACAAAAATT
GAGCTTATTAATTATAATTGAGAAGAAAAAAAATC

Wild-type Solyc06g074350 SP
Nucleic acid sequence of wild-type
Solyc06g074350 SP promoter
(upstream region of start codon (ATG))
(SEQ ID NO: 149)

GATGATTGTTCTTTTGATTATGATTACTCATGTGA
TTCATCCTTTTATGATATCAATCCTGATATACATG
TTTGTCCTACTTCACCTCATCTTGGATCTGATTCA
TATTCTGATGCACATATGATGCCTACTTCAGTAGA
AGTTGCTTCAGTAGAGGTTCCTATTATACCTTCTA
CTGATAGTTCCTATAATCCTCCAAGAAGGTCTCAA
AGAGTGTCCTCTAGACCTCTCTGGATGACAGATTA
TGTGACTGCACCATCTGGGAATTCTGTACAATATC
CCATACAAGACTATATGTCCTATATAGGCTTGTCA
GCTTCACACTATAGTTTTTTGAGCATGCTGAACAC
TGTGGTTGAACCATCTACTTATCAACAGGCTTCAC
AAGACCCTCGTTGGATAGATGCTATGAATGCTGAG

-continued

ATACAAGCCTTGCAGGATAATCATACTTGGGACTC

TTTACCTCAAGGGAAACATCCTATAGGTTGTAAAT

GGGTATATAAAGTTAAACTTCAGGCCAATGGTGAC

ATAGAAAGGTTTAAGGCTCGTCTTGTGGCAAAAGG

GTATAATCAAACGGAAGGTCTTGATTACAATGAGA

CTTTTTCTCCAGTTGTCAAAATTGCTACTGCGAGA

ACTGTATTATCTATAGCTGCTCAACATGACTGGCA

TATTCATCAACTTGATGTCTATAATGCATTTCTTC

AAGGGGATCTTCATGATGAAGTATATATGCAGTTG

CCACAAGGTTTTCCAAGTCAGGGGGAGTCTATAGT

TTGTAGACTTGTTAAATCCTTGTATGGGCTCAAGC

AAGCAAGTAGACAATGGAATGTAAAGTTAACAGAA

GCCTTGCTGCATTCTCAATTTCAACAGAGCAAATT

GGATCATTCATTGTTTATAAAAAGAGAAGGTAAAA

GCACTGTGATCATCCTTATTTATGTGGATGATATG

TTGGTAACAGGGAATGATTTGGAGTTGATTAGAAG

GACCAAGGAAGAATTACACAAAGCATTCAAGATCA

AAGATTTAGGAAATTTGAAATATTTTCTTGGTATG

GAGTTTAGCAGGTAAAAGAAAGGAATATTAATCAA

TCAAAGAAAATACGCATTAGAGATAATCTCAGAAA

CAGGACTAGGGGGAGCTAAACCTGCATGGACACCA

TTAGAAATAAATGAGAAGTTGACAGCAATTGAGTT

AGACAAGCTTACTGGAAAGGAAGATGATGACATGT

TAGAAGATGTAGGATAGTATCAAAGAGTCATTGGA

AGATTATTGTACTTGACTTTAACAAGACCTGATAT

AGCATTCTCAGTACAAACTCTTAGTCAATTTTTAC

AGCAGCCAAAGAAATCTCATTGGGATGCAGCAATG

AGGATAATCAGATATGTCAAGAGACAGCCAGGCCT

TGGAATTTTGATGAGTAGTTAATAAATCTAATACT

ATGGTAGTATACTGTGATTCAGATTGGGCATCATG

TCCAAATACAAGAAGGTCGGTATCAGGTTTTTTGG

TCAAGTATGGAGATTCATTGATTTCTTGGAAGTCA

AAGAAACAAACCACTGTGTCTAGGAGTTCAGCAGA

GGCTGAATACAGAAGTATGGGAAGTGCAGTAGCTG

AGATAGTATGGTTGACAACTCTAATGAAAGAATTG

GAGGCTGGAATTGAGATACCTGTTAAAGTTTACAG

TGACAGCAAAGCTGCATTGCAAATTGCTGCAAACC

CTGTGTTTCACGAGAGAACAAAGCACATTGAAATT

GATTGCCATTTTATTAGGCAGAAAATTCAAGAGGG

GTTAGTAAAGACTGAACATGTGGGAACTAAGGATC

-continued

AAACAGCAGACATATTGACAAAAGGGCTTCCAAGA

GTACAACATGAACATTTAGTTGGCAAGCTGGGAAT

GCTTAACATTTTTGCACCTGCCAGCTTGAGGGGGA

GTGATGAAATAGGAATAGGTTGAAGTAAATATAAT

TAGTGAGTTAGTTAGTCTTTTATCAAGTTAGTTAG

AAATTAGTTATTAGCATCTTAACTTGCACATGATA

GGTAGTTAGATATAATTAGTCACATTATAAATATG

CTGTAACAAACCAATATTGTAATTCAATTTTCTGC

AATATACAATACACAGTTTTCTCAATGATTTTTTC

TTCTTCTTCATCTTCTCCATCTTCTATTCTCTTCA

TCTTCATAGATTTAGTTACAGATTTTCAATAATTC

AACAACCATCACCATACTCACAATTACTACCACCT

CCACCATCACTATCAACCACTACAATCCTTGCGAT

CAATCTCTACTACAAACCAATGAACCATTTTCATT

ATCATAACTAGCACAGCTACTATCATCAACACATC

ATCAATTACCATATATATTCTTCACCCATCGCTGT

TAATATCACTAACTATTAATATCAATCAACTTCAC

CAGGACAATCACCATCACCACTATTAAATGTCATC

ATCACACCAGTCATTACAAAACTAACAGTCTCCAA

CATTACCAGTAATCACTAACAACAACCATTATTAC

AAACAATCTCTACTTATTTACTTTTATTCAAATAT

TTATTTAGACAAAACTGATTTTAGTAAAACAAATG

AGATCAATCTTTTTCTCGTGATTAATTTTTAAGTT

GGAATTAGTTCCAAAATACATTTAATATAGACAAA

TATGATACTCCCACCGTCCCATTTTATGTAAAAAA

ACACGTCTCATTTTCTTATATGGTAAGTATTTAAA

GGTATAATTTCTCTTTTTTACCTTTATTGATCTTA

ATTTTCTAATACATTTATGAGAAGAGAGAAAAATG

AGTTACTTTTTTAAAGAACGATTTGATAAATATTT

TAAAATCTTCATTATTTCTTAAATTTTGTGCCAGA

TCAAATGTTGTCACATAAAATGAGACGGAAAAAGT

AAAACATATCAAACACACCCTTAATTTAAAATAGT

GTAGGTACTACCTAAAAGTGGAAGTTAATTATTTG

TTTCCCCAAAATTAAATTTTACCCTTGGACAGCAA

TTCCTGTTTAAGGGTTAATTGTATAGGGACATACA

TTTTCTTCTAATAGTCCAGGGTAGTTTGGTTTTCG

ATATGTGGAAAATTATCTCGACATAAAATGCTACA

GTAACTAATTAGTACAATATTTAGTTTGTATTTAC

CATTACATTTAGCTCCACATTCACATAAATTGGTA

GTACAACATTTAATCTTCTAATTTGTACTATAACA

TTTTCATTAATAAAAAGTATGGTTTCTATCTTCAC

-continued

CATTAGCGTAACGTTCGAGTAGAGATATACATATT

TATTATTATAATATACGATTGCAAATGCCAAAGAT

GGCTAATTTTGTTTTGAGAGACTACTGCATTAAGT

AAATTTTTTCAGAGACATGTATAAGATTAAGTCTA

TTGCCAATTCTCAAATATTACTCTTTTTTACTTAT

TGTGGTTATTTATACATATTAAGTGAACTTTCTTT

TAAGACAAAAATGTGAAAGAAATGAATTTCAAATT

TGATTCAATTCCATAAAATAGCTCAAATCGGAGGA

GGAATTAATATTCAAGTCTTATAAGGAAATTATTC

ATCGATCATGATTATTTTTCCATGTTAAATTGATT

AAATCTTTTTTCATTCTTCAACATATCTAATCTTC

TACCCTACAACAAGCTCTCACCTTTCATAGTATTT

ATATAGACTATATATTCGTATAAAATATTTTTCTT

CATATCGAACACACATGATCTTTTTAGGATAGAGG

GAGTATTTTTTAAAAAAAAAATAATGGGGCAAACG

CAAATAAAATAGAACACATATATATTCTTTCTCTA

GCTGCTAATTAAGCTATGACTTTATAATTTTGTAG

CACGAGAAGAGAATAACCTTTTTGTGCTTTTCATT

TCTTTAATTTGGTTCCCCATTTTTTGAACTATCAA

TATTTAGTCCCTATCCCATCTGACTCTCTAATGA

TCTTAGGGCCACTATAAATATTGGTATTTTGCTCT

TCTTTTCTCCACCAAAAAACAACTACAACTCTTTA

AGTAGATTTTGTTTTGTTTCTTATAATTAATTAAT

AATTAACTCTAAATATATAT

In order that the disclosure may be more fully understood, the following examples are set forth. The examples described in this application are offered to illustrate the plants and methods provided herein and are not to be construed in any way as limiting their scope.

EXAMPLES

The following materials and methods were used to accomplish the examples included herein:

Plant Materials and Growth Conditions.

Seeds of tomato cultivar M82, Sweet100, MicroTom, and short internode (si)[21] were from stocks produced in-lab. The short pedicel 1 (spd1) and short pedicel 2 (spd2) mutants were obtained from Dani Zamir and Naomi Ori at Hebrew University, Israel. Seed of sler mutant in the MicroTom background (TOMJPE5066-1) was provided by the University of Tsukuba, Gene Research Center, through the National Bio-Resource Project (NBRP) of the AMED, Japan (tomatoma.nbrp.jp).

Tomato seeds were sown directly in soil in 96-cell plastic flats and grown to ~4 week-old seedling stage according to standard protocols. Seedlings were transplanted to pots in the greenhouse or fields 28-40 days after sowing. Briefly, plants were grown in a greenhouse under long-day conditions (16 h light, 26-28° C. /8 h dark, 18-20° C.; 40-60% relative humidity) supplemented with artificial light from high-pressure sodium bulbs (~250 mol $m^{-2}$ $s^{-1}$), the agricultural fields at Cold Spring Harbor Laboratory, the Cornell Long Island Horticultural Experiment Station, Riverhead, New York, and the Gulf Coast Research and Education Center, Wimauma, Florida. Plants were grown under drip irrigation and standard fertilizer regimes. Damaged or diseased plants were marked and excluded from data analyses.

CRISPR-Cas9 Mutagenesis and Plant Transformation.

CRISPR-Cas9 mutagenesis for tomato was performed as described previously[20,30-32]. Briefly, gRNAs were designed using the CRISPRdirect software[33] (https://crispr.dbcls.jp/) and binary vectors were built through Golden Gate cloning as described[34,35]. The final binary plasmids were introduced into the tomato cultivar M82 and Sweet100 seedlings by *Agrobacterium tumefaciens*-mediated transformation as described previously[31,32]. Transplanting first-generation (TO) transgenic plants and genotyping of CRISPR-generated mutations were performed as previously described[20,36].

Plant Phenotyping.

Quantification data on tomato shoots and inflorescences were obtained from the individual plants grown in greenhouses and fields at Cold Spring Harbor Laboratory. Prior to phenotyping, all CRISPR-generated null mutants were backcrossed at least once to the M82 or Sweet100 cultivar, and genotyped by PCR and sprayed by 400 mg/liter kanamycin to confirm absence of the transgene. All phenotyping was conducted on non-transgenic homozygous plants from selfing or backcrossing with WT plants. Pedicels were manually measured, peduncles and inflorescence internodes when at least half of the flowers were opened in the inflorescences. Mature red fruits were used for measurement of fruit size and mass. All measurements were taken with an electronic digital caliper (Fowler). Shoot lengths and heights were evaluated with standard 30 cm and 100 cm rulers. Fruit mass was quantified by a digital scale (OHAUS). Data for flowering time, flower, inflorescence and fruit number were quantified from matched staged plants and inflorescences. For analyses of flowering time, leaf numbers on the primary shoot were counted before initiation of the first inflorescence as described previously[7]. Exact numbers of individuals for the quantification are indicated in all figures.

Mapping-by-Sequencing.

To map the locus underlying condensed shoot and inflorescence of spd1, an $F_2$ segregating population was generated by crossing spd1 with the wild progenitor of tomato, *S. pimpinellifolium*. From a total of 96 spd1 x S. pimpinellifolium $F_2$ plants, 16 segregating spd1 mutants and 12 WT siblings were selected for tissue collection and DNA extraction. Tissue collection, library preparation, whole genome sequencing, mapping-by-sequencing and data analyses were followed as previously described[36]. The difference in allele frequency (ΔSNP index) between WT and spd1 was evaluated for all pairwise comparisons. By plotting across the 12 tomato chromosomes, one large genomic region on chromosome 8 surpassed a genome-wide 95% cut-off in SNP index. Despite a large mapping interval, SlER was the top candidate gene.

The mapping of spd2 was performed with an spd2 x S. pimpinellifolium $F_2$ population. Bulked and individual mutant and WT sibling plants were used for mapping with a core set of PCR markers that scanned the genome. The candidate region was narrowed down to 564kbp in chromosome 4, and the SlSERK1 candidate gene was sequenced from all EMS alleles, which revealed coding sequence mutations.

RNA Extraction, cDNA Synthesis and Transcriptome Profiling.

For RNA extraction, leaf tissue was collected and immediately flash-frozen in liquid nitrogen. Total RNA from leaves was extracted using the RNeasy Plant Mini Kit (QIAGEN) according to the manufacturer's instructions. 1 g of total RNA was used for reverse transcriptase PCR using the SuperScript III First-Strand Synthesis System (Invitrogen).

Tissue-specific expression patterns for SlER, SlERL1 and SlSERK1 were obtained from the tomato tissue RNA sequencing database. All data from different tissues and meristems were procured from the tomato genome project transcriptome profiling data sets deposited in the Sequence Read Archive (SRA) under accession SRP010775 and a tomato meristem maturation expression atlas[37] produced in-lab.

Yield Trials Under Agricultural Field Conditions.

Tomato yield trials were performed as previously described with slight modification[7]. The yield trial for M82 sp, sp sp5g, sp sp5g sler, $sp^{CR}$ and $sp^{CR}$ $sler^{CR\text{-}1}$ was conducted on plants grown in the fields of the Gulf Coast Research and Education Center, Wimauma, Florida (May 21, 2019). The yield trial for Sweet100 sp, sp sp5g and sp sp5g sler was conducted on plants grown in the field of Cornell Long Island Horticultural Experiment Station, Riverhead, New York (Aug. 9, 2019). Seeds were germinated in 96-cell flats in greenhouses and grown for 40 days in the greenhouse (Florida) or 30 (New York). Yield trials for this project were performed under higher-density planting of 2 plants/$m^2$ (Florida and New York) and 4 plants/$m^2$ (New York), with standard fertilizer regimes and drip irrigation. Each genotype was represented by ten biological replicates (Florida), and twelve biological replicates for yield per individual plant (New York). For block yield (randomized replicated block design), eight plants were planted in each block, and eight replicated blocks (2 plants/$m^2$ and 4 plants/$m^2$) were analyzed (New York). To evaluate fruit yield and plant weight, fruits and plants were manually separated from the plant and the soil, respectively. Total fruit yield was the sum of green and mature fruits (Red and breakers) from each plant. Harvest indices were calculated by dividing the total fruit weight by the vegetative biomass. Sugar content in fruit juice was determined by measuring the Brix value (percentage) with a digital Brix refractometer (ATAGO Palette). Exact numbers for individuals (n) of the yield trials are presented in all figures.

Growth Conditions of LED Growth Chamber and Hydroponic Vertical Farm.

To grow Sweet100 triple-determinate tomatoes in an LED growth chamber, seeds were sown in soil in flats with 32-cell plastic inserts. Seedlings were transplanted to pots in the LED growth chamber 17 and 20 days after sowing. Briefly, plants were grown under long-day conditions (16 h light, 26-28° C. /8 h dark, 18-20° C.; ambient humidity) with artificial light from LED (475 mol $m^{-2}$ $s^{-1}$) with 4000k color temperature at Cornell University, Ithaca, New York. The chamber dimensions were 1.12 m (width)×0.74 m (depth)×1.32 m (height). A total 18 pots were evenly distributed in the growth chamber for high-density planting (1 plant/0.05 $m^2$). Plants were grown under overhead watering and standard fertilizer regimes.

To demonstrate the potential of Sweet100 triple-determinate tomatoes for hydroponic vertical farming, seeds were sown in both peat moss plugs (Grow-tech) and peat/coco plugs (iHort) in flats with plastic 200-cell inserts. Seedlings were grown in a greenhouse at Cold Spring Harbor Laboratory and also a self-contained hydroponic farm inside of an upcycled insulated shipping container designed and manufactured by Freight Farms based in Boston, MA. Seedlings were grown under long-day conditions (16 h light, 26-28° C./8 h dark, 18-20° C.; 40-60% relative humidity) and with sub-irrigation containing 50 ppm of JR Peters 15-5-15 Cal-Mg fertilizer. Seedlings in the hydroponic farm were grown with artificial light from red/blue LED (150-200 mol $m^{-2}$ $s^{-1}$). Five-week old seedlings were transplanted into 128 adjacent vertical growing columns for higher-density planting (1 plant/0.03 $m^2$) and 64 vertical growing columns in an alternating pattern comprised of a column of plants next to a column with no plants for lower-density planting (1 plant/0.06 $m^2$). Equal numbers of columns containing 6 or 7 evenly spaced plants were transplanted into each section. Plants in the columns were grown with artificial light from red/blue LED (200 mol $m^{-2}$ $s^{-1}$) and the same long-day conditions. Automated irrigation systems were operated with JR Peters 15-5-15 Cal-Mg fertilizer (pH 6.0-6.4) on a 45-90 min on/30 min off cycle during the day cycle and with one 30-minute irrigation cycle in the middle of the night cycle. The concentrations of the fertilizer were gradually increased from 150 ppm to 350 ppm in accordance with plant age and size.

Phylogenetic Analysis.

Coding and peptide sequences were obtained for tomato, Arabidopsis and rice ER family members from the Phytozome v12.1 database (phytozome.jgi.doe.gov)[38]. Full length peptide sequences of Arabidopsis, rice, tomato, and *Amborella* ER family members were aligned with MAFFT version 7 (L-ins-i algorithm)[39]. Model selection and phylogenetic inference were both conducted using IQTree as implemented on CIPRES[40,41]. Full name of AmTr_v1.0_scaffold00069.214 and AmTr_v1.0_scaffold00024.267 are evm_27.model.AmTr_v1.0_scaffold00069.214 and evm_27.model.AmTr_v1.0_scaffold00024.267, respectively.

Statistical Analyses.

For quantitative analyses, exact numbers of individuals (n) are presented in all figures. Statistical calculations were performed using Microsoft Excel and R[42]. Statistical analyses were performed using a two-tailed, two-sample t-test and a one-way analysis of variance (ANOVA) with Tukey test, whenever appropriate.

Example 1. Characterization of SlERECTA (SlER)

Figure 5A:
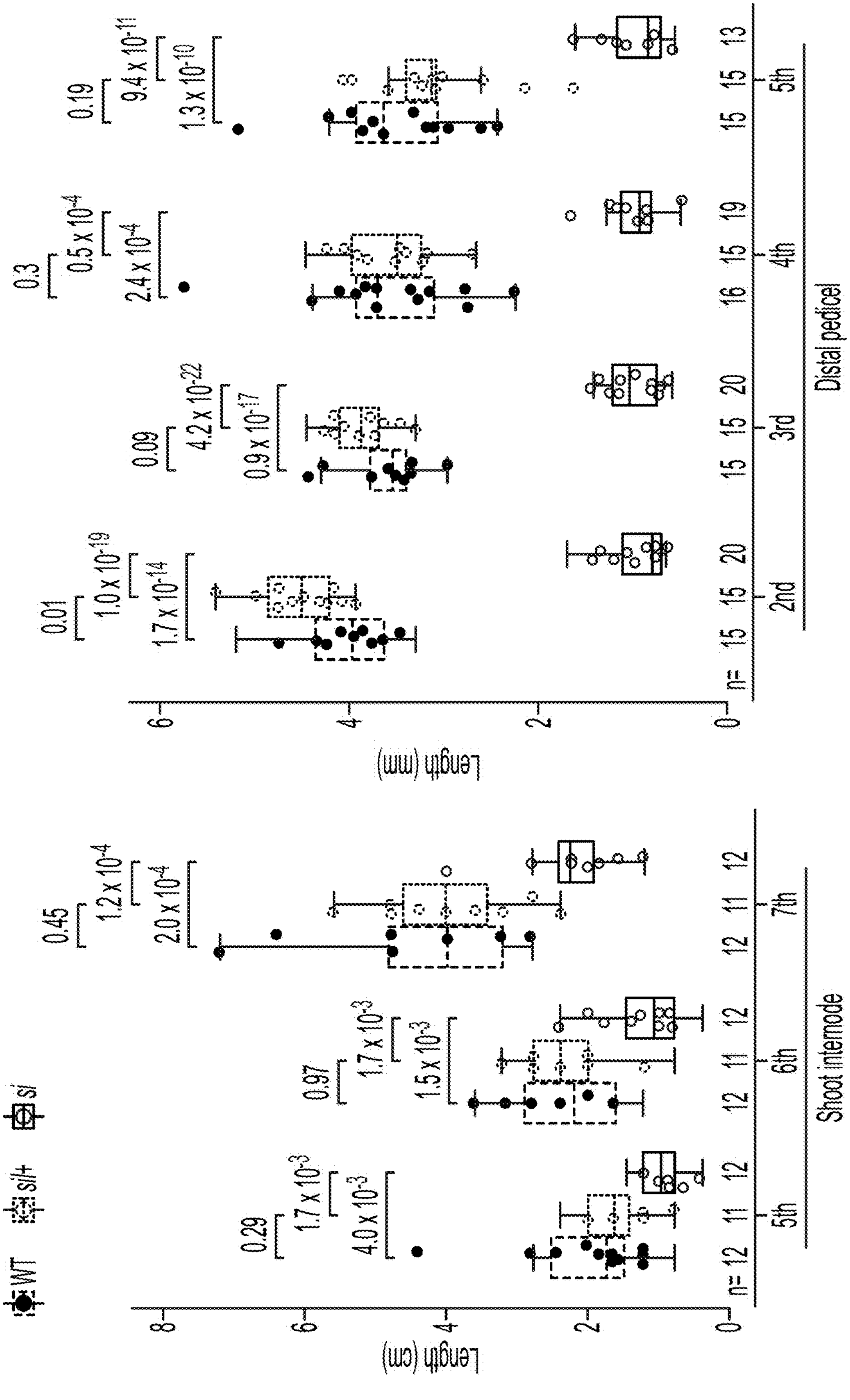
Figure 5B:
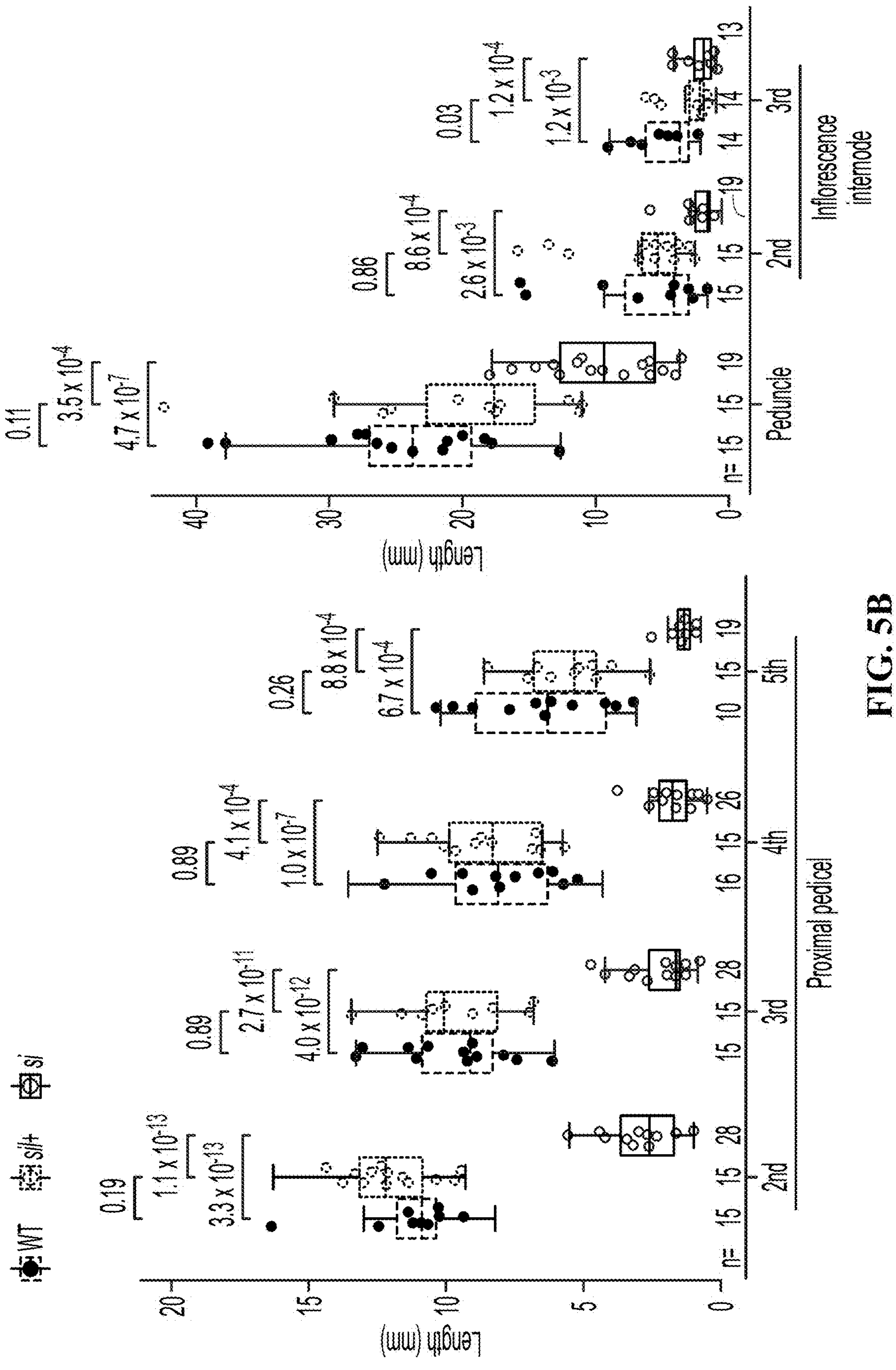
Figure 5C:
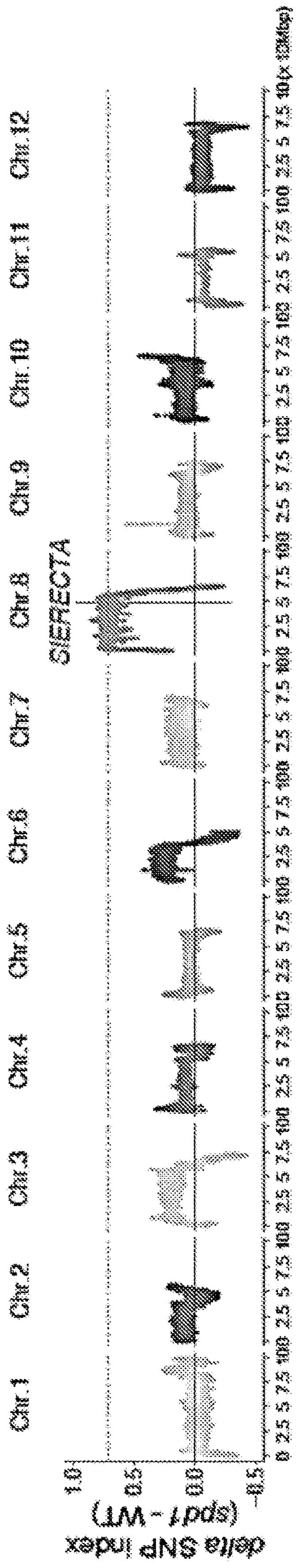
Figure 5F:
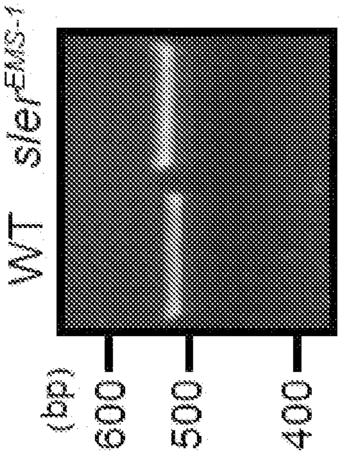
Figure 5G:
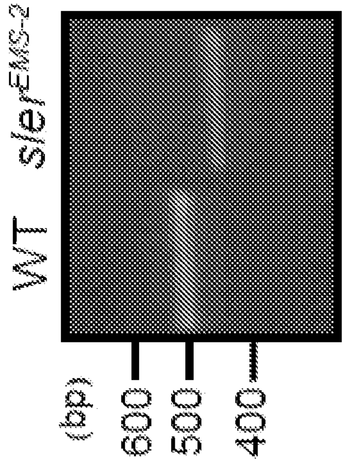
Figure 5H:
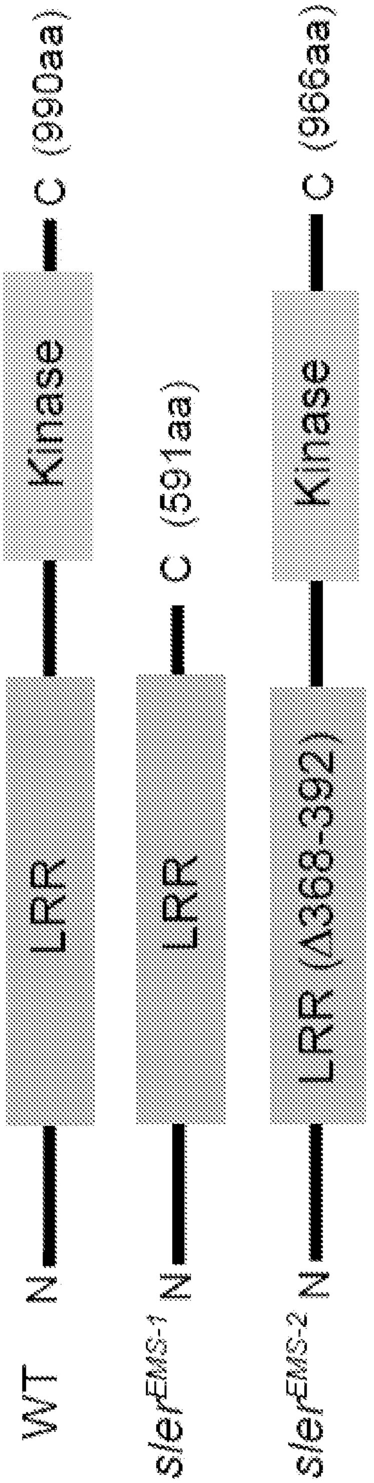
Figure 5I:
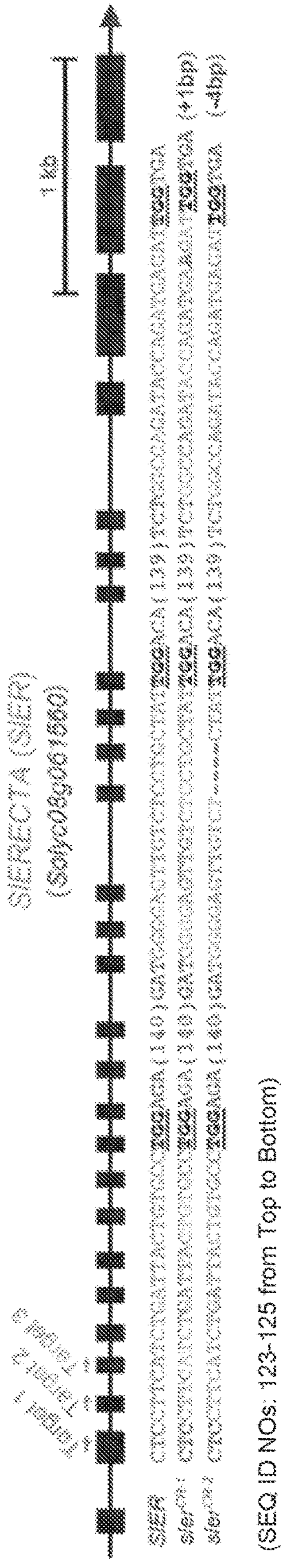
Figure 5K:
Figure 5J:
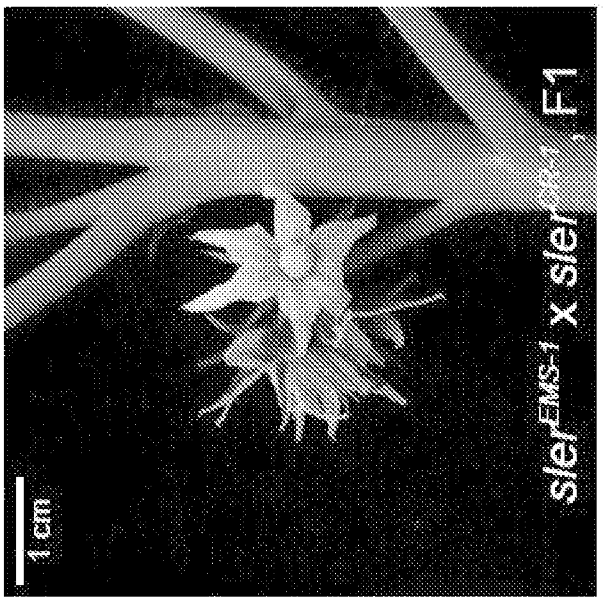
Figure 6A:
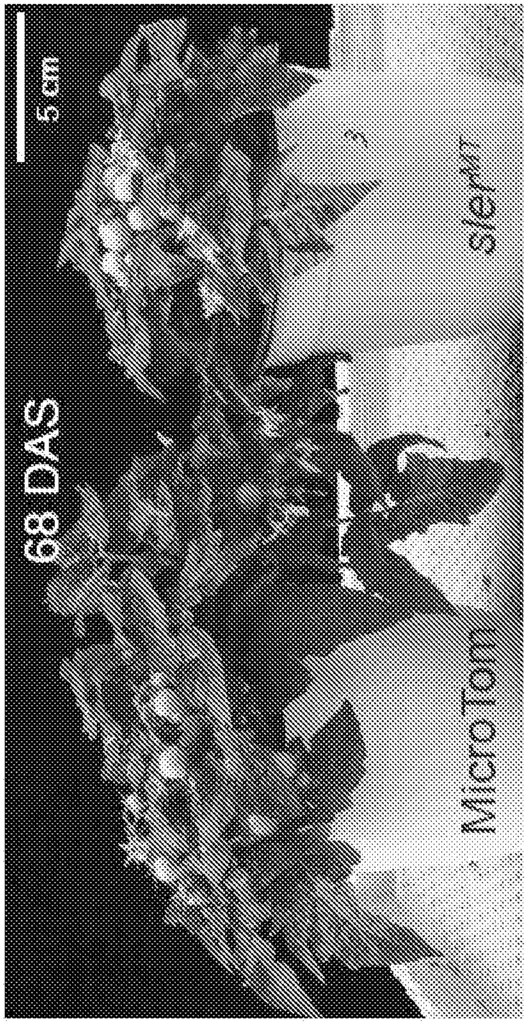
FIGS. 6A-6D show the ultra-compact plant architecture of the classical tomato cultivar "MicroTom" and its enhancement by sler.
Figure 5L:
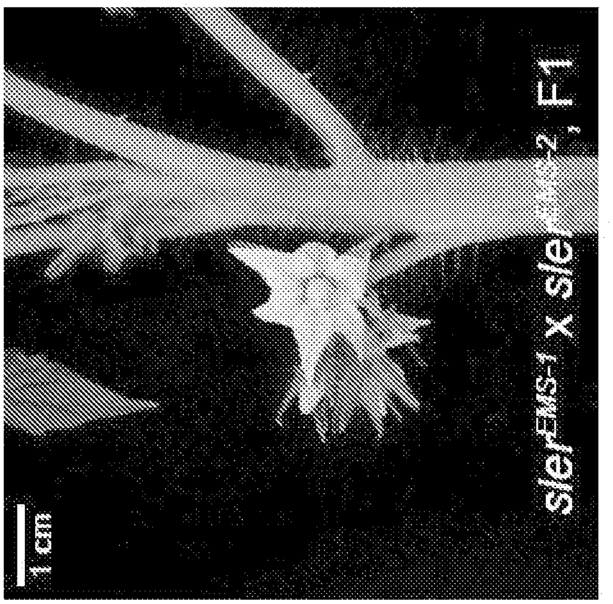
Figure 6B:
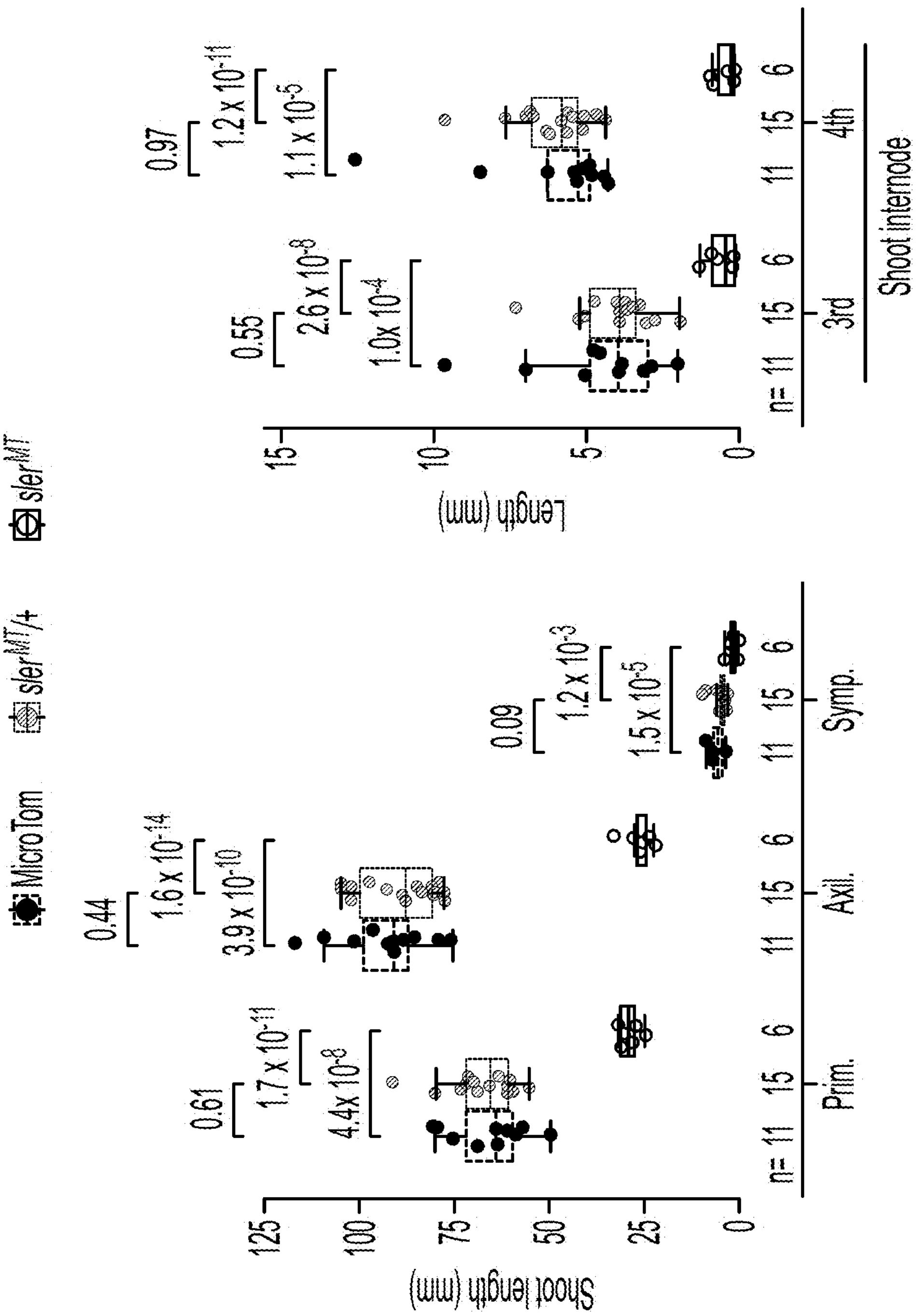
Figure 6C:
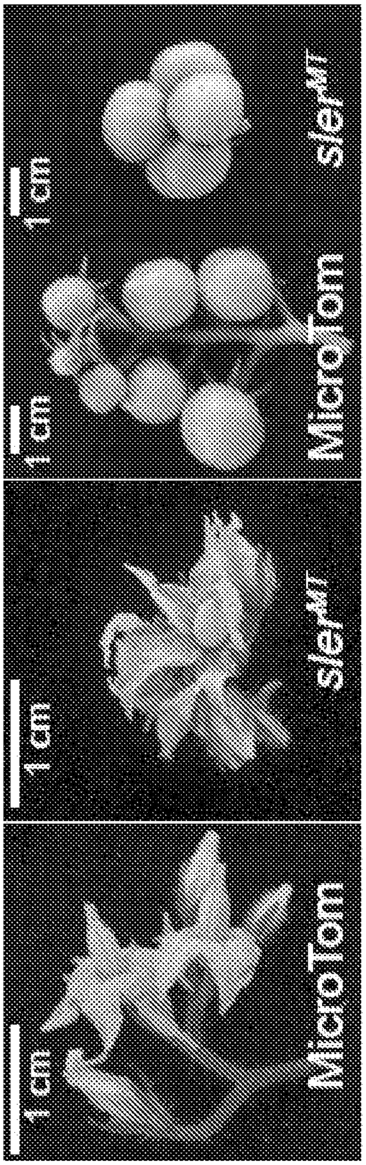
Figure 6D:
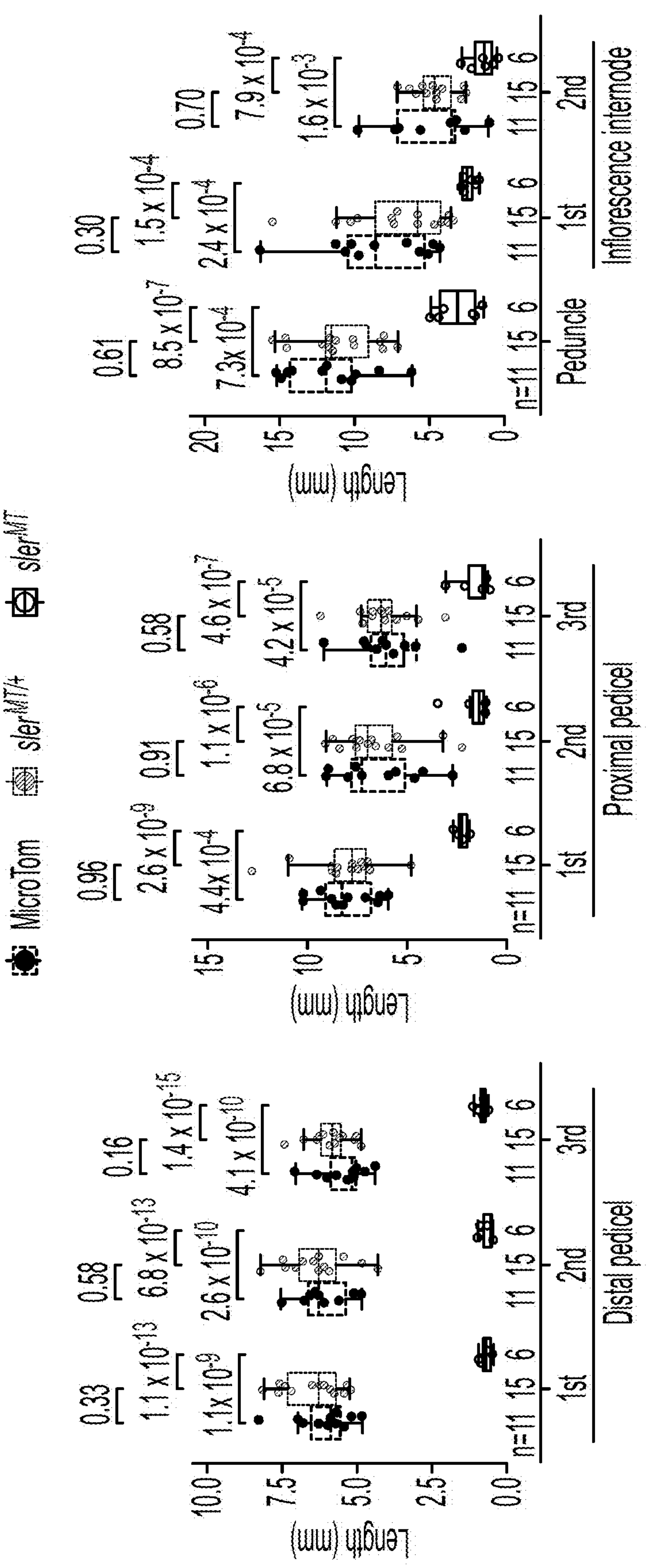

It was hypothesized that decreasing stem length between leaves and flowers (internodes) would further enhance the compactness of sp sp5g double-determinate plants without compromising productivity. In a previous ethyl methanesulfonate (EMS) mutagenesis experiment of the standard plum tomato variety "M82" [8], a dwarf mutant was identified that showed shortened internodes and extremely compact inflorescences that form tight clusters of fruits (FIGS. 1A-1D). This mutant, designated short internodes (si), showed good fruit set and high fertility, and all vegetative and reproductive internodes and flower/fruit stems (pedicels) were substantially shorter than wild-type (WT) plants and sil+ heterozygotes (FIGS. 1A-1D, FIG. 5A). These phenotypes closely resembled a monogenic recessive mutant called short pedicel 1 (spd1) that was isolated in a separate M82 mutagenesis[9,10]. Allelism was confirmed, and mapping-by-sequencing positioned silspd1 to a large interval on chromosome 8 (FIG. 5B). This region included the tomato ortholog of the classical Arabidopsis ERECTA (ER) gene, which is known to control internode length[11]. Notably, three EMS alleles, including one from a mutagenesis in the dwarf "MicroTom" genotype[12], carried point mutations that caused splicing defects and a premature stop codon (FIG. 1E and FIGS. 5C-5G, FIG. 6). In addition, CRISPR-Cas9 mutagenesis of tomato (denoted with "Sl" prefix) ER (SlER) resulted in null mutants with identical phenotypes as si/spd1, and these alleles also failed to complement the EMS mutants (FIG. 1E and FIGS. 5H-5K).

Example 2. Mutations in the Tomato Ortholog of SOMATIC EMBRYOGENESIS RECEPTOR KINASE 1 (SlSERKI)

Figure 1F:
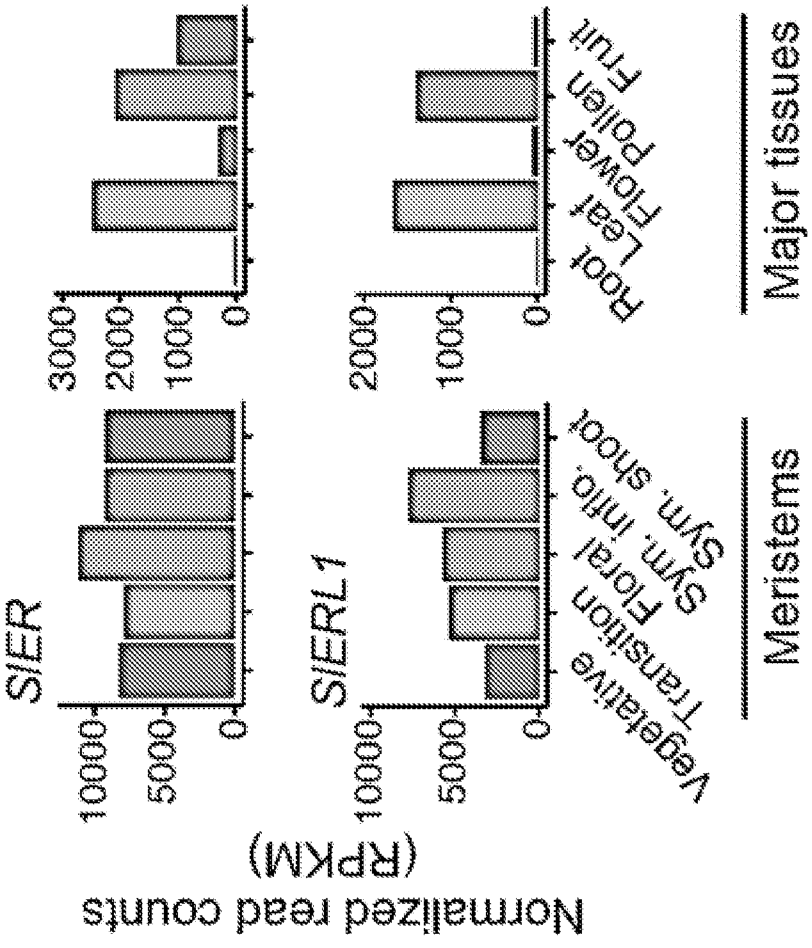
Figure 1G:
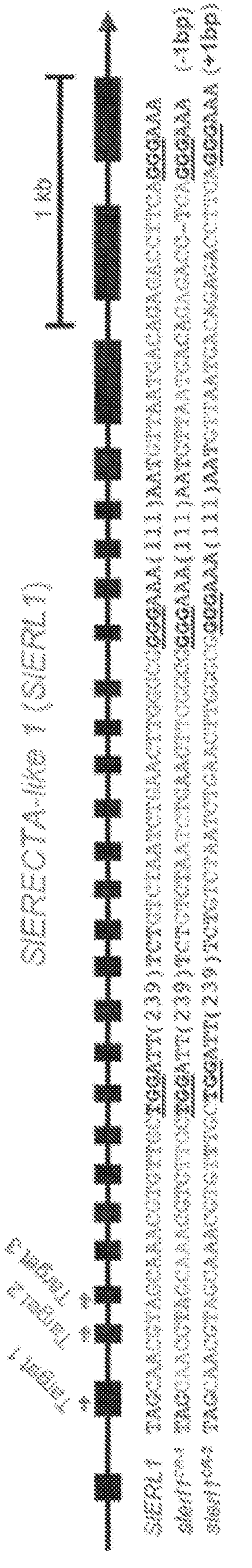
Figure 1I:
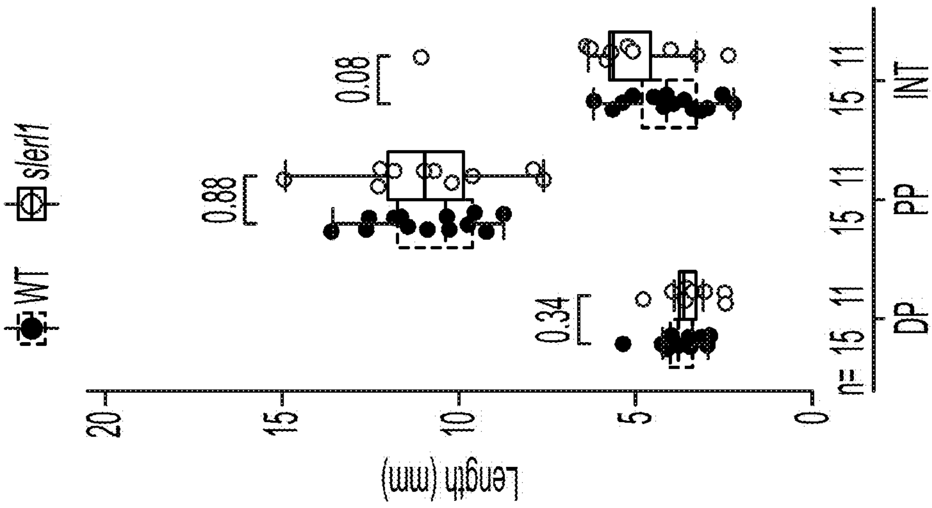
Figure 1H:
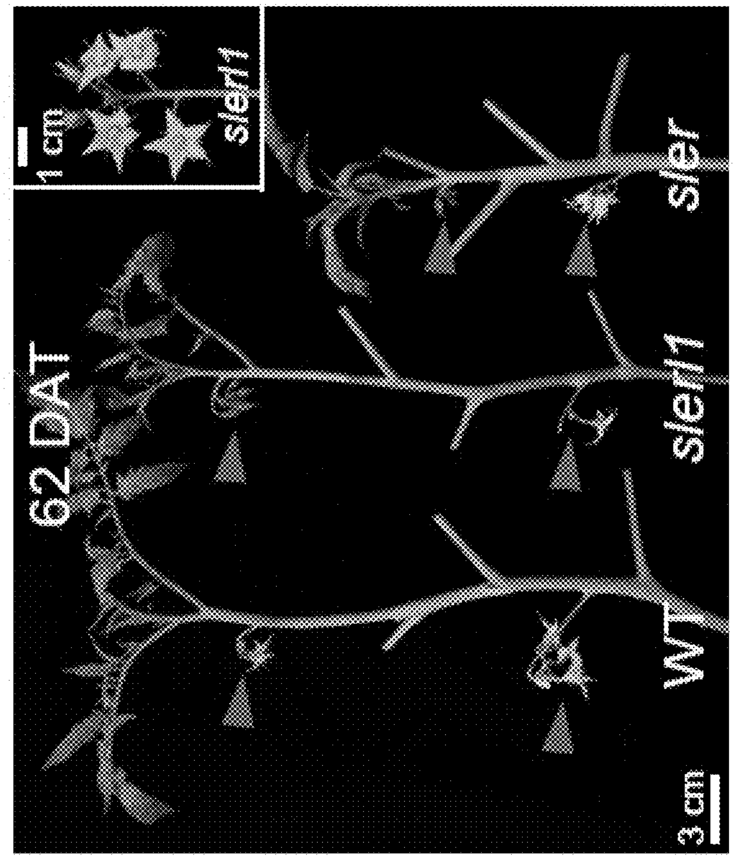
Figure 1J:
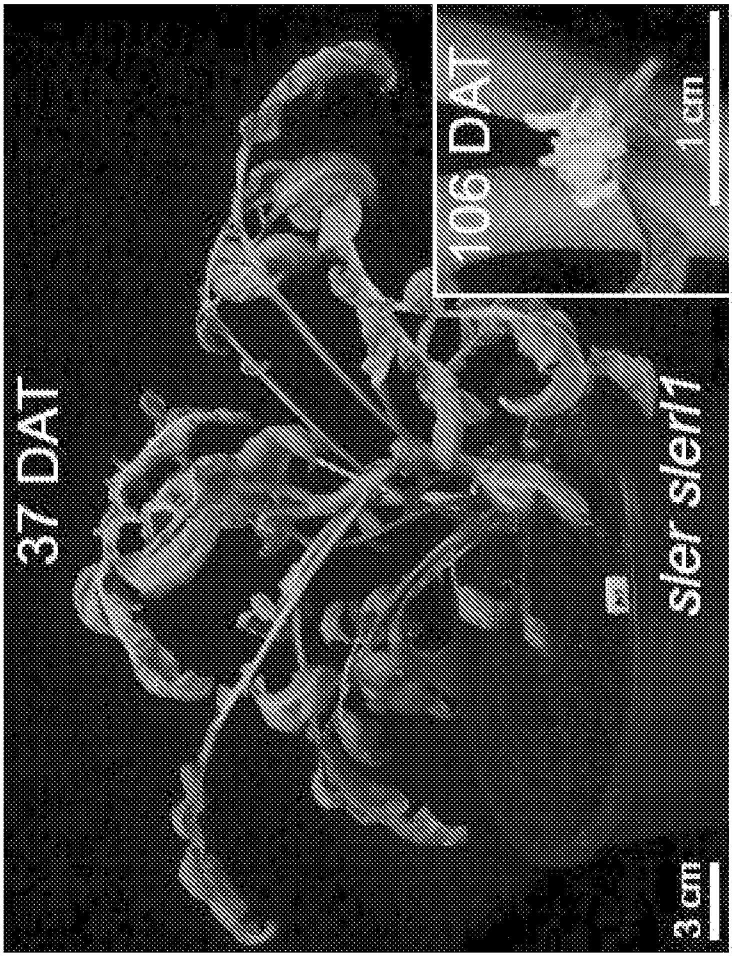
Figure 7A:
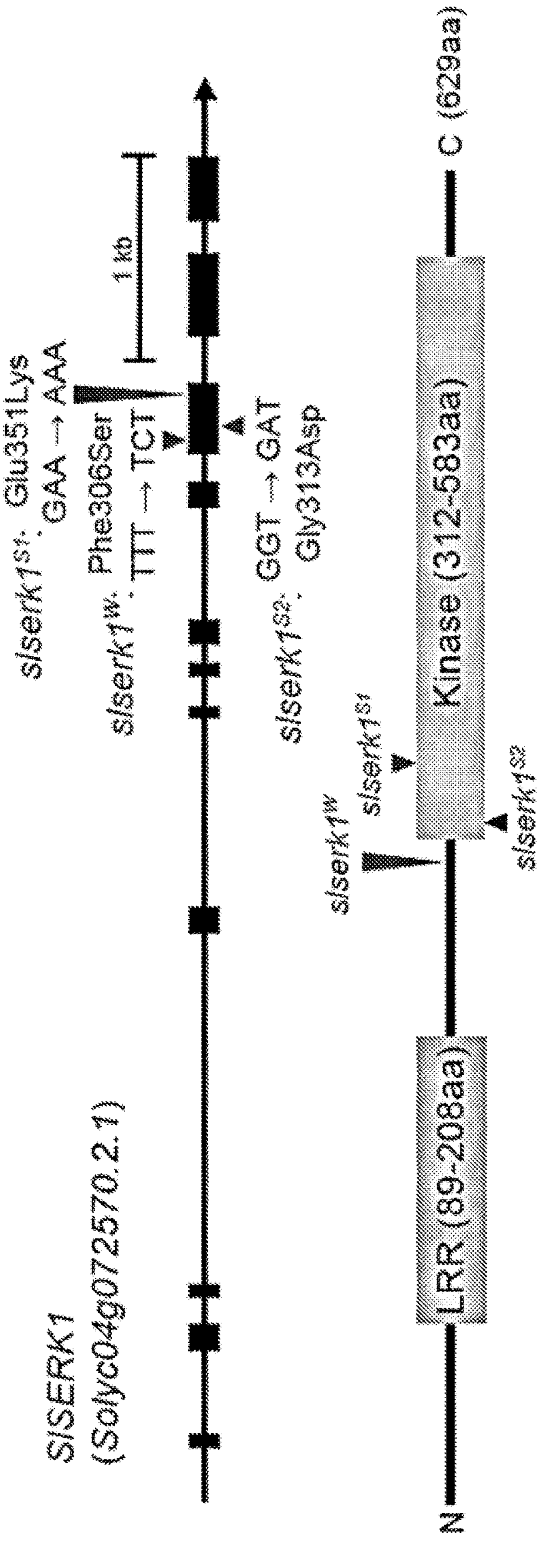
FIGS. 7A-7K show mutations in the tomato ortholog of SOMATIC EMBRYOGENESIS RECEPTOR KINASE 1 (SlSERK1) and additional phenotypic characterization of sler, slerl1 and sler slerl1 mutants.
Figure 7B:
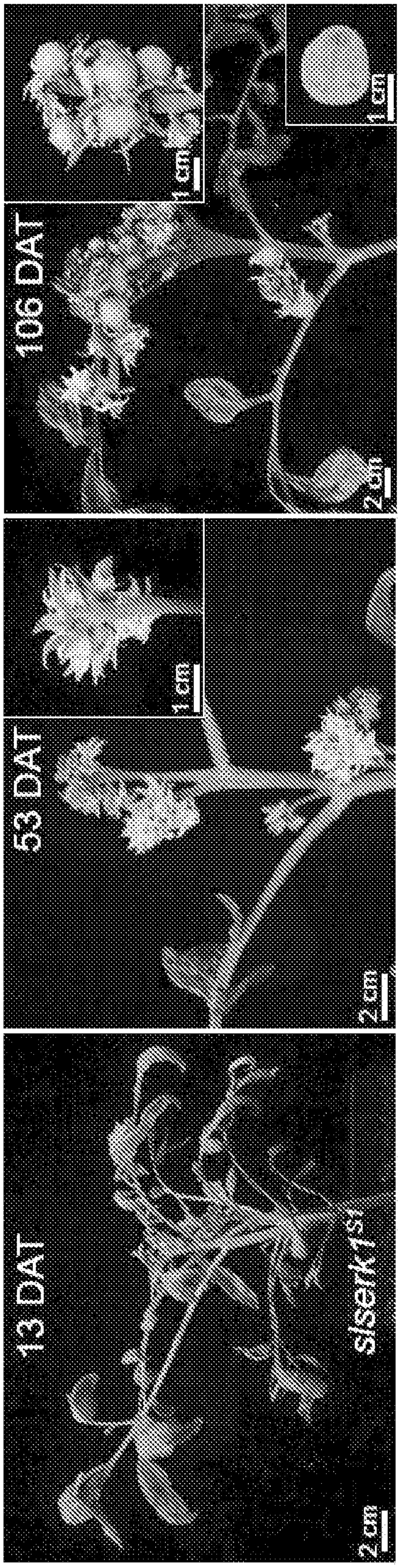
Figure 7C:
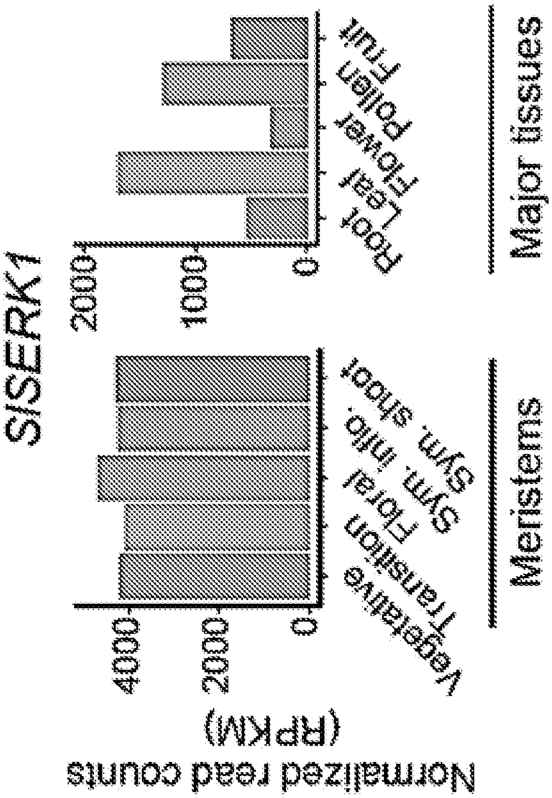
Figure 7D:
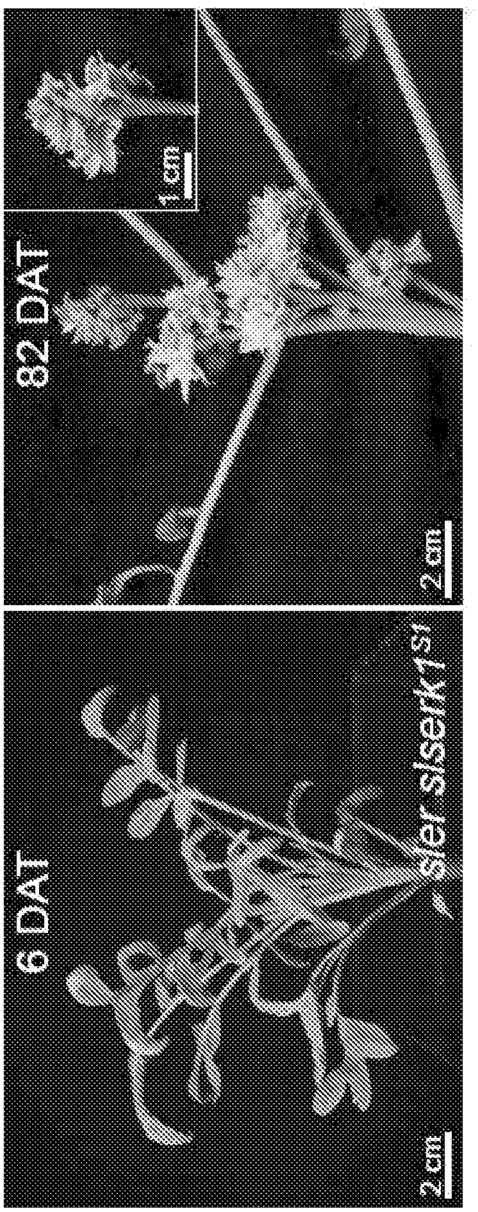
Figure 7E:
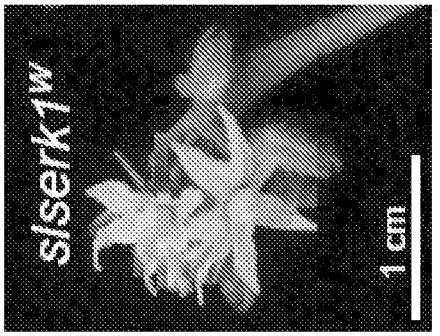
Figure 7F:
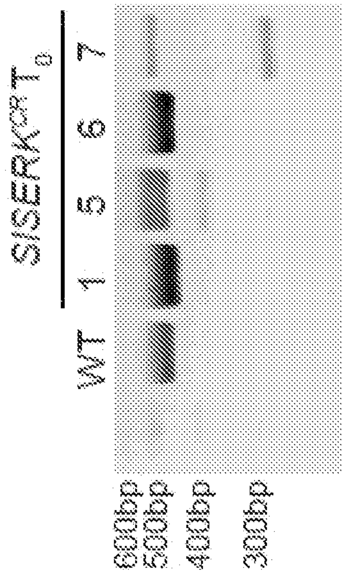
Figure 7G:
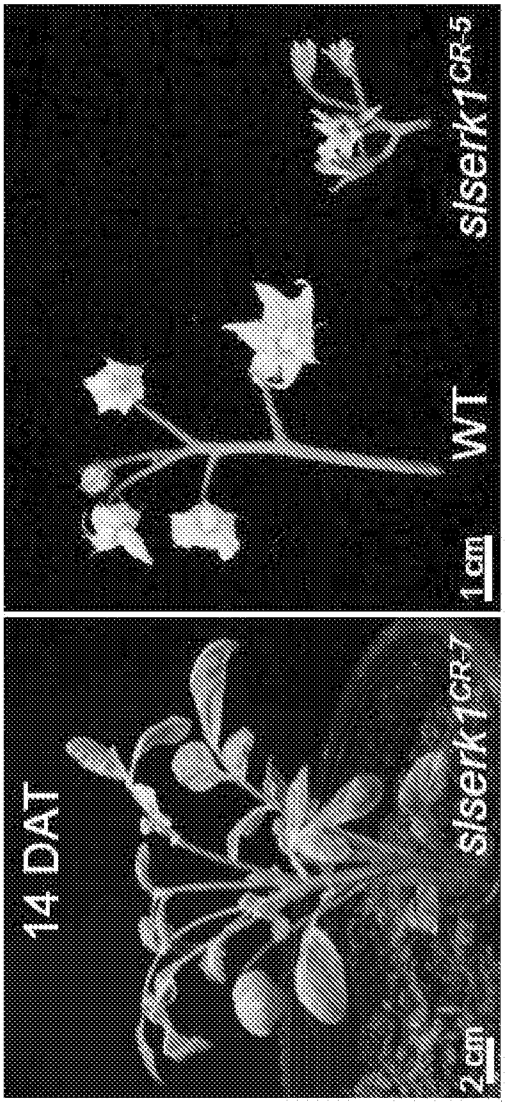
Figure 7H:
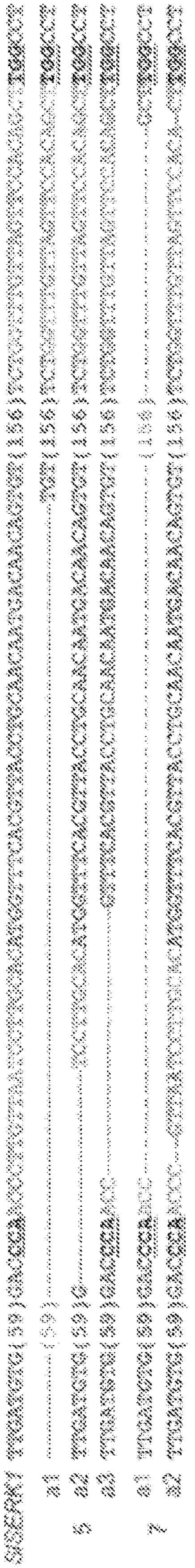
Figure 7I:
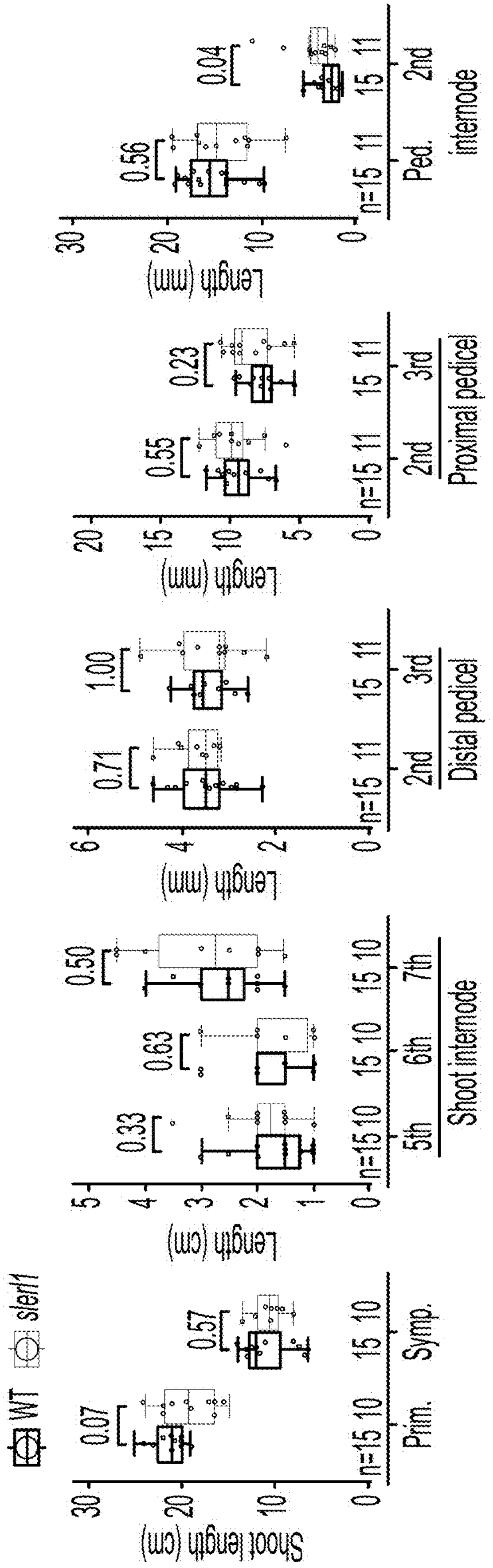
Figure 7J:
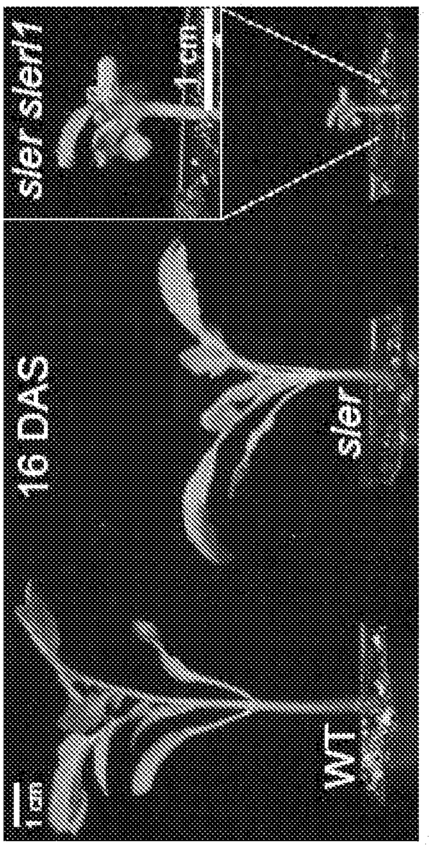
Figure 7K:
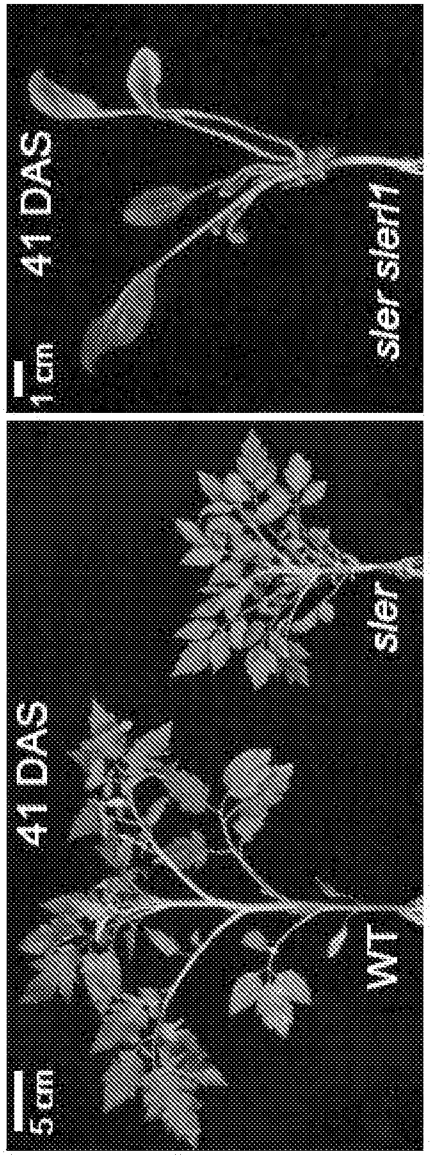

The gene underlying spd2 was also identified, a short internode mutant in the same class as sler, but with additional developmental defects that make it unsuitable for agriculture, including sterility[10]. Mapping and cloning showed three EMS alleles had mutations in the tomato homolog of Arabidopsis SOMATIC EMBRYOGENESIS RECEPTOR KINASE 1 (SERK1) on chromosome 4, which in Arabidopsis functions in a complex with ER (FIG. 7A)[13]. It was found that slserk1 mutants showed severe developmental defects including fused stems and inflorescences, and parthenocarpic fruits, and less complex leaves (FIG. 7B). The expression patterns of SlSERK1 were similar to those of SlER, and sler slserk1 double mutants showed slserk1 is epistatic to sler (FIGS. 7C-7D). SlSERK1 was mutagenized by CRISPR-Cas9 and several To individuals that were chimeric for large deletion mutations were developed. These individuals showed a range of severity similar to the EMS alleles (FIGS. 7F-7H). Finally, SlER-like 1 (SlERL1) was mutated, a paralog of SlER that shares a similar expression pattern (FIGS. 1F, 1G). While CRISPR-Cas9 generated slerl1 mutants were indistinguishable from WT plants, sler slerl1 double mutants showed severe pleiotropic growth defects resembling spd2/slserk1 (FIGS. 1H-1J, FIGS. 7I-7K).

Example 3. Creation of a Modified Tomato Using Genome Editing

Figure 2A:
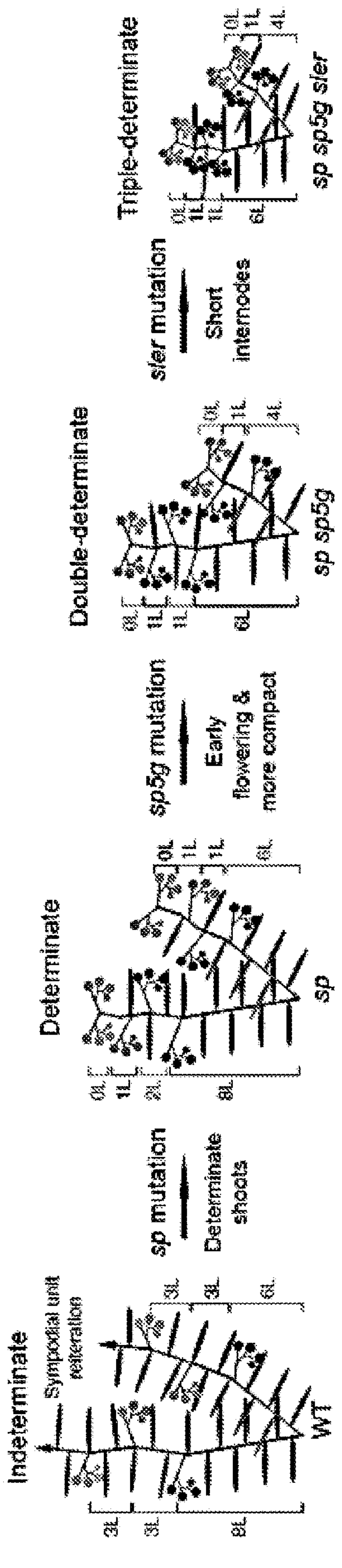
FIGS. 2A-2D show the creation of highly compact, rapid flowering tomatoes by genome editing.
Figure 2B:
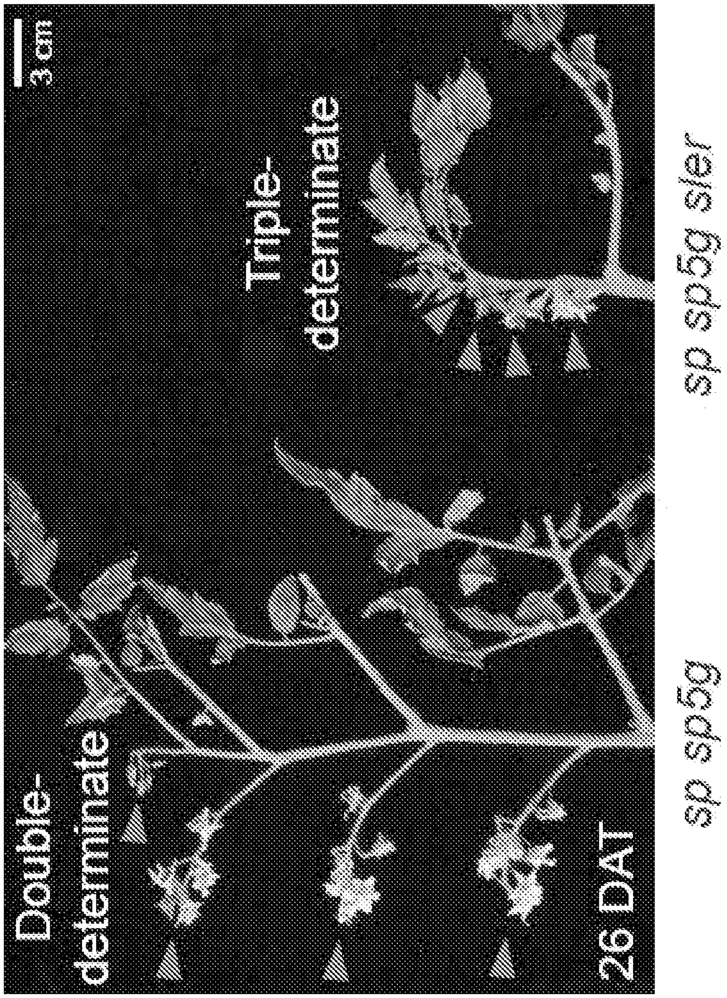
Figure 2C:
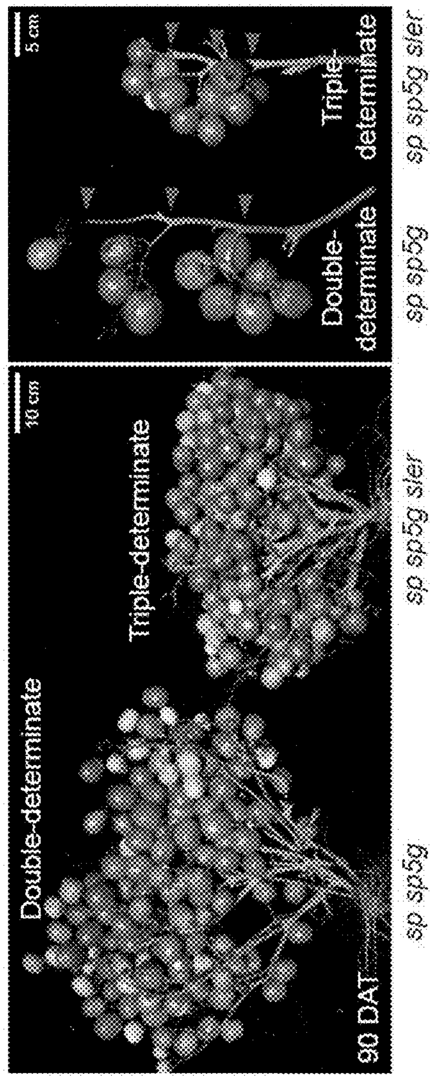
Figure 2D:
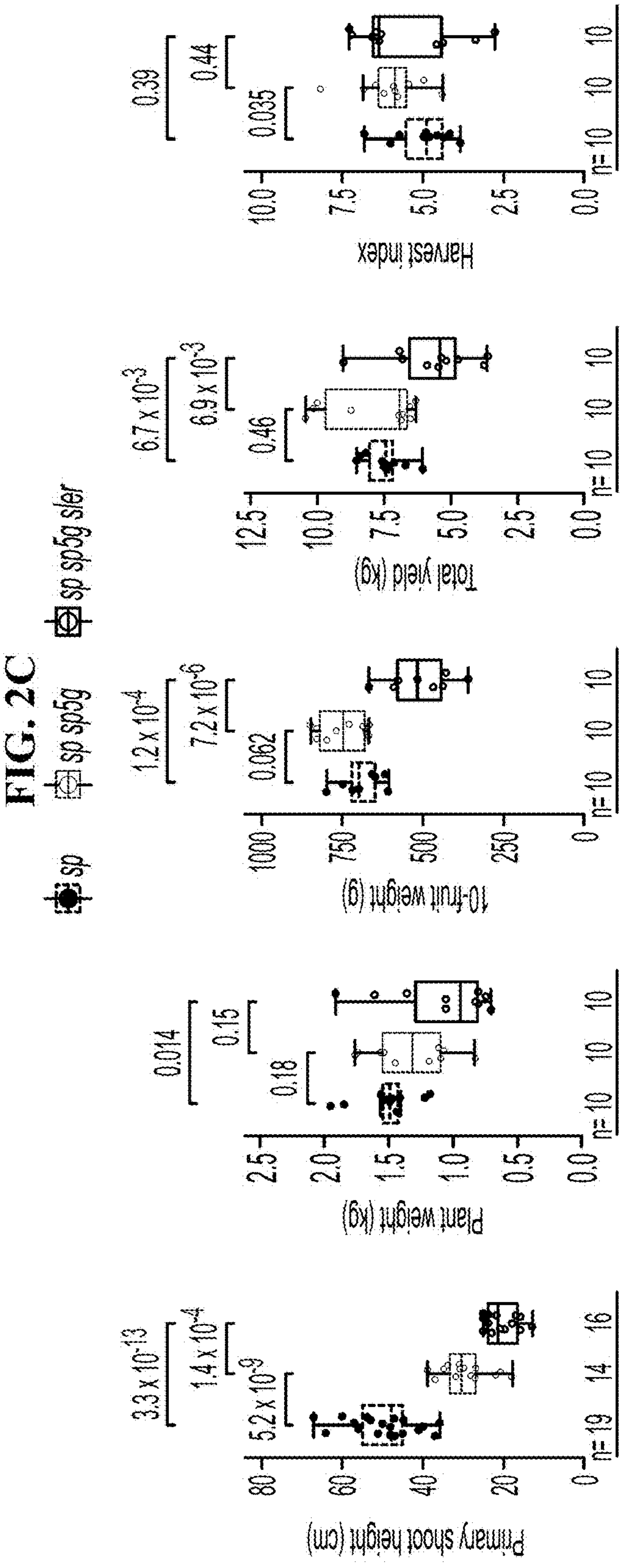
Figures 8A, 8B:
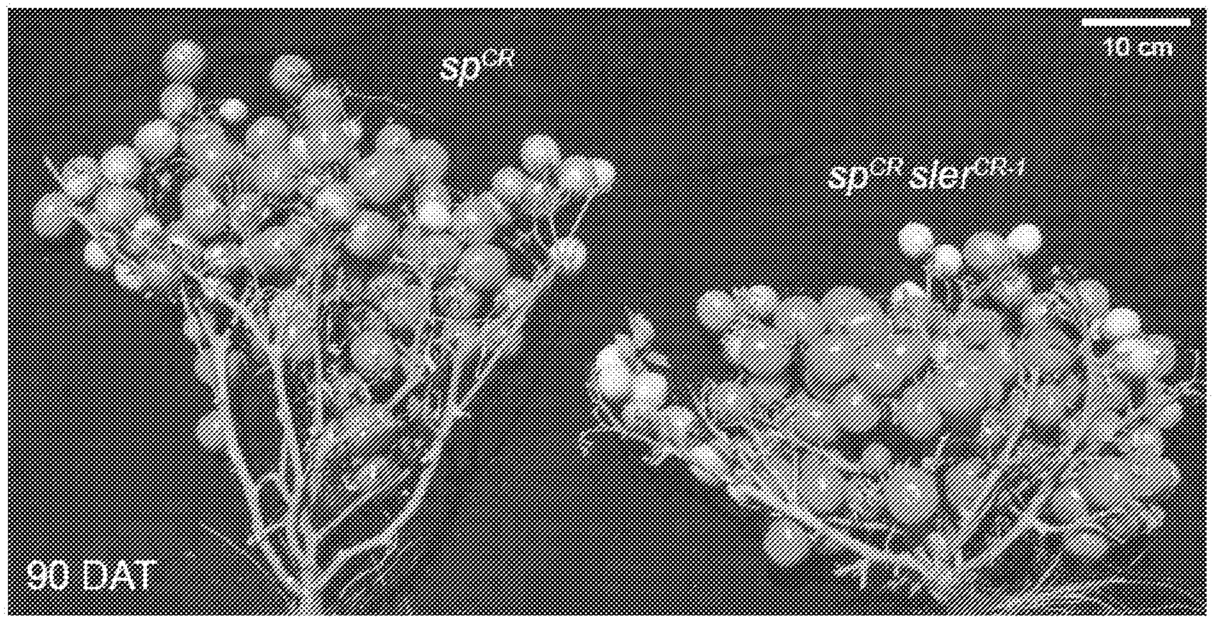
FIGS. 8A-8D show comparison of field-grown mature plants of sp$^{CR}$ single mutants and sp$^{CR}$ sler$^{CR\text{-}1}$ double mutants, and additional comparisons between sp determinate, sp sp5g double-determinate and sp sp5g sler triple-determinate plants.
Figure 8C:
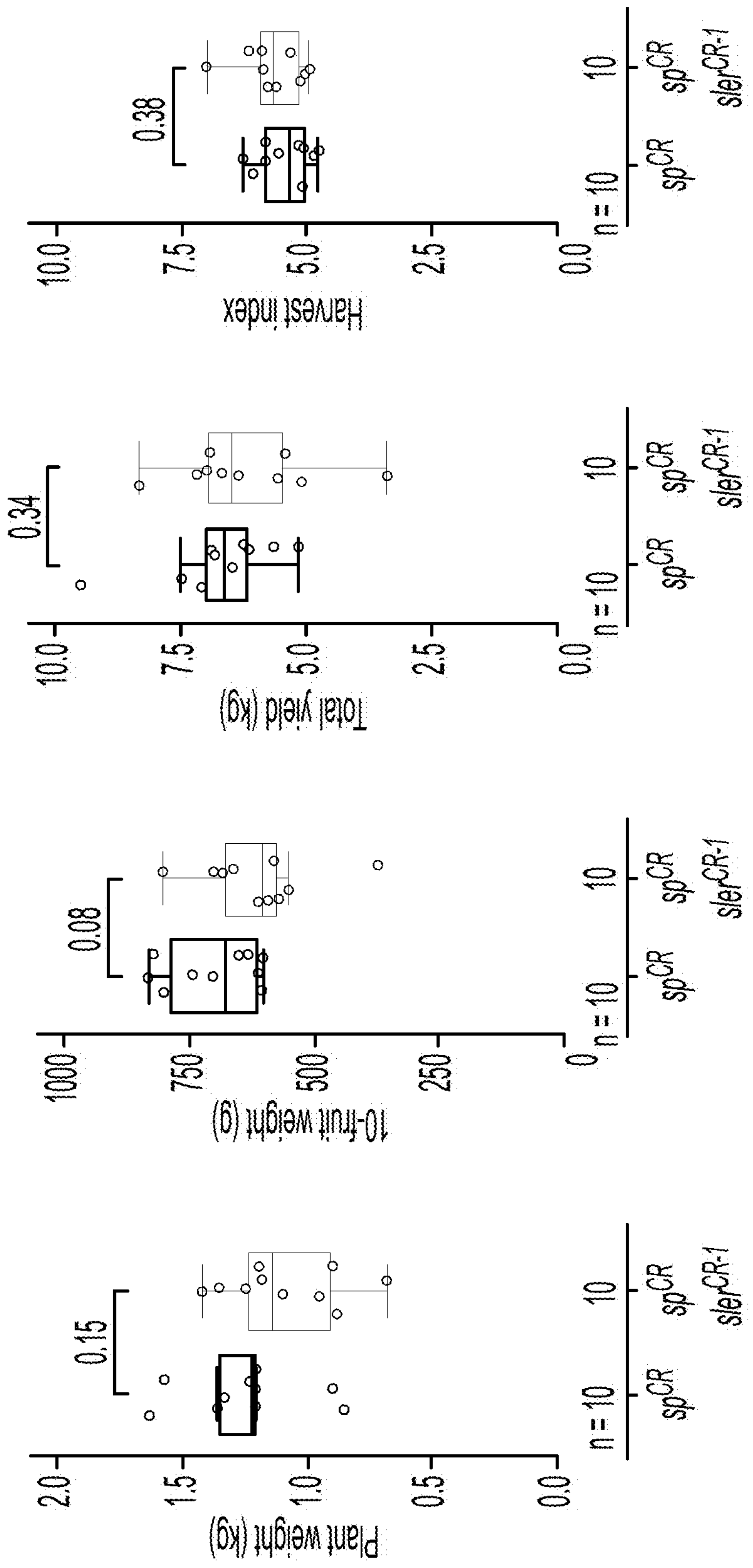
Figure 8D:
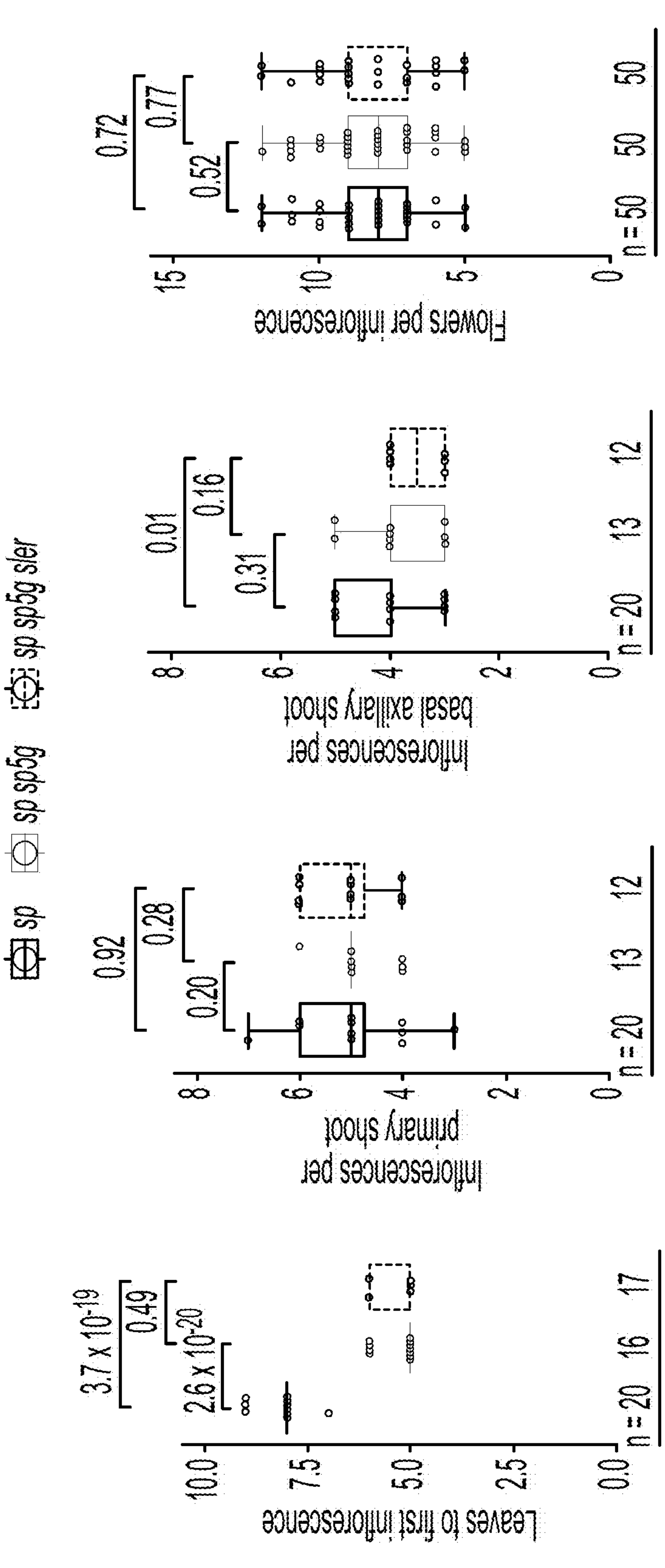

This example describes a comparison of field-grown mature plants of $sp^{CR}$ single mutants and $sp^{CR}$ $sler^{CR-1}$ double mutants, and additional comparisons between sp determinate, sp sp5g double-determinate and sp sp5g sler triple-determinate plants. The results show conservation of function for ER and two of its interacting receptors, but for the purpose of agricultural application the primary interest was in the specific phenotype of short internodes caused by mutations in SlER. However, ER has been shown to have multiple roles in plant development, for example in meristem maintenance and stomatal patterning44-8, which could impact agricultural productivity. To test agricultural performance of the sler mutant, specifically its potential to increase compactness of double determinate sp sp5g plants (FIG. 2A), all combinations of double and triple sp, sp5g, and sler mutants in the M82 background were generated and shoot architecture and yield components in greenhouses and agricultural fields were evaluated (FIG. 2). Compared to sp determinate plants, sp sler plants surprisingly produced condensed shoots with no yield loss (FIGS. 8A-8C). Notably, the sp sp5g sler triple mutants were the most compact of all genotypes (FIGS. 2B-2D), and these "triple-determinate" plants were still early flowering and produced the same number of inflorescences and flowers as sp sp5g double-determinates (FIG. 8D). Though a smaller fruit size caused a reduction in yield, harvest index (defined as the total yield per plant weight) of the triple-determinates exceeded sp determinate plants and matched sp sp5g double determinates (FIG. 2D). Together, these results suggest that CRISPR-Cas9 targeting of only three genes, controlling flowering time (SP5G), growth termination (SP), and stem length (SlER), can transform any tomato genotype into a compact, early yielding form.

Example 4. CRISPR-Cas9 Generation of a Tomato Variety

Figure 3A:
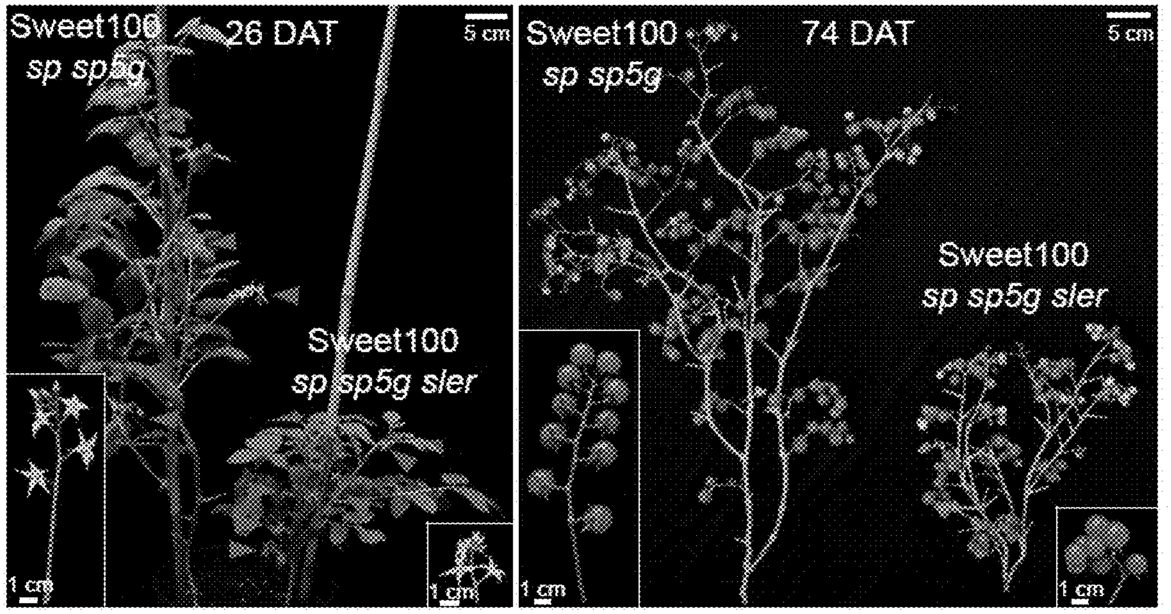
FIGS. 3A-3F show CRISPR-Cas9 generation of a rapid cycling, highly compact cherry tomato variety.
Figure 3B:
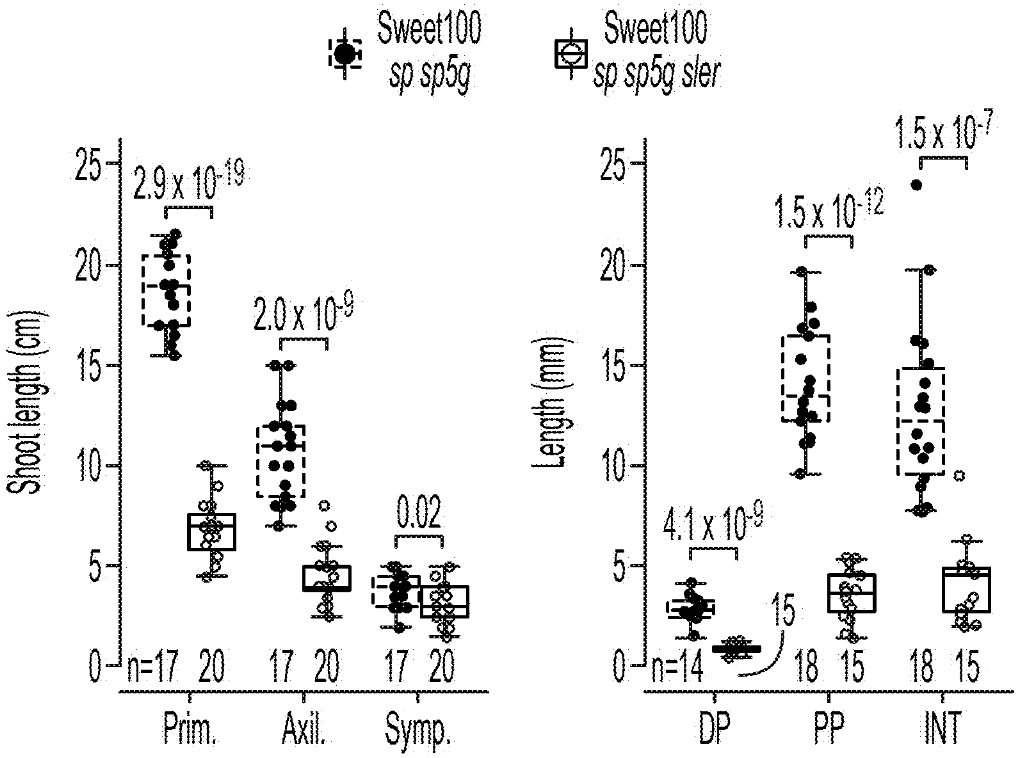
Figure 3C:
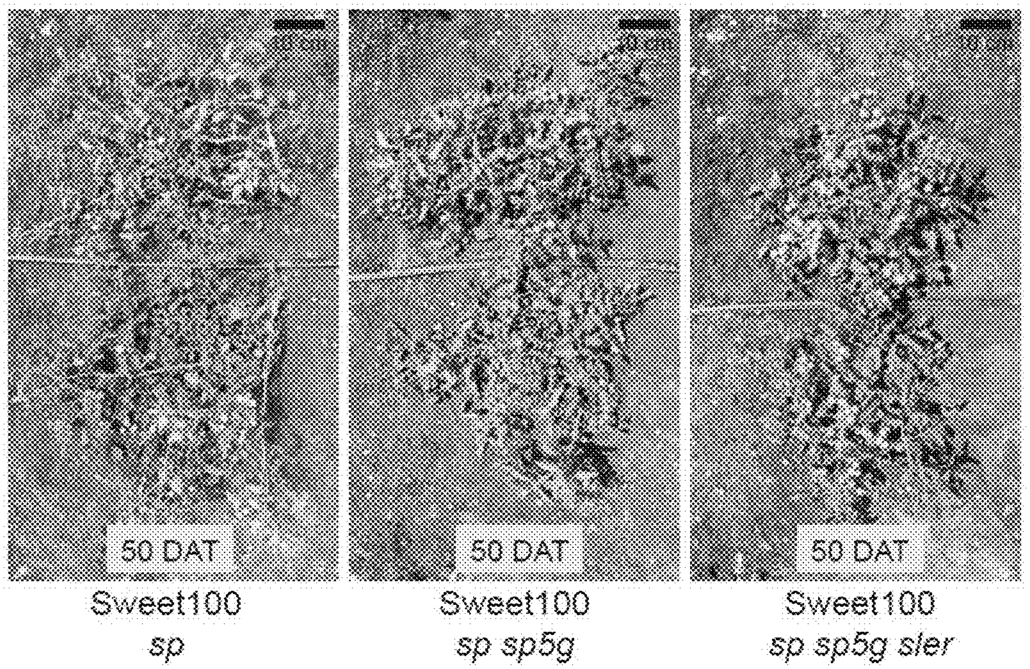
Figure 3D:
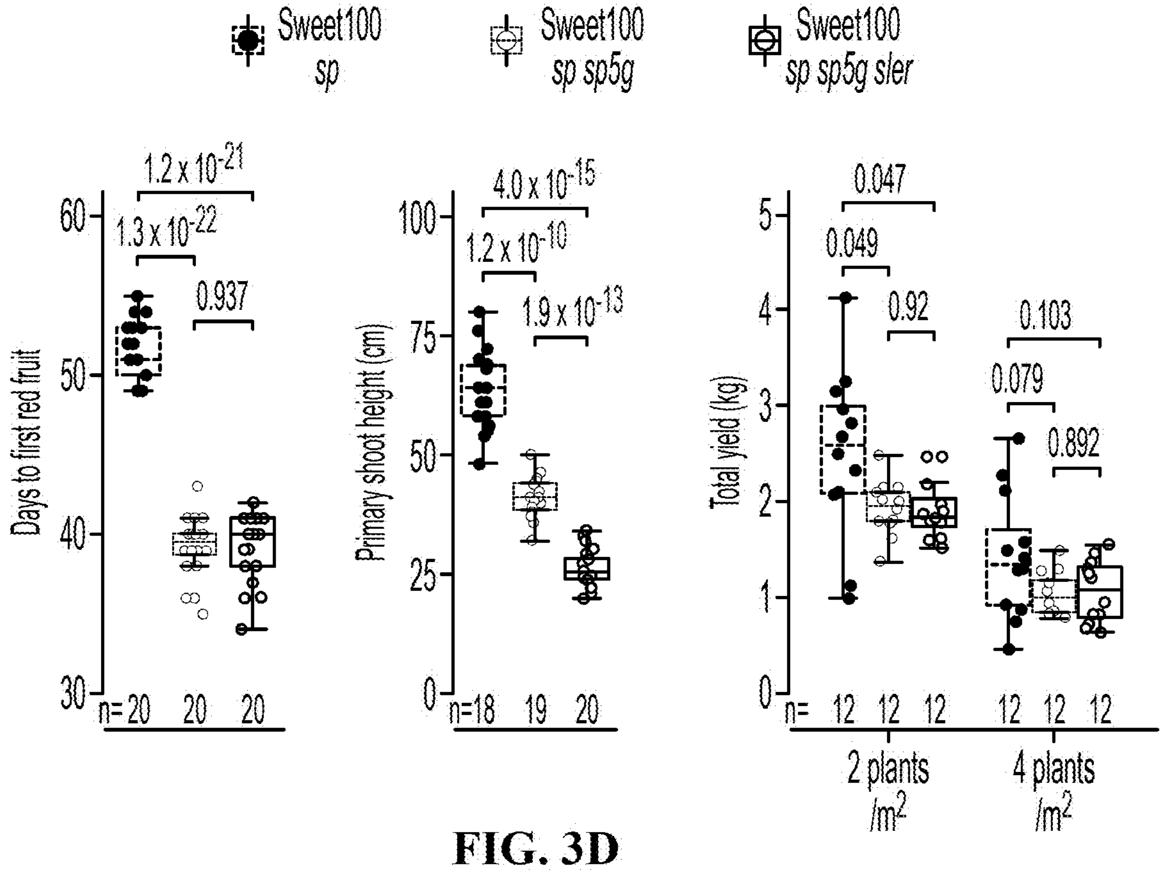
Figure 3E:
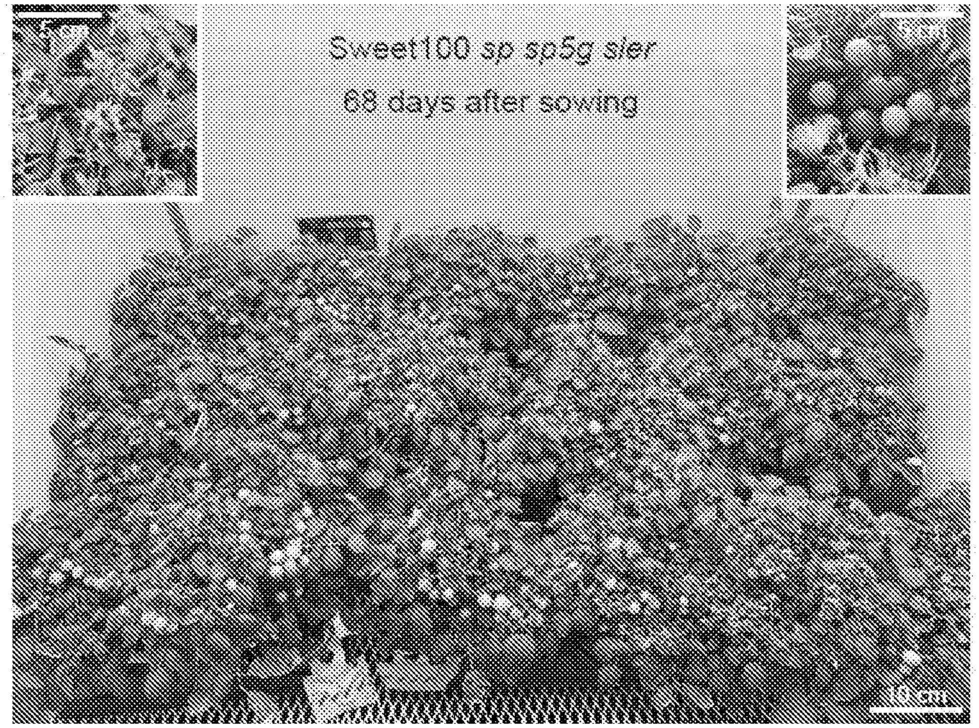
Figure 3F:
Figure 4:
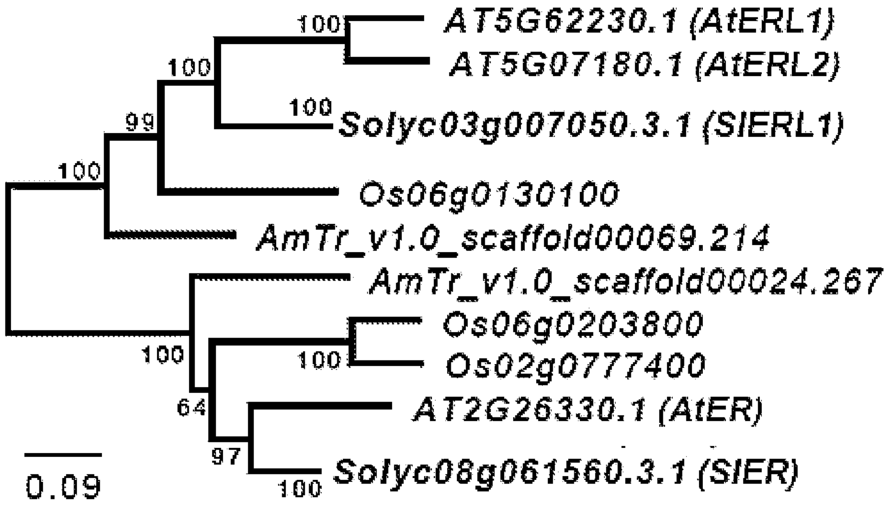
FIG. 4 shows the phylogenetic tree of the ER gene family in Arabidopsis, tomato, rice, and *Amborella* (*A. trichopoda*).
Figures 9A, 9B:
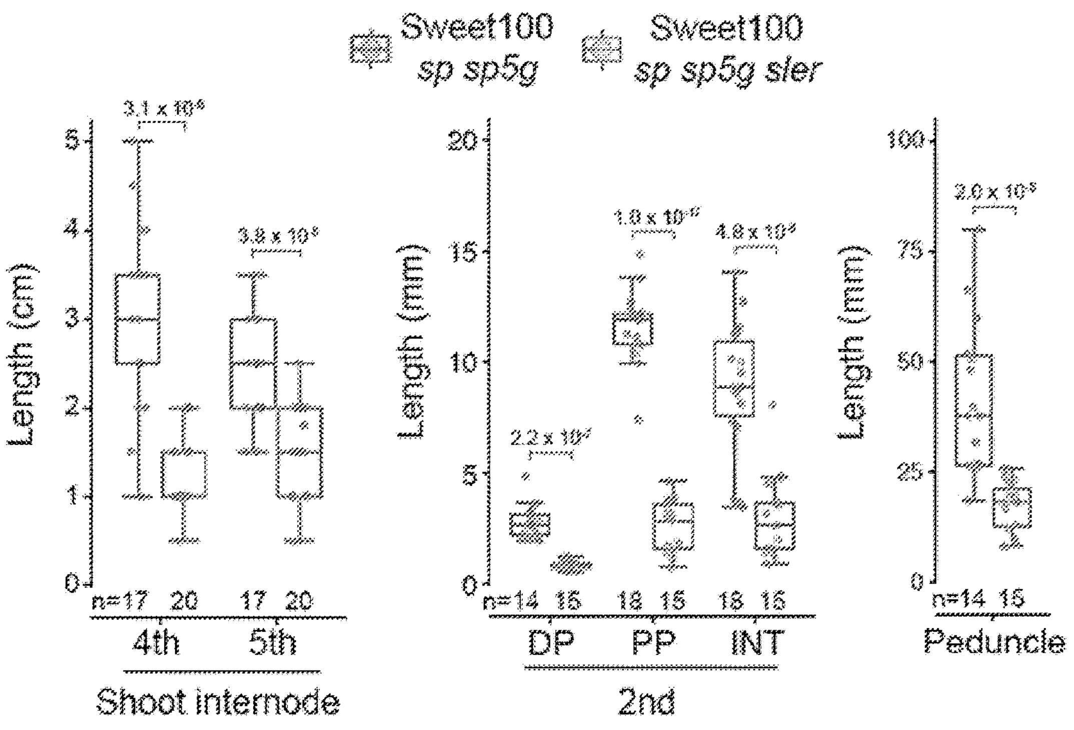
FIGS. 9A-9E show CRISPR-Cas9 mutagenesis of SlER in the cherry tomato cultivar Sweet100 and additional comparisons between Sweet100 sp determinate, sp sp5g double-determinate and sp sp5g sler triple-determinate plants.
Figure 9C:
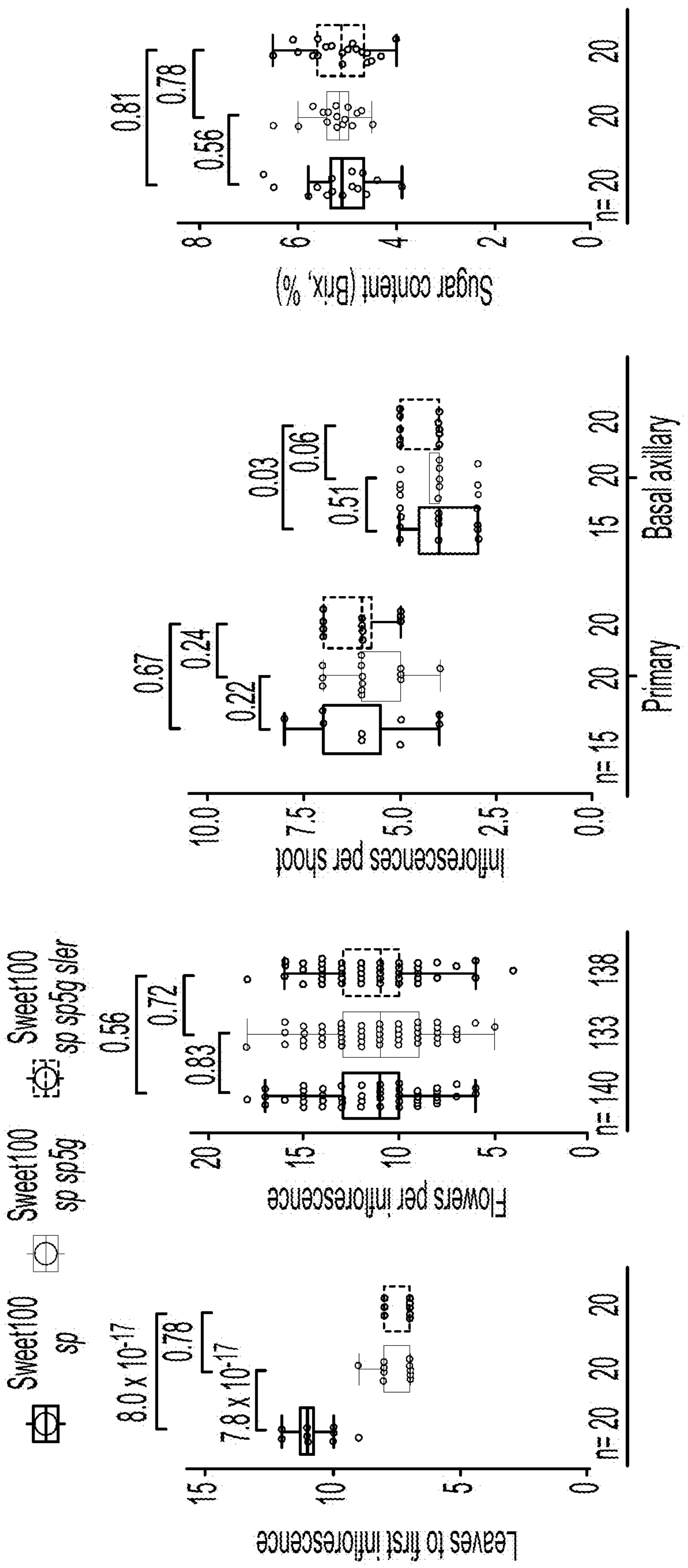
Figure 9D:
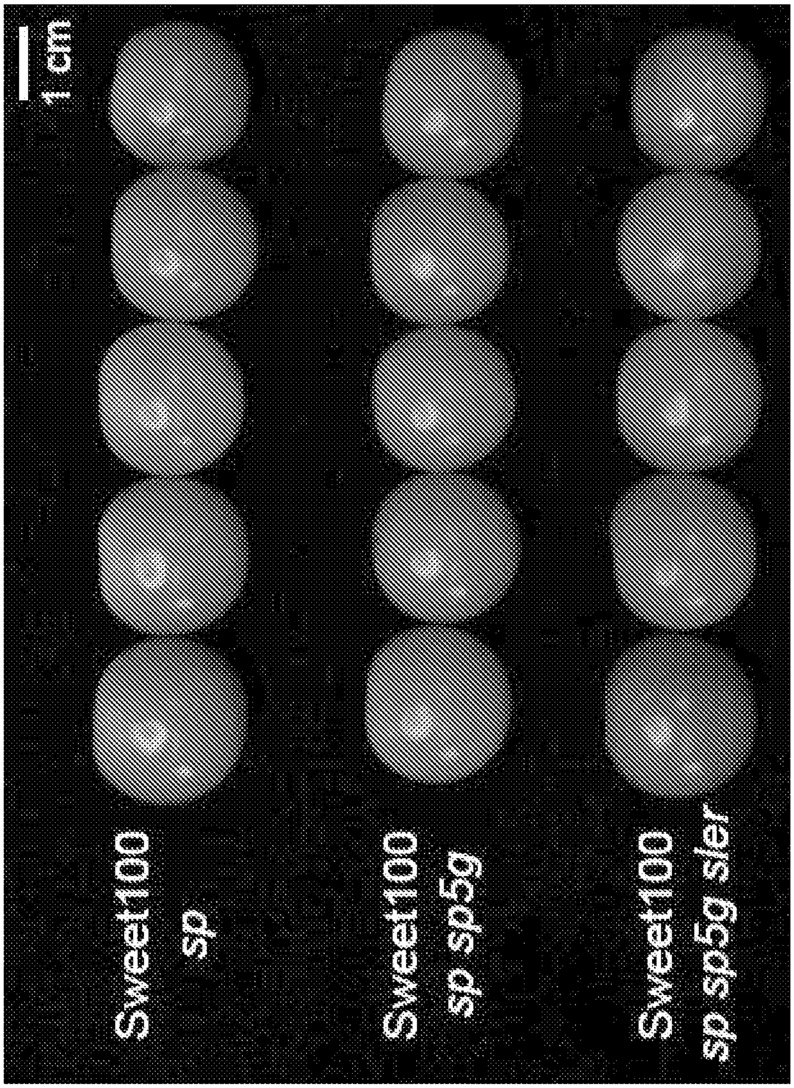
Figure 9E:
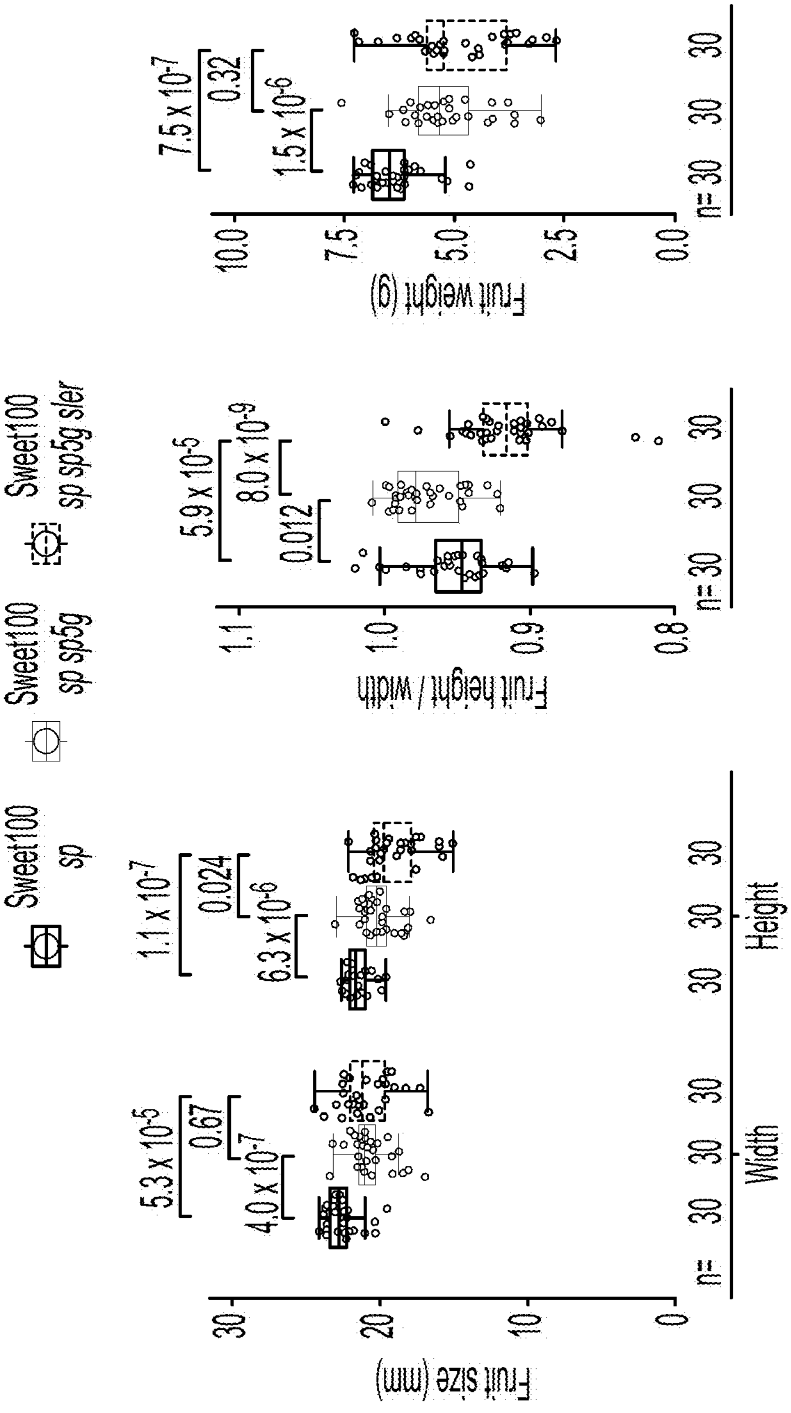
Figure 10A:
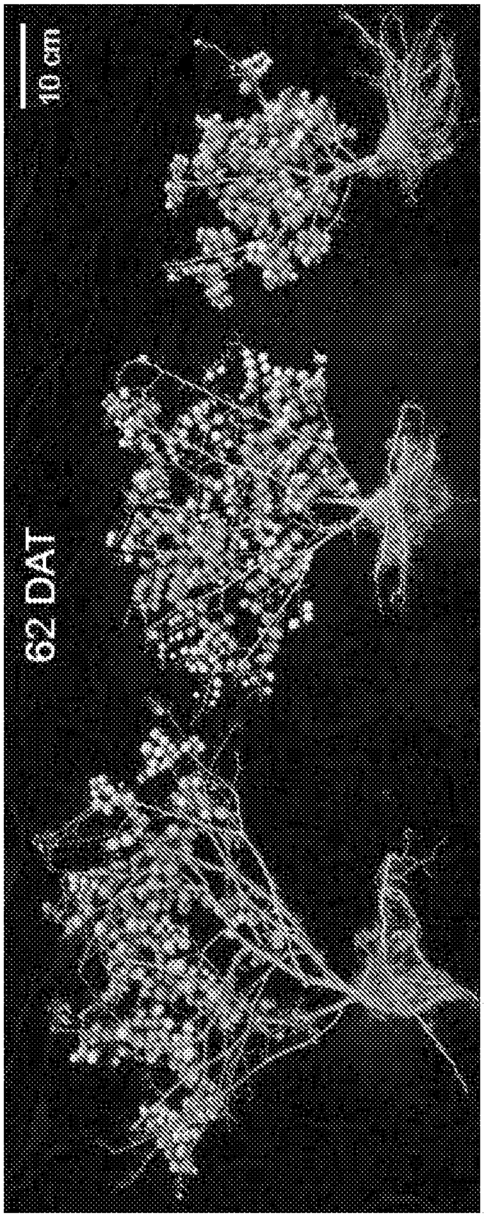
FIGS. 10A-10C show yield trials of Sweet100 sp determinate, sp sp5g double-determinate and sp sp5g sler triple-determinate plants in higher-density planting.
Figure 10B:
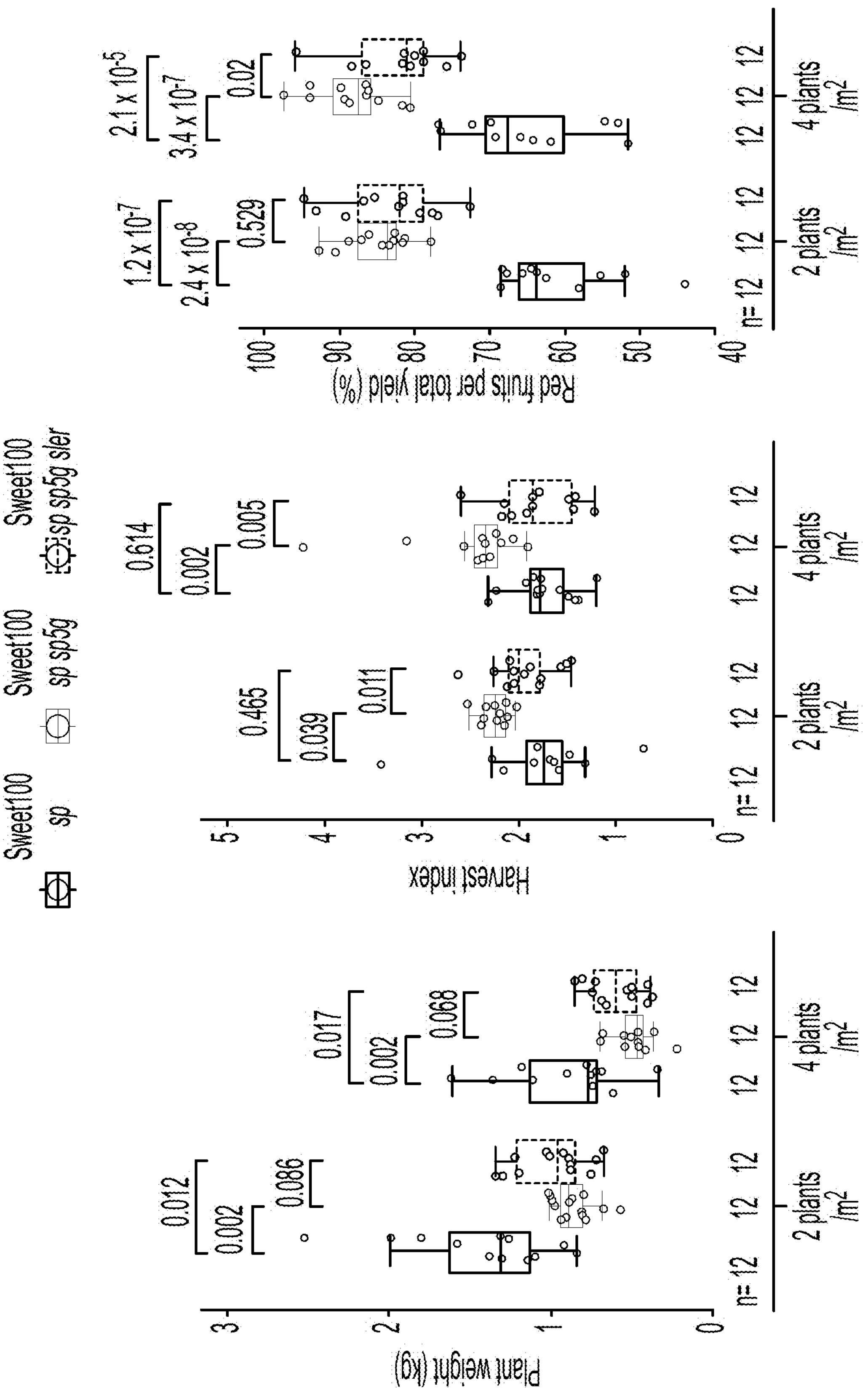
Figure 10C:
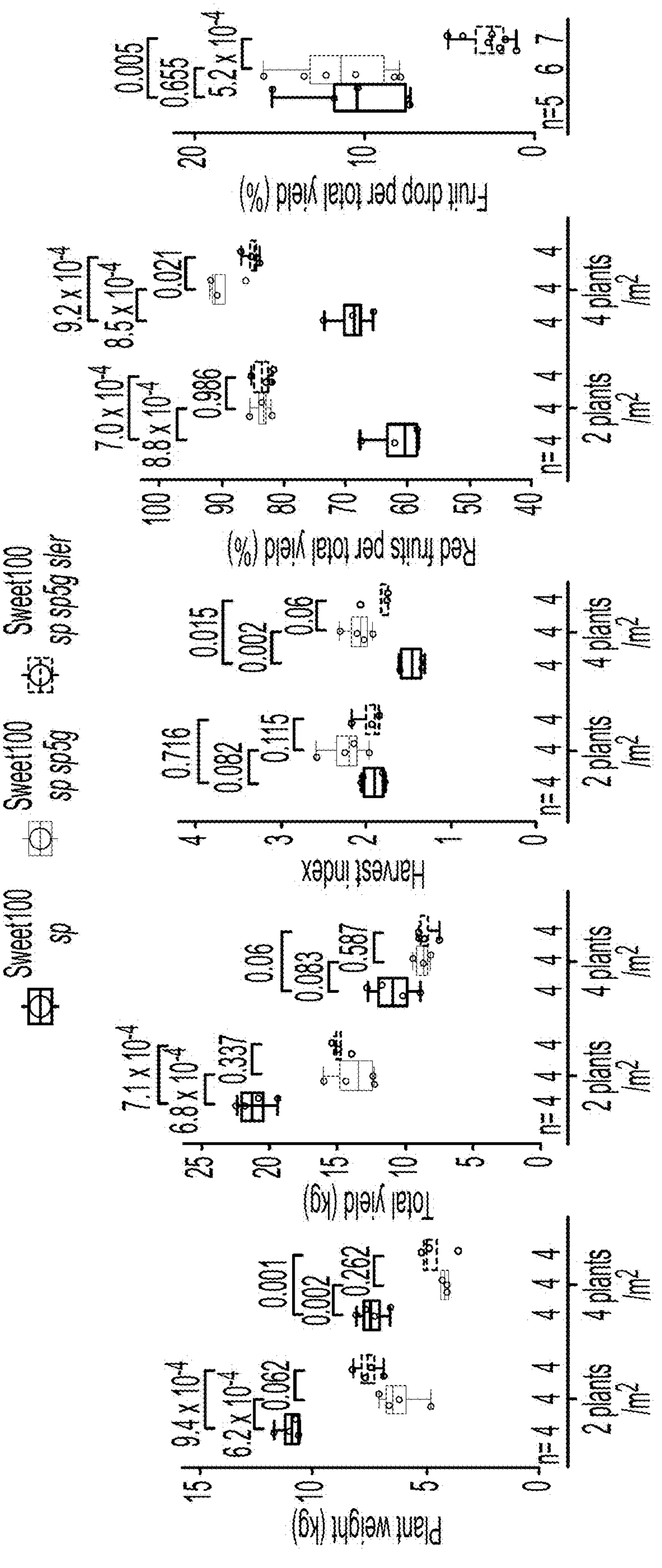

This example shows CRISPR-Cas9 mutagenesis of SlER in the cherry tomato cultivar Sweetl00, and additional comparisons between Sweet100 sp determinate, sp sp5g double-determinate and sp sp5g sler triple-determinate plants. Breeding medium and large-fruited varieties such as M82 for urban agriculture is not practical, because larger plants are needed to support the high metabolic and structural demands of fruits that also require more time to develop and ripen. The focus herein was therefore on using CRISPR-Cas9 to generate a triple-determinate small-fruited variety. SlER was targeted in "Sweetl00" double-determinate plants[7] (generated in-lab), and the resulting plants showed a triple-determinate form (FIGS. 3A, 3B and FIGS. 9A, 9B). Important agronomic traits including flowering time, flower number, and sugar content (Brix) were the same as double-determinates, though fruit size was slightly decreased (FIGS. 9C-9E). Testing was conducted to determine if Sweetl00 triple-determinate plants perform well under restricted space conditions by performing a high-density yield trial in agricultural fields. Less than 40 days after transplanting, both double-determinate and triple-determinate plants produced their first ripe fruits, providing early yield and rapid cycling (FIGS. 3C, 3D). Importantly, triple-determinate plants had the smallest stature of all Sweet100 genotypes in all conditions, and yields were the same as double-determinates (FIG. 3D and FIG. 10). It was also found that the highly compact fruit clusters minimized fruit drop during harvest (FIG. 10C). Finally, it was demonstrated that the first steps for cultivating a Sweet100 triple-determinate variety (produced in-lab) in both a light-emitting diode (LED) growth chamber and a self-contained, climate-controlled LED hydroponic vertical farm system (FIGS. 3E, 3F). Together, these results demonstrate that high performing triple-determinate small-fruited tomato varieties can be developed to accommodate the growth restrictions of urban agriculture.

Example 5. Generation of F2 Populations

Figure 11A:
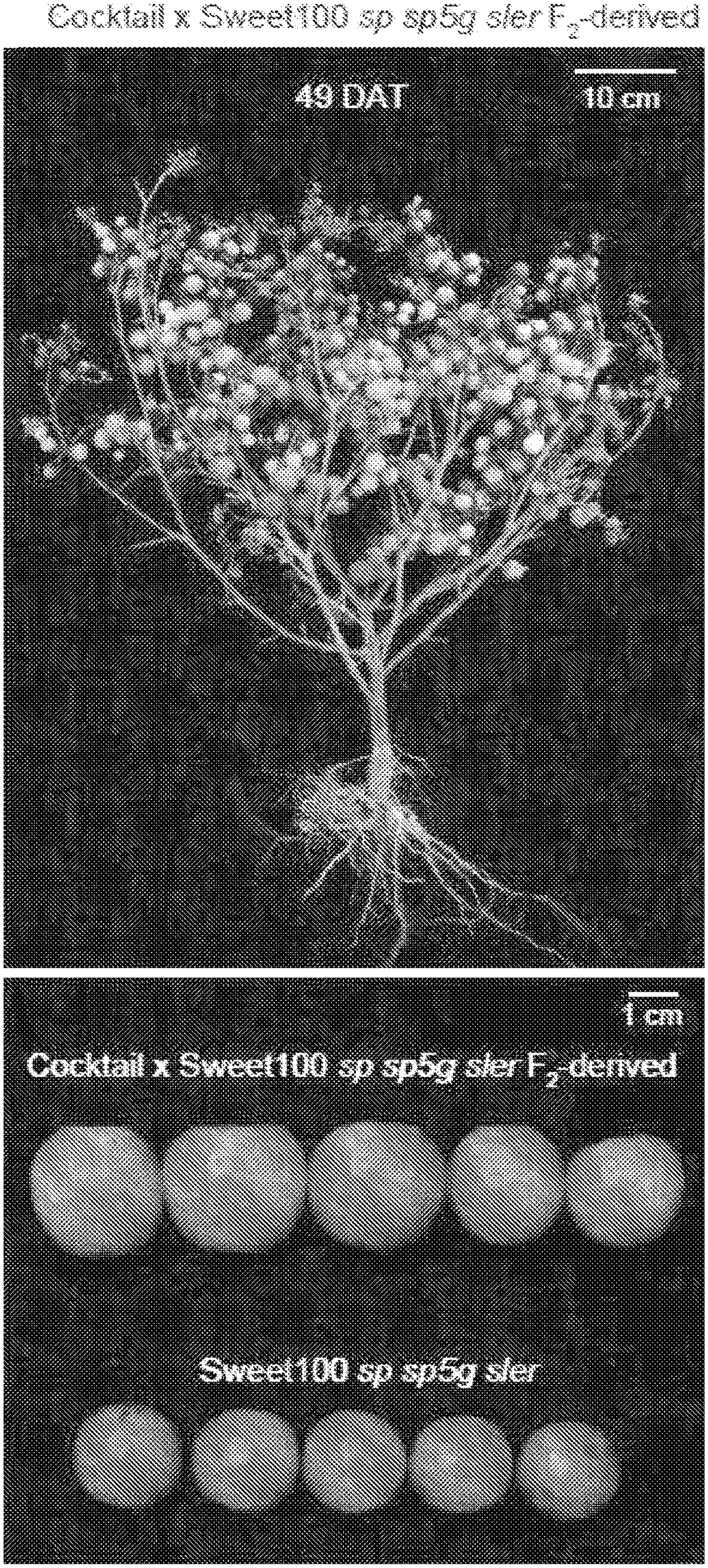
Figure 11B:
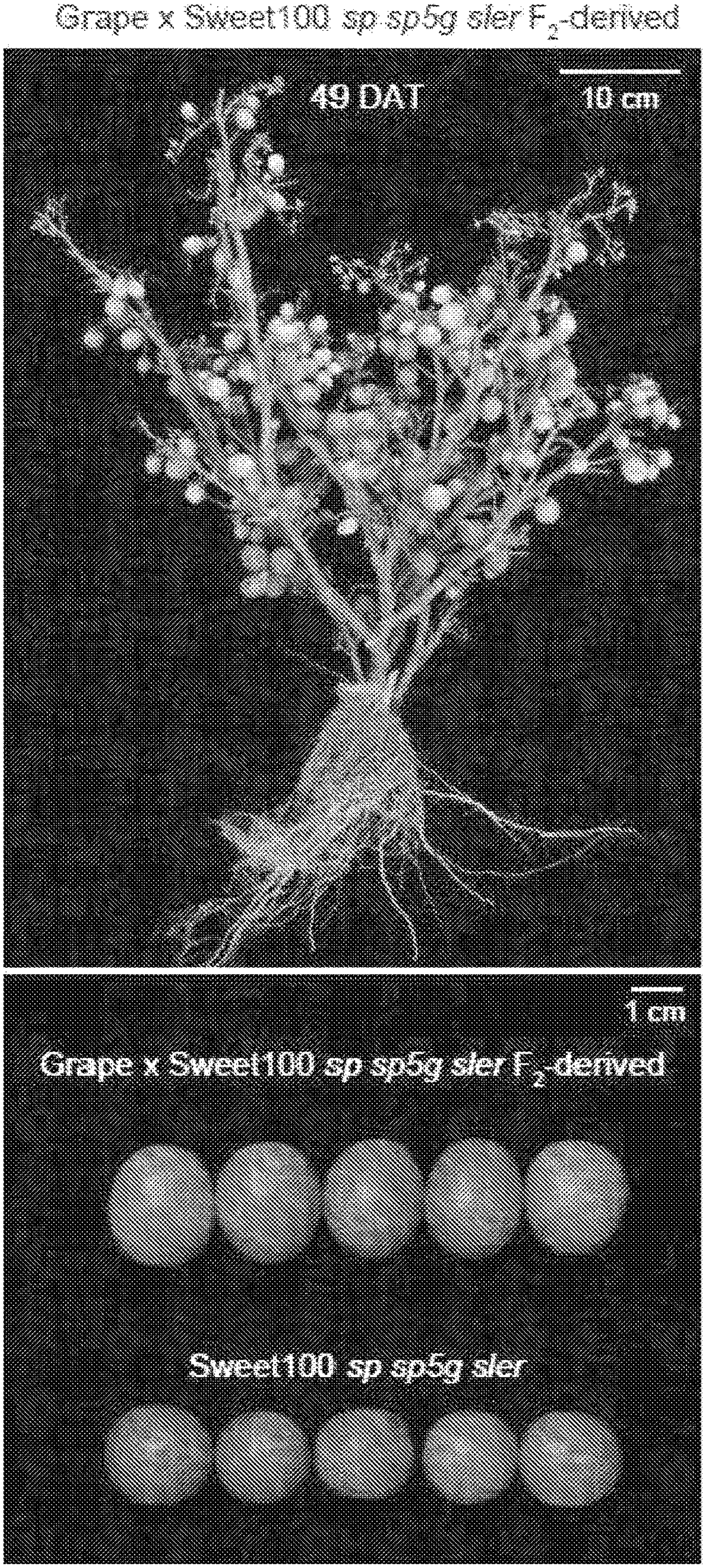
Figure 12A:
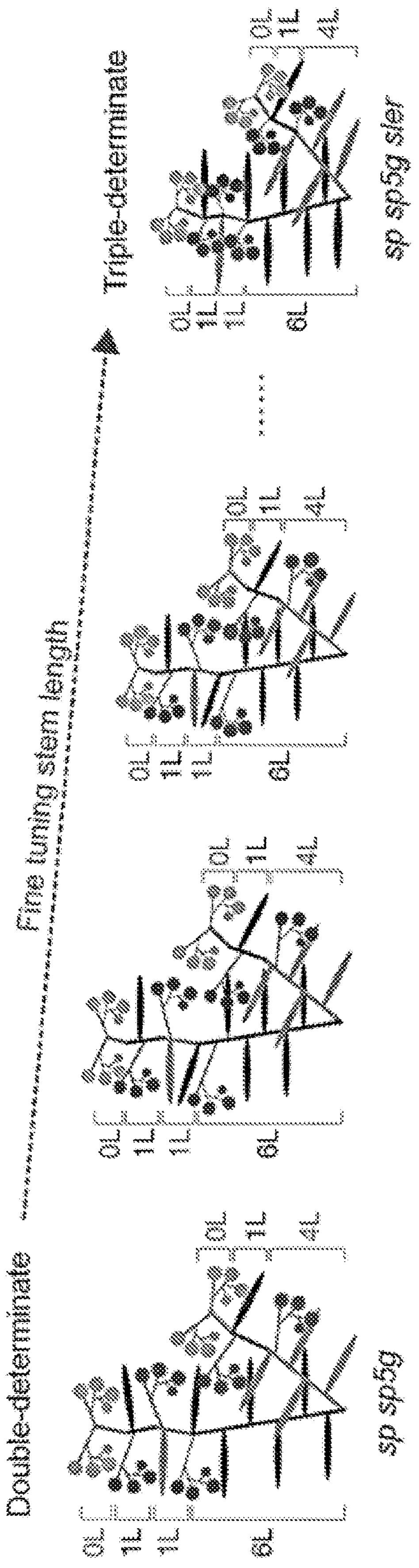
FIGS. 12A-12H show fine-tuning stem length from an in-frame mutation in the SlER coding sequence and by targeting the SlER promoter region.
Figure 12B:
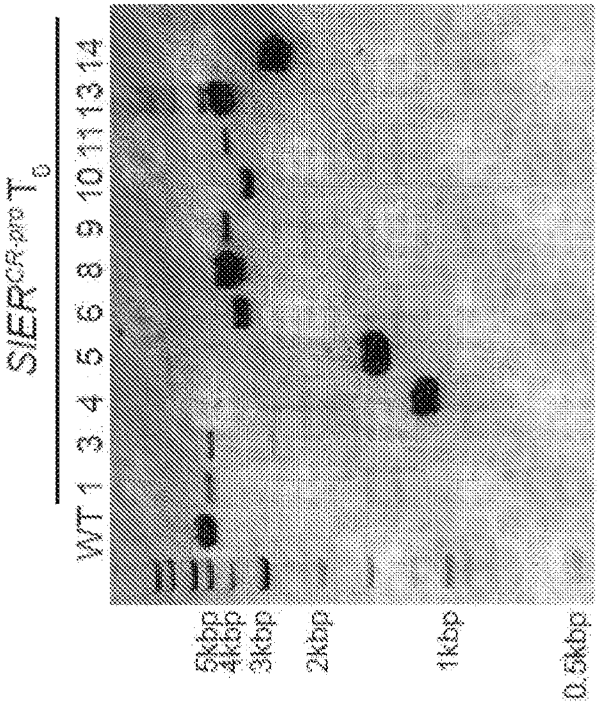
Figure 12C:
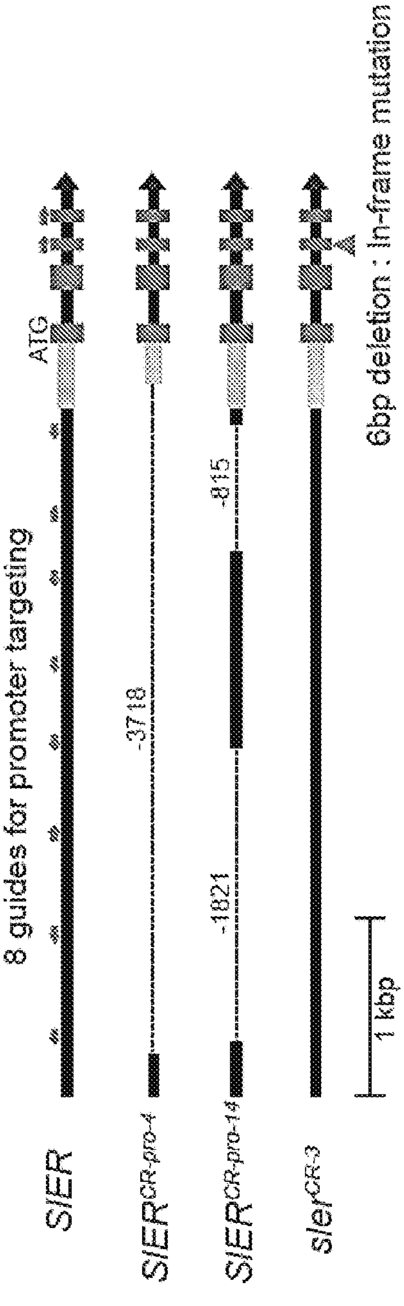
Figure 12D:
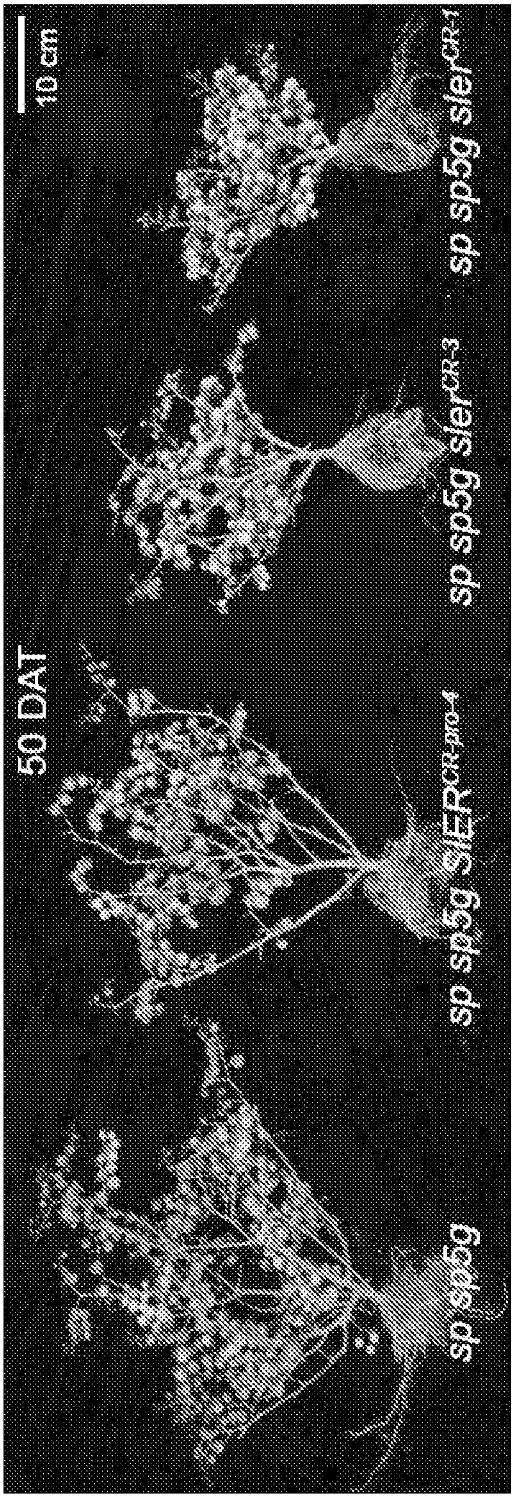
Figure 12E:
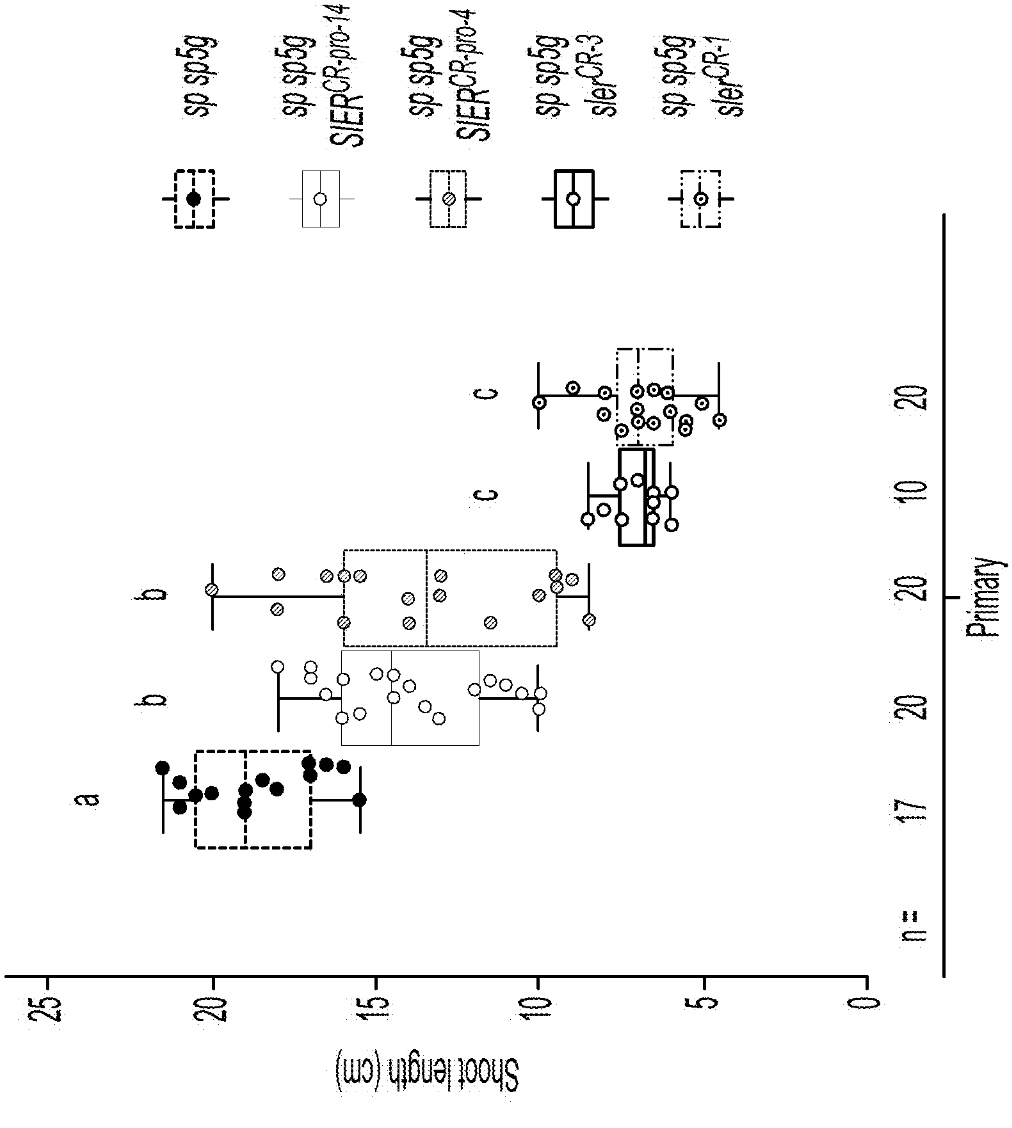
Figure 12F:
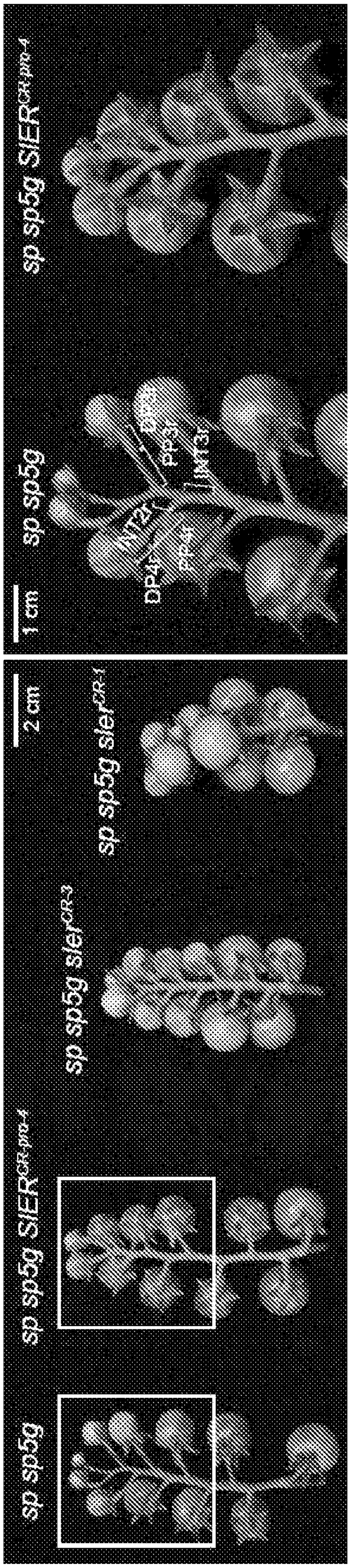
Figure 12G:
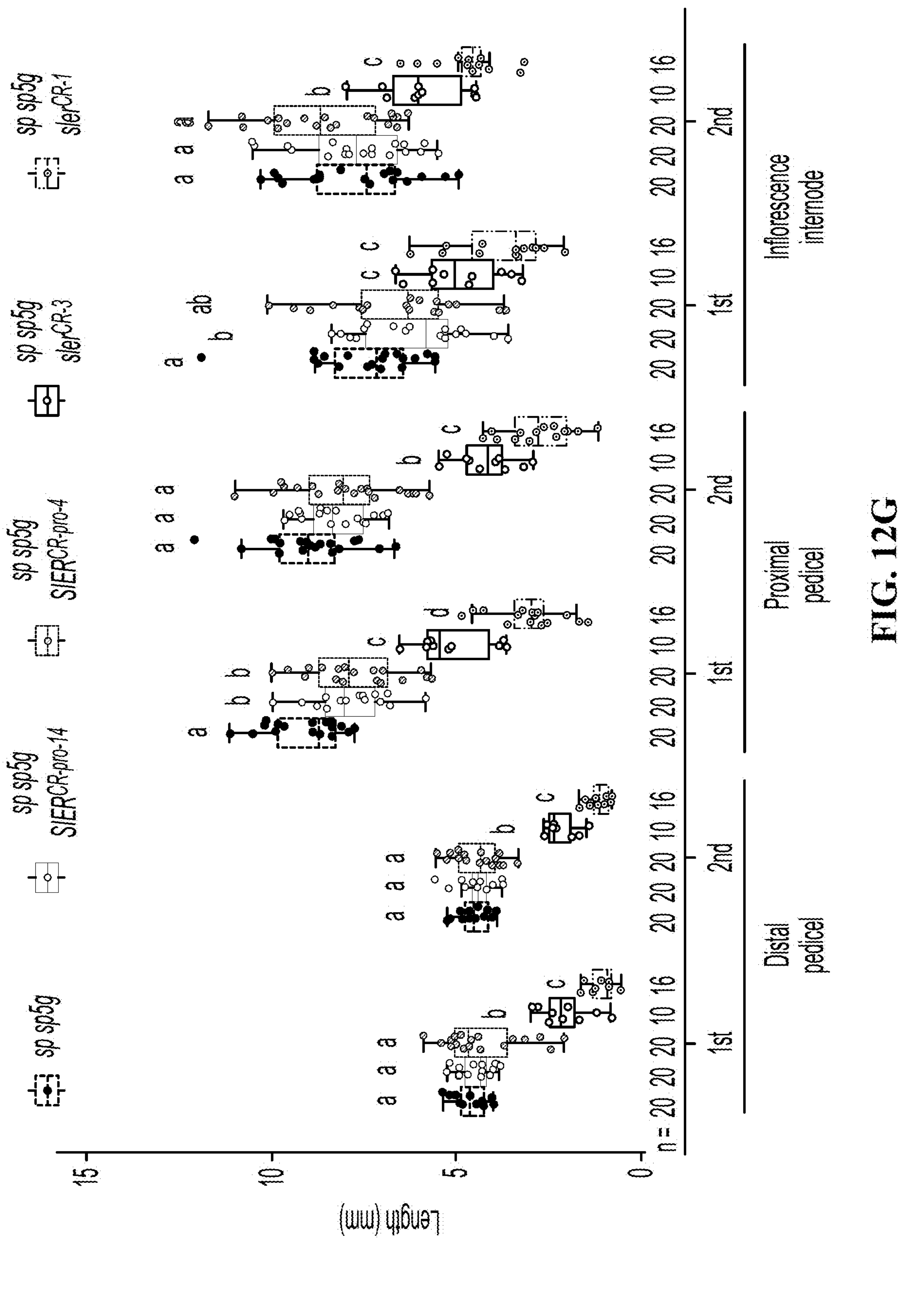
Figure 12H:
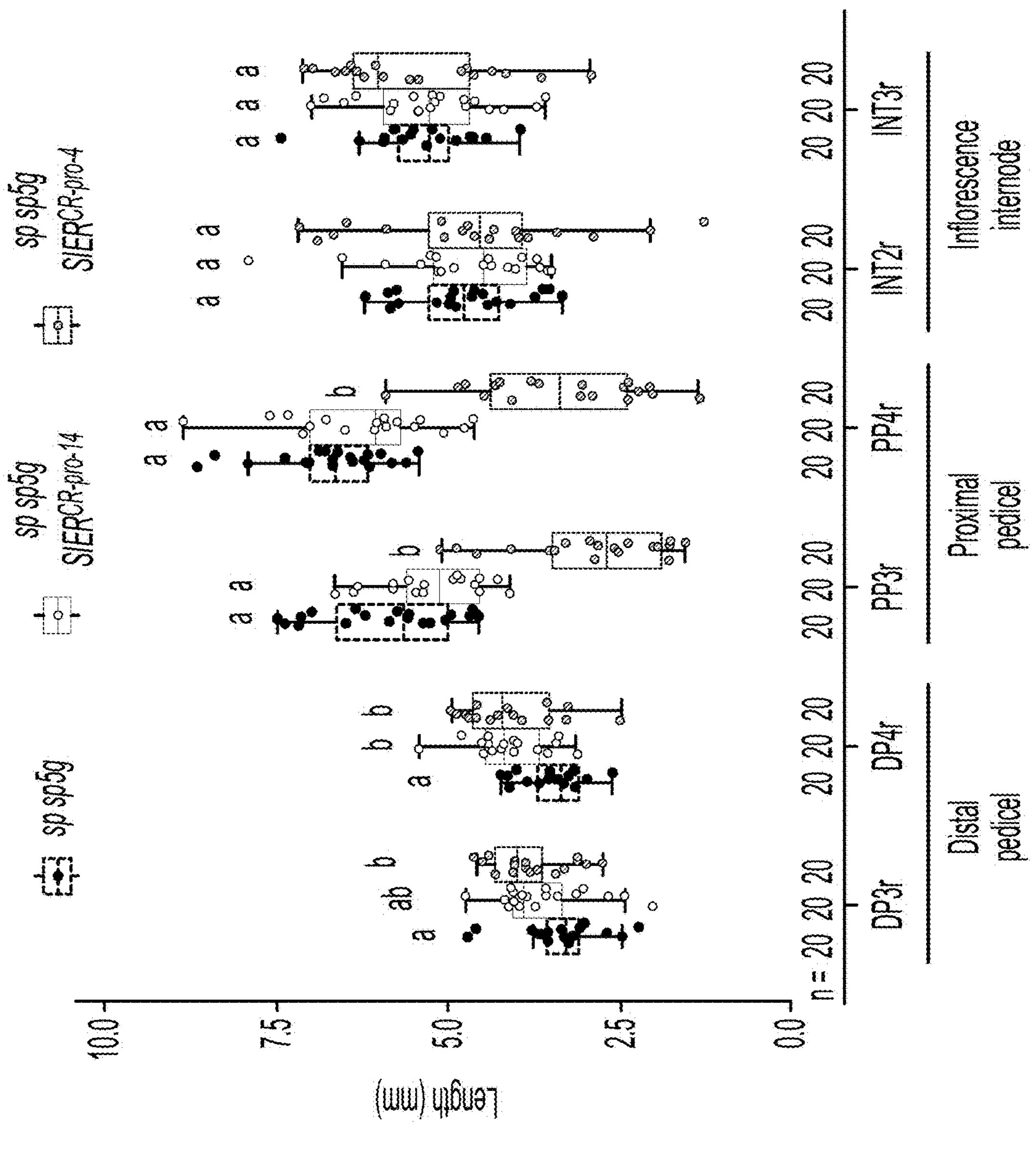

The results herein have demonstrated a straightforward genetic path that allowed rapid adaptation of a Solanaceae fruit crop to the most challenging agronomic parameters of urban agriculture: rapid cycling and compact plant size. The CRISPR-Cas9 based approach disclosed will allow rapid modification of many other small-fruited tomato varieties into a triple-determinate growth habit by generating loss-of-function alleles of SP, SP5G and SlER in elite breeding lines. Alternatively, in cases where resources for genome editing are not available, the novel genetic diversity generated, as disclosed, in these genes in a "plum" and "cherry" variety can easily be incorporated into traditional breeding programs. To appeal to consumers, small-fruited tomato varieties have been bred for diverse colors, shapes, sizes, and flavor profiles, and crossing these genotypes with the triple determinate plants disclosed would allow rapid selection for these highly desirable and heritable fruit quality traits. To demonstrate this, $F_2$ populations between Sweet100 triple determinates and a "cocktail" and a "grape" tomato variety were generated, and new triple determinate genotypes with larger and elongated fruits, respectively, were selected (FIG. 11). The alleles disclosed could also be used to customize plant compactness for specific agronomic needs. For example, sp5g and sler mutations could be combined to develop early yielding and shorter indeterminate varieties for urban greenhouses. In such cases, particularly when larger-fruited varieties are sought, a more subtle change in internode length might be beneficial, which could be achieved with weak sler alleles. Notably, one of the CRISPR-Cas9 alleles disclosed was a 6 bp in-frame mutation in the SlER LRR domain that resulted in a weaker effect on stem and pedicel length. Weak alleles were also generated by targeting the promoter of SlER (FIG. 12)[22].

REFERENCES

1. Benke, K. & Tomkins, B. Future food-production systems: vertical farming and controlled-environment agriculture. Sustain. *Sci. Pract. Policy* 13, 13-26 (2017).
2. Pearson, L. J., Pearson, L. & Pearson, C. J. Sustainable urban agriculture: stocktake and opportunities. *Int. J. Agric. Sustain.* 8, 7-19 (2010).
3. Martellozzo, F. et al. Urban agriculture: a global analysis of the space constraint to meet urban vegetable demand. *Environ. Res. Lett.* 9, 064025 (2014).
4. Banerjee, C. & Adenaeuer, L. Up, Up and Away! The Economics of Vertical Farming. *J. Agric. Stud.* 2, 40-60 (2014).
5. Touliatos, D., Dodd, I. C. & McAinsh, M. Vertical farming increases lettuce yield per unit area compared to conventional horizontal hydroponics. *Food Energy Secur.* 5, 184-191 (2016).
6. Pnueli, L. et al. The SELF-PRUNING gene of tomato regulates vegetative to reproductive switching of sympodial meristems and is the ortholog of CEN and TFL1. *Development* 125, 1979-1989 (1998).
7. Soyk, S. et al. Variation in the flowering gene SELF PRUNING 5G promotes day-neutrality and early yield in tomato. *Nat. Genet.* 49, 162-168 (2017).
8. Xu, C. et al. A cascade of arabinosyltransferases controls shoot meristem size in tomato. *Nat. Genet.* 47, 784-792 (2015).
9. Menda, N., Semel, Y., Peled, D., Eshed, Y. & Zamir, D. In silico screening of a saturated mutation library of tomato. *Plant J.* 38, 861-872 (2004).
10. Brand, A., Shirding, N., Shleizer, S. & Ori, N. Meristem maintenance and compound-leaf patterning utilize common genetic mechanisms in tomato. *Planta* 226, 941-951 (2007).
11. Torii, K. U. et al. The Arabidopsis ERECTA gene encodes a putative receptor protein kinase with extracellular leucine-rich repeats. *Plant Cell* 8, 735-746 (1996).
12. Saito, T. et al. TOMATOMA: A Novel Tomato Mutant Database Distributing MicroTom Mutant Collections. *Plant Cell Physiol.* 52, 283-296 (2011).
13. aan den Toorn, M., Albrecht, C. & de Vries, S. On the Origin of SERKs: Bioinformatics Analysis of the Somatic Embryogenesis Receptor Kinases. *Mol. Plant* 8, 762-782 (2015).
14. Shpak, E. D. Diverse Roles of *ERECTA* Family Genes in Plant Development. *J. Integr. Plant Biol.* 55, 1238-1250 (2013).
15. Shpak, E. D., McAbee, J. M., Pillitteri, L. J. & Torii, K. U. Stomatal Patterning and Differentiation by Synergistic Interactions of Receptor Kinases. *Science* 309, 290-293 (2005).
16. Masle, J., Gilmore, S. R. & Farquhar, G. D. The ERECTA gene regulates plant transpiration efficiency in Arabidopsis. *Nature* 436, 866-870 (2005).
17. Mandel, T. et al. The ERECTA receptor kinase regulates Arabidopsis shoot apical meristem size, phyllotaxy and floral meristem identity. *Development* 141, 830-841 (2014).
18. Kimura, Y., Tasaka, M., Torii, K. U. & Uchida, N. ERECTA-family genes coordinate stem cell functions between the epidermal and internal layers of the shoot apical meristem. *Development* 145, dev156380 (2018).
19. Zhang, Y. et al. Phylogenetic and CRISPR/Cas9 Studies in Deciphering the Evolutionary Trajectory and Phenotypic Impacts of Rice ERECTA Genes. *Front. Plant Sci.* 9, 473 (2018).
20. Lemmon, Z. H. et al. Rapid improvement of domestication traits in an orphan crop by genome editing. *Nat. Plants* 4, 766-770 (2018).
21. Martinez, M. The correct application of Physalis pruinosa L. (Solanaceae). *TAXON* 42, 103-104 (1993).
22. Rodriguez-Leal, D., Lemmon, Z. H., Man, J., Bartlett, M. E. & Lippman, Z. B. Engineering Quantitative Trait Variation for Crop Improvement by Genome Editing. *Cell* 171, 470-480.e8 (2017).
23. Elitzur, T. et al. Co-ordinated regulation of flowering time, plant architecture and growth by FASCICULATE: the pepper ortholog of SELF PRUNING. *J. Exp. Bot.* 60, 869-880 (2009).
24. Varkonyi-Gasic, E. et al. Mutagenesis of kiwifruit CENTRORADIALIS-like genes transforms a climbing woody perennial with long juvenility and axillary flowering into a compact plant with rapid terminal flowering. *Plant Biotechnol. J.* 17, 869-880 (2019).
25. Wen, C. et al. CsTFL1 inhibits determinate growth and terminal flower formation through interaction with CsNOT2a in cucumber. *Development* 146, dev180166 (2019).
26. Eshed, Y. & Lippman, Z. B. Revolutions in agriculture chart a course for targeted breeding of old and new crops. *Science* eaax0025 (2019) doi:10.1126/science.aax0025.
27. Tomlinson, L. et al. Using CRISPR/Cas9 genome editing in tomato to create a gibberellin-responsive dominant dwarf DELLA allele. *Plant Biotechnol. J.* 17, 132-140 (2019).
28. Wheeler, R. M. Agriculture for Space: People and Places Paving the Way. *Open Agric.* 2, 14-32 (2017).
29. Wang, M., Dong, C. & Gao, W. Evaluation of the growth, photosynthetic characteristics, antioxidant capacity, biomass yield and quality of tomato using aeroponics, hydroponics and porous tube-vermiculite systems in bio-regenerative life support systems. *Life Sci. Space Res.* 22, 68-75 (2019).
30. Brooks, C., Nekrasov, V., Lippman, Z. B. & Van Eck, J. Efficient gene editing in tomato in the first generation using the clustered regularly interspaced short palindromic repeats/CRISPR-associated9 system. *Plant Physiol.* 166, 1292-1297 (2014).
31. Van Eck, J., Keen, P. & Tjahjadi, M. Agrobacterium tumefaciens-Mediated Transformation of Tomato. in *Transgenic Plants: Methods and Protocols* (eds. Kumar, S., Barone, P. & Smith, M.) 225-234 (Springer New York, 2019). doi:10.1007/978-1-4939-8778-8_16.

32. Swartwood, K. & Van Eck, J. Development of plant regeneration and Agrobacterium tumefaciens-mediated transformation methodology for Physalis pruinosa. *Plant Cell Tissue Organ Cult. PCTOC* 137, 465-472 (2019).
33. Naito, Y., Hino, K., Bono, H. & Ui-Tei, K. CRISPRdirect: software for designing CRISPR/Cas guide RNA with reduced off-target sites. *Bioinformatics* 31, 1120-1123 (2015).
34. Werner, S., Engler, C., Weber, E., Gruetzner, R. & Marillonnet, S. Fast track assembly of multigene constructs using Golden Gate cloning and the MoClo system. *Bioeng. Bugs* 3, 38-43 (2012).
35. Rodriguez-Leal, D. et al. Evolution of buffering in a genetic circuit controlling plant stem cell proliferation. *Nat. Genet.* 51, 786-792 (2019).
36. Soyk, S. et al. Duplication of a domestication locus neutralized a cryptic variant that caused a breeding barrier in tomato. *Nat. Plants* 5, 471 (2019).
37. Park, S. J., Jiang, K., Schatz, M. C. & Lippman, Z. B. Rate of meristem maturation determines inflorescence architecture in tomato. *Proc. Natl. Acad. Sci. U.S.A* 109, 639-644 (2012).
38. Goodstein, D. M. et al. Phytozome: a comparative platform for green plant genomics. *Nucleic Acids Res.* 40, D1178-D1186 (2012).
39. Katoh, K. & Standley, D. M. MAFFT multiple sequence alignment software version 7: improvements in performance and usability. *Mol. Biol. Evol.* 30, 772-780 (2013).
40. Miller, M. A. et al. A RESTful API for Access to Phylogenetic Tools via the CIPRES Science Gateway. *Evol. Bioinforma. Online* 11, 43-48 (2015).
41. Nguyen, L.-T., Schmidt, H. A., von Haeseler, A. & Minh, B. Q. IQ-TREE: A Fast and Effective Stochastic Algorithm for Estimating Maximum-Likelihood Phylogenies. *Mol. Biol. Evol.* 32, 268-274 (2015).
42. R Core Team (2015). R: *A language and environment for statistical computing*. (R Found. Stat. Comput. Vienna, Austria.).

Those skilled in the art will recognize, or be able to ascertain using no more than routine experimentation, many equivalents to the specific embodiments disclosed. Such equivalents are intended to be encompassed by the following claims.

What is claimed is:

1. A tomato plant comprising:

a genetically-altered, mutant *Solanum lycopersicum ERECTA* (sler) gene comprising a sequence that has at least 99% identity with the nucleic acid sequence of SEQ ID NO: 1, wherein the genetically-altered mutant sler gene is a null allele or a hypomorphic allele; and a mutant SELF-PRUNING (sp) gene comprising a sequence that has at least 99% identity with the nucleic acid sequence of SEQ ID NO: 67, wherein the mutant sp gene is a null allele or hypomorphic allele, wherein the tomato plant has reduced stem length between leaves and flowers (internodes) relative to a reference tomato plant without such mutation in a non-coding, cis-regulatory element of the sler gene.

2. The tomato plant of claim 1 further comprising:

a mutant SELF-PRUNING 5G (sp5g) gene comprising a sequence that has at least 99% identity with the nucleic acid sequence of SEQ ID NO: 52, and wherein the mutant sp5g gene is a null allele or hypomorphic allele.

3. The tomato plant of claim 1, wherein the mutant sler gene is a null allele.

4. The tomato plant of claim 1, wherein the tomato plant is homozygous for the mutant sler gene.

5. The tomato plant of claim 2, wherein the tomato plant is homozygous for the mutant sp5g gene and homozygous for the mutant sp gene, and wherein each is a null allele.

6. A crop harvested from the tomato plant of claim 1.

7. A seed produced by the tomato plant of claim 1, wherein the seed comprises the mutant sler gene and the mutant sp gene.

8. The tomato plant of claim 1, wherein the tomato plant is heterozygous for the mutant sler gene.

9. A crop harvested from the tomato plant of claim 2.

10. A seed produced by the tomato plant of claim 2, wherein the seed comprises the mutant sler gene, the mutant sp gene, and the mutant sp5g gene.

* * * * *